United States Patent
Griffin et al.

(10) Patent No.: US 10,744,117 B2
(45) Date of Patent: *Aug. 18, 2020

(54) PPARG MODULATORS FOR THE TREATMENT OF OSTEOPOROSIS

(71) Applicants: The Scripps Research Institute, La Jolla, CA (US); University of Toledo, Toledo, OH (US)

(72) Inventors: Patrick R. Griffin, Jupiter, FL (US); Theodore Kamenecka, Palm Beach Gardens, FL (US); Beata Lecka-Czernik, Toledo, OH (US)

(73) Assignees: The Scripps Research Institute, La Jolla, CA (US); The University of Toledo, Toledo, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/028,730

(22) Filed: Jul. 6, 2018

(65) Prior Publication Data
US 2018/0369196 A1  Dec. 27, 2018

Related U.S. Application Data

(63) Continuation of application No. 15/302,862, filed as application No. PCT/US2015/026226 on Apr. 16, 2015, now Pat. No. 10,016,394.

(60) Provisional application No. 61/980,444, filed on Apr. 16, 2014.

(51) Int. Cl.
| | | |
|---|---|---|
| A61K 31/404 | (2006.01) |
| A61K 31/4045 | (2006.01) |
| A61K 31/41 | (2006.01) |
| A61K 31/4245 | (2006.01) |
| A61K 31/4439 | (2006.01) |
| A61K 31/454 | (2006.01) |
| A61K 31/4709 | (2006.01) |
| A61K 31/5377 | (2006.01) |
| C07D 209/08 | (2006.01) |
| C07D 209/18 | (2006.01) |

(52) U.S. Cl.
CPC ........ *A61K 31/404* (2013.01); *A61K 31/4045* (2013.01); *A61K 31/41* (2013.01); *A61K 31/4245* (2013.01); *A61K 31/4439* (2013.01); *A61K 31/454* (2013.01); *A61K 31/4709* (2013.01); *A61K 31/5377* (2013.01); *C07D 209/08* (2013.01); *C07D 209/18* (2013.01)

(58) Field of Classification Search
CPC .................................................... A61K 31/404
See application file for complete search history.

(56) References Cited

U.S. PATENT DOCUMENTS 10,016,394 B2 * 7/2018 Griffin ................. C07D 209/08

FOREIGN PATENT DOCUMENTS

WO   WO-9710219 A1 * 3/1997  ........... C07D 235/06

OTHER PUBLICATIONS

Oku et al., WO 97/10219 A1 (Mar. 20, 1997), SciFinder abstract retrieved from database CAPLUS (Acc. No. 1997:315042).*

* cited by examiner

*Primary Examiner* — Brian J Davis
(74) *Attorney, Agent, or Firm* — Hugh Wang; Thomas Fitting

(57) ABSTRACT

The invention provides methods of treatment of a progressive bone disease, such as osteoporosis, Paget's Disease, multiple myeloma, or hyperparathyroidism, comprising administration of an effective amount of a non-agonist PPARG modulator to a patient afflicted with the disease.

14 Claims, 15 Drawing Sheets

Figure 4

Top Indole Acids

| SR# | IC50 (nM) Lantha | 1EC50 (nM) GAL_4 | 1EC50 (nM) PPRE | 1EC50 (nM) PPARα | 3T3-L1 Cell Data | % inhibition 20μM | P-PPAR 2μM | Mouse In Vivo 2[plasma] μM, 2h | Mouse In Vivo [plasma] μM, 6h | Rat In Vivo 3Clp (mL/min/kg) | Rat In Vivo T1/2 (h) | Rat In Vivo Vd (L/kg) | Rat In Vivo AUC (μM·h) | Rat In Vivo %F |
|---|---|---|---|---|---|---|---|---|---|---|---|---|---|---|
| SR-10167 | 60 | No activity | No activity | 1446 (2x) | non-agonist | NT | | 13 | 8 | 1 | 5 | 1 | 8 | 15 |
| SR-10171 | 126 | 7260 (4%) | No activity | 1499 (x10) | non-agonist | 54 | 12 | 79 | 34 | 2 | 5 | 0.33 | 18 | 21 |
| SR-11023 | 108 | 2761 (10%) | No activity | No activity | non-agonist | 77 | 25 | 35 | 5 | 19 | 3.7 | 5 | 1.4 | 16 |
| SR-11789 | 17 | 3000 (5%) | No activity | No activity | non-agonist | NT | | 30 | 6 | 13 | 3.7 | 3.9 | 1.4 | 28 |
| SR-11658 | 144 | No activity | No activity | No activity | non-agonist | NT | | 32 | 16 | 31 | 5.4 | 13 | 0.7 | 4 |

1 % transactivation at 10μM; 2 20mg/kg PO; 3 rat PK: 1mg/kg IV, 2mg/kg PO; 4 cannot fit PO curves; NT = not tested

| SR# | CYP inhibition (%) 1A2 | 2C9 | 2D6 | 3A4 | 1Microsome Stability (t1/2 minutes) Mouse | Rat | Human | Log D |
|---|---|---|---|---|---|---|---|---|
| 10171 | 20 | 81 | -2 | -8 | 71 | 37 | 28 | 3.35 |
| 11023 | 8 | 78 | -7 | 13 | 89 | 111 | 61 | 3.43 |

Log D was measured, differs from calculated

1 Sutent: 37, 18, 49 min (mouse, rat, human)

Figure 5

Bone and metabolic effect of SR10171 and Rosi in C57BL/6 mice with DIO

- C57BL/6 mice, males, 4 mo old
- DIO and glucose intolerance achieved after 4 wks of HFD
- Mice received SR10171 and Rosi as supplementation of HFD for 4 weeks
- Drug intake calculated at the end of exp:
  - SR10171 – 22.1 mg/kg/day
  - Rosi – 24.2 mg/kg/day
- Drug was well tolerated and no obvious toxicity observed with chronic dosing for 4 weeks. Liver weight was increased as expected due to the PPARA activity of SR10171. Weight loss was primarily due to loss of fat and serum FGF21 was elevated likely due to PPARA activity. However, interesting positive effects on bone where observed which have been shown previously to not be related to activation of PPARA.

Done in collaboration with Lecka-Czernik's lab

Updated: Feb. 10, 2014

Osmium staining for fat (yellow) in whole tibia and juxtaposed trabecular bone (gray) and fat (yellow) in proximal tibia Figure 13
A. 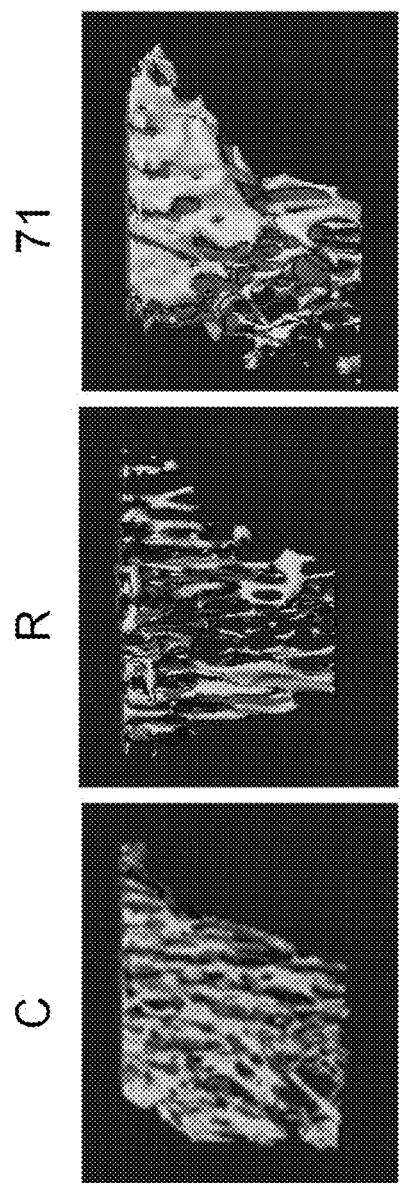
B. 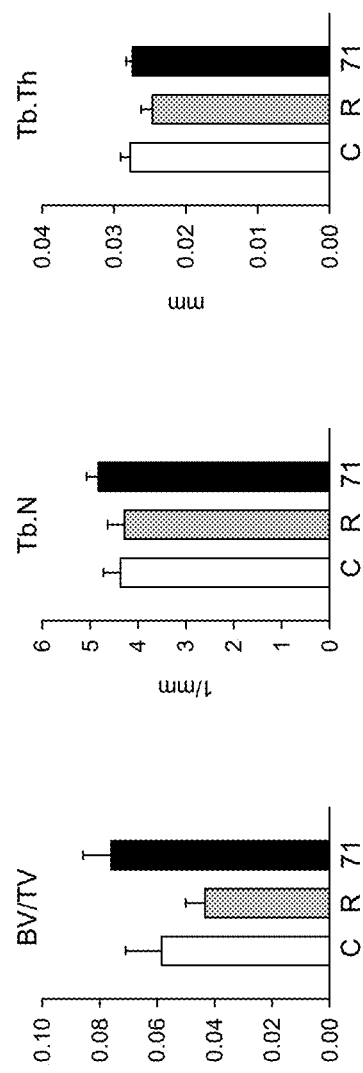

Figure 14
A.
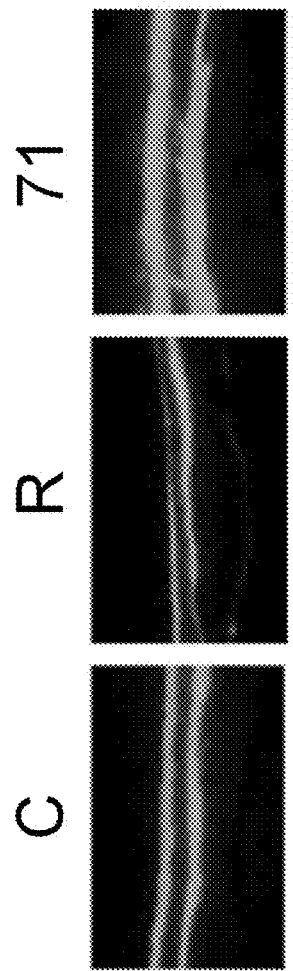
B.
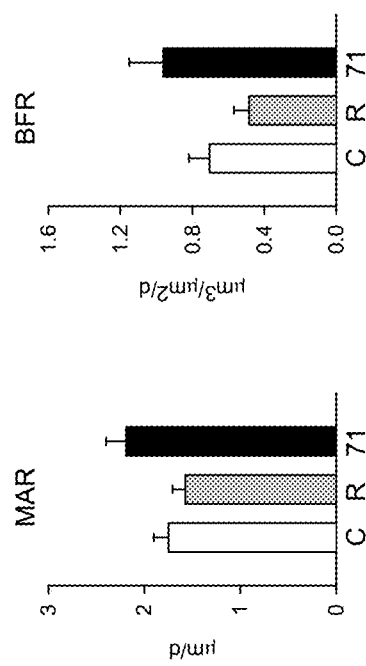

PPARG MODULATORS FOR THE TREATMENT OF OSTEOPOROSIS

CROSS-REFERENCE TO RELATED APPLICATIONS

This application claims the benefit of priority to U.S. Provisional Patent Application No. 61/980,444, which was filed on Apr. 16, 2014, the entire contents of which are incorporated by reference as if fully set forth herein. The disclosed subject matter herein is related to the subject matter of U.S. Ser. No. 13/490,324 published as US-2012-0309757, Ser. Nos. 13/811,965, 13/490,342 published as US-2012-0309769, Ser. Nos. 13/811,969, and 13/811,973, the disclosures of which are incorporated by reference herein in their entireties.

BACKGROUND

The peroxisome proliferator active receptors (PPARs), members of the nuclear hormone receptor superfamily, comprise several subtypes such as PPARα, PPARβ, and PPARγ. The PPARγ subtype, also referred to as PPARG, is the target of the glitazone pharmaceutical agents used for treatment of type II diabetes. PPARG is also known as NR1C3 (the gene ID) and there exist PPARG1 and PPARG2, the two major isoforms of PPARG. The glitazones, such as pioglitazone and rosiglitazone, act as PPARG receptor agonists. However, other classes of pharmaceutical agents, such as Telmisartan, have been reported to act as partial agonists, binding in a different mode to PPARG and having different cofactor requirements. See Y. Lamotte, et al., *Bioorg. Med. Chem. Lett.* (2010), 20, 1399-1404.

SUMMARY

The present invention is directed to methods of use of compounds that are non-activating (non-agonist) PPARG modulators, compounds of formula (I) including compounds of formula (IA) and of formula (IB) as described herein, in modulating the activity of PPARG, in treatment of conditions wherein non-activating modulation of PPARG is medically indicated, such as for treatment of a progressive bone disease. Compounds of the invention can block kinase-mediated, such as cdk5-mediated, phosphorylation of PPARG, but are not agonists of the receptor itself. By avoiding agonism of the receptor, it is believed that the compounds may exhibit no or reduced side effects associated with administration of full and partial agonists of PPARG, such as significant weight gain, edema, impairment of bone growth or formation, or cardiac hypertrophy, or any combination thereof, in the mammal receiving the compound. For instance, in practice of a method of treatment of a progressive bone disease in a patient, such as treatment of osteoporosis, Paget's Disease, multiple myeloma, hyperparathyroidism, and related progressive bone diseases, administration of an effective amount of a compound of formula (I) as disclosed herein can be used to treat the disease, wherein the effective dose of the compound acts to inhibit bone resorption, improve bone formation, or both, in the patient. For example, the method of treatment of the invention for the progressive bone disease can act to increase FGF21 while increasing bone health.

BRIEF DESCRIPTION OF THE FIGURES

FIG. 4 provides bioactivity details for compounds effective for carrying out a method of the invention.

FIG. 5 indicates the results of a 4-week study of SR10171, a compound effective for carrying out a method of the invention, in comparison with rosiglitazone.

FIG. 13 shows (A) mCT renderings and (B) measurements of trabecular bone in proximal tibia in lean C57BL/6 mice (BV/TV—bone mass; Tb.N—number of trabeculae; Tb.Th—trabecular thickness; C=control; R=rosiglitazone; 71=SR10171).

FIG. 14 shows dynamic histomorphometry of trabecular bone in proximal tibia double-labeled with calcein in lean C57BL/6 mice: (A) representative microphotographs of bone surface labeled with calcein, and (B) quantification of marrow apposition rate (MAR) and bone formation rate (BFR) (C=control; R=rosiglitazone; 71=SR10171).

DETAILED DESCRIPTION

Definitions

Figure 1:
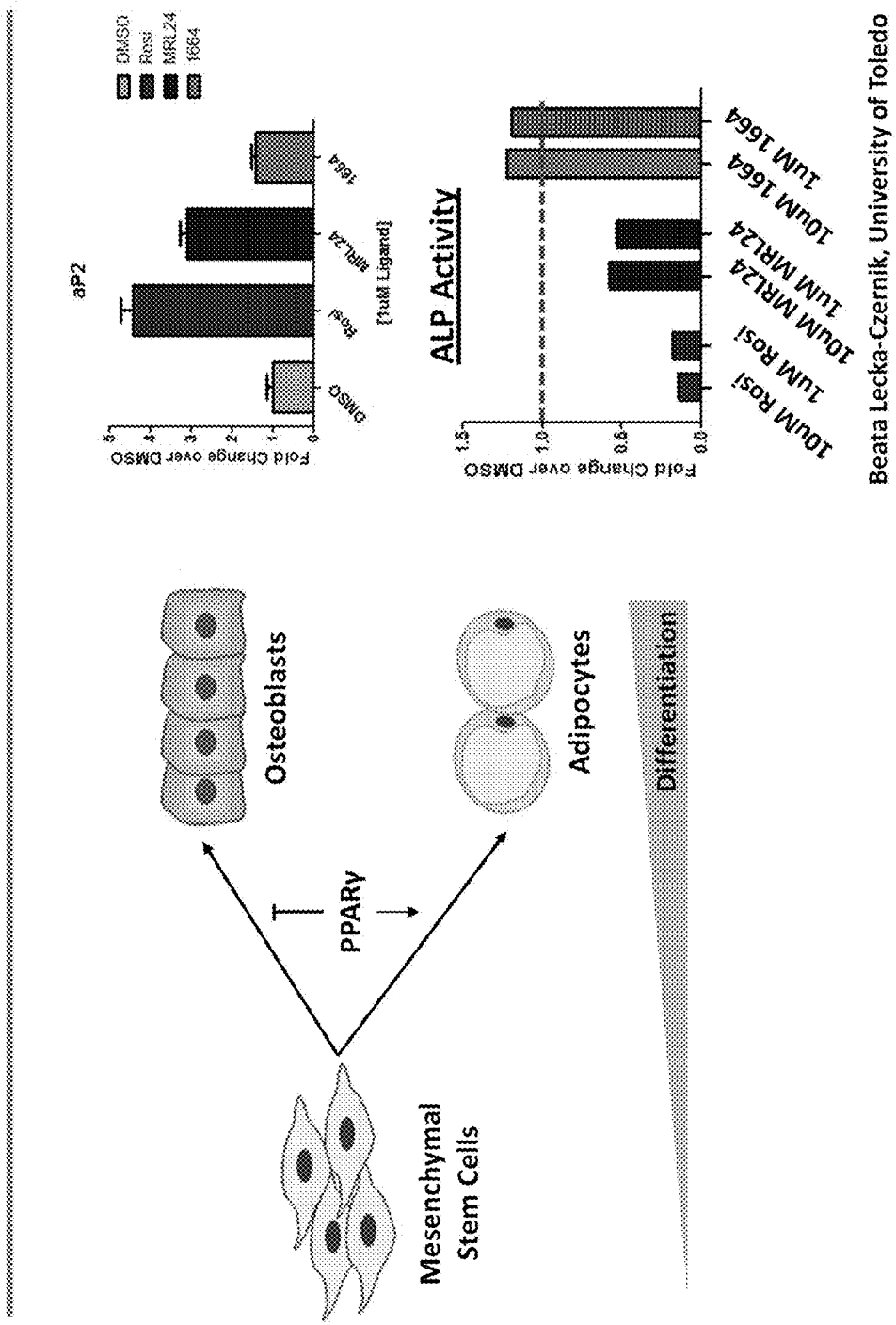
FIG. 1 is a schematic showing the differentiation of mesenchymal stem cells into osteoblasts and adipocytes under mediation of PPARG, along with bar graphs showing relative effects on PPARG target genes aP2 and ALP induced by rosiglitazone, MRL24 (a Merck PPARG partial agonist) and a compound of formula (I), SR1664.
Figure 2:
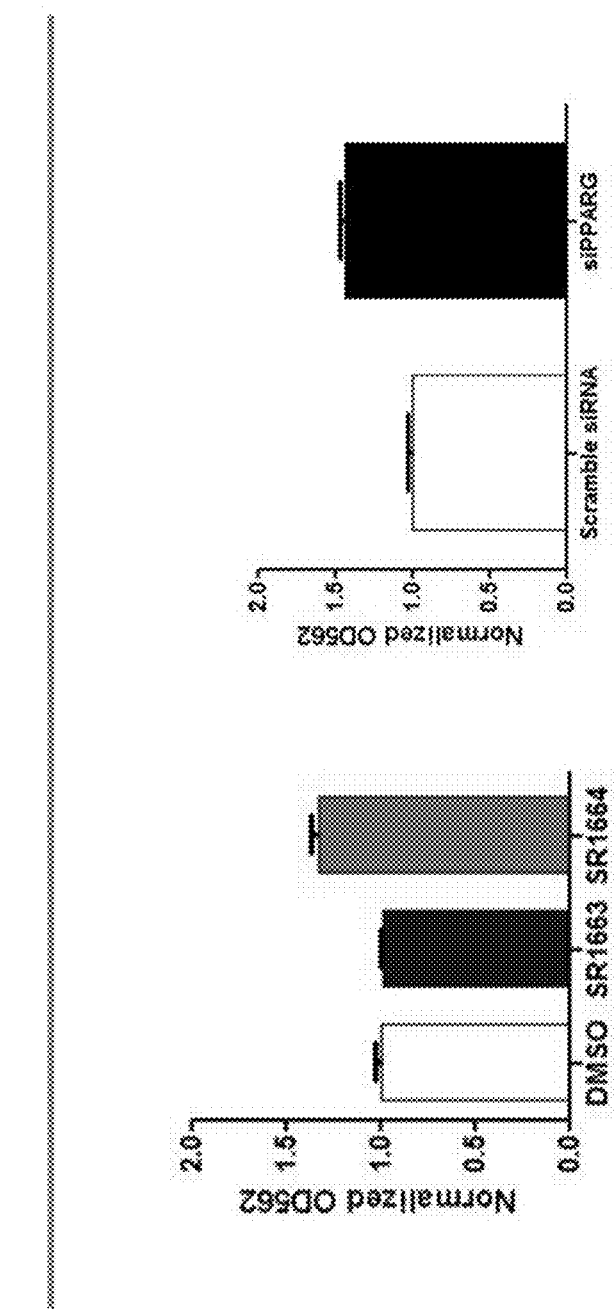
FIG. 2 is a bar graph showing the extent of bone formation marker in human mesenchymal stem cells upon treatment with a compound effective for practice of a method of the invention.
Figure 3:
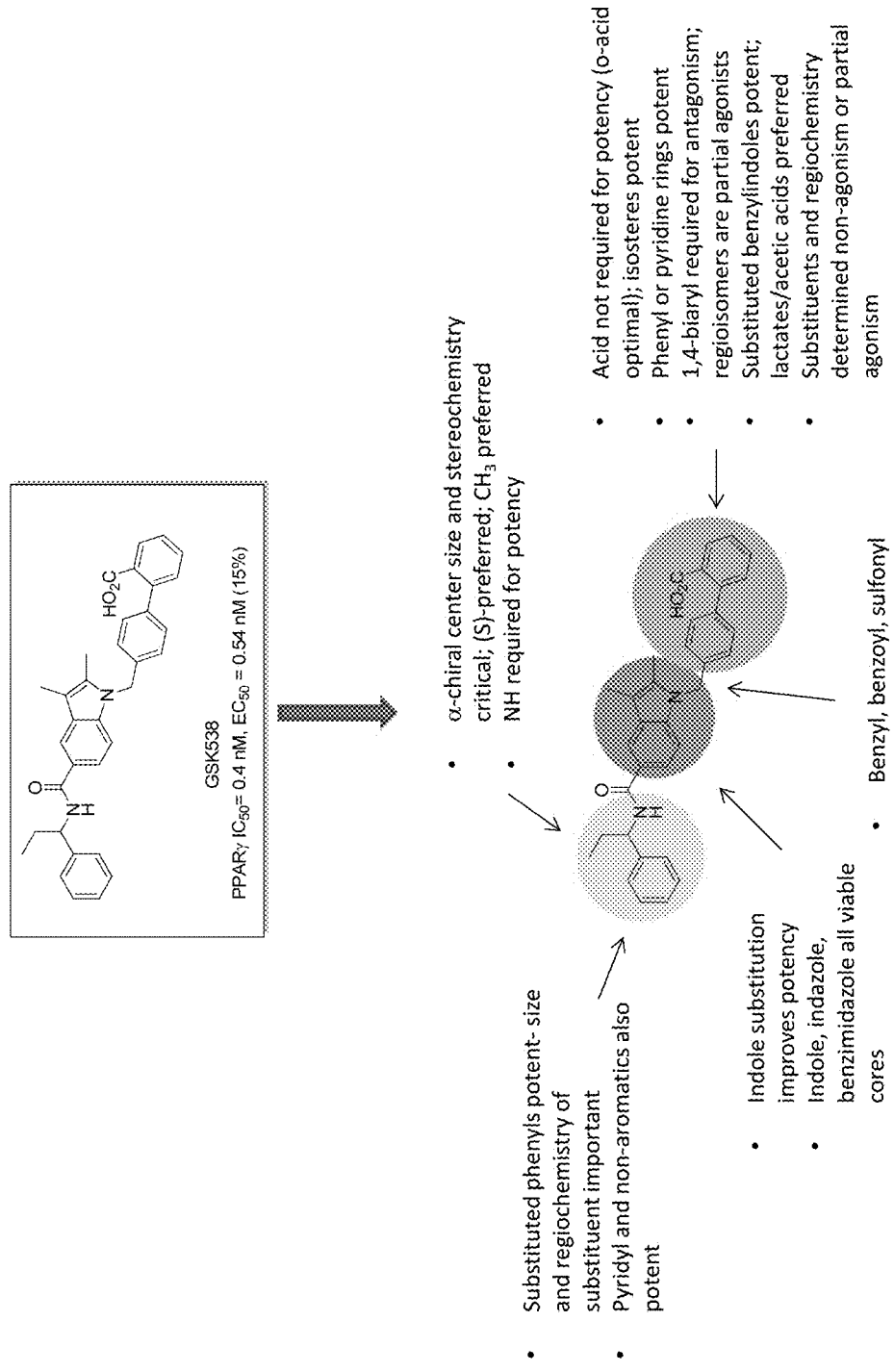
FIG. 3 schematically shows desirable molecular features of compounds for practicing a method of the invention.
Figure 6:
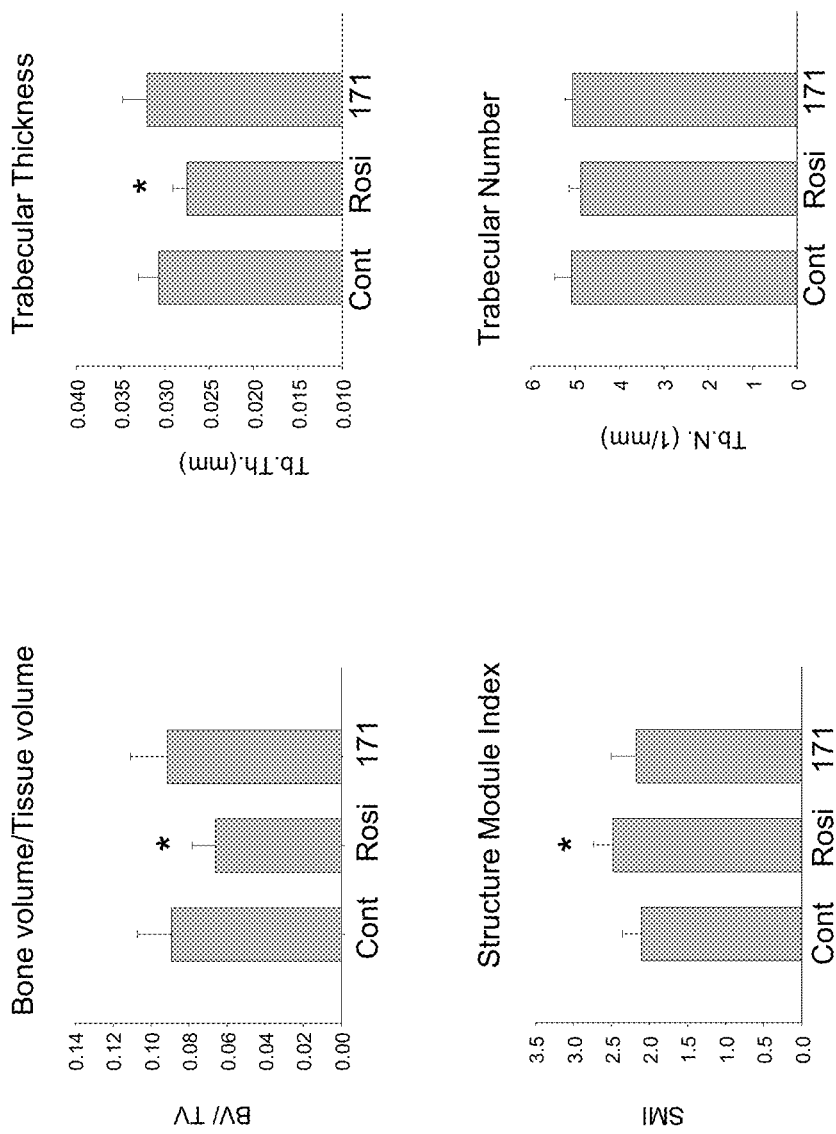
FIG. 6 shows bar graphs related to bone development, relative to control, of SR10171, a compound effective for carrying out a method of the invention, in comparison with rosiglitazone.
Figure 7:
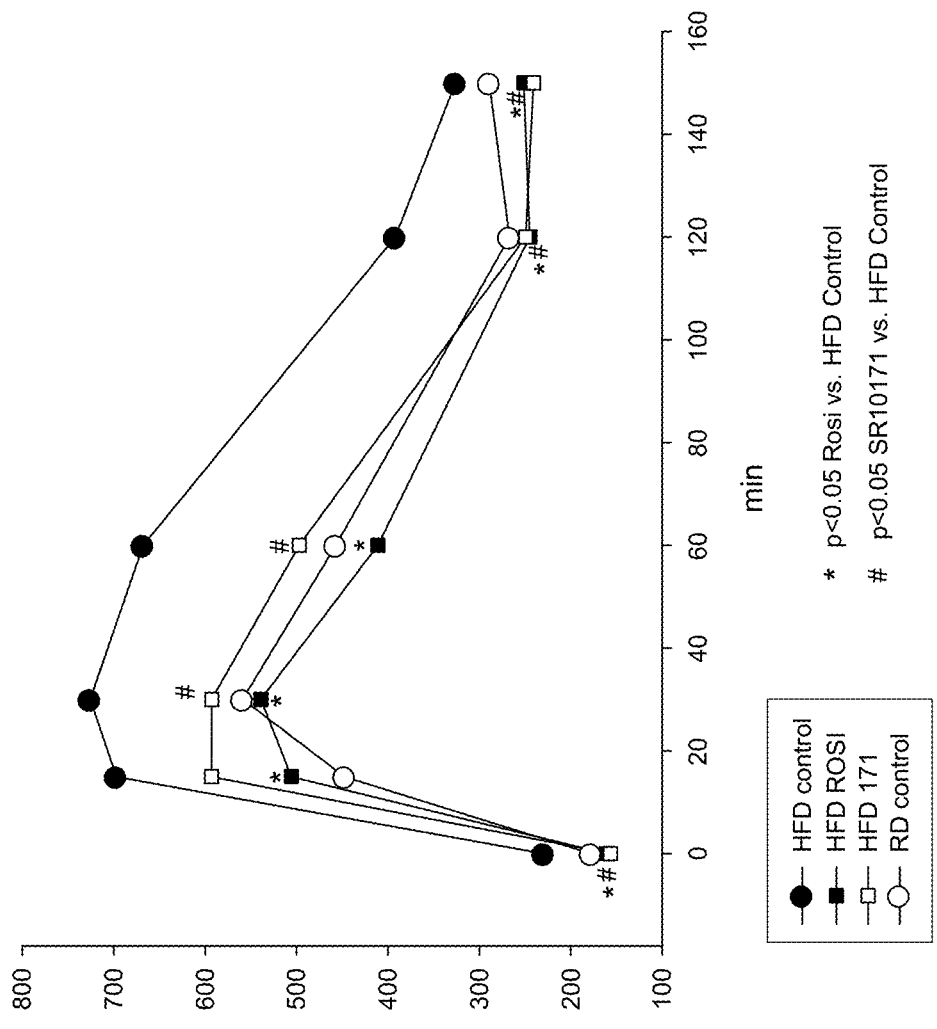
FIG. 7 shows the results of a glucose tolerance test on mice fed a regular chow diet (RD) or obese mice fed a high fat diet (HFD). Mice were fasted overnight and then administered a bolus of glucose. At several time intervals plasma glucose was measured. The data confirms the insulin sensitization effects and improved glucose disposal for TZD rosiglitazone treated mice. Similar results were obtained with SR10171 demonstrating that this compound is an insulin sensitizer. Both drug treated arms resulted in similar glucose disposal rates as the lean mice on RD.
Figure 8:
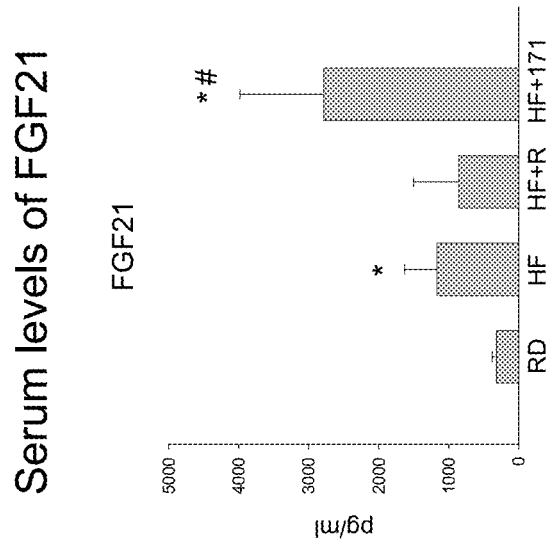
FIG. 8 shows serum levels of FGF21, a liver-secreted hormone believed to have beneficial effects in terms of metabolism, although over-expression of FGF21 can be detrimental to bone. From Wei et al PNAS 2012 "The endocrine hormone fibroblast growth factor 21 (FGF21) is a powerful modulator of glucose and lipid metabolism and a promising drug for type 2 diabetes. Here we identify FGF21 as a potent regulator of skeletal homeostasis. Both genetic and pharmacologic FGF21 gains of function lead to a striking decrease in bone mass. In contrast, FGF21 loss of function leads to a reciprocal high-bone-mass phenotype. Mechanistically, FGF21 inhibits osteoblastogenesis and stimulates adipogenesis from bone marrow mesenchymal stem cells by potentiating the activity of peroxisome proliferator-activated receptor γ (PPAR-γ). Consequently, FGF21 deletion prevents the deleterious bone loss side effect of the PPAR-γ agonist rosiglitazone. Therefore, FGF21 is a critical rheostat for bone turnover and a key integrator of bone and energy metabolism. These results reveal that skeletal fragility may be an undesirable consequence of chronic FGF21 administration." Thus, while our compounds increase FGF21 expression likely due to activation of PPARA, we inhibit the bad effects by blocking PPARG.
Figure 9:
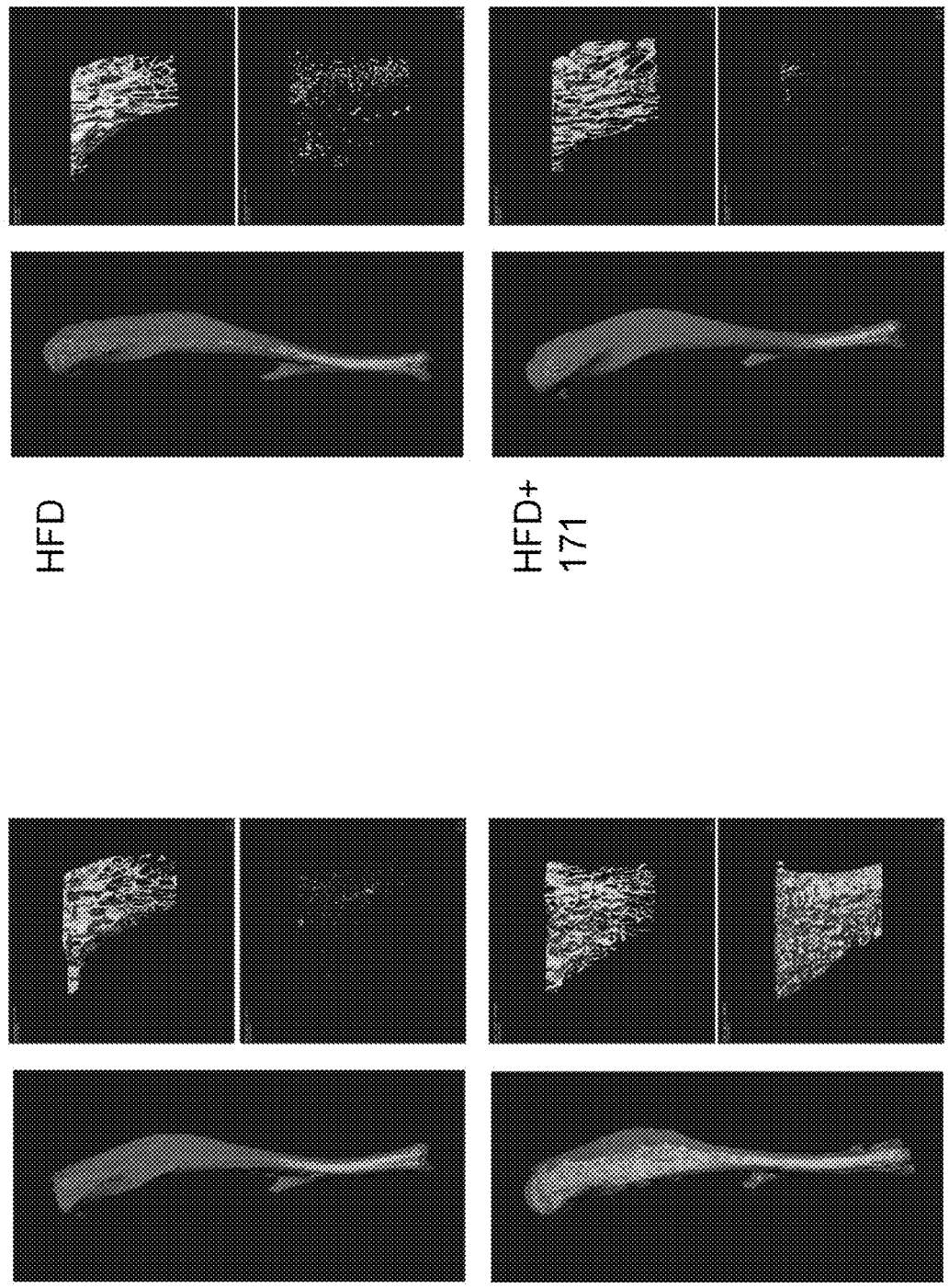
FIG. 9 shows photographs depicting results of osmium staining in whole tibia and juxtaposed trabecular bone (gray) and fat (yellow) in proximal tibia. RD is regular diet (normal chow) and HFD is high fat diet (chow is 45% fat). Mice on HFD have increased fat accumulation in the bone marrow as compared to lean controls. Mice on HFD and treated with a TZD, rosiglitazone, have significant fat accumulation in the bone marrow. Treatment of mice with SR10171 reduces the fat accumulation in bone marrow to that below vehicle controls on high fat diet alone.
Figure 10:
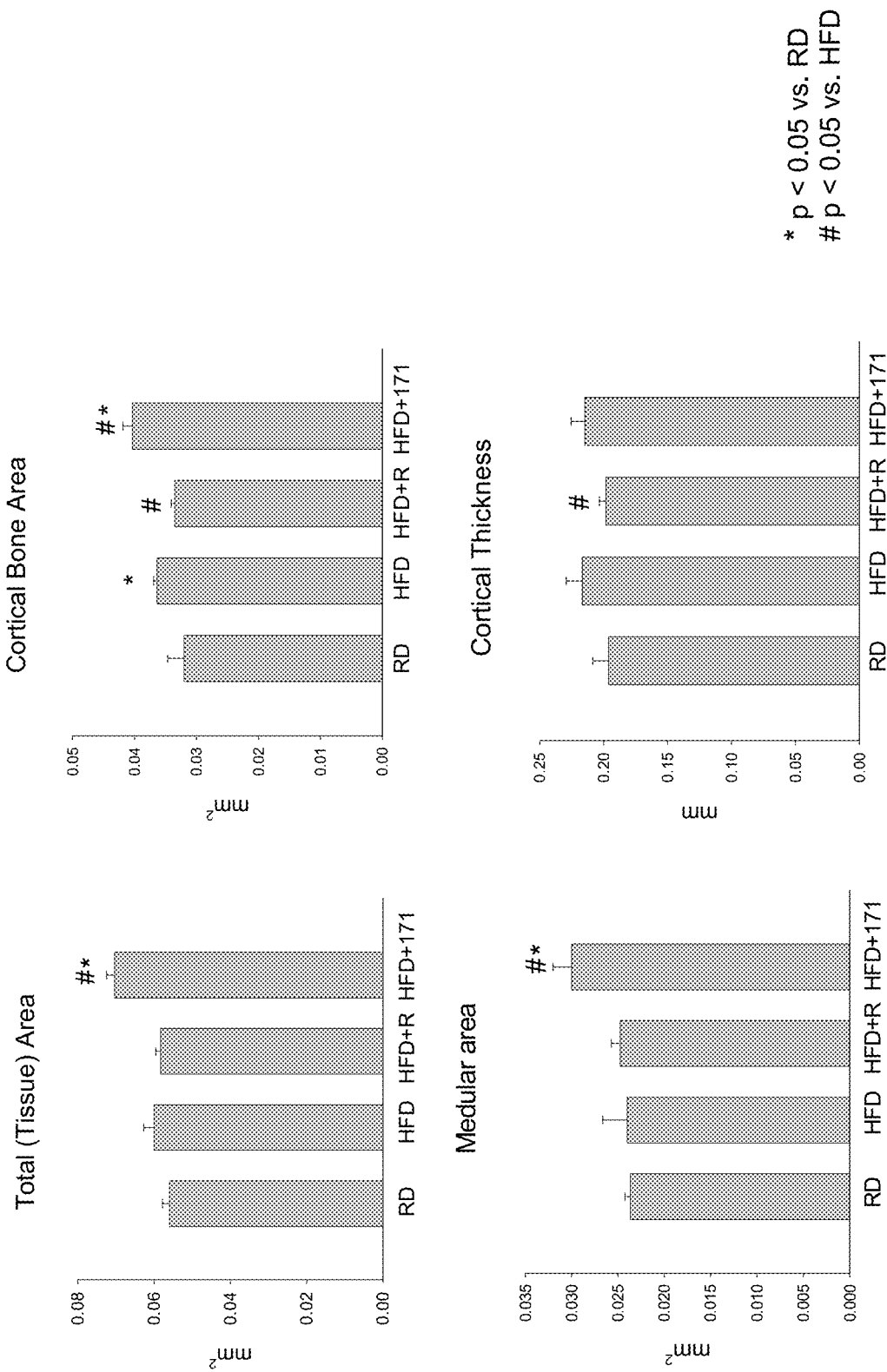
FIG. 10 shows quantitation of cortical bone mass from the midshaft tibia from mice treated under the conditions described above in FIG. 7. Treatment of mice with SR10171 resulted in a statistically significant increase in total tissue area, cortical bone area, and medular area.
Figure 11:
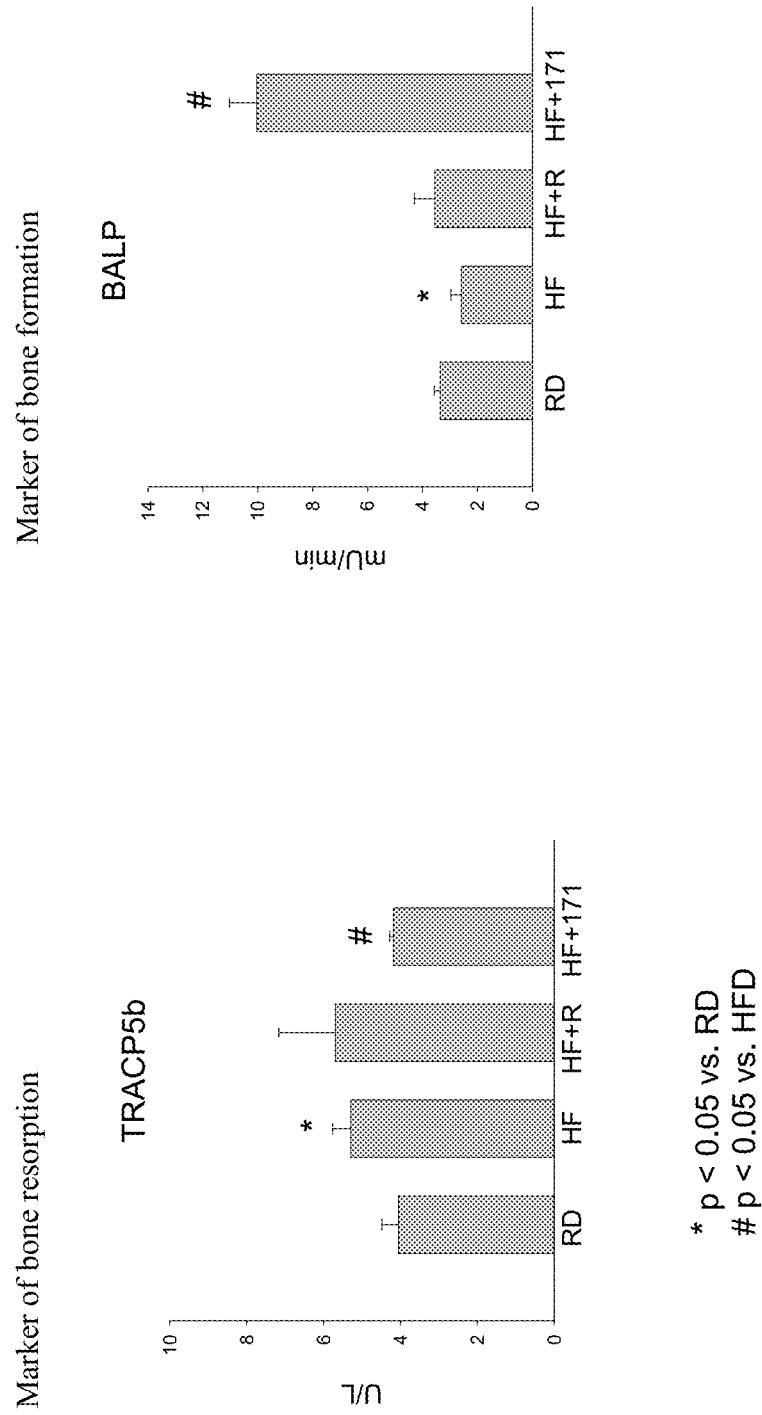
FIG. 11 shows quantitative data on serum markers of bone resorption (TRACP5b) and bone formation (BALP) in mice treated under the conditions described in FIG. 7. Treatment of mice on HFD with SR10171 reduced the level of TRACP5b to that of lean mice on normal chow diet. Likewise SR10171 increase BALP significantly over the other treatment arms.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein PPARG plays a role in the biochemical mechanisms involved in the disease or condition or symptom(s) thereof such that a therapeutically beneficial effect can be achieved by acting on PPARG. "Acting on" PPARG, or "modulating" PPARG, can include binding to PPARG and/or inhibiting the bioactivity of PPARG and/or allosterically regulating the bioactivity of PPARG in vivo. When the term "modulator" is used herein, the term alludes to a compound of the invention, and it is understood that the terms "modulator" and "compound" or "compound of the invention" are synonymous when the context indicates that a compound of the present invention is being referred to.

In various embodiments, the compounds of the invention are not agonists of PPARG, i.e., binding of the compound to PPARG does not activate the receptor, as discussed in greater detail below. In various embodiments, compounds of the invention bring about inhibition of cdk5-mediated phosphorylation of PPARG while being devoid of classical agonism. Such compounds are referred to herein as "non-agonist PPARG modulatory compounds."

The expression "effective amount", when used to describe therapy to an individual suffering from a disorder, refers to the amount of a compound of the invention that is effective to inhibit or otherwise act on PPARG in the individual's tissues wherein PPARG involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result.

A therapeutically effective amount is also one in which any toxic or detrimental effects of compounds of the invention are outweighed by the therapeutically beneficial effects. Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units. As to any of the groups described herein, which contain one or more substituents, it is understood that such groups do not contain any substitution or substitution patterns which are sterically impractical and/or synthetically non-feasible. In addition, the compounds of this disclosed subject matter include all stereochemical isomers arising from the substitution of these compounds.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON (R')$_2$, N(R')SO$_2$R', N(R')SO$_2$N(R')$_2$, N(R')C(O)OR', N(R')C (O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group.

When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

C(O) and $S(O)_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a $S(O)_2$ group is bound to one carbon and one nitrogen atom, the resulting unit is termed a "sulfonamide." When a $S(O)_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$CC(CH$_3$), and —CH$_2$CC(CH$_2$CH$_3$) among others.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl or arylalkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group.

The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl.

Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int. J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention
Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

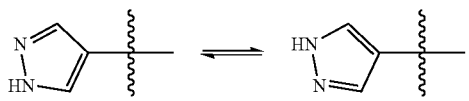 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

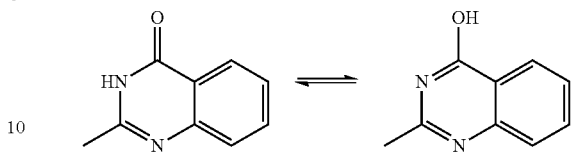

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer. The solid wedge indicates that the atom bonded thereby projects toward the viewer out of the plane of the paper, and a dashed wedge indicates that the atom bonded thereby projects away from the viewer out of the plan of the paper, i.e., the plane "of the paper" being defined by atoms A, C, and the chiral carbon atom for the (R) configuration shown below.

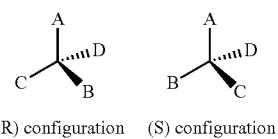

(R) configuration    (S) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

There are various conventions for depicting chiral structures using solid and dashed wedges. For example, for the (R) configuration shown above, the following two depictions are equivalent:

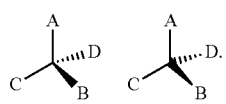

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Description

The invention is directed, in various embodiments, to a method for treatment of a patient afflicted by a progressive bone disease, comprising administering to the patient an effective dose of a compound of formula (I)

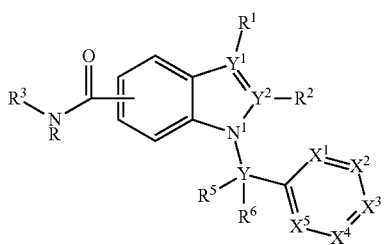

(I)

wherein:

R is H, $(C_1-C_6)$alkyl, $(C_3-C_9)$cycloalkyl, or $(C_3-C_9)$cycloalkyl$(C_1-C_6)$alkyl;

$Y^1$ or $Y^2$ are each independently C or N, provided that when $Y^1$ or $Y^2$ is N, $R^1$ or $R^2$, respectively, is absent;

$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or multi-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, oxo, $(C_1-C_6)$haloalkyl, nitro, cyano-$(C_0-C_6)$alkyl, R'$O_2$C—$(C_0-C_6)$alkyl, methylenedioxy, R'O—$(C_0-C_6)$alkyl, $(R')_2$N—$(C_0-C_6)$alkyl, $(R')_2$NC(=O)—$(C_0-C_6)$alkyl, R'C(=O)N(R')—$(C_0-C_6)$alkyl, $(C_1-C_6)$alkyl-S(O)$_q(C_0-C_6)$alkyl, aryl, aroyl, or $SO_2NR'_2$;

$R^3$ is optionally mono- or multi-substituted $(C_1-C_6)$alkyl, $(C_1-C_6)$alkenyl, $(C_1-C_6)$alkynyl, $(C_6-C_{10})$aryl, $(C_6-C_{10})$aryl$(C_1-C_6)$alkyl, (3-9 membered)heterocyclyl, (3-9 membered) heterocyclyl$(C_1-C_6)$alkyl, (3-9 membered)heteroaryl, or (3-9 membered)heteroaryl$(C_1-C_6)$alkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, oxo, haloalkyl, haloalkoxy, nitro, cyano, $CO_2$R', methylenedioxy, OR', N(R')$_2$, C(O)N(R')$_2$, $(C_1-C_6)$alkyl-S(O)$_q$, $SO_2NR'2$, and $(C_1-C_6)$alkoxyl; and provided that group $R^3$N(R')C(=O)— can be bonded to any one of the four carbon atoms of the phenyl ring not bonded to $N^1$ or $Y^1$;

wherein each R' is independently H, $(C_1-C_6)$ alkyl, $(C_3-C_9)$cycloalkyl, $(C_3-C_9)$cycloalkyl$(C_1-C_6)$alkyl, $(C_6-C_{10})$aryl, or $(C_6-C_{10})$aryl$(C_1-C_6)$ alkyl, or wherein two R' bonded to an atom together with the atom form a 3-9 membered ring optionally further comprising a heteroatom selected from the group consisting of O, NR', and S(O)$_q$;

wherein any alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, oxo, aryl, or aroyl;

each of $X^1$-$X^5$ is independently N or CH, or is C substituted with an independently selected $R^4$ or is C substituted with Z, provided that no more than two of $X^1$-$X^5$ are N, and provided that there is no more than one Z group bonded to the ring comprising $X^1$-$X^5$;

each $R^4$ is independently halo, nitro, $(C_1-C_6)$fluoroalkyl, R'—$(C_0-C_6)$alkyl, R'O$_2$C—$(C_0-C_6)$alkyl, NC—$(C_0-C_6)$alkyl, R'O—$(C_0-C_6)$alkyl, $(R')_2$N—$(C_0-C_6)$alkyl, $(R')_2$NC(=O)—$(C_0-C_6)$alkyl, R'C(=O)N(R')—$(C_0-C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1-C_6)$alkyl-S(O)$_q$$(C_0-C_6)$alkyl, R'S(O)$_2$NHC(O), R'C(O)NHS(O)$_2$, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with R', OR', N(R')$_2$, C-bonded tetrazolyl, $(C_1-C_6)$alkyl-S(O)$_q$$(C_0-C_6)$alkyl, an unsubstituted or substituted aryl, or an unsubstituted or substituted heteroaryl; or $R^4$ is —(C(R")$_2$)$_m$CO$_2$R', —(C(R")$_2$)$_m$CON(R')$_2$, —(C(R")$_2$)$_m$CN, —O(C(R")$_2$)$_m$CO$_2$R', —O(C(R")$_2$)$_m$CON(R')$_2$, or —O(C(R")$_2$)$_m$CN, wherein m is 1, 2, or 3;

R" is H, halo, $(C_1-C_6)$ alkyl, $(C_1-C_6)$ haloalkyl, $(C_3-C_9)$cycloalkyl, $(C_3-C_9)$cycloalkyl$(C_1-C_6)$alkyl, $(C_6-C_{10})$aryl, or $(C_6-C_{10})$aryl$(C_1-C_6)$ alkyl, or two R" together with an atom to which they are bonded form a 3- to 9-membered ring;

Z is a group of formula

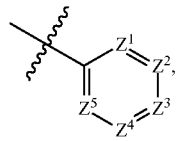

wherein a wavy line indicates a point of bonding, each of $Z^1$-$Z^5$ is independently N or is C substituted with an independently selected H or $R^4$; provided that no more than two of $Z^1$-$Z^5$ are N;

Y is (C$_1$-C$_2$)alkyl, or sulfur;

when Y is (C$_1$-C$_2$)alkyl, R$^5$ and R$^6$ are independently H or (C$_1$-C$_4$)alkyl or independently each R$^5$ and R$^6$ together with the carbon atom to which they are bonded form a carbonyl, or, one R$^5$ group can further be bonded to X$^5$ to form a 4- to 8-membered ring; and, when Y is sulfur, R$^5$ and R$^6$ are both oxygen;

or a pharmaceutically acceptable salt thereof;

wherein the effective dose of the compound acts to inhibit bone resorption, improve bone formation, or both, in the patient.

For example, in various embodiments of practice of a method of the invention, for a compound of formula (I), Y$^1$ or Y$^2$ can each be C, providing an indole nucleus. R$^1$ and R$^2$ can be independently H or methyl. In other embodiments, Y$^1$ is N and Y$^2$ is C, providing a benzimidazole nucleus, or Y$^1$ is C and Y$^2$ is N, providing an indazole nucleus for the compound of formula (I) used in a method of the invention.

More specifically, R$^3$ can be benzyl, α-phenethyl, α-phenpropyl, cycloalkyl or cycloalkylalkyl, any of which can be unsubstituted or substituted, as described herein. Or, R$^3$ can be heterocyclyl, heterocyclylalkyl, heteroaryl, or heteroarylalkyl, any of which can be unsubstituted or substituted. For instance, R$^3$ can be any one of:

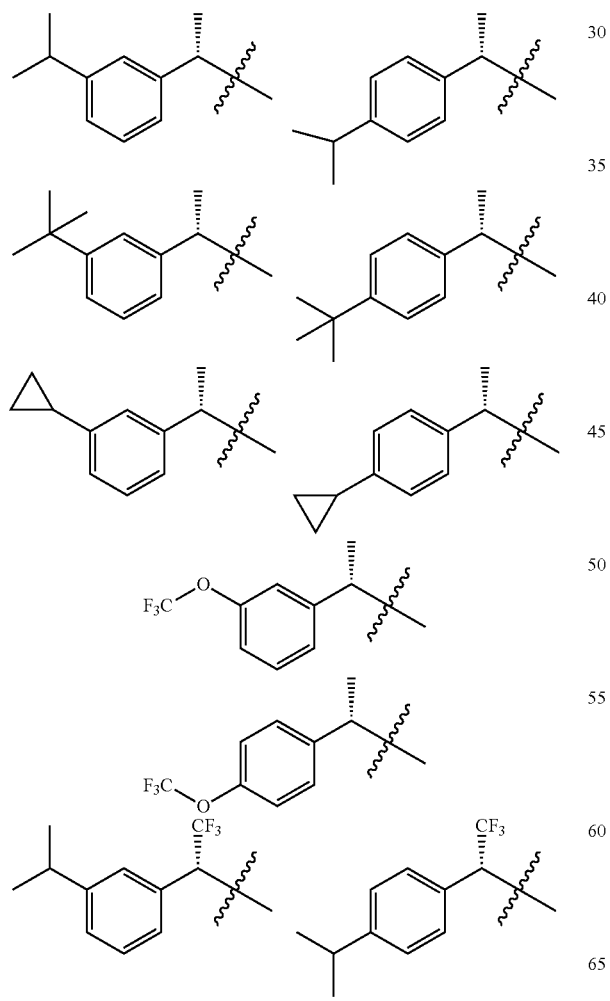

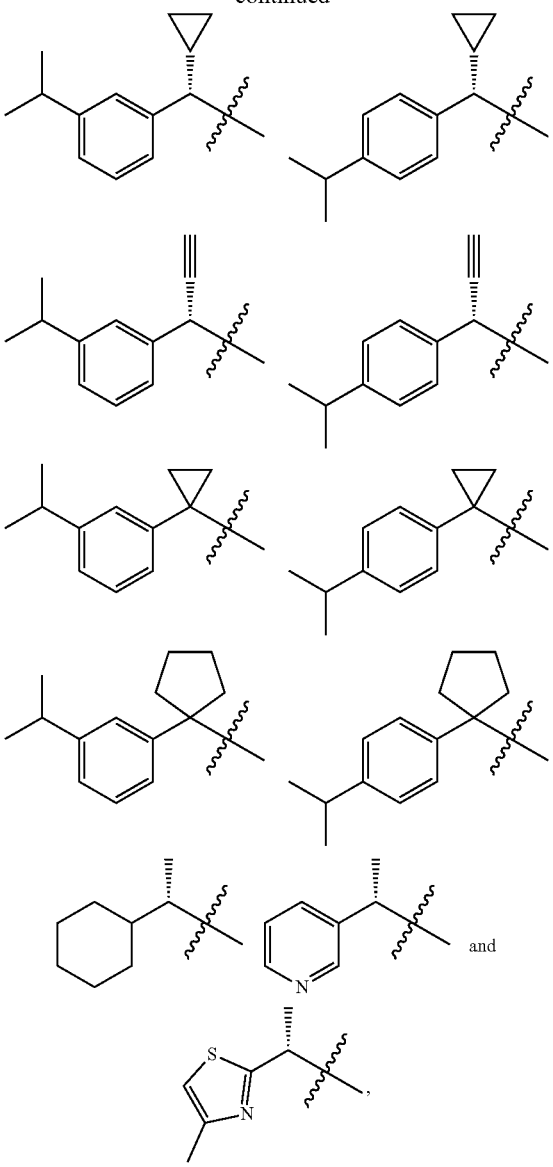

wherein a wavy line indicates a point of attachment.

In various embodiments for practice of a method of the invention, for a compound of formula (I), YR$^5$R$^6$ can be SO$_2$. In other embodiments, Y can be C$_1$-alkyl; and R$^5$ and R$^6$ be H, or Y can be C$_2$-alkyl, and R$^5$ and R$^6$ be H.

Further embodiments for practice of a method of the invention comprise the use of an effective dose of a compound of formula (I) wherein R$^4$ is —CO$_2$H, —(CH$_2$)$_m$CO$_2$H, —O(CH$_2$)$_m$CO$_2$H, —CN, —(CH$_2$)$_m$CN, —O(CH$_2$)$_m$CN, —C(CH$_3$)$_2$CO$_2$H, —C(CH$_3$)$_2$CN, —OC(CH$_3$)$_2$CO$_2$H, —OC(CH$_3$)$_2$CN, —CH(CH$_3$)CO$_2$H, —CH(CH$_3$)CN, —OCH(CH$_3$)CO$_2$H, —OCH(CH$_3$)CN; —CH(CH$_2$CH$_3$)CO$_2$H, —CH(CH$_2$CH$_3$)CN, —OCH(CH$_2$CH$_3$)CO$_2$H, —OCH(CH$_2$CH$_3$)CN; —CH(i-Pr)CO$_2$H, —CH(i-Pr)CN, —OCH(i-Pr)CO$_2$H, —OCH(i-Pr)CN, wherein iPr indicates isopropyl; —CH(t-Bu)CO$_2$H, —CH(t-Bu)CN, —OCH(t-Bu)CO$_2$H, —OCH(t-Bu)CN, wherein t-Bu indicates t-butyl; or —(CHR")$_m$C(=O)N(R")$_2$, —O(CHR")$_m$C(=O)N(R")$_2$,

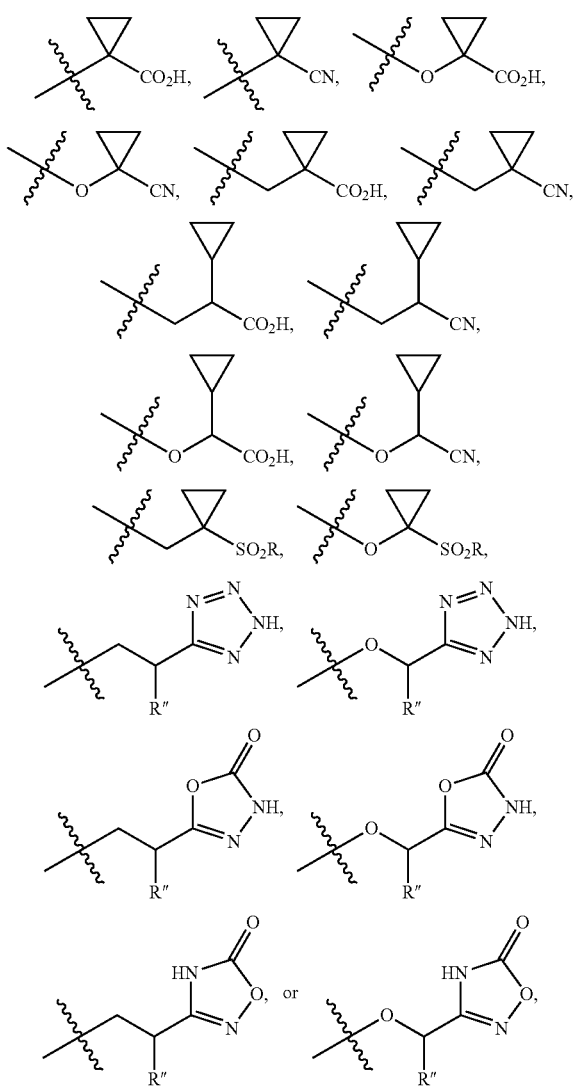

wherein a wavy line indicates a point of attachment.

In various embodiments for practice of a method of the invention, for the compound of formula (I), no Z group is present on the ring comprising $X^1$-$X^5$, providing a compound of formula (IA), which can be an N-benzyl-indole, an N-benzyl-benzimidazole, or an N-benzyl-indazole, or an analog thereof.

More specifically, for practice of a method of the invention, the compound of formula (IA) can be any one of:

IA-1

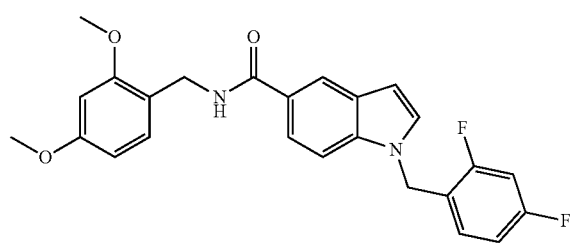

IA-2

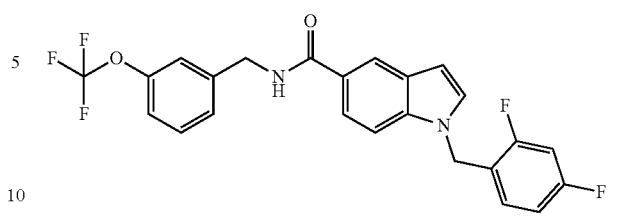

IA-3

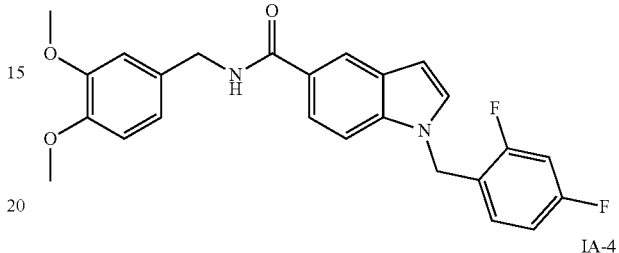

IA-4

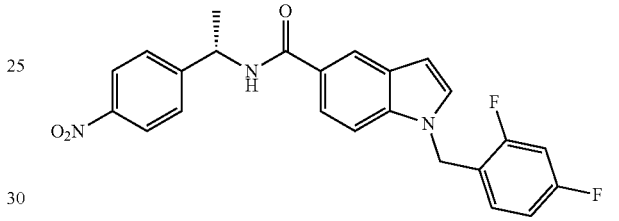

IA-5

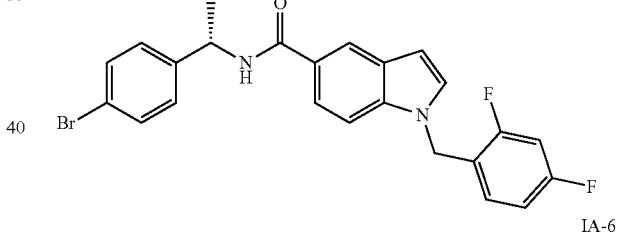

IA-6

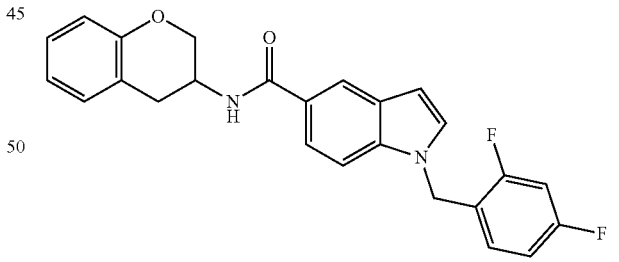

IA-7

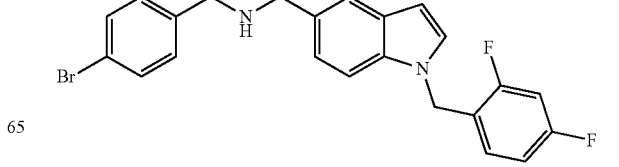

IA-8
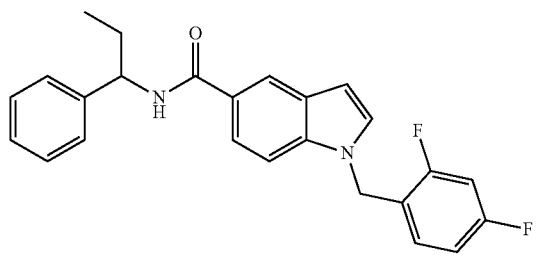
IA-9
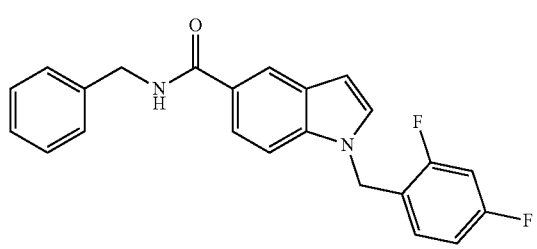
IA-10
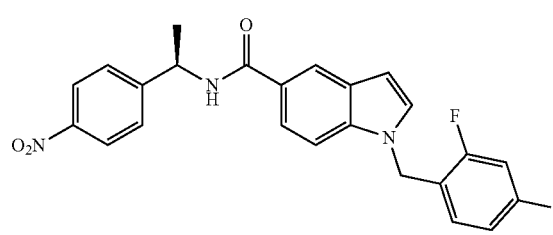
IA-11
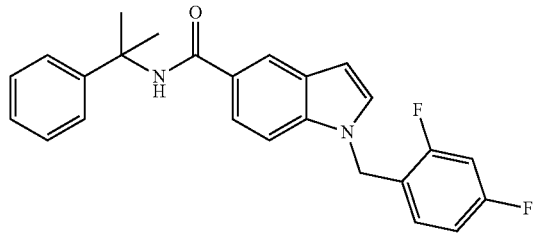
IA-12
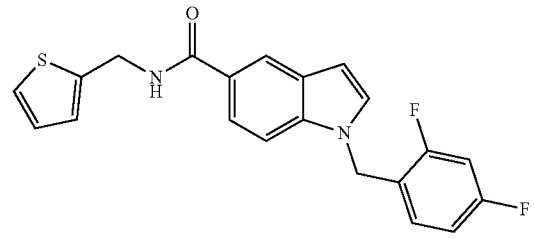
IA-13
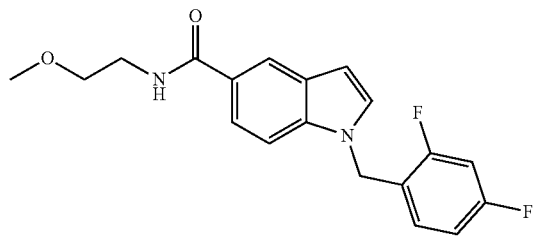
IA-14
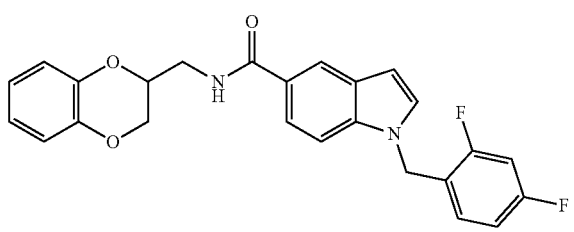
IA-15
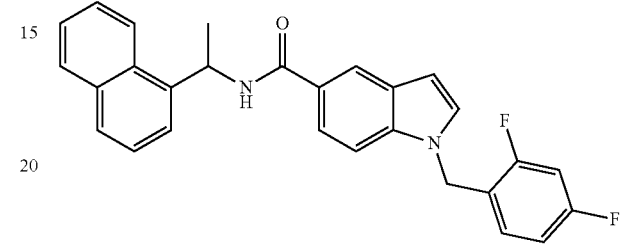
IA-16
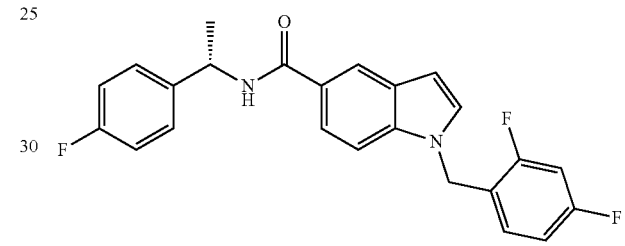
IA-17
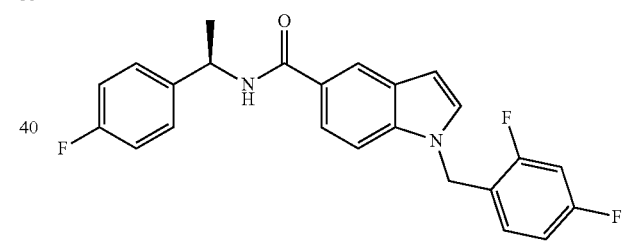
IA-18
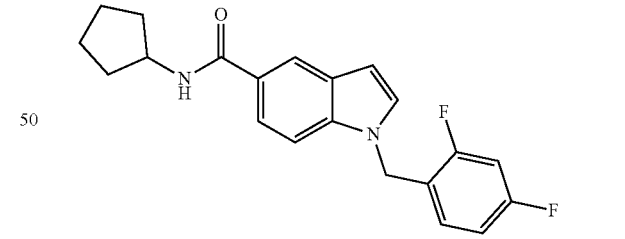
IA-19
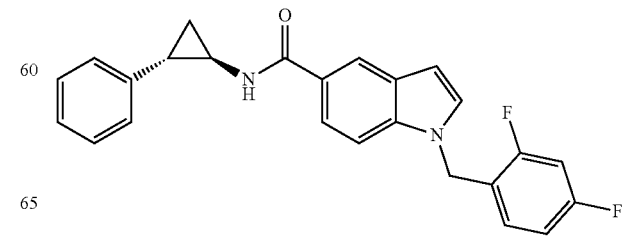

IA-20
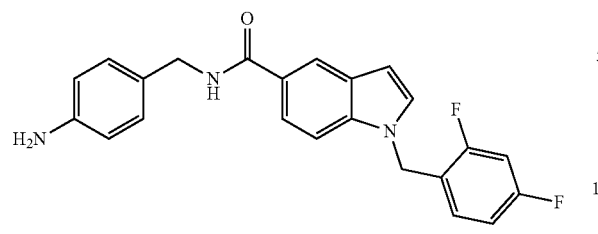
IA-26
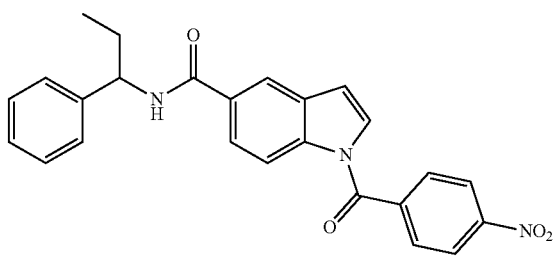
IA-21
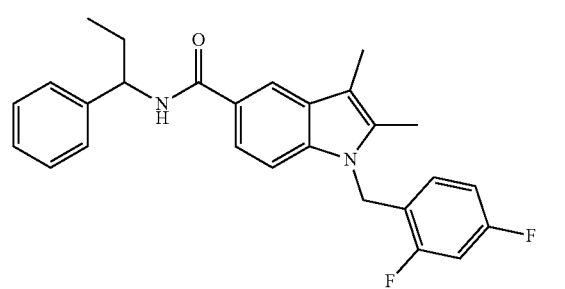
IA-27
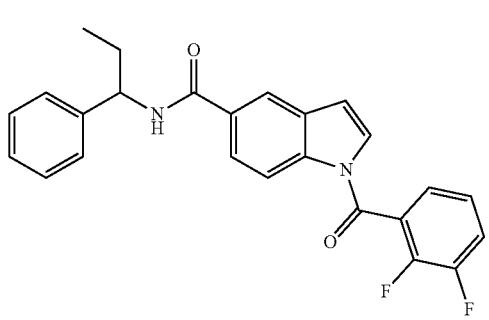
IA-22
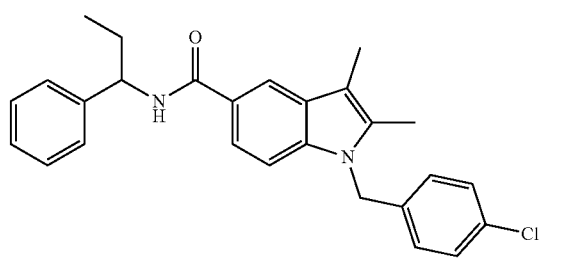
IA-28
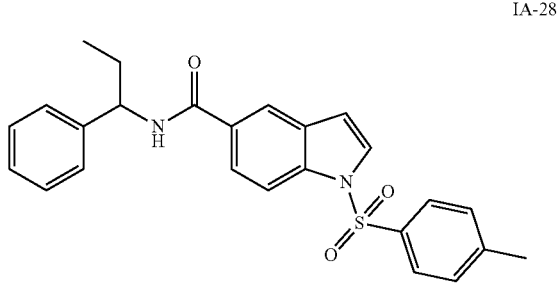
IA-24
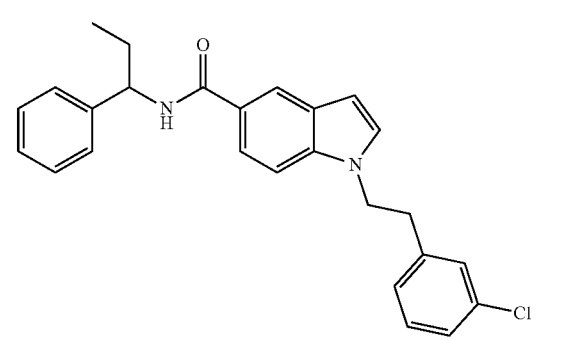
IA-30
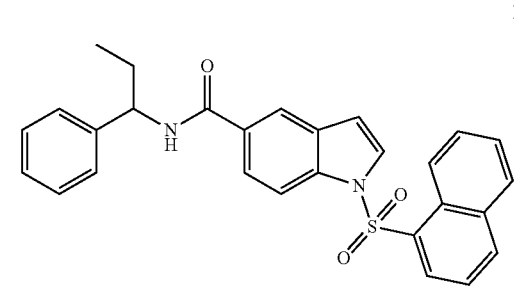
IA-25
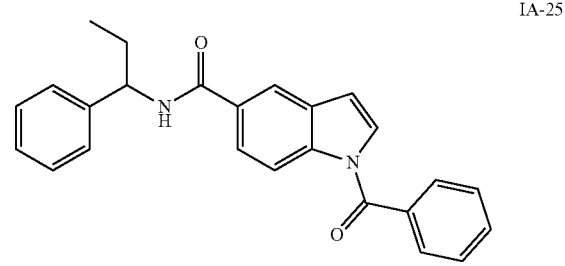
IA-31
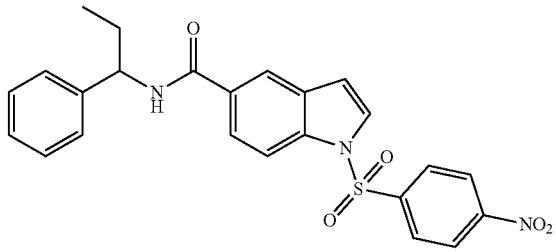

IA-32
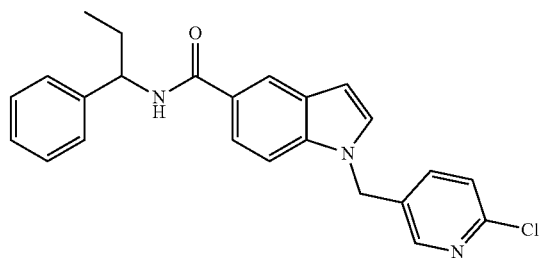
IA-33
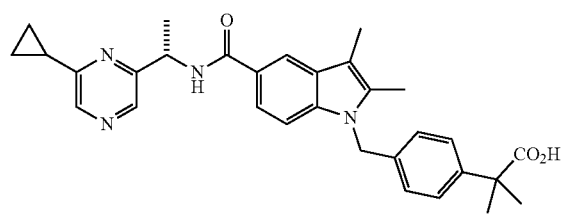
IA-34
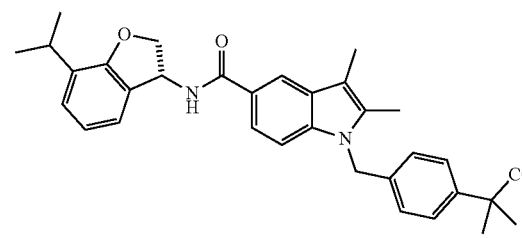
IA-35
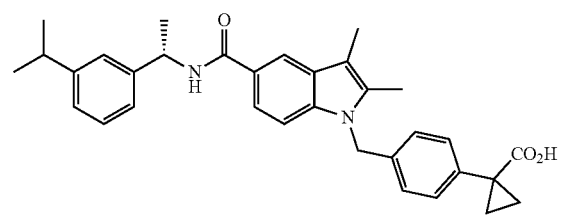
IA-36
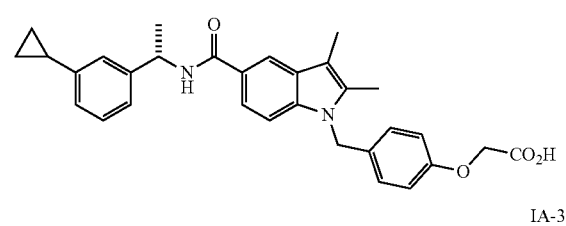
IA-37
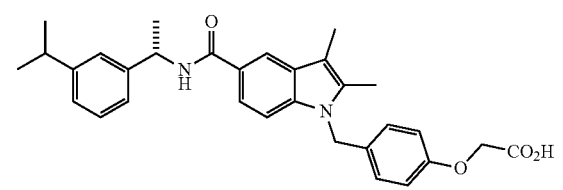
IA-38
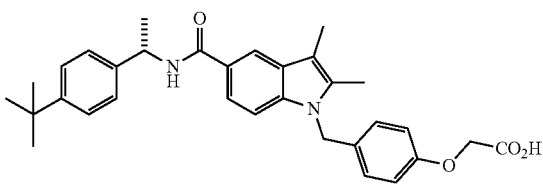
IA-39
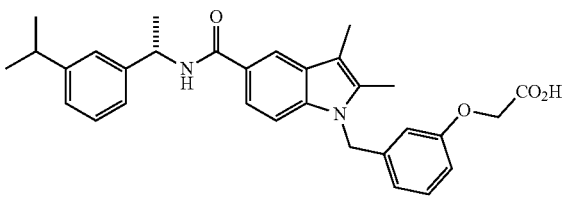
IA-40
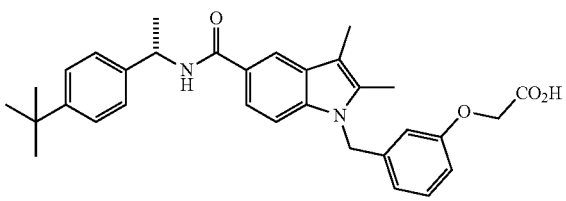
IA-41
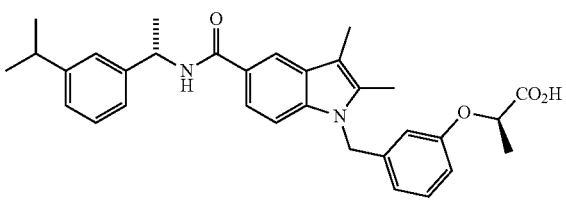
IA-42
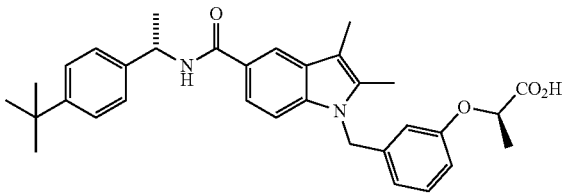
IA-43
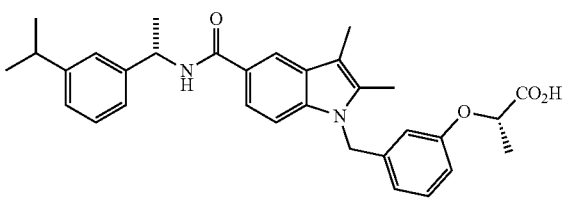
IA-44

IA-45
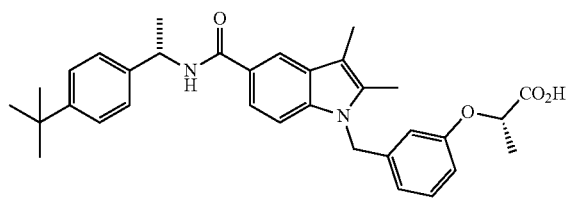
IA-52
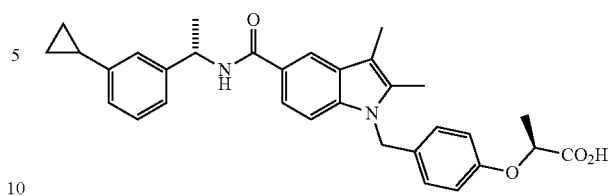
IA-46
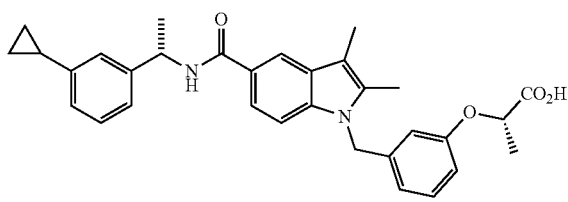
IA-53
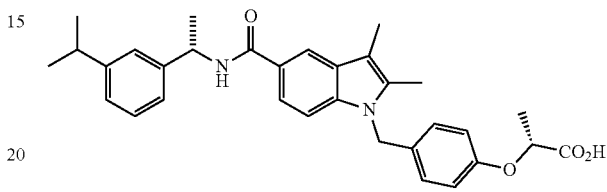
IA-47
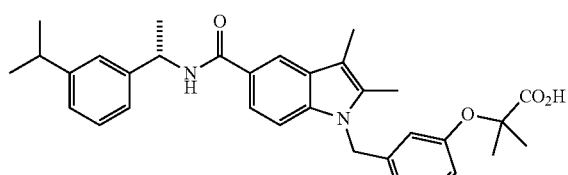
IA-54
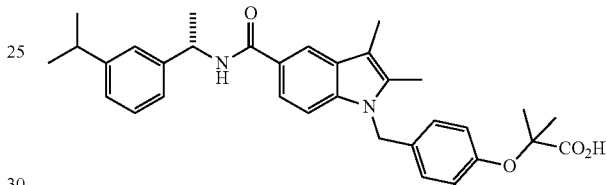
IA-48/SR10171
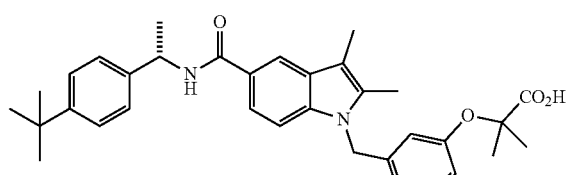
IA-55
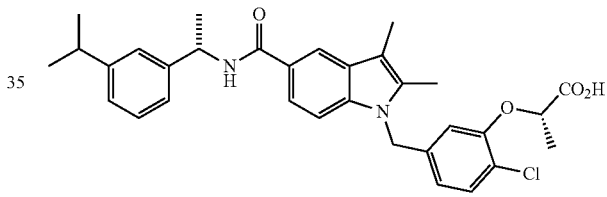
IA-49
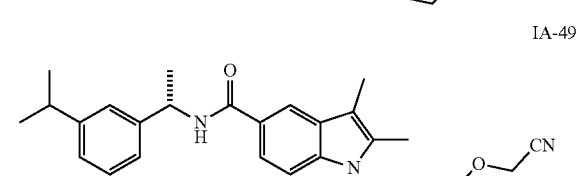
IA-56
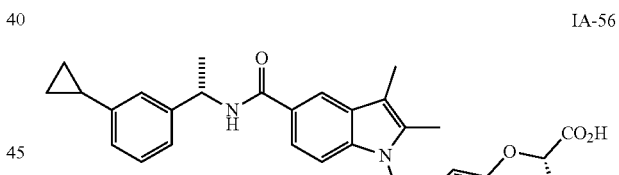
IA-50
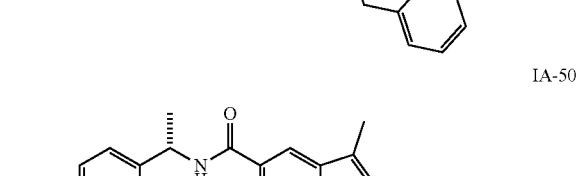
IA-57
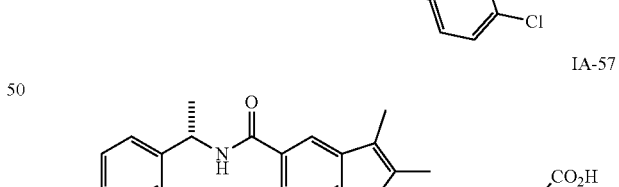
IA-51
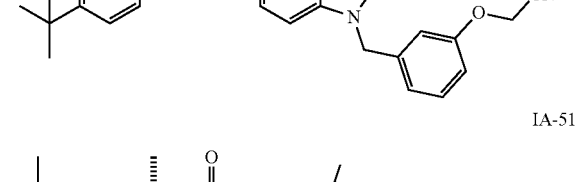
IA-58
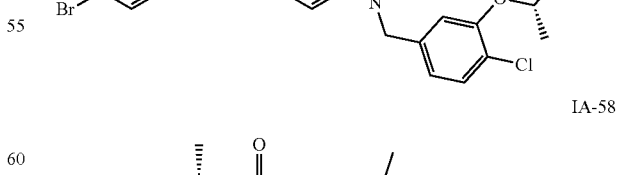

IA-59
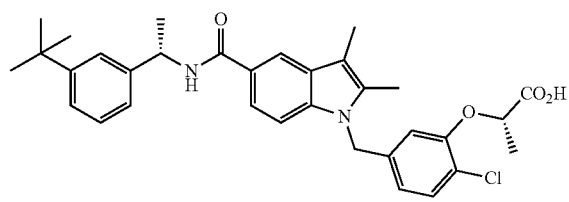
IA-60
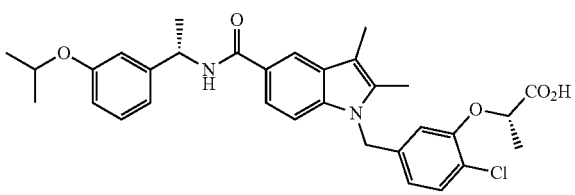
IA-61
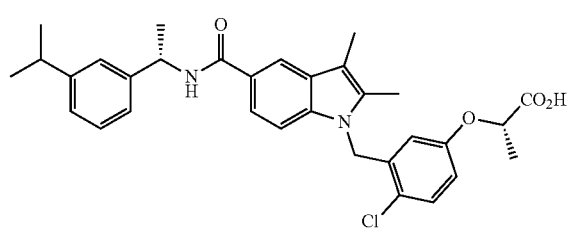
IA-62
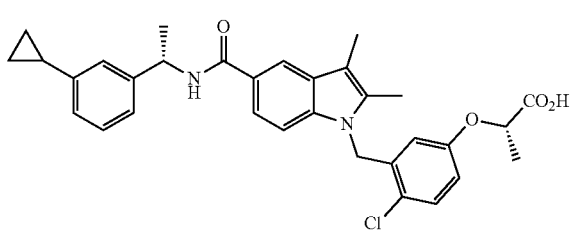
IA-63
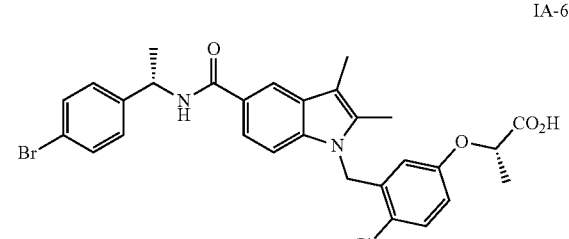
IA-64
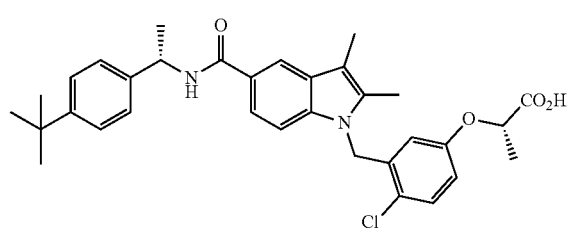
IA-65
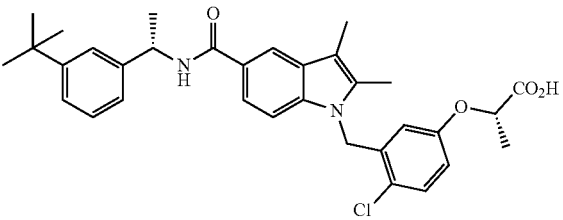
IA-66
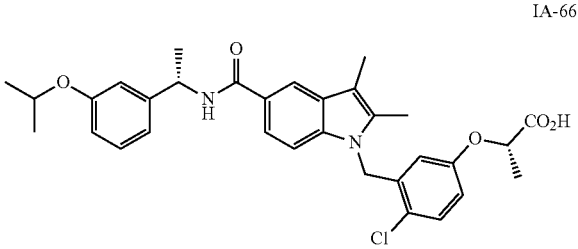
IA-67
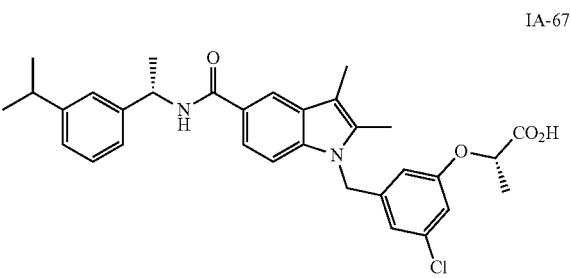
IA-68
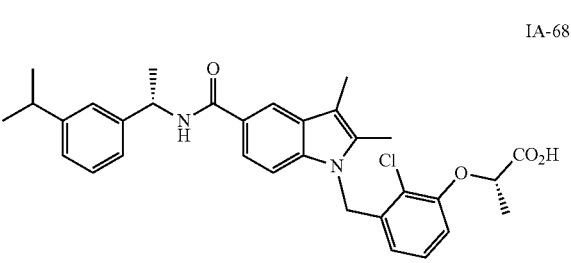
IA-69
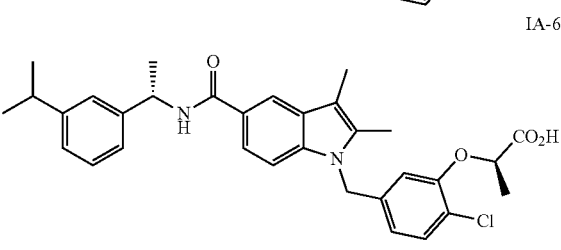
IA-70
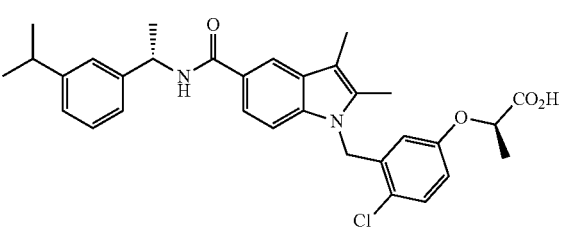

IA-71
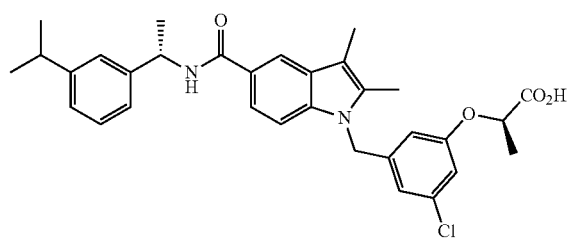
IA-72
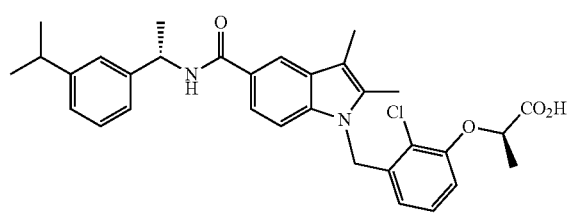
IA-73
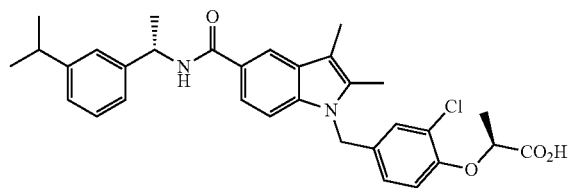
IA-74
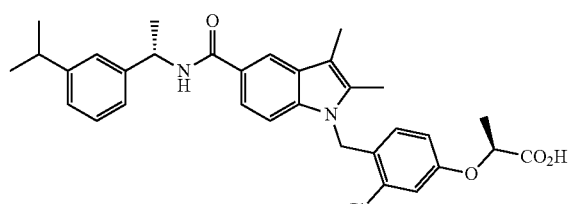
IA-75
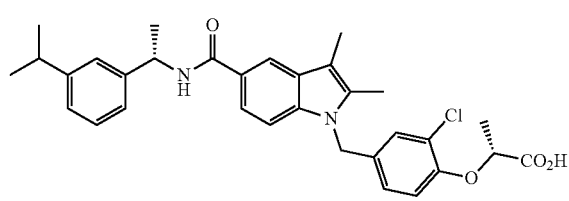
IA-76
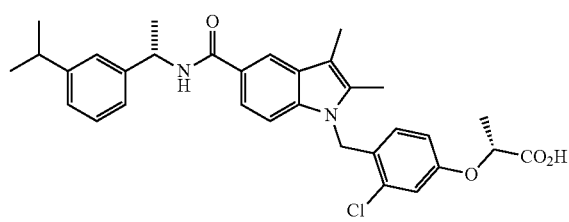
IA-77
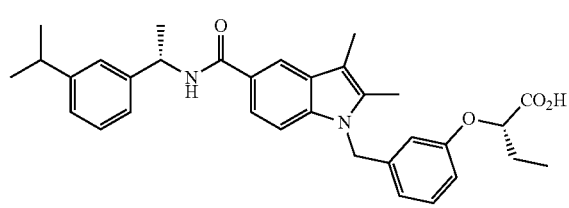
IA-78
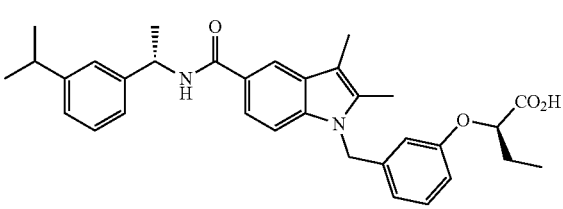
IA-79
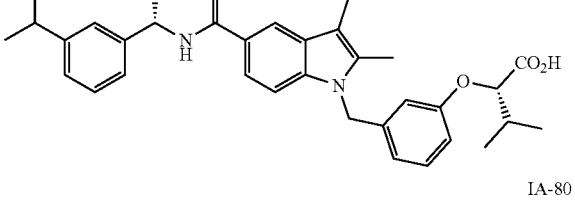
IA-80
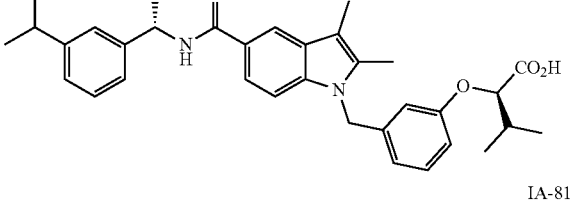
IA-81
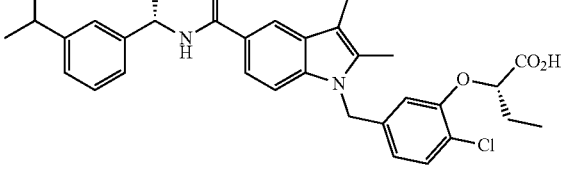
IA-82
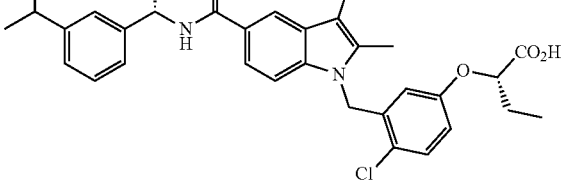
IA-83
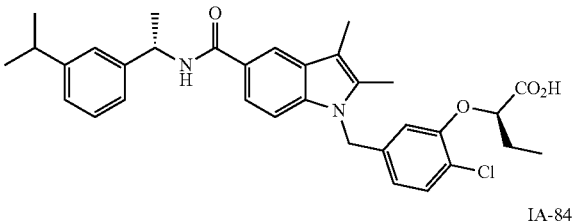
IA-84
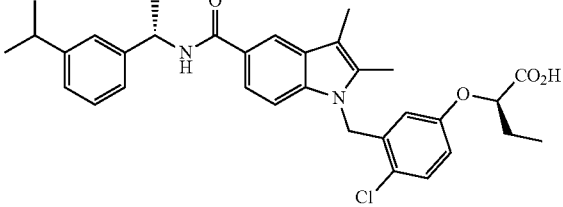

IA-85
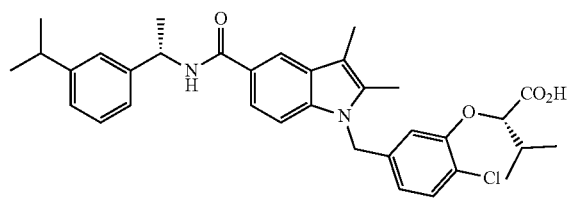
IA-86
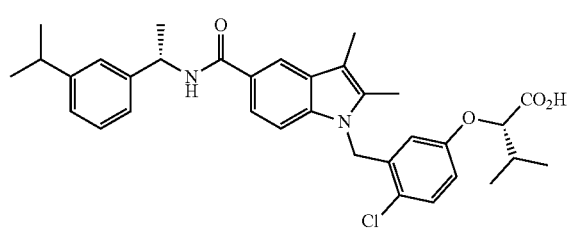
IA-87
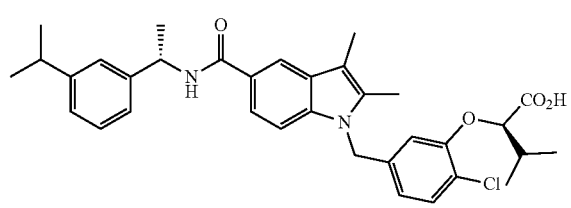
IA-88
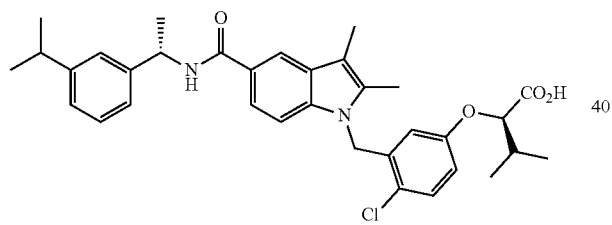
IA-89
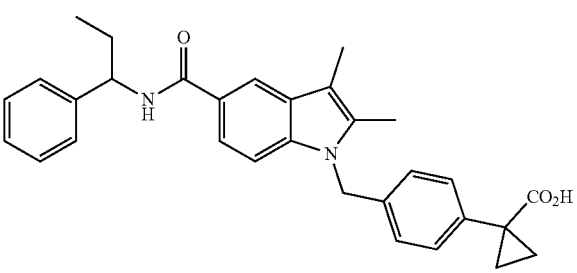
IA-90
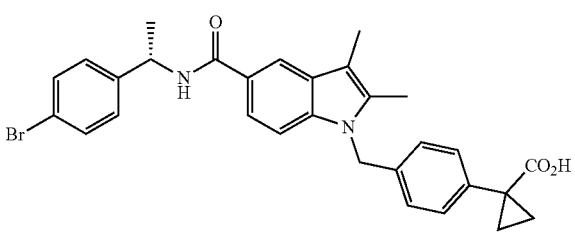
IA-91
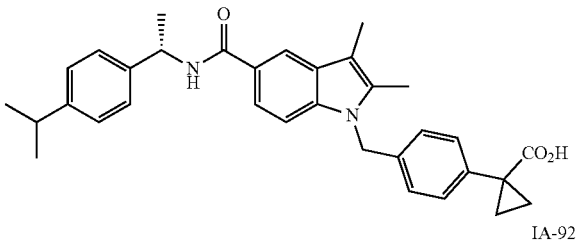
IA-92, IA-93, IA-94, IA-95, IA-96, IA-97
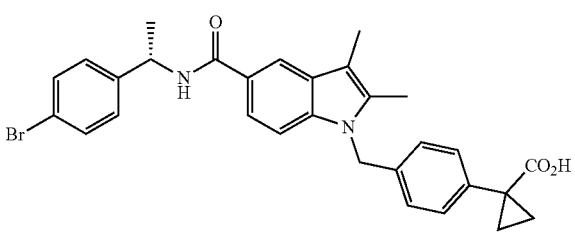

IA-98
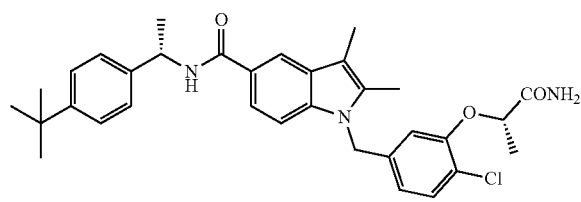
IA-99
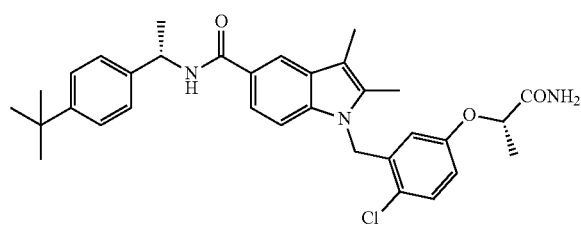
IA-100
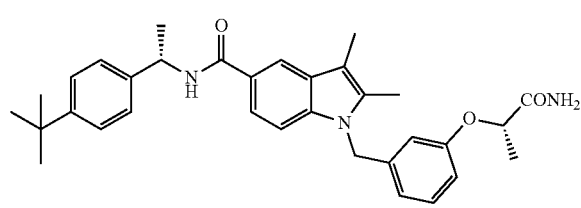
IA-101
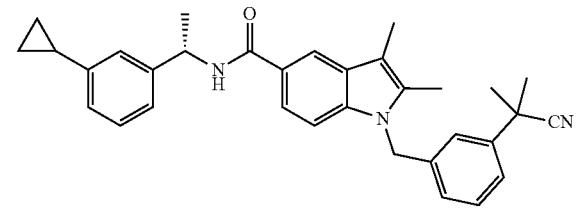
IA-102
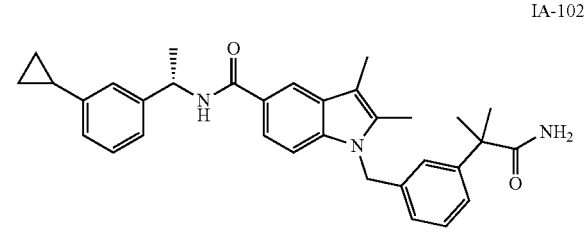
IA-103
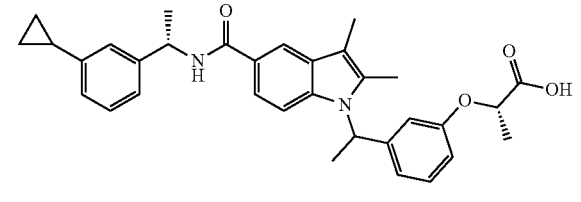
IA-104
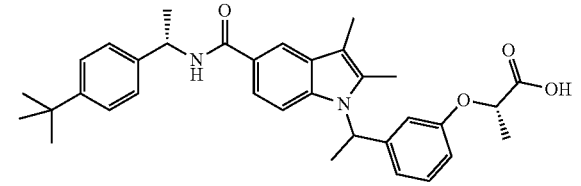
IA-105
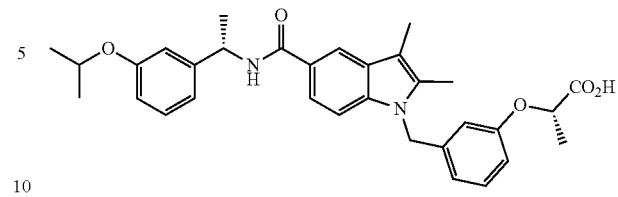
IA-106
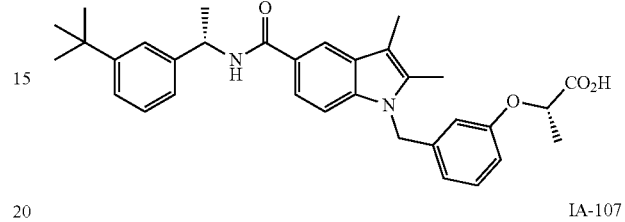
IA-107
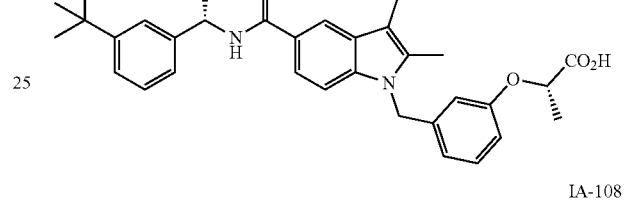
IA-108
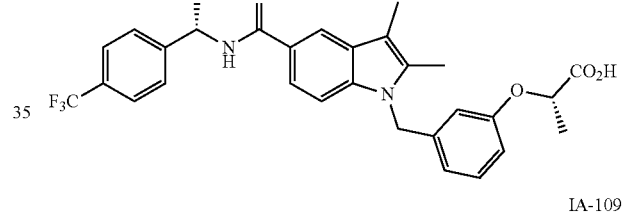
IA-109
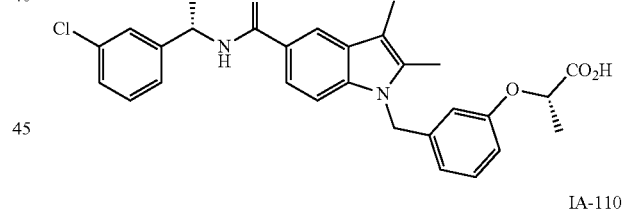
IA-110
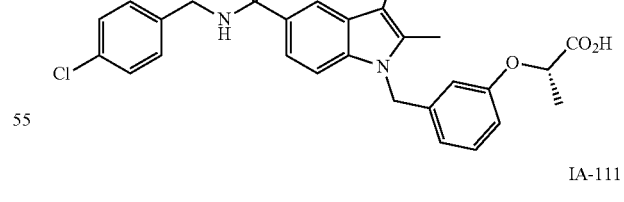
IA-111
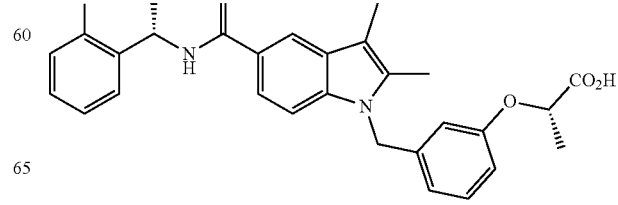

IA-112
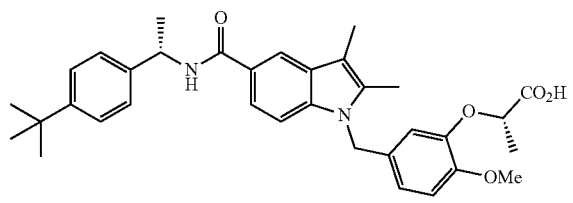
IA-113
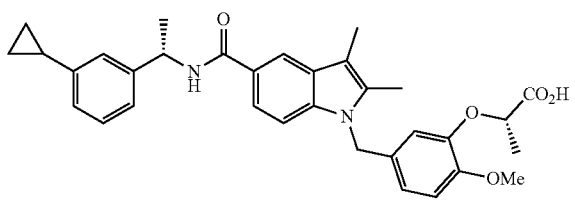
IA-114
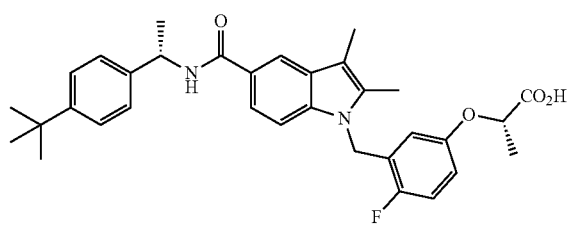
IA-115
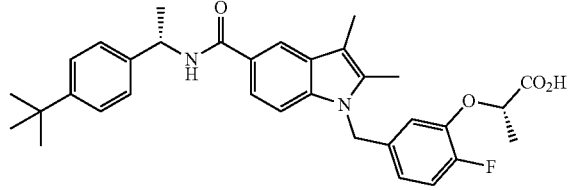
IA-116
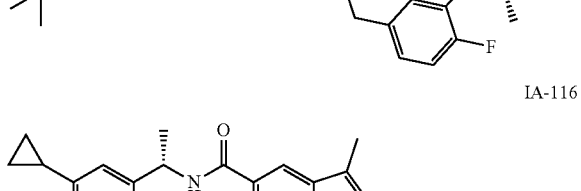
IA-117
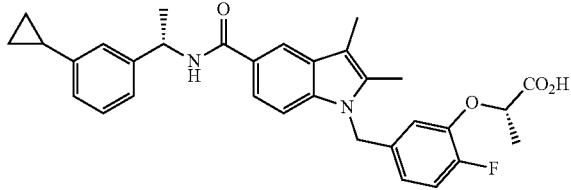
IA-118
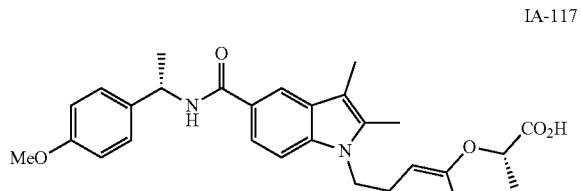
IA-119
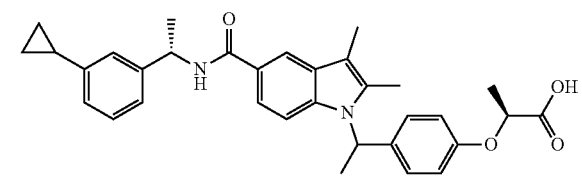
IA-120
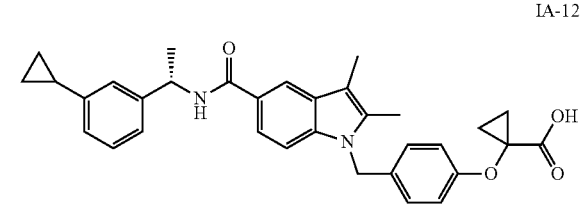
IA-121
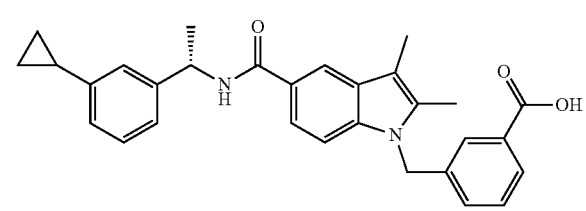
IA-122
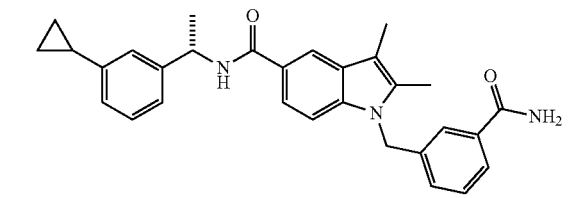
IA-123
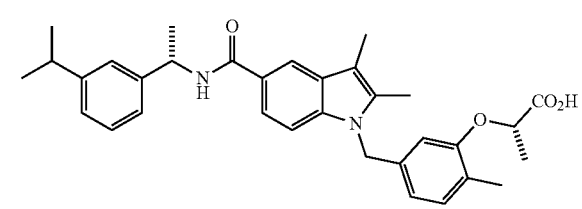
IA-124
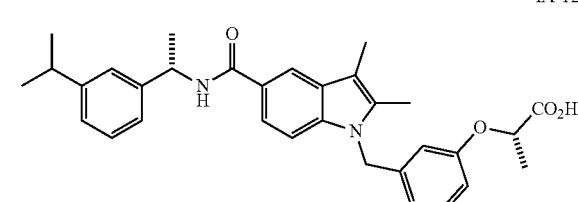
IA-125
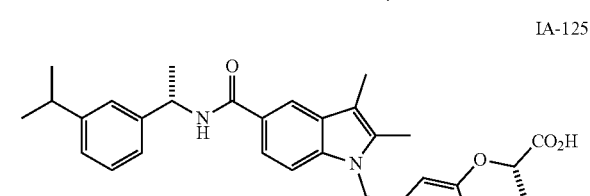

IA-126
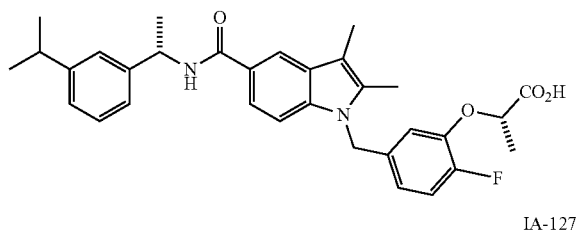
IA-127
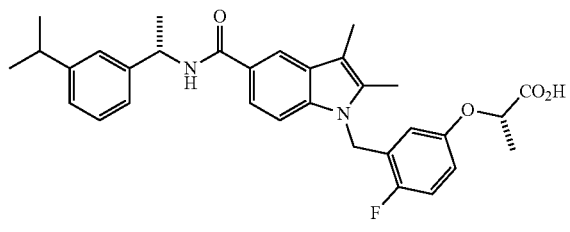
IA-128
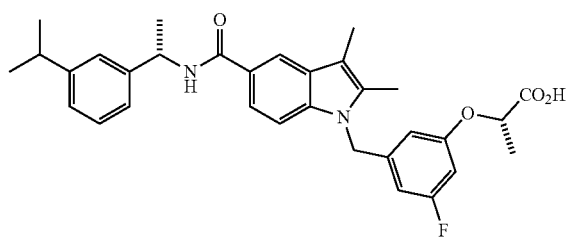
IA-129
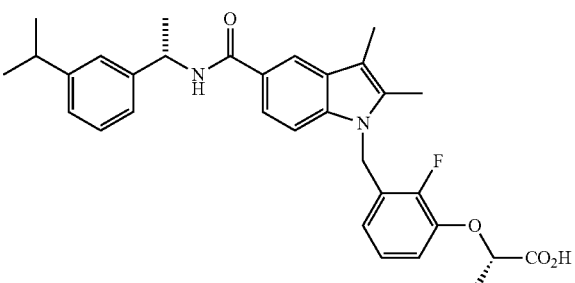
IA-130
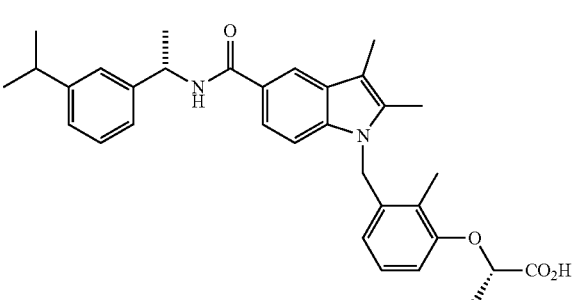
IA-131
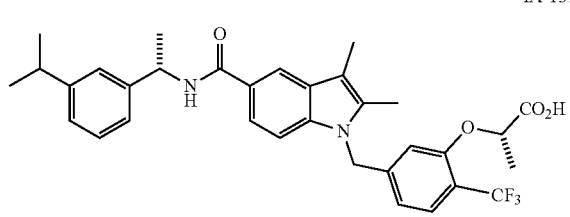
IA-132
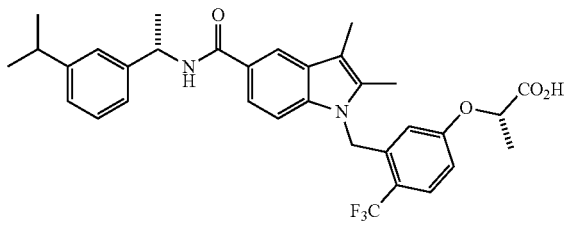
IA-133
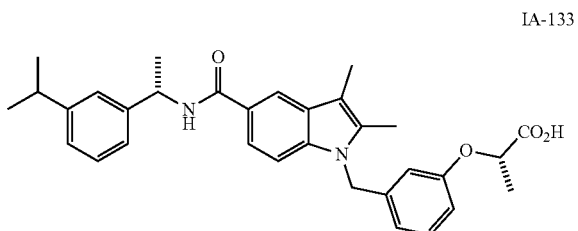
IA-134
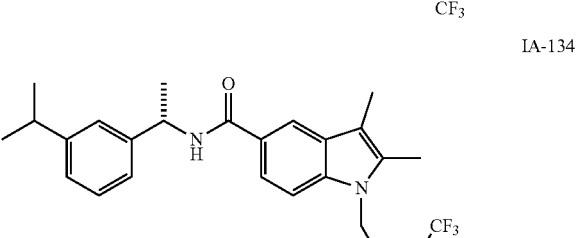
IA-135
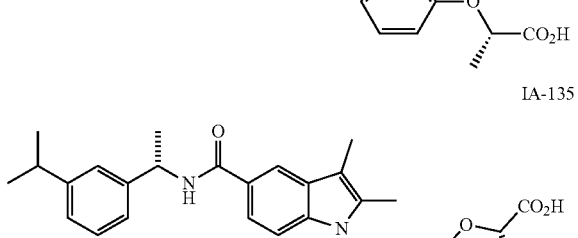
IA-136
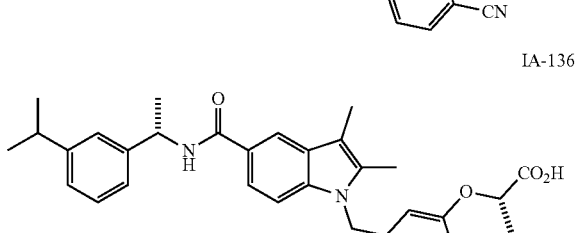
IA-137
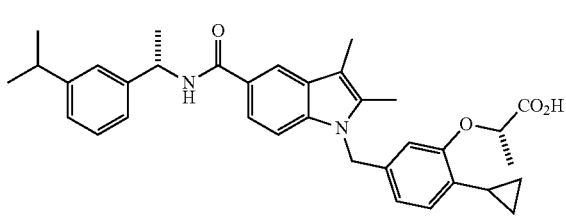

IA-138
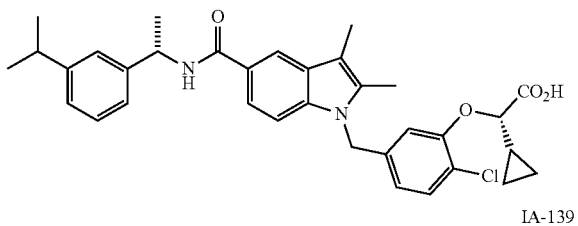
IA-139
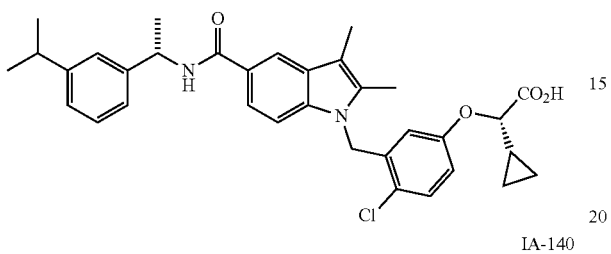
IA-140
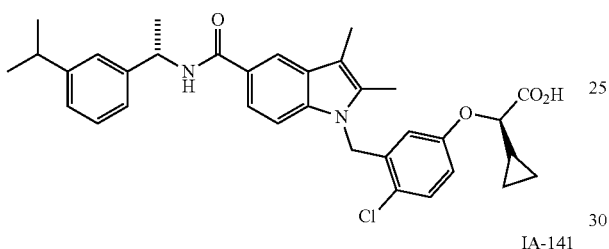
IA-141
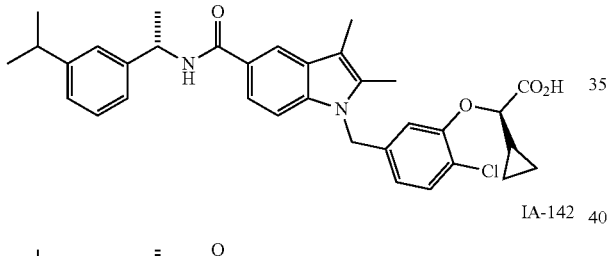
IA-142
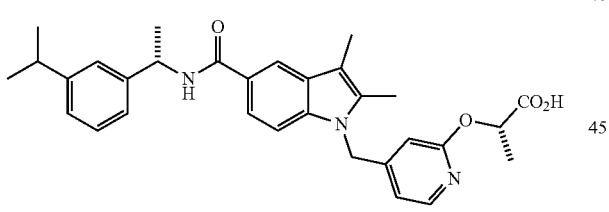
IA-143
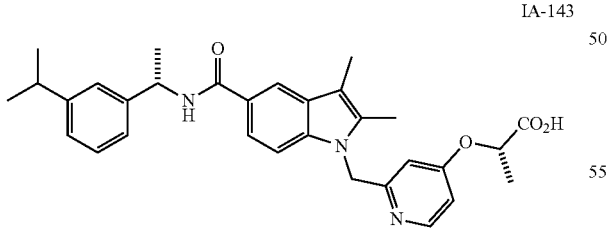
IA-144
IA-145
IA-146
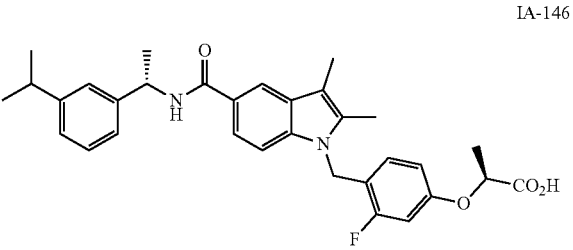
IA-147
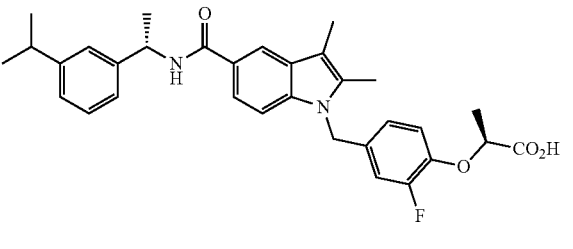
IA-148
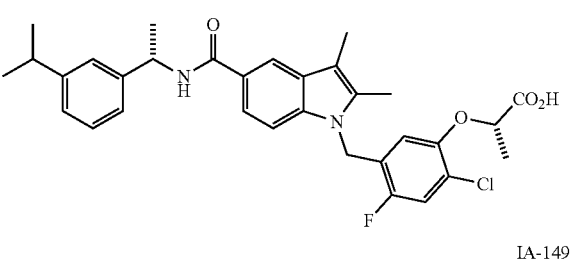
IA-149
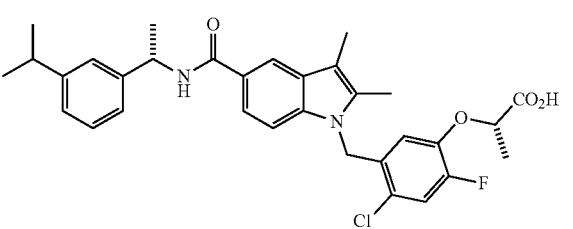
IA-150
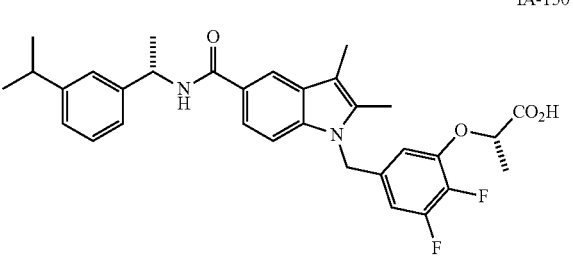

IA-151
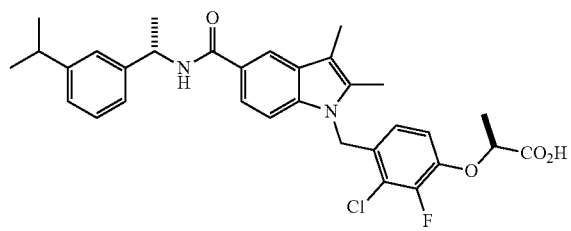
IA-152
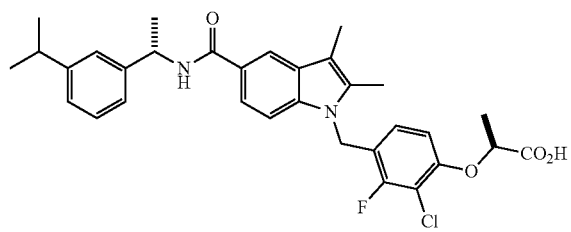
IA-153
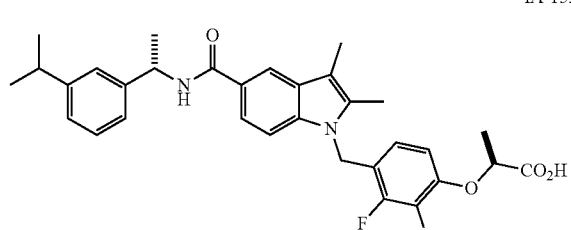
IA-154
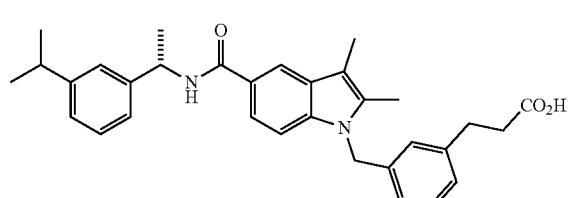
IA-155
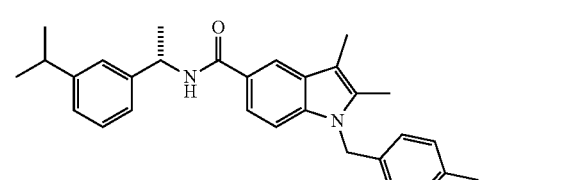
IA-156
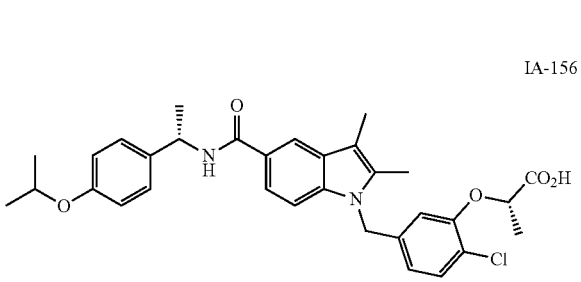
IA-157
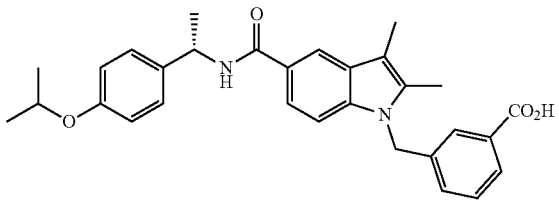
IA-158
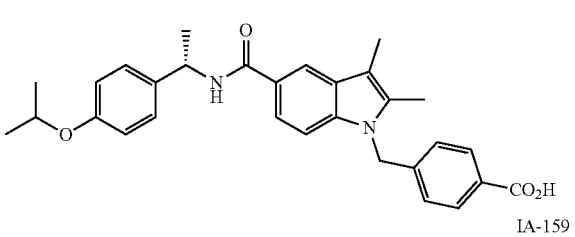
IA-159
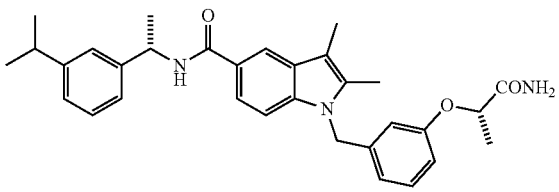
IA-160
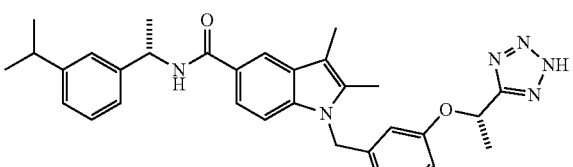
IA-161
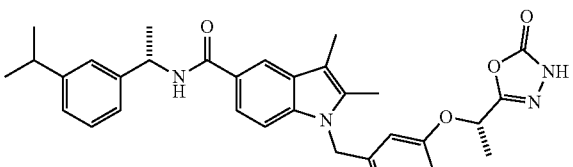
IA-162
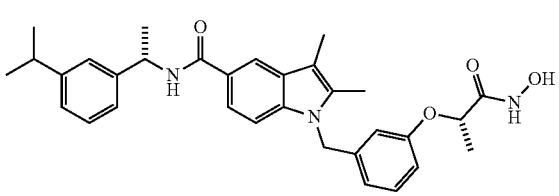
IA-163

IA-164
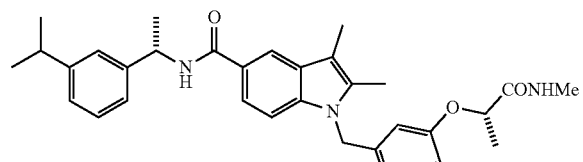

IA-165
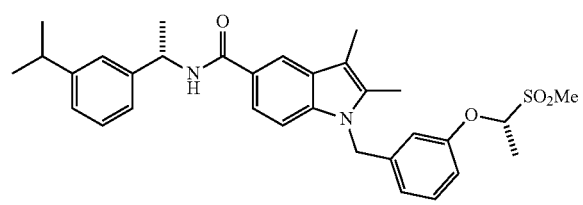

IA-166
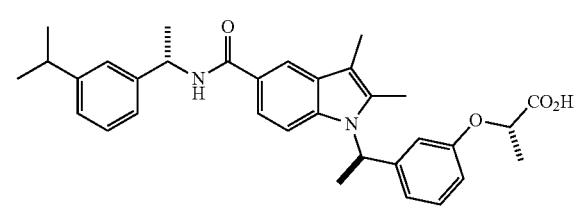

IA-167
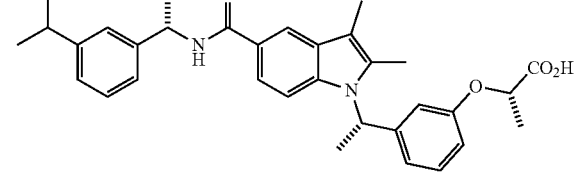

IA-168
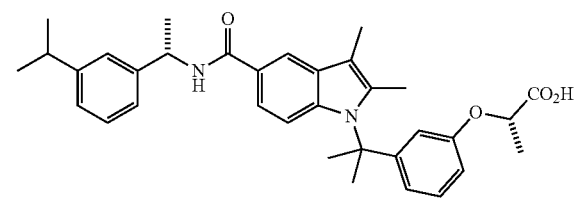

IA-169
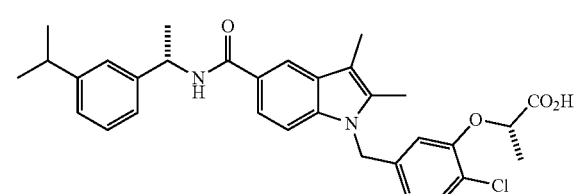

IA-170
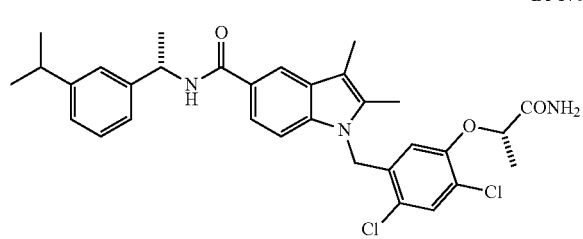

IA-171
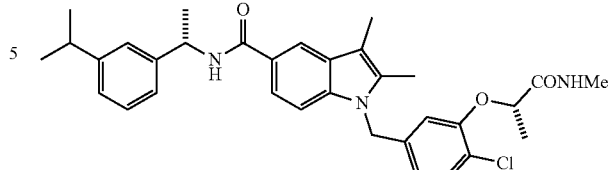

IA-172
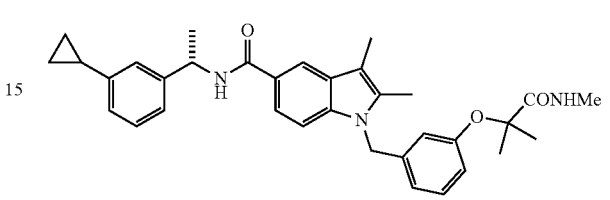

IA-173
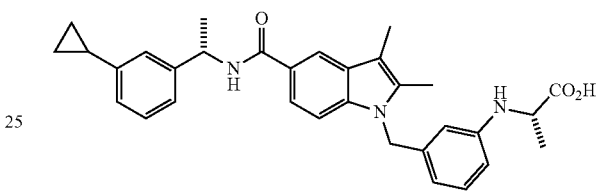

IA-174
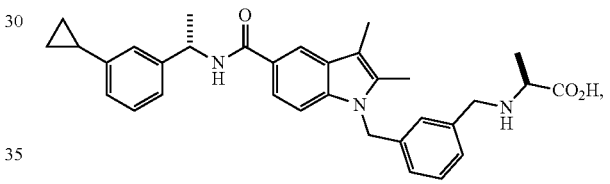

IA-175
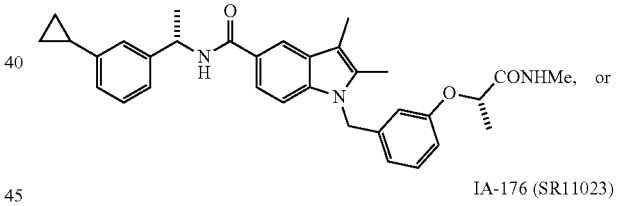

IA-176 (SR11023)
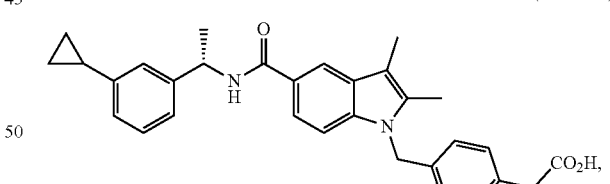

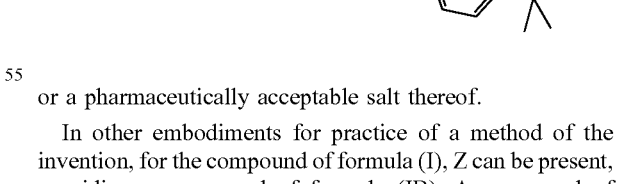

or a pharmaceutically acceptable salt thereof.

In other embodiments for practice of a method of the invention, for the compound of formula (I), Z can be present, providing a compound of formula (IB). A compound of formula (IB) can be an N-biphenylmethyl-indole, an N-biphenylmethyl-benzimidazole, an N-biphenylmethyl-indazole, or an analog thereof. For instance, in various embodiments, $Z^1$-$Z^5$ can all be carbon. In other embodiments, one of two of $Z^1$-$Z^5$ can be nitrogen.

In specific embodiments for practice of a method of the invention, the compound of formula (IB) can be any one of:

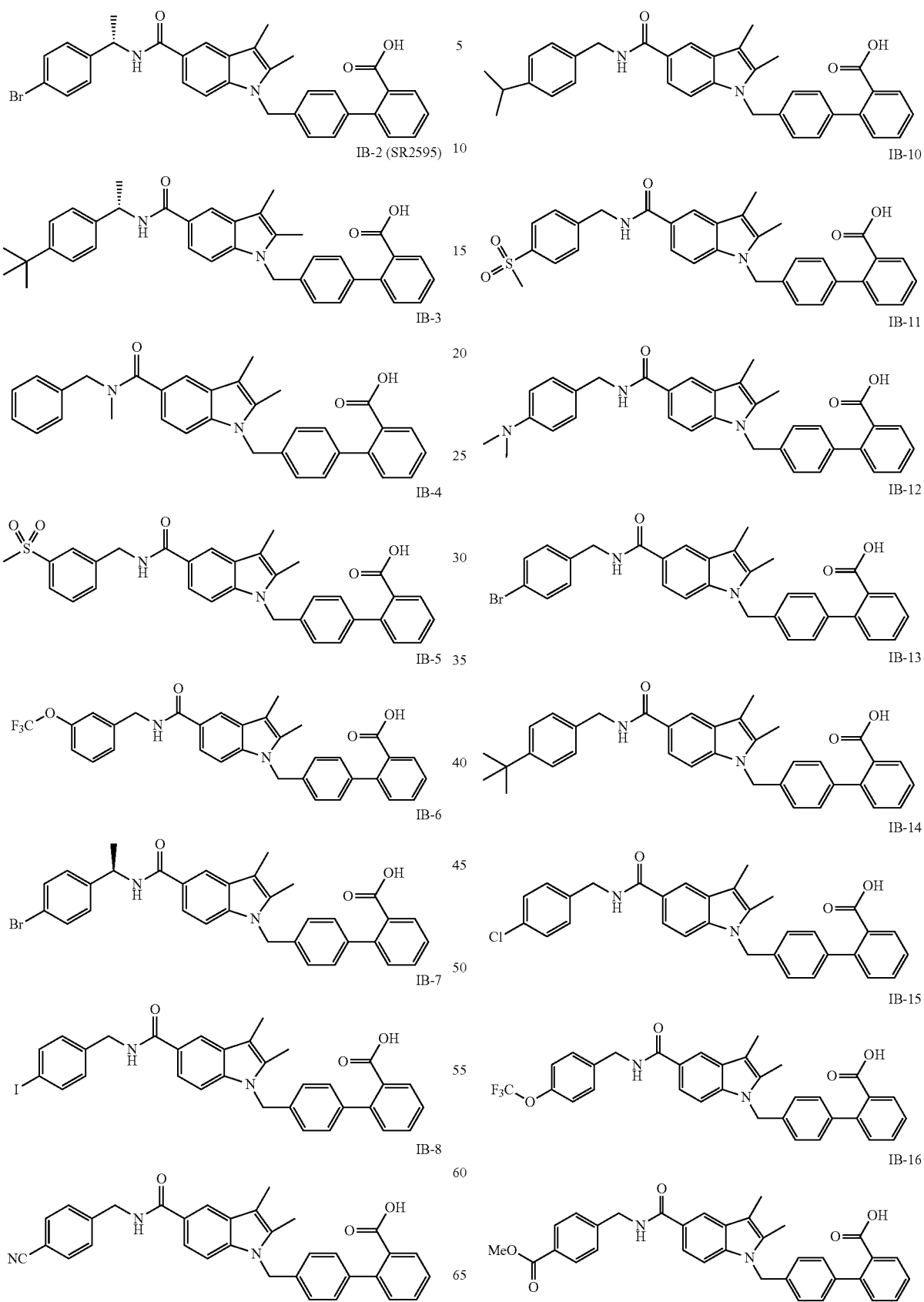

IB-17
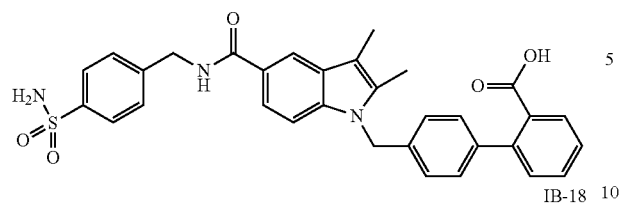
IB-18
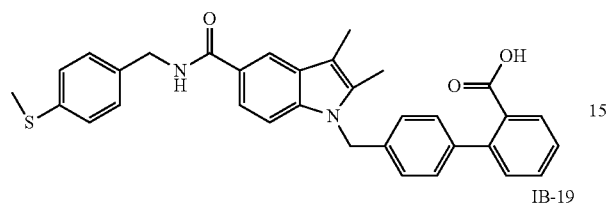
IB-19
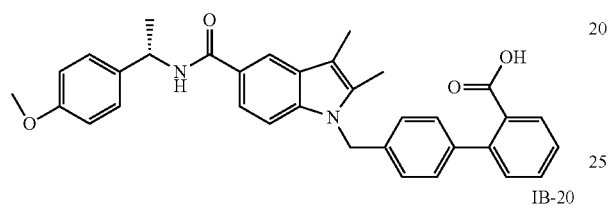
IB-20

IB-21
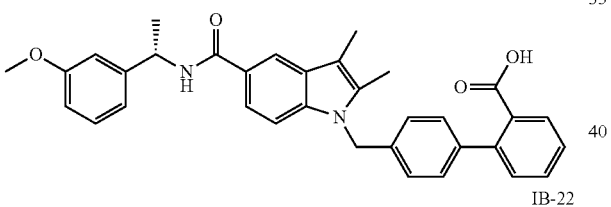
IB-22
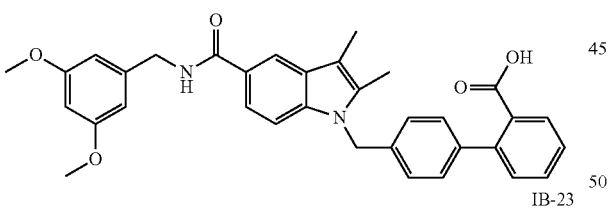
IB-23
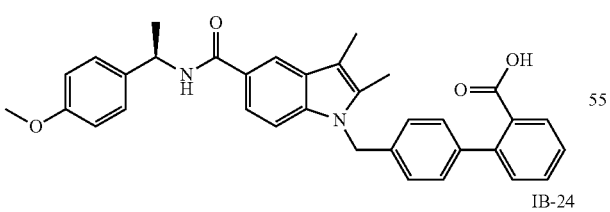
IB-24
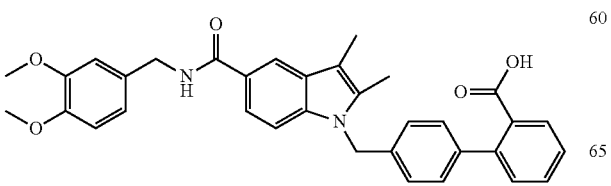
IB-25
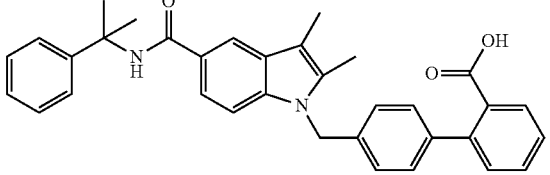
IB-26
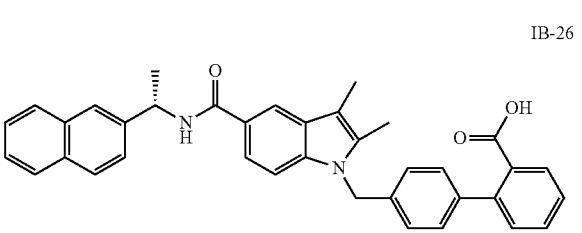
IB-27

IB-30

IB-31
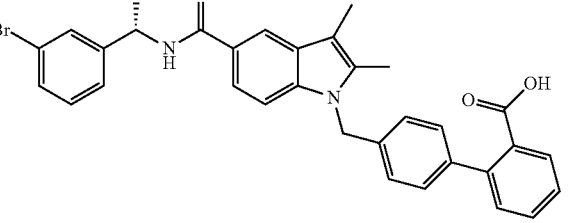
IB-34
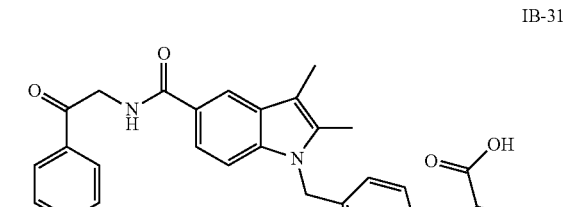
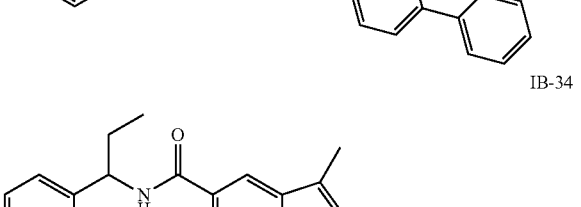
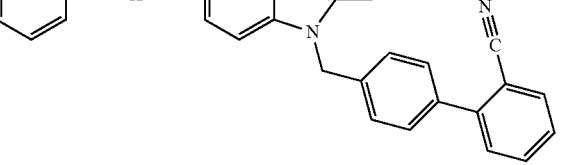

IB-35
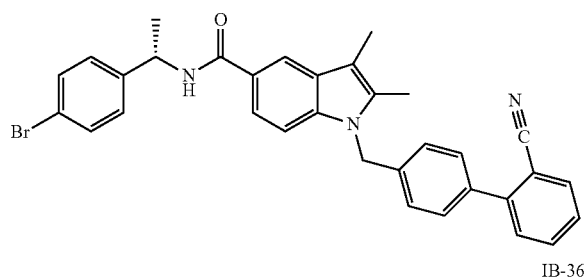
IB-36
IB-37
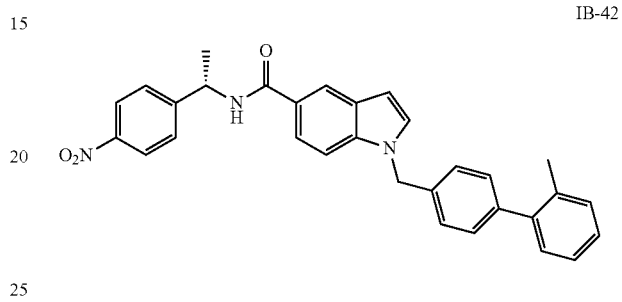
IB-38

IB-39
IB-40
IB-41
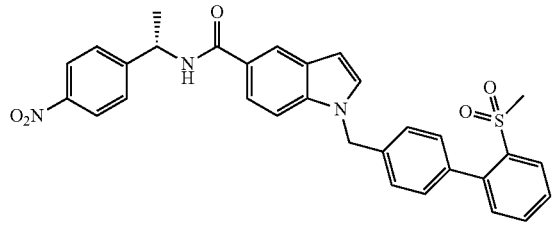
IB-42
IB-43

IB-44
IB-45
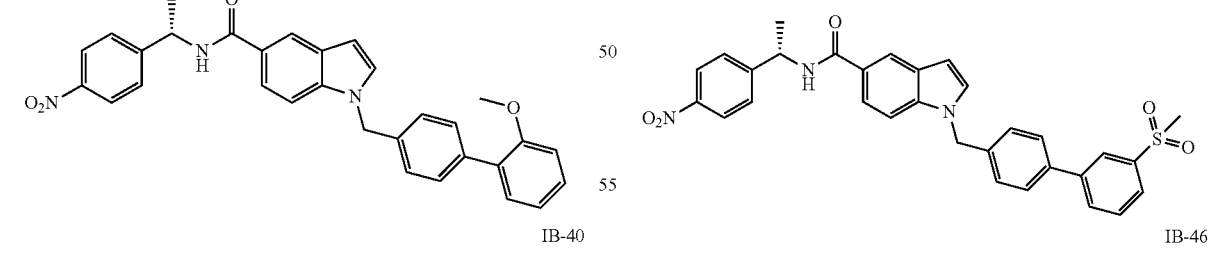
IB-46
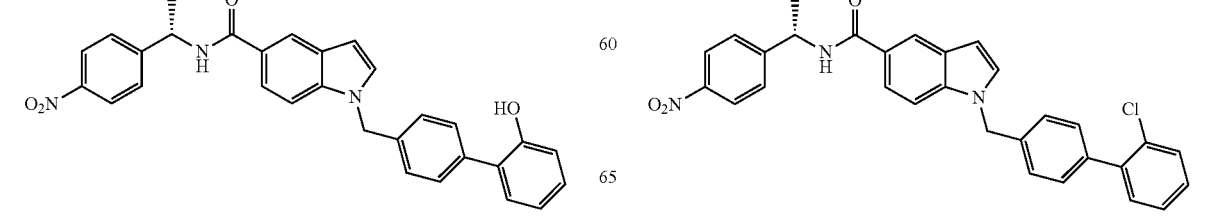

IB-47
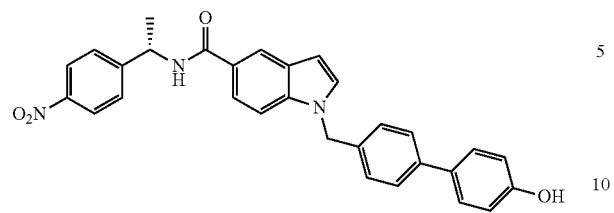
IB-53
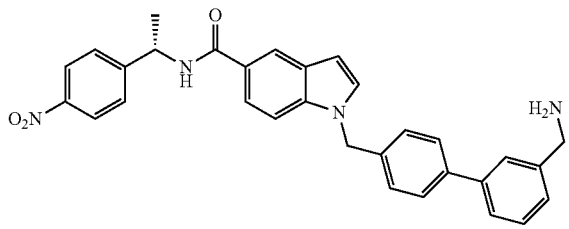
IB-48
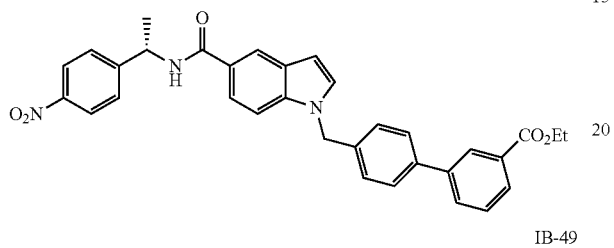
IB-54
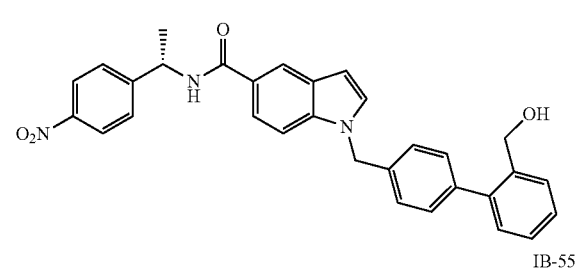
IB-49
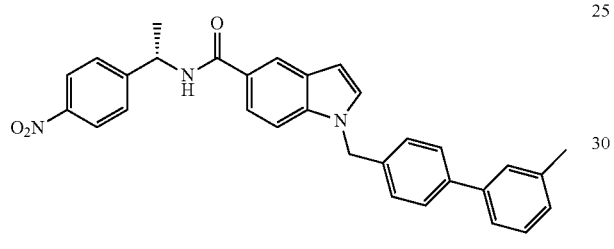
IB-55
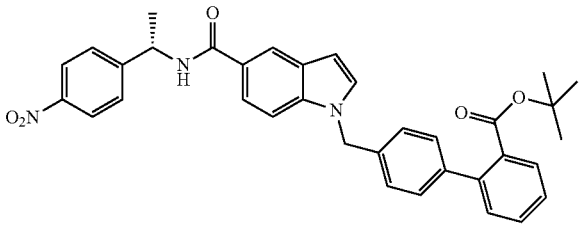
IB-50
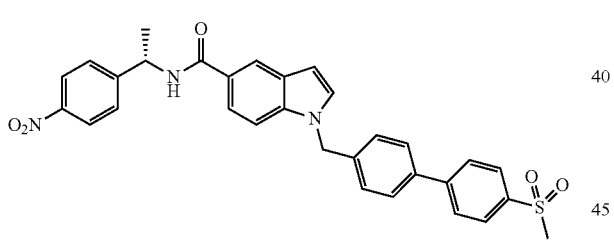
IB-56
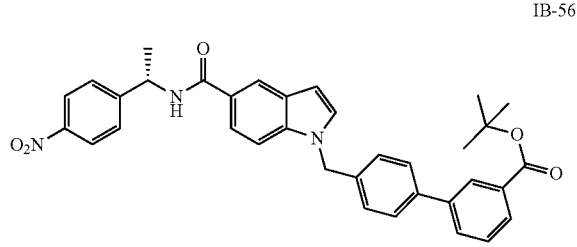
IB-51
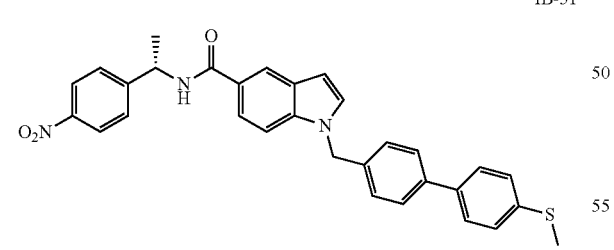
IB-52
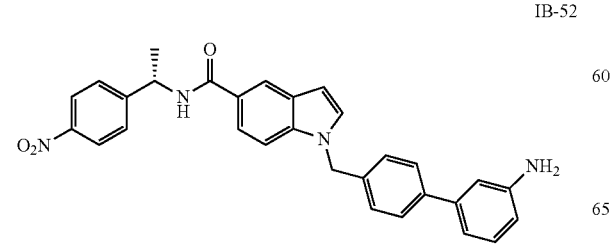
IB-57
IB-58
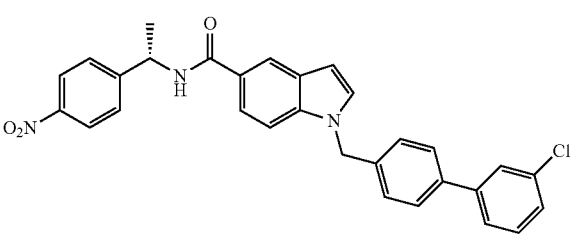

IB-59
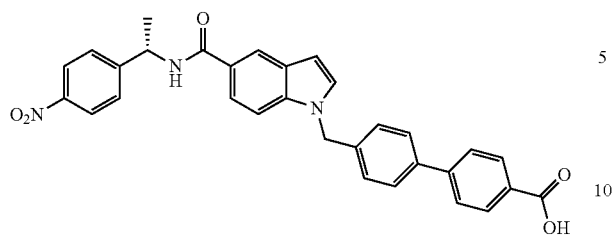
IB-60
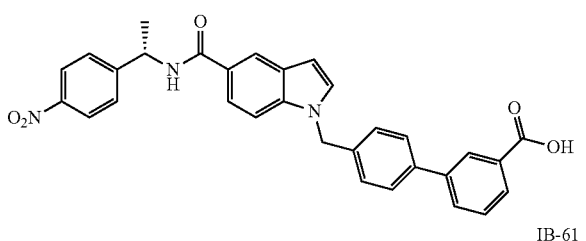
IB-61
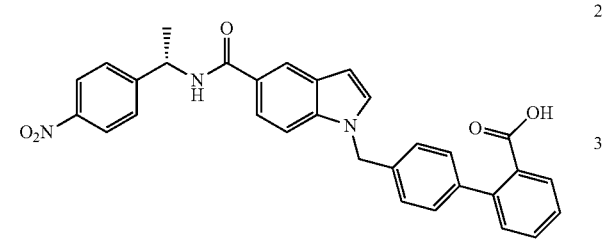
IB-62
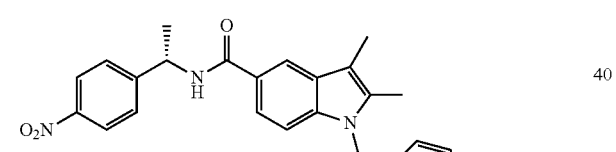
IB-63
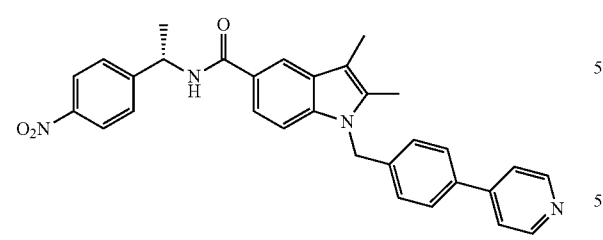
IB-64
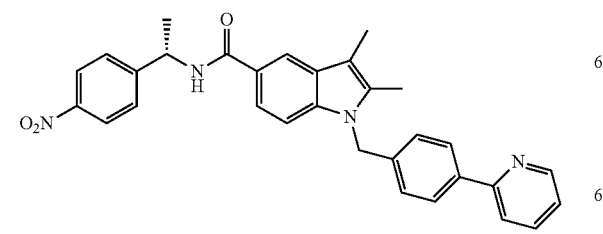
IB-65
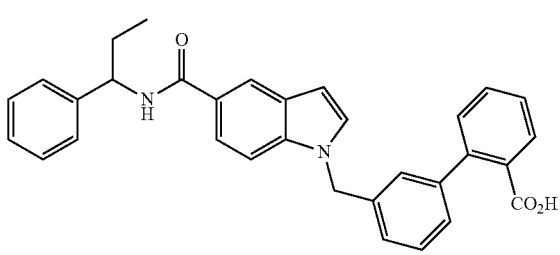
IB-66
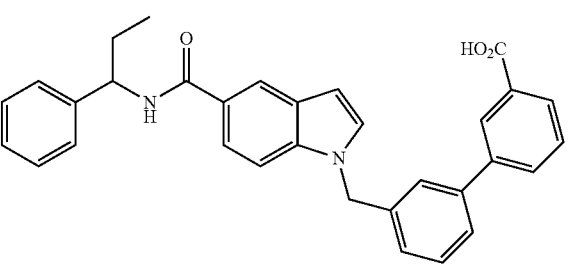
IB-67
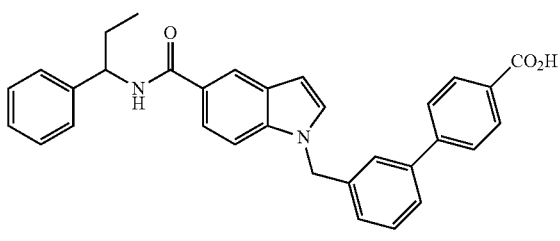
IB-68
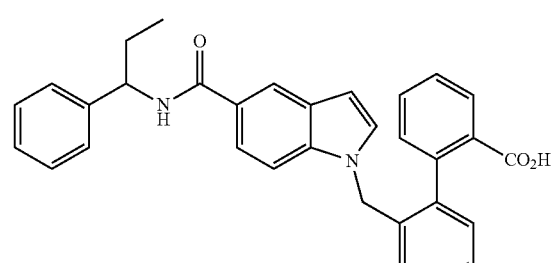
IB-69
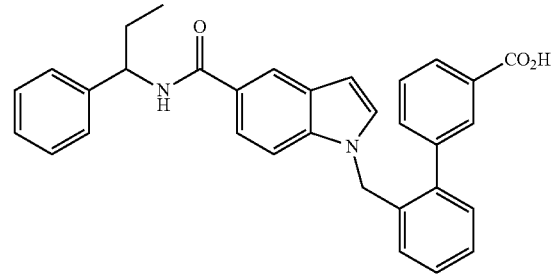

IB-70
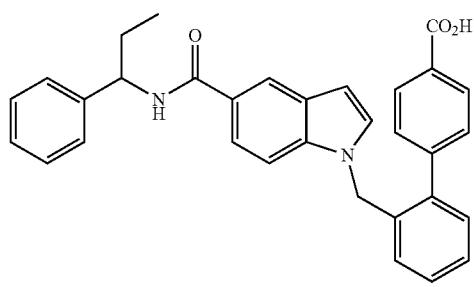
IB-72
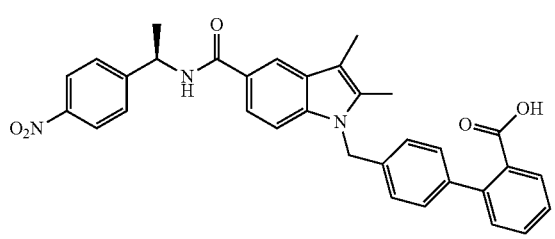
IB-73 (SR1664)
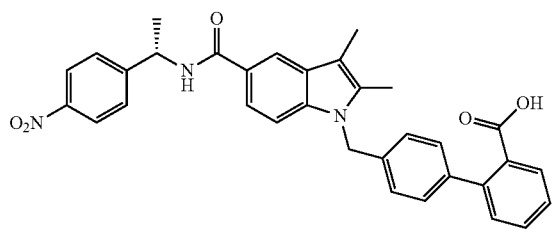
IB-74
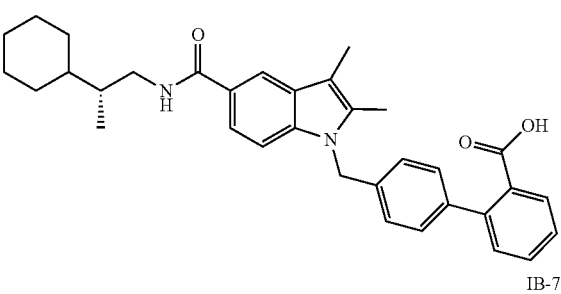
IB-75
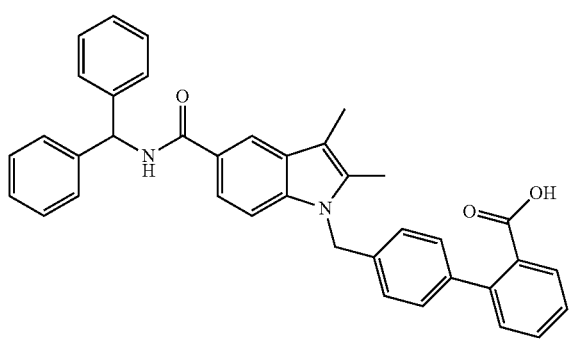
IB-76
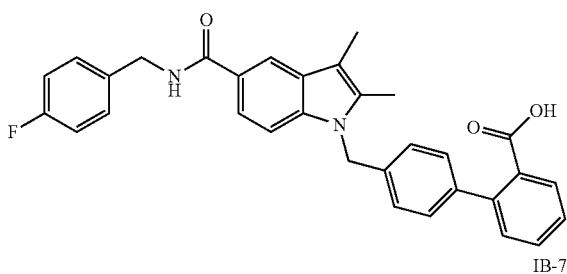
IB-77
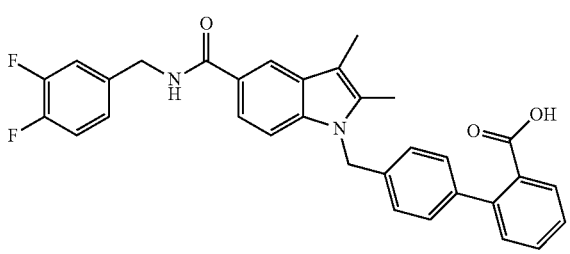
IB-78
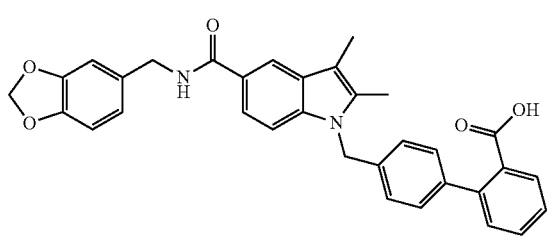
IB-79
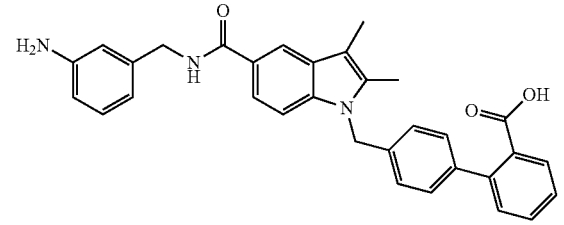
IB-80
IB-81
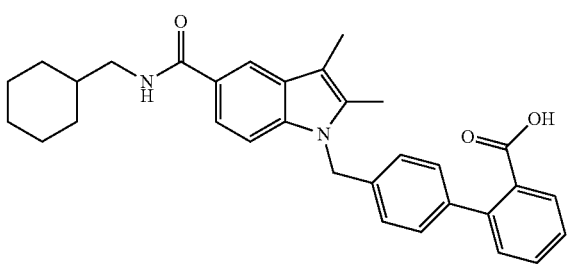

IB-82
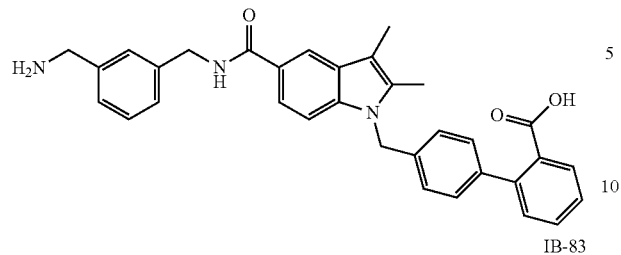
IB-83
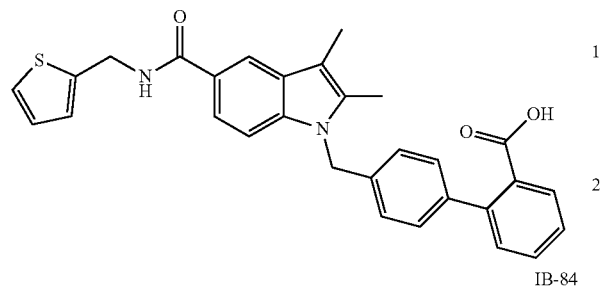
IB-84
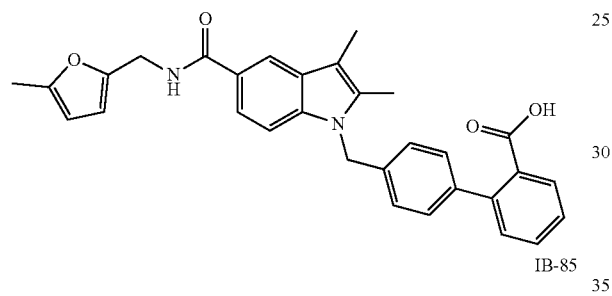
IB-85
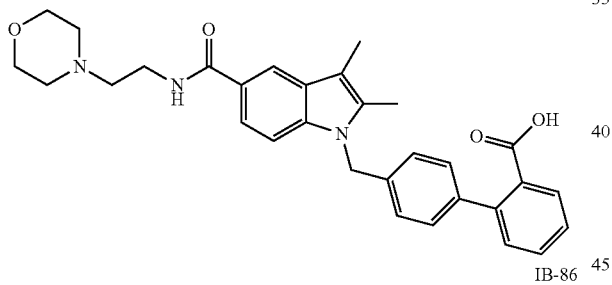
IB-86
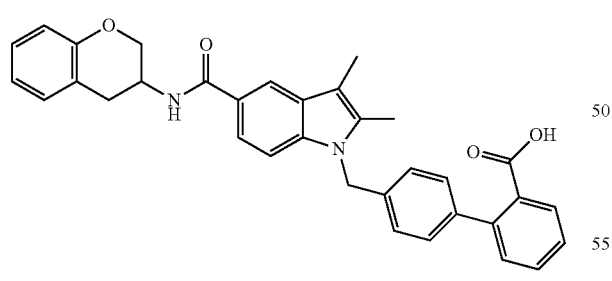
IB-87
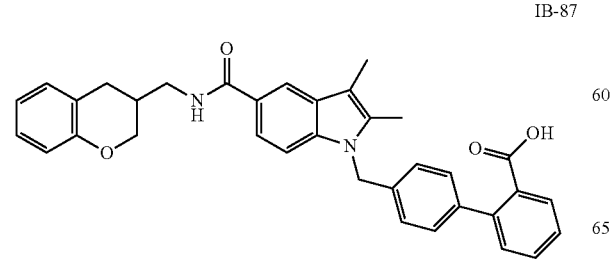
IB-88
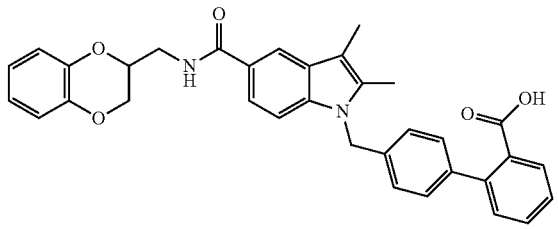
IB-89
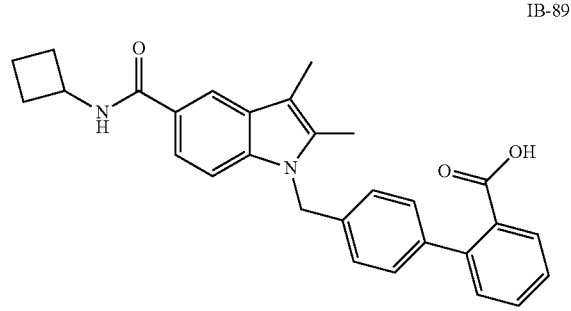
IB-90
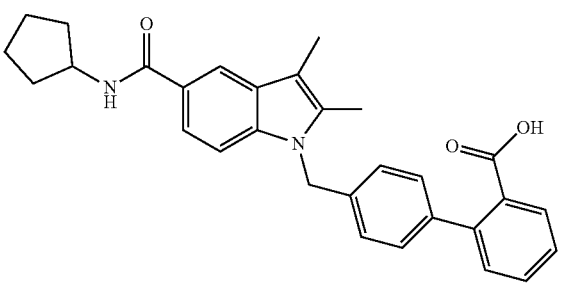
IB-91
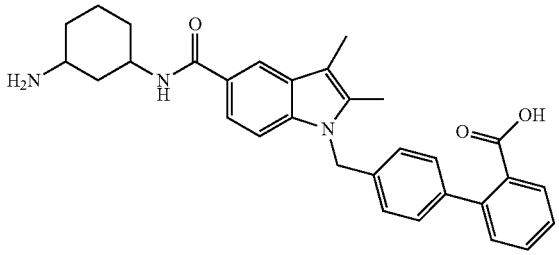
IB-92
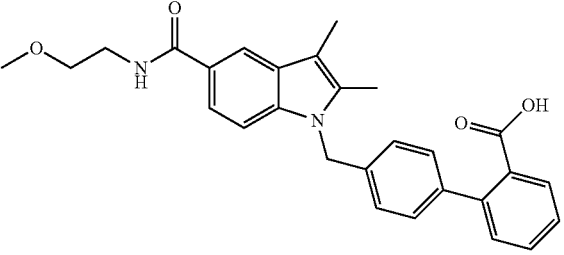

IB-93
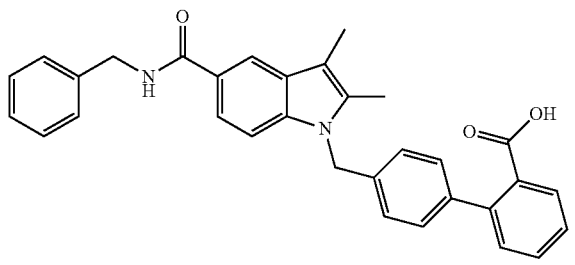
IB-94
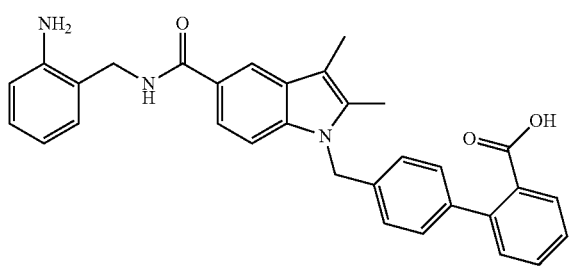
IB-95
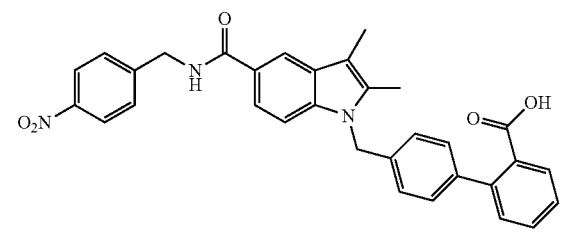
IB-96
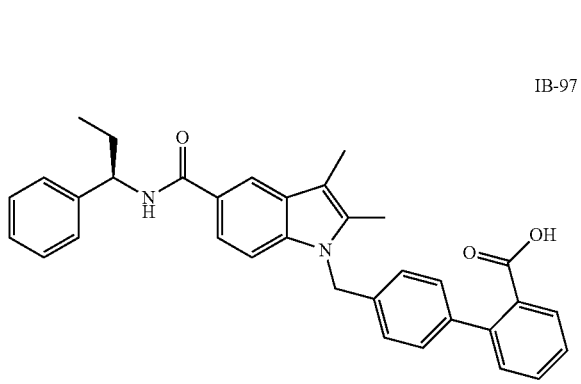
IB-97
IB-98
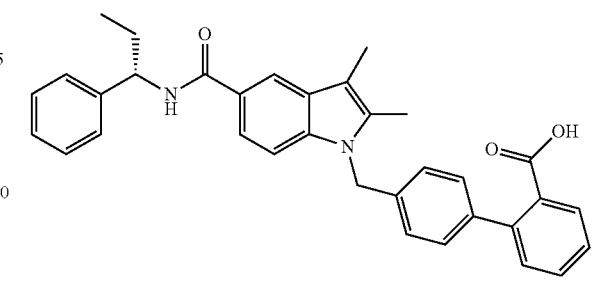
IB-99
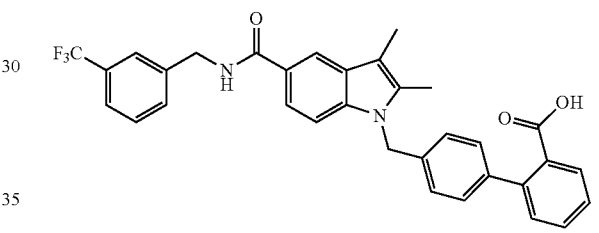
IB-100
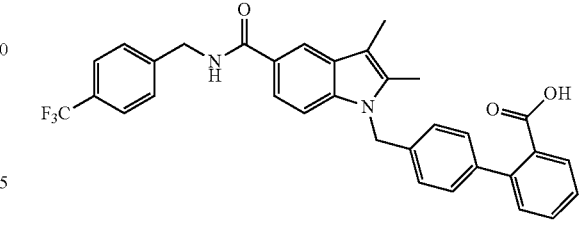
IB-101
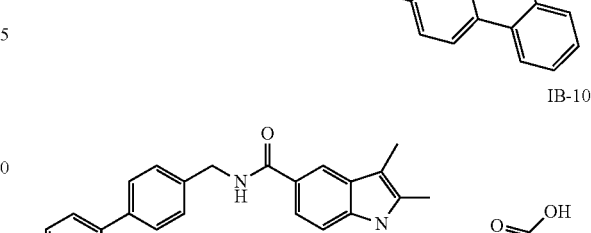
IB-102
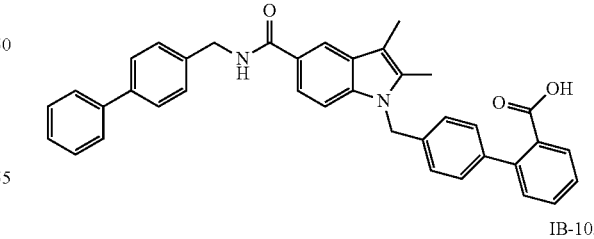
IB-103
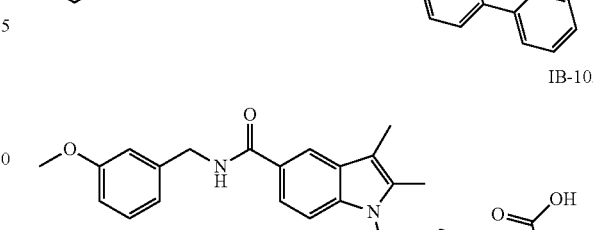

IB-104
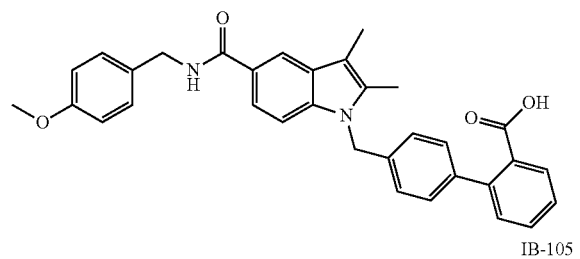
IB-105
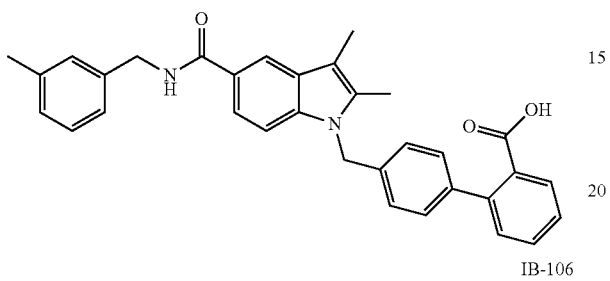
IB-106
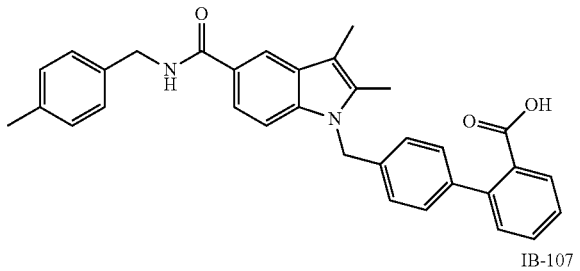
IB-107
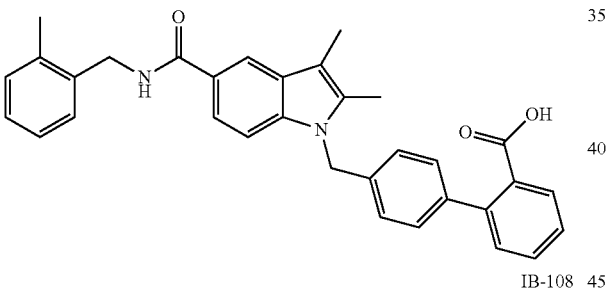
IB-108
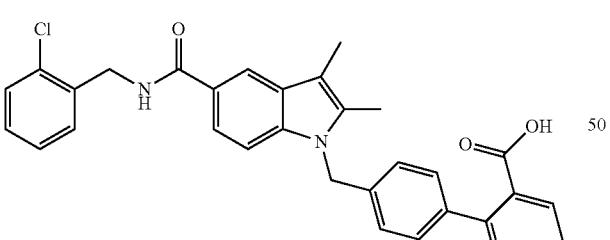
IB-109
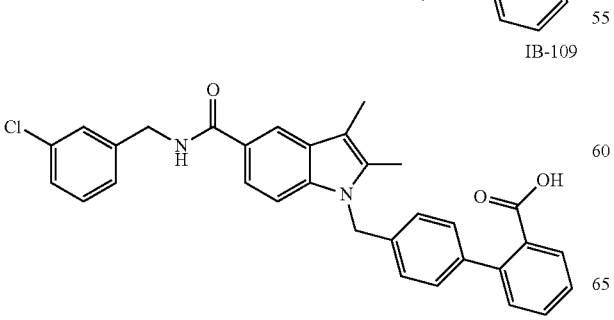
IB-110
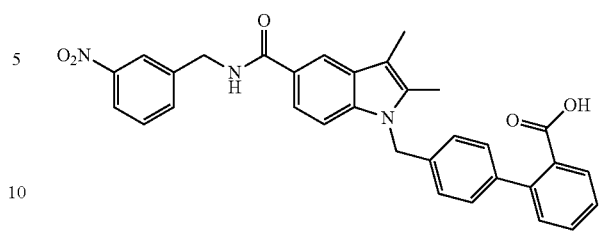
IB-111
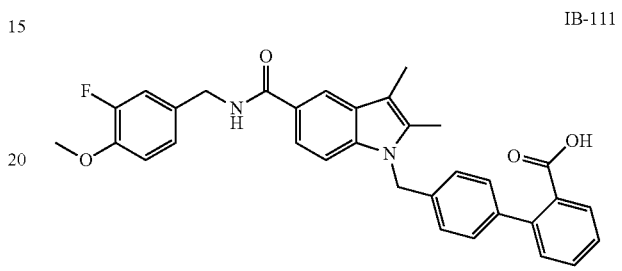
IB-112
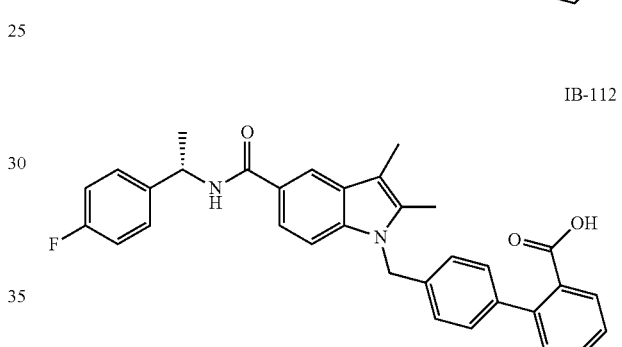
IB-113
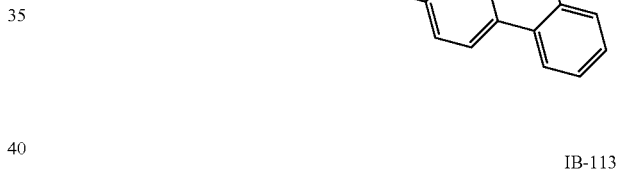
IB-114
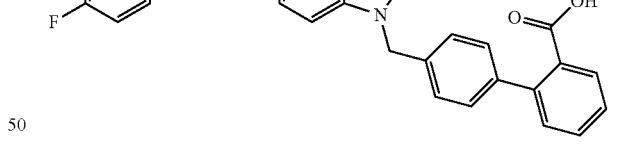
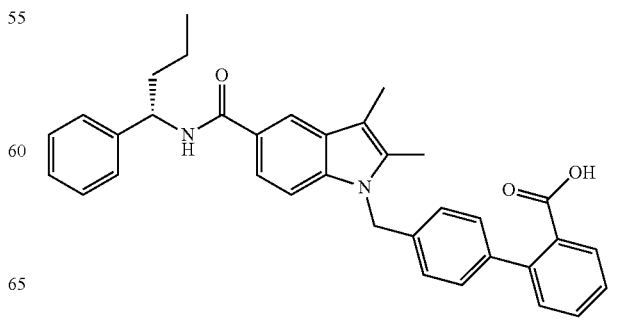

-continued
IB-115
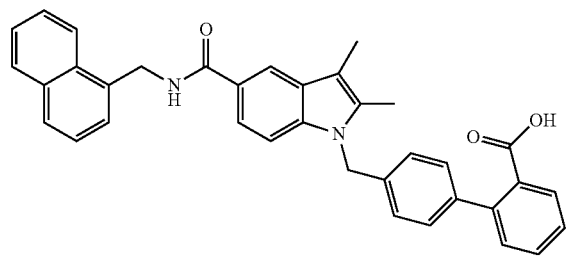
IB-116
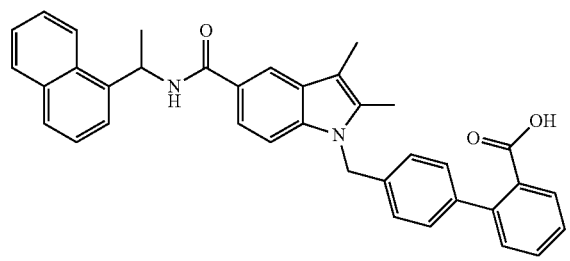
IB-117
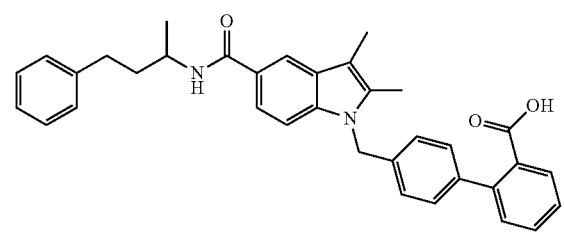
IB-118
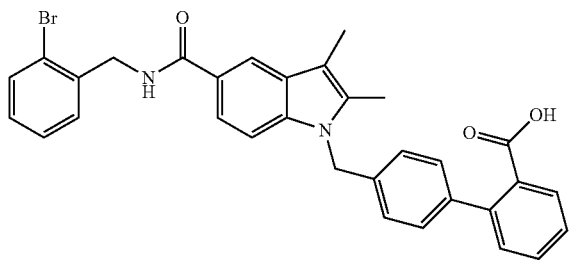
IB-119
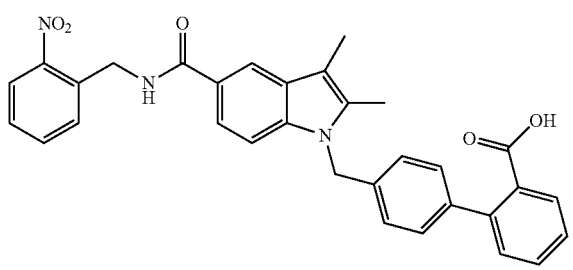
-continued
IB-120
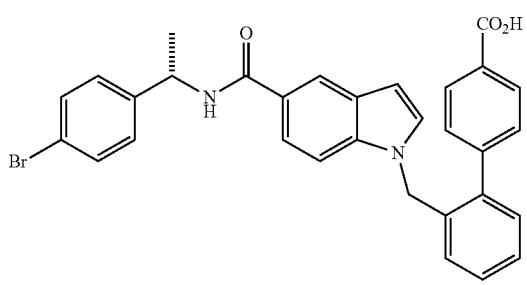
IB-121
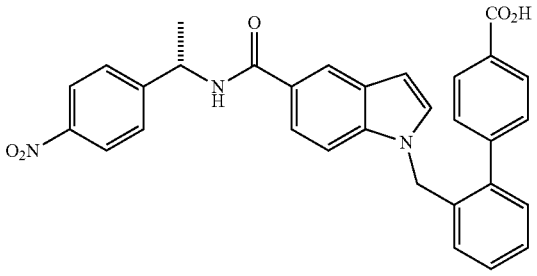
IB-122
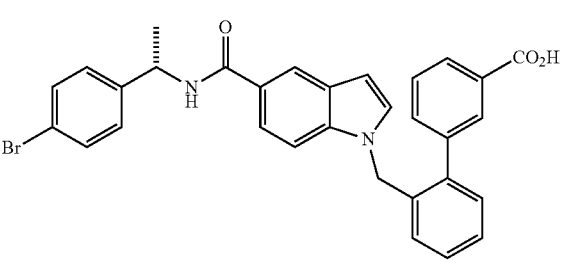
IB-123
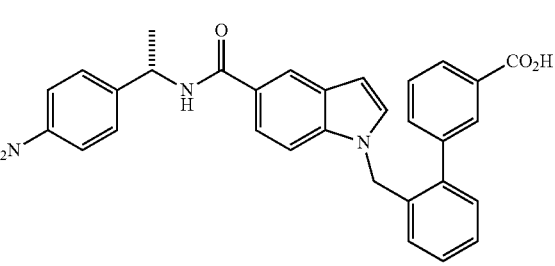
IB-124
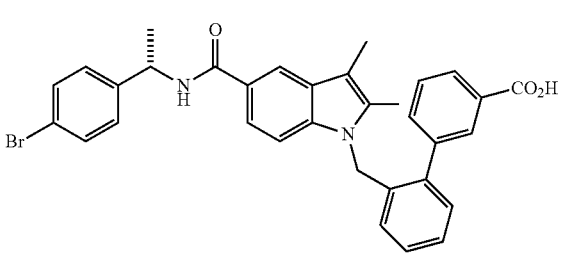

IB-125
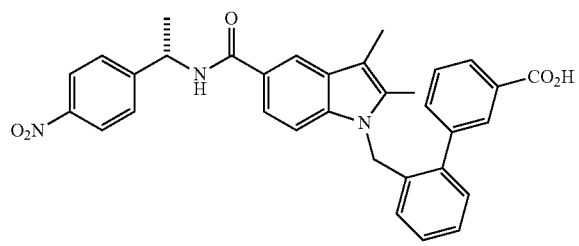
IB-130
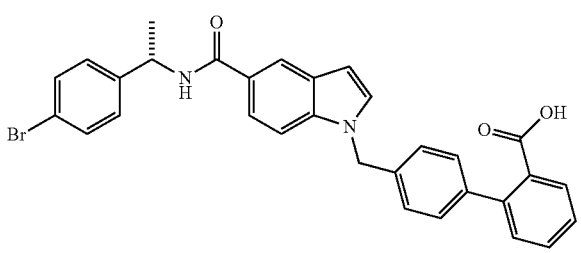
IB-126
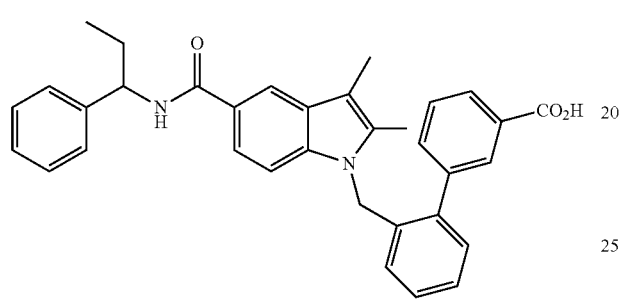
IB-131
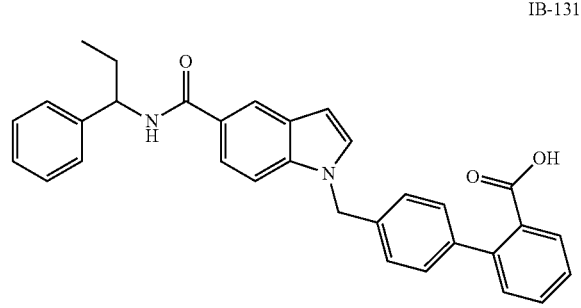
IB-127
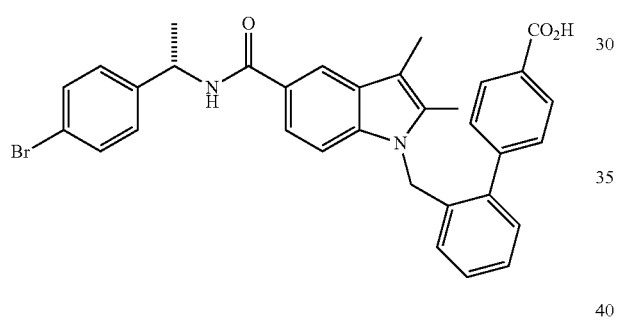
IB-132
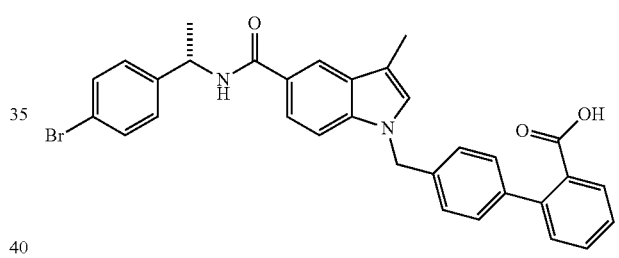
IB-128
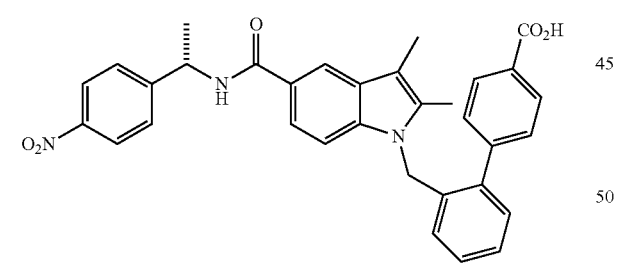
IB-133
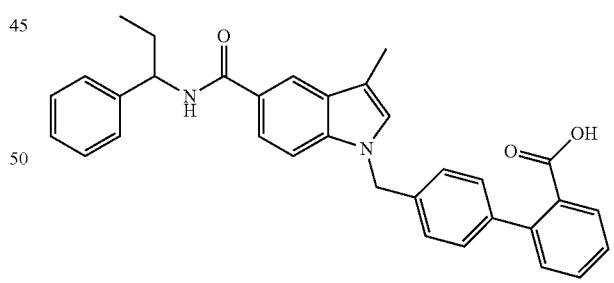
IB-129
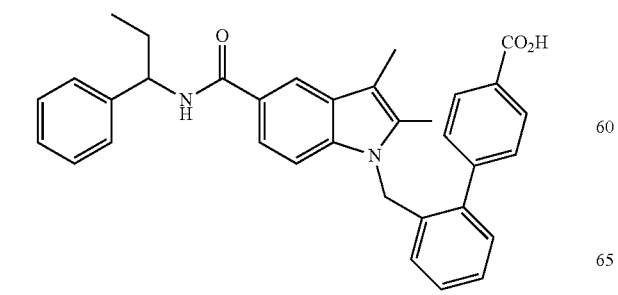
IB-134
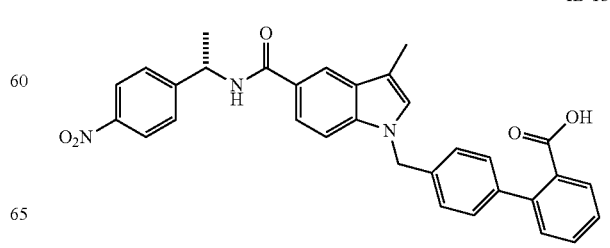

IB-135
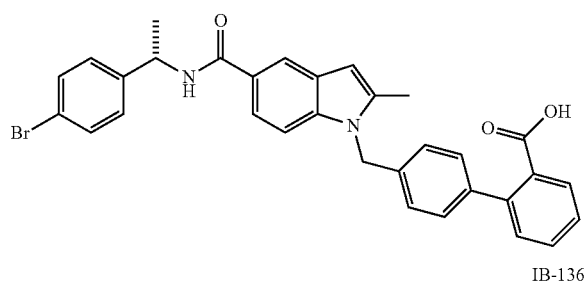
IB-136
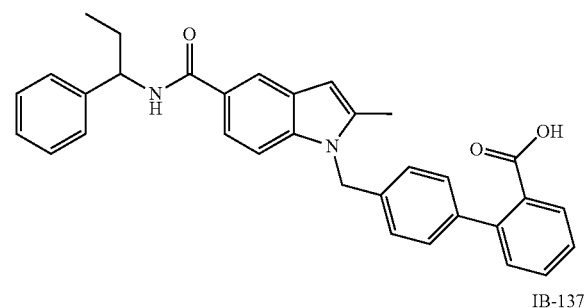
IB-137
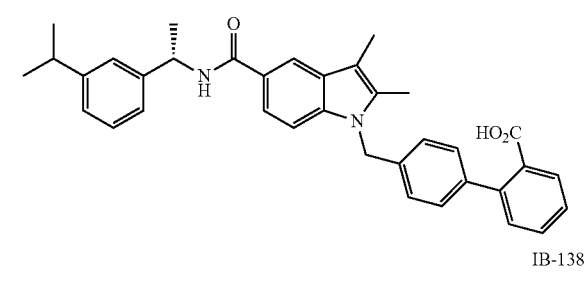
IB-138
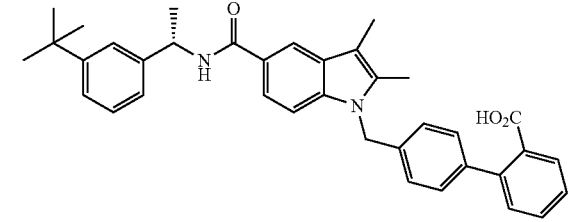
IB-139
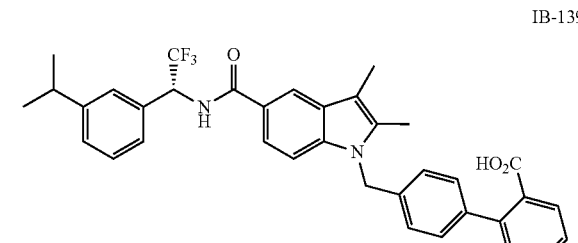
IB-140
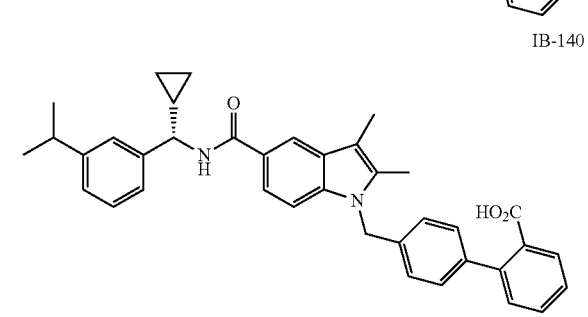
IB-141
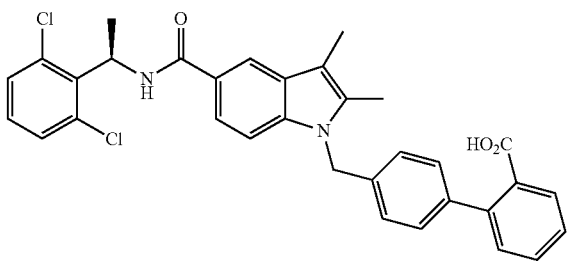
IB-142
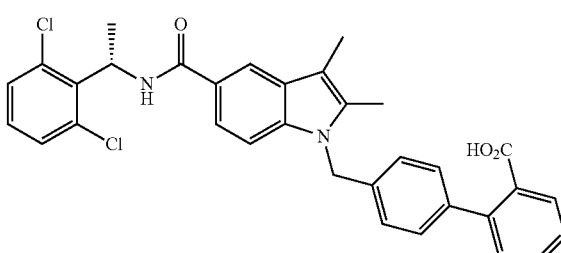
IB-143
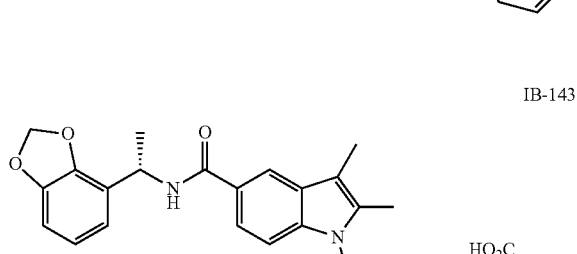
IB-144
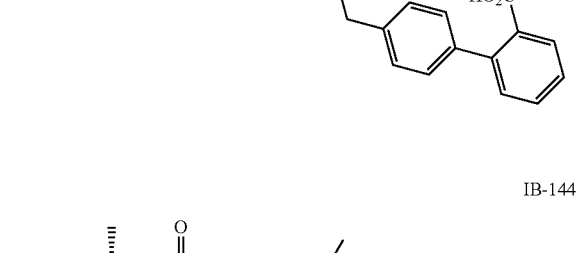
IB-144
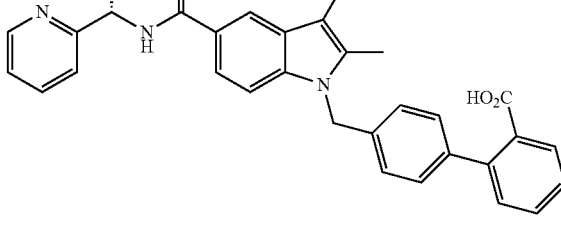
IB-145
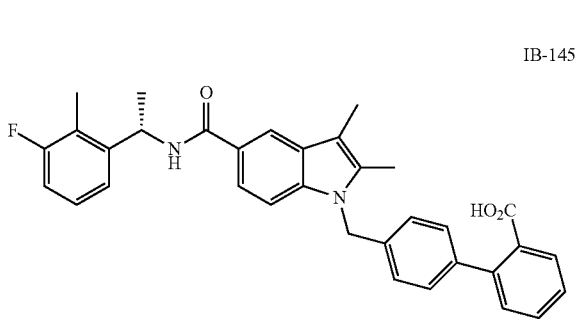

IB-146
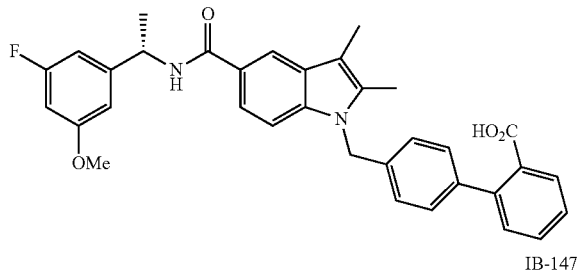
IB-147
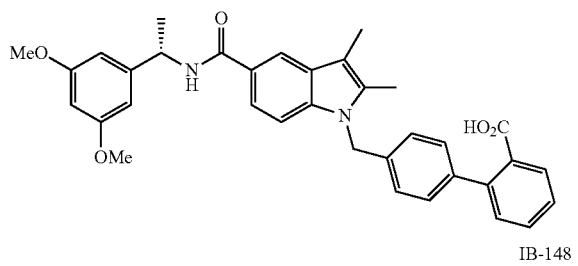
IB-148
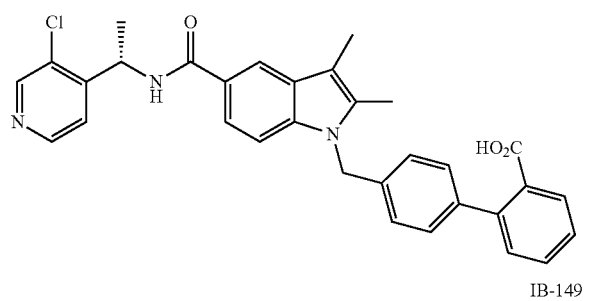
IB-149
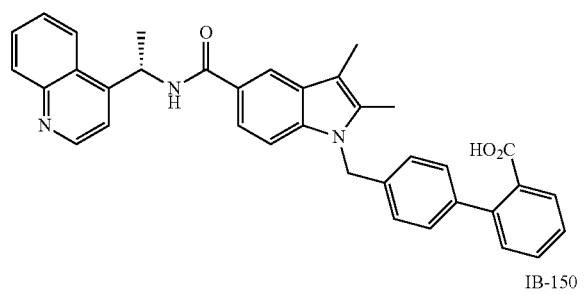
IB-150
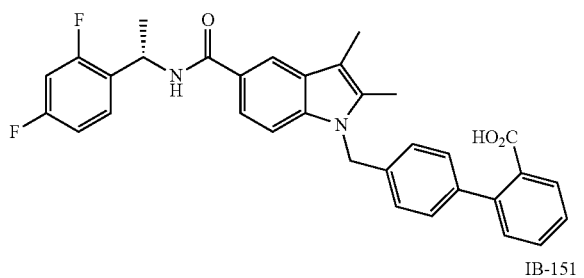
IB-151
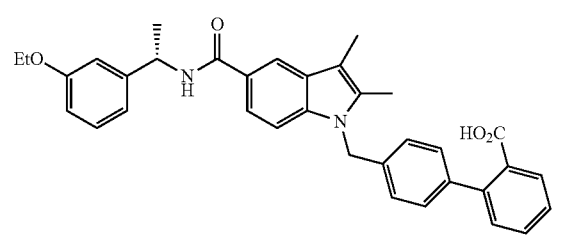
IB-152
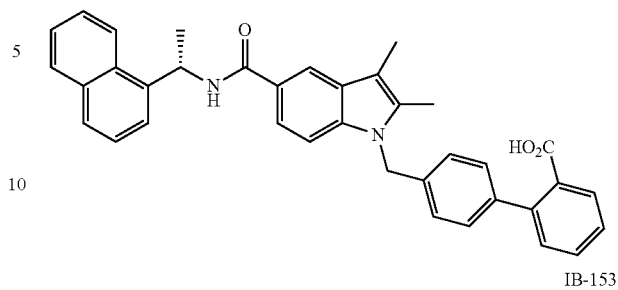
IB-153
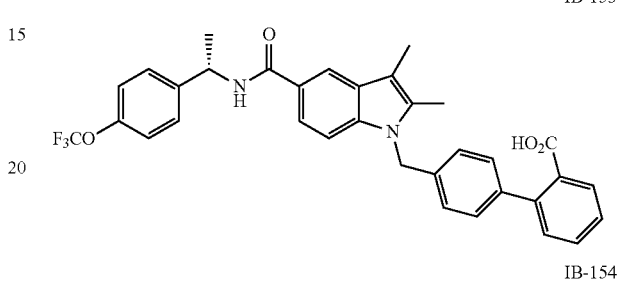
IB-154
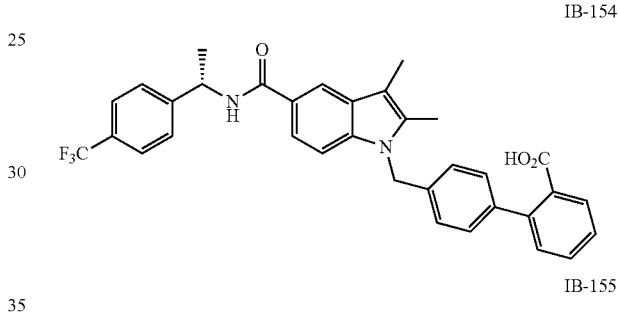
IB-155
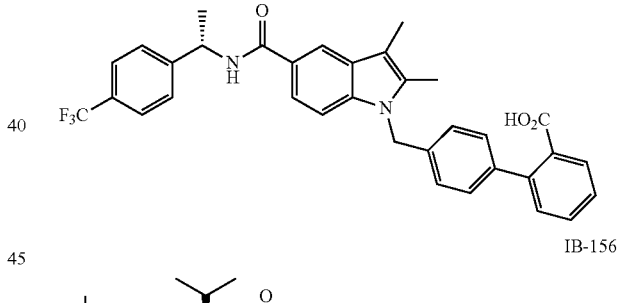
IB-156
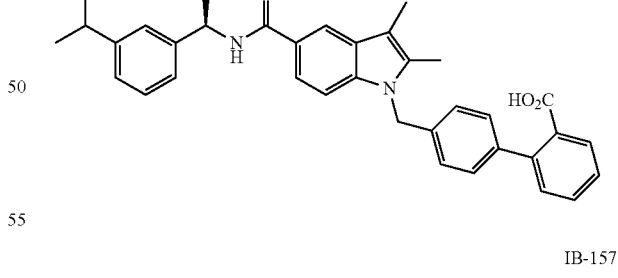
IB-157
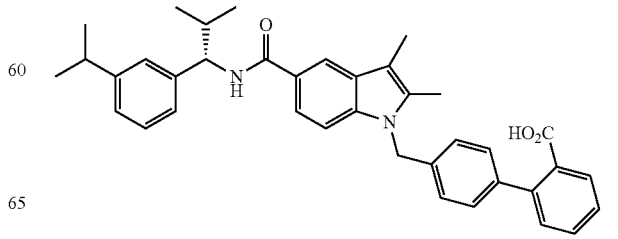

75
-continued
IB-158

IB-159

IB-160
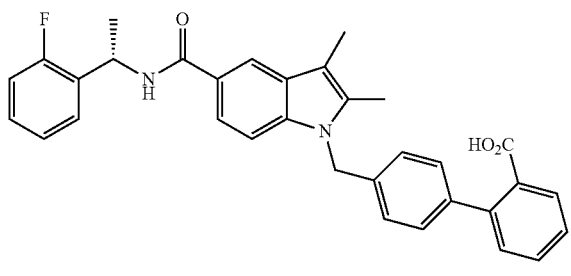
IB-161
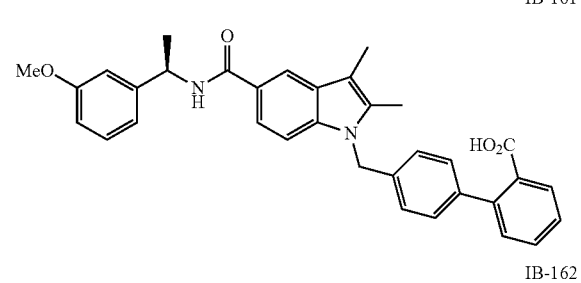
IB-162
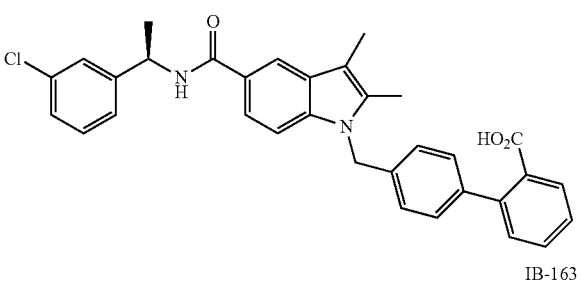
IB-163
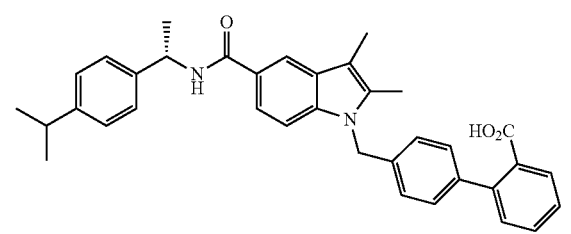
76
-continued
IB-164
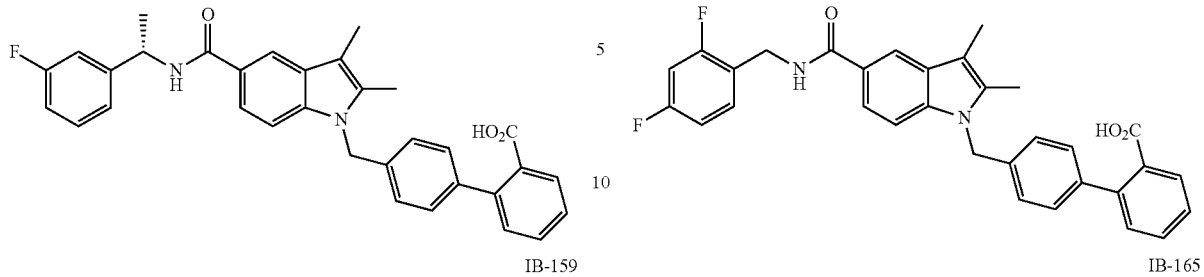
IB-165
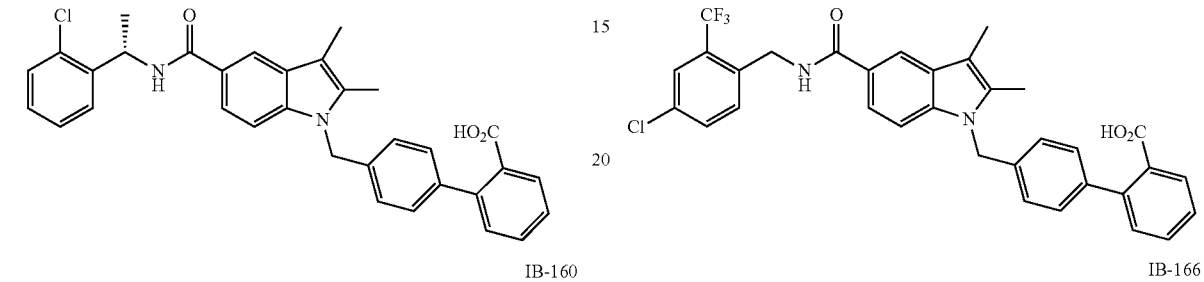
IB-166
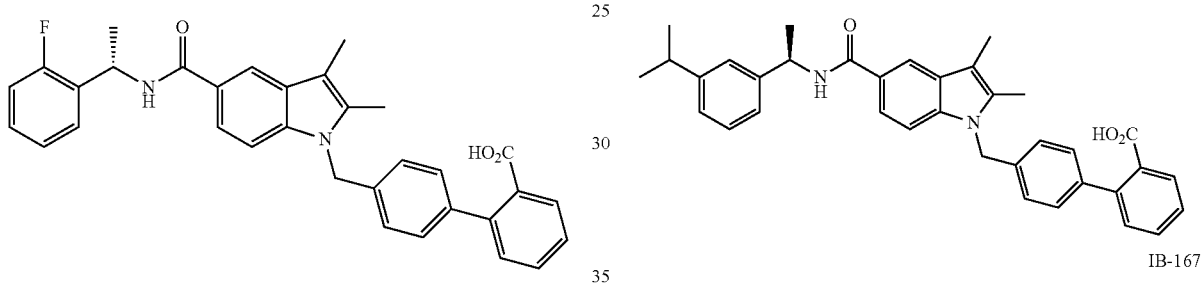
IB-167
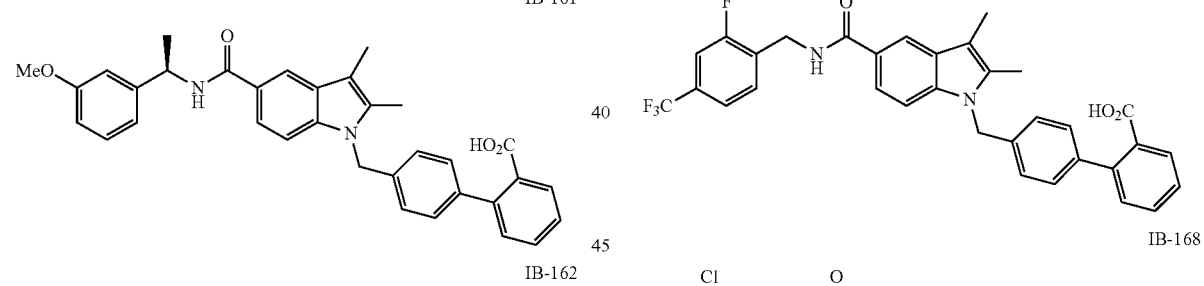
IB-168
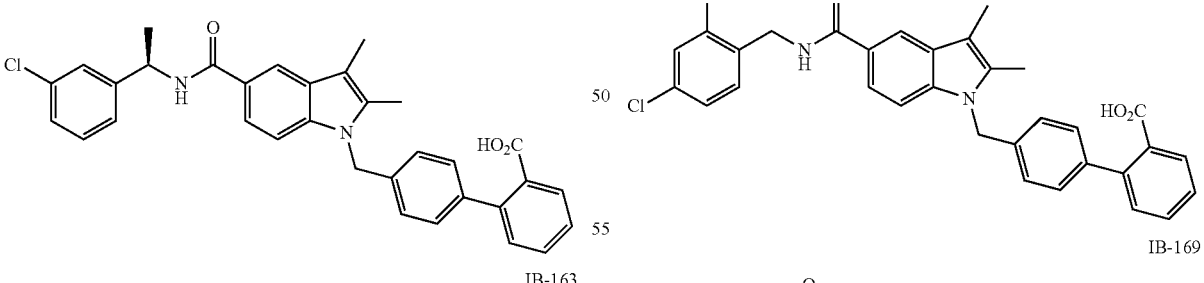
IB-169
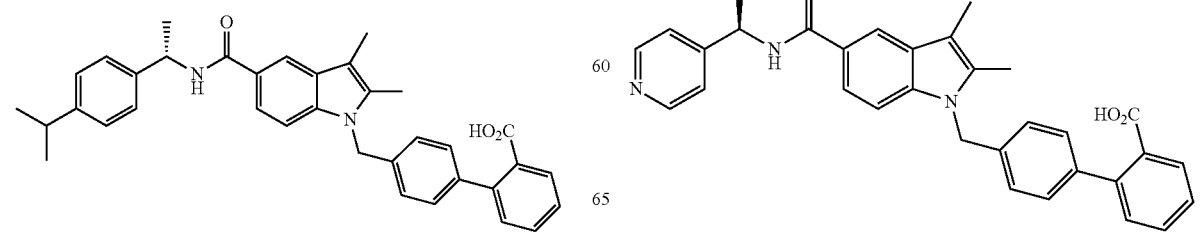

IB-170
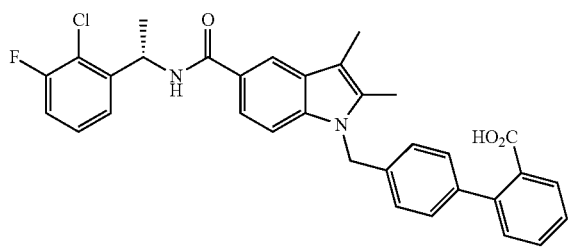
IB-175
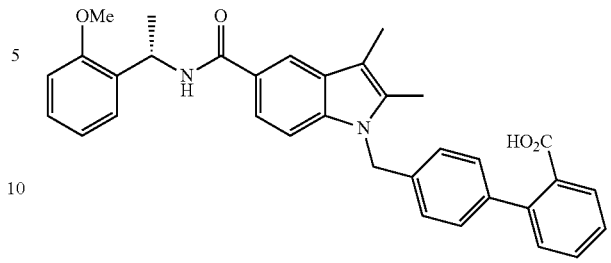
IB-171
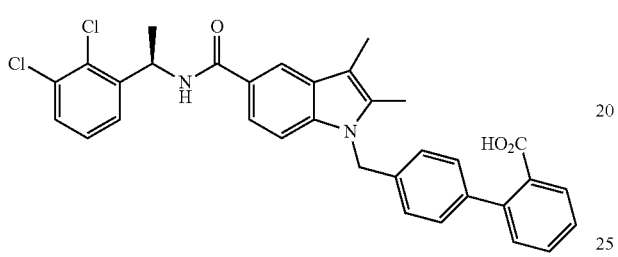
IB-176
IB-172
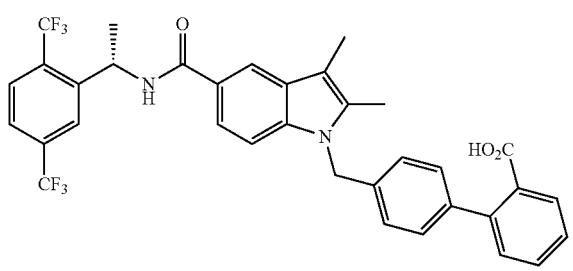
IB-177
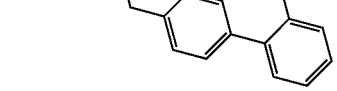
IB-173
IB-178
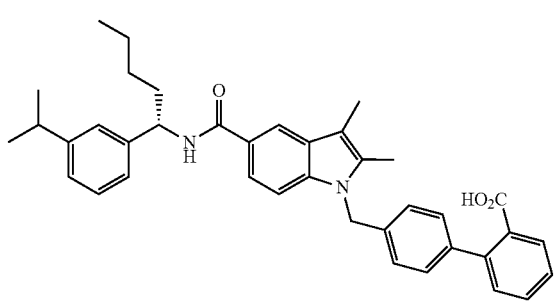
IB-174
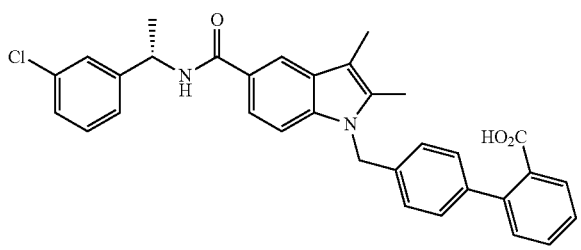
IB-179

IB-180
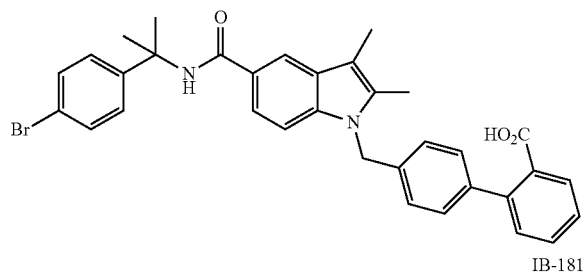
IB-181
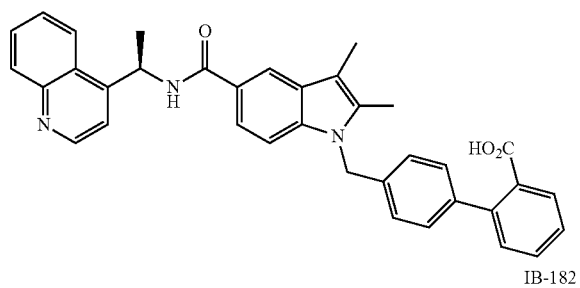
IB-182
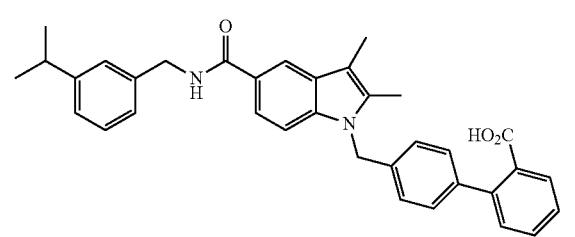
IB-183
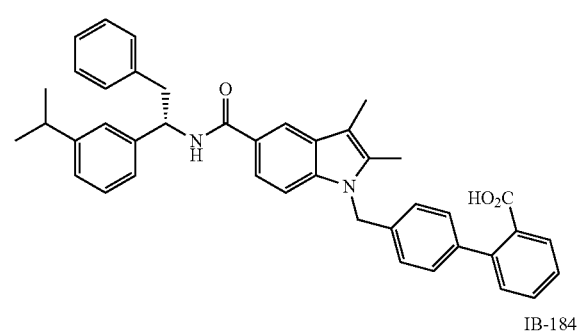
IB-184
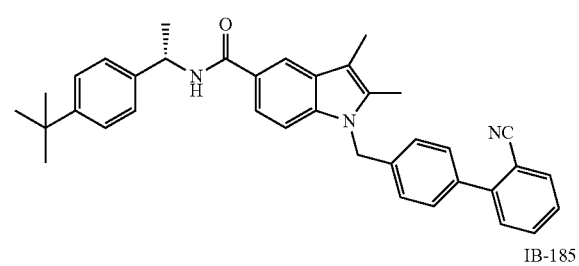
IB-185
IB-186
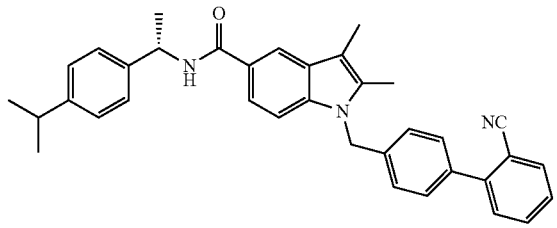
IB-187
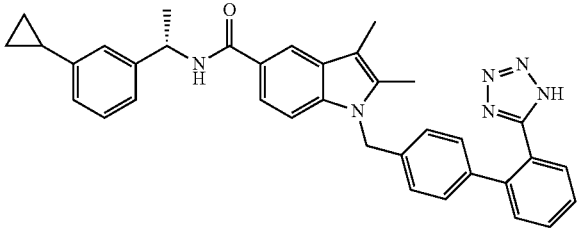
IB-188
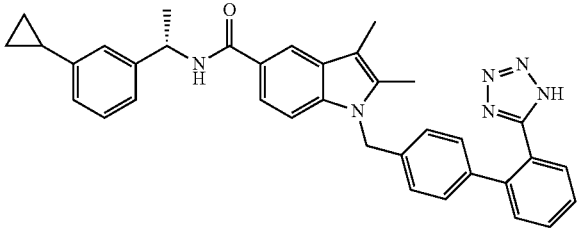
IB-189
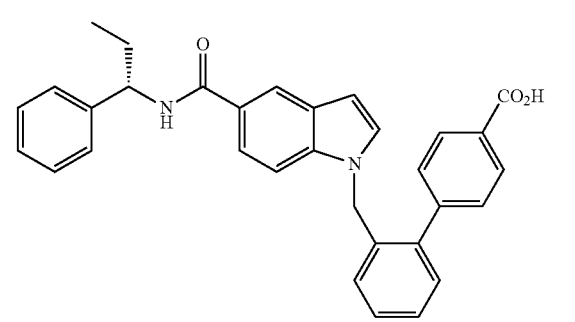
IB-190
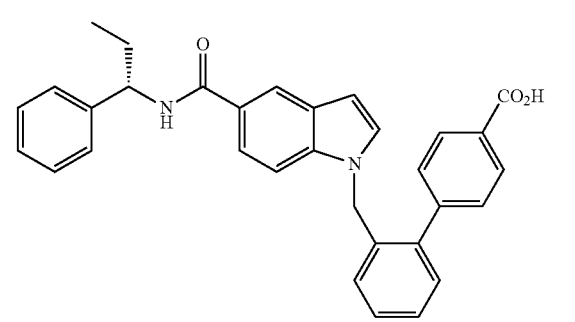

IB-191
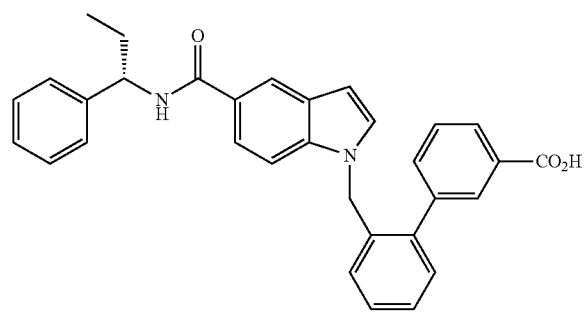
IB-192
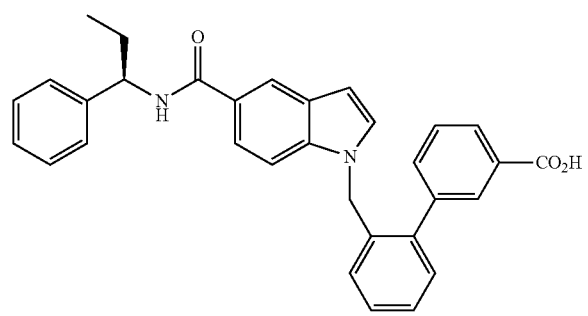
IB-193
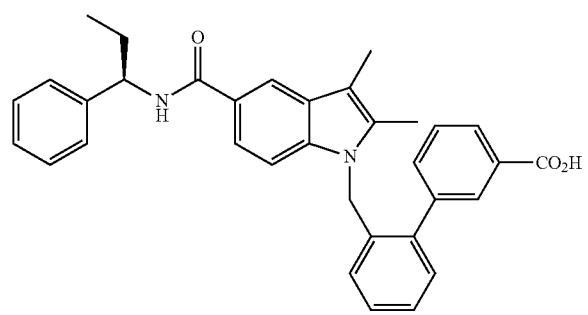
IB-194
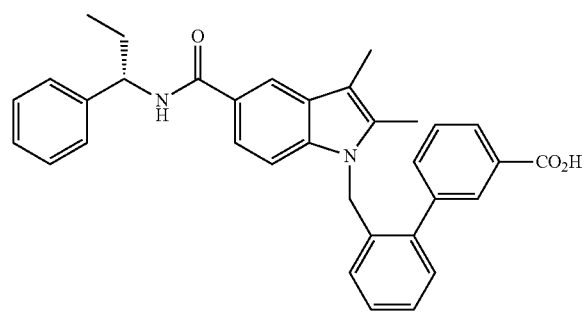
IB-195
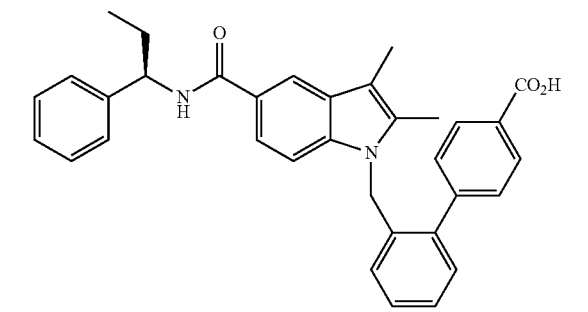
IB-196
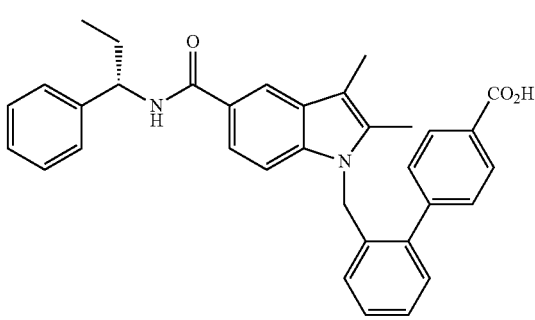
IB-197
IB-198
IB-199
IB-200
IB-201

IB-202
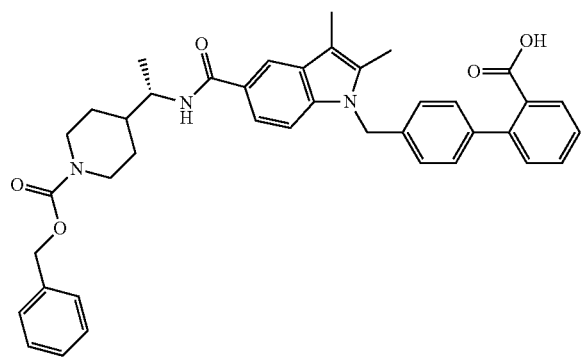
IB-203
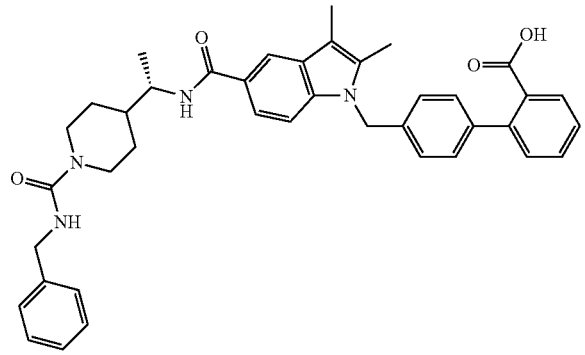
IB-204
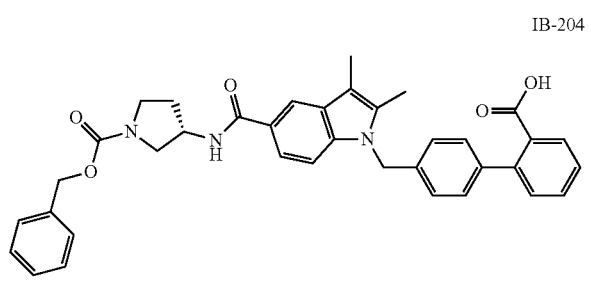
IB-205
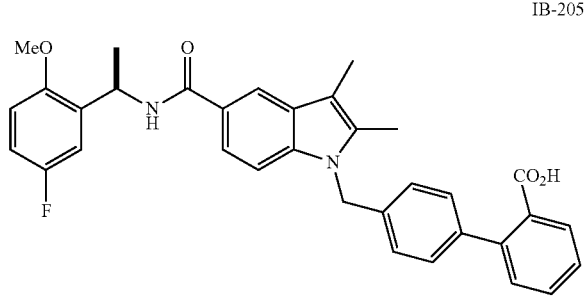
IB-206
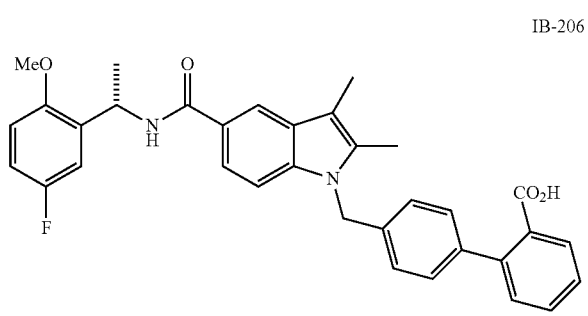
IB-207
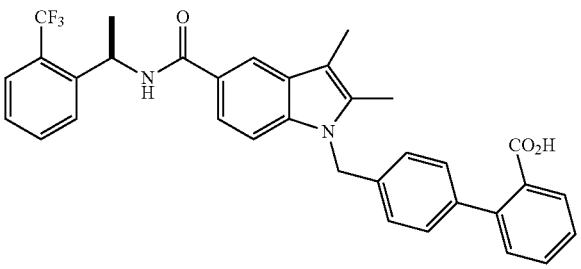
IB-208
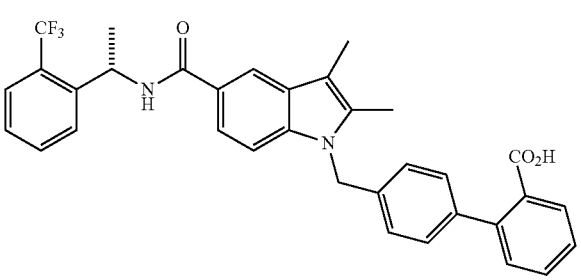
IB-209
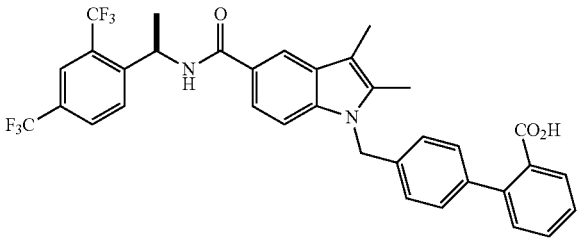
IB-210
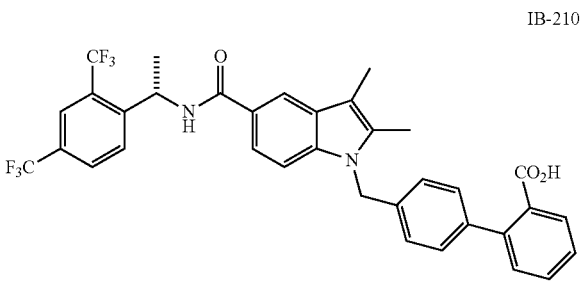
IB-211
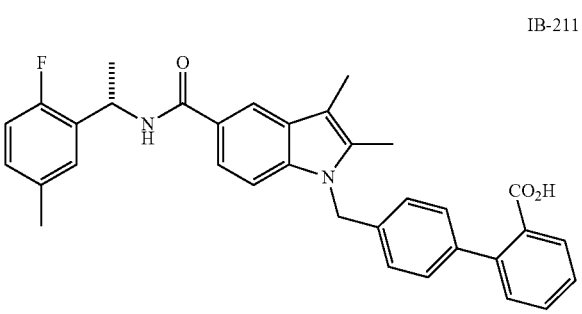

IB-212
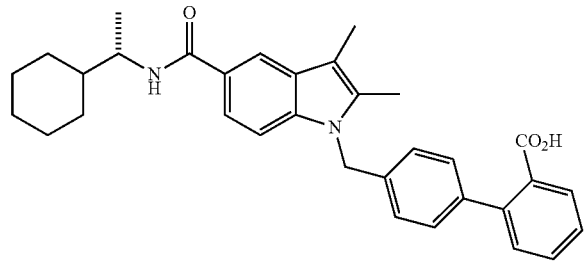
IB-213
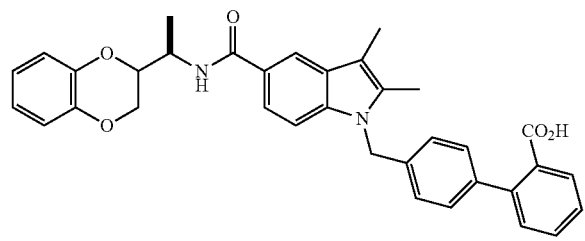
IB-214
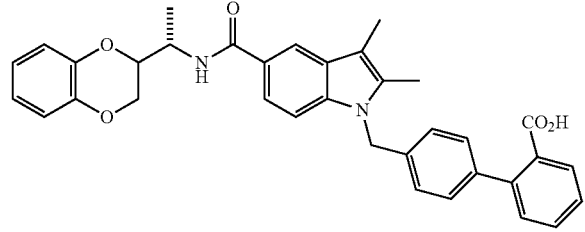
IB-215
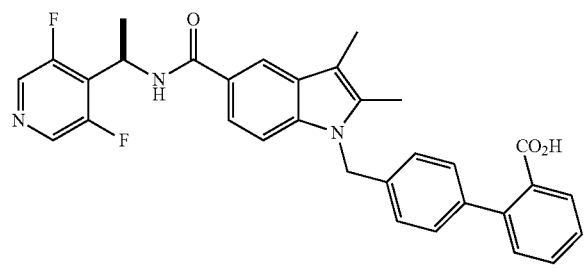
IB-216
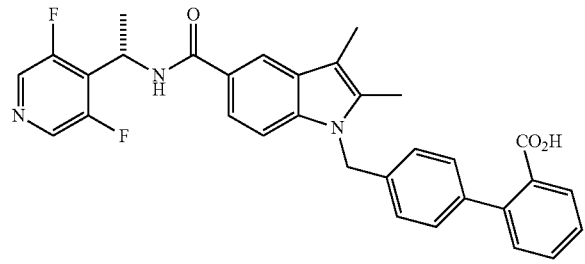
IB-217
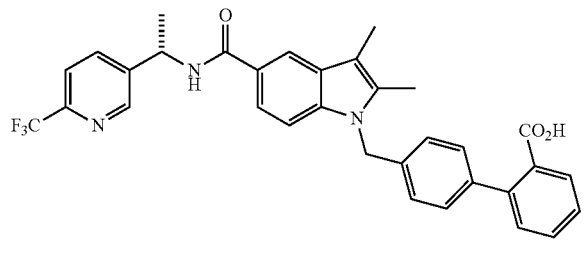
IB-218
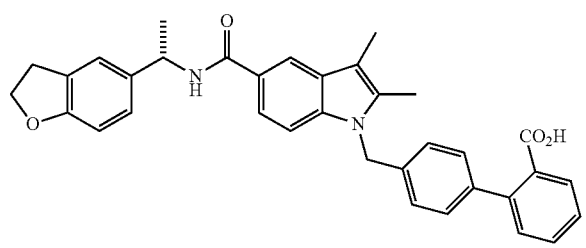
IB-219
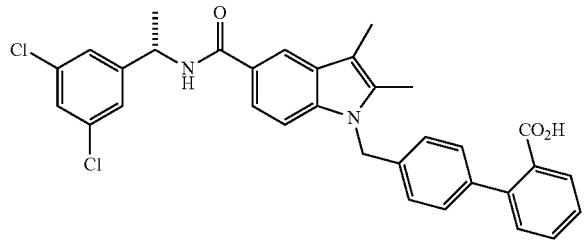
IB-220
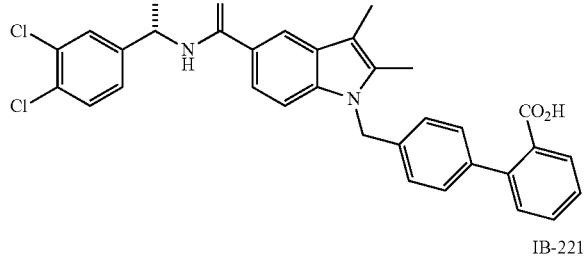
IB-221
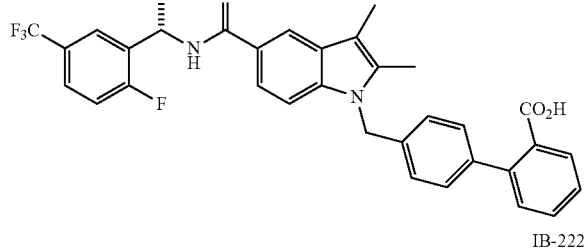
IB-222
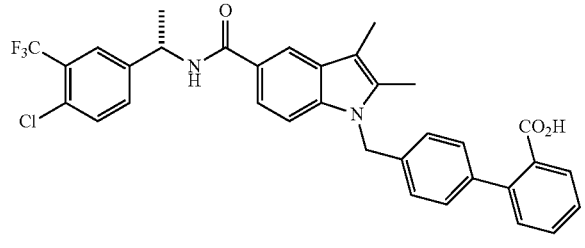

IB-223
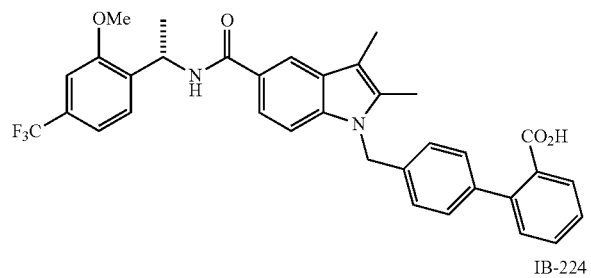
IB-224

IB-225
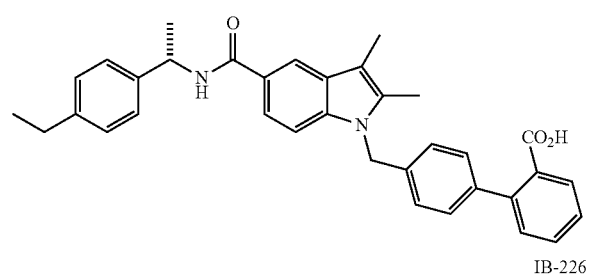
IB-226

IB-227
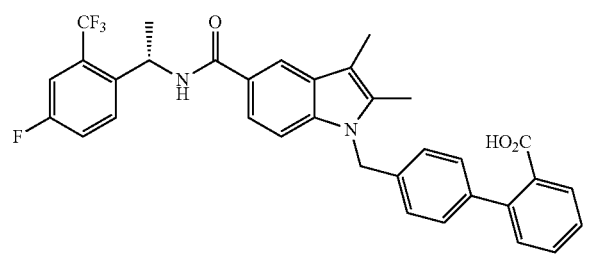
IB-228
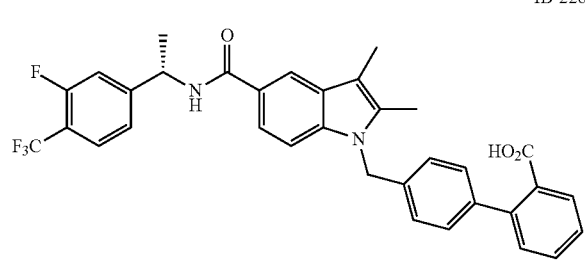
IB-229
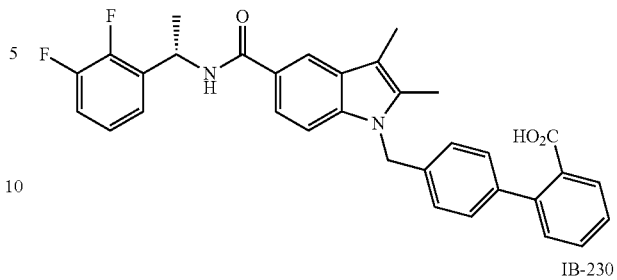
IB-230
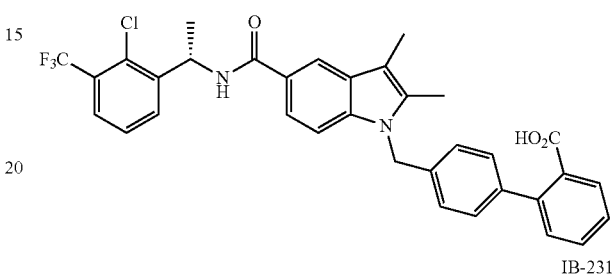
IB-231

IB-232
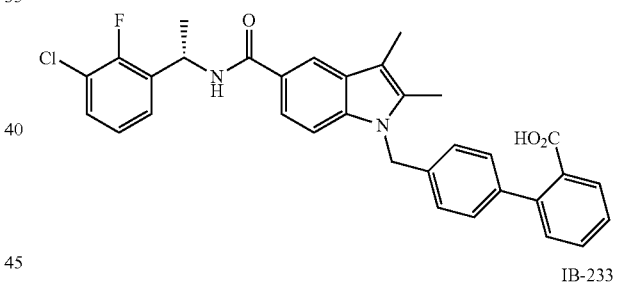
IB-233
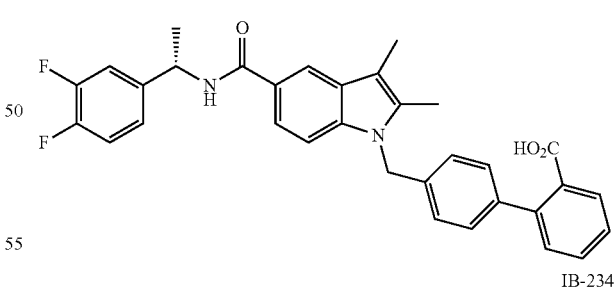
IB-234
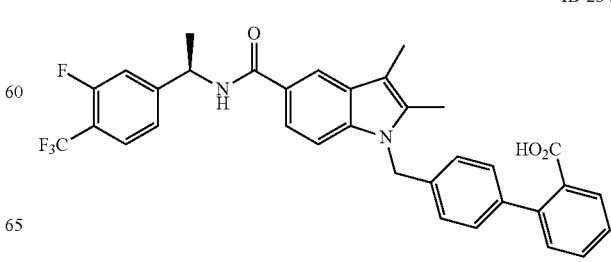

IB-235
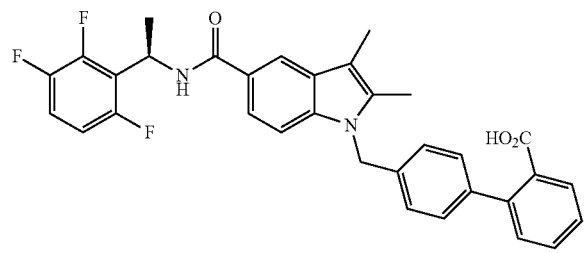
IB-240
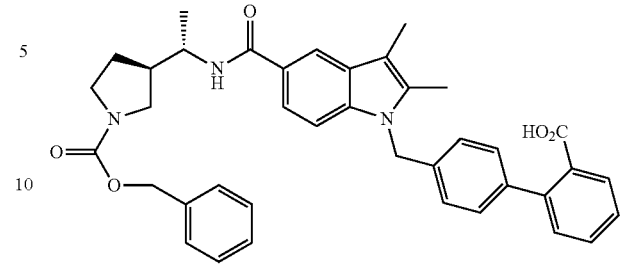
IB-236
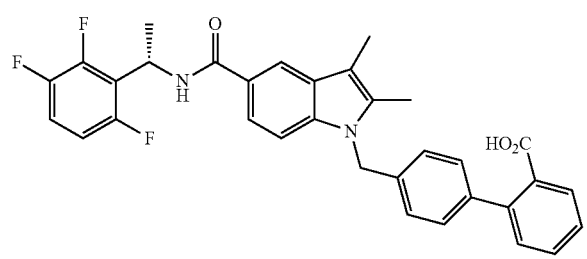
IB-241
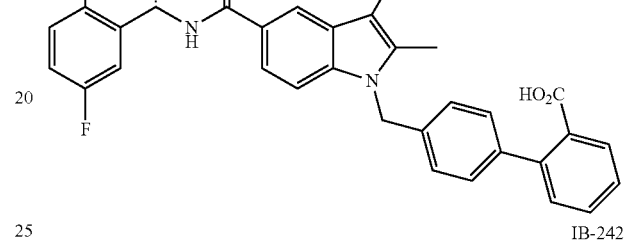
IB-237
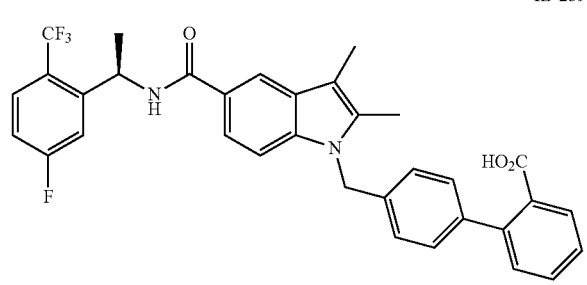
IB-242

IB-238
IB-243

IB-239
IB-244
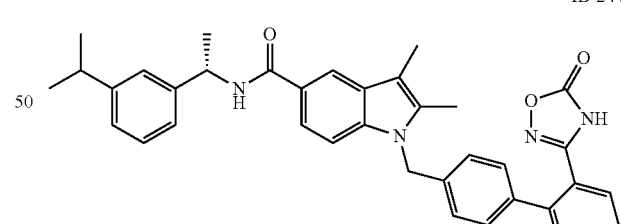
IB-245
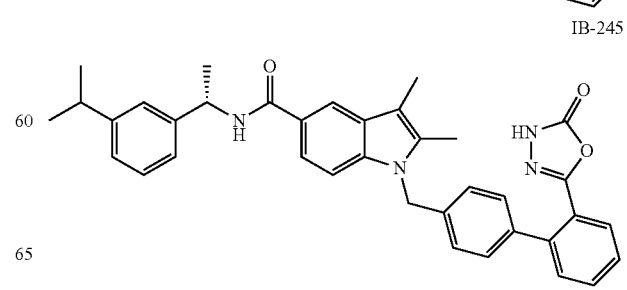

IB-246
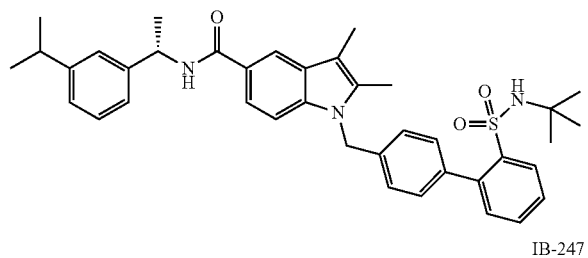
IB-247
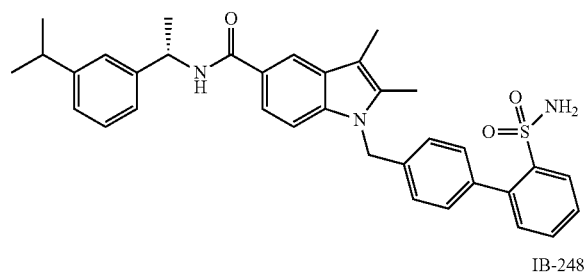
IB-248

IB-249
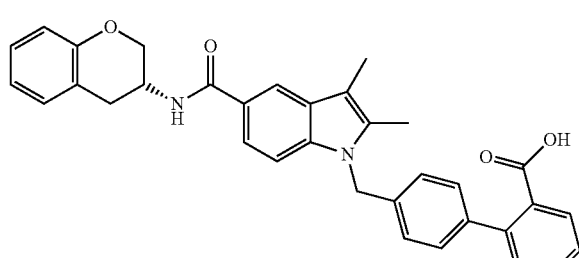
IB-250
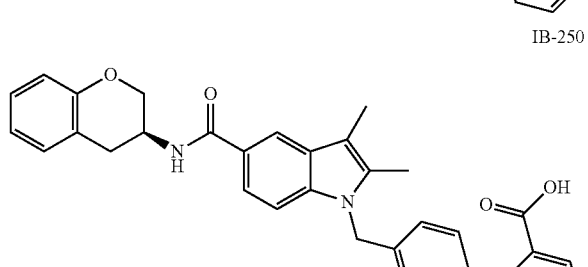
IB-251
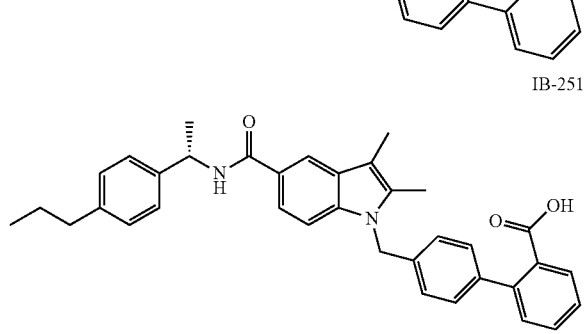
IB-252
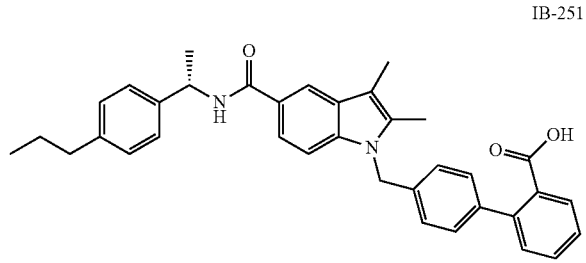
IB-253

IB-254
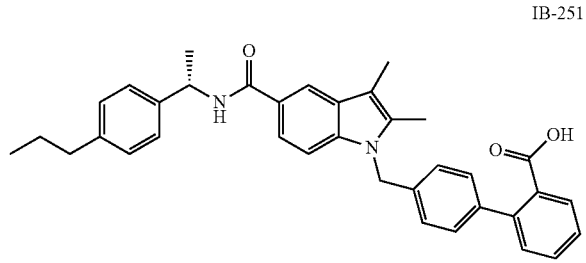
IB-255
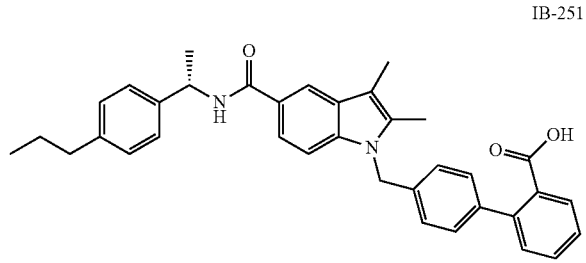
IB-256
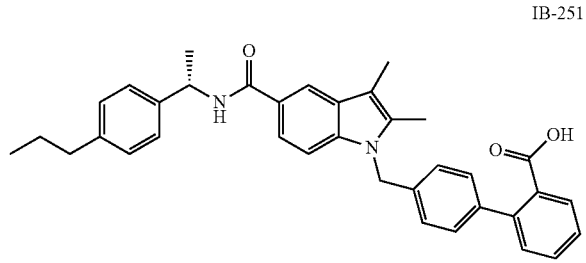

IB-257
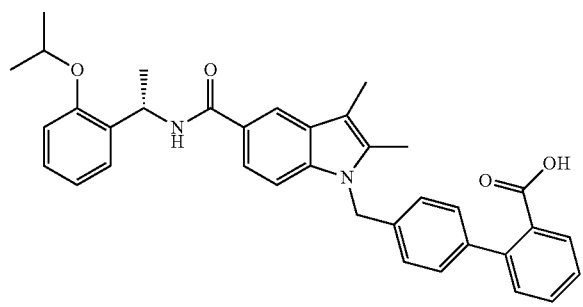
IB-262
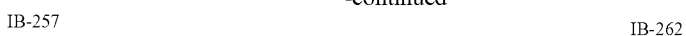
IB-258
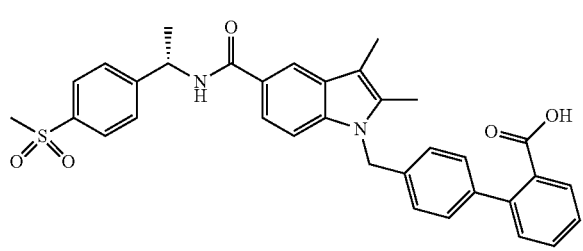
IB-263
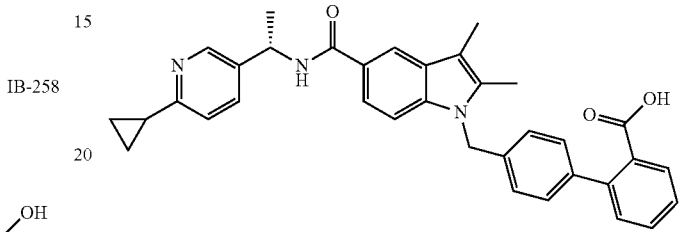
IB-259
IB-264
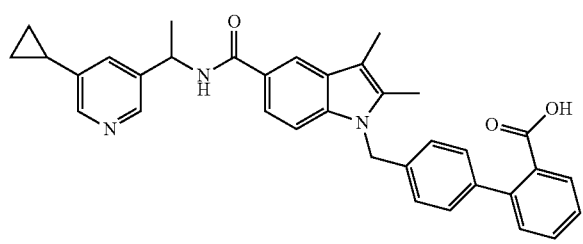
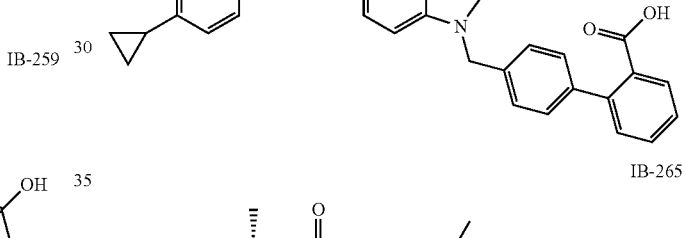
IB-260
IB-265
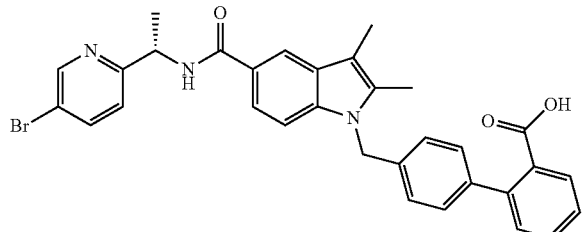
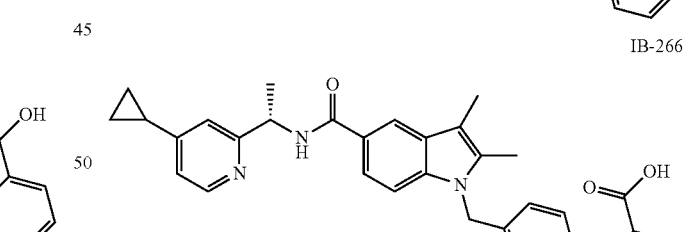
IB-261
IB-266
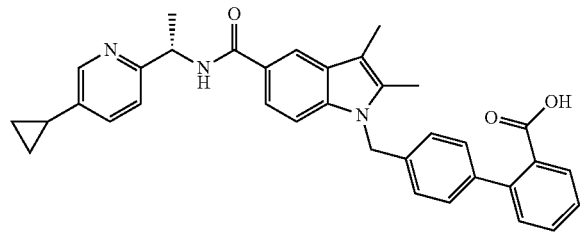
IB-267
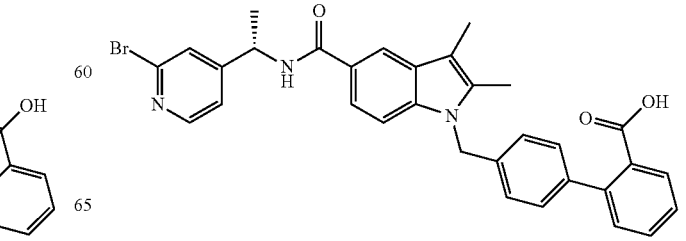

IB-268
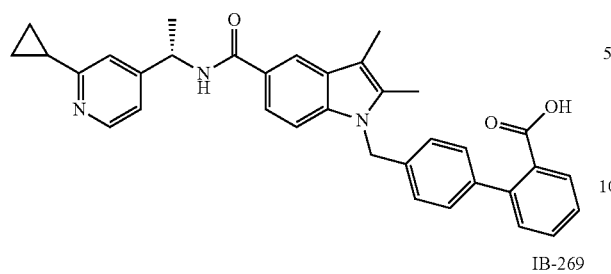
IB-269
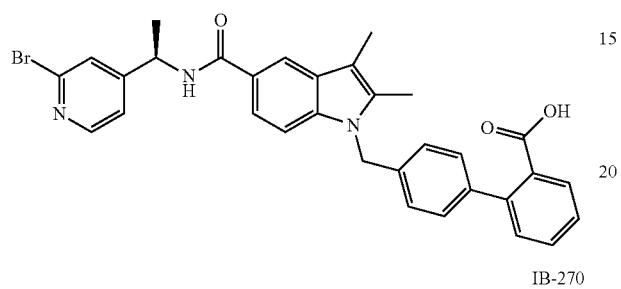
IB-270
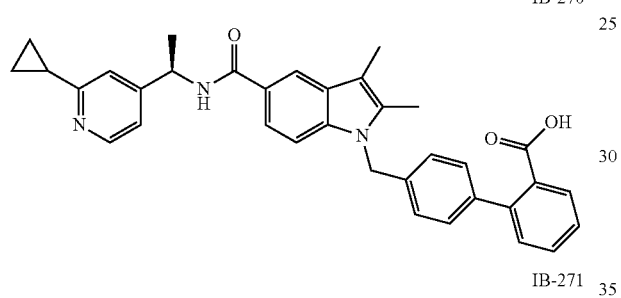
IB-271

IB-272
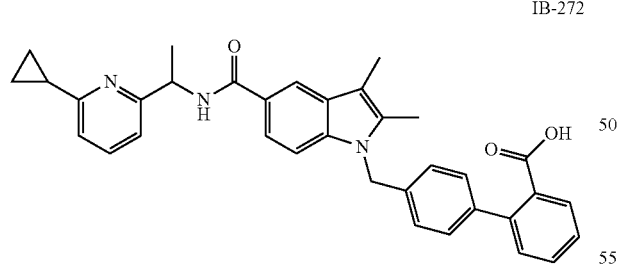
IB-273
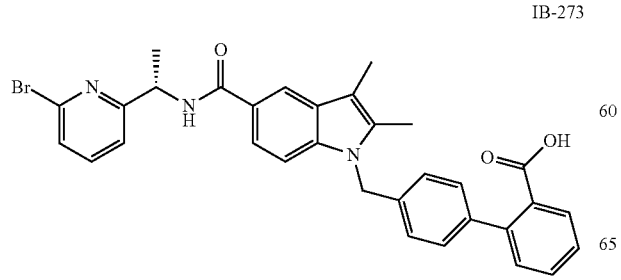
IB-274
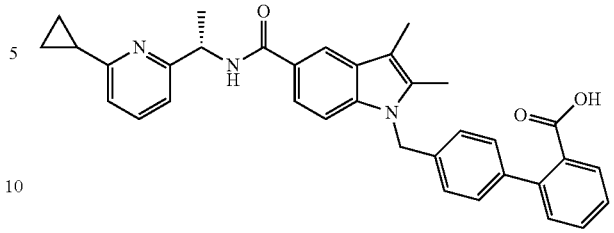
IB-275
IB-276
IB-277
IB-278
IB-279

IB-280
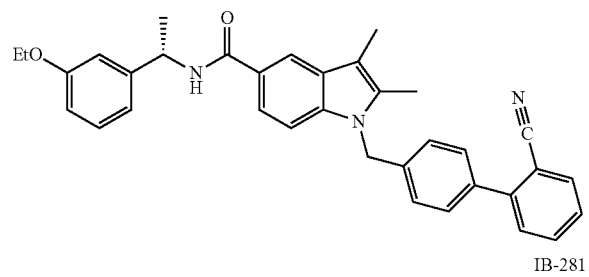
IB-281
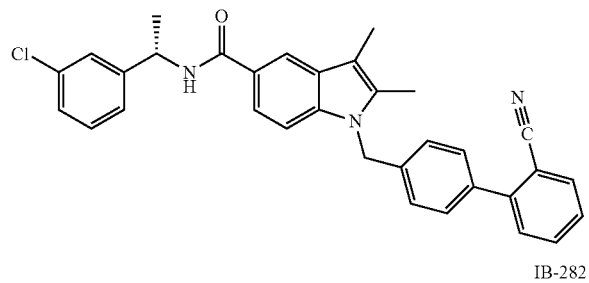
IB-282
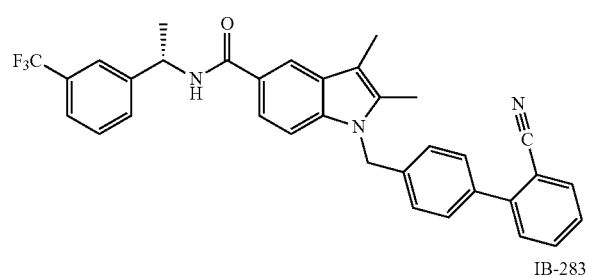
IB-283
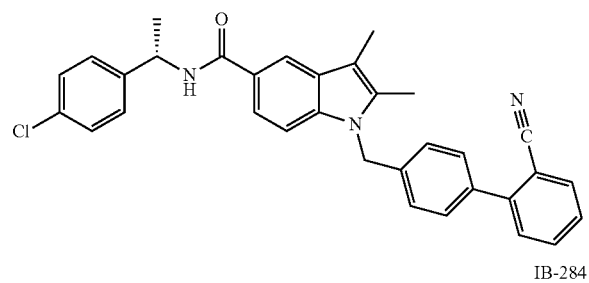
IB-284

IB-285
IB-286
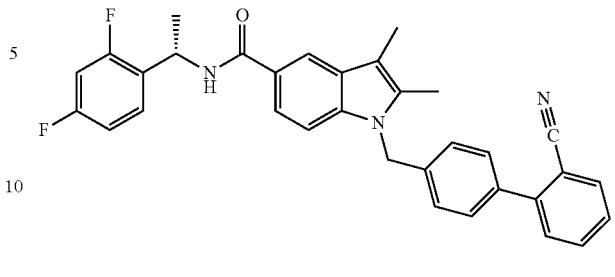
IB-287

IB-288
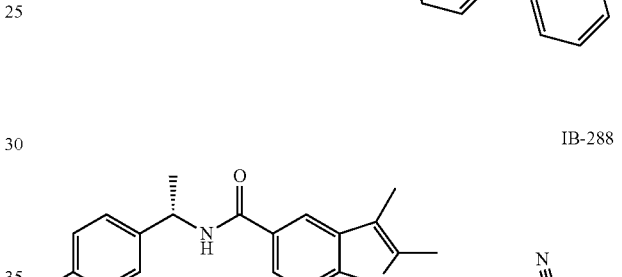
IB-289
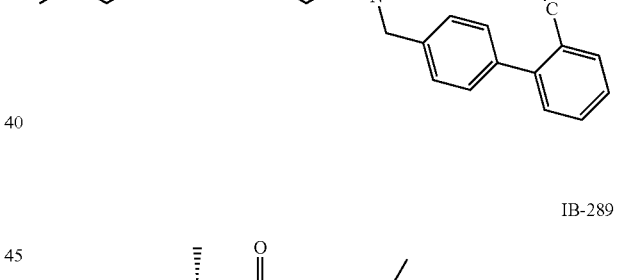
IB-290

IB-291
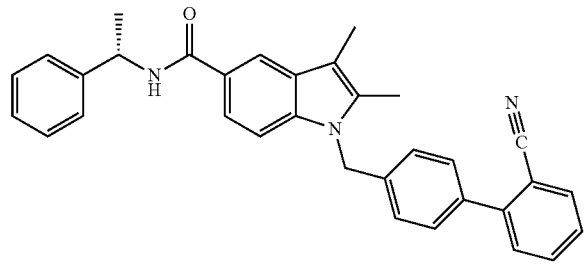
IB-297
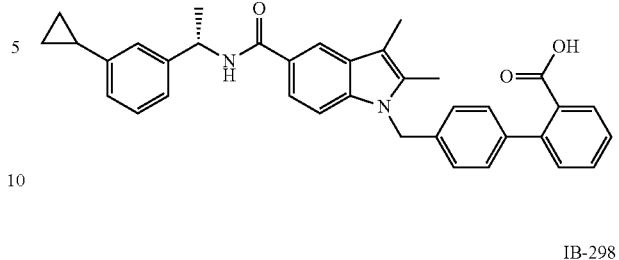
IB-292
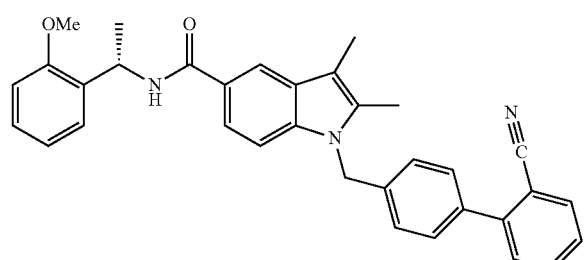
IB-298
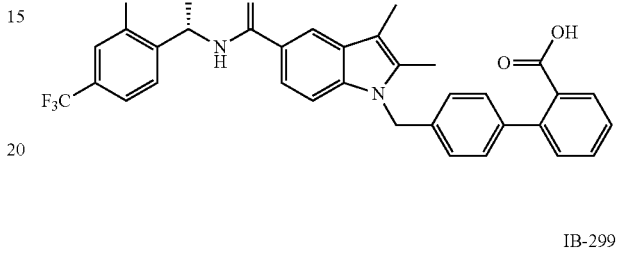
IB-293
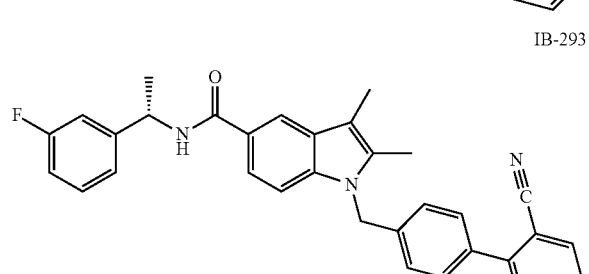
IB-299
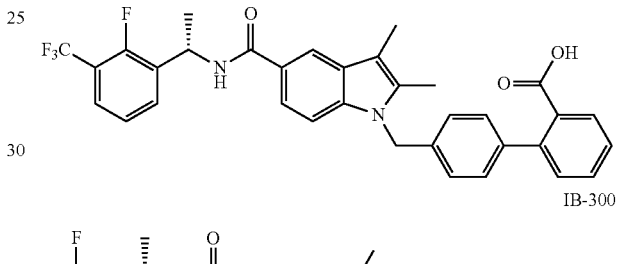
IB-294
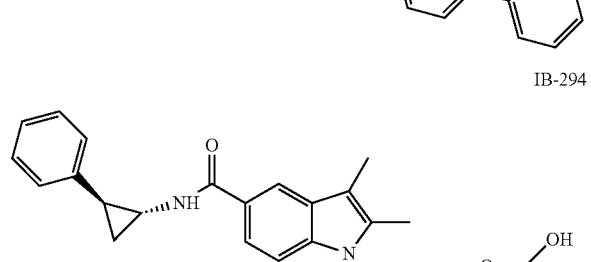
IB-300
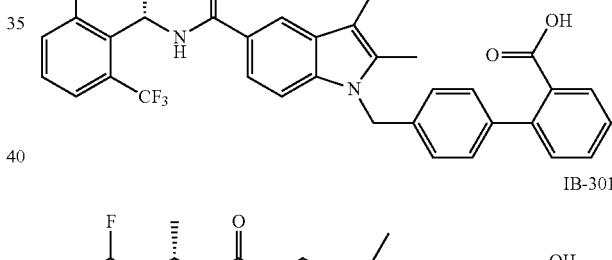
IB-295
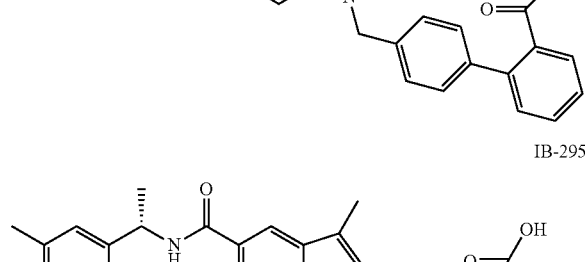
IB-301
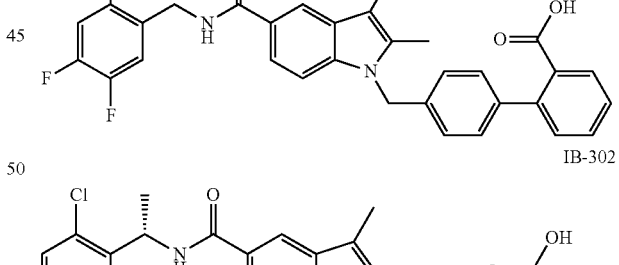
IB-296
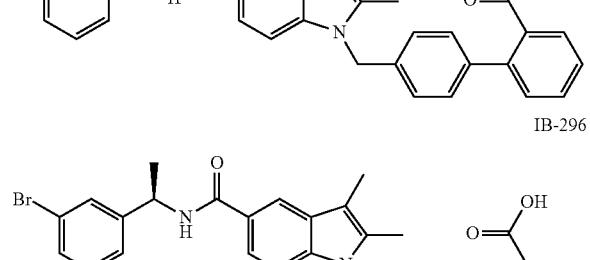
IB-302
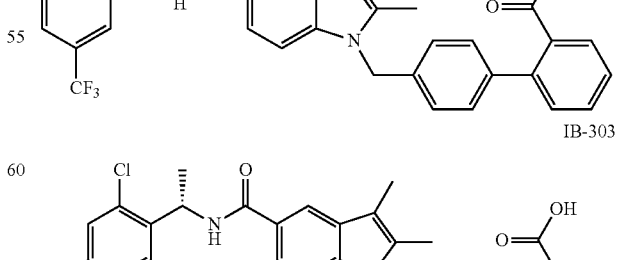
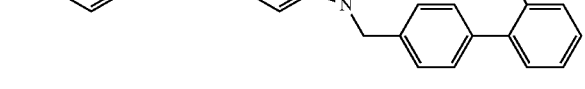
IB-303
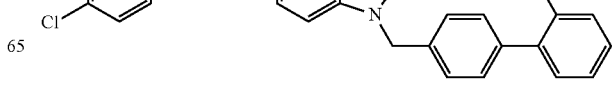

IB-304
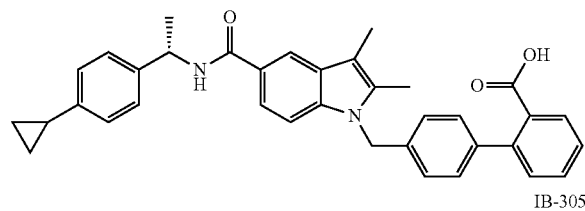
IB-305
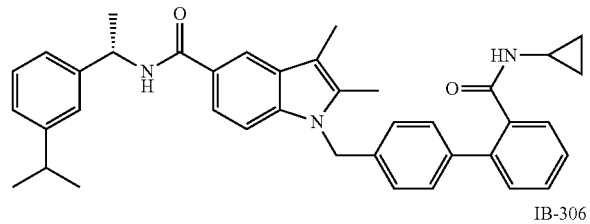
IB-306
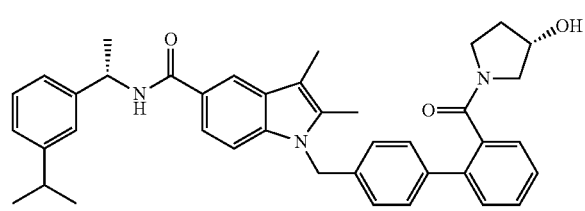
IB-307
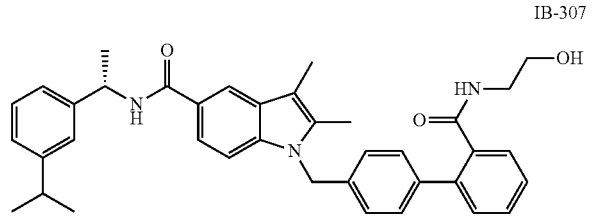
IB-308
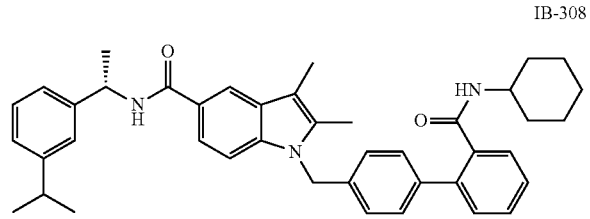
IB-309

IB-310
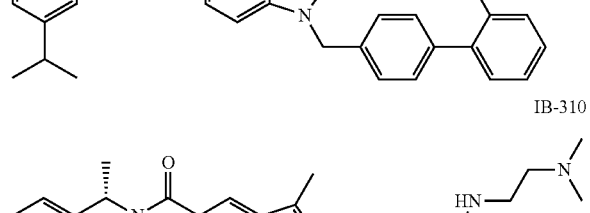
IB-311
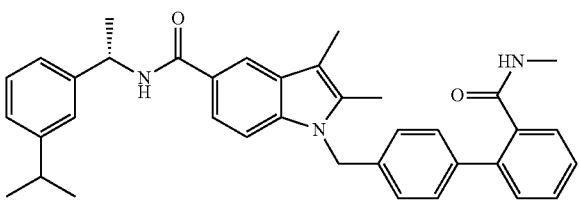
IB-312
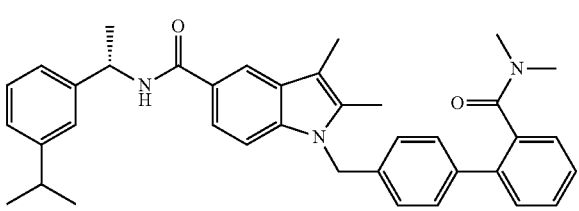
IB-313
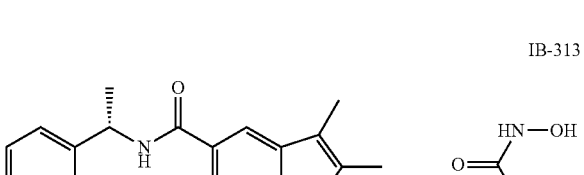
IB-314
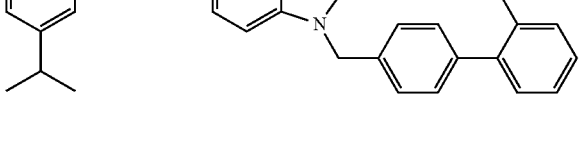
IB-315
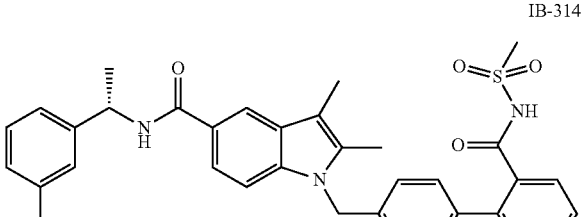
IB-316
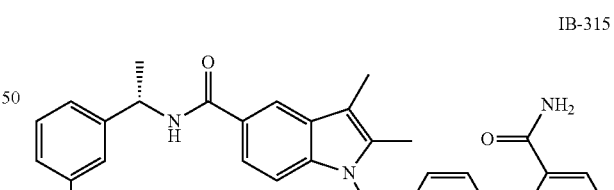
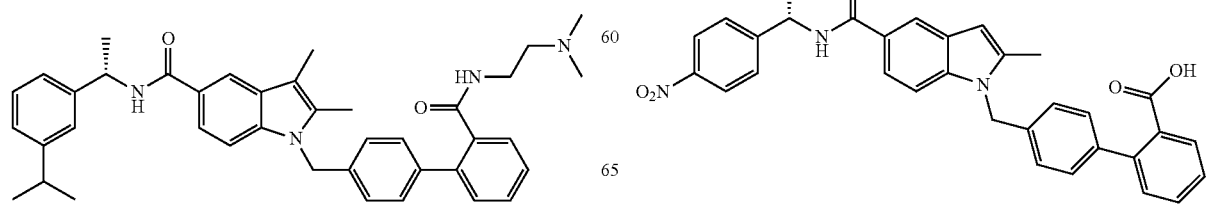

IB-317
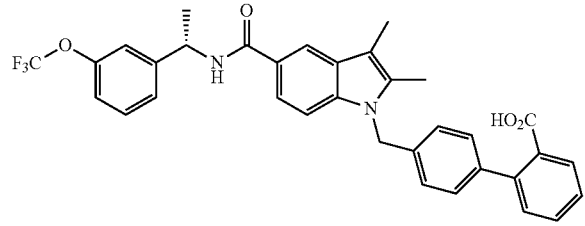
IB-322
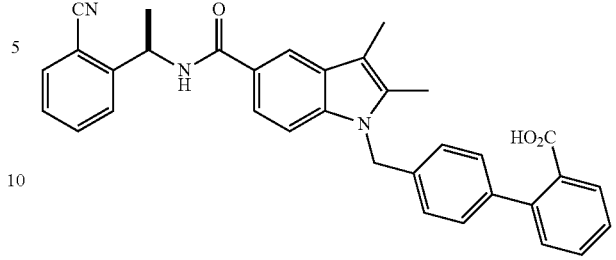
IB-318
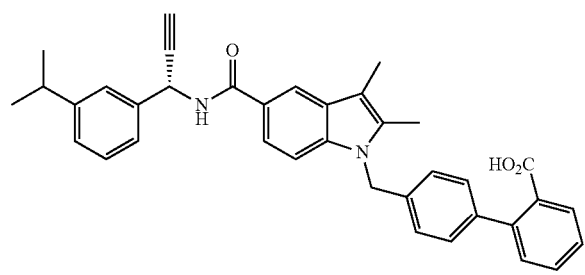
IB-323
IB-319
IB-324
IB-320
IB-325
IB-321
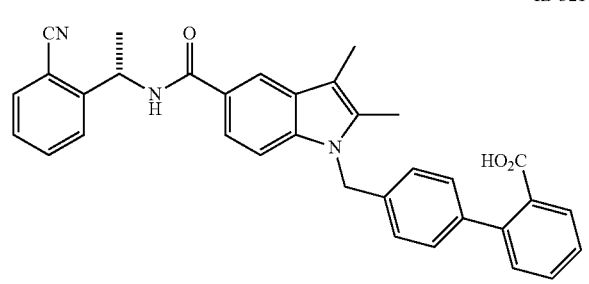
IB-326

IB-327
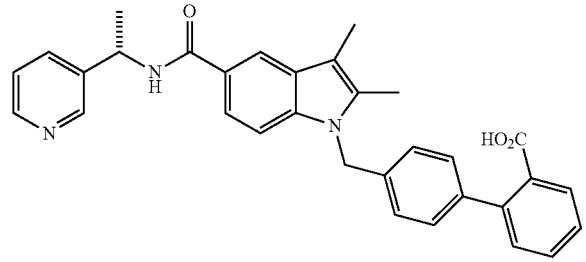
IB-328
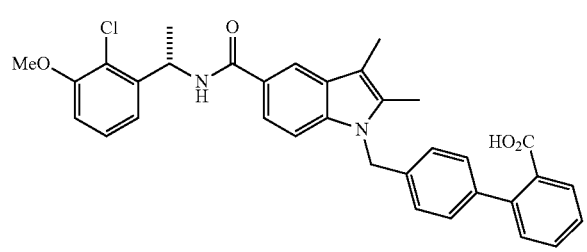
IB-329
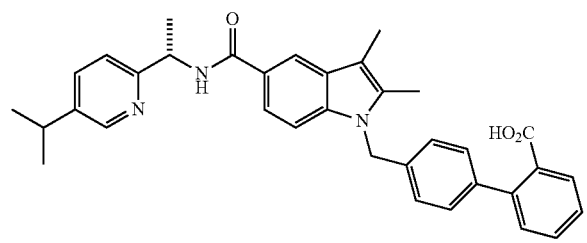
IB-330
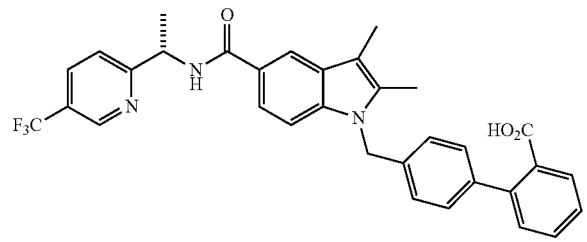
IB-331
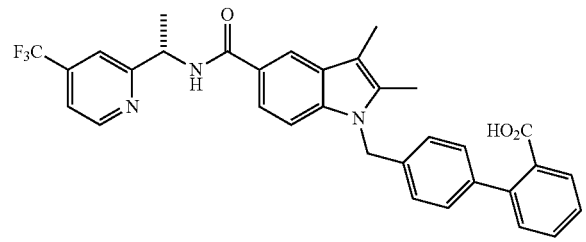
IB-332
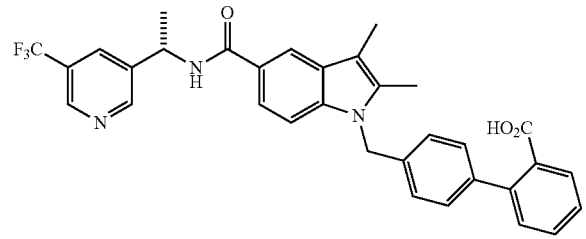
IB-333
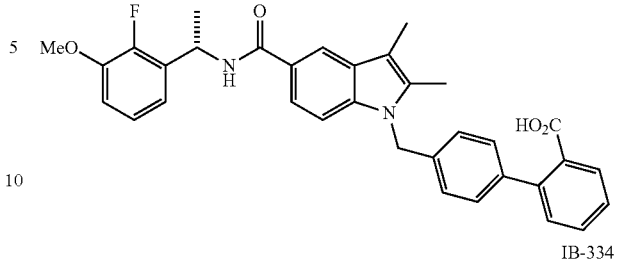
IB-334
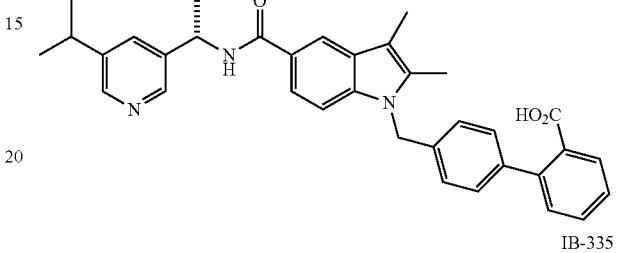
IB-335
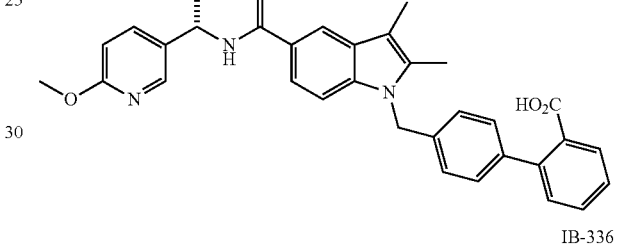
IB-336
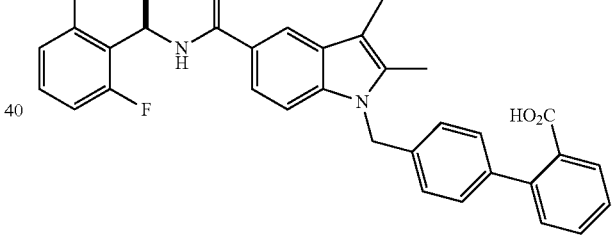
IB-337
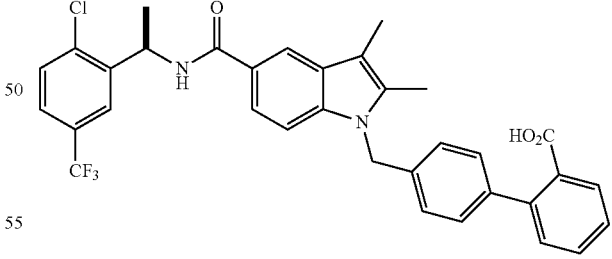
IB-338
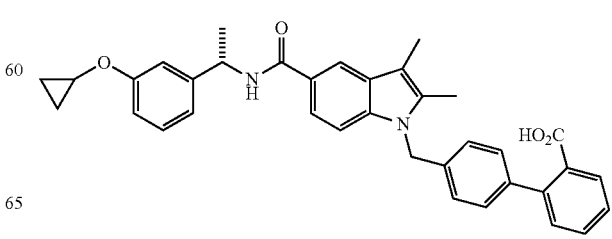

IB-339
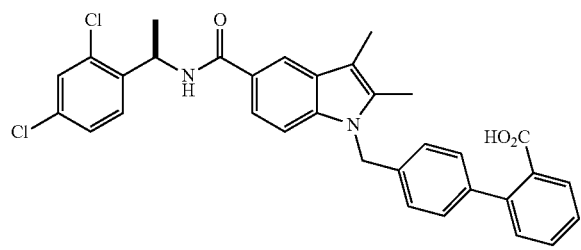
IB-340
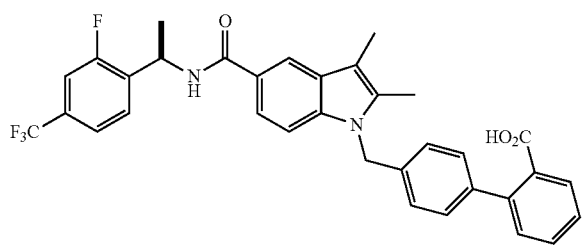
IB-341
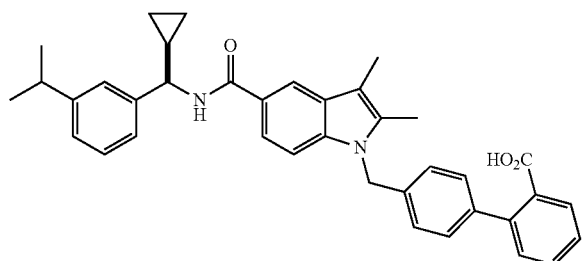
IB-342
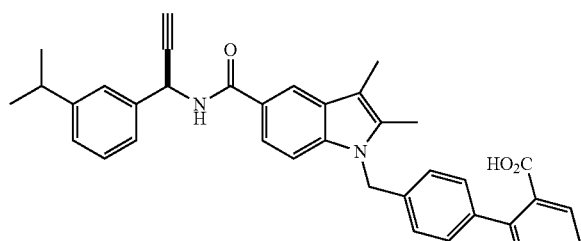
IB-343
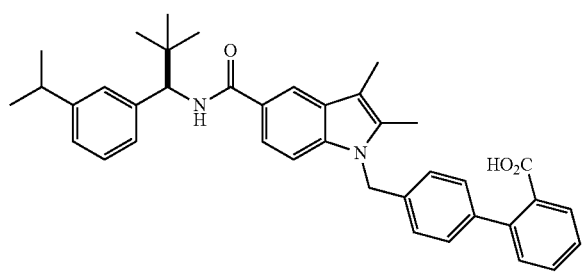
IB-344
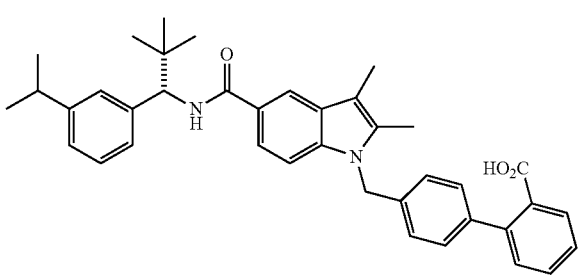
IB-345
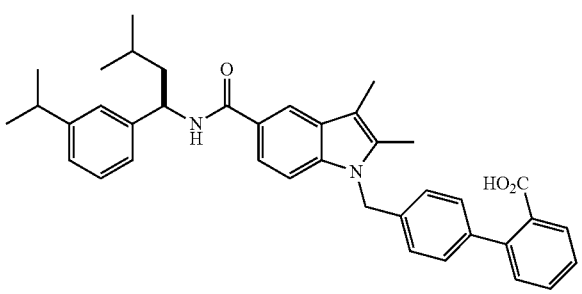
IB-346
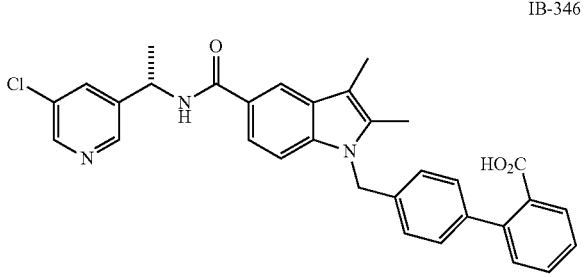
IB-347
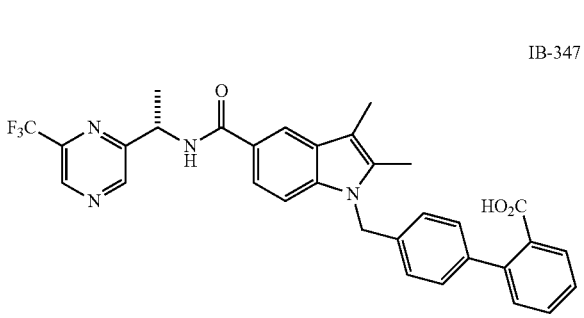
IB-348
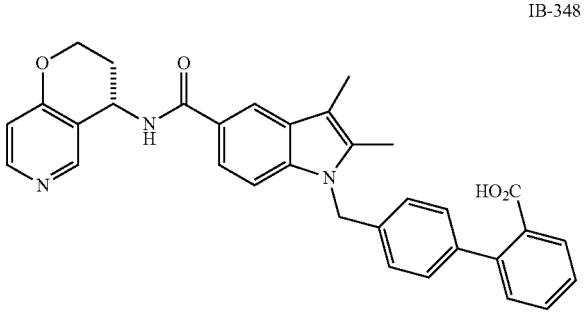

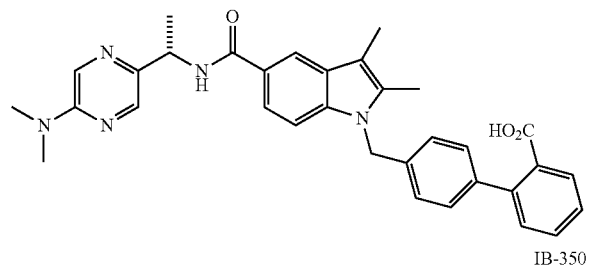
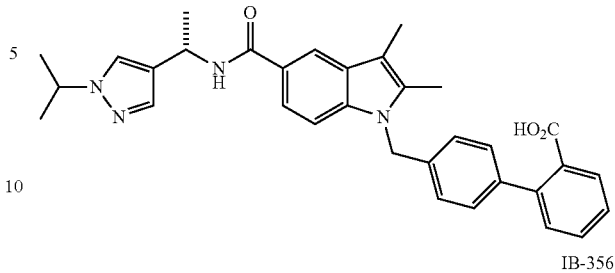
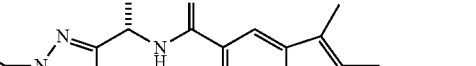
or a pharmaceutically acceptable salt thereof.

The invention provides, in various embodiments, methods of treatment of a progressive bone disease, wherein the progressive bone disease is osteoporosis, Paget's Disease, multiple myeloma, or hyperparathyroidism. For instance, administration of the compound of formula (I) acts to increase FGF21 while increasing bone health.

In various embodiments, the invention provides the use of a compound of formula (I) for treatment of a progressive bone disease, wherein the compound of formula (I) is

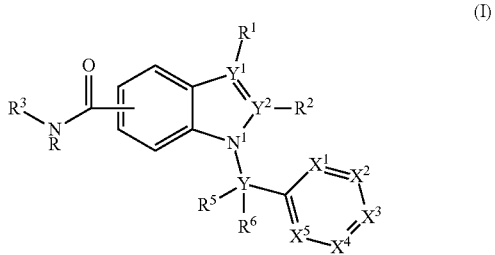

wherein:

R is H, $(C_1-C_6)$alkyl, $(C_3-C_9)$cycloalkyl, or $(C_3-C_9)$cycloalkyl$(C_1-C_6)$alkyl;

$Y^1$ or $Y^2$ are each independently C or N, provided that when $Y^1$ or $Y^2$ is N, $R^1$ or $R^2$, respectively, is absent;

$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or multi-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, oxo, $(C_1-C_6)$haloalkyl, nitro, cyano-$(C_0-C_6)$alkyl, R'O$_2$C—$(C_0-C_6)$alkyl, methylenedioxy, R'O—$(C_0-C_6)$alkyl, (R')$_2$N—$(C_0-C_6)$alkyl, (R')$_2$NC(=O)—$(C_0-C_6)$alkyl, R'C(=O)N(R')—$(C_0-C_6)$alkyl, $(C_1-C_6)$alkyl-S(O)$_q$$(C_0-C_6)$alkyl, aryl, aroyl, or SO$_2$NR'2;

$R^3$ is optionally mono- or multi-substituted $(C_1-C_6)$alkyl, $(C_1-C_6)$alkenyl, $(C_1-C_6)$alkynyl, $(C_6-C_{10})$aryl, $(C_6-C_{10})$aryl$(C_1-C_6)$alkyl, (3-9 membered)heterocyclyl, (3-9 membered)heterocyclyl$(C_1-C_6)$alkyl, (3-9 membered)heteroaryl, or (3-9 membered)heteroaryl$(C_1-C_6)$alkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, oxo, haloalkyl, haloalkoxy, nitro, cyano, CO$_2$R', methylenedioxy, OR', N(R')$_2$, C(O)N(R')$_2$, $(C_1-C_6)$alkyl-S(O)$_q$, SO$_2$NR'2, and $(C_1-C_6)$alkoxyl; and provided that group $R^3$N(R')C(=O)— can be bonded to any one of the four carbon atoms of the phenyl ring not bonded to $N^1$ or $Y^1$;

wherein each R' is independently H, $(C_1-C_6)$ alkyl, $(C_3-C_9)$cycloalkyl, $(C_3-C_9)$cycloalkyl$(C_1-C_6)$alkyl, $(C_6-C_{10})$ aryl, or $(C_6-C_{10})$aryl$(C_1-C_6)$ alkyl, or wherein two R' bonded to an atom together with the atom form a 3-9 membered ring optionally further comprising a heteroatom selected from the group consisting of O, NR', and S(O)$_q$;

wherein any alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, oxo, aryl, or aroyl;

each of $X^1$-$X^5$ is independently N or CH, or is C substituted with an independently selected $R^4$ or is C substituted with Z, provided that no more than two of $X^1$-$X^5$ are N, and provided that there is no more than one Z group bonded to the ring comprising $X^1$-$X^5$;

each $R^4$ is independently halo, nitro, $(C_1-C_6)$fluoroalkyl, R'—$(C_0-C_6)$alkyl, R'O$_2$C—$(C_0-C_6)$alkyl, NC—$(C_0-C_6)$alkyl, R'O—$(C_0-C_6)$alkyl, (R')$_2$N—$(C_0-C_6)$alkyl, (R')$_2$NC(=O)—$(C_0-C_6)$alkyl, R'C(=O)N(R')—$(C_0-C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1-C_6)$alkyl-S(O)$_q$$(C_0-C_6)$alkyl, R'S(O)$_2$NHC(O), R'C(O)NHS(O)$_2$, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with R', OR', N(R')$_2$, C-bonded tetrazolyl, $(C_1-C_6)$alkyl-S(O)$_q$$(C_0-C_6)$alkyl, an unsubstituted or substituted aryl, or an unsubstituted or substituted heteroaryl; or $R^4$ is —(C(R")$_2$)$_m$CO$_2$R', —(C(R")$_2$)$_m$CON(R')$_2$, —(C(R")$_2$)$_m$CN, —O(C(R")$_2$)$_m$CO$_2$R', —O(C(R")$_2$)$_m$CON(R')$_2$, or —O(C(R")$_2$)$_m$CN, wherein m is 1, 2, or 3;

R" is H, halo, $(C_1-C_6)$ alkyl, $(C_1-C_6)$ haloalkyl, $(C_3-C_9)$cycloalkyl, $(C_3-C_9)$cycloalkyl$(C_1-C_6)$alkyl, $(C_6-C_{10})$aryl, or $(C_6-C_{10})$aryl$(C_1-C_6)$ alkyl, or two R" together with an atom to which they are bonded form a 3- to 9-membered ring;

Z is a group of formula

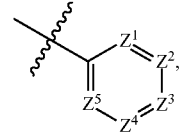

wherein a wavy line indicates a point of bonding, each of $Z^1$-$Z^5$ is independently N or is C substituted with an independently selected H or $R^4$; provided that no more than two of $Z^1$-$Z^5$ are N;

Y is $(C_1-C_2)$alkyl, or sulfur;

when Y is $(C_1-C_2)$alkyl, $R^5$ and $R^6$ are independently H or $(C_1-C_4)$alkyl or independently each $R^5$ and $R^6$ together with the carbon atom to which they are bonded form a carbonyl, or, one $R^5$ group can further be bonded to $X^5$ to form a 4- to 8-membered ring; and, when Y is sulfur, $R^5$ and $R^6$ are both oxygen;

or a pharmaceutically acceptable salt thereof;

wherein the effective dose of the compound acts to inhibit bone resorption, improve bone formation, or both, in the patient.

For instance, the progressive bone disease can be osteoporosis, Paget's Disease, multiple myeloma, or hyperparathyroidism. For instance, administration of the compound of formula (I) acts to increase FGF21 while increasing bone health.

In various embodiments, the invention provides a compound of formula

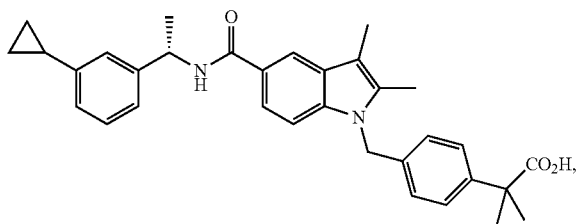

IA-176 (SR11023)

or a pharmaceutically acceptable salt thereof.

The invention provides a method for practice of the invention wherein the compound of formula (I) is

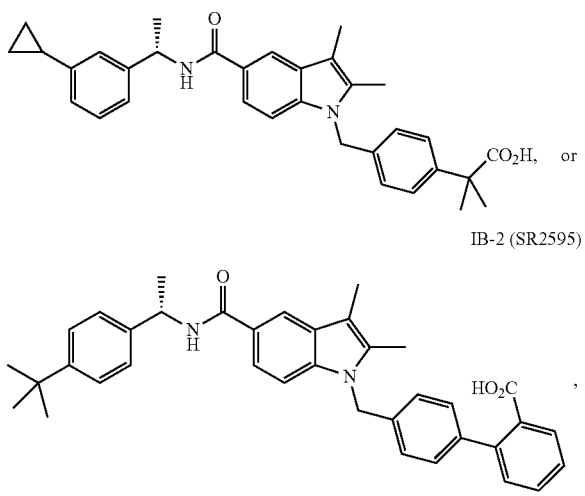

IA-176 (SR11023)

IB-2 (SR2595)

or a pharmaceutically acceptable salt thereof.

The invention provides a use of a compound of formula (I), wherein the compound is

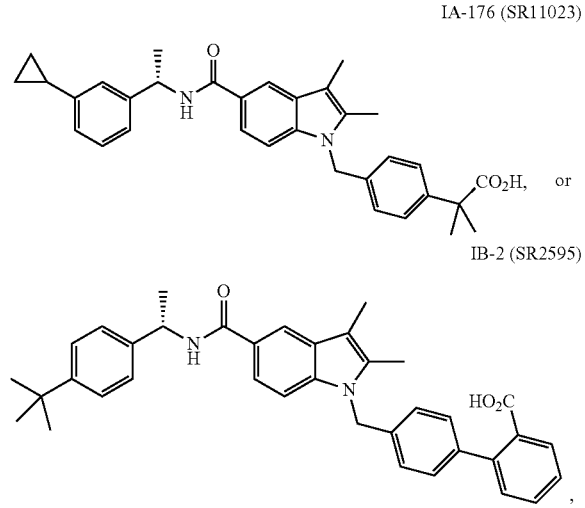 [SMILES: Cc1c(C)n(Cc2ccc(C(C)(C)C(=O)O)cc2)c2ccc(C(=O)N[C@@H](C)c3cccc(C4CC4)c3)cc12 ; "or" ; Cc1c(C)n(Cc2ccc(-c3ccccc3C(=O)O)cc2)c2ccc(C(=O)N[C@@H](C)c3ccc(C(C)(C)C)cc3)cc12 ; ","]

IA-176 (SR11023)

IB-2 (SR2595)

or a pharmaceutically acceptable salt thereof, for treatment of a progressive bone disease, for instance, for treatment of osteoporosis, Paget's Disease, multiple myeloma, or hyperparathyroidism.

EXAMPLES

Synthetic Methods
The following abbreviations are used throughout this document.
BOP Benzotriazol-1-yl-oxy-tris-(dimethylamino)phosphonium hexafluorophosphate
CDI Carbonyl diimidazole
DBU Diazabicycloundecane
DCM Dichloromethane
DIPEA, $^iPr_2EtN$ N,N-Diisopropylethylamine
DMAP 4-(N,N-dimethylamino)pyridine
DMF N,N-Dimethylformamide
DMSO Dimethylsulfoxide
EDAC 1-Ethyl-3-(3-dimethylaminopropyl)carbodiimide hydrochloride
eq Equivalents
$Et_2O$ Diethyl ether
EtOAc Ethyl acetate
h Hours
HATU O-(7-Azabenzotriazole-1-yl)-N, N,N'N'-tetramethyluronium hexafluorophosphate
HCl Hydrochloric acid
HOAT Hydroxyazabenztriazole
HOBT Hydroxybenzotriazole
LiHDMS Lithium hexamethyldisilazide
LiOH Lithium hydroxide
mg Milligrams
min Minutes
mL Milliliters
μL Microliters
mmole Millimoles
MS Mass spectroscopy
MeOH Methanol
$NaBH_3CN$ Sodium cyanoborohydride
NaH Sodium hydride
$NaIO_4$ Sodium periodate
NMM N-Methylmorpholine
rb Round-bottom
RT, rt Room temperature
sat. Saturated
TEA Triethylamine
TFA Trifluoroacetic acid
THF Tetrahydrofuran

SYNTHETIC EXAMPLES

Compounds of Formula (IA)

Example 1: 1-(2,4-Difluorobenzyl)-N-(2,4-dimethoxybenzyl)-1H-indole-5-carboxamide

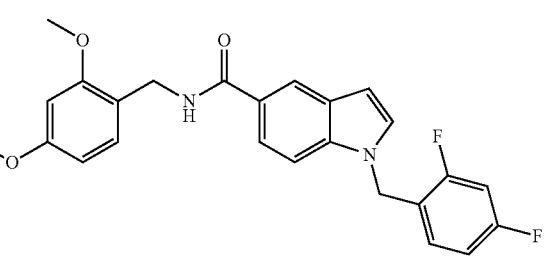

Step 1: Methyl 1H-indole-5-carboxylate

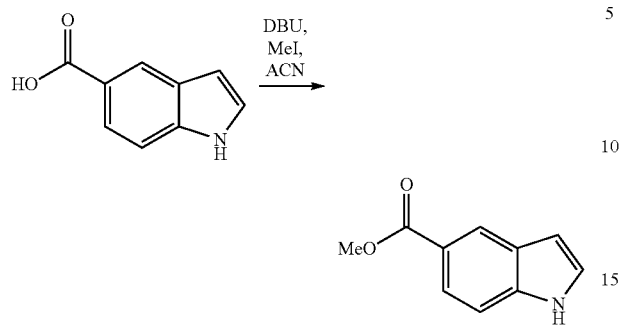

To a solution of 1H-indole-5-carboxylic acid (1 g, 6.2 mmol, 1.0 equiv) in acetonitrile (40 mL) were added 1,8-Diazabicyclo[5.4.0]undec-7-ene (1.1 mL, 7.4 mmol, 1.2 equiv) and iodomethane (2.3 mL, 37.2 mmol, 6 equiv). The solution was stirred under reflux overnight. The reaction mixture was concentrated in vacuo. The residue was dissolved in AcOEt, washed with a 0.5 N HCl aqueous solution, a saturated NaHCO₃ solution and brine, dried over MgSO₄ and concentrated in vacuo. The obtained oil was used in the next step without further purification.

Step 2: Methyl 1-(2,4-difluorobenzyl)-1H-indole-5-carboxylate

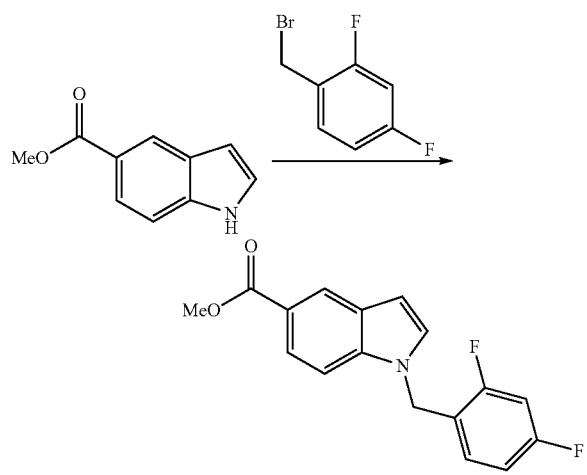

To a solution of methyl 1H-indole-5-carboxylate (2 g, 11.4 mmol, 1 equiv) and 1-(bromomethyl)-2,4-difluorobenzene (1.61 mL, 12.6 mmol, 1.1 equiv) in anhydrous DMF (50 mL) under argon atmosphere was added sodium hydride (913 mg, 22.8 mmol, 2 equiv) in small portions. The mixture was stirred 2 h at room temperature. The reaction mixture was then neutralized by addition of methanol and concentrated in vacuo. The residue was dissolved in AcOEt, washed with brine and dried over MgSO₄. The crude was purified by flash chromatography (Hexane/AcOEt 7/3) to afford the title compound as a colorless oil (3.14 g, 10.4 mmol, 91%). ESI-MS (m/z): 302 [M+H]$^+$.

Step 3: 1-(2,4-Difluorobenzyl)-1H-indole-5-carboxylic acid

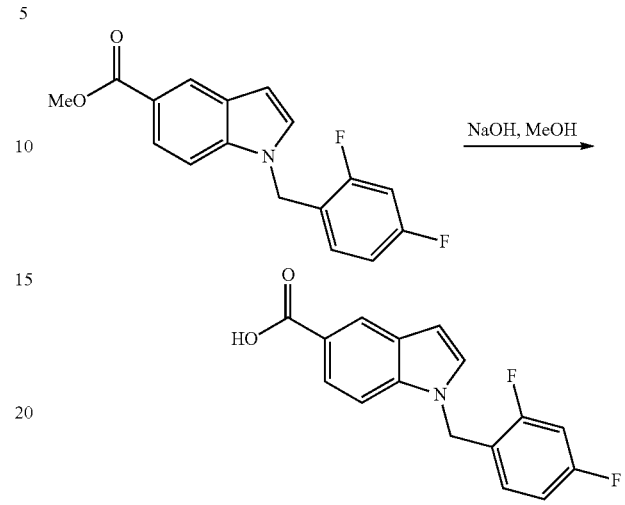

To a solution of methyl 1-(2,4-difluorobenzyl)-1H-indole-5-carboxylate (3.14 g, 10.4 mmol, 1 equiv) in methanol (50 mL) was added a 5 N NaOH solution (50 mL, 104 mmol, 10 equiv). The reaction mixture was stirred 2 h at 40° C. The mixture was then acidified and extracted with DCM. After concentration in vacuo, the title compound was precipitated in Et₂O to afford a white powder (2.82 g, 9.8 mmol, 96%). ESI-MS (m/z): 288 [M+H]$^+$.

Step 4: 1-(2,4-Difluorobenzyl)-N-(2,4-dimethoxybenzyl)-1H-indole-5-carboxamide

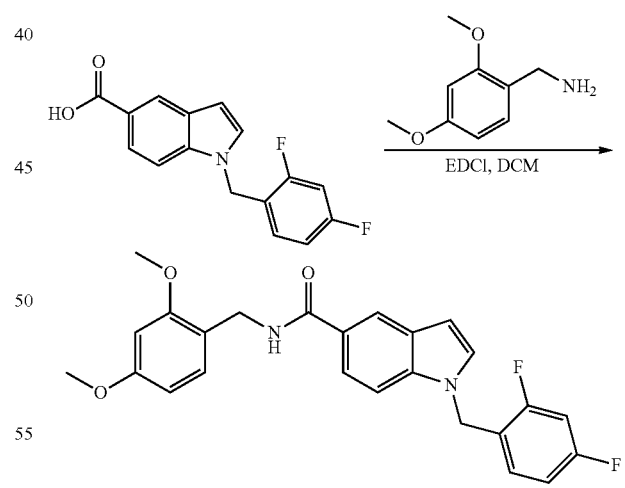

To a solution of 1-(2,4-difluorobenzyl)-1H-indole-5-carboxylic acid (50 mg, 0.17 mmol, 1 equiv) in DCM (2 mL) were added the (2,4-dimethoxyphenyl)methanamine (27 μL, 0.18 mmol, 1.05 equiv) and 1-Ethyl-3-(3-dimethylaminopropyl)carbodiimide (35 mg, 0.18 mmol, 1.05 equiv). The reaction mixture was stirred 2 h at room temperature. The solvent was removed in vacuo. The residue was dissolved in AcOEt and washed with a 0.5 N HCl aqueous solution, a saturated NaHCO₃ solution and brine, dried over MgSO₄ and concentrated in vacuo to afford a beige powder (56 mg, 0.13 mmol, 76%). ESI-MS (m/z): 437 [M+H]$^+$.

Example 2: 1-(2,4-Difluorobenzyl)-N-(3-(trifluoromethoxy)benzyl)-1H-indole-5-carboxamide

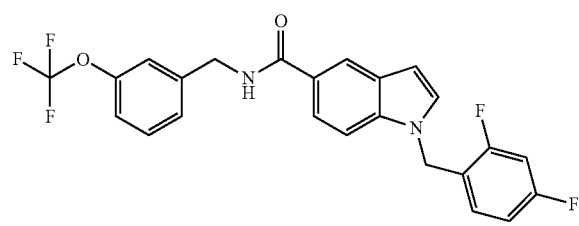 [SMILES: O=C(NCc1cccc(OC(F)(F)F)c1)c1ccc2c(ccn2Cc2ccc(F)cc2F)c1]

The title compound was prepared following the same general protocol as described in Step 4, Example 1, using (3-(trifluoromethoxy)phenyl)methanamine instead of the (2,4-dimethoxyphenyl)methanamine. A white powder was obtained (55 mg, 0.12 mmol, 70%). ESI-MS (m/z): 461 [M+H]$^+$.

Example 3: 1-(2,4-Difluorobenzyl)-N-(3,4-dimethoxybenzyl)-1H-indole-5-carboxamide

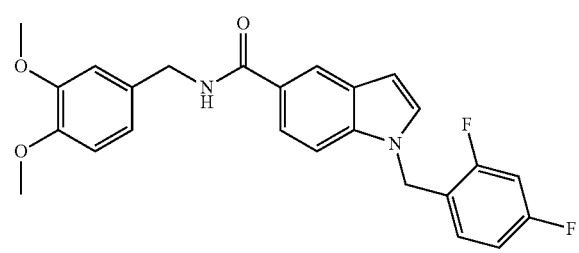 [SMILES: COc1ccc(CNC(=O)c2ccc3c(ccn3Cc3ccc(F)cc3F)c2)cc1OC]

The title compound was prepared following the same general protocol as described in Step 4, Example 1, using (3,4-dimethoxyphenyl)methanamine instead of the (2,4-dimethoxyphenyl)methanamine. A white powder was obtained (44 mg, 0.10 mmol, 59%). ESI-MS (m/z): 437 [M+H]$^+$.

Example 4: (S)-1-(2,4-Difluorobenzyl)-N-(1-(4-nitrophenyl)ethyl)-1H-indole-5-carboxamide

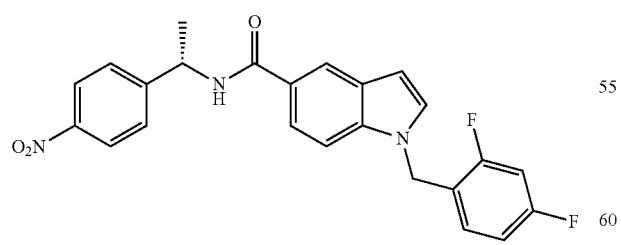

The title compound was prepared following the same general protocol as described in Step 4, Example 1, using (S)-1-(4-nitrophenyl)ethanamine instead of the (2,4-dimethoxyphenyl)methanamine. A beige powder was obtained (46 mg, 0.11 mmol, 62%). ESI-MS (m/z): 436 [M+H]$^+$.

Example 5: (S)—N-(1-(4-Bromophenyl)ethyl)-1-(2,4-difluorobenzyl)-1H-indole-5-carboxamide

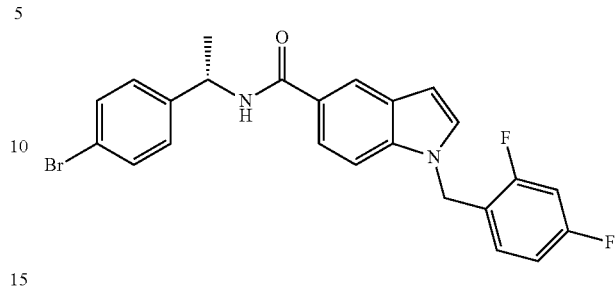

The title compound was prepared following the same general protocol as described in Step 4, Example 1, using (S)-1-(4-bromophenyl)ethanamine instead of the (2,4-dimethoxyphenyl)methanamine. A white powder was obtained (50 mg, 0.11 mmol, 63%). ESI-MS (m/z): 469/471 [M+H]$^+$.

Example 6: N-(Chroman-3-yl)-1-(2,4-difluorobenzyl)-1H-indole-5-carboxamide

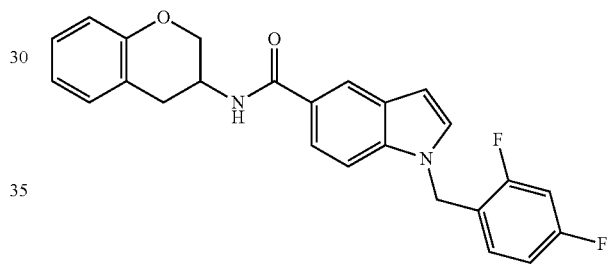

The title compound was prepared following the same general protocol as described in Step 4, Example 1, using chroman-3-amine instead of the (2,4-dimethoxyphenyl)methanamine. A white powder was obtained (52 mg, 0.12 mmol, 73%). ESI-MS (m/z): 419 [M+H]$^+$.

Example 7: (R)—N-(1-(4-Bromophenyl)ethyl)-1-(2,4-difluorobenzyl)-1H-indole-5-carboxamide

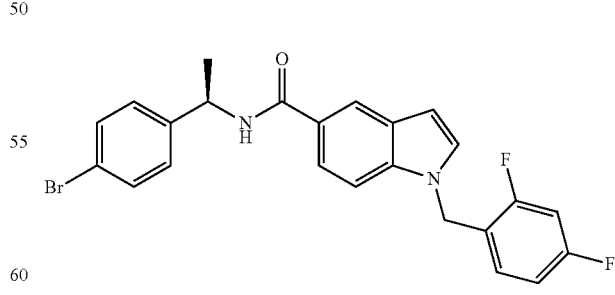

The title compound was prepared following the same general protocol as described in Step 4, Example 1, using (R)-1-(4-bromophenyl)ethanamine instead of the (2,4-dimethoxyphenyl)methanamine. A white powder was obtained (55 mg, 0.12 mmol, 69%). ESI-MS (m/z): 469/471 [M+H]$^+$.

Example 8: 1-(2,4-Difluorobenzyl)-N-(1-phenylpropyl)-1H-indole-5-carboxamide

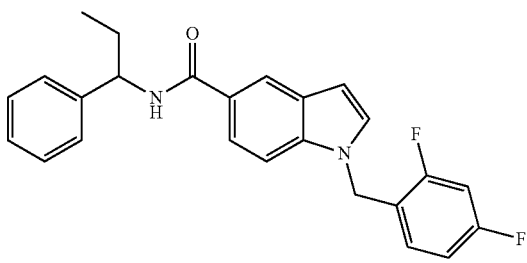 [SMILES: CCC(NC(=O)c1ccc2c(ccn2Cc2ccc(F)cc2F)c1)c1ccccc1]

The title compound was prepared following the same general protocol as described in Step 4, Example 1, using 1-phenylpropan-1-amine instead of the (2,4-dimethoxyphenyl)methanamine. A beige powder was obtained (46 mg, 0.12 mmol, 67%). ESI-MS (m/z): 405 [M+H]$^+$.

Example 9: N-Benzyl-1-(2,4-difluorobenzyl)-1H-indole-5-carboxamide

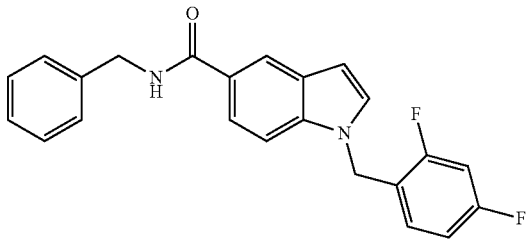 [SMILES: O=C(NCc1ccccc1)c1ccc2c(ccn2Cc2ccc(F)cc2F)c1]

The title compound was prepared following the same general protocol as described in Step 4, Example 1, using phenylmethanamine instead of the (2,4-dimethoxyphenyl)methanamine. A light green powder was obtained (49 mg, 0.13 mmol, 77%). ESI-MS (m/z): 377 [M+H]$^+$.

Example 10: (R)-1-(2,4-Difluorobenzyl)-N-(1-(4-nitrophenyl)ethyl)-1H-indole-5-carboxamide

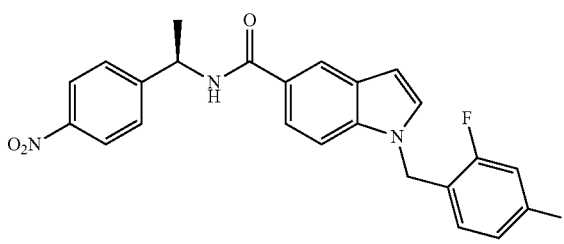

The title compound was prepared following the same general protocol as described in Step 4, Example 1, using (R)-1-(4-nitrophenyl)ethanamine instead of the (2,4-dimethoxyphenyl)methanamine. A beige powder was obtained (45 mg, 0.10 mmol, 60%). ESI-MS (m/z): 436 [M+H]$^+$.

Example 11: 1-(2,4-Difluorobenzyl)-N-(2-phenylpropan-2-yl)-1H-indole-5-carboxamide

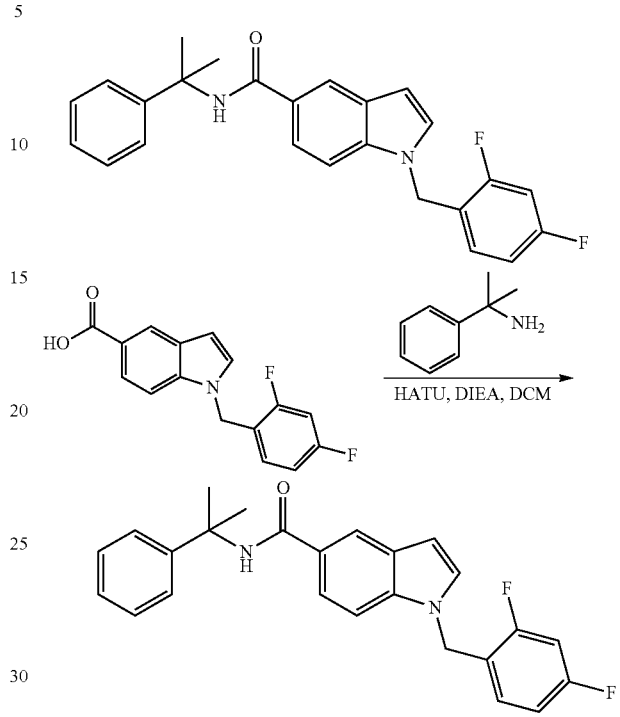

To a solution of 1-(2,4-difluorobenzyl)-1H-indole-5-carboxylic acid (50 mg, 0.17 mmol, 1 equiv) in DCM (2 mL) was added 2-phenylpropane-2-amine (27 µL, 0.18 mmol, 1.05 equiv), DIEA (30 µL, 0.17 mmol, 1 equiv) and HATU (68 mg, 0.18 mmol, 1.05 equiv). The reaction mixture was stirred 2 h at room temperature. The solvent was removed in vacuo. The residue was dissolved in AcOEt and washed with a 0.5N HCl aqueous solution, a saturated NaHCO$_3$ solution and brine, dried over MgSO$_4$ and concentrated in vacuo to afford a white powder (63 mg, 0.15 mmol, 92%). ESI-MS (m/z): 405 [M+H]$^+$.

Example 12: 1-(2,4-Difluorobenzyl)-N-(thiophen-2-ylmethyl)-1H-indole-5-carboxamide

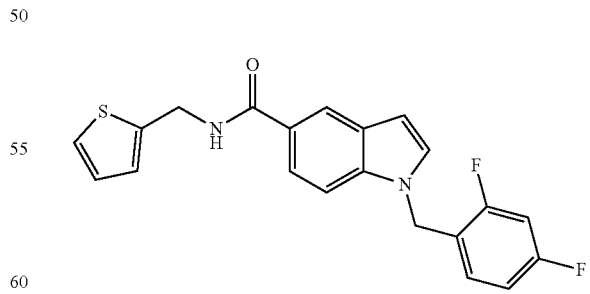

The title compound was prepared following the same general protocol as described in Step 4, Example 1, using thiophen-2-ylmethanamine instead of the (2,4-dimethoxyphenyl)methanamine. A white powder was obtained (45 mg, 0.12 mmol, 69%). ESI-MS (m/z): 383 [M+H]$^+$.

Example 13: 1-(2,4-Difluorobenzyl)-N-(2-methoxyethyl)-1H-indole-5-carboxamide

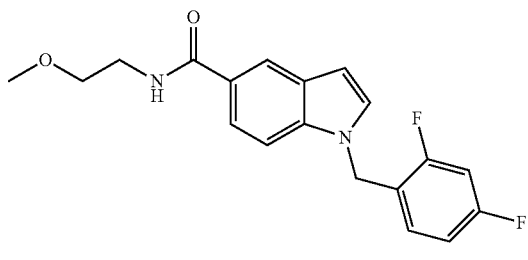 [SMILES: COCCNC(=O)c1ccc2c(ccn2Cc2ccc(F)cc2F)c1]

The title compound was prepared following the same general protocol as described in Step 4, Example 1, using 2-methoxyethanamine instead of the (2,4-dimethoxyphenyl)methanamine. A light green powder was obtained (47 mg, 0.14 mmol, 80%). ESI-MS (m/z): 345 [M+H]$^+$.

Example 14: 1-(2,4-Difluorobenzyl)-N-((2,3-dihydrobenzo[b][1,4]dioxin-2-yl)methyl)-1H-indole-5-carboxamide

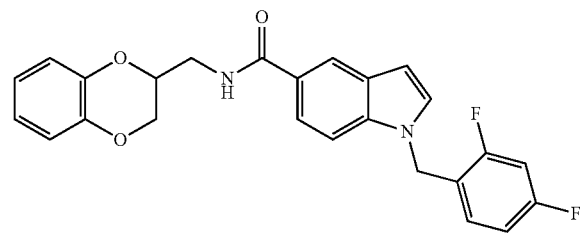 [SMILES: O=C(NCC1COc2ccccc2O1)c1ccc2c(ccn2Cc2ccc(F)cc2F)c1]

The title compound was prepared following the same general protocol as described in Step 4, Example 1, using (2,3-dihydrobenzo[b][1,4]dioxin-2-yl)methanamine instead of the (2,4-dimethoxyphenyl)methanamine. A beige powder was obtained (65 mg, 0.15 mmol, 88%). ESI-MS (m/z): 435 [M+H]$^+$.

Example 15: 1-(2,4-Difluorobenzyl)-N-(1-(naphthalen-1-yl)ethyl)-1H-indole-5-carboxamide

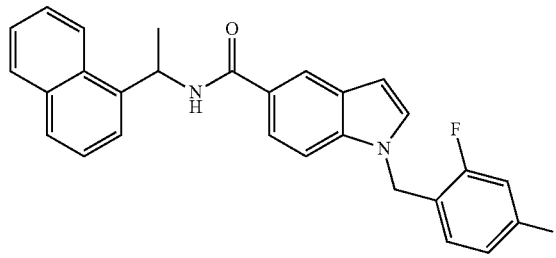

The title compound was prepared following the same general protocol as described in Step 4, Example 1, using 1-(naphthalen-1-yl)ethanamine instead of the (2,4-dimethoxyphenyl)methanamine. A white powder was obtained (55 mg, 0.12 mmol, 73%). ESI-MS (m/z): 441 [M+H]$^+$.

Example 16: (S)-1-(2,4-Difluorobenzyl)-N-(1-(4-fluorophenyl)ethyl)-1H-indole-5-carboxamide

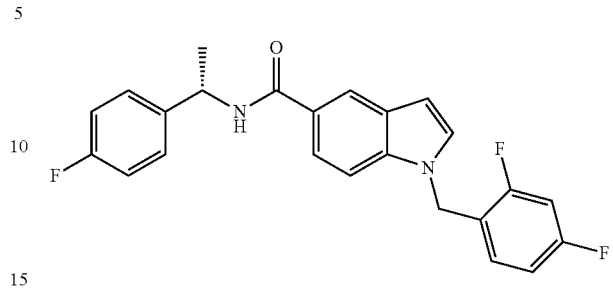

The title compound was prepared following the same general protocol as described in Step 4, Example 1, using (S)-1-(4-fluorophenyl)ethanamine instead of the (2,4-dimethoxyphenyl)methanamine. A white powder was obtained (45 mg, 0.11 mmol, 65%). ESI-MS (m/z): 409 [M+H]$^+$.

Example 17: (R)-1-(2,4-Difluorobenzyl)-N-(1-(4-fluorophenyl)ethyl)-1H-indole-5-carboxamide

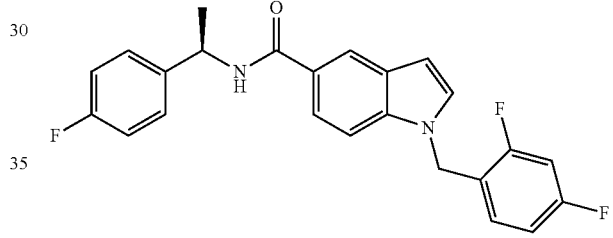

The title compound was prepared following the same general protocol as described in Step 4, Example 1, using (R)-1-(4-fluorophenyl)ethanamine instead of the (2,4-dimethoxyphenyl)methanamine. A white powder was obtained (41 mg, 0.10 mmol, 59%). ESI-MS (m/z): 409 [M+H]$^+$.

Example 18: N-Cyclopentyl-1-(2,4-difluorobenzyl)-1H-indole-5-carboxamide

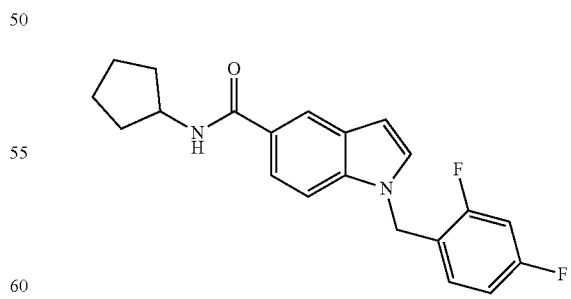

The title compound was prepared following the same general protocol as described in Step 4, Example 1, using cyclopentanamine instead of the (2,4-dimethoxyphenyl)methanamine. A white powder was obtained (35 mg, 0.10 mmol, 58%). ESI-MS (m/z): 355 [M+H]$^+$.

Example 19: 1-(2,4-Difluorobenzyl)-N-((1R,2S)-2-phenylcyclopropyl)-1H-indole-5-carboxamide

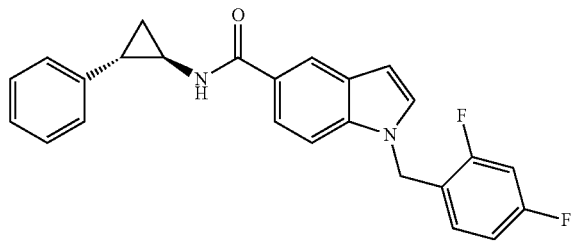 [SMILES: O=C(N[C@@H]1C[C@H]1c1ccccc1)c1ccc2c(ccn2Cc2ccc(F)cc2F)c1]

The title compound was prepared following the same general protocol as described in Step 4, Example 1, using (1R,2S)-2-phenylcyclopropanamine instead of the (2,4-dimethoxyphenyl)methanamine. A beige powder was obtained (49 mg, 0.12 mmol, 72%). ESI-MS (m/z): 403 [M+H]$^+$.

Example 20: N-(4-Aminobenzyl)-1-(2,4-difluorobenzyl)-1H-indole-5-carboxamide

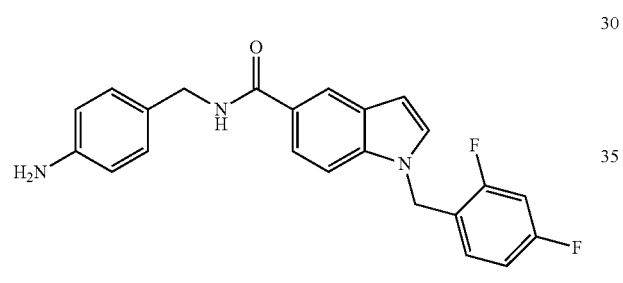

The title compound was prepared following the same general protocol as described in Example 11, using 4-(aminomethyl)aniline instead of the 2-phenylpropane-2-amine. A yellow powder was obtained (19 mg, 0.05 mmol, 29%). ESI-MS (m/z): 392 [M+H]$^+$.

Example 21: 1-(2,4-difluorobenzyl)-2,3-dimethyl-N-(1-phenylpropyl)-1H-indole-5-carboxamide

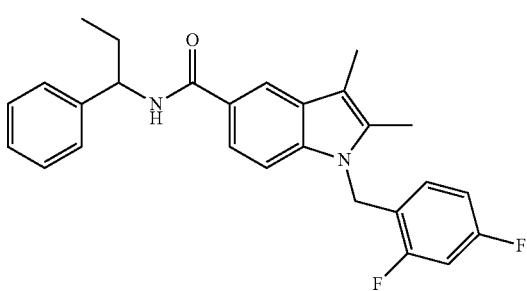 [SMILES: CCC(NC(=O)c1ccc2c(c1)c(C)c(C)n2Cc1ccc(F)cc1F)c1ccccc1]

Step 1: ethyl 1-(2,4-difluorobenzyl)-2,3-dimethyl-1H-indole-5-carboxylate

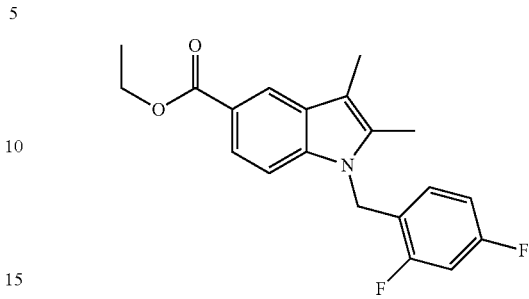

NaH (1.1 equiv) was added to a solution of ethyl 2,3-dimethyl-1H-indole-5-carboxylate in DMF at room temperature. After 30 min, 2,4-difluorobenzyl bromide (1.1 equiv) was added to the reaction mixture and stirred for 1 h. After the reaction was completed, the solvent was removed in vacuo to obtain the crude which was purified by flash chromatography to obtain the compound. LC-MS 344 (M+H).

Step 2: 1-(2,4-difluorobenzyl)-2,3-dimethyl-1H-indole-5-carboxylic acid

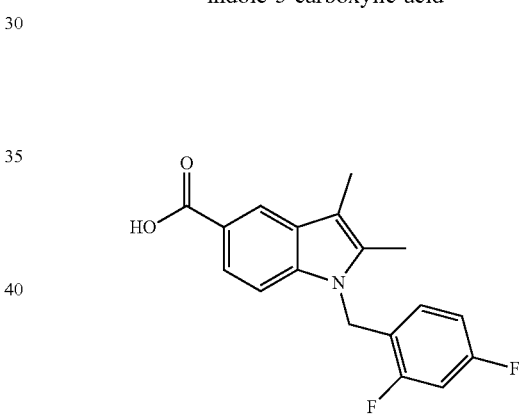

A mixture of above compound and NaOH (10 equiv) in EtOH was refluxed at 100° C. for 2 h. The reaction mixture was cooled to rt, then acidified to pH-4 with sat'd citric acid. The mixture was evaporated in vacuo to obtain the crude, which was precipitated in water and filtered to obtain the compound. LC-MS 316 (M+H).

Step 3: 1-(2,4-difluorobenzyl)-2,3-dimethyl-N-(1-phenylpropyl)-1H-indole-5-carboxamide To a mixture of 1-(2,4-difluorobenzyl)-2,3-dimethyl-1H-indole-5-carboxylic acid in DMF was added DIPEA (1.3 equiv) and HATU (1.2 equiv). The mixture was stirred for 5 min, and then α-ethylbenzylamine (1.1 equiv) was added. The reaction mixture was stirred at rt for 1 h. After the reaction was completed, the solvent was removed in vacuo to obtain the crude which was purified by flash chromatography to obtain the title compound. LC-MS 433 (M+H).

Example 22: 1-(4-chlorobenzyl)-2,3-dimethyl-N-(1-phenylpropyl)-1H-indole-5-carboxamide

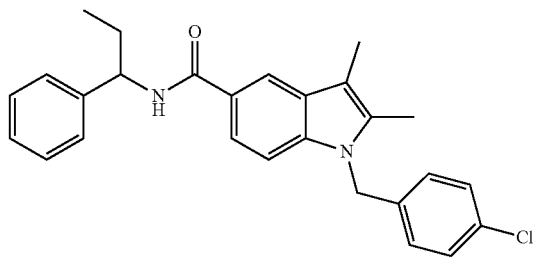 [SMILES: CCC(NC(=O)c1ccc2c(c1)c(C)c(C)n2Cc1ccc(Cl)cc1)c1ccccc1]

The title compound was prepared following the same general protocol as described in Steps 1, 2, and 3 of Example 21, using 4-chloro-benzylchloride and ethyl 2,3-dimethyl-1H-indole-5-carboxylate. LC-MS 431 (M+H).

Example 24: 1-(3-chlorophenethyl)-N-(1-phenylpropyl)-1H-indole-5-carboxamide

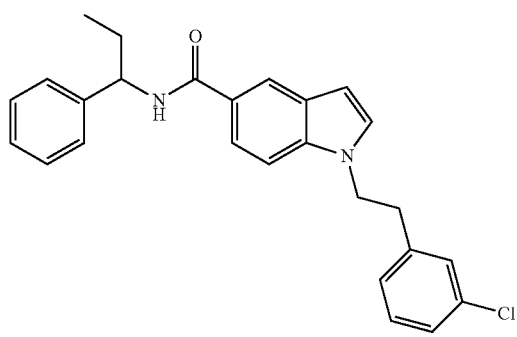 [SMILES: CCC(NC(=O)c1ccc2c(ccn2CCc2cccc(Cl)c2)c1)c1ccccc1]

The title compound was prepared following the same general protocol as described in Step 1 of Example 21, using 2-(3-chlorophenyl)ethyl chloride and N-(1-phenylpropyl)-1H-indole-5-carboxamide. LC-MS 417 (M+H).

Example 25: 1-benzoyl-N-(1-phenylpropyl)-1H-indole-5-carboxamide

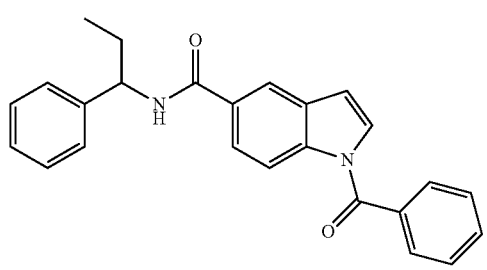 [SMILES: CCC(NC(=O)c1ccc2c(ccn2C(=O)c2ccccc2)c1)c1ccccc1]

Benzoyl chloride (1.1 equiv) was added to a solution of N-(1-phenylpropyl)-1H-indole-5-carboxamide in CH$_2$Cl$_2$, Et$_3$N (1.3 equiv) at room temperature. After the reaction was completed, the solvent was evaporated and the residual was purified by silica gel column chromatography to get the product. LC-MS 383 (M+H).

Example 26: 1-(4-nitrobenzoyl)-N-(1-phenylpropyl)-1H-indole-5-carboxamide

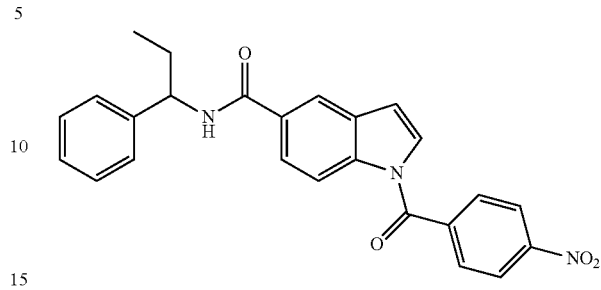

The title compound was prepared following the same general protocol as described in Example 25, using 4-nitrobenzoylchloride and N-(1-phenylpropyl)-1H-indole-5-carboxamide. LC-MS 428 (M+H)

Example 27: 1-(2,3-difluorobenzoyl)-N-(1-phenylpropyl)-1H-indole-5-carboxamide

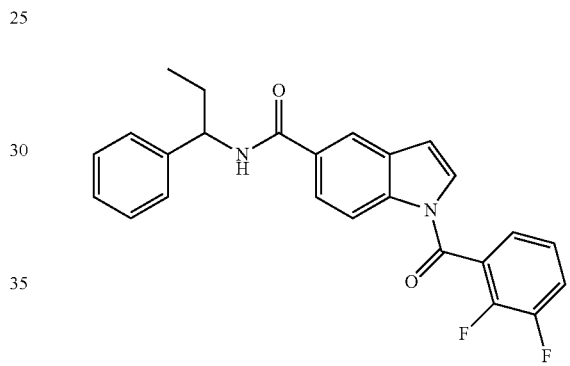

The title compound was prepared following the same general protocol as described in Example 25, using 2,3-difluorobenzoylchloride and N-(1-phenylpropyl)-1H-indole-5-carboxamide. LC-MS 419 (M+H).

Example 28: N-(1-phenylpropyl)-1-tosyl-1H-indole-5-carboxamide

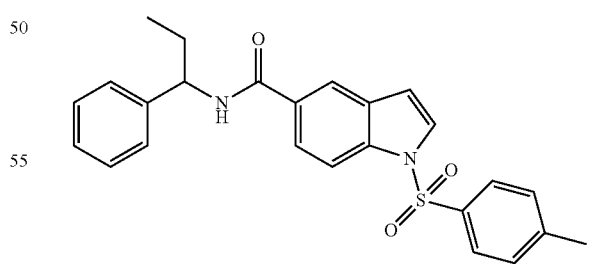

Tosyl chloride (1.1 equiv), benzyltriethylammonium chloride (0.5 equiv) was added to a solution of N-(1-phenylpropyl)-1H-indole-5-carboxamide in CH$_2$Cl$_2$, KOH (1.3 equiv) at room temperature. After the reaction was completed, the solvent was evaporated and the residual was purified by silica gel column chromatography to get the product. LC-MS 433 (M+H).

Example 30: 1-(naphthalen-1-ylsulfonyl)-N-(1-phenylpropyl)-1H-indole-5-carboxamide

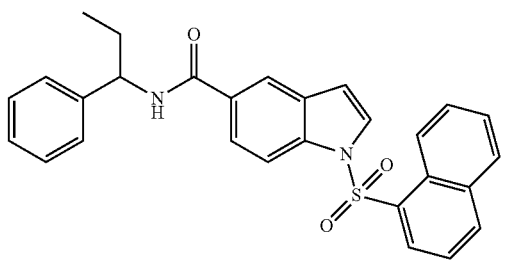 [SMILES: CCC(NC(=O)c1ccc2c(ccn2S(=O)(=O)c2cccc3ccccc23)c1)c1ccccc1]

The title compound was prepared following the same general protocol as described in Example 28, using 1-naphthyl sulfonyl chloride and N-(1-phenylpropyl)-1H-indole-5-carboxamide. LC-MS 469 (M+H).

Example 31: 1-(4-nitrophenylsulfonyl)-N-(1-phenylpropyl)-1H-indole-5-carboxamide

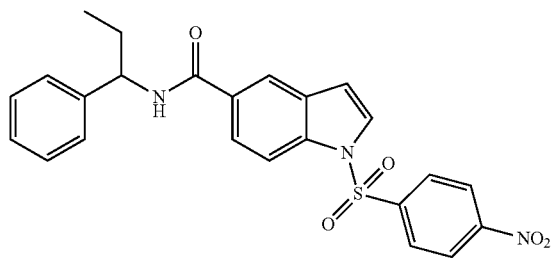 [SMILES: CCC(NC(=O)c1ccc2c(ccn2S(=O)(=O)c2ccc([N+](=O)[O-])cc2)c1)c1ccccc1]

The title compound was prepared following the same general protocol as described in Example 28, using 4-nitrophenylsulfonyl chloride and N-(1-phenylpropyl)-1H-indole-5-carboxamide. LC-MS 464 (M+H).

Example 32: 1-((6-chloropyridin-3-yl)methyl)-N-(1-phenylpropyl)-1H-indole-5-carboxamide

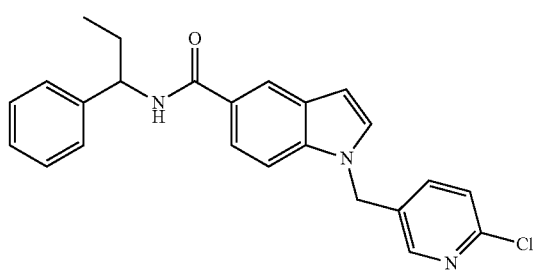 [SMILES: CCC(NC(=O)c1ccc2c(ccn2Cc2ccc(Cl)nc2)c1)c1ccccc1]

The title compound was prepared following the same general protocol as described in Step 1, Example 21, using 5-(bromomethyl)-2-chloropyridine and N-(1-phenylpropyl)-1H-indole-5-carboxamide. LC-MS 404 (M+H).

Examples 33, 34

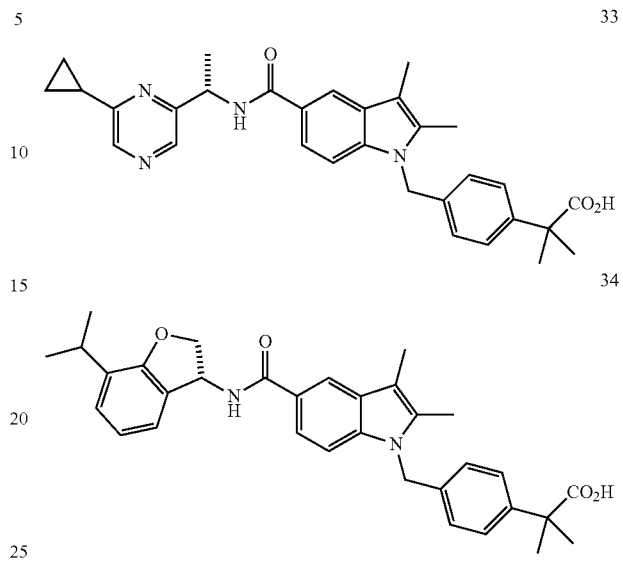

The title compounds can be prepared analogously to Example 35, below, but substituting

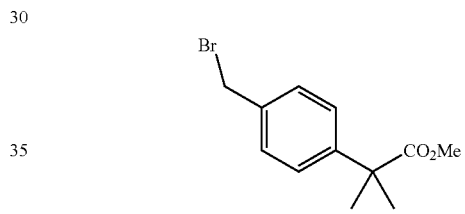

This bromomethyl compound can be prepared as described in Example 35, step 2, below, substituting methyl 1-methyl-1-(p-tolyl)-propionate for methyl 1-(p-tolyl)cyclopropanecarboxylate in the bromination reaction. Alternatively the bromomethyl compound can be purchased from Chinglu Pharmaceutical Research LLC, 705 North Mountain Rd., Suite C115, Newington, Conn.

Various compounds such as 33 and 34 can then be prepared, as is apparent to a person of skill in the art, by use of the appropriate precursors and reagents as indicated in Example 35, steps 3-8.

Example 35: (S)-1-(4-((5-((1-(3-Isopropylphenyl)ethyl)carbamoyl)-2,3-dimethyl-1H-indol-1-yl)methyl)phenyl)cyclopropanecarboxylic acid

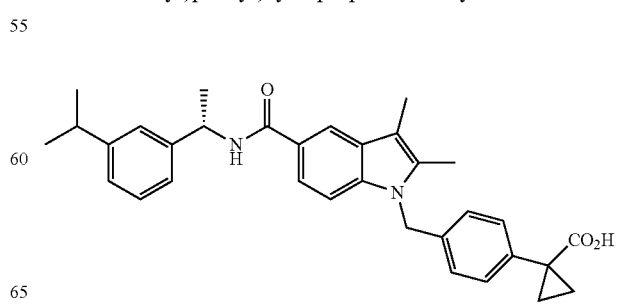

Step 1: Methyl 1-(p-tolyl)cyclopropanecarboxylate

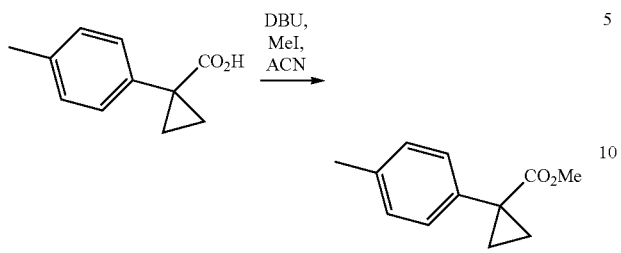

To a solution of 1-(p-tolyl)cyclopropanecarboxylic acid (900 mg, 5.1 mmol) in acetonitrile (20 mL) was added DBU (917 μL) followed by methyl iodide (1.91 mL). The resulting solution was heated at reflux overnight, and then diluted with AcOEt. The mixture was washed with a 0.5 N HCl solution, a saturated solution of NaHCO$_3$, and brine, dried on MgSO$_4$, and concentrated. The resulting colorless oil was purified by chromatography on silica gel (Hexane/ethyl acetate 9/1) to afford the title compound as a colorless oil (622 mg, 64%).

Step 2: Methyl 1-(4-(bromomethyl)phenyl)cyclopropanecarboxylate

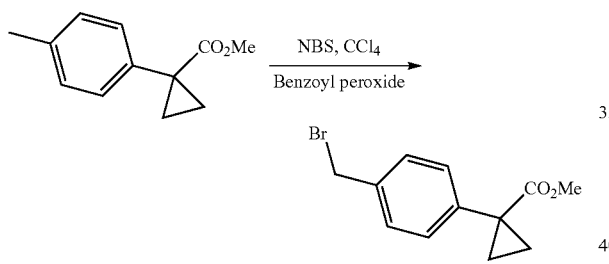

To a solution of methyl 1-(p-tolyl)cyclopropanecarboxylate (622 mg, 3.27 mmol) in carbon tetrachloride (16 mL) was added N-bromosuccinimide (611 mg) followed by benzoyl peroxide (40 mg). The resulting solution was heated at reflux overnight, and then diluted with methylene chloride. The mixture was washed with brine, dried on MgSO$_4$, and concentrated to afford a colorless oil (860 mg, 97%).

Step 3: 2,3-Dimethyl-1H-indole-5-carboxylic acid

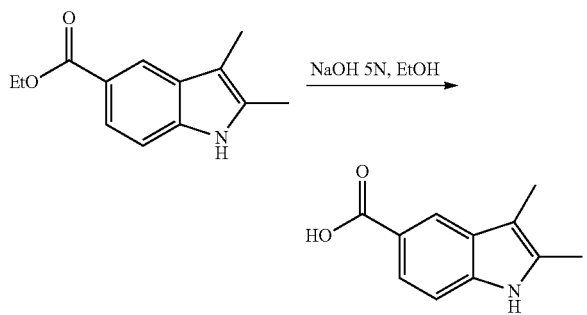

To a solution of ethyl 2,3-dimethyl-1H-indole-5-carboxylate (500 mg, 2.3 mmol) in ethanol (10 mL) was added a 5N NaOH solution (9.2 mL). The resulting solution was heated at 50° C. for 4 h, and then quenched carefully by addition of a 6N HCl solution (10 mL). The mixture was diluted with ethyl acetate, washed with a 0.5 N HCl solution and brine, dried on MgSO$_4$, and concentrated to afford a yellow powder (500 mg, 100%). ESI-MS (m/z): 190 [MH]$^+$

Step 4: 1-(4-(1-(Methoxycarbonyl)cyclopropyl)benzyl)-2,3-dimethyl-1H-indole-5-carboxylic acid

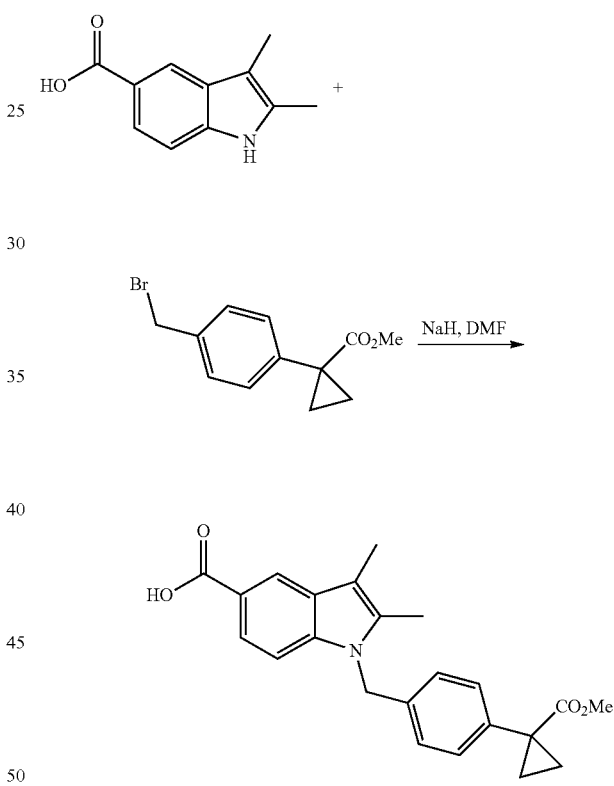

To a solution of 2,3-dimethyl-1H-indole-5-carboxylic acid (500 mg, 2.3 mmol) in anhydrous DMF (20 mL) was added methyl 1-(4-(bromomethyl)phenyl)cyclopropanecarboxylate (620 mg) followed by NaH (230 mg). The resulting solution was allowed to stir overnight under argon atmosphere. The remaining NaH was hydrolyzed by the careful addition of a 0.5 N HCl solution. The mixture was diluted with ethyl acetate, washed with a 0.5 N HCl solution and brine, dried on MgSO$_4$, and concentrated. The crude residue was purified by chromatography on silica gel (Hexane/Ethyl acetate 5/5) to afford an orange powder (361 mg). ESI-MS (m/z): 378 [MH]$^+$ Step 5: (S)-Methyl 1-(4-((5-((1-(3-bromophenyl)ethyl)carbamoyl)-2,3-dimethyl-1H-indol-1-yl)methyl)phenyl)cyclopropanecarboxylate

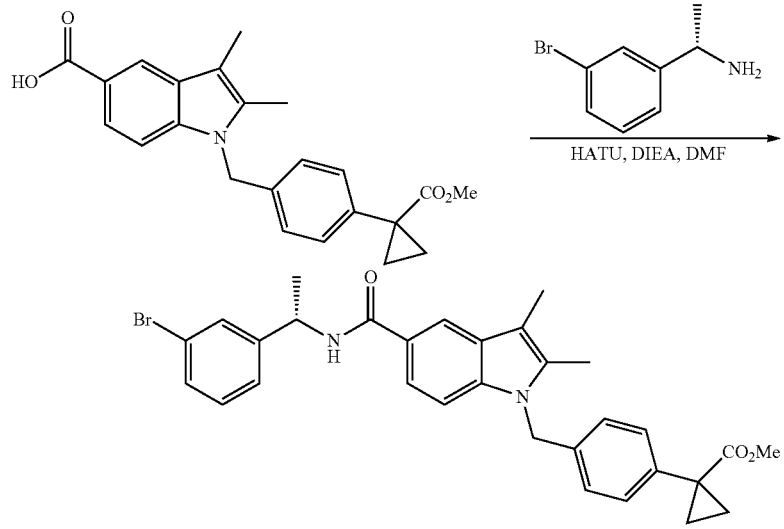

To a solution of 1-(4-(1-(methoxycarbonyl)cyclopropyl)benzyl)-2,3-dimethyl-1H-indole-5-carboxylic acid (50 mg, 0.13 mmol) in DMF (1 mL) was added (S)-1-(3-bromophenyl)ethylamine (21 μL), DIEA (45 μL) and HATU (54 mg). The reaction mixture was allowed to stir at rt for 30 min, and then was diluted by ethyl acetate. The resulting mixture was washed with a 0.5 N HCl solution, a saturated solution of NaHCO$_3$, and brine, dried on MgSO$_4$, and concentrated to afford a yellow oil (73 mg) which was directly used without further purification. ESI-MS (m/z): 559/561 [MH]$^+$ Step 6: (S)-Methyl 1-(4-((2,3-dimethyl-5-((1-(3-(prop-1-en-2-yl)phenyl)ethyl)carbamoyl)-1H-indol-1-yl)methyl)phenyl)cyclopropanecarboxylate To a solution of (S)-methyl 1-(4-((5-((1-(3-bromophenyl)ethyl)carbamoyl)-2,3-dimethyl-1H-indol-1-yl)methyl)phenyl)cyclopropanecarboxylate (73 mg) in dioxane/water (1.2 mL/0.3 mL) was added isopropenylboronic acid pinacol ester (49 μL), K$_2$CO$_3$ (36 mg) and Pd(PPh$_3$)$_4$ (15 mg). The solution was degassed with argon and then stirred for 1 h at 100° C. under microwave. The resulting mixture was diluted with ethyl acetate washed with a 0.5 N HCl solution, a saturated solution of NaHCO$_3$, and brine, dried on MgSO$_4$, and concentrated to afford a yellow oil which was directly used without further purification. ESI-MS (m/z): 521 [MH]$^+$

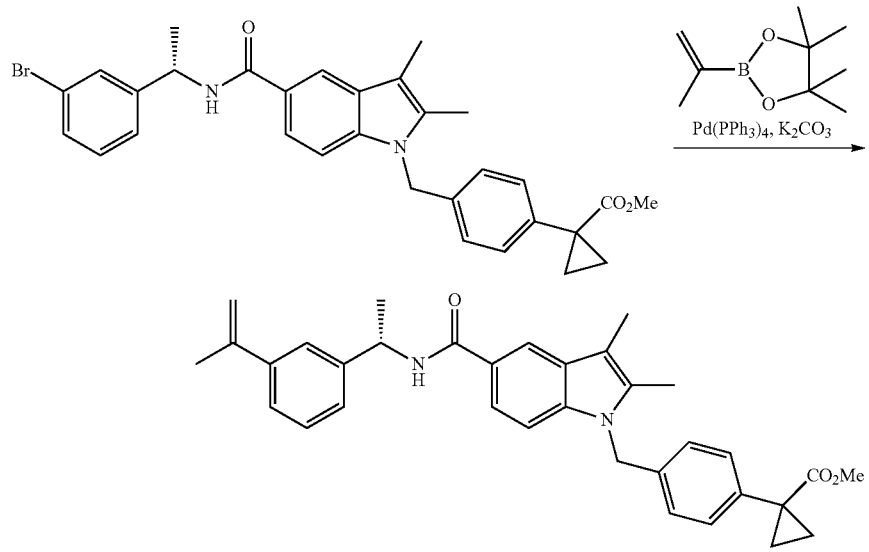

Step 7: (S)-Methyl 1-(4-((5-((1-(3-isopropylphenyl)ethyl)carbamoyl)-2,3-dimethyl-1H-indol-1-yl)methyl)phenyl)cyclopropanecarboxylate

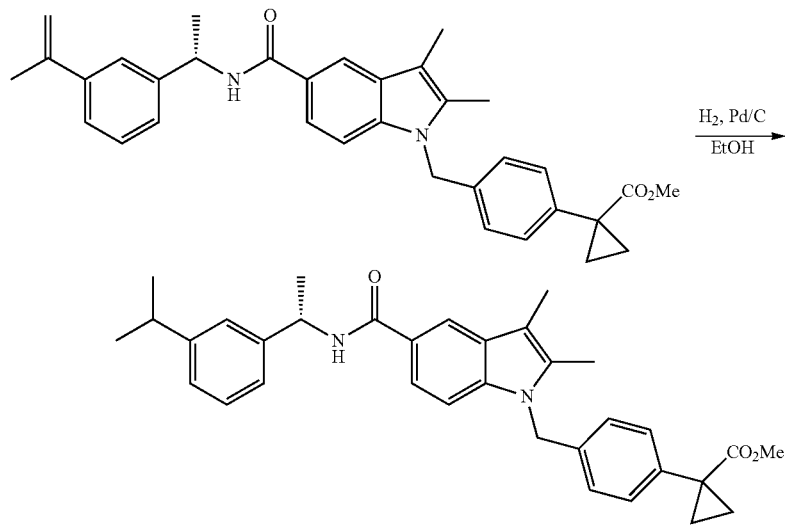

To a solution of (S)-methyl 1-(4-((2,3 methyl-5-((1-(3-(prop-1-en-2-yl)phenyl)ethyl)carbamoyl)-1H-indol-1-yl)methyl)phenyl)cyclopropanecarboxylate in EtOH (5 mL) was added Pd/C 10%. The resulting mixture was stirred for 5 h under hydrogen atmosphere. The solution was then filtered and concentrated to afford a yellow oil which was directly used without further purification. ESI-MS (m/z): 523 [MH]+

Step 8: (S)-1-(4-((5-((1-(3-Isopropylphenyl)ethyl)carbamoyl)-2,3-dimethyl-1H-indol-1-yl)methyl)phenyl)cyclopropanecarboxylic acid To a solution of (S)-1-(4-((5-((1-(3-isopropylphenyl)ethyl)carbamoyl)-2,3-dimethyl-1H-indol-1-yl)methyl)phenyl)cyclopropanecarboxylic acid in methanol (1 mL) was added a 5 N NaOH solution (1 mL). The resulting solution was heated at 50° C. for 4 h, and then quenched carefully by addition of a 6 N HCl solution (1 mL). The mixture was diluted with ethyl acetate, washed with a 0.5 N HCl solution and brine, dried on MgSO4, and concentrated. The resulting oil was purified by preparative HPLC to afford a white powder (9 mg). ESI-MS (m/z): 509 [MH]+

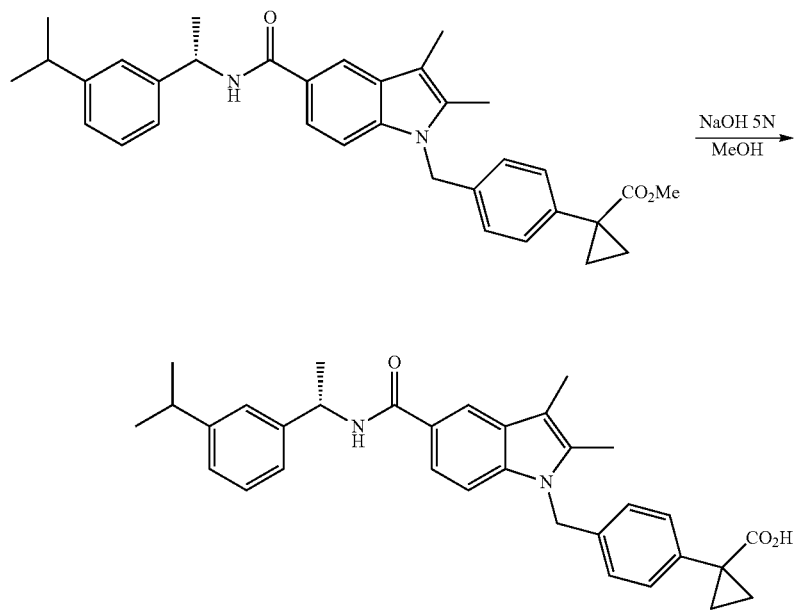

Example 36: (S)-2-(4-((5-((1-(3-Cyclopropylphenyl)ethyl)carbamoyl)-2,3-dimethyl-1H-indol-1-yl)methyl)phenoxy)acetic acid

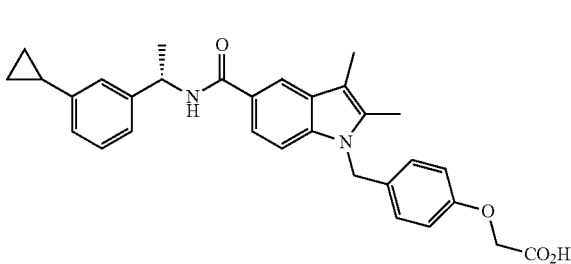 [SMILES: Cc1c(C)n(Cc2ccc(OCC(=O)O)cc2)c2ccc(C(=O)N[C@@H](C)c3cccc(C4CC4)c3)cc12]

Step 1: Methyl 2-(p-tolyloxy)acetate

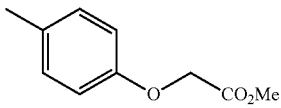

To a solution of p-cresol (2 mL, 19.1 mmol) in anhydrous DMF (50 mL) were added $Cs_2CO_3$ (8.1 g, 24.9 mmol) and methyl bromoacetate (1.9 mL, 20.1 mmol). The suspension was stirred at room temperature for 3 h. After dilution with ethyl acetate, the reaction mixture was washed with a 0.5 N HCl solution, a saturated solution of $NaHCO_3$, and brine, dried on $MgSO_4$, and concentrated. The resulting oil was purified by chromatography on silica gel (Hexane/ethyl acetate 8/2) to afford the title compound as a colorless oil (3.10 g, 90%).

Step 2: Methyl 2-(4-(bromomethyl)phenoxy)acetate

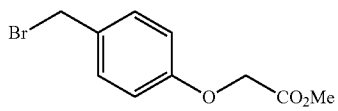 [SMILES: COC(=O)COc1ccc(CBr)cc1]

To a solution of the methyl 2-(p-tolyloxy)acetate (3.10 g, 17.2 mmol) in carbon tetrachloride (60 mL) was added N-bromosuccinimide (3.57 g, 20 mmol) followed by benzoyl peroxide (463 mg, 1.9 mmol). The resulting solution was heated at reflux overnight, and then diluted with methylene chloride. The mixture was washed with brine, dried on $MgSO_4$, and concentrated. The resulting colorless oil was purified by chromatography on silica gel (Hexane/ethyl acetate 9/1) to afford a colorless oil (2.5 g, 56%).

Step 3: Allyl 1-(4-(2-methoxy-2-oxoethoxy)benzyl)-2,3-dimethyl-1H-indole-5-carboxylate

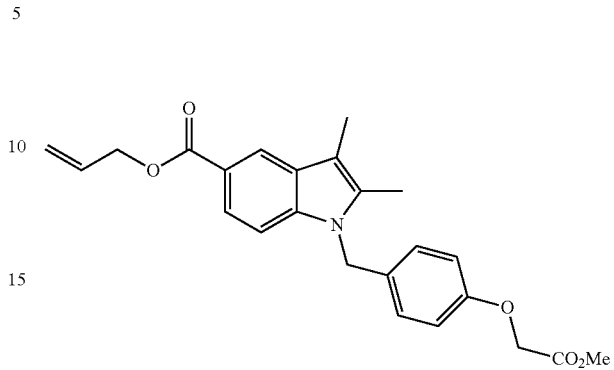

To a solution of the allyl 2,3-dimethyl-1H-indole-5-carboxylate (500 mg, 2.2 mmol) in anhydrous DMF (20 mL) was added the methyl 2-(4-(bromomethyl)phenoxy)acetate (565 mg, 2.2 mmol) followed by NaH (131 mg, 3.3 mmol). The resulting solution was allowed to stir overnight under argon atmosphere. The remaining NaH was hydrolyzed by the careful addition of a 0.5 N HCl solution. The mixture was diluted with ethyl acetate, washed with a 0.5 N HCl solution and brine, dried on $MgSO_4$, and concentrated. The crude residue was purified by chromatography on silica gel (Hexane/Ethyl acetate 5/5) to afford yellow oil (536 mg, 61%). ESI-MS (m/z): 408 $[M+H]^+$

Step 4: 1-(4-(2-Methoxy-2-oxoethoxy)benzyl)-2,3-dimethyl-1H-indole-5-carboxylic acid

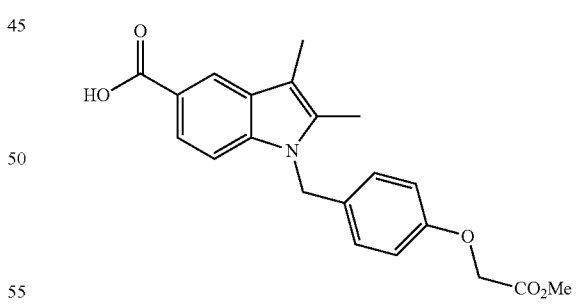

A solution of the allyl 1-(4-(2-methoxy-2-oxoethoxy)benzyl)-2,3-dimethyl-1H-indole-5-carboxylate (536 mg, 1.3 mmol) and morpholine (1.14 mL, 13.2 mmol) in anhydrous THF was degassed with argon. Then $Pd(PPh_3)_4$ (152 mg, 0.13 mmol) was added and the reaction stirred under argon protection for 1.5 h. The reaction mixture was diluted with ethyl acetate, washed with brine, concentrated. The title compound was precipitated in ethyl ether as a beige powder (430 mg, 89%). ESI-MS (m/z): 368 $[M+H]^+$.

Step 5: (S)-Methyl 2-(4-((5-((1-(3-cyclopropylphenyl)ethyl)carbamoyl)-2,3-dimethyl-1H-indol-1-yl)methyl)phenoxy)acetate

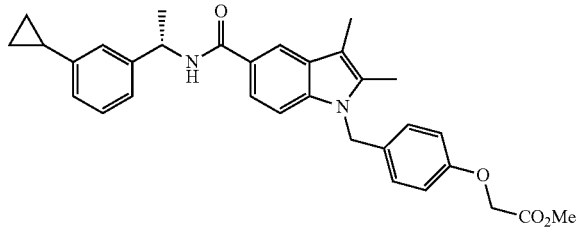 [SMILES: COC(=O)COc1ccc(Cn2c(C)c(C)c3cc(C(=O)N[C@@H](C)c4cccc(C5CC5)c4)ccc32)cc1]

To a solution of the 1-(4-(2-methoxy-2-oxoethoxy)benzyl)-2,3-dimethyl-1H-indole-5-carboxylic acid (50 mg, 0.14 mmol) in DCM (1 mL) was added the (S)-1-(3-cyclopropylphenyl)ethanamine hydrochloride (28 mg), DIEA (73 μL) and HATU (53 mg). The reaction mixture was allowed to stir at rt for 30 min, and then was diluted by ethyl acetate. The resulting mixture was washed with a 0.5 N HCl solution, a saturated solution of NaHCO₃, and brine, dried on MgSO₄, and concentrated to afford a yellow oil (73 mg) which was directly used without further purification. ESI-MS (m/z): 497 [M+H]⁺

Step 6: (S)-2-(4-((5-((1-(3-Cyclopropylphenyl)ethyl)carbamoyl)-2,3-dimethyl-1H-indol-1-yl)methyl)phenoxy)acetic acid

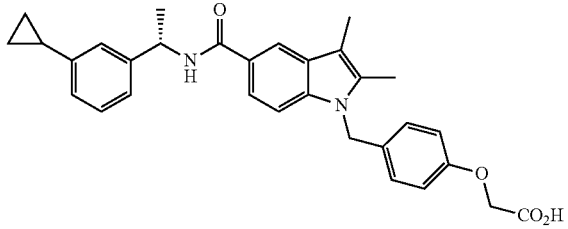 [SMILES: Cc1c(C)n(Cc2ccc(OCC(=O)O)cc2)c2ccc(C(=O)N[C@@H](C)c3cccc(C4CC4)c3)cc12]

To a solution of the (S)-methyl 2-(4-((5-((1-(3-cyclopropylphenyl)ethyl)carbamoyl)-2,3-dimethyl-1H-indol-1-yl)methyl)phenoxy)acetate in methanol (1 mL) was added a 5N NaOH solution (1 mL). The resulting solution was heated at 50° C. for 4 h, and then quenched carefully by addition of a 6N HCl solution (1 mL). The mixture was diluted with ethyl acetate, washed with a 0.5 N HCl solution and brine, dried on MgSO₄, and concentrated. The resulting oil was purified by preparative HPLC to afford a white powder (46 mg). ESI-MS (m/z): 497 [MH]⁺

Example 37: (S)-2-(4-((5-((1-(3-Isopropylphenyl)ethyl)carbamoyl)-2,3-dimethyl-1H-indol-1-yl)methyl)phenoxy)acetic acid

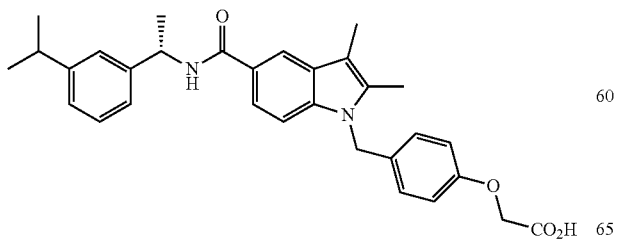

Step 1: (S)-Methyl 2-(4-((5-((1-(3-isopropylphenyl)ethyl)carbamoyl)-2,3-dimethyl-1H-indol-1-yl)methyl)phenoxy)acetate

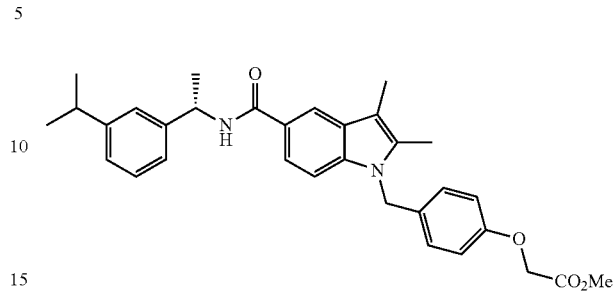

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride.

Step 2: (S)-2-(4-((5-((1-(3-Isopropylphenyl)ethyl)carbamoyl)-2,3-dimethyl-1H-indol-1-yl)methyl)phenoxy)acetic acid

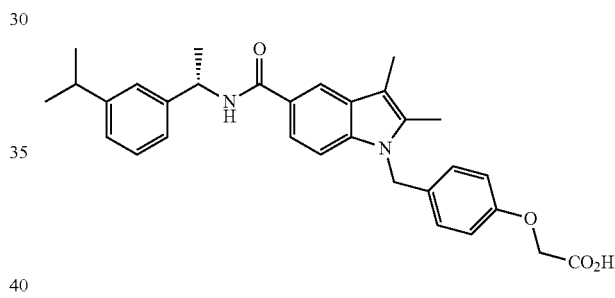

The title compound was prepared following the same protocol as described in Step 6, Example 36, using the (S)-methyl 2-(4-((5-((1-(3-isopropylphenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 499 [MH]⁺

Example 38: (S)-2-(4-((5-((1-(4-(tert-Butyl)phenyl)ethyl)carbamoyl)-2,3-dimethyl-1H-indol-1-yl)methyl)phenoxy)acetic acid

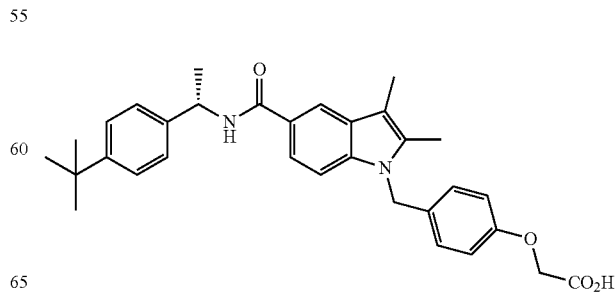

Step 1: (S)-Methyl 2-(4-((5-((1-(4-(tert-butyl)phe-nyl)ethyl)carbamoyl)-2,3-dimethyl-1H-indol-1-yl)methyl)phenoxy)acetate

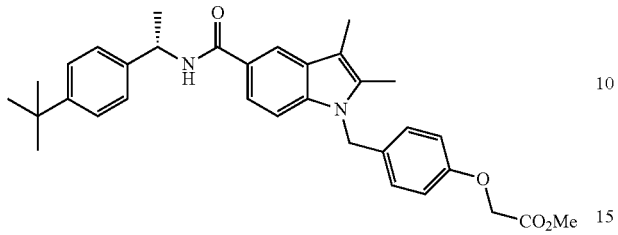

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride.

Step 2: (S)-2-(4-((5-((1-(4-(tert-Butyl)phenyl)ethyl)carbamoyl)-2,3-dimethyl-1H-indol-1-yl)methyl)phenoxy)acetic acid

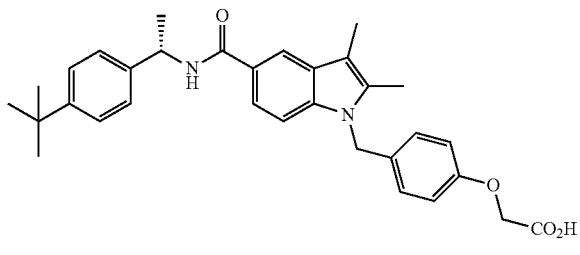 [SMILES: Cc1c(C)n(Cc2ccc(OCC(=O)O)cc2)c2ccc(C(=O)N[C@@H](C)c3ccc(C(C)(C)C)cc3)cc12]

The title compound was prepared following the same protocol as described in Step 6, Example 36, using the (S)-methyl 2-(4-((5-((1-(4-(tert-butyl)phenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]$^+$

Example 39: (S)-2-(3-((5-((1-(3-Cyclopropylphenyl)ethyl)carbamoyl)-2,3-dimethyl-1H-indol-1-yl)methyl)phenoxy)acetic acid

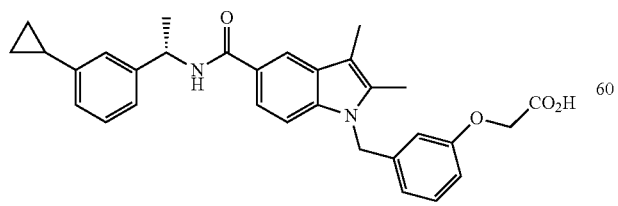

Step 1: Methyl 2-(m-tolyloxy)acetate

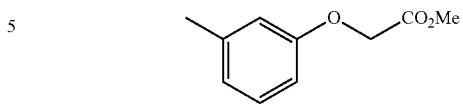

The title compound was prepared following the same protocol as described in Step 1, Example 36, using the m-cresol instead of the p-cresol.

Step 2: Methyl 2-(3-(bromomethyl)phenoxy)acetate

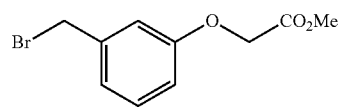 [SMILES: COC(=O)COc1cccc(CBr)c1]

The title compound was prepared following the same protocol as described in Step 2, Example 36, using the methyl 2-(m-tolyloxy)acetate instead of the methyl 2-(p-tolyloxy)acetate.

Step 3: Allyl 1-(3-(2-methoxy-2-oxoethoxy)benzyl)-2,3-dimethyl-1H-indole-5-carboxylate

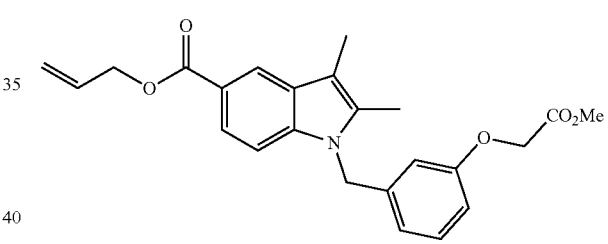

The title compound was prepared following the same general protocol as described in Step 3, Example 36, using the methyl 2-(3-(bromomethyl)phenoxy)acetate instead of the methyl 2-(4-(bromomethyl)phenoxy)acetate. ESI-MS (m/z): 408 [M+H]$^+$.

Step 4: 1-(3-(2-Methoxy-2-oxoethoxy)benzyl)-2,3-dimethyl-1H-indole-5-carboxylic acid

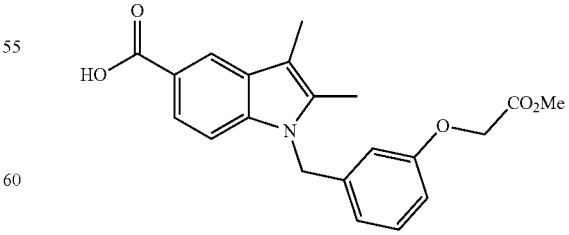

The title compound was prepared following the same general protocol as described in Step 4, Example 36, using the allyl 1-(3-(2-methoxy-2-oxoethoxy)benzyl)-2,3-dimethyl-1H-indole-5-carboxylate instead of the allyl 1-(4-(2- methoxy-2-oxoethoxy)benzyl)-2,3-dimethyl-1H-indole-5-carboxylate. ESI-MS (m/z): 368 [M+H]+.

Step 5: (S)-Methyl 2-(3-((5-((1-(3-cyclopropylphenyl)ethyl)carbamoyl)-2,3-dimethyl-1H-indol-1-yl)methyl)phenoxy)acetate

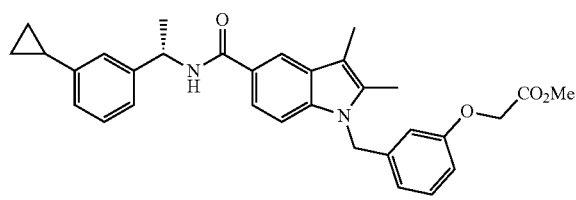 [SMILES: COC(=O)COc1cccc(Cn2c(C)c(C)c3cc(C(=O)N[C@@H](C)c4cccc(C5CC5)c4)ccc32)c1]

The title compound was prepared following the same protocol as described in Step 5, Example 36, using the 1-(3-(2-methoxy-2-oxoethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-((1-(3-Cyclopropylphenyl)ethyl)carbamoyl)-2,3-dimethyl-1H-indol-1-yl)methyl)phenoxy)acetic acid

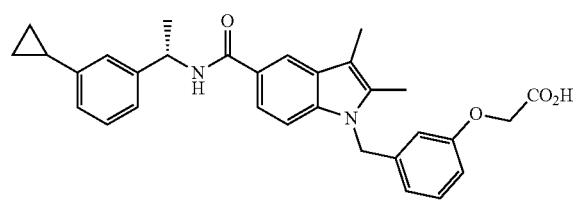 [SMILES: Cc1c(C)n(Cc2cccc(OCC(=O)O)c2)c2ccc(C(=O)N[C@@H](C)c3cccc(C4CC4)c3)cc12]

The title compound was prepared following the same protocol as described in Step 6, Example 36, using the (S)-methyl 2-(3-((5-((1-(3-cyclopropylphenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 497 [MH]+

Example 40: (S)-2-(3-((5-((1-(3-Isopropylphenyl)ethyl)carbamoyl)-2,3-dimethyl-1H-indol-1-yl)methyl)phenoxy)acetic acid

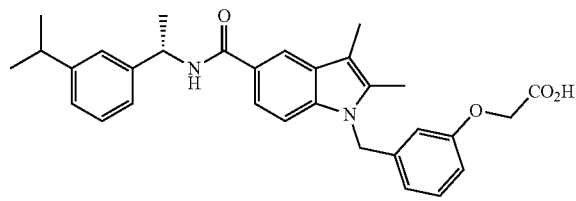 [SMILES: Cc1c(C)n(Cc2cccc(OCC(=O)O)c2)c2ccc(C(=O)N[C@@H](C)c3cccc(C(C)C)c3)cc12]

Step 1: (S)-Methyl 2-(3-((5-((1-(3-isopropylphenyl)ethyl)carbamoyl)-2,3-dimethyl-1H-indol-1-yl)methyl)phenoxy)acetate

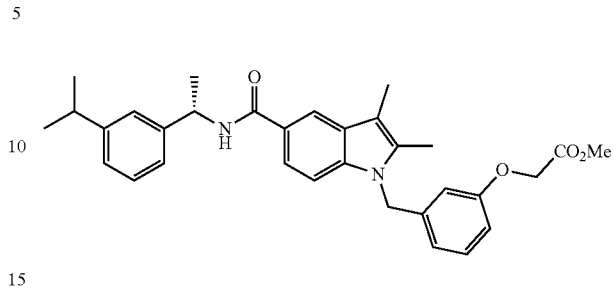

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(3-(2-methoxy-2-oxoethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-((1-(3-Isopropylphenyl)ethyl)carbamoyl)-2,3-dimethyl-1H-indol-1-yl)methyl)phenoxy)acetic acid

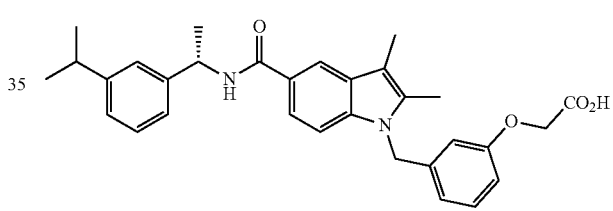

The title compound was prepared following the same protocol as described in Step 6, Example 36, using the (S)-methyl 2-(3-((5-((1-(3-isopropylphenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 499 [MH]+

Example 41: (S)-2-(3-((5-((1-(4-(tert-Butyl)phenyl)ethyl)carbamoyl)-2,3-dimethyl-1H-indol-1-yl)methyl)phenoxy)acetic acid

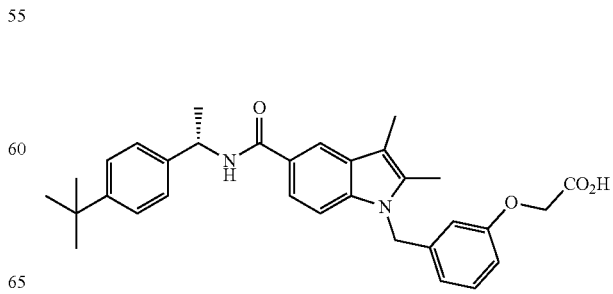

Step 1: (S)-Methyl 2-(3-((5-((1-(4-(tert-butyl)phenyl)ethyl)carbamoyl)-2,3-dimethyl-1H-indol-1-yl)methyl)phenoxy)acetate

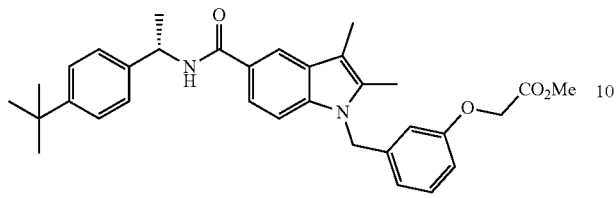

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the 1-(3-(2-methoxy-2-oxoethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-((1-(4-(tert-Butyl)phenyl)ethyl)carbamoyl)-2,3-dimethyl-1H-indol-1-yl)methyl)phenoxy)acetic acid

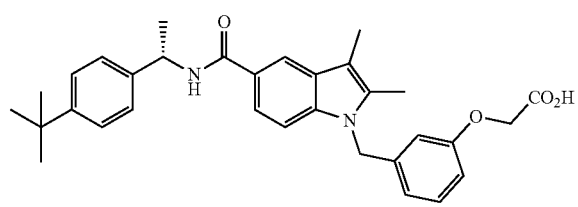 [SMILES: Cc1c(C)n(Cc2cccc(OCC(=O)O)c2)c2ccc(C(=O)N[C@@H](C)c3ccc(C(C)(C)C)cc3)cc12]

The title compound was prepared following the same protocol as described in Step 6, Example 36, using the (S)-methyl 2-(3-((5-((1-(4-(tert-butyl)phenyl)ethyl)carbamoyl)-2,3-dimethyl-1H-indol-1-yl)methyl)phenoxy)acetate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [M+H]$^+$ Example 42: (R)-2-(3-((5-(((S)-1-(3-Isopropylphenyl)ethyl)carbamoyl)-2,3-dimethyl-1H-indol-1-yl)methyl)phenoxy)propanoic acid

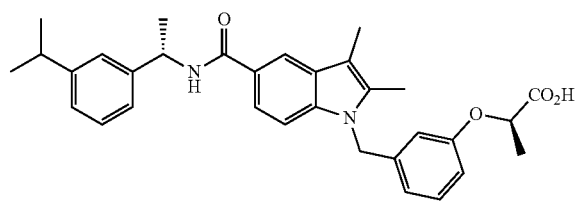 [SMILES: Cc1c(C)n(Cc2cccc(O[C@H](C)C(=O)O)c2)c2ccc(C(=O)N[C@@H](C)c3cccc(C(C)C)c3)cc12]

Step 1: (R)-Methyl 2-(m-tolyloxy)propanoate

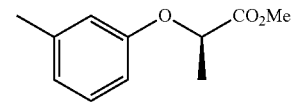

To a solution of the m-cresol (1.0 g, 9.2 mmol) in anhydrous THF (15 mL) at 0° C. under argon protection was added triphenylphosphine (2.55 g, 9.7 mmol), followed by addition of the (S)-methyl 2-hydroxypropanoate (926 µL, 9.7 mmol). Then diisopropylazodicarboxylate (DIAD) (2.85 mL, 13.8 mmol) was added dropwise at 0° C. The reaction mixture was stirred at room temperature overnight. The resulting mixture was diluted by ethyl acetate, washed with a 0.5 N HCl solution, a saturated solution of NaHCO$_3$, and brine, dried on MgSO$_4$, and concentrated. The obtained oil was purified by flash chromatography (Hexane/Ethyl acetate 0~50%) to afford a colorless oil (820 mg, 46%).

Step 2: (R)-Methyl 2-(3-(bromomethyl)phenoxy)propanoate

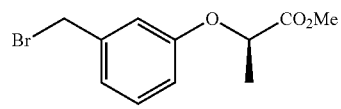

The title compound was prepared following the same protocol as described in Step 2, Example 36, using the (R)-methyl 2-(m-tolyloxy)propanoate instead of the methyl 2-(p-tolyloxy)acetate.

Step 3: (R)-Allyl 1-(3-((1-methoxy-1-oxopropan-2-yl)oxy)benzyl)-2,3-dimethyl-1H-indole-5-carboxylate

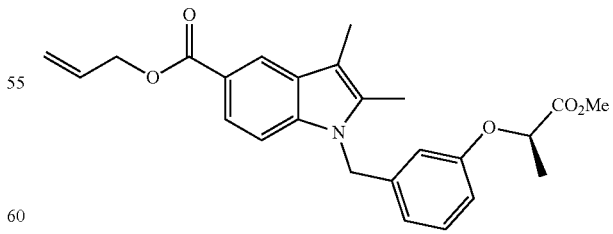

The title compound was prepared following the same general protocol as described in Step 3, Example 36, using the (R)-methyl 2-(3-(bromomethyl)phenoxy)propanoate instead of the methyl 2-(4-(bromomethyl)phenoxy)acetate. ESI-MS (m/z): 422 [M+H]$^+$.

Step 4: (R)-1-(3-((1-Methoxy-1-oxopropan-2-yl)oxy)benzyl)-2,3-dimethyl-1H-indole-5-carboxylic acid

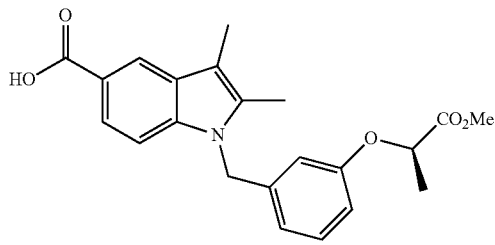 [SMILES: COC(=O)[C@@H](C)Oc1cccc(Cn2c(C)c(C)c3cc(C(=O)O)ccc32)c1]

The title compound was prepared following the same general protocol as described in Step 4, Example 36, using the (R)-allyl 1-(3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]$^+$.

Step 5: (R)-Methyl 2-(3-((5-(((S)-1-(3-isopropylphenyl)ethyl)carbamoyl)-2,3-dimethyl-1H-indol-1-yl)methyl)phenoxy)propanoate

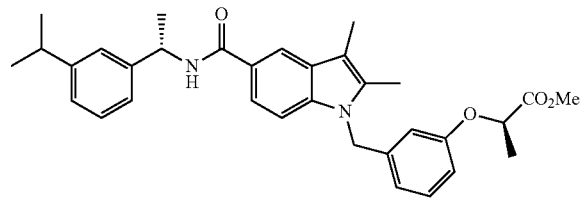 [SMILES: COC(=O)[C@@H](C)Oc1cccc(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(3-Isopropylphenyl)ethyl)carbamoyl)-2,3-dimethyl-1H-indol-1-yl)methyl)phenoxy)propanoic acid

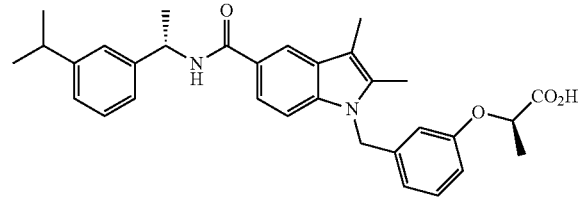 [SMILES: Cc1c(C)n(Cc2cccc(O[C@H](C)C(=O)O)c2)c2ccc(C(=O)N[C@@H](C)c3cccc(C(C)C)c3)cc12]

The title compound was prepared following the same protocol as described in Step 6, Example 36, using the (R)-methyl 2-(3-((5-(((S)-1-(3-isopropylphenyl)ethyl)carbamoyl)-2,3-dimethyl-1H-indol-1-yl)methyl)phenoxy)propanoate instead of the (S)-methyl 2-(4(5-((1-(3-cyclopropylphenyl)ethyl)carbamoyl)-2,3-dimethyl-1H-indol-1-yl)methyl)phenoxy)acetate. ESI-MS (m/z): 513 [MH]$^+$ Example 43: (R)-2-(3-((5-(((S)-1-(4-(tert-Butyl)phenyl)ethyl)carbamoyl)-2,3-dimethyl-1H-indol-1-yl)methyl)phenoxy)propanoic acid

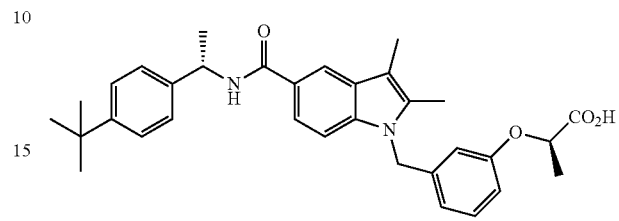

Step 1: (R)-Methyl 2-(3-((5-(((S)-1-(4-(tert-butyl)phenyl)ethyl)carbamoyl)-2,3-dimethyl-1H-indol-1-yl)methyl)phenoxy)propanoate

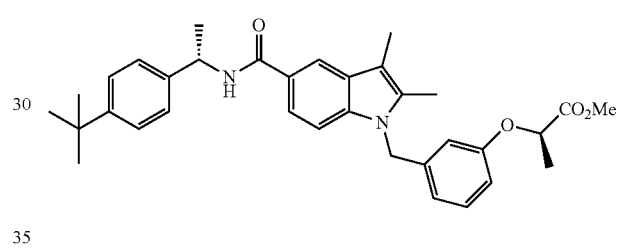

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the (R)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (R)-2-(3-((5-(((S)-1-(4-(tert-Butyl)phenyl)ethyl)carbamoyl)-2,3-dimethyl-1H-indol-1-yl)methyl)phenoxy)propanoic acid

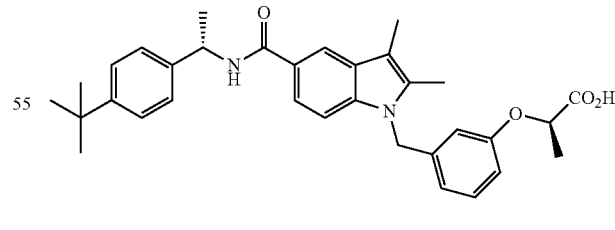

The title compound was prepared following the same protocol as described in Step 6, Example 36, using the (R)-methyl 2-(3-((5-(((S)-1-(4-(tert-butyl)phenyl)ethyl)carbamoyl)-2,3-dimethyl-1H-indol-1-yl)methyl)phenoxy)propanoate instead of the (S)-methyl 2-(4(5-((1-(3-cyclopropylphenyl)ethyl)carbamoyl)-2,3-dimethyl-1H-indol-1-yl)methyl)phenoxy)acetate. ESI-MS (m/z): 527 [MH]$^+$ Example 44: (S)-2-(3-((5-(((S)-1-(3-Isopropylphenyl)ethyl)carbamoyl)-2,3-dimethyl-1H-indol-1-yl)methyl)phenoxy)propanoic acid

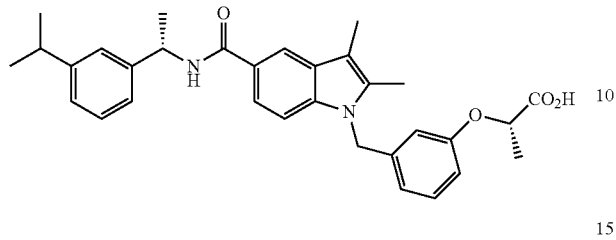

Step 1: (S)-Methyl 2-(m-tolyloxy)propanoate

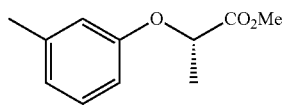

The title compound was prepared following the same protocol as described in Step 1, Example 42, using the (R)-methyl 2-hydroxypropanoate instead of the (S)-methyl 2-hydroxypropanoate.

Step 2: (S)-Methyl 2-(3-(bromomethyl)phenoxy)propanoate

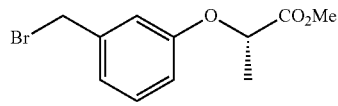

The title compound was prepared following the same protocol as described in Step 2, Example 36, using the (S)-methyl 2-(m-tolyloxy)propanoate instead of the methyl 2-(p-tolyloxy)acetate.

Step 3: (S)-Allyl 1-(3-((1-methoxy-1-oxopropan-2-yl)oxy)benzyl)-2,3-dimethyl-1H-indole-5-carboxylate

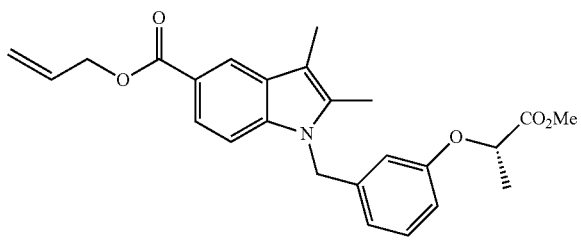 [SMILES: C=CCOC(=O)c1ccc2c(c1)c(C)c(C)n2Cc1cccc(O[C@@H](C)C(=O)OC)c1]

The title compound was prepared following the same general protocol as described in Step 3, Example 36, using the (S)-methyl 2-(3-(bromomethyl)phenoxy)propanoate instead of the methyl 2-(4-(bromomethyl)phenoxy)acetate. ESI-MS (m/z): 422 [M+H]⁺.

Step 4: (S)-1-(3-((1-Methoxy-1-oxopropan-2-yl)oxy)benzyl)-2,3-dimethyl-1H-indole-5-carboxylic acid

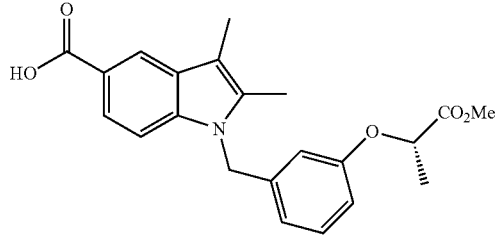 [SMILES: COC(=O)[C@H](C)Oc1cccc(Cn2c(C)c(C)c3cc(C(=O)O)ccc32)c1]

The title compound was prepared following the same general protocol as described in Step 4, Example 36, using the (S)-allyl 1-(3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]⁺.

Step 5: (S)-Methyl 2-(3-((5-(((S)-1-(3-isopropylphenyl)ethyl)carbamoyl)-2,3-dimethyl-1H-indol-1-yl)methyl)phenoxy)propanoate

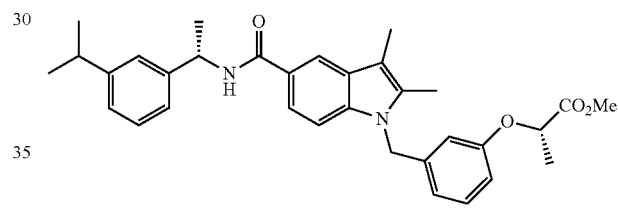

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-(((S)-1-(3-Isopropylphenyl)ethyl)carbamoyl)-2,3-dimethyl-1H-indol-1-yl)methyl)phenoxy)propanoic acid

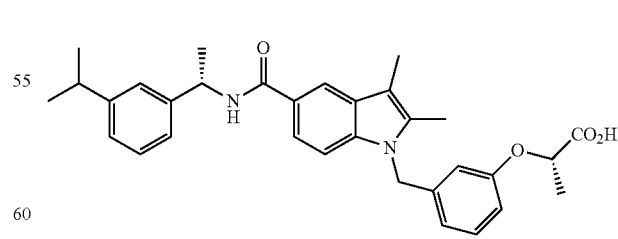

The title compound was prepared following the same protocol as described in Step 6, Example 36, using the (S)-methyl 2-(3-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 513 [M+H]+

Example 45: (S)-2-(3-((5-(((S)-1-(4-(tert-Butyl)phenyl)ethyl)carbamoyl)-2,3-dimethyl-1H-indol-1-yl)methyl)phenoxy)propanoic acid

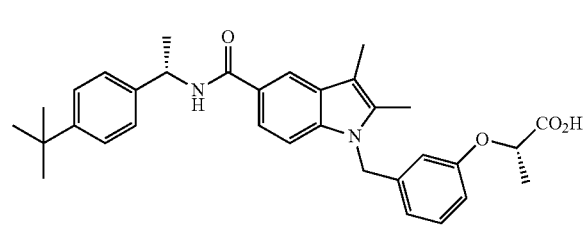 [SMILES: Cc1c(C)n(Cc2cccc(O[C@@H](C)C(=O)O)c2)c2ccc(C(=O)N[C@@H](C)c3ccc(C(C)(C)C)cc3)cc12]

Step 1: (S)-Methyl 2-(3-((5-(((S)-1-(4-(tert-butyl)phenyl)ethyl)carbamoyl)-2,3-dimethyl-1H-indol-1-yl)methyl)phenoxy)propanoate

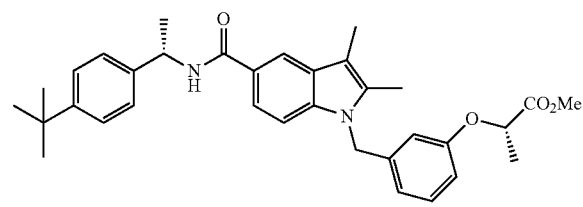 [SMILES: COC(=O)[C@H](C)Oc1cccc(Cn2c(C)c(C)c3cc(C(=O)N[C@@H](C)c4ccc(C(C)(C)C)cc4)ccc32)c1]

The title compound was prepared following the same protocol as described in Step 5, Example 36, using the (S)-1-(4-(tert-Butyl)phenyl)ethanamine hydrochloride instead of the (S)-1-(3-cyclopropylphenyl)ethanamine hydrochloride and the (S)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(4-(tert-Butyl)phenyl)ethyl)carbamoyl)-2,3-dimethyl-1H-indol-1-yl)methyl)phenoxy)propanoic acid

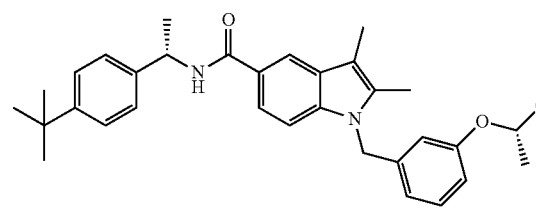

The title compound was prepared following the same protocol as described in Step 6, Example 36, using the (S)-methyl 2-(3-((5-(((S)-1-(4-(tert-Butyl)phenyl)ethyl)carbamoyl)-2,3-dimethyl-1H-indol-1-yl)methyl)phenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 527 [MH]+

Example 46: (S)-2-(3-((5-(((S)-1-(3-Cyclopropylphenyl)ethyl)carbamoyl)-2,3-dimethyl-1H-indol-1-yl)methyl)phenoxy)propanoic acid


Step 1: (S)-Methyl 2-(3-((5-(((S)-1-(3-cyclopropylphenyl)ethyl)carbamoyl)-2,3-dimethyl-1H-indol-1-yl)methyl)phenoxy)propanoate

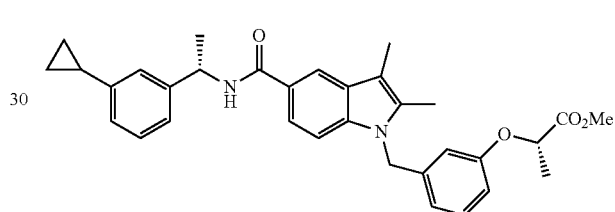

The title compound was prepared following the same protocol as described in Step 5, Example 36, using the (S)-1-(3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(3-Cyclopropylphenyl)ethyl)carbamoyl)-2,3-dimethyl-1H-indol-1-yl)methyl)phenoxy)propanoic acid

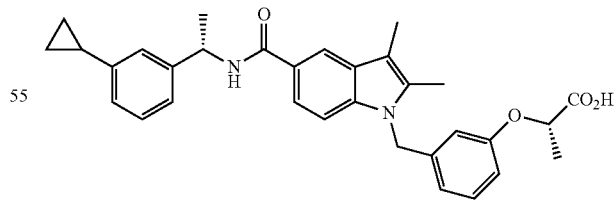

The title compound was prepared following the same protocol as described in Step 6, Example 36, using the (S)-methyl 2-(3-((5-(((S)-1-(3-cyclopropylphenyl)ethyl)carbamoyl)-2,3-dimethyl-1H-indol-1-yl)methyl)phenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 511 [MH]+

Example 47: (S)-2-(3-((5-((1-(3-Isopropylphenyl)ethyl)carbamoyl)-2,3-dimethyl-1H-indol-1-yl)methyl)phenoxy)-2-methylpropanoic acid

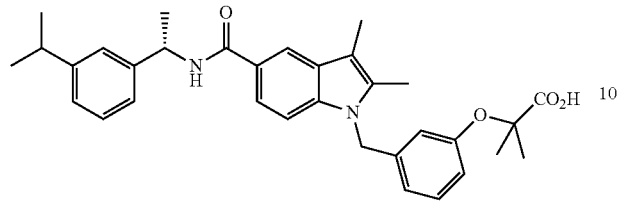

Step 1: Methyl 2-methyl-2-(m-tolyloxy)propanoate

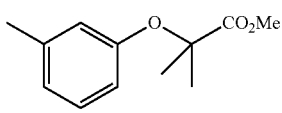

The title compound was prepared following the same protocol as described in Step 1, Example 36, using the m-cresol instead of the p-cresol and the methyl α-bromoisobutyrate instead of the methyl bromoacetate.

Step 2: Methyl 2-(3-(bromomethyl)phenoxy)-2-methylpropanoate

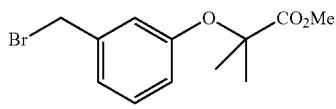 [SMILES: COC(=O)C(C)(C)Oc1cccc(CBr)c1]

The title compound was prepared following the same protocol as described in Step 2, Example 36, using the methyl 2-methyl-2-(m-tolyloxy)propanoate instead of the methyl 2-(p-tolyloxy)acetate.

Step 3: Allyl 1-(3-((1-methoxy-2-methyl-1-oxopropan-2-yl)oxy)benzyl)-2,3-dimethyl-1H-indole-5-carboxylate

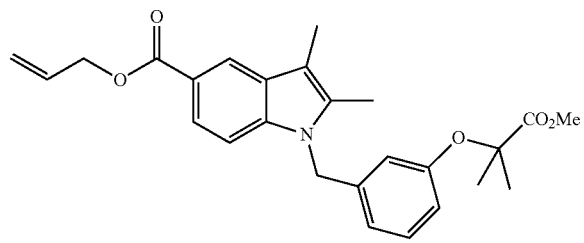 [SMILES: C=CCOC(=O)c1ccc2c(c1)c(C)c(C)n2Cc1cccc(OC(C)(C)C(=O)OC)c1]

The title compound was prepared following the same general protocol as described in Step 3, Example 36, using the methyl 2-(3-(bromomethyl)phenoxy)-2-methylpropanoate instead of the methyl 2-(4-(bromomethyl)phenoxy)acetate. ESI-MS (m/z): 436 [M+H]$^+$.

Step 4: 1-(3-((1-Methoxy-2-methyl-1-oxopropan-2-yl)oxy)benzyl)-2,3-dimethyl-1H-indole-5-carboxylic acid

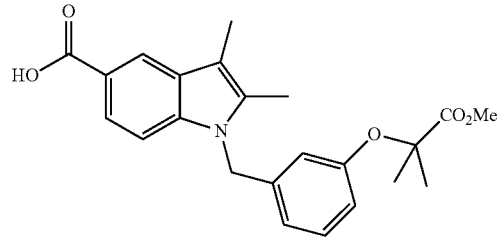 [SMILES: COC(=O)C(C)(C)Oc1cccc(Cn2c(C)c(C)c3cc(C(=O)O)ccc32)c1]

The title compound was prepared following the same general protocol as described in Step 4, Example 36, using the allyl 1-(3-((1-methoxy-2-methyl-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 396 [M+H]$^+$.

Step 5: (S)-Methyl 2-(3-((5-((1-(3-isopropylphenyl)ethyl)carbamoyl)-2,3-dimethyl-1H-indol-1-yl)methyl)phenoxy)-2-methylpropanoate

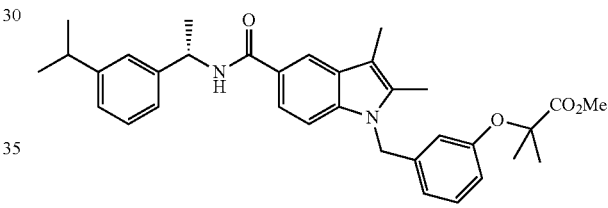

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(3-((1-methoxy-2-methyl-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-((1-(3-Isopropylphenyl)ethyl)carbamoyl)-2,3-dimethyl-1H-indol-1-yl)methyl)phenoxy)-2-methylpropanoic acid

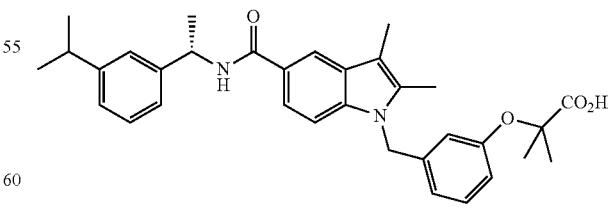

The title compound was prepared following the same protocol as described in Step 6, Example 36, using the (S)-methyl 2-(3-((5-((1-(3-isopropylphenyl)ethyl)carbamoyl)-2,3-dimethyl-1H-indol-1-yl)methyl)phenoxy)-2-methylpropanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [MH]+

Example 48: (S)-2-(3-((5-((1-(4-(tert-Butyl)phenyl)ethyl)carbamoyl)-2,3-dimethyl-1H-indol-1-yl)methyl)phenoxy)-2-methylpropanoic acid

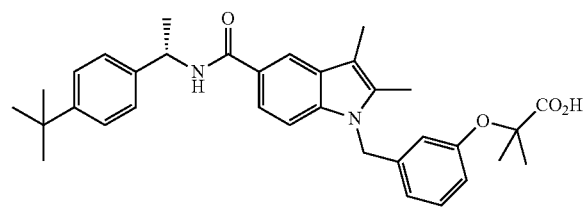 [SMILES: Cc1c(C)n(Cc2cccc(OC(C)(C)C(=O)O)c2)c2ccc(C(=O)N[C@@H](C)c3ccc(C(C)(C)C)cc3)cc12]

Step 1: (S)-Methyl 2-(3-((5-((1-(4-(tert-butyl)phenyl)ethyl)carbamoyl)-2,3-dimethyl-1H-indol-1-yl)methyl)phenoxy)-2-methylpropanoate

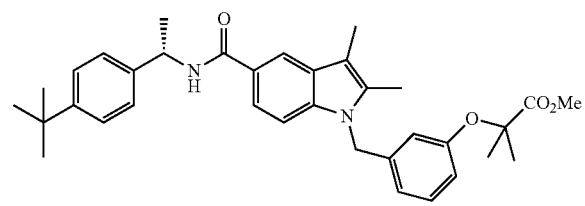 [SMILES: COC(=O)C(C)(C)Oc1cccc(Cn2c(C)c(C)c3cc(C(=O)N[C@@H](C)c4ccc(C(C)(C)C)cc4)ccc32)c1]

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the 1-(3-(1-methoxy-2-methyl-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-((1-(4-(tert-Butyl)phenyl)ethyl)carbamoyl)-2,3-dimethyl-1H-indol-1-yl)methyl)phenoxy)-2-methylpropanoic acid

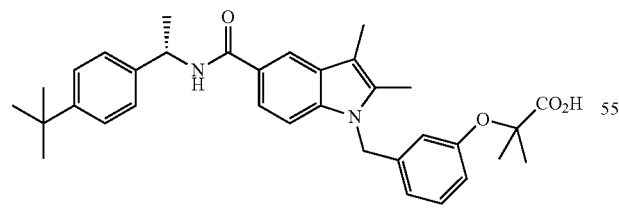

The title compound was prepared following the same protocol as described in Step 6, Example 36, using the (S)-methyl 2-(3-((5-((1-(4-(tert-butyl)phenyl)ethyl)carbamoyl)-2,3-dimethyl-1H-indol-1-yl)methyl)phenoxy)-2-methylpropanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 541 [MH]+

Example 49: (S)-1-(3-(Cyanomethoxy)benzyl)-N-(1-(3-isopropylphenyl)ethyl)-2,3-dimethyl-1H-indole-5-carboxamide

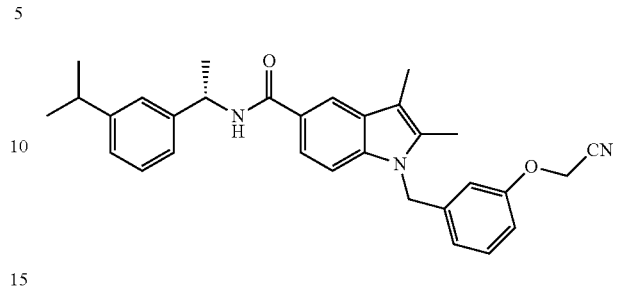

Step 1: 2-(m-Tolyloxy)acetonitrile

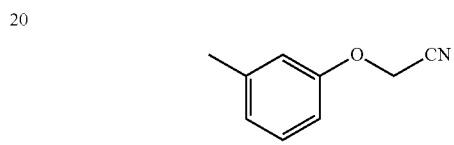

The title compound was prepared following the same protocol as described in Step 1, Example 36, using the m-cresol instead of the p-cresol and the bromoacetonitrile instead of the methyl bromoacetate.

Step 2: 2-(3-(Bromomethyl)phenoxy)acetonitrile

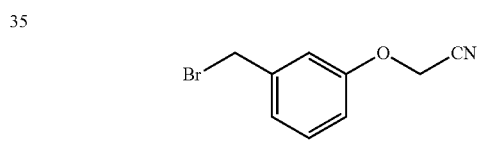

The title compound was prepared following the same protocol as described in Step 2, Example 36, using the 2-(m-Tolyloxy)acetonitrile instead of the methyl 2-(p-tolyloxy)acetate.

Step 3: Allyl 1-(3-(cyanomethoxy)benzyl)-2,3-dimethyl-1H-indole-5-carboxylate

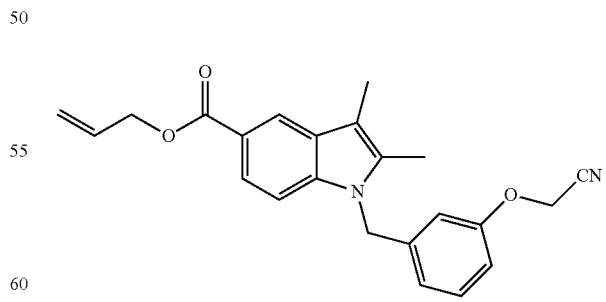

The title compound was prepared following the same general protocol as described in Step 3, Example 36, using the 2-(3-(Bromomethyl)phenoxy)acetonitrile instead of the methyl 2-(4-(bromomethyl)phenoxy)acetate. ESI-MS (m/z): 375 [M+H]+.

Step 4: 1-(3-(Cyanomethoxy)benzyl)-2,3-dimethyl-1H-indole-5-carboxylic acid

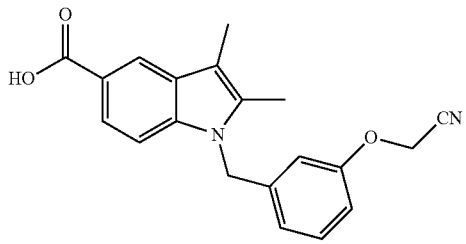 [SMILES: Cc1c(C)n(Cc2cccc(OCC#N)c2)c2ccc(C(=O)O)cc12]

The title compound was prepared following the same general protocol as described in Step 4, Example 36, using the allyl 1-(3-(cyanomethoxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 335 [M+H]+.

Step 5: (S)-1-(3-(Cyanomethoxy)benzyl)-N-(1-(3-isopropylphenyl)ethyl)-2,3-dimethyl-1H-indole-5-carboxamide

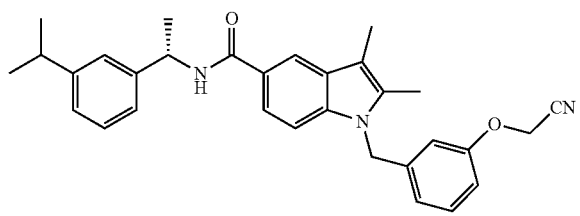 [SMILES: Cc1c(C)n(Cc2cccc(OCC#N)c2)c2ccc(C(=O)N[C@@H](C)c3cccc(C(C)C)c3)cc12]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(3-(cyanomethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid. ESI-MS (m/z): 480 [M+H]+.

Example 50: (S)—N-(1-(4-(tert-Butyl)phenyl)ethyl)-1-(3-(cyanomethoxy)benzyl)-2,3-dimethyl-1H-indole-5-carboxamide

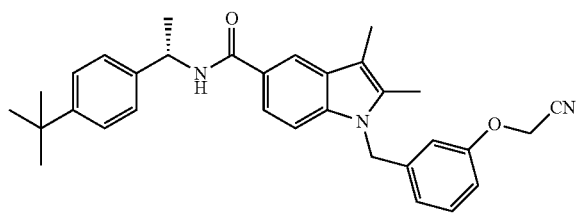 [SMILES: Cc1c(C)n(Cc2cccc(OCC#N)c2)c2ccc(C(=O)N[C@@H](C)c3ccc(C(C)(C)C)cc3)cc12]

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride and the 1-(3-(cyanomethoxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid. ESI-MS (m/z): 494 [M+H]+.

Example 51: (S)-2-(4-((5-(((S)-1-(3-Isopropylphenyl)ethyl)carbamoyl)-2,3-dimethyl-1H-indol-1-yl)methyl)phenoxy)propanoic acid

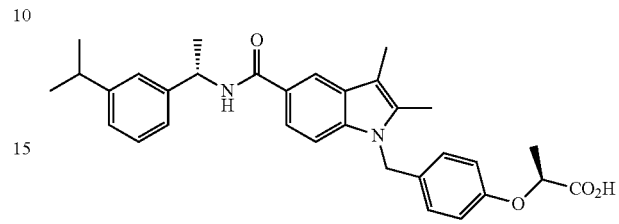

Step 1: (S)-Methyl 2-(p-tolyloxy)propanoate

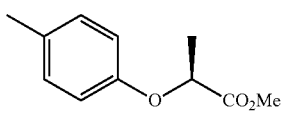

The title compound was prepared following the same protocol as described in Step 1, Example 42, using the p-cresol instead of the m-cresol and the (R)-methyl 2-hydroxypropanoate instead of the (S)-methyl 2-hydroxypropanoate.

Step 2: (S)-Methyl 2-(4-(bromomethyl)phenoxy)propanoate

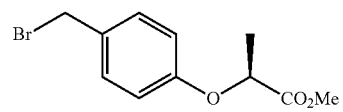

The title compound was prepared following the same protocol as described in Step 2, Example 36, using the (S)-methyl 2-(p-tolyloxy)propanoate instead of the methyl 2-(p-tolyloxy)acetate.

Step 3: (S)-Allyl 1-(4-((1-methoxy-1-oxopropan-2-yl)oxy)benzyl)-2,3-dimethyl-1H-indole-5-carboxylate

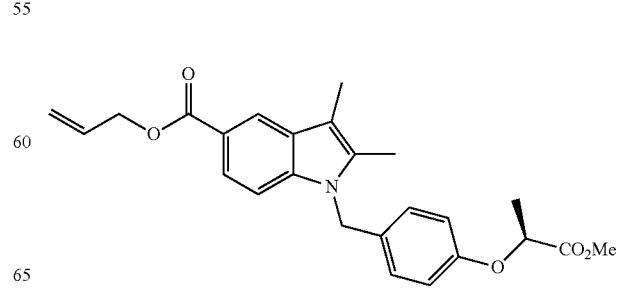

The title compound was prepared following the same general protocol as described in Step 3, Example 36, using the (S)-methyl 2-(4-(bromomethyl)phenoxy)propanoate instead of the methyl 2-(4-(bromomethyl)phenoxy)acetate. ESI-MS (m/z): 422 [M+H]+.

Step 4: (S)-1-(4-((1-Methoxy-1-oxopropan-2-yl)oxy)benzyl)-2,3-dimethyl-1H-indole-5-carboxylic acid

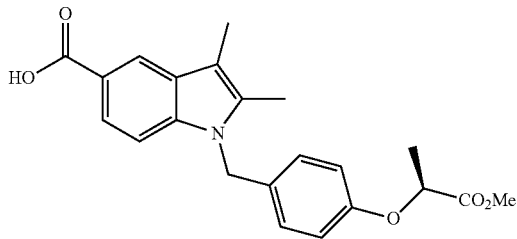 [SMILES: COC(=O)[C@H](C)Oc1ccc(Cn2c(C)c(C)c3cc(C(=O)O)ccc32)cc1]

The title compound was prepared following the same general protocol as described in Step 4, Example 36, using the (S)-allyl 1-(4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]+.

Step 5: (S)-Methyl 2-(4-((5-(((S)-1-(3-isopropylphenyl)ethyl)carbamoyl)-2,3-dimethyl-1H-indol-1-yl)methyl)phenoxy)propanoate

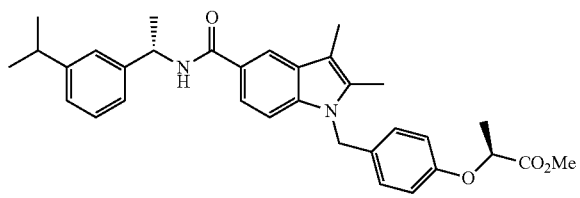 [SMILES: COC(=O)[C@H](C)Oc1ccc(Cn2c(C)c(C)c3cc(C(=O)N[C@@H](C)c4cccc(C(C)C)c4)ccc32)cc1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(4-(1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-((5-(((S)-1-(4-Isopropylphenyl)ethyl)carbamoyl)-2,3-dimethyl-1H-indol-1-yl)methyl)phenoxy)propanoic acid

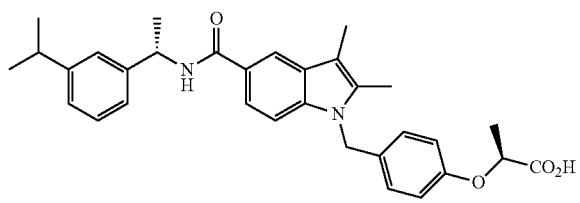 [SMILES: Cc1c(C)n(Cc2ccc(O[C@@H](C)C(=O)O)cc2)c2ccc(C(=O)N[C@@H](C)c3cccc(C(C)C)c3)cc12]

The title compound was prepared following the same protocol as described in Step 6, Example 36, using the (S)-methyl 2-(4-(((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]+

Example 52: (S)-2-(4-((5-(((S)-1-(3-Cyclopropylphenyl)ethyl)carbamoyl)-2,3-dimethyl-1H-indol-1-yl)methyl)phenoxy)propanoic acid

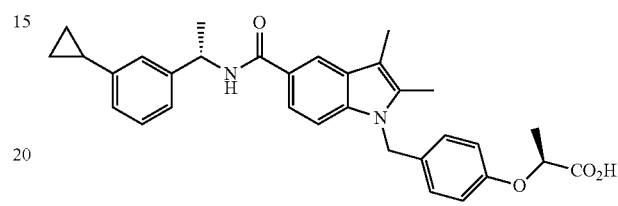

Step 1: (S)-Methyl 2-(4-((5-(((S)-1-(3-cyclopropylphenyl)ethyl)carbamoyl)-2,3-dimethyl-1H-indol-1-yl)methyl)phenoxy)propanoate

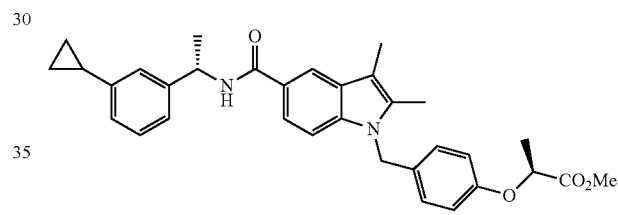

The title compound was prepared following the same protocol as described in Step 5, Example 36, using the (S)-1-(4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(4(5-(((S)-1-(3-Cyclopropylphenyl)ethyl)carbamoyl)-2,3-dimethyl-1H-indol-1-yl)methyl)phenoxy)propanoic acid

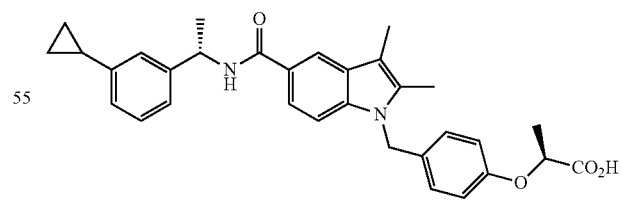

The title compound was prepared following the same protocol as described in Step 6, Example 36, using the (S)-methyl 2-(4-(((5-(((S)-1-(3-cyclopropylphenyl)ethyl)carbamoyl)-2,3-dimethyl-1H-indol-1-yl)methyl)phenoxy) propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 511 [MH]+

Example 53: (R)-2-(4-((5-(((S)-1-(3-Isopropylphenyl)ethyl)carbamoyl)-2,3-dimethyl-1H-indol-1-yl)methyl)phenoxy)propanoic acid

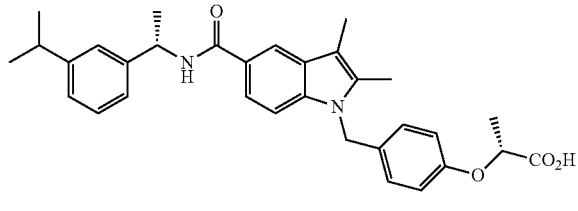

Step 1: (R)-Methyl 2-(p-tolyloxy)propanoate

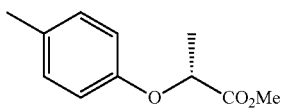

The title compound was prepared following the same protocol as described in Step 1, Example 42, using the p-cresol instead of the m-cresol.

Step 2: (R)-Methyl 2-(4-(bromomethyl)phenoxy)propanoate

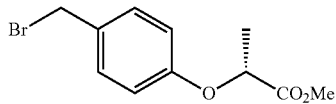

The title compound was prepared following the same protocol as described in Step 2, Example 36, using the (R)-methyl 2-(p-tolyloxy)propanoate instead of the methyl 2-(p-tolyloxy)acetate.

Step 3: (R)-Allyl 1-(4-((1-methoxy-1-oxopropan-2-yl)oxy)benzyl)-2,3-dimethyl-1H-indole-5-carboxylate

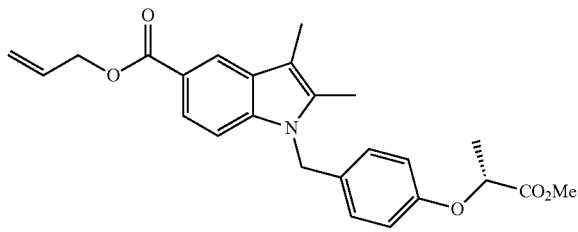 [SMILES: C=CCOC(=O)c1ccc2c(c1)c(C)c(C)n2Cc1ccc(O[C@H](C)C(=O)OC)cc1]

The title compound was prepared following the same general protocol as described in Step 3, Example 36, using the (R)-methyl 2-(4-(bromomethyl)phenoxy)propanoate instead of the methyl 2-(4-(bromomethyl)phenoxy)acetate. ESI-MS (m/z): 422 [M+H]$^+$.

Step 4: (R)-1-(4-((1-Methoxy-1-oxopropan-2-yl)oxy)benzyl)-2,3-dimethyl-1H-indole-5-carboxylic acid

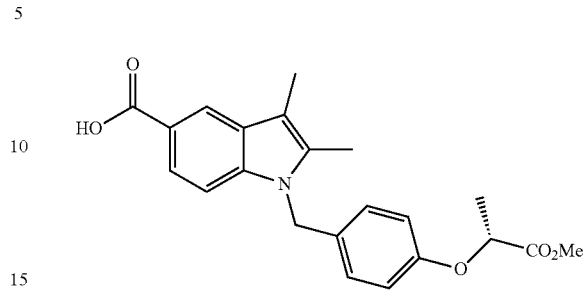

The title compound was prepared following the same general protocol as described in Step 4, Example 36, using the (R)-allyl 1-(4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 368 [M+H]$^+$.

Step 5: (R)-Methyl 2-(4-((5-(((S)-1-(3-isopropylphenyl)ethyl)carbamoyl)-2,3-dimethyl-1H-indol-1-yl)methyl)phenoxy)propanoate

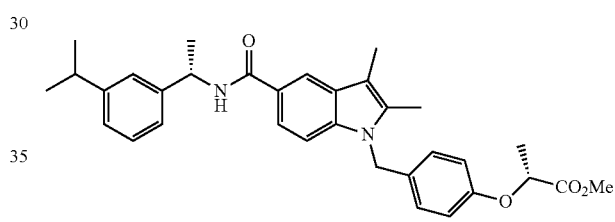

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(4-Isopropylphenyl)ethyl)carbamoyl)-2,3-dimethyl-1H-indol-1-yl)methyl)phenoxy)propanoic acid

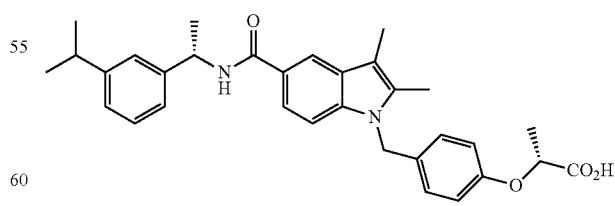

The title compound was prepared following the same protocol as described in Step 6, Example 36, using the (R)-methyl 2-(4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 513 [MH]+

Example 54: (S)-2-(4-((5-((1-(3-Isopropylphenyl)ethyl)carbamoyl)-2,3-dimethyl-1H-indol-1-yl)methyl)phenoxy)-2-methylpropanoic acid

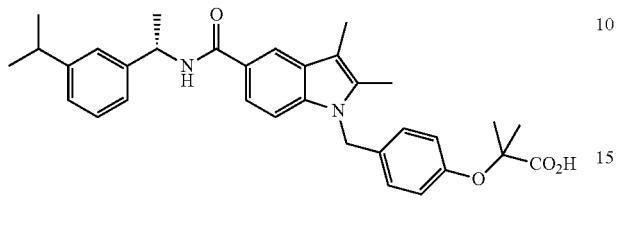

Step 1: Methyl 2-methyl-2-(p-tolyloxy)propanoate

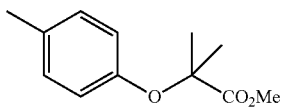

The title compound was prepared following the same protocol as described in Step 1, Example 36, using the methyl α-bromoisobutyrate instead of the methyl bromoacetate.

Step 2: Methyl 2-(4-(bromomethyl)phenoxy)-2-methylpropanoate

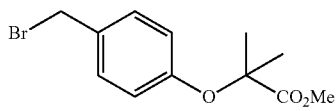 [SMILES: COC(=O)C(C)(C)Oc1ccc(CBr)cc1]

The title compound was prepared following the same protocol as described in Step 2, Example 36, using the methyl 2-methyl-2-(p-tolyloxy)propanoate instead of the methyl 2-(p-tolyloxy)acetate Step 3: Allyl 1-(4-((1-methoxy-2-methyl-1-oxopropan-2-yl)oxy)benzyl)-2,3-dimethyl-1H-indole-5-carboxylate

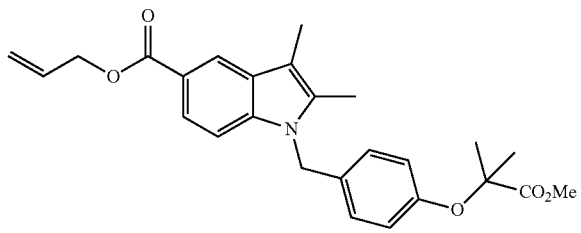 [SMILES: C=CCOC(=O)c1ccc2c(c1)c(C)c(C)n2Cc1ccc(OC(C)(C)C(=O)OC)cc1]

The title compound was prepared following the same general protocol as described in Step 3, Example 36, using the methyl 2-(4-(bromomethyl)phenoxy)-2-methylpropanoate instead of the methyl 2-(4-(bromomethyl)phenoxy)acetate. ESI-MS (m/z): 436 [M+H]+.

Step 4: 1-(4-((1-Methoxy-2-methyl-1-oxopropan-2-yl)oxy)benzyl)-2,3-dimethyl-1H-indole-5-carboxylic acid

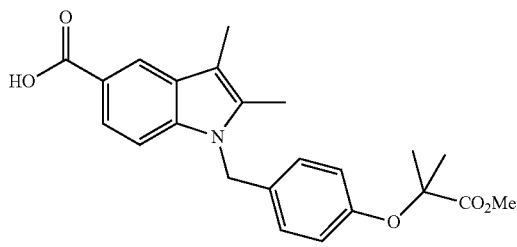 [SMILES: COC(=O)C(C)(C)Oc1ccc(Cn2c(C)c(C)c3cc(C(=O)O)ccc32)cc1]

The title compound was prepared following the same general protocol as described in Step 4, Example 36, using the allyl 1-(4-(1-methoxy-2-methyl-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 396 [M+H]+.

Step 5: (S)-Methyl 2-(4-((5-((1-(3-isopropylphenyl)ethyl)carbamoyl)-2,3-dimethyl-1H-indol-1-yl)methyl)phenoxy)-2-methylpropanoate

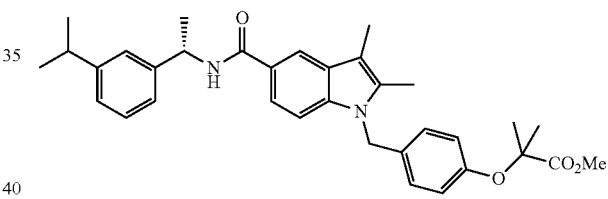

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the 1-(4-((1-methoxy-2-methyl-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-((5-((1-(3-Isopropylphenyl)ethyl)carbamoyl)-2,3-dimethyl-1H-indol-1-yl)methyl)phenoxy)-2-methylpropanoic acid

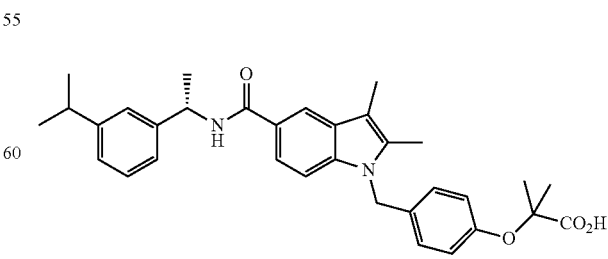

The title compound was prepared following the same protocol as described in Step 6, Example 36, using the (S)-methyl 2-(4-(((5-((1-(3-isopropylphenyl)ethyl)carbamoyl)-2,3-dimethyl-1H-indol-1-yl)methyl)phenoxy)-2-methylpropanoate instead of the (S)-methyl 2-(4(5-((1-(3-cyclopropylphenyl)ethyl)carbamoyl)-2,3-dimethyl-1H-indol-1-yl)methyl)phenoxy)acetate. ESI-MS (m/z): 527 [MH]⁺

Example 55: (S)-2-(2-Chloro-5-((5-(((S)-1-(3-isopropylphenyl)ethyl)carbamoyl)-2,3-dimethyl-1H-indol-1-yl)methyl)phenoxy)propanoic acid

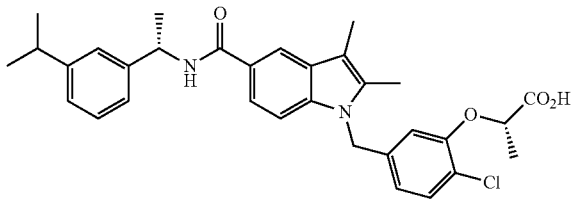 [SMILES: Cc1c(C)n(Cc2ccc(Cl)c(O[C@@H](C)C(=O)O)c2)c2ccc(C(=O)N[C@@H](C)c3cccc(C(C)C)c3)cc12]

Step 1: (S)-Methyl 2-(2-chloro-5-methylphenoxy)propanoate

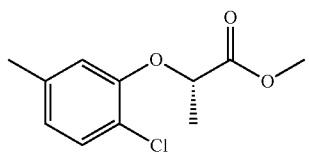

To a solution of the 2-chloro-5-methylphenol (4.0 g, 28 mmol) in anhydrous THF (24 mL) at 0° C. under argon protection was added triphenylphosphine (9.5 g, 36.4 mmol), followed by addition of the (R)-methyl 2-hydroxypropanoate (3.89 g, 31 mmol). Then DIAD (8.2 mL, 42 mmol) was added slowly to the solution at 0° C. The reaction mixture was stirred at room temperature for 20 h. The solvent was removed and the crude was purified by flash chromatography (AcOEt/hexane 0~30%) to obtain the title compound.

Step 2: (S)-Methyl 2-(5-(bromomethyl)-2-chlorophenoxy)propanoate

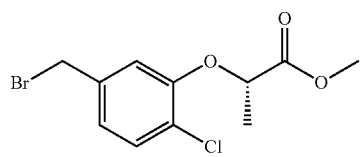 [SMILES: COC(=O)[C@H](C)Oc1cc(CBr)ccc1Cl]

To (S)-methyl 2-(2-chloro-5-methylphenoxy)propanoate (2.4 g, 10.5 mmol) in CCl₄ (20 mL) was added NBS (1.92 g, 11.55 mmol) and AIBN (0.35 g, 2.1 mmol). The mixture was refluxed overnight. The reaction mixture was cooled and the solvent was removed to obtain the crude. The crude was purified by flash chromatography (AcOEt/Hexane 0~30%) to obtain the title compound.

Step 3: (S)-Allyl 1-(4-chloro-3-((1-methoxy-1-oxopropan-2-yl)oxy)benzyl)-2,3-dimethyl-1H-indole-5-carboxylate

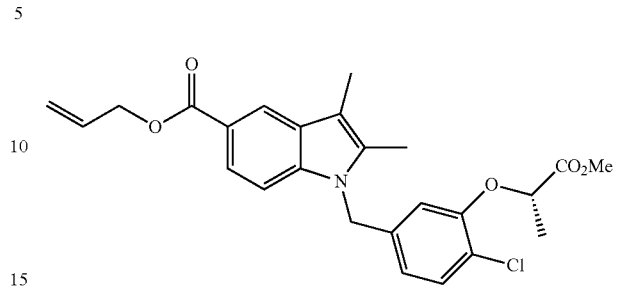

The title compound was prepared following the same general protocol as described for the synthesis of the (S)-allyl 1-(2-chloro-5-((1-methoxy-1-oxopropan-2-yl)oxy)benzyl)-2,3-dimethyl-1H-indole-5-carboxylate (Step 3, Example 26), using the (S)-methyl 2-(5-(bromomethyl)-2-chlorophenoxy)propanoate instead of the (S)-methyl 2-(3-(bromomethyl)-4-chlorophenoxy)propanoate ESI-MS (m/z): 456 [M+1]⁺.

Step 4: (S)-1-(4-Chloro-3-((1-methoxy-1-oxopropan-2-yl)oxy)benzyl)-2,3-dimethyl-1H-indole-5-carboxylic acid

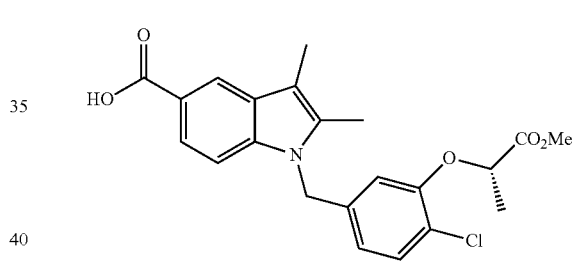

The title compound was prepared following the same general protocol as described for the synthesis of the (S)-1-(2-chloro-5-((1-methoxy-1-oxopropan-2-yl)oxy)benzyl)-2,3-dimethyl-1H-indole-5-carboxylic acid (Step 4, Example 26), using the (S)-allyl 1-(4-chloro-3-((1-methoxy-1-oxopropan-2-yl)oxy)benzyl)-2,3-dimethyl-1H-indole-5-carboxylate instead of the (5)-allyl 1-(2-chloro-5-((1-methoxy-1-oxopropan-2-yl)oxy)benzyl)-2,3-dimethyl-1H-indole-5-carboxylate. ESI-MS (m/z): 416 [M+1]⁺.

Step 5: (S)-Methyl 2-(2-chloro-5-((5-(((S)-1-(3-isopropylphenyl)ethyl)carbamoyl)-2,3-dimethyl-1H-indol-1-yl)methyl)phenoxy)propanoate

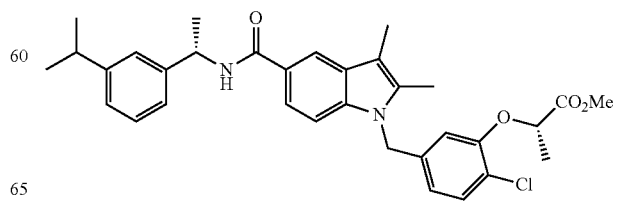

The (S)-1-(4-chloro-3-((1-methoxy-1-oxopropan-2-yl)oxy)benzyl)-2,3-dimethyl-1H-indole-5-carboxylic acid (55 mg, 0.13 mmol), the (S)-1-(3-isopropylphenyl)ethanamine hydrochloride (37 mg, 0.19 mmol) and HATU (61 mg, 0.16 mmol) were dissolved in DMF (3 mL) and DIEA (0.1 mL). It was stirred for 15 h. The solution was filtered and purified by preparative HPLC.

Step 6: (S)-2-(2-Chloro-5-((5-(((S)-1-(3-isopropylphenyl)ethyl)carbamoyl)-2,3-dimethyl-1H-indol-1-yl)methyl)phenoxy)propanoic acid

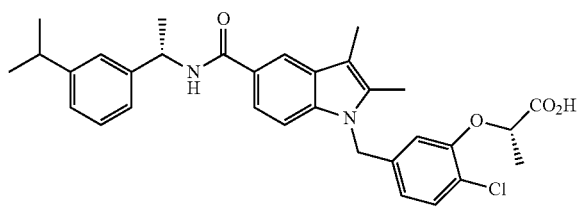 [SMILES: Cc1c(C)n(Cc2ccc(Cl)c(O[C@@H](C)C(=O)O)c2)c2ccc(C(=O)N[C@@H](C)c3cccc(C(C)C)c3)cc12]

The (S)-methyl 2-(2-chloro-5-((5-(((S)-1-(3-isopropylphenyl)ethyl)carbamoyl)-2,3-dimethyl-1H-indol-1-yl)methyl)phenoxy)propanoate was dissolved in methanol (1.5 mL), DMSO (~1.5 mL) and water (0.1 mL) then NaOH (2 N, 0.1 mL) was added dropwise. The reaction was monitored by LC/MS. It was stirred until all the starting material was consumed (~3 h). It was acidified with trifluoroacetic acid, filtered and purified by preparative HPLC to yield the title compound. ESI-MS (m/z): 547.1 [M+H]$^+$.

Example 56: (S)-2-(2-Chloro-5-((5-(((S)-1-(3-cyclopropylphenyl)ethyl)carbamoyl)-2,3-dimethyl-1H-indol-1-yl)methyl)phenoxy)propanoic acid

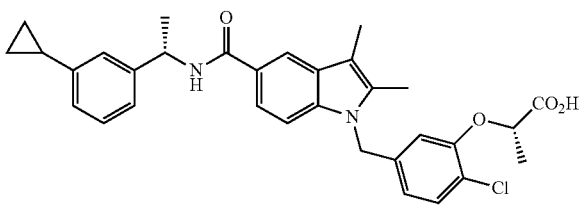

A similar procedure was followed as described in the previous example (Example 20) to yield the title compound. ESI-MS (m/z): 545.1 [M+H]$^+$.

Example 57: (S)-2-(5-((5-(((S)-1-(4-Bromophenyl)ethyl)carbamoyl)-2,3-dimethyl-1H-indol-1-yl)methyl)-2-chlorophenoxy)propanoic acid

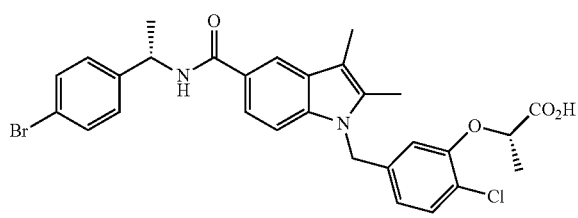 [SMILES: Cc1c(C)n(Cc2ccc(Cl)c(O[C@@H](C)C(=O)O)c2)c2ccc(C(=O)N[C@@H](C)c3ccc(Br)cc3)cc12]

A similar procedure was followed as described in the previous example (Example 20) using (S)-1-(4-bromophenyl)ethanamine to yield the title compound. ESI-MS (m/z): 585.0 [M+H]$^+$.

Example 58: (S)-2-(5-((5-(((S)-1-(4-(tert-Butyl)phenyl)ethyl)carbamoyl)-2,3-dimethyl-1H-indol-1-yl)methyl)-2-chlorophenoxy)propanoic acid

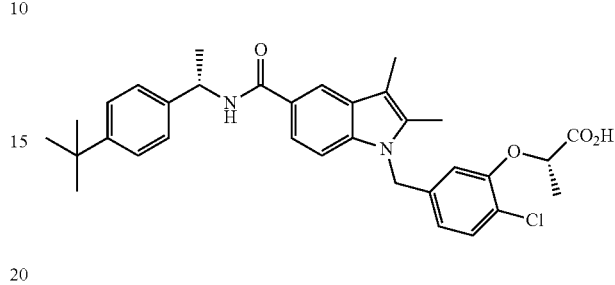

Step 1: (S)-Methyl 2-(5-((5-(((S)-1-(4-(tert-butyl)phenyl)ethyl)carbamoyl)-2,3-dimethyl-1H-indol-1-yl)methyl)-2-chlorophenoxy)propanoate

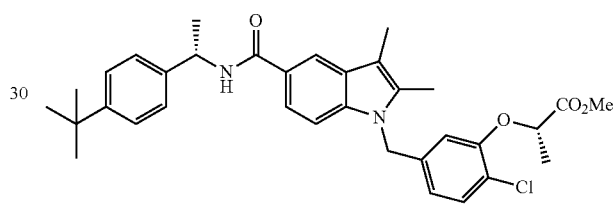

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride the (S)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(5-((5-(((S)-1-(4-(tert-Butyl)phenyl)ethyl)carbamoyl)-2,3-dimethyl-1H-indol-1-yl)methyl)-2-chlorophenoxy)propanoic acid

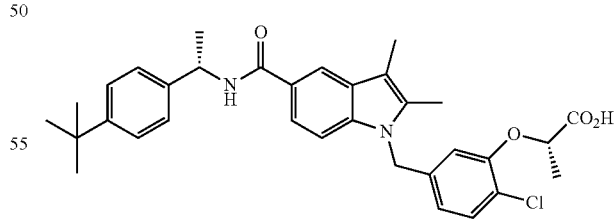

The title compound was prepared following the same protocol as described in Step 6, Example 36, using the (S)-methyl 2-(5-((5-(((S)-1-(4-(tert-butyl)phenyl)ethyl)carbamoyl)-2,3-dimethyl-1H-indol-1-yl)methyl)-2-chlorophenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 59: (S)-2-(5-((5-(((S)-1-(3-(tert-Butyl)phenyl)ethyl)carbamoyl)-2,3-dimethyl-1H-indol-1-yl)methyl)-2-chlorophenoxy)propanoic acid Example 60: (S)-2-(2-Chloro-5-((5-(((S)-1-(3-isopropoxyphenyl)ethyl)carbamoyl)-2,3-dimethyl-1H-indol-1-yl)methyl)phenoxy)propanoic acid

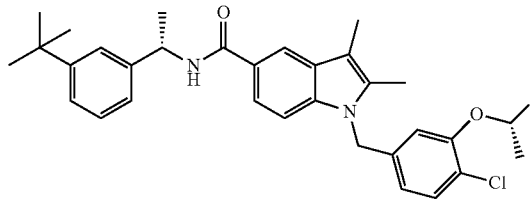

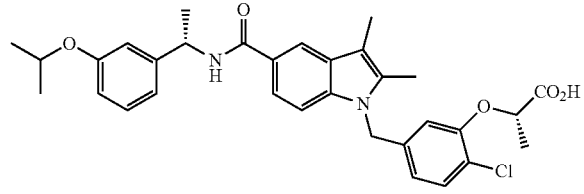

Step 1: (S)-Methyl 2-(5-((5-(((S)-1-(3-(tert-butyl)phenyl)ethyl)carbamoyl)-2,3-dimethyl-1H-indol-1-yl)methyl)-2-chlorophenoxy)propanoate Step 1: (S)-Methyl 2-(5-((5-(((S)-1-(3-isopropoxyphenyl)ethyl)carbamoyl)-2,3-dimethyl-1H-indol-1-yl)methyl)-2-chlorophenoxy)propanoate

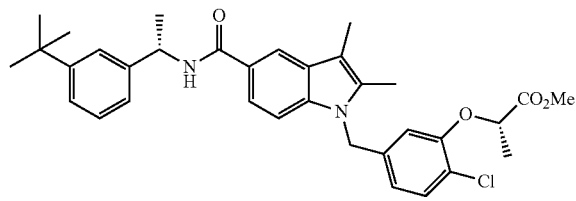 [SMILES: COC(=O)[C@H](C)Oc1cc(Cn2c(C)c(C)c3cc(C(=O)N[C@@H](C)c4cccc(C(C)(C)C)c4)ccc32)ccc1Cl]

The title compound was prepared following the same protocol as described in Step 5, Example 36, using the (S)-1-(3-(tert-butyl)phenyl)ethanamine hydrochloride instead of the (S)-1-(3-cyclopropylphenyl)ethanamine hydrochloride the (S)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

The title compound was prepared following the same protocol as described in Step 5, Example 36, using the (S)-1-(3-isopropoxyphenyl)ethanamine hydrochloride instead of the (S)-1-(3-cyclopropylphenyl)ethanamine hydrochloride and (S)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(5-((5-(((S)-1-(3-(tert-Butyl)phenyl)ethyl)carbamoyl)-2,3-dimethyl-1H-indol-1-yl)methyl)-2-chlorophenoxy)propanoic acid Step 2: (S)-2-(5-((5-(((S)-1-(3-isopropoxyphenyl)ethyl)carbamoyl)-2,3-dimethyl-1H-indol-1-yl)methyl)-2-chlorophenoxy)propanoic acid

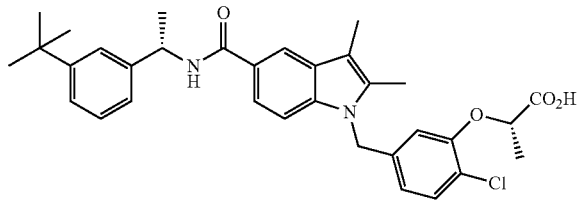 [SMILES: Cc1c(C)n(Cc2ccc(Cl)c(O[C@@H](C)C(=O)O)c2)c2ccc(C(=O)N[C@@H](C)c3cccc(C(C)(C)C)c3)cc12]

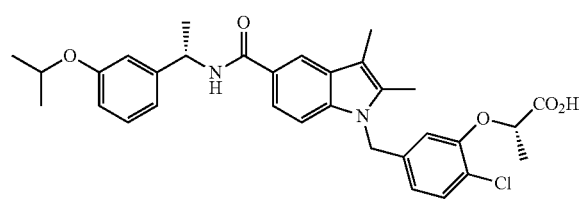 [SMILES: Cc1c(C)n(Cc2ccc(Cl)c(O[C@@H](C)C(=O)O)c2)c2ccc(C(=O)N[C@@H](C)c3cccc(OC(C)C)c3)cc12]

The title compound was prepared following the same protocol as described in Step 6, Example 36, using the (S)-methyl 2-(5-((5-(((S)-1-(4-(tert-butyl)phenyl)ethyl)carbamoyl)-2,3-dimethyl-1H-indol-1-yl)methyl)-2-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ The title compound was prepared following the same protocol as described in Step 6, Example 36, using the (S)-methyl 2-(5-((5-(((S)-1-(3-isopropoxyphenyl)ethyl)carbamoyl)-2,3-dimethyl-1H-indol-1-yl)methyl)-2-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 61: (S)-2-(4-Chloro-3-((5-(((S)-1-(3-iso-propylphenyl)ethyl)carbamoyl)-2,3-dimethyl-1H-indol-1-yl)methyl)phenoxy)propanoic acid

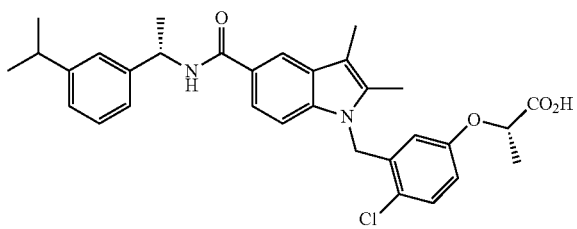 [SMILES: Cc1c(C)n(Cc2cc(O[C@@H](C)C(=O)O)ccc2Cl)c2ccc(C(=O)N[C@@H](C)c3cccc(C(C)C)c3)cc12]

Step 1: (S)-Methyl 2-(4-chloro-3-methylphenoxy)propanoate

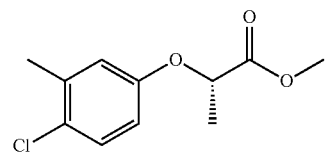

The title compound was prepared following the same general protocol as described for the synthesis of the (S)-methyl 2-(2-chloro-5-methylphenoxy)propanoate (Step 1, Example 55), using the 4-chloro-3-methylphenol instead of the 2-chloro-5-methylphenol.

Step 2: (S)-Methyl 2-(3-(bromomethyl)-4-chlorophenoxy)propanoate

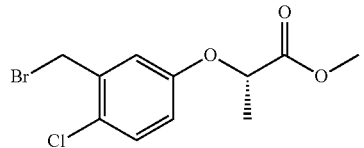 [SMILES: COC(=O)[C@H](C)Oc1ccc(Cl)c(CBr)c1]

The title compound was prepared following the same general protocol as described for the synthesis of the (S)-methyl 2-(5-(bromomethyl)-2-chlorophenoxy)propanoate (Step 2, Example 55), using the (S)-methyl 2-(4-chloro-3-methylphenoxy)propanoate instead of the (S)-methyl 2-(2-chloro-5-methylphenoxy)propanoate.

Step 3: (S)-Allyl 1-(2-chloro-5-((1-methoxy-1-oxopropan-2-yl)oxy)benzyl)-2,3-dimethyl-1H-indole-5-carboxylate

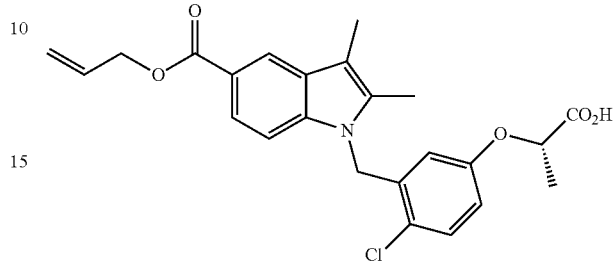

To a solution of the allyl 2,3-dimethyl-1H-indole-5-carboxylate (0.34 g, 1.483 mmol) in anhydrous DMF (3 mL) at 0° C. under argon protection was added NaH (0.08 g, 2.22 mmol). The mixture was stirred at rt for 30 min and re-cooled to 0° C., and then the (S)-methyl 2-(3-(bromomethyl)-4-chlorophenoxy)propanoate (0.55 g, 1.78 mmol) was added. The reaction was stirred at rt for another 1 h. The solvent was removed to obtain the crude, which was dissolved in EtOAc, then washed with water and brine and dried over $Na_2SO_4$. The solvent was removed to obtain the crude. The crude was purified by flash chromatography (AcOEt/Hexane 0~100%) to obtain the title compound. ESI-MS (m/z): 456 [M+1]$^+$.

Step 4: (S)-1-(2-Chloro-5-((1-methoxy-1-oxopropan-2-yl)oxy)benzyl)-2,3-dimethyl-1H-indole-5-carboxylic acid

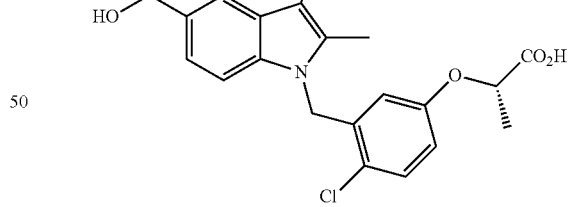

A solution of (S)-allyl 1-(2-chloro-5-((1-methoxy-1-oxopropan-2-yl)oxy)benzyl)-2,3-dimethyl-1H-indole-5-carboxylate (0.327 g, 0.72 mmol) and morpholine (0.63 mL, 7.2 mmol) in anhydrous THF (10 mL) was degassed, then Pd(PPh$_3$)$_4$ (0.083 g, 0.072 mmol) was added under argon protection. The reaction mixture was stirred at rt for 1 h. The solvent was removed and the resulting crude was dissolved in MeOH. The mixture was acidified with 2 N HCl to pH 3. The mixture was filtered and the solid was washed with water. The solid was dried for the next Step with no further purification. ESI-MS (m/z): 416 [M+1]$^+$.

Step 5: (S)-Methyl 2-(4-chloro-3-((5-(((S)-1-(3-isopropylphenyl)ethyl)carbamoyl)-2,3-dimethyl-1H-indol-1-yl)methyl)phenoxy)propanoate


The (S)-1-(2-chloro-5-((1-methoxy-1-oxopropan-2-yl)oxy)benzyl)-2,3-dimethyl-1H-indole-5-carboxylic acid (71 mg, 0.17 mmol), the (S)-1-(3-isopropylphenyl)ethanamine hydrochloride (53 mg, 0.27 mmol) and HATU (88 mg, 0.23 mmol) were dissolved in DMF (3 mL) and DIEA (0.15 mL). It was stirred for 15 h. The solution was filtered and purified by preparative HPLC.

Step 6: (S)-2-(4-Chloro-3-((5-(((S)-1-(3-isopropylphenyl)ethyl)carbamoyl)-2,3-dimethyl-1H-indol-1-yl)methyl)phenoxy)propanoic acid


The (S)-methyl 2-(4-chloro-3-((5-(((S)-1-(3-isopropylphenyl)ethyl)carbamoyl)-2,3-dimethyl-1H-indol-1-yl)methyl)phenoxy)propanoate was dissolved in methanol (1.5 mL) and DMSO (~1 mL), water (0.1 mL) and NaOH (2 N, 0.1 mL) were added dropwise. The reaction was monitored by LC/MS. It was stirred until all the starting material was consumed (~3 h). It was acidified with trifluoroacetic acid, filtered and purified by preparative HPLC to yield the title compound. ESI-MS (m/z): 547.1 [M+H]⁺.

Example 62: (S)-2-(4-Chloro-3-((5-(((S)-1-(3-cyclopropylphenyl)ethyl)carbamoyl)-2,3-dimethyl-1H-indol-1-yl)methyl)phenoxy)propanoic acid

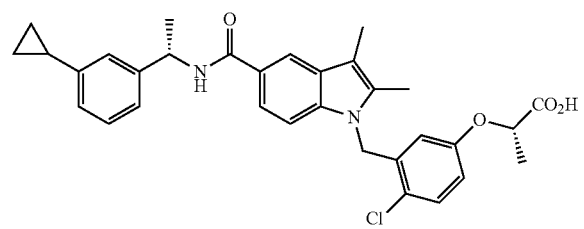 [SMILES: Cc1c(C)n(Cc2cc(O[C@@H](C)C(=O)O)ccc2Cl)c2ccc(C(=O)N[C@@H](C)c3cccc(C4CC4)c3)cc12]

A similar procedure was followed as described in the previous example (Example 61) to yield the title compound. ESI-MS (m/z): 545.1 [M+H]⁺.

Example 63: (S)-2-(3-((5-(((S)-1-(4-Bromophenyl)ethyl)carbamoyl)-2,3-dimethyl-1H-indol-1-yl)methyl)-4-chlorophenoxy)propanoic acid

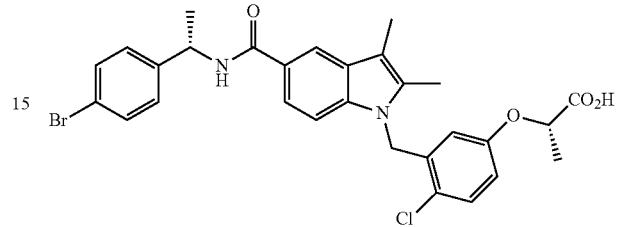

A similar procedure was followed as described in the previous example (Example 61) to yield the title compound. ESI-MS (m/z): 585.0 [M+H]⁺.

Example 64: (S)-2-(3-((5-(((S)-1-(4-(tert-Butyl)phenyl)ethyl)carbamoyl)-2,3-dimethyl-1H-indol-1-yl)methyl)-4-chlorophenoxy)propanoic acid

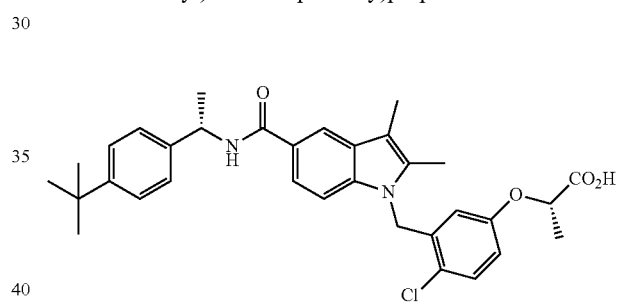

Step 1: (S)-Methyl 2-(3-((5-(((S)-1-(4-(tert-butyl)phenyl)ethyl)carbamoyl)-2,3-dimethyl-1H-indol-1-yl)methyl)-4-chlorophenoxy)propanoate

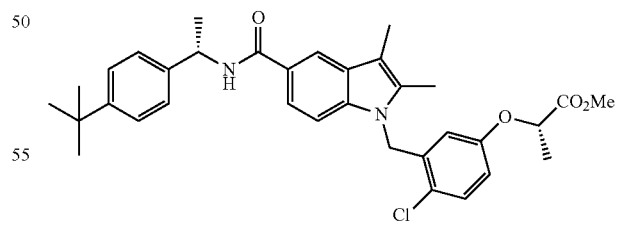

The title compound was prepared following the same protocol as described in Step 5, Example 36, using the (S)-1-(4-(tert-butyl)phenyl)ethanamine hydrochloride instead of the (S)-1-(3-cyclopropylphenyl)ethanamine hydrochloride the (S)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(4-(tert-Butyl)phenyl)ethyl)carbamoyl)-2,3-dimethyl-1H-indol-1-yl)methyl)-4-chlorophenoxy)propanoic acid

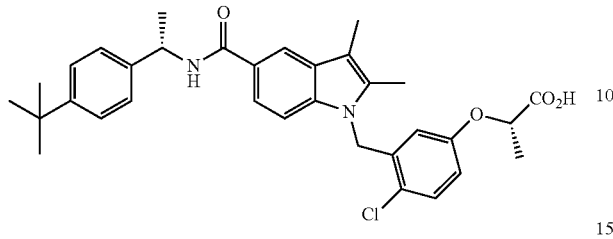

The title compound was prepared following the same protocol as described in Step 6, Example 36, using the (S)-methyl 2-(3-((5-(((S)-1-(4-(tert-butyl)phenyl)ethyl)carbamoyl)-2,3-dimethyl-1H-indol-1-yl)methyl)-4-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 65: (S)-2-(3-((5-(((S)-1-(3-(tert-Butyl)phenyl)ethyl)carbamoyl)-2,3-dimethyl-1H-indol-1-yl)methyl)-4-chlorophenoxy)propanoic acid

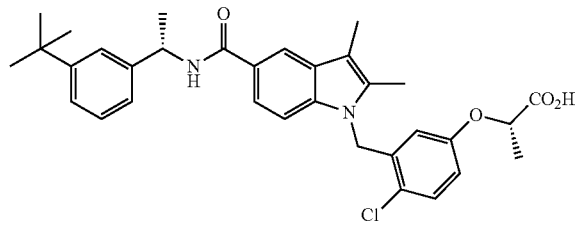 [SMILES: Cc1c(C)n(Cc2cc(O[C@@H](C)C(=O)O)ccc2Cl)c2ccc(C(=O)N[C@@H](C)c3cccc(C(C)(C)C)c3)cc12]

Step 1: (S)-Methyl 2-(3-((5-(((S)-1-(3-(tert-butyl)phenyl)ethyl)carbamoyl)-2,3-dimethyl-1H-indol-1-yl)methyl)-4-chlorophenoxy)propanoate

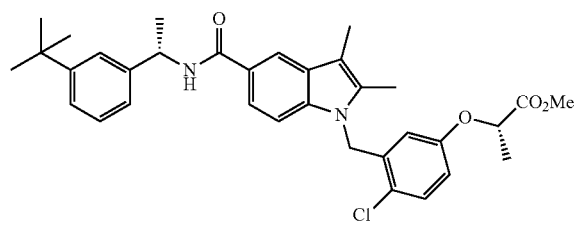 [SMILES: COC(=O)[C@H](C)Oc1ccc(Cl)c(Cn2c(C)c(C)c3cc(C(=O)N[C@@H](C)c4cccc(C(C)(C)C)c4)ccc32)c1]

The title compound was prepared following the same protocol as described in Step 5, Example 36, using the (S)-1-(3-(tert-butyl)phenyl)ethanamine hydrochloride instead of the (S)-1-(3-cyclopropylphenyl)ethanamine hydrochloride the (S)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(3-((5-(((S)-1-(3-(tert-Butyl)phenyl)ethyl)carbamoyl)-2,3-dimethyl-1H-indol-1-yl)methyl)-4-chlorophenoxy)propanoic acid

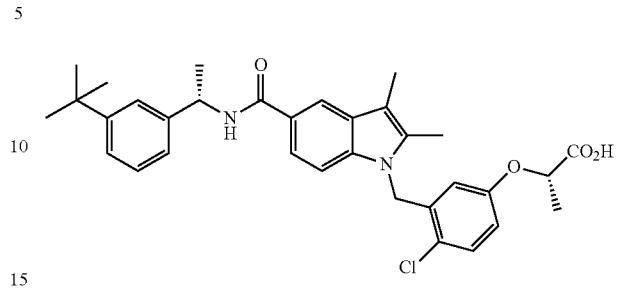

The title compound was prepared following the same protocol as described in Step 6, Example 36, using the (S)-methyl 2-(3-((5-(((S)-1-(4-(tert-butyl)phenyl)ethyl)carbamoyl)-2,3-dimethyl-1H-indol-1-yl)methyl)-4-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 66: (S)-2-(4-Chloro-3-((5-(((S)-1-(3-isopropoxyphenyl)ethyl)carbamoyl)-2,3-dimethyl-1H-indol-1-yl)methyl)phenoxy)propanoic acid

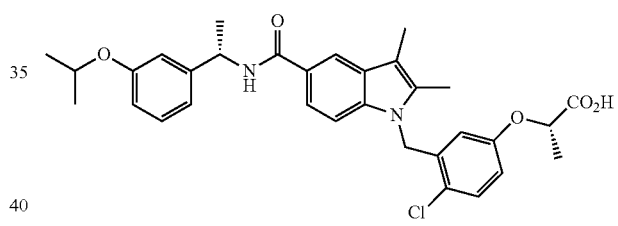

Step 1: (S)-Methyl 2-(3-((5-(((S)-1-(3-isopropoxyphenyl)ethyl)carbamoyl)-2,3-dimethyl-1H-indol-1-yl)methyl)-4-chlorophenoxy)propanoate

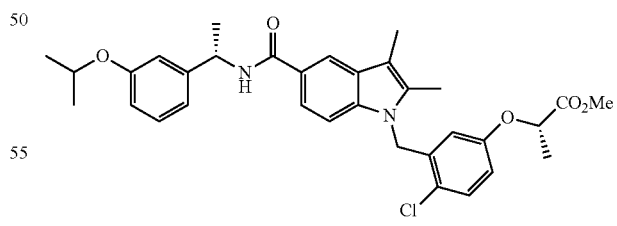

The title compound was prepared following the same protocol as described in Step 5, Example 36, using the (S)-1-(3-isopropoxyphenyl)ethanamine hydrochloride instead of the (S)-1-(3-cyclopropylphenyl)ethanamine hydrochloride the (S)-1-(2-chloro-5-(1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 2: (S)-2-(4-Chloro-3-((5-(((S)-1-(3-isopropoxyphenyl)ethyl)carbamoyl)-2,3-dimethyl-1H-indol-1-yl)methyl)phenoxy)propanoic acid

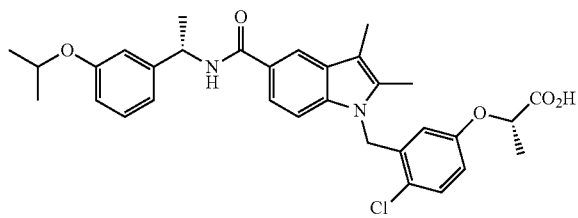 [SMILES: Cc1c(C)n(Cc2cc(O[C@@H](C)C(=O)O)ccc2Cl)c2ccc(C(=O)N[C@@H](C)c3cccc(OC(C)C)c3)cc12]

The title compound was prepared following the same protocol as described in Step 6, Example 36, using the (S)-methyl 2-(3-((5-(((S)-1-(3-isopropoxyphenyl)ethyl)carbamoyl)-2,3-dimethyl-1H-indol-1-yl)methyl)-4-chlorophenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 67: (S)-2-(3-chloro-5-((5-(((S)-1-(3-isopropylphenyl)ethyl)carbamoyl)-2,3-dimethyl-1H-indol-1-yl)methyl)phenoxy)propanoic acid

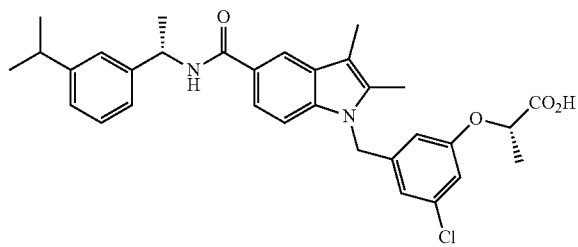 [SMILES: Cc1c(C)n(Cc2cc(Cl)cc(O[C@@H](C)C(=O)O)c2)c2ccc(C(=O)N[C@@H](C)c3cccc(C(C)C)c3)cc12]

Step 1: (S)-Methyl 2-(3-chloro-5-methylphenoxy)propanoate

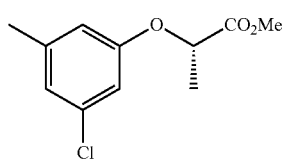

The title compound was prepared following the same protocol as described in Step 1, Example 42, using the 3-chloro-5-methylphenol instead of the m-cresol and the (R)-methyl 2-hydroxypropanoate instead of the (S)-methyl 2-hydroxypropanoate.

Step 2: (S)-Methyl 2-(3-(bromomethyl)-5-chlorophenoxy)propanoate

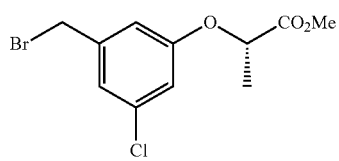 [SMILES: COC(=O)[C@H](C)Oc1cc(Cl)cc(CBr)c1]

The title compound was prepared following the same protocol as described in Step 2, Example 36, using the (S)-methyl 2-(3-chloro-5-methylphenoxy)propanoate instead of the methyl 2-(p-tolyloxy)acetate.

Step 3: (S)-Allyl 1-(3-chloro-5-((1-methoxy-1-oxopropan-2-yl)oxy)benzyl)-2,3-dimethyl-1H-indole-5-carboxylate

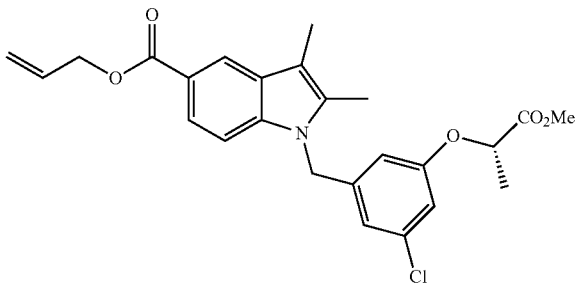 [SMILES: C=CCOC(=O)c1ccc2c(c1)c(C)c(C)n2Cc1cc(Cl)cc(O[C@@H](C)C(=O)OC)c1]

The title compound was prepared following the same general protocol as described in Step 3, Example 36, using the (S)-methyl 2-(3-(bromomethyl)-5-chlorophenoxy)propanoate instead of the methyl 2-(4-(bromomethyl)phenoxy)acetate. ESI-MS (m/z): 456/457/458 [M+H]$^+$.

Step 4: (S)-1-(3-Chloro-5-((1-methoxy-1-oxopropan-2-yl)oxy)benzyl)-2,3-dimethyl-1H-indole-5-carboxylic acid

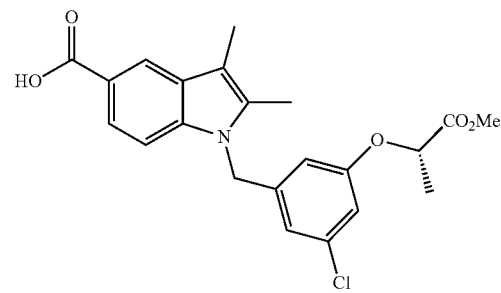 [SMILES: COC(=O)[C@H](C)Oc1cc(Cl)cc(Cn2c(C)c(C)c3cc(C(=O)O)ccc32)c1]

The title compound was prepared following the same general protocol as described in Step 4, Example 36, using the (S)-allyl 1-(3-chloro-5-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]$^+$.

Step 5: (S)-methyl 2-(3-chloro-5-((5-(((S)-1-(3-isopropylphenyl)ethyl)carbamoyl)-2,3-dimethyl-1H-indol-1-yl)methyl)phenoxy)propanoate

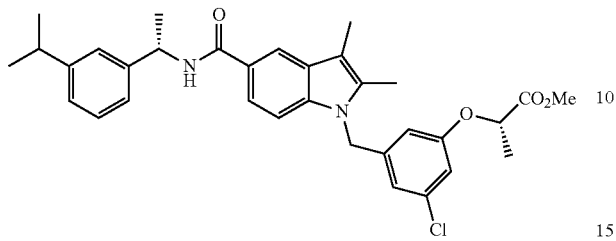

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-chloro-5-(1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-chloro-5-((5-(((S)-1-(3-isopropylphenyl)ethyl)carbamoyl)-2,3-dimethyl-1H-indol-1-yl)methyl)phenoxy)propanoic acid

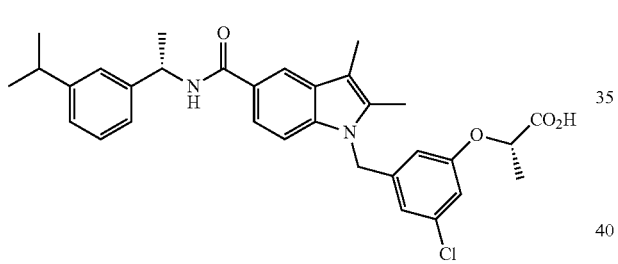

The title compound was prepared following the same protocol as described in Step 6, Example 36, using the (S)-methyl 2-(3-chloro-5-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]$^+$ Example 68: (S)-2-(2-chloro-3-((5-(((S)-1-(3-isopropylphenyl)ethyl)carbamoyl)-2,3-dimethyl-1H-indol-1-yl)methyl)phenoxy)propanoic acid

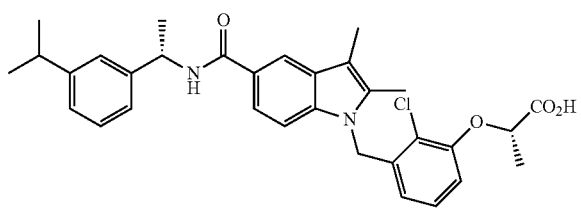 [SMILES: Cc1c(C)n(Cc2cccc(O[C@@H](C)C(=O)O)c2Cl)c2ccc(C(=O)N[C@@H](C)c3cccc(C(C)C)c3)cc12]

Step 1: (S)-Methyl 2-(2-chloro-3-methylphenoxy)propanoate

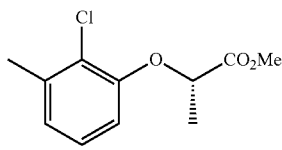

The title compound was prepared following the same protocol as described in Step 1, Example 42, using the 2-chloro-3-methylphenol instead of the m-cresol and the (R)-methyl 2-hydroxypropanoate instead of the (S)-methyl 2-hydroxypropanoate.

Step 2: (S)-Methyl 2-(3-(bromomethyl)-2-chlorophenoxy)propanoate

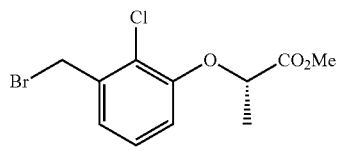

The title compound was prepared following the same protocol as described in Step 2, Example 36, using the (S)-methyl 2-(2-chloro-3-methylphenoxy)propanoate instead of the methyl 2-(p-tolyloxy)acetate.

Step 3: (S)-Allyl 1-(2-chloro-3-((1-methoxy-1-oxopropan-2-yl)oxy)benzyl)-2,3-dimethyl-1H-indole-5-carboxylate

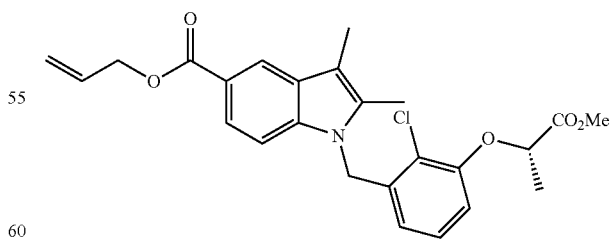

The title compound was prepared following the same general protocol as described in Step 3, Example 36, using the (S)-methyl 2-(3-(bromomethyl)-2-chlorophenoxy)propanoate instead of the methyl 2-(4-(bromomethyl)phenoxy)acetate. ESI-MS (m/z): 456/457/458 [M+H]$^+$.

Step 4: (S)-1-(2-Chloro-3-((1-methoxy-1-oxopropan-2-yl)oxy)benzyl)-2,3-dimethyl-1H-indole-5-carboxylic acid

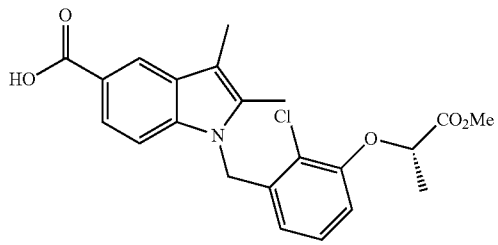 [SMILES: COC(=O)[C@H](C)Oc1cccc(Cn2c(C)c(C)c3cc(C(=O)O)ccc32)c1Cl]

The title compound was prepared following the same general protocol as described in Step 4, Example 36, using the (S)-allyl 1-(2-chloro-3-(1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]+.

Step 5: (S)-methyl 2-(2-chloro-3-((5-(((S)-1-(3-isopropylphenyl)ethyl)carbamoyl)-2,3-dimethyl-1H-indol-1-yl)methyl)phenoxy)propanoate

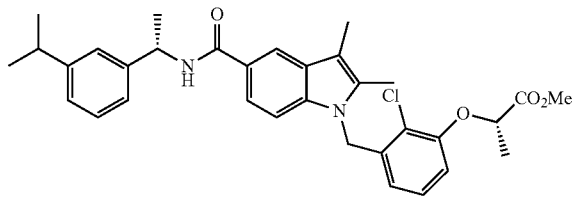 [SMILES: COC(=O)[C@H](C)Oc1cccc(Cn2c(C)c(C)c3cc(C(=O)N[C@@H](C)c4cccc(C(C)C)c4)ccc32)c1Cl]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-3-(1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-chloro-3-((5-(((S)-1-(3-isopropylphenyl)ethyl)carbamoyl)-2,3-dimethyl-1H-indol-1-yl)methyl)phenoxy)propanoic acid

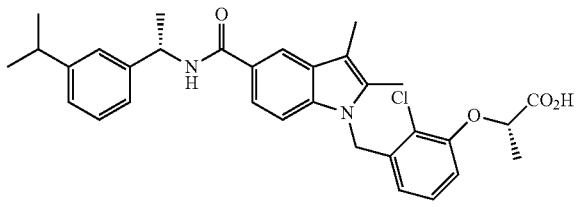 [SMILES: Cc1c(C)n(Cc2cccc(O[C@@H](C)C(=O)O)c2Cl)c2ccc(C(=O)N[C@@H](C)c3cccc(C(C)C)c3)cc12]

The title compound was prepared following the same protocol as described in Step 6, Example 36, using the (S)-methyl 2-(2-chloro-3-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 547/548/549 [M+H]+

Example 69: (R)-2-(2-Chloro-5-((5-(((S)-1-(3-isopropylphenyl)ethyl)carbamoyl)-2,3-dimethyl-1H-indol-1-yl)methyl)phenoxy)propanoic acid

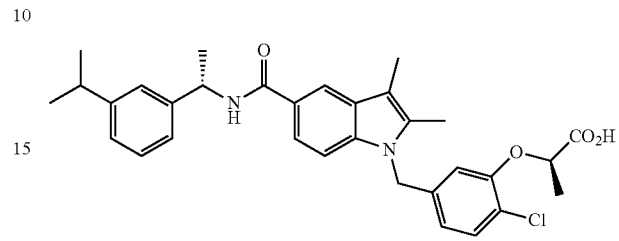

Step 1: (R)-Methyl 2-(2-chloro-5-methylphenoxy)propanoate

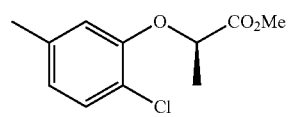

The title compound was prepared following the same protocol as described in Step 1, Example 42, using the 2-chloro-5-methylphenol instead of the m-cresol.

Step 2: (R)-Methyl 2-(5-(bromomethyl)-2-chlorophenoxy)propanoate

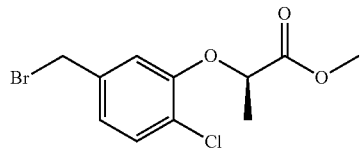 [SMILES: COC(=O)[C@@H](C)Oc1cc(CBr)ccc1Cl]

The title compound was prepared following the same protocol as described in Step 2, Example 36, using the (R)-methyl 2-(2-chloro-5-methylphenoxy)propanoate instead of the methyl 2-(p-tolyloxy)acetate.

Step 3: (R)-Allyl 1-(4-chloro-3-((1-methoxy-1-oxopropan-2-yl)oxy)benzyl)-2,3-dimethyl-1H-indole-5-carboxylate

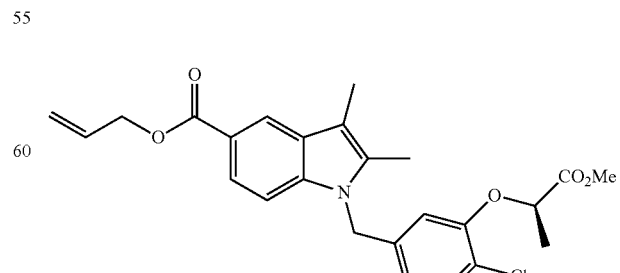

The title compound was prepared following the same general protocol as described in step 3, Example 36, using the (R)-methyl 2-(5-(bromomethyl)-2-chlorophenoxy)propanoate instead of the methyl 2-(4-(bromomethyl)phenoxy)acetate ESI-MS (m/z): 456 [M+1]⁺.

Step 4: (R)-1-(4-Chloro-3-((1-methoxy-1-oxopropan-2-yl)oxy)benzyl)-2,3-dimethyl-1H-indole-5-carboxylic acid

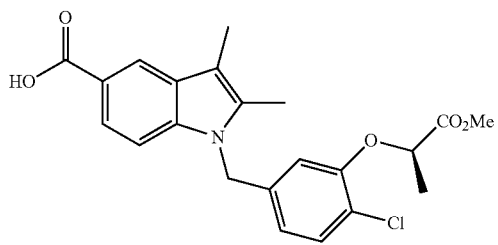 [SMILES: COC(=O)[C@@H](C)Oc1cc(Cn2c(C)c(C)c3cc(C(=O)O)ccc32)ccc1Cl]

The title compound was prepared following the same general protocol as described in Step 4, Example 36, using the (R)-allyl 1-(4-chloro-3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416 [M+1]⁺.

Step 5: (R)-Methyl 2-(2-chloro-5-((5-(((S)-1-(3-isopropylphenyl)ethyl)carbamoyl)-2,3-dimethyl-1H-indol-1-yl)methyl)phenoxy)propanoate

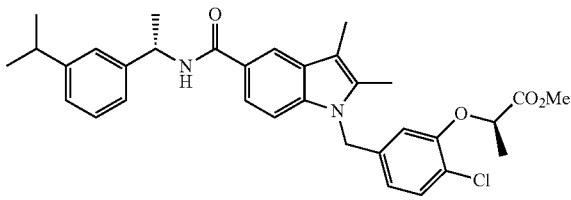 [SMILES: COC(=O)[C@@H](C)Oc1cc(Cn2c(C)c(C)c3cc(C(=O)N[C@@H](C)c4cccc(C(C)C)c4)ccc32)ccc1Cl]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-Chloro-5-((5-(((S)-1-(3-isopropylphenyl)ethyl)carbamoyl)-2,3-dimethyl-1H-indol-1-yl)methyl)phenoxy)propanoic acid

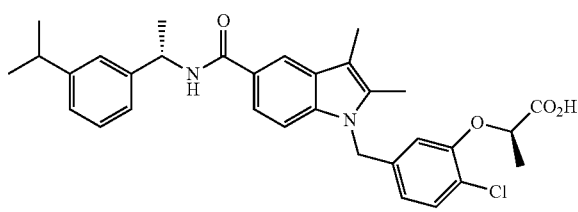 [SMILES: Cc1c(C)n(Cc2ccc(Cl)c(O[C@H](C)C(=O)O)c2)c2ccc(C(=O)N[C@@H](C)c3cccc(C(C)C)c3)cc12]

The title compound was prepared following the same protocol as described in Step 6, Example 36, using the (R)-methyl 2-(2-chloro-5-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]⁺

Example 70: (R)-2-(4-Chloro-3-((5-(((S)-1-(3-isopropylphenyl)ethyl)carbamoyl)-2,3-dimethyl-1H-indol-1-yl)methyl)phenoxy)propanoic acid

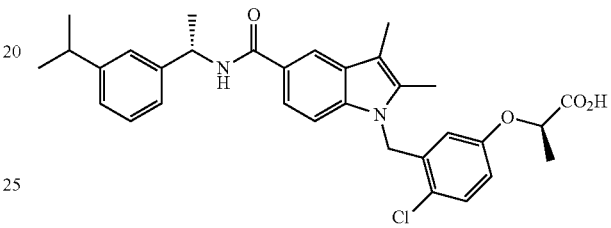

Step 1: (R)-Methyl 2-(4-chloro-3-methylphenoxy)propanoate

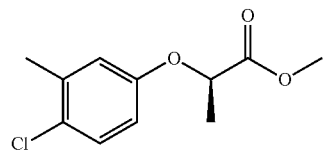

The title compound was prepared following the same protocol as described in Step 1, Example 42, using the 4-chloro-3-methylphenol instead of the m-cresol Step 2: (R)-Methyl 2-(3-(bromomethyl)-4-chlorophenoxy)propanoate

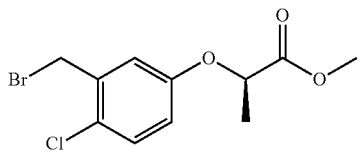 [SMILES: COC(=O)[C@@H](C)Oc1ccc(Cl)c(CBr)c1]

The title compound was prepared following the same protocol as described in Step 2, Example 36, using the (R)-methyl 2-(4-chloro-3-methylphenoxy)propanoate instead of the methyl 2-(p-tolyloxy)acetate.

Step 3: (R)-Allyl 1-(2-chloro-5-((1-methoxy-1-oxo-propan-2-yl)oxy)benzyl)-2,3-dimethyl-1H-indole-5-carboxylate

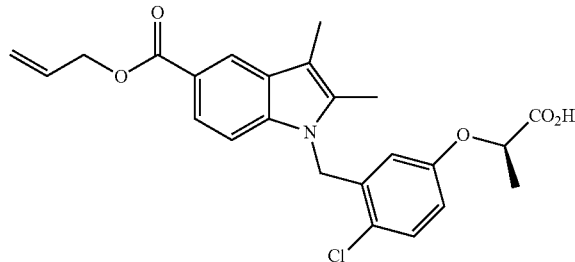 [SMILES: C=CCOC(=O)c1ccc2c(c1)c(C)c(C)n2Cc1cc(O[C@H](C)C(=O)O)ccc1Cl]

The title compound was prepared following the same general protocol as described in step 3, Example 36, using the (R)-methyl 2-(3-(bromomethyl)-4-chlorophenoxy)propanoate instead of the methyl 2-(4-(bromomethyl)phenoxy)acetate ESI-MS (m/z): 456 [M+1]$^+$.

Step 4: (R)-1-(2-Chloro-5-((1-methoxy-1-oxopropan-2-yl)oxy)benzyl)-2,3-dimethyl-1H-indole-5-carboxylic acid

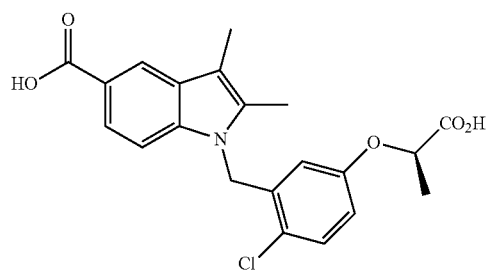 [SMILES: Cc1c(C)n(Cc2cc(O[C@H](C)C(=O)O)ccc2Cl)c2ccc(C(=O)O)cc12]

The title compound was prepared following the same general protocol as described in Step 4, Example 36, using the (R)-allyl 1-(2-chloro-5-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416 [M+1]$^+$.

Step 5: (R)-Methyl 2-(3-chloro-4-((5-(((S)-1-(3-isopropylphenyl)ethyl)carbamoyl)-2,3-dimethyl-1H-indol-1-yl)methyl)phenoxy)propanoate

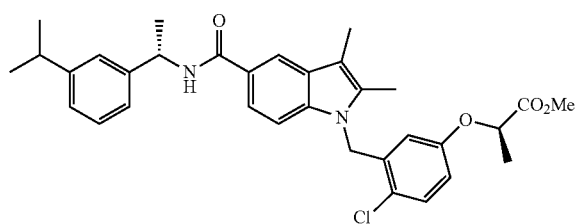 [SMILES: COC(=O)[C@@H](C)Oc1ccc(Cl)c(Cn2c(C)c(C)c3cc(C(=O)N[C@@H](C)c4cccc(C(C)C)c4)ccc32)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-Chloro-4-((5-(((S)-1-(3-isopropylphenyl)ethyl)carbamoyl)-2,3-dimethyl-1H-indol-1-yl)methyl)phenoxy)propanoic acid

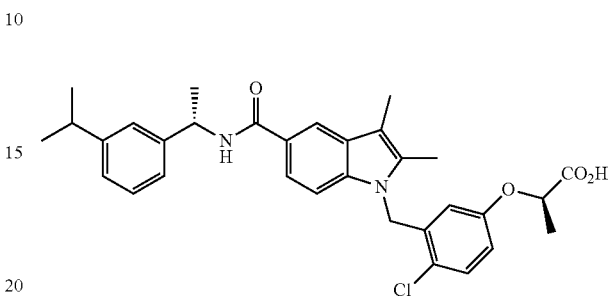

The title compound was prepared following the same protocol as described in Step 6, Example 36, using the (R)-methyl 2-(3-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]$^+$

Example 71: (R)-2-(3-chloro-5-((5-(((S)-1-(3-isopropylphenyl)ethyl)carbamoyl)-2,3-dimethyl-1H-indol-1-yl)methyl)phenoxy)propanoic acid

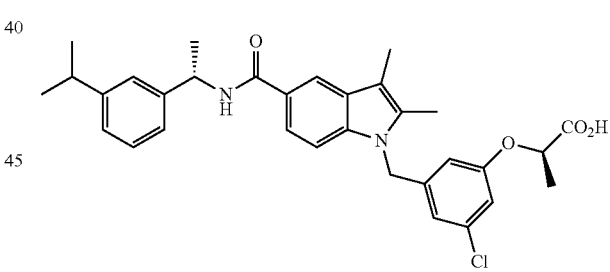

Step 1: (R)-Methyl 2-(3-chloro-5-methylphenoxy)propanoate

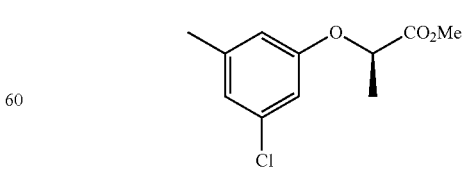

The title compound was prepared following the same protocol as described in Step 1, Example 42, using the 3-chloro-5-methylphenol instead of the m-cresol.

Step 2: (R)-Methyl 2-(3-(bromomethyl)-5-chlorophenoxy)propanoate

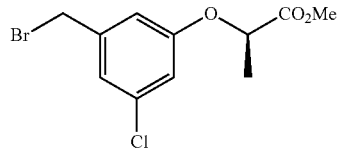 [SMILES: COC(=O)[C@@H](C)Oc1cc(Cl)cc(CBr)c1]

The title compound was prepared following the same protocol as described in Step 2, Example 36, using the (R)-methyl 2-(3-chloro-5-methylphenoxy)propanoate instead of the methyl 2-(p-tolyloxy)acetate.

Step 3: (R)-Allyl 1-(3-chloro-5-((1-methoxy-1-oxopropan-2-yl)oxy)benzyl)-2,3-dimethyl-1H-indole-5-carboxylate

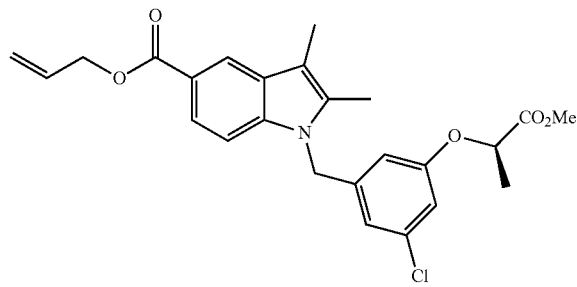 [SMILES: C=CCOC(=O)c1ccc2c(c1)c(C)c(C)n2Cc1cc(Cl)cc(O[C@H](C)C(=O)OC)c1]

The title compound was prepared following the same general protocol as described in Step 3, Example 36, using the (R)-methyl 2-(3-(bromomethyl)-5-chlorophenoxy)propanoate instead of the methyl 2-(4-(bromomethyl)phenoxy)acetate. ESI-MS (m/z): 456/457/458 [M+H]+.

Step 4: (R)-1-(3-Chloro-5-((1-methoxy-1-oxopropan-2-yl)oxy)benzyl)-2,3-dimethyl-1H-indole-5-carboxylic acid

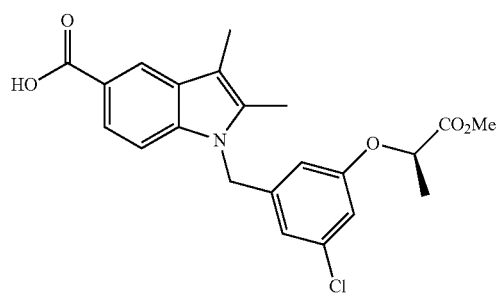 [SMILES: COC(=O)[C@@H](C)Oc1cc(Cl)cc(Cn2c(C)c(C)c3cc(C(=O)O)ccc32)c1]

The title compound was prepared following the same general protocol as described in Step 4, Example 36, using the (R)-allyl 1-(3-chloro-5-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]+.

Step 5: (R)-methyl 2-(3-chloro-5-((5-(O)-1-(3-isopropylphenyl)ethyl)carbamoyl)-2,3-dimethyl-1H-indol-1-yl)methyl)phenoxy)propanoate

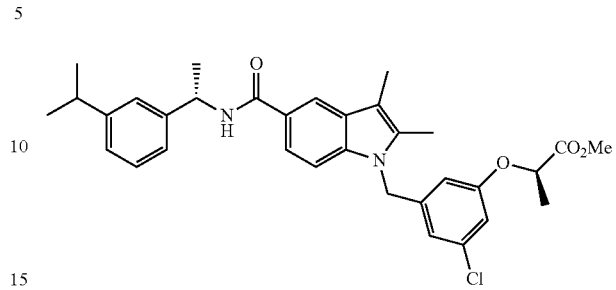

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-chloro-5-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-chloro-5-((5-(((S)-1-(3-isopropylphenyl)ethyl)carbamoyl)-2,3-dimethyl-1H-indol-1-yl)methyl)phenoxy)propanoic acid

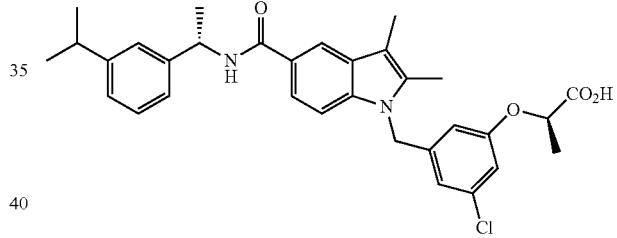

The title compound was prepared following the same protocol as described in Step 6, Example 36, using the (R)-methyl 2-(3-chloro-5-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]+

Example 72: (R)-2-(2-chloro-3-((5-(((S)-1-(3-isopropylphenyl)ethyl)carbamoyl)-2,3-dimethyl-1H-indol-1-yl)methyl)phenoxy)propanoic acid

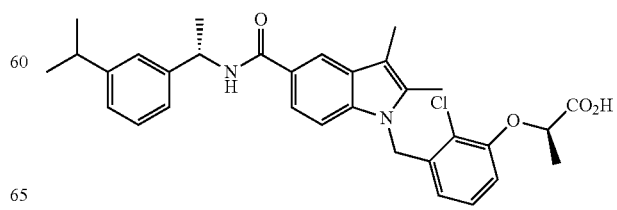

Step 1: (R)-Methyl 2-(2-chloro-3-methylphenoxy)propanoate

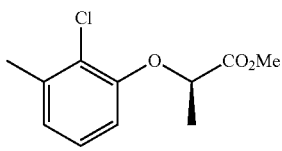

The title compound was prepared following the same protocol as described in Step 1, Example 42, using the 2-chloro-3-methylphenol instead of the m-cresol.

Step 2: (R)-Methyl 2-(3-(bromomethyl)-2-chlorophenoxy)propanoate

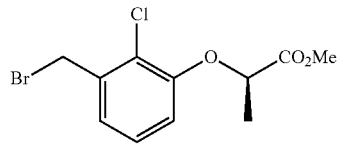 [SMILES: COC(=O)[C@@H](C)Oc1cccc(CBr)c1Cl]

The title compound was prepared following the same protocol as described in Step 2, Example 36, using the (R)-methyl 2-(2-chloro-3-methylphenoxy)propanoate instead of the methyl 2-(p-tolyloxy)acetate.

Step 3: (R)-Allyl 1-(2-chloro-3-((1-methoxy-1-oxopropan-2-yl)oxy)benzyl)-2,3-dimethyl-1H-indole-5-carboxylate

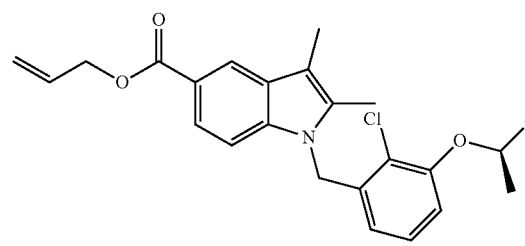

The title compound was prepared following the same general protocol as described in Step 3, Example 36, using the (R)-methyl 2-(3-(bromomethyl)-2-chlorophenoxy)propanoate instead of the methyl 2-(4-(bromomethyl)phenoxy)acetate. ESI-MS (m/z): 456/457/458 [M+H]$^+$.

Step 4: (R)-1-(2-Chloro-3-((1-methoxy-1-oxopropan-2-yl)oxy)benzyl)-2,3-dimethyl-1H-indole-5-carboxylic acid

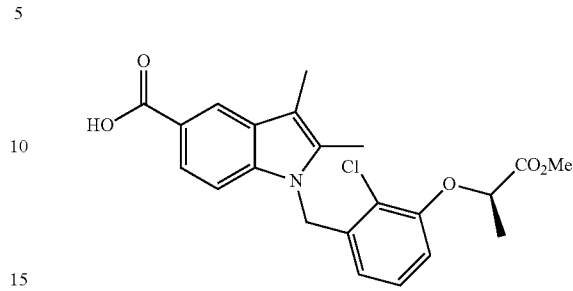

The title compound was prepared following the same general protocol as described in Step 4, Example 36, using the (R)-allyl 1-(2-chloro-3-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]$^+$.

Step 5: (R)-methyl 2-(2-chloro-3-((5-(O)-1-(3-isopropylphenyl)ethyl)carbamoyl)-2,3-dimethyl-1H-indol-1-yl)methyl)phenoxy)propanoate

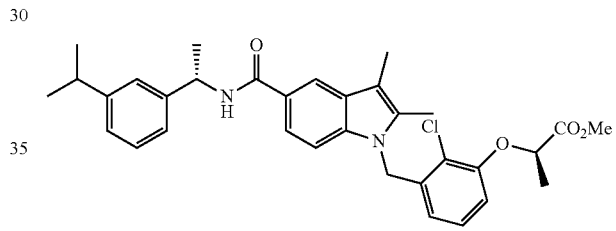

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-chloro-3-((5-(((S)-1-(3-isopropylphenyl)ethyl)carbamoyl)-2,3-dimethyl-1H-indol-1-yl)methyl)phenoxy)propanoic acid

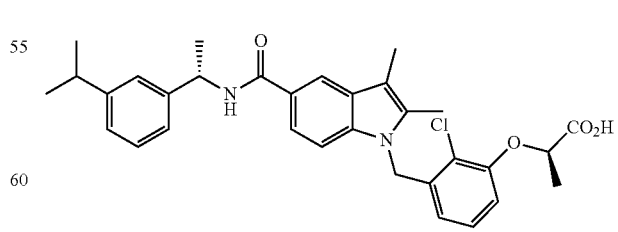

The title compound was prepared following the same protocol as described in Step 6, Example 36, using the (R)-methyl 2-(2-chloro-3-((5-(((S)-1-(3-isopropylphenyl)ethyl)carbamoyl)-2,3-dimethyl-1H-indol-1-yl)methyl)phenoxy)propanoate instead of the (S)-methyl 2-(4-(((5-((1-(3-cyclopropylphenyl)ethyl)carbamoyl)-2,3-dimethyl-1H-indol-1-yl)methyl)phenoxy)acetate. ESI-MS (m/z): 547/548/549 [M+H]⁺

Example 73: (S)-2-(2-chloro-4-((5-(((S)-1-(3-Isopropylphenyl)ethyl)carbamoyl)-2,3-dimethyl-1H-indol-1-yl)methyl)phenoxy)propanoic acid

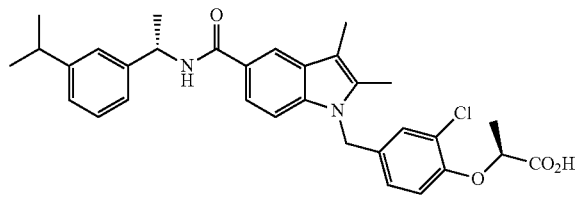 [SMILES: Cc1c(C)n(Cc2ccc(O[C@@H](C)C(=O)O)c(Cl)c2)c2ccc(C(=O)N[C@@H](C)c3cccc(C(C)C)c3)cc12]

Step 1: (S)-Methyl 2-(2-chloro-4-methylphenoxy)propanoate

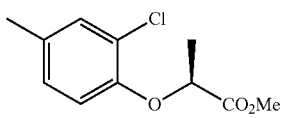

The title compound was prepared following the same protocol as described in Step 1, Example 42, using the 2-chloro-4-methylphenol instead of the m-cresol and the (R)-methyl 2-hydroxypropanoate instead of the (S)-methyl 2-hydroxypropanoate.

Step 2: (S)-Methyl 2-(4-(bromomethyl)-2-chlorophenoxy)propanoate

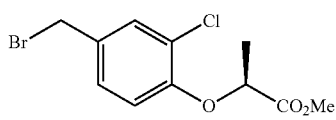

The title compound was prepared following the same protocol as described in Step 2, Example 36, using the (S)-methyl 2-(2-chloro-4-methylphenoxy)propanoate instead of the methyl 2-(p-tolyloxy)acetate.

Step 3: (S)-Allyl 1-(3-chloro-4-((1-methoxy-1-oxopropan-2-yl)oxy)benzyl)-2,3-dimethyl-1H-indole-5-carboxylate

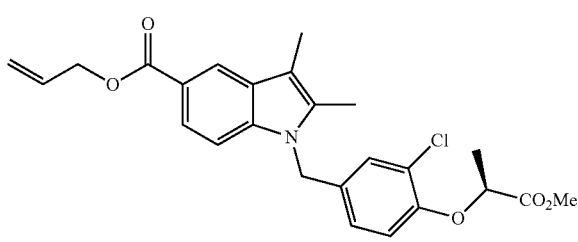 [SMILES: C=CCOC(=O)c1ccc2c(c1)c(C)c(C)n2Cc1ccc(O[C@@H](C)C(=O)OC)c(Cl)c1]

The title compound was prepared following the same general protocol as described in Step 3, Example 36, using the (S)-methyl 2-(4-(bromomethyl)-2-chlorophenoxy)propanoate instead of the methyl 2-(4-(bromomethyl)phenoxy) acetate. ESI-MS (m/z): 456/457/458 [M+H]⁺.

Step 4: (S)-1-(3-chloro-4-((1-Methoxy-1-oxopropan-2-yl)oxy)benzyl)-2,3-dimethyl-1H-indole-5-carboxylic acid

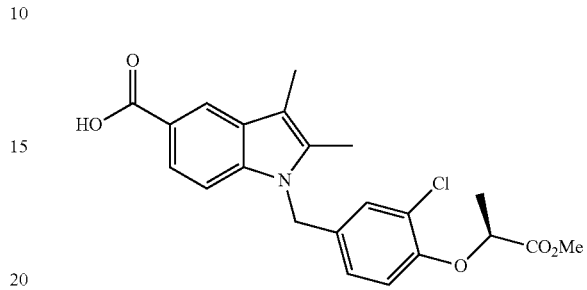

The title compound was prepared following the same general protocol as described in Step 4, Example 36, using the (S)-allyl 1-(3-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]⁺.

Step 5: (S)-Methyl 2-(2-chloro-4-((5-(((S)-1-(3-isopropylphenyl)ethyl)carbamoyl)-2,3-dimethyl-1H-indol-1-yl)methyl)phenoxy)propanoate

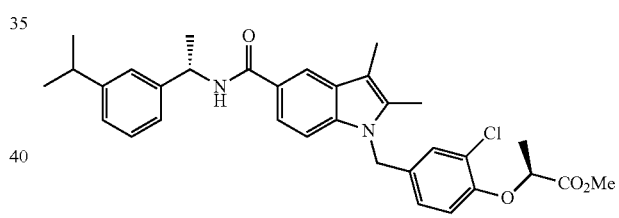

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-chloro-4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-chloro-4-((5-(((S)-1-(3-Isopropylphenyl)ethyl)carbamoyl)-2,3-dimethyl-1H-indol-1-yl)methyl)phenoxy)propanoic acid

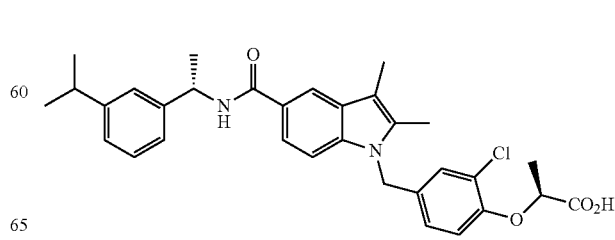

The title compound was prepared following the same protocol as described in Step 6, Example 36, using the (S)-methyl 2-(2-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [MH]+

Example 74: (S)-2-(3-chloro-4-((5-(((S)-1-(3-Isopropylphenyl)ethyl)carbamoyl)-2,3-dimethyl-1H-indol-1-yl)methyl)phenoxy)propanoic acid

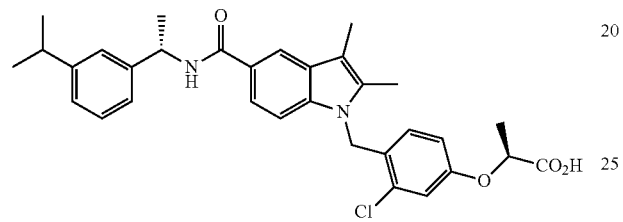

Step 1: (S)-Methyl 2-(3-chloro-4-methylphenoxy)propanoate

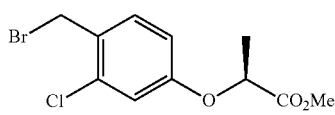

The title compound was prepared following the same protocol as described in Step 1, Example 42, using the 3-chloro-4-methylphenol instead of the m-cresol and the (R)-methyl 2-hydroxypropanoate instead of the (S)-methyl 2-hydroxypropanoate.

Step 2: (S)-Methyl 2-(4-(bromomethyl)-3-chlorophenoxy)propanoate

The title compound was prepared following the same protocol as described in Step 2, Example 36, using the (S)-methyl 2-(3-chloro-4-methylphenoxy)propanoate instead of the methyl 2-(p-tolyloxy)acetate.

Step 3: (S)-Allyl 1-(2-chloro-4-((1-methoxy-1-oxopropan-2-yl)oxy)benzyl)-2,3-dimethyl-1H-indole-5-carboxylate

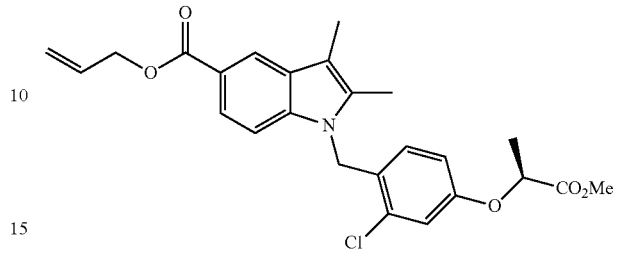

The title compound was prepared following the same general protocol as described in Step 3, Example 36, using the (S)-methyl 2-(4-(bromomethyl)-3-chlorophenoxy)propanoate instead of the methyl 2-(4-(bromomethyl)phenoxy)acetate. ESI-MS (m/z): 456/457/458 [M+H]+.

Step 4: (S)-1-(2-chloro-4-((1-Methoxy-1-oxopropan-2-yl)oxy)benzyl)-2,3-dimethyl-1H-indole-5-carboxylic acid

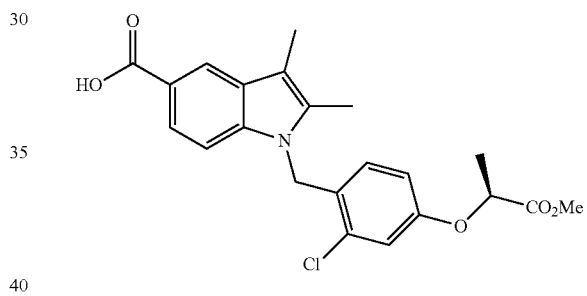

The title compound was prepared following the same general protocol as described in Step 4, Example 36, using the (S)-allyl 1-(2-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]+.

Step 5: (S)-Methyl 2-(3-chloro-4-((5-(((S)-1-(3-isopropylphenyl)ethyl)carbamoyl)-2,3-dimethyl-1H-indol-1-yl)methyl)phenoxy)propanoate

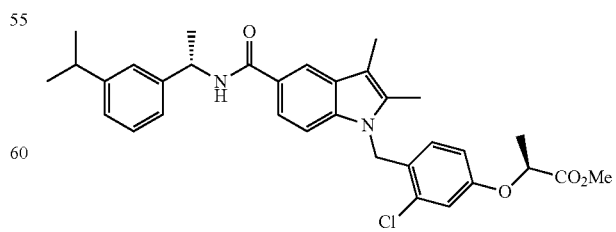

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-4-(1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-chloro-4-((5-(((S)-1-(3-Isopropylphenyl)ethyl)carbamoyl)-2,3-dimethyl-1H-indol-1-yl)methyl)phenoxy)propanoic acid

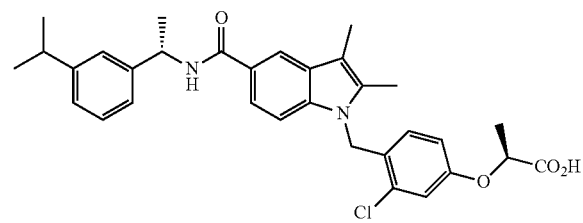 [SMILES: Cc1c(C)n(Cc2ccc(O[C@@H](C)C(=O)O)cc2Cl)c2ccc(C(=O)N[C@@H](C)c3cccc(C(C)C)c3)cc12]

The title compound was prepared following the same protocol as described in Step 6, Example 36, using the (S)-methyl 2-(3-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 547/548/549 [MH]+

Example 75: (R)-2-(2-chloro-4-((5-(((S)-1-(3-Isopropylphenyl)ethyl)carbamoyl)-2,3-dimethyl-1H-indol-1-yl)methyl)phenoxy)propanoic acid

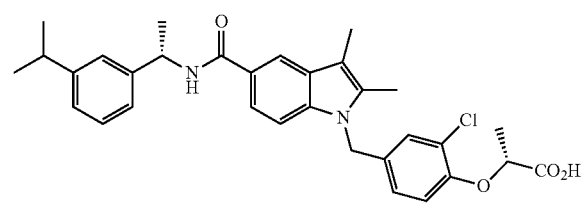 [SMILES: Cc1c(C)n(Cc2ccc(O[C@H](C)C(=O)O)c(Cl)c2)c2ccc(C(=O)N[C@@H](C)c3cccc(C(C)C)c3)cc12]

Step 1: (R)-Methyl 2-(2-chloro-4-methylphenoxy)propanoate

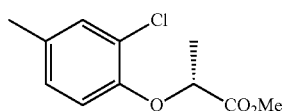

The title compound was prepared following the same protocol as described in Step 1, Example 42, using the 2-chloro-4-methylphenol instead of the m-cresol.

Step 2: (R)-Methyl 2-(4-(bromomethyl)-2-chlorophenoxy)propanoate

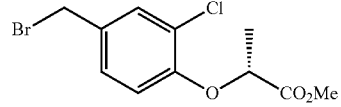

The title compound was prepared following the same protocol as described in Step 2, Example 36, using the (R)-methyl 2-(2-chloro-4-methylphenoxy)propanoate instead of the methyl 2-(p-tolyloxy)acetate.

Step 3: (R)-Allyl 1-(3-chloro-4-((1-methoxy-1-oxopropan-2-yl)oxy)benzyl)-2,3-dimethyl-1H-indole-5-carboxylate

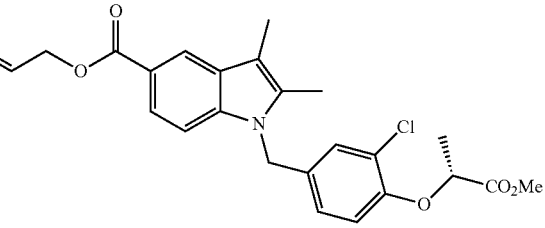

The title compound was prepared following the same general protocol as described in Step 3, Example 36, using the (R)-methyl 2-(4-(bromomethyl)-2-chlorophenoxy)propanoate instead of the methyl 2-(4-(bromomethyl)phenoxy)acetate. ESI-MS (m/z): 456/457/458 [M+H]+.

Step 4: (R)-1-(3-chloro-4-((1-Methoxy-1-oxopropan-2-yl)oxy)benzyl)-2,3-dimethyl-1H-indole-5-carboxylic acid

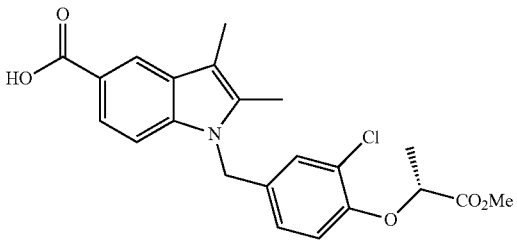 [SMILES: COC(=O)[C@@H](C)Oc1ccc(Cn2c(C)c(C)c3cc(C(=O)O)ccc32)cc1Cl]

The title compound was prepared following the same general protocol as described in Step 4, Example 36, using the (R)-allyl 1-(3-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]+.

Step 5: (R)-Methyl 2-(2-chloro-4-((5-(((S)-1-(3-isopropylphenyl)ethyl)carbamoyl)-2,3-dimethyl-1H-indol-1-yl)methyl)phenoxy)propanoate

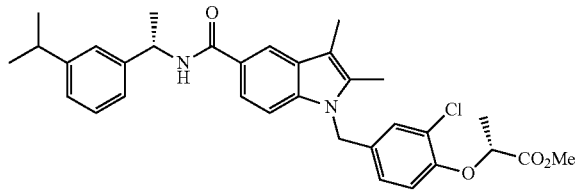

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-chloro-4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-chloro-4-((5-(((S)-1-(3-Isopropylphenyl)ethyl)carbamoyl)-2,3-dimethyl-1H-indol-1-yl)methyl)phenoxy)propanoic acid

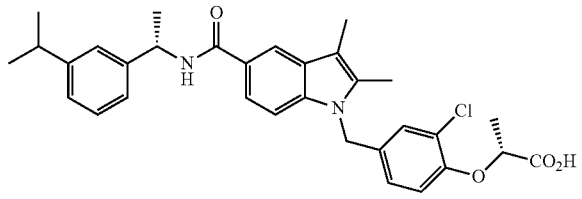 [SMILES: Cc1c(C)n(Cc2ccc(O[C@H](C)C(=O)O)c(Cl)c2)c2ccc(C(=O)N[C@@H](C)c3cccc(C(C)C)c3)cc12]

The title compound was prepared following the same protocol as described in Step 6, Example 36, using the (R)-methyl 2-(2-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 547/548/549 [MH]$^+$ Example 76: (R)-2-(3-chloro-4-((5-(((S)-1-(3-Isopropylphenyl)ethyl)carbamoyl)-2,3-dimethyl-1H-indol-1-yl)methyl)phenoxy)propanoic acid

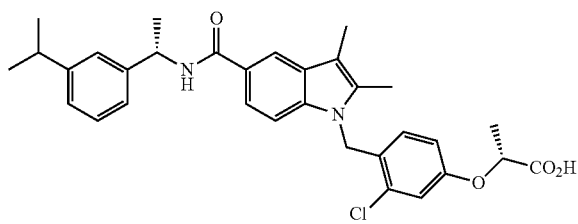 [SMILES: Cc1c(C)n(Cc2ccc(O[C@H](C)C(=O)O)cc2Cl)c2ccc(C(=O)N[C@@H](C)c3cccc(C(C)C)c3)cc12]

Step 1: (R)-Methyl 2-(3-chloro-4-methylphenoxy)propanoate

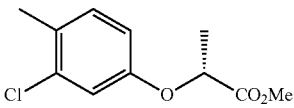

The title compound was prepared following the same protocol as described in Step 1, Example 42, using the 3-chloro-4-methylphenol instead of the m-cresol.

Step 2: (R)-Methyl 2-(4-(bromomethyl)-3-chlorophenoxy)propanoate

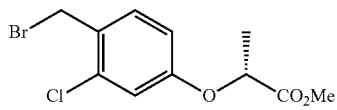

The title compound was prepared following the same protocol as described in Step 2, Example 36, using the (R)-methyl 2-(3-chloro-4-methylphenoxy)propanoate instead of the methyl 2-(p-tolyloxy)acetate.

Step 3: (R)-Allyl 1-(2-chloro-4-((1-methoxy-1-oxopropan-2-yl)oxy)benzyl)-2,3-dimethyl-1H-indole-5-carboxylate

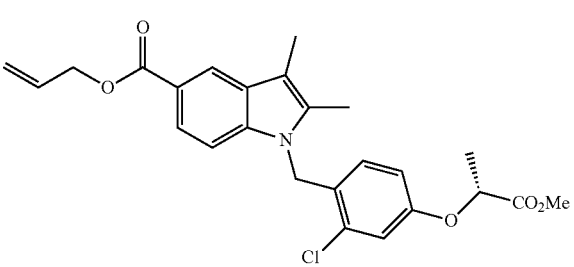 [SMILES: C=CCOC(=O)c1ccc2c(c1)c(C)c(C)n2Cc1ccc(O[C@H](C)C(=O)OC)cc1Cl]

The title compound was prepared following the same general protocol as described in Step 3, Example 36, using the (R)-methyl 2-(4-(bromomethyl)-3-chlorophenoxy)propanoate instead of the methyl 2-(4-(bromomethyl)phenoxy)acetate. ESI-MS (m/z): 456/457/458 [M+H]$^+$.

Step 4: (R)-1-(2-chloro-4-((1-Methoxy-1-oxopropan-2-yl)oxy)benzyl)-2,3-dimethyl-1H-indole-5-carboxylic acid

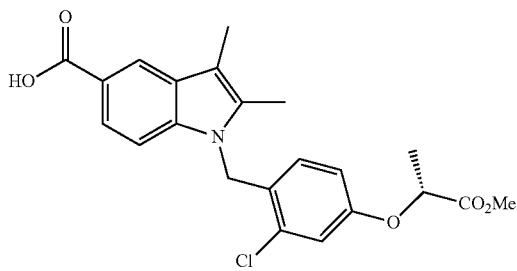 [SMILES: COC(=O)[C@@H](C)Oc1ccc(Cn2c(C)c(C)c3cc(C(=O)O)ccc32)c(Cl)c1]

The title compound was prepared following the same general protocol as described in Step 4, Example 36, using the (R)-allyl 1-(2-chloro-4-((1-methoxy-1-oxopropan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 416/417/418 [M+H]+.

Step 5: (R)-Methyl 2-(3-chloro-4-((5-(((S)-1-(3-isopropylphenyl)ethyl)carbamoyl)-2,3-dimethyl-1H-indol-1-yl)methyl)phenoxy)propanoate

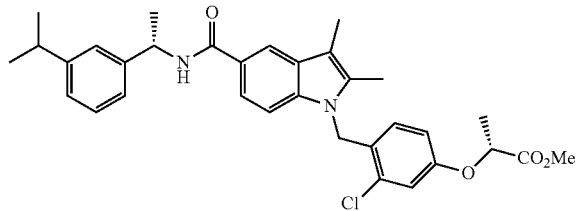 [SMILES: COC(=O)[C@@H](C)Oc1ccc(Cn2c(C)c(C)c3cc(C(=O)N[C@@H](C)c4cccc(C(C)C)c4)ccc32)c(Cl)c1]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-4-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-chloro-4-((5-(((S)-1-(3-Isopropylphenyl)ethyl)carbamoyl)-2,3-dimethyl-1H-indol-1-yl)methyl)phenoxy)propanoic acid

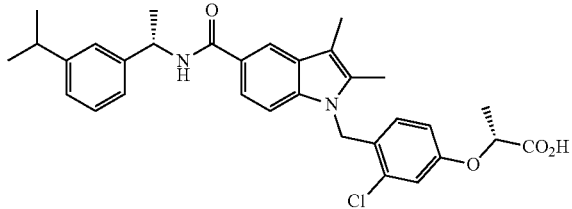 [SMILES: Cc1c(C)n(Cc2ccc(O[C@H](C)C(=O)O)cc2Cl)c2ccc(C(=O)N[C@@H](C)c3cccc(C(C)C)c3)cc12]

The title compound was prepared following the same protocol as described in Step 6, Example 36, using the (R)-methyl 2-(3-chloro-4-((5-(((S)-1-(3-isopropylphenyl)ethyl)carbamoyl)-2,3-dimethyl-1H-indol-1-yl)methyl)phenoxy)propanoate instead of the (S)-methyl 2-(4-((5-(((1-(3-cyclopropylphenyl)ethyl)carbamoyl)-2,3-dimethyl-1H-indol-1-yl)methyl)phenoxy)acetate. ESI-MS (m/z): 547/548/549 [MH]+

Example 77: (S)-2-(3-((5-(((S)-1-(3-Isopropylphenyl)ethyl)carbamoyl)-2,3-dimethyl-1H-indol-1-yl)methyl)phenoxy)butanoic acid

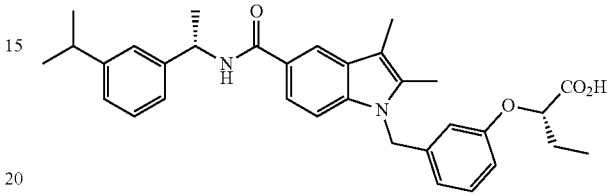

Step 1: (S)-Methyl 2-(m-tolyloxy)butanoate

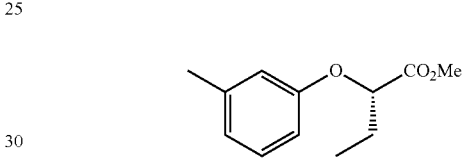

The title compound was prepared following the same protocol as described in Step 1, Example 42, using the (R)-methyl 2-hydroxybutanoate instead of the (S)-methyl 2-hydroxypropanoate.

Step 2: (S)-Methyl 2-(3-(bromomethyl)phenoxy)butanoate

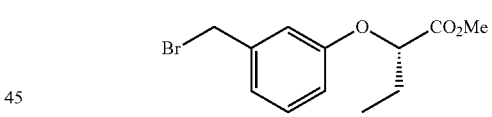

The title compound was prepared following the same protocol as described in Step 2, Example 36, using the (S)-methyl 2-(m-tolyloxy)butanoate instead of the methyl 2-(p-tolyloxy)acetate.

Step 3: (S)-Allyl 1-(3-((1-methoxy-1-oxobutan-2-yl)oxy)benzyl)-2,3-dimethyl-1H-indole-5-carboxylate

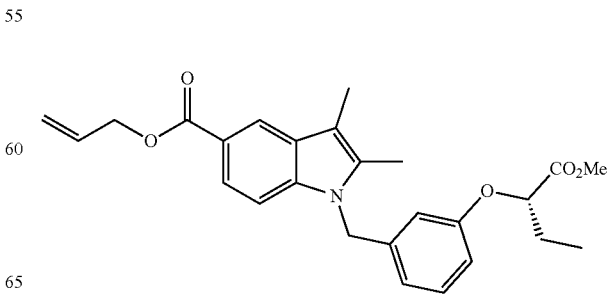

The title compound was prepared following the same general protocol as described in Step 3, Example 36, using the (S)-methyl 2-(3-(bromomethyl)phenoxy)butanoate instead of the methyl 2-(4-(bromomethyl)phenoxy)acetate. ESI-MS (m/z): 436 [M+H]+.

Step 4: (S)-1-(3-((1-Methoxy-1-oxobutan-2-yl)oxy)benzyl)-2,3-dimethyl-1H-indole-5-carboxylic acid

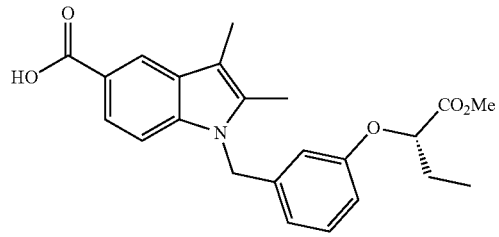 [SMILES: CC[C@H](Oc1cccc(Cn2c(C)c(C)c3cc(C(=O)O)ccc32)c1)C(=O)OC]

The title compound was prepared following the same general protocol as described in Step 4, Example 36, using the (S)-allyl 1-(3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 382 [M+H]+.

Step 5: (S)-Methyl 2-(3-((5-(((S)-1-(3-isopropylphenyl)ethyl)carbamoyl)-2,3-dimethyl-1H-indol-1-yl)methyl)phenoxy)butanoate

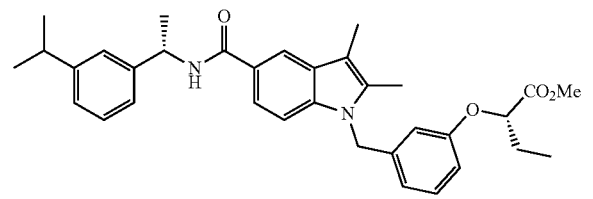 [SMILES: CC[C@H](Oc1cccc(Cn2c(C)c(C)c3cc(C(=O)N[C@@H](C)c4cccc(C(C)C)c4)ccc32)c1)C(=O)OC]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-(((S)-1-(3-Isopropylphenyl)ethyl)carbamoyl)-2,3-dimethyl-1H-indol-1-yl)methyl)phenoxy)butanoic acid

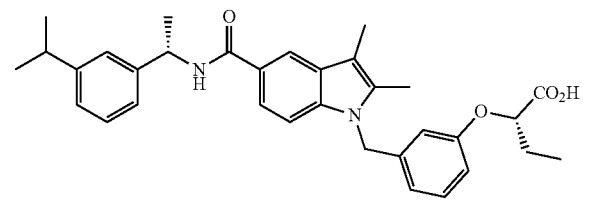 [SMILES: CC[C@H](Oc1cccc(Cn2c(C)c(C)c3cc(C(=O)N[C@@H](C)c4cccc(C(C)C)c4)ccc32)c1)C(=O)O]

The title compound was prepared following the same protocol as described in Step 6, Example 36, using the (S)-methyl 2-(3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [M+H]+

Example 78: (R)-2-(3-((5-(((S)-1-(3-Isopropylphenyl)ethyl)carbamoyl)-2,3-dimethyl-1H-indol-1-yl)methyl)phenoxy)butanoic acid

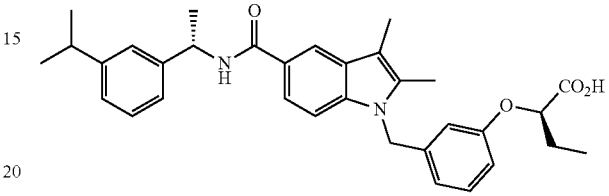

Step 1: (R)-Methyl 2-(m-tolyloxy)butanoate

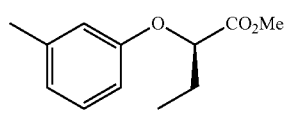

The title compound was prepared following the same protocol as described in Step 1, Example 42, using the (S)-methyl 2-hydroxybutanoate instead of the (S)-methyl 2-hydroxypropanoate.

Step 2: (R)-Methyl 2-(3-(bromomethyl)phenoxy)butanoate

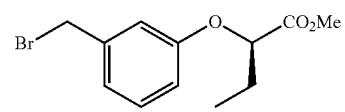 [SMILES: CC[C@@H](Oc1cccc(CBr)c1)C(=O)OC]

The title compound was prepared following the same protocol as described in Step 2, Example 36, using the (R)-methyl 2-(m-tolyloxy)butanoate instead of the methyl 2-(p-tolyloxy)acetate.

Step 3: (R)-Allyl 1-(3-((1-methoxy-1-oxobutan-2-yl)oxy)benzyl)-2,3-dimethyl-1H-indole-5-carboxylate

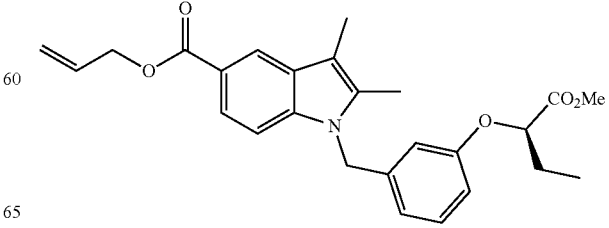

The title compound was prepared following the same general protocol as described in Step 3, Example 36, using the (R)-methyl 2-(3-(bromomethyl)phenoxy)butanoate instead of the methyl 2-(4-(bromomethyl)phenoxy)acetate. ESI-MS (m/z): 436 [M+H]⁺.

Step 4: (R)-1-(3-((1-Methoxy-1-oxobutan-2-yl)oxy)benzyl)-2,3-dimethyl-1H-indole-5-carboxylic acid

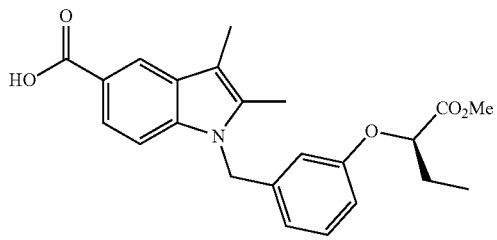 [SMILES: CC[C@@H](Oc1cccc(Cn2c(C)c(C)c3cc(C(=O)O)ccc32)c1)C(=O)OC]

The title compound was prepared following the same general protocol as described in Step 4, Example 36, using the (R)-allyl 1-(3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 382 [M+H]⁺.

Step 5: (R)-Methyl 2-(3-((5-(((S)-1-(3-isopropylphenyl)ethyl)carbamoyl)-2,3-dimethyl-1H-indol-1-yl)methyl)phenoxy)butanoate

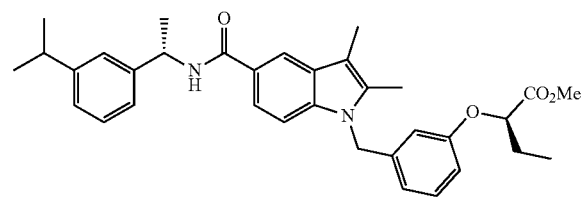 [SMILES: CC[C@@H](Oc1cccc(Cn2c(C)c(C)c3cc(C(=O)N[C@@H](C)c4cccc(C(C)C)c4)ccc32)c1)C(=O)OC]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(3-Isopropylphenyl)ethyl)carbamoyl)-2,3-dimethyl-1H-indol-1-yl)methyl)phenoxy)butanoic acid

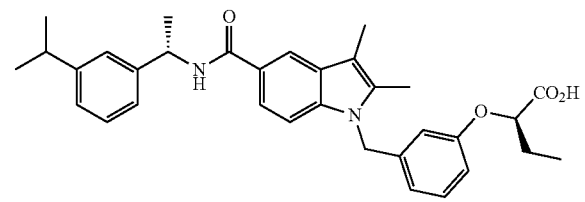 [SMILES: CC[C@@H](Oc1cccc(Cn2c(C)c(C)c3cc(C(=O)N[C@@H](C)c4cccc(C(C)C)c4)ccc32)c1)C(=O)O]

The title compound was prepared following the same protocol as described in Step 6, Example 36, using the (R)-methyl 2-(3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 527 [M+H]⁺

Example 79: (S)-2-(3-((5-(((S)-1-(3-Isopropylphenyl)ethyl)carbamoyl)-2,3-dimethyl-1H-indol-1-yl)methyl)phenoxy)-3-methylbutanoic acid

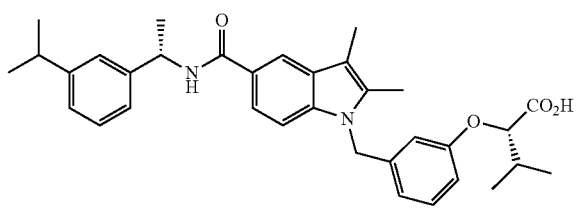 [SMILES: Cc1c(C)n(Cc2cccc(O[C@H](C(=O)O)C(C)C)c2)c2ccc(C(=O)N[C@@H](C)c3cccc(C(C)C)c3)cc12]

Step 1: (S)-Methyl 3-methyl-2-(m-tolyloxy)butanoate

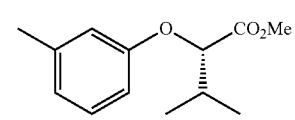 [SMILES: COC(=O)[C@@H](Oc1cccc(C)c1)C(C)C]

The title compound was prepared following the same protocol as described in Step 1, Example 42, using the (R)-methyl 2-hydroxy-3-methylbutanoate instead of the (S)-methyl 2-hydroxypropanoate.

Step 2: (S)-Methyl 2-(3-(bromomethyl)phenoxy)-3-methylbutanoate

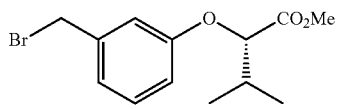 [SMILES: COC(=O)[C@@H](Oc1cccc(CBr)c1)C(C)C]

The title compound was prepared following the same protocol as described in Step 2, Example 36, using the (S)-methyl 3-methyl-2-(m-tolyloxy)butanoate instead of the methyl 2-(p-tolyloxy)acetate.

Step 3: (S)-Allyl 1-(3-((1-methoxy-3-methyl-1-oxobutan-2-yl)oxy)benzyl)-2,3-dimethyl-1H-indole-5-carboxylate

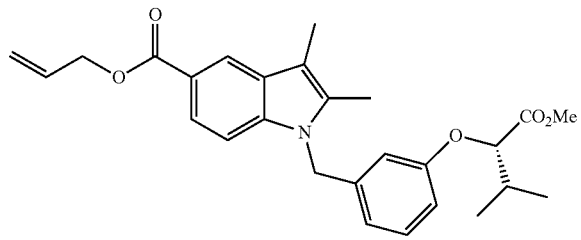 [SMILES: C=CCOC(=O)c1ccc2c(c1)c(C)c(C)n2Cc1cccc(O[C@H](C(=O)OC)C(C)C)c1]

The title compound was prepared following the same general protocol as described in Step 3, Example 36, using the (S)-methyl 2-(3-(bromomethyl)phenoxy)-3-methylbutanoate instead of the methyl 2-(4-(bromomethyl)phenoxy)acetate. ESI-MS (m/z): 450 [M+H]⁺.

Step 4: (S)-1-(3-((1-Methoxy-3-methyl-1-oxobutan-2-yl)oxy)benzyl)-2,3-dimethyl-1H-indole-5-carboxylic acid

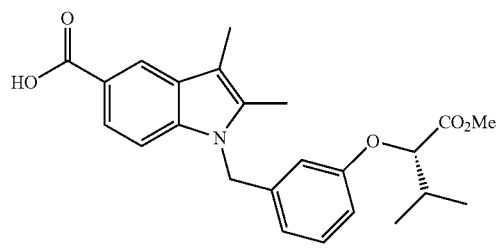 [SMILES: COC(=O)[C@@H](Oc1cccc(Cn2c(C)c(C)c3cc(C(=O)O)ccc32)c1)C(C)C]

The title compound was prepared following the same general protocol as described in Step 4, Example 36, using the (S)-allyl 1-(3-(1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 396 [M+H]⁺.

Step 5: (S)-Methyl 2-(3-((5-(((S)-1-(3-isopropylphenyl)ethyl)carbamoyl)-2,3-dimethyl-1H-indol-1-yl)methyl)phenoxy)-3-methylbutanoate

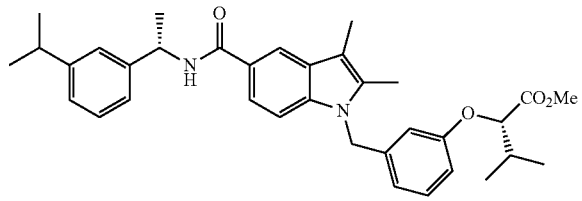 [SMILES: COC(=O)[C@@H](Oc1cccc(Cn2c(C)c(C)c3cc(C(=O)N[C@@H](C)c4cccc(C(C)C)c4)ccc32)c1)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(3-(1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(3-((5-(((S)-1-(3-Isopropylphenyl)ethyl)carbamoyl)-2,3-dimethyl-1H-indol-1-yl)methyl)phenoxy)-3-methylbutanoic acid

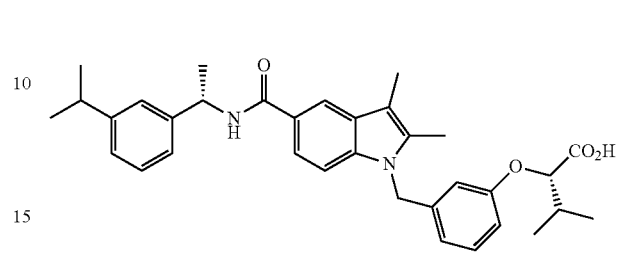

The title compound was prepared following the same protocol as described in Step 6, Example 36, using the (S)-methyl 2-(3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 541 [M+H]⁺

Example 80: (R)-2-(3-((5-(((S)-1-(3-Isopropylphenyl)ethyl)carbamoyl)-2,3-dimethyl-1H-indol-1-yl)methyl)phenoxy)-3-methylbutanoic acid

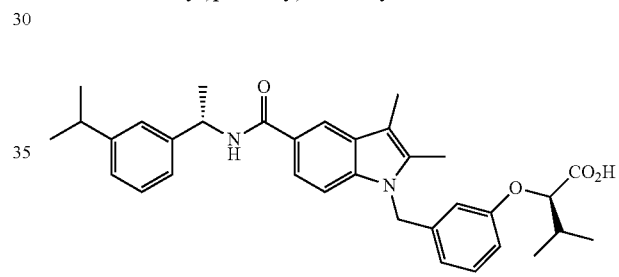

Step 1: (R)-Methyl 3-methyl-2-(m-tolyloxy)butanoate

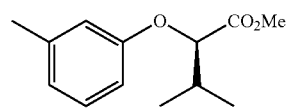 [SMILES: COC(=O)[C@H](Oc1cccc(C)c1)C(C)C]

The title compound was prepared following the same protocol as described in Step 1, Example 42, using the (S)-methyl 2-hydroxy-3-methylbutanoate instead of the (S)-methyl 2-hydroxypropanoate.

Step 2: (R)-Methyl 2-(3-(bromomethyl)phenoxy)₃-methylbutanoate

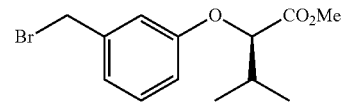 [SMILES: COC(=O)[C@H](Oc1cccc(CBr)c1)C(C)C]

The title compound was prepared following the same protocol as described in Step 2, Example 36, using the (R)-methyl 3-methyl-2-(m-tolyloxy)butanoate instead of the methyl 2-(p-tolyloxy)acetate.

Step 3: (R)-Allyl 1-(3-((1-methoxy-3-methyl-1-oxobutan-2-yl)oxy)benzyl)-2,3-dimethyl-1H-indole-5-carboxylate

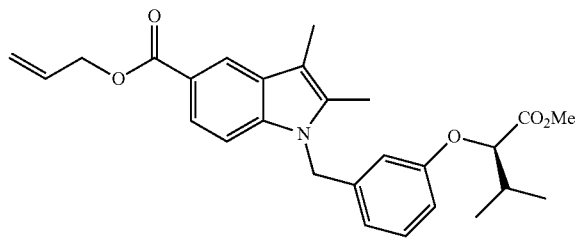 [SMILES: C=CCOC(=O)c1ccc2c(c1)c(C)c(C)n2Cc1cccc(O[C@@H](C(=O)OC)C(C)C)c1]

The title compound was prepared following the same general protocol as described in Step 3, Example 36, using the (R)-methyl 2-(3-(bromomethyl)phenoxy)-3-methylbutanoate instead of the methyl 2-(4-(bromomethyl)phenoxy)acetate. ESI-MS (m/z): 450 [M+H]$^+$.

Step 4: (R)-1-(3-((1-Methoxy-3-methyl-1-oxobutan-2-yl)oxy)benzyl)-2,3-dimethyl-1H-indole-5-carboxylic acid

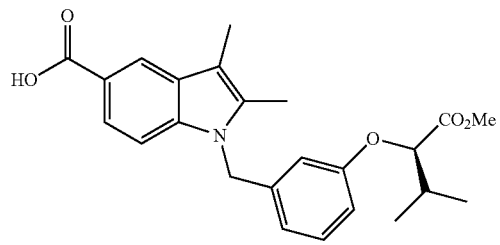 [SMILES: COC(=O)[C@H](Oc1cccc(Cn2c(C)c(C)c3cc(C(=O)O)ccc32)c1)C(C)C]

The title compound was prepared following the same general protocol as described in Step 4, Example 36, using the (R)-allyl 1-(3-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 396 [M+H]$^+$.

Step 5: (R)-Methyl 2-(3-((5-(((S)-1-(3-isopropylphenyl)ethyl)carbamoyl)-2,3-dimethyl-1H-indol-1-yl)methyl)phenoxy)-3-methylbutanoate

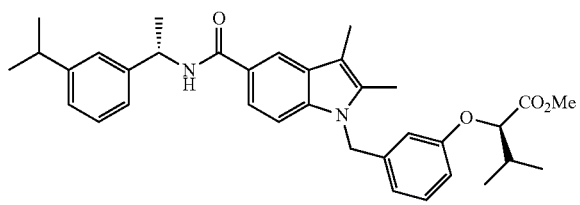 [SMILES: COC(=O)[C@H](Oc1cccc(Cn2c(C)c(C)c3cc(C(=O)N[C@@H](C)c4cccc(C(C)C)c4)ccc32)c1)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(3-((5-(((S)-1-(3-Isopropylphenyl)ethyl)carbamoyl)-2,3-dimethyl-1H-indol-1-yl)methyl)phenoxy)-3-methylbutanoic acid

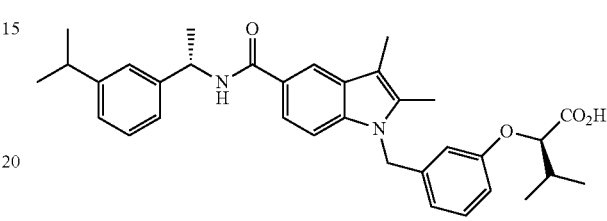

The title compound was prepared following the same protocol as described in Step 6, Example 36, using the (R)-methyl 2-(3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 541 [M+H]$^+$ Example 81: (S)-2-(2-Chloro-5-((5-(((S)-1-(3-isopropylphenyl)ethyl)carbamoyl)-2,3-dimethyl-1H-indol-1-yl)methyl)phenoxy)butanoic acid

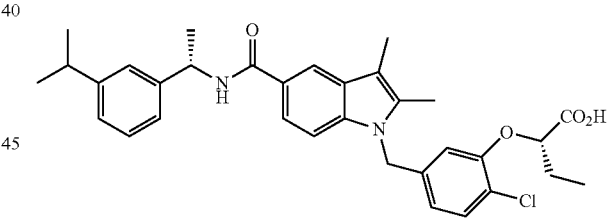

Step 1: (S)-Methyl 2-(2-chloro-5-methylphenoxy)butanoate

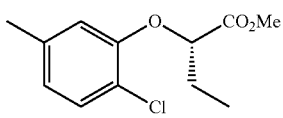 [SMILES: CC[C@H](Oc1cc(C)ccc1Cl)C(=O)OC]

The title compound was prepared following the same protocol as described in Step 1, Example 42, using the (R)-methyl 2-hydroxybutanoate instead of the (S)-methyl 2-hydroxypropanoate and the 2-chloro-5-methylphenol instead of the m-cresol.

Step 2: (S)-Methyl 2-(5-(bromomethyl)-2-chlorophenoxy)butanoate

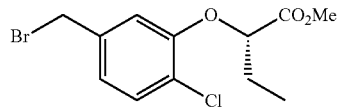 [SMILES: CC[C@H](Oc1cc(CBr)ccc1Cl)C(=O)OC]

The title compound was prepared following the same protocol as described in Step 2, Example 36, using the (S)-methyl 2-(2-chloro-5-methylphenoxy)butanoate instead of the methyl 2-(p-tolyloxy)acetate.

Step 3: (S)-Allyl 1-(4-chloro-3-((1-methoxy-1-oxobutan-2-yl)oxy)benzyl)-2,3-dimethyl-1H-indole-5-carboxylate

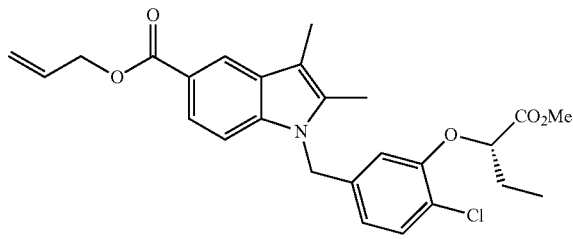 [SMILES: C=CCOC(=O)c1ccc2c(c1)c(C)c(C)n2Cc1ccc(Cl)c(O[C@@H](CC)C(=O)OC)c1]

The title compound was prepared following the same general protocol as described in Step 3, Example 36, using the (S)-methyl 2-(5-(bromomethyl)-2-chlorophenoxy)butanoate instead of the methyl 2-(4-(bromomethyl)phenoxy)acetate. ESI-MS (m/z): 470/471/472 [M+H]$^+$.

Step 4: (S)-1-(4-Chloro-3-((1-methoxy-1-oxobutan-2-yl)oxy)benzyl)-2,3-dimethyl-1H-indole-5-carboxylic acid

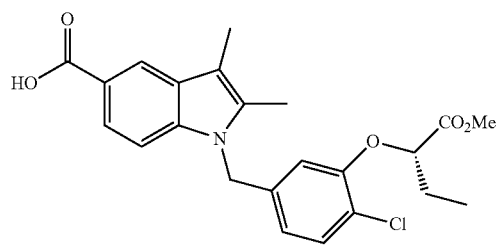 [SMILES: CC[C@H](Oc1cc(Cn2c(C)c(C)c3cc(C(=O)O)ccc32)ccc1Cl)C(=O)OC]

The title compound was prepared following the same general protocol as described in Step 4, Example 36, using the (S)-allyl 1-(4-chloro-3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (S)-Methyl 2-(2-chloro-5-((5-(((S)-1-(3-isopropylphenyl)ethyl)carbamoyl)-2,3-dimethyl-1H-indol-1-yl)methyl)phenoxy)butanoate

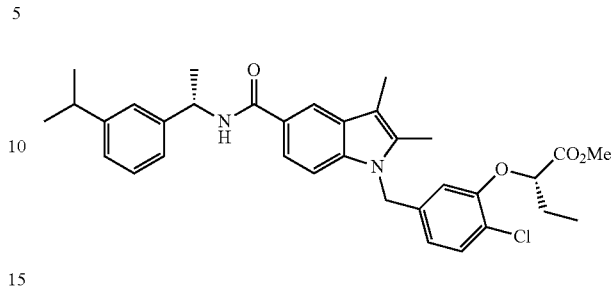

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(4-chloro-3-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-Chloro-5-((5-(((S)-1-(3-isopropylphenyl)ethyl)carbamoyl)-2,3-dimethyl-1H-indol-1-yl)methyl)phenoxy)butanoic acid

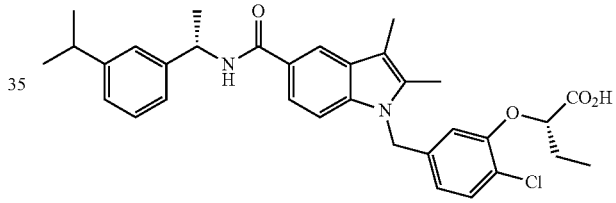

The title compound was prepared following the same protocol as described in Step 6, Example 36, using the (S)-methyl 2-(2-chloro-5-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$

Example 82: (S)-2-(4-Chloro-3-((5-(((S)-1-(3-isopropylphenyl)ethyl)carbamoyl)-2,3-dimethyl-1H-indol-1-yl)methyl)phenoxy)butanoic acid

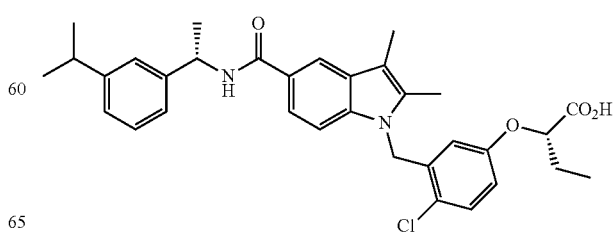

Step 1: (S)-Methyl 2-(4-chloro-3-methylphenoxy)butanoate

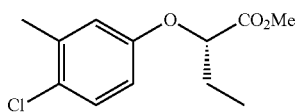 [SMILES: CC[C@H](Oc1ccc(Cl)c(C)c1)C(=O)OC]

The title compound was prepared following the same protocol as described in Step 1, Example 42, using the (R)-methyl 2-hydroxybutanoate instead of the (S)-methyl 2-hydroxypropanoate and the 4-chloro-3-methylphenol instead of the m-cresol.

Step 2: (S)-Methyl 2-(3-(bromomethyl)-4-chlorophenoxy)butanoate

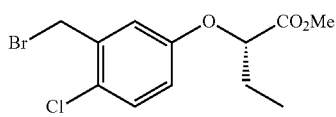 [SMILES: CC[C@H](Oc1ccc(Cl)c(CBr)c1)C(=O)OC]

The title compound was prepared following the same protocol as described in Step 2, Example 36, using the (S)-methyl 2-(4-chloro-3-methylphenoxy)butanoate instead of the methyl 2-(p-tolyloxy)acetate.

Step 3: (S)-Allyl 1-(2-chloro-5-((1-methoxy-1-oxobutan-2-yl)oxy)benzyl)-2,3-dimethyl-1H-indole-5-carboxylate

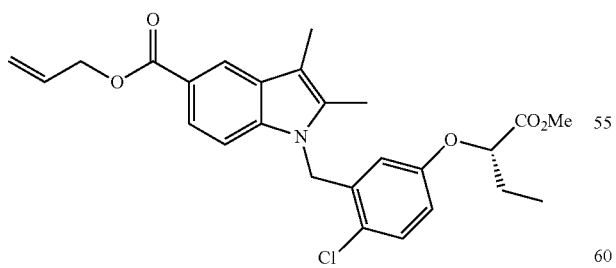

The title compound was prepared following the same general protocol as described in Step 3, Example 36, using the (S)-methyl 2-(3-(bromomethyl)-4-chlorophenoxy)butanoate instead of the methyl 2-(4-(bromomethyl)phenoxy)acetate. ESI-MS (m/z): 470/471/472 [M+H]$^+$.

Step 4: (S)-1-(2-Chloro-5-((1-methoxy-1-oxobutan-2-yl)oxy)benzyl)-2,3-dimethyl-1H-indole-5-carboxylic acid

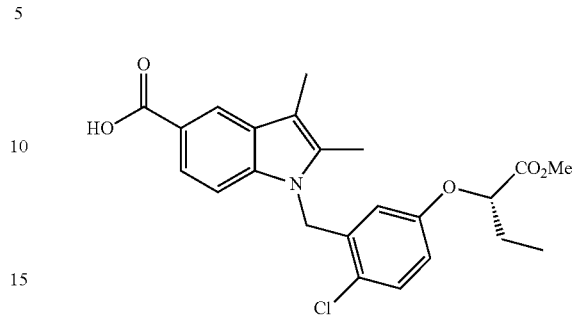

The title compound was prepared following the same general protocol as described in Step 4, Example 36, using the (S)-allyl 1-(2-chloro-5-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (S)-Methyl 2-(4-chloro-3-((5-(((S)-1-(3-isopropylphenyl)ethyl)carbamoyl)-2,3-dimethyl-1H-indol-1-yl)methyl)phenoxy)butanoate

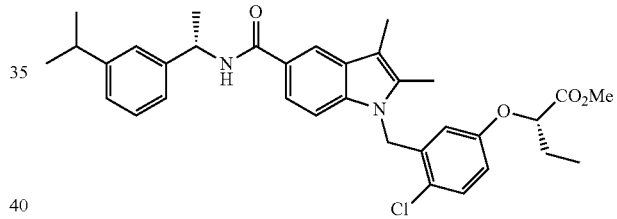

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-5-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-Chloro-3-((5-(((S)-1-(3-isopropylphenyl)ethyl)carbamoyl)-2,3-dimethyl-1H-indol-1-yl)methyl)phenoxy)butanoic acid


The title compound was prepared following the same protocol as described in Step 6, Example 36, using the (S)-methyl 2-(4-chloro-3-((5-(((S)-1-(3-isopropylphenyl)ethyl)carbamoyl)-2,3-dimethyl-1H-indol-1-yl)methyl)phenoxy)butanoate instead of the (S)-methyl 2-(4-(((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]⁺

Example 83: (R)-2-(2-Chloro-5-((5-(((S)-1-(3-isopropylphenyl)ethyl)carbamoyl)-2,3-dimethyl-1H-indol-1-yl)methyl)phenoxy)butanoic acid

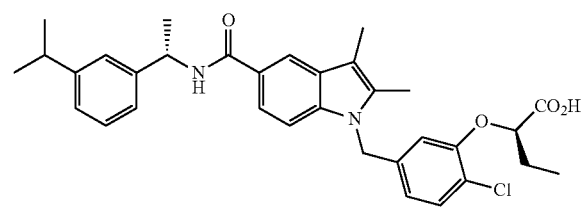 [SMILES: CC[C@@H](Oc1cc(Cn2c(C)c(C)c3cc(C(=O)N[C@@H](C)c4cccc(C(C)C)c4)ccc32)ccc1Cl)C(=O)O]

Step 1: (R)-Methyl 2-(2-chloro-5-methylphenoxy)butanoate

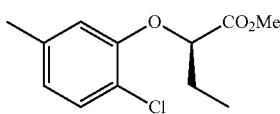 [SMILES: CC[C@@H](Oc1cc(C)ccc1Cl)C(=O)OC]

The title compound was prepared following the same protocol as described in Step 1, Example 42, using the (S)-methyl 2-hydroxybutanoate instead of the (S)-methyl 2-hydroxypropanoate and the 2-chloro-5-methylphenol instead of the m-cresol.

Step 2: (R)-Methyl 2-(5-(bromomethyl)-2-chlorophenoxy)butanoate

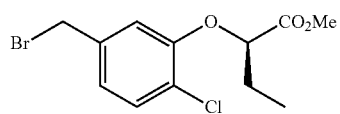 [SMILES: CC[C@@H](Oc1cc(CBr)ccc1Cl)C(=O)OC]

The title compound was prepared following the same protocol as described in Step 2, Example 36, using the (R)-methyl 2-(2-chloro-5-methylphenoxy)butanoate instead of the methyl 2-(p-tolyloxy)acetate.

Step 3: (R)-Allyl 1-(4-chloro-3-((1-methoxy-1-oxobutan-2-yl)oxy)benzyl)-2,3-dimethyl-1H-indole-5-carboxylate

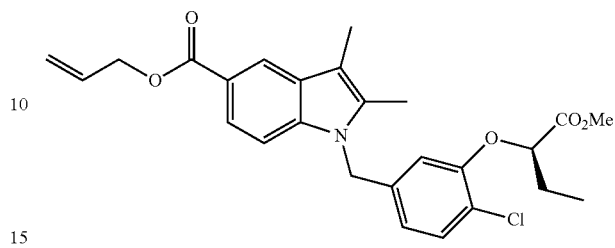

The title compound was prepared following the same general protocol as described in Step 3, Example 36, using the (R)-methyl 2-(5-(bromomethyl)-2-chlorophenoxy)butanoate instead of the methyl 2-(4-(bromomethyl)phenoxy)acetate. ESI-MS (m/z): 470/471/472 [M+H]⁺.

Step 4: (R)-1-(4-Chloro-3-((1-methoxy-1-oxobutan-2-yl)oxy)benzyl)-2,3-dimethyl-1H-indole-5-carboxylic acid

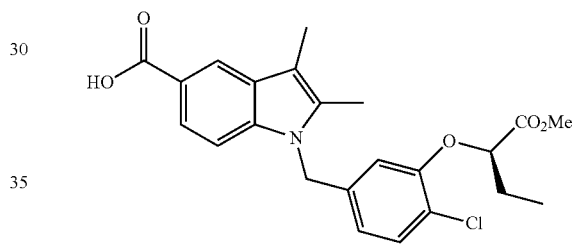

The title compound was prepared following the same general protocol as described in Step 4, Example 36, using the (R)-allyl 1-(4-chloro-3-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]⁺.

Step 5: (R)-Methyl 2-(2-chloro-5-((5-(((S)-1-(3-isopropylphenyl)ethyl)carbamoyl)-2,3-dimethyl-1H-indol-1-yl)methyl)phenoxy)butanoate

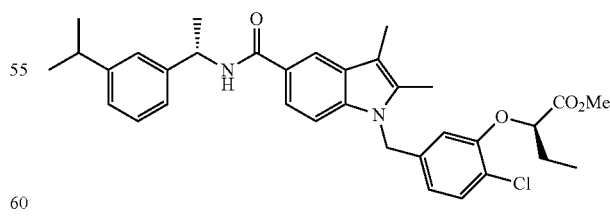

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-chloro-3-((1-methoxy-1-oxobutan-2-yl)oxy)benzyl)-2,3-dimethyl-1H-indole-5-carboxylic acid

Step 6: (R)-2-(2-chloro-5-((5-(((S)-1-(3-Isopropylphenyl)ethyl)carbamoyl)-2,3-dimethyl-1H-indol-1-yl)methyl)phenoxy)butanoic acid

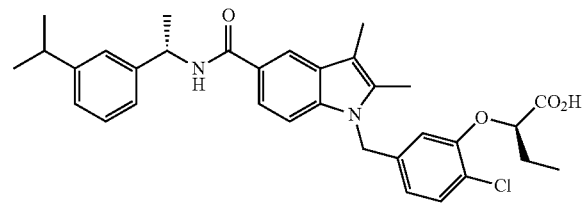 [SMILES: CC[C@@H](Oc1cc(Cn2c(C)c(C)c3cc(C(=O)N[C@@H](C)c4cccc(C(C)C)c4)ccc32)ccc1Cl)C(=O)O]

The title compound was prepared following the same protocol as described in Step 6, Example 36, using the (R)-methyl 2-(2-chloro-5-((5-(((S)-1-(3-isopropylphenyl)ethyl)carbamoyl)-2,3-dimethyl-1H-indol-1-yl)methyl)phenoxy)butanoate instead of the (S)-methyl 2-(4-(((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$

Example 84: (R)-2-(4-Chloro-3-((5-(((S)-1-(3-isopropylphenyl)ethyl)carbamoyl)-2,3-dimethyl-1H-indol-1-yl)methyl)phenoxy)butanoic acid

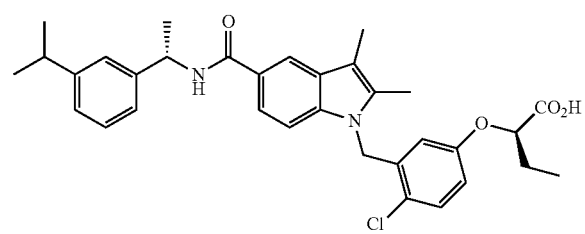 [SMILES: CC[C@@H](Oc1ccc(Cl)c(Cn2c(C)c(C)c3cc(C(=O)N[C@@H](C)c4cccc(C(C)C)c4)ccc32)c1)C(=O)O]

Step 1: (R)-Methyl 2-(4-chloro-3-methylphenoxy)butanoate

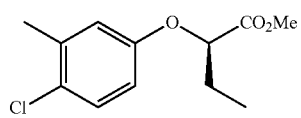 [SMILES: CC[C@@H](Oc1ccc(Cl)c(C)c1)C(=O)OC]

The title compound was prepared following the same protocol as described in Step 1, Example 42, using the (S)-methyl 2-hydroxybutanoate instead of the (S)-methyl 2-hydroxypropanoate and the 4-chloro-3-methylphenol instead of the m-cresol.

Step 2: (R)-Methyl 2-(3-(bromomethyl)-4-chlorophenoxy)butanoate

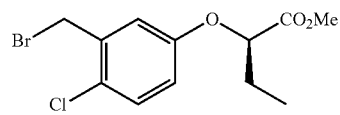

The title compound was prepared following the same protocol as described in Step 2, Example 36, using the (R)-methyl 2-(4-chloro-3-methylphenoxy)butanoate instead of the methyl 2-(p-tolyloxy)acetate.

Step 3: (R)-Allyl 1-(2-chloro-5-((1-methoxy-1-oxobutan-2-yl)oxy)benzyl)-2,3-dimethyl-1H-indole-5-carboxylate

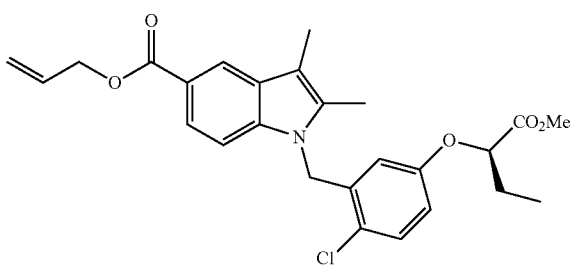 [SMILES: C=CCOC(=O)c1ccc2c(c1)c(C)c(C)n2Cc1cc(O[C@H](CC)C(=O)OC)ccc1Cl]

The title compound was prepared following the same general protocol as described in Step 3, Example 36, using the (R)-methyl 2-(3-(bromomethyl)-4-chlorophenoxy)butanoate instead of the methyl 2-(4-(bromomethyl)phenoxy)acetate. ESI-MS (m/z): 470/471/472 [M+H]$^+$.

Step 4: (R)-1-(2-Chloro-5-((1-methoxy-1-oxobutan-2-yl)oxy)benzyl)-2,3-dimethyl-1H-indole-5-carboxylic acid

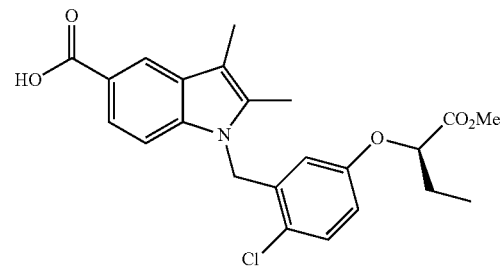 [SMILES: CC[C@@H](Oc1ccc(Cl)c(Cn2c(C)c(C)c3cc(C(=O)O)ccc32)c1)C(=O)OC]

The title compound was prepared following the same general protocol as described in Step 4, Example 36, using the (R)-allyl 1-(2-chloro-5-((1-methoxy-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (R)-Methyl 2-(4-chloro-3-((5-(((S)-1-(3-isopropylphenyl)ethyl)carbamoyl)-2,3-dimethyl-1H-indol-1-yl)methyl)phenoxy)butanoate

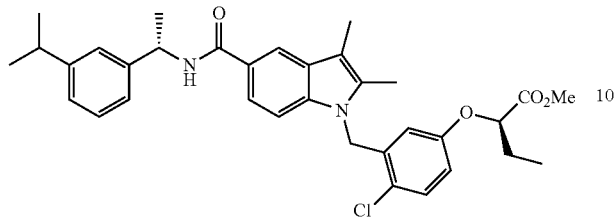

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-5-((1-methoxy-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(4-Chloro-3-((5-(((S)-1-(3-isopropylphenyl)ethyl)carbamoyl)-2,3-dimethyl-1H-indol-1-yl)methyl)phenoxy)butanoic acid

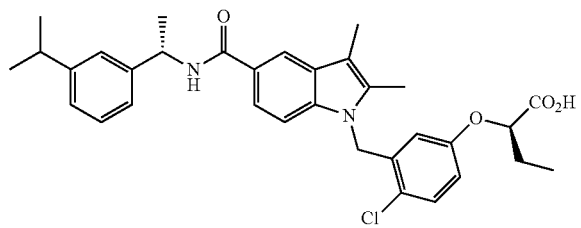 [SMILES: CC[C@@H](Oc1ccc(Cl)c(Cn2c(C)c(C)c3cc(C(=O)N[C@@H](C)c4cccc(C(C)C)c4)ccc32)c1)C(=O)O]

The title compound was prepared following the same protocol as described in Step 6, Example 36, using the (R)-methyl 2-(4-chloro-3-((5-(((S)-1-(3-isopropylphenyl)ethyl)carbamoyl)-2,3-dimethyl-1H-indol-1-yl)methyl)phenoxy)butanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]+

Example 85: (S)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

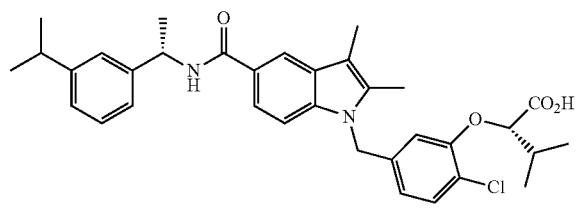 [SMILES: Cc1c(C)n(Cc2ccc(Cl)c(O[C@H](C(=O)O)C(C)C)c2)c2ccc(C(=O)N[C@@H](C)c3cccc(C(C)C)c3)cc12]

Step 1: (S)-Methyl 2-(2-chloro-5-methylphenoxy)-3-methylbutanoate

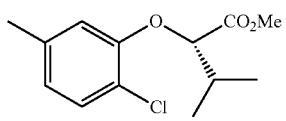 [SMILES: COC(=O)[C@@H](Oc1cc(C)ccc1Cl)C(C)C]

The title compound was prepared following the same protocol as described in Step 1, Example 42, using the (R)-methyl 2-hydroxy-3-methylbutanoate instead of the (S)-methyl 2-hydroxypropanoate and the 2-chloro-5-methylphenol instead of the m-cresol.

Step 2: (S)-Methyl 2-(5-(bromomethyl)-2-chlorophenoxy)-3-methylbutanoate

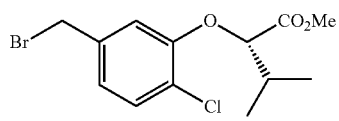 [SMILES: COC(=O)[C@@H](Oc1cc(CBr)ccc1Cl)C(C)C]

The title compound was prepared following the same protocol as described in Step 2, Example 36, using the (S)-methyl 2-(2-chloro-5-methylphenoxy)-3-methylbutanoate instead of the methyl 2-(p-tolyloxy)acetate.

Step 3: (S)-Allyl 1-(4-chloro-3-((1-methoxy-3-methyl-1-oxobutan-2-yl)oxy)benzyl)-2,3-dimethyl-1H-indole-5-carboxylate

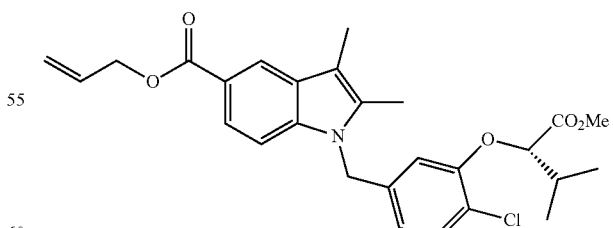

The title compound was prepared following the same general protocol as described in Step 3, Example 36, using the (S)-methyl 2-(5-(bromomethyl)-2-chlorophenoxy)-3-methylbutanoate instead of the methyl 2-(4-(bromomethyl)phenoxy)acetate. ESI-MS (m/z): 470/471/472 [M+H]+.

Step 4: (S)-1-(4-Chloro-3-((1-methoxy-3-methyl-1-oxobutan-2-yl)oxy)benzyl)-2,3-dimethyl-1H-indole-5-carboxylic acid

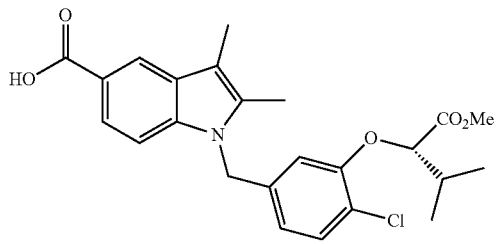 [SMILES: COC(=O)[C@@H](Oc1cc(Cn2c(C)c(C)c3cc(C(=O)O)ccc32)ccc1Cl)C(C)C]

The title compound was prepared following the same general protocol as described in Step 4, Example 36, using the (S)-allyl 1-(4-chloro-3-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (S)-Methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate

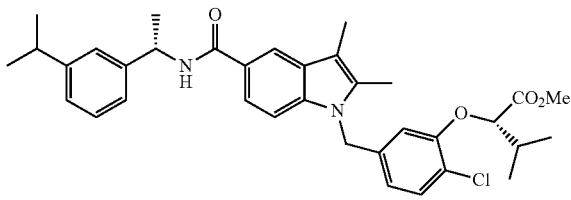 [SMILES: COC(=O)[C@@H](Oc1cc(Cn2c(C)c(C)c3cc(C(=O)N[C@@H](C)c4cccc(C(C)C)c4)ccc32)ccc1Cl)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(4-chloro-3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

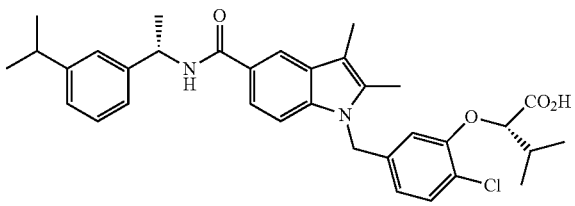 [SMILES: Cc1c(C)n(Cc2ccc(Cl)c(O[C@H](C(=O)O)C(C)C)c2)c2ccc(C(=O)N[C@@H](C)c3cccc(C(C)C)c3)cc12]

The title compound was prepared following the same protocol as described in Step 6, Example 36, using the (S)-methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$

Example 86: (S)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

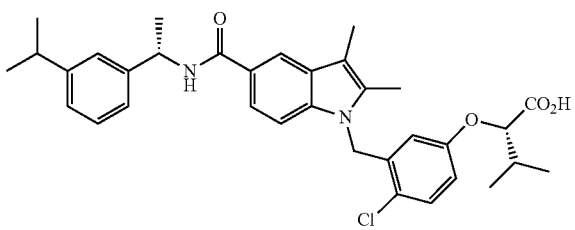

Step 1: (S)-Methyl 2-(4-chloro-3-methylphenoxy)-3-methylbutanoate

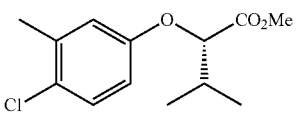 [SMILES: COC(=O)[C@@H](Oc1ccc(Cl)c(C)c1)C(C)C]

The title compound was prepared following the same protocol as described in Step 1, Example 42, using the (R)-methyl 2-hydroxy-3-methylbutanoate instead of the (S)-methyl 2-hydroxypropanoate and the 4-chloro-3-methylphenol instead of the m-cresol.

Step 2: (S)-Methyl 2-(3-(bromomethyl)-4-chlorophenoxy)-3-methylbutanoate

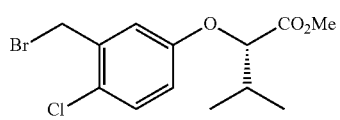

The title compound was prepared following the same protocol as described in Step 2, Example 36, using the (S)-methyl 2-(4-chloro-3-methylphenoxy)-3-methylbutanoate instead of the methyl 2-(p-tolyloxy)acetate.

Step 3: (S)-Allyl 1-(2-chloro-5-((1-methoxy-3-methyl-1-oxobutan-2-yl)oxy)benzyl)-2,3-dimethyl-1H-indole-5-carboxylate

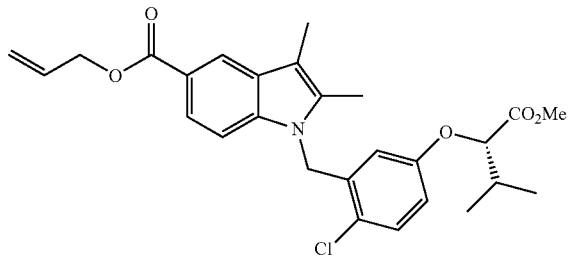 [SMILES: C=CCOC(=O)c1ccc2c(c1)c(C)c(C)n2Cc1cc(O[C@H](C(=O)OC)C(C)C)ccc1Cl]

The title compound was prepared following the same general protocol as described in Step 3, Example 36, using the (S)-methyl 2-(3-(bromomethyl)-4-chlorophenoxy)-3-methylbutanoate instead of the methyl 2-(4-(bromomethyl)phenoxy)acetate. ESI-MS (m/z): 470/471/472 $[M+H]^+$.

Step 4: (S)-1-(2-Chloro-5-((1-methoxy-3-methyl-1-oxobutan-2-yl)oxy)benzyl)-2,3-dimethyl-1H-indole-5-carboxylic acid

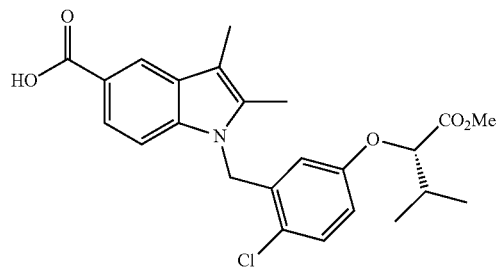 [SMILES: COC(=O)[C@@H](Oc1ccc(Cl)c(Cn2c(C)c(C)c3cc(C(=O)O)ccc32)c1)C(C)C]

The title compound was prepared following the same general protocol as described in Step 4, Example 36, using the (S)-allyl 1-(2-chloro-5-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 $[M+H]^+$.

Step 5: (S)-Methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate

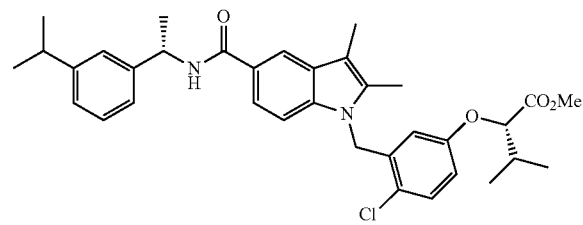 [SMILES: COC(=O)[C@@H](Oc1ccc(Cl)c(Cn2c(C)c(C)c3cc(C(=O)N[C@@H](C)c4cccc(C(C)C)c4)ccc32)c1)C(C)C]

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (S)-1-(2-chloro-5-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (S)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

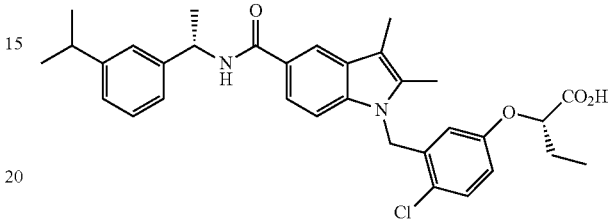

The title compound was prepared following the same protocol as described in Step 6, Example 36, using the (S)-methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-(((5-((1-(3-cyclopropylphenyl)ethyl)carbamoyl)-2,3-dimethyl-1H-indol-1-yl)methyl)phenoxy)acetate. ESI-MS (m/z): 561/562/563 $[M+H]^+$

Example 87: (R)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

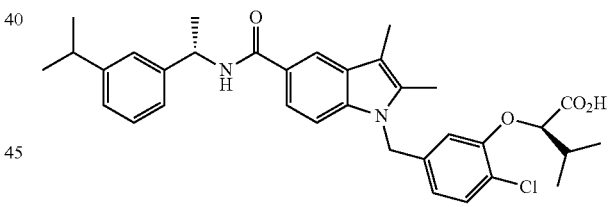

Step 1: (R)-Methyl 2-(2-chloro-5-methylphenoxy)-3-methylbutanoate

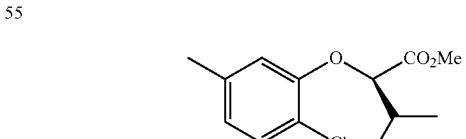

The title compound was prepared following the same protocol as described in Step 1, Example 42, using the (S)-methyl 2-hydroxy-3-methylbutanoate instead of the (S)-methyl 2-hydroxypropanoate and the 2-chloro-5-methylphenol instead of the m-cresol.

Step 2: (R)-Methyl 2-(5-(bromomethyl)-2-chlorophenoxy)-3-methylbutanoate

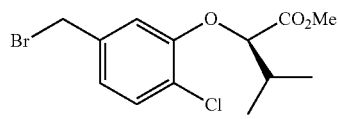 [SMILES: COC(=O)[C@H](Oc1cc(CBr)ccc1Cl)C(C)C]

The title compound was prepared following the same protocol as described in Step 2, Example 36, using the (R)-methyl 2-(2-chloro-5-methylphenoxy)-3-methylbutanoate instead of the methyl 2-(p-tolyloxy)acetate.

Step 3: (R)-Allyl 1-(4-chloro-3-((1-methoxy-3-methyl-1-oxobutan-2-yl)oxy)benzyl)-2,3-dimethyl-1H-indole-5-carboxylate

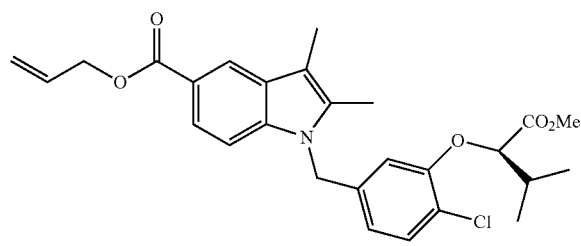 [SMILES: C=CCOC(=O)c1ccc2c(c1)c(C)c(C)n2Cc1ccc(Cl)c(O[C@@H](C(=O)OC)C(C)C)c1]

The title compound was prepared following the same general protocol as described in Step 3, Example 36, using the (R)-methyl 2-(5-(bromomethyl)-2-chlorophenoxy)-3-methylbutanoate instead of the methyl 2-(4-(bromomethyl)phenoxy)acetate. ESI-MS (m/z): 470/471/472 [M+H]$^+$.

Step 4: (R)-1-(4-Chloro-3-((1-methoxy-3-methyl-1-oxobutan-2-yl)oxy)benzyl)-2,3-dimethyl-1H-indole-5-carboxylic acid

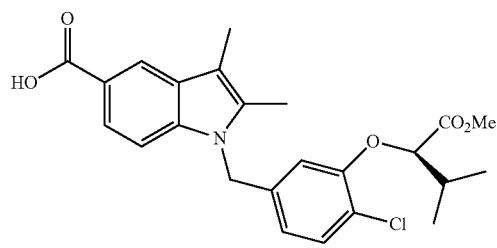 [SMILES: COC(=O)[C@H](Oc1cc(Cn2c(C)c(C)c3cc(C(=O)O)ccc32)ccc1Cl)C(C)C]

The title compound was prepared following the same general protocol as described in Step 4, Example 36, using the (R)-allyl 1-(4-chloro-3-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (R)-Methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate

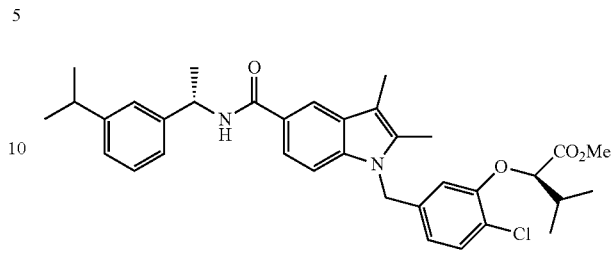

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(4-chloro-3-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(2-Chloro-5-((5-(((S)-1-(3-isopropylphenyl)ethyl)carbamoyl)-2,3-dimethyl-1H-indol-1-yl)methyl)phenoxy)-3-methylbutanoic acid

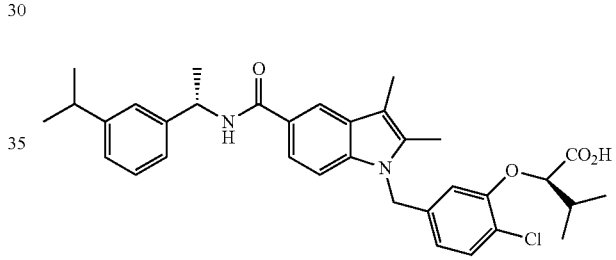

The title compound was prepared following the same protocol as described in Step 6, Example 36, using the (R)-methyl 2-(2-chloro-5-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$ Example 88: (R)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

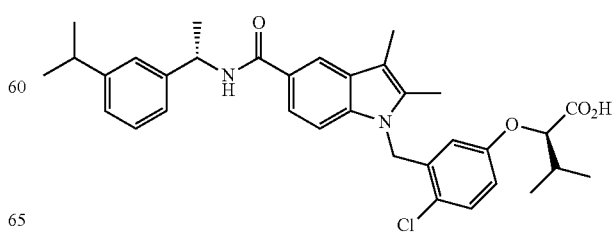

Step 1: (R)-Methyl 2-(4-chloro-3-methylphenoxy)-3-methylbutanoate

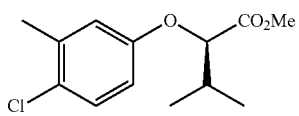 [SMILES: COC(=O)[C@H](Oc1ccc(Cl)c(C)c1)C(C)C]

The title compound was prepared following the same protocol as described in Step 1, Example 42, using the (S)-methyl 2-hydroxybutanoate instead of the (S)-methyl 2-hydroxy-3-methylpropanoate and the 4-chloro-3-methylphenol instead of the m-cresol.

Step 2: (R)-Methyl 2-(3-(bromomethyl)-4-chlorophenoxy)-3-methylbutanoate

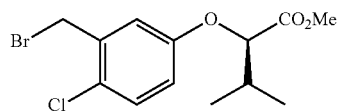 [SMILES: COC(=O)[C@H](Oc1ccc(Cl)c(CBr)c1)C(C)C]

The title compound was prepared following the same protocol as described in Step 2, Example 36, using the (R)-methyl 2-(4-chloro-3-methylphenoxy)-3-methylbutanoate instead of the methyl 2-(p-tolyloxy)acetate.

Step 3: (R)-Allyl 1-(2-chloro-5-((1-methoxy-3-methyl-1-oxobutan-2-yl)oxy)benzyl)-2,3-dimethyl-1H-indole-5-carboxylate

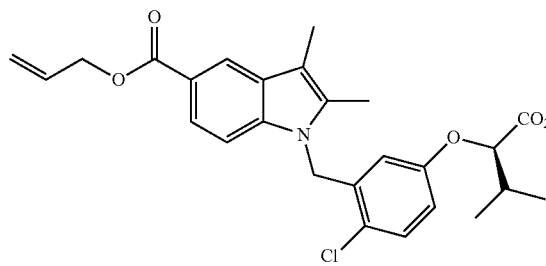

The title compound was prepared following the same general protocol as described in Step 3, Example 36, using the (R)-methyl 2-(3-(bromomethyl)-4-chlorophenoxy)-3-methylbutanoate instead of the methyl 2-(4-(bromomethyl)phenoxy)acetate. ESI-MS (m/z): 470/471/472 [M+H]$^+$.

Step 4: (R)-1-(2-Chloro-5-((1-methoxy-3-methyl-1-oxobutan-2-yl)oxy)benzyl)-2,3-dimethyl-1H-indole-5-carboxylic acid

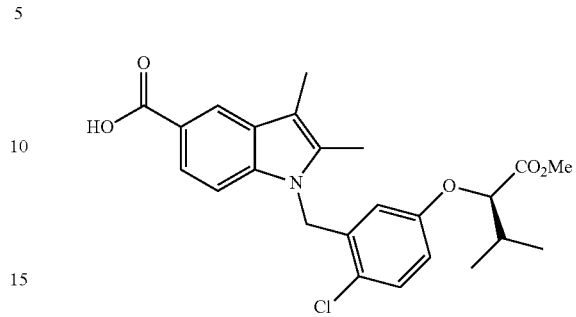

The title compound was prepared following the same general protocol as described in Step 4, Example 36, using the (R)-allyl 1-(2-chloro-5-((1-methoxy-3-methyl-1-oxobutan-2-yl)oxy)benzyl)-2,3-dimethyl-1H-indole-5-carboxylate instead of the allyl 1-(4-(2-methoxy-2-oxoethoxy)benzyl)-2,3-dimethyl-1H-indole-5-carboxylate. ESI-MS (m/z): 430/431/432 [M+H]$^+$.

Step 5: (R)-Methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate

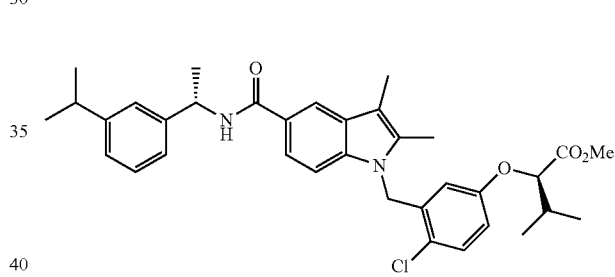

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and the (R)-1-(2-chloro-5-((1-methoxy-3-methyl-1-oxobutan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid.

Step 6: (R)-2-(4-Chloro-3-((5-(((S)-1-(3-isopropylphenyl)ethyl)carbamoyl)-2,3-dimethyl-1H-indol-1-yl)methyl)phenoxy)-3-methylbutanoic acid

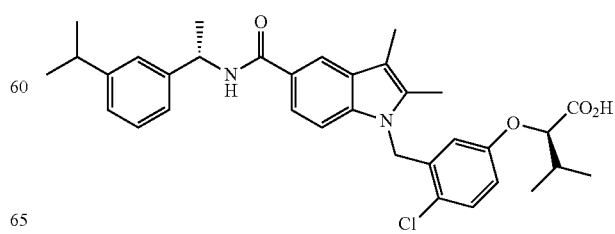

The title compound was prepared following the same protocol as described in Step 6, Example 36, using the (R)-methyl 2-(4-chloro-3-((5-(((S)-1-(3-isopropylphenyl)ethyl)carbamoyl)-2,3-dimethyl-1H-indol-1-yl)methyl)phenoxy)-3-methylbutanoate instead of the (S)-methyl 2-(4-((5-((1-(3-cyclopropylphenyl)ethyl)carbamoyl)-2,3-dimethyl-1H-indol-1-yl)methyl)phenoxy)acetate. ESI-MS (m/z): 561/562/563 [M+H]$^+$.

Example 89: 1-(4-((2,3-dimethyl-5-((1-phenylpropyl)carbamoyl)-1H-indol-1-yl)methyl)phenyl)cyclopropanecarboxylic acid

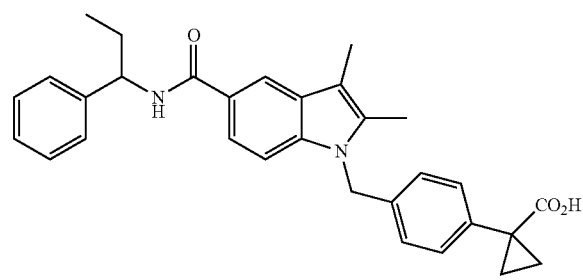 [SMILES: CCC(NC(=O)c1ccc2c(c1)c(C)c(C)n2Cc1ccc(C2(C(=O)O)CC2)cc1)c1ccccc1]

The title compound was prepared following the same protocol as described in Step 5 and 8, Example 35, using the 1-phenylpropanamine instead of the (S)-1-(3-bromophenyl)ethanamine. ESI-MS (m/z): 481 [MH]$^+$.

Example 90: (S)-1-(4-(((5-((1-(4-bromophenyl)ethyl)carbamoyl)-2,3-dimethyl-1H-indol-1-yl)methyl)phenyl)cyclopropanecarboxylic acid

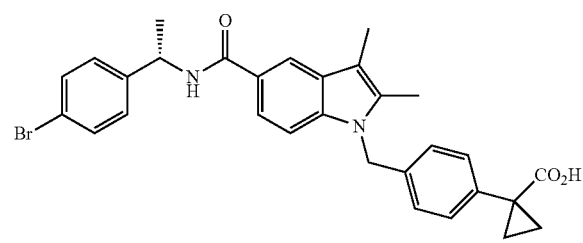 [SMILES: Cc1c(C)n(Cc2ccc(C3(C(=O)O)CC3)cc2)c2ccc(C(=O)N[C@@H](C)c3ccc(Br)cc3)cc12]

The title compound was prepared following the same protocol as described in Step 5 and 8, Example 35, using the (S)-1-(4-bromophenyl)ethanamine instead of the (S)-1-(3-bromophenyl)ethanamine. ESI-MS (m/z): 545/547 [MH]$^+$.

Example 91: (S)-1-(4-(((5-((1-(4-isopropylphenyl)ethyl)carbamoyl)-2,3-dimethyl-1H-indol-1-yl)methyl)phenyl)cyclopropanecarboxylic acid

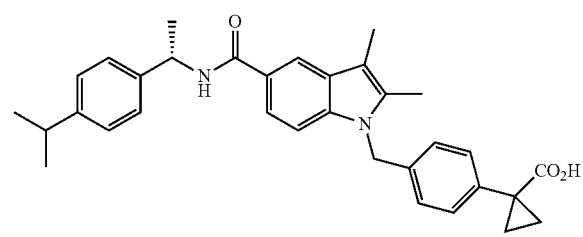 [SMILES: Cc1c(C)n(Cc2ccc(C3(C(=O)O)CC3)cc2)c2ccc(C(=O)N[C@@H](C)c3ccc(C(C)C)cc3)cc12]

The title compound was prepared following the same protocol as described in Step 5-8, Example 35, using the (S)-1-(4-bromophenyl)ethanamine instead of the (S)-1-(3-bromophenyl)ethanamine. ESI-MS (m/z): 509 [MH]$^+$.

Example 92: (S)-2-(3-chloro-5-((5-(((S)-1-(3-cyclopropylphenyl)ethyl)carbamoyl)-2,3-dimethyl-1H-indol-1-yl)methyl)phenoxy)propanoic acid

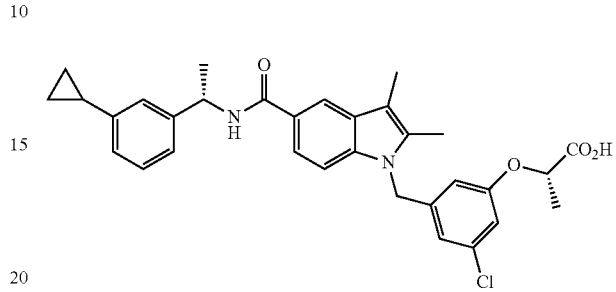

The title compound was prepared following the same protocol as described in Step 5-6, Example 67, using the (S)-1-(3-cyclopropylphenyl)ethanamine hydrochloride instead of the (S)-1-(3-isopropylphenyl)ethanamine hydrochloride. ESI-MS (m/z): 545/546/547 [MH]$^+$.

Example 93: (S)-2-(3-((5-(((S)-1-(4-(tert-butyl)phenyl)ethyl)carbamoyl)-2,3-dimethyl-1H-indol-1-yl)methyl)-5-chlorophenoxy)propanoic acid

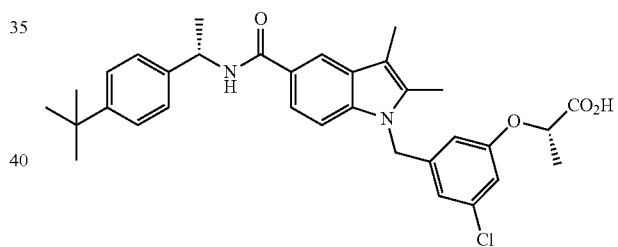

The title compound was prepared following the same protocol as described in Step 5-6, Example 67, using the (S)-1-(4-tert-butylphenyl)ethanamine hydrochloride instead of the (S)-1-(3-isopropylphenyl)ethanamine hydrochloride. ESI-MS (m/z): 561/562/563 [MH]$^+$.

Example 94: (S)-2-(2-chloro-4-((5-(((S)-1-(3-cyclopropylphenyl)ethyl)carbamoyl)-2,3-dimethyl-1H-indol-1-yl)methyl)phenoxy)propanoic acid


The title compound was prepared following the same protocol as described in Step 5-6, Example 73, using the (S)-1-(3-cyclopropylphenyl)ethanamine hydrochloride instead of the (S)-1-(3-isopropylphenyl)ethanamine hydrochloride. ESI-MS (m/z): 545/546/547 [MH]$^+$.

Example 95: (S)-2-(4-((5-(((S)-1-(4-(tert-butyl)phenyl)ethyl)carbamoyl)-2,3-dimethyl-1H-indol-1-yl)methyl)-2-chlorophenoxy)propanoic acid

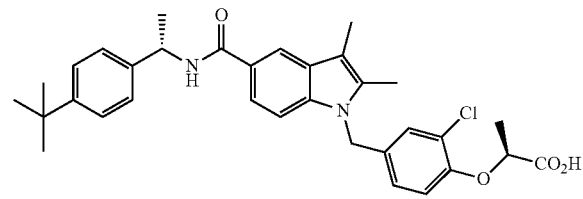 [SMILES: Cc1c(C)n(Cc2ccc(O[C@@H](C)C(=O)O)c(Cl)c2)c2ccc(C(=O)N[C@@H](C)c3ccc(C(C)(C)C)cc3)cc12]

The title compound was prepared following the same protocol as described in Step 5-6, Example 73, using the (S)-1-(4-tert-butylphenyl)ethanamine hydrochloride instead of the (S)-1-(3-isopropylphenyl)ethanamine hydrochloride. ESI-MS (m/z): 561/562/563 [MH]$^+$.

Example 96: (S)-2-(2-chloro-3-((5-(((S)-1-(3-cyclopropylphenyl)ethyl)carbamoyl)-2,3-dimethyl-1H-indol-1-yl)methyl)phenoxy)propanoic acid

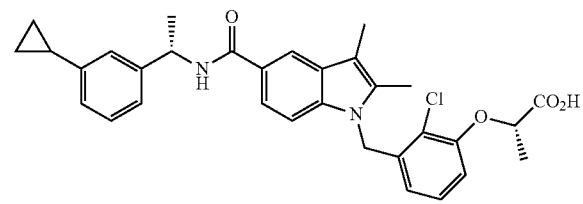 [SMILES: Cc1c(C)n(Cc2cccc(O[C@@H](C)C(=O)O)c2Cl)c2ccc(C(=O)N[C@@H](C)c3cccc(C4CC4)c3)cc12]

The title compound was prepared following the same protocol as described in Step 5-6, Example 68, using the (S)-1-(3-cyclopropylphenyl)ethanamine hydrochloride instead of the (S)-1-(3-isopropylphenyl)ethanamine hydrochloride. ESI-MS (m/z): 545/546/547 [MH]$^+$.

Example 97: (S)-2-(3-((5-(((S)-1-(4-(tert-butyl)phenyl)ethyl)carbamoyl)-2,3-dimethyl-1H-indol-1-yl)methyl)-2-chlorophenoxy)propanoic acid

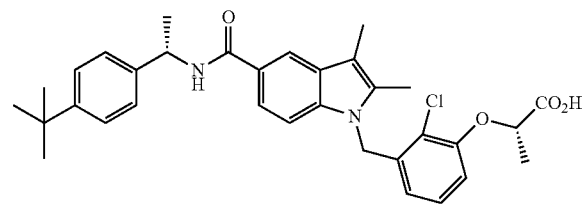 [SMILES: Cc1c(C)n(Cc2cccc(O[C@@H](C)C(=O)O)c2Cl)c2ccc(C(=O)N[C@@H](C)c3ccc(C(C)(C)C)cc3)cc12]

The title compound was prepared following the same protocol as described in Step 5-6, Example 68, using the (S)-1-(4-tert-butylphenyl)ethanamine hydrochloride instead of the (S)-1-(3-isopropylphenyl)ethanamine hydrochloride. ESI-MS (m/z): 561/562/563 [MH]$^+$.

Example 98: 1-(3-(((S)-1-amino-1-oxopropan-2-yl)oxy)-4-chlorobenzyl)-N—((S)-1-(4-(tert-butyl)phenyl)ethyl)-2,3-dimethyl-1H-indole-5-carboxamide

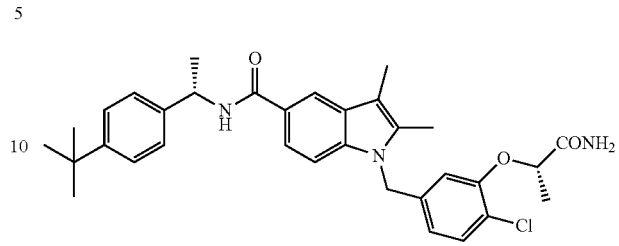

A solution of (S)-2-(5-((5-(((S)-1-(4-(tert-butyl)phenyl)ethyl)carbamoyl)-2,3-dimethyl-1H-indol-1-yl)methyl)-2-chlorophenoxy)propanoic acid (20 mg, 0.036 mmol), NH$_4$C$_1$ (19 mg, 0.36 mmol), HATU (14 mg, 0.036 mmol) and DIEA (25 µl, 0.144 mmol) in DCM (0.5 ml) was stirred at rt for 1 h. After concentration, the obtained oil was purified by reverse phase prep-HPLC (MeOH/Acetonitrile/water) to afford a white powder (18 mg). ESI-MS (m/z): 560/561/562 [MH]$^+$.

Example 99: 1-(5-(((S)-1-amino-1-oxopropan-2-yl)oxy)-2-chlorobenzyl)-N—((S)-1-(4-(tert-butyl)phenyl)ethyl)-2,3-dimethyl-1H-indole-5-carboxamide

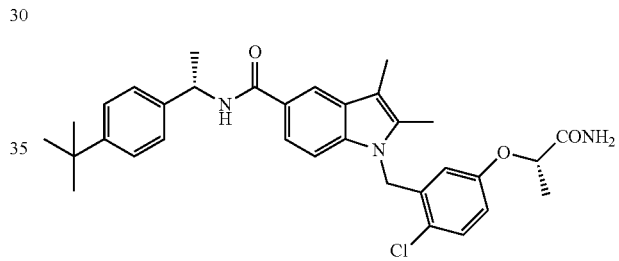

A solution of (S)-2-(3-((5-(((S)-1-(4-(tert-butyl)phenyl)ethyl)carbamoyl)-2,3-dimethyl-1H-indol-1-yl)methyl)-4-chlorophenoxy)propanoic acid (20 mg, 0.036 mmol), NH$_4$C$_1$ (19 mg, 0.36 mmol), HATU (14 mg, 0.036 mmol) and DIEA (25 µl, 0.144 mmol) in DCM (0.5 ml) was stirred at rt for 1 h. After concentration, the obtained oil was purified by reverse phase prep-HPLC (MeOH/Acetonitrile/water) to afford a white powder (18 mg). ESI-MS (m/z): 560/561/562 [MH]$^+$.

Example 100: 1-(3-(((S)-1-amino-1-oxopropan-2-yl)oxy)benzyl)-N—((S)-1-(4-(tert-butyl)phenyl)ethyl)-2,3-dimethyl-1H-indole-5-carboxamide

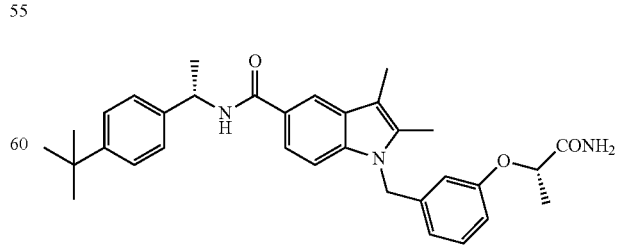

A solution of (S)-2-(3-((5-(((S)-1-(4-(tert-butyl)phenyl)ethyl)carbamoyl)-2,3-dimethyl-1H-indol-1-yl)methyl)phenoxy)propanoic acid (20 mg, 0.036 mmol), NH₄C₁ (19 mg, 0.36 mmol), HATU (14 mg, 0.036 mmol) and DIEA (25 μl, 0.144 mmol) in DCM (0.5 ml) was stirred at rt for 1 h. After concentration, the obtained oil was purified by reverse phase prep-HPLC (MeOH/Acetonitrile/water) to afford a white powder (18 mg). ESI-MS (m/z): 526 [MH]⁺.

Example 101: (S)-1-(3-(2-cyanopropan-2-yl)benzyl)-N-(1-(3-cyclopropylphenyl)ethyl)-2,3-dimethyl-1H-indole-5-carboxamide

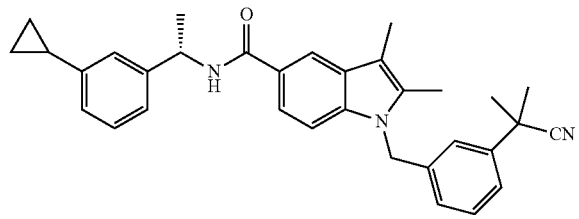 [SMILES: Cc1c(C)n(Cc2cccc(C(C)(C)C#N)c2)c2ccc(C(=O)N[C@@H](C)c3cccc(C4CC4)c3)cc12]

Step 1: 2-methyl-2-(m-tolyl)propanenitrile

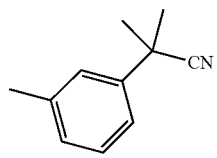

2-(m-tolyl)acetonitrile (3.75 g, 28.6 mmol) in dry THF (20 mL) was cooled at ice bath, and then NaH (60% in dispension, 2.9 g, 71.5 mmol) was added gradually. The mixture was stirred at room temperature for 30 min, and recooled at ice bath. MeI (3.91 mL, 62.8 mmol) was then added dropwise. The reaction mixture was stirred at room temperature for 16 hr. isopropanol was carefully added to the mixture followed by ethyl acetate. The organic layer was washed with water and brine, dried over anhydrous sodium sulfate. The solvent was removed and the residue was purified by silica gel to obtain the title compound. ¹H NMR (400 MHz, CDCl₃) δ 7.28-7.24 (m, 3H), 7.11 (s, 1H), 2.36 (s, 3H), 1.70 (s, 6H)

Step 2: 2-(3-(bromomethyl)phenyl)-2-methylpropanenitrile

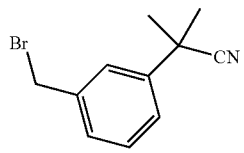

The title compound was prepared following the same general protocol as described in Step 2, Example 35, using 2-methyl-2-(m-tolyl)propanenitrile.

Step 3: allyl 1-(3-(2-cyanopropan-2-yl)benzyl)-2,3-dimethyl-1H-indole-5-carboxylate

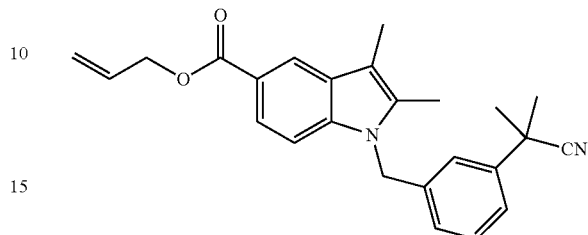

The title compound was prepared following the same general protocol as described in Step 2, Example 1, using 2-(3-(bromomethyl)phenyl)-2-methylpropanenitrile and allyl 2,3-dimethyl-1H-indole-5-carboxylate. ESI-MS (m/z): 387 [M+H]⁺.

Step 4: 1-(3-(2-cyanopropan-2-yl)benzyl)-2,3-dimethyl-1H-indole-5-carboxylic acid

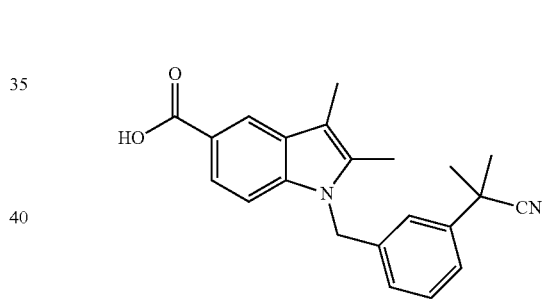

The mixture of allyl 1-(3-(2-cyanopropan-2-yl)benzyl)-2,3-dimethyl-1H-indole-5-carboxylate (0.688 g, 1.78 mmol) and morpholine (1.6 mL, 17.8 mmol) in THF (5 mL) was degassed and then Pd(PPh₃)₄ (0.21 g, 0.18 mmol) was added. The mixture was stirred at room temperature for 1 h. The solvent was removed and the residue was dissolved in Methanol and acidified to pH4. The solvent was removed and the residue was purified by silica gel to obtain the title compound. ESI-MS (m/z): 347 [M+H]⁺.

Step 5: (S)-1-(3-(2-cyanopropan-2-yl)benzyl)-N-(1-(3-cyclopropylphenyl)ethyl)-2,3-dimethyl-1H-indole-5-carboxamide The title compound was prepared following the same general protocol as described in Step 4, Example 1, using (S)-1-(3-cyclopropylphenyl)ethanamine hydrochloride and 1-(3-(2-cyanopropan-2-yl)benzyl)-2,3-dimethyl-1H-indole-5-carboxylic acid. ESI-MS (m/z): 490 [M+H]⁺.

Example 102: (S)-1-(3-(1-amino-2-methyl-1-oxo-propan-2-yl)benzyl)-N-(1-(3-cyclopropylphenyl)ethyl)-2,3-dimethyl-1H-indole-5-carboxamide and (S)-2-(3-((5-((1-(3-cyclopropylphenyl)ethyl)carbamoyl)-2,3-dimethyl-1H-indol-1-yl)methyl)phenyl)-2-methylpropanoic acid

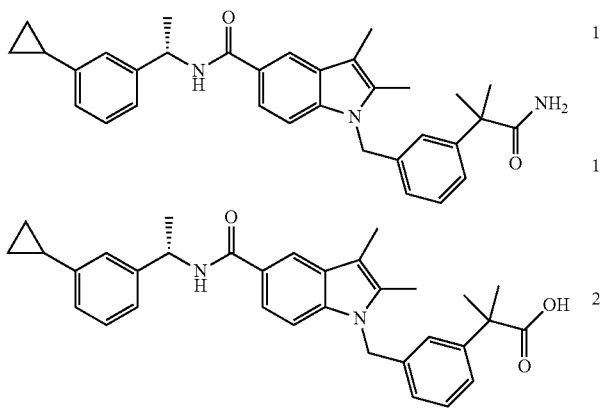

To (S)-1-(3-(2-cyanopropan-2-yl)benzyl)-N-(1-(3-cyclopropylphenyl)ethyl)-2,3-dimethyl-1H-indole-5-carboxamide (0.1 g, 0.2 mmol) in ethanol added NaOH (5 N, 1 mL). The mixture was heated at 130° C. oil bath for 2 days. The mixture was cooled to room temperature and acidified to pH 4. The solvent was removed and residue was purified by preparative-HPLC to obtain the title compounds. (S)-1-(3-(1-amino-2-methyl-1-oxopropan-2-yl)benzyl)-N-(1-(3-cyclopropylphenyl)ethyl)-2,3-dimethyl-1H-indole-5-carboxamide ESI-MS (m/z): 508 [M+H]$^+$; (S)-2-(3-((5-((1-(3-cyclopropylphenyl)ethyl)carbamoyl)-2,3-dimethyl-1H-indol-1-yl)methyl)phenyl)-2-methylpropanoic acid. ESI-MS (m/z): 509 [M+H]$^+$.

Example 103: (2S)-2-(3-(1-(5-(((S)-1-(3-cyclopropylphenyl)ethyl)carbamoyl)-2,3-dimethyl-1H-indol-1-yl)ethyl)phenoxy)propanoic acid

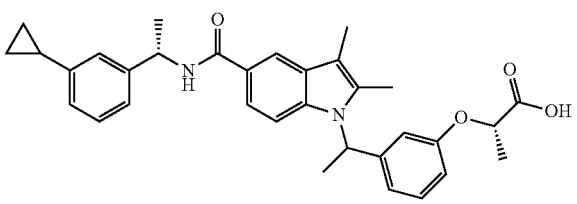 [SMILES: Cc1c(C)n(C(C)c2cccc(O[C@@H](C)C(=O)O)c2)c2ccc(C(=O)N[C@@H](C)c3cccc(C4CC4)c3)cc12]

Step 1: (S)-methyl 2-(3-ethylphenoxy)propanoate

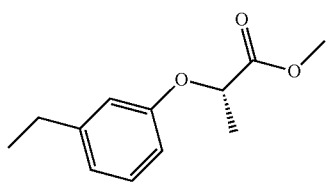

To 3-ethylphenol (3.42 g, 28 mmol) in THF (20 mL) at ice bath was added triphenylphosphine (9.5 g, 36.4 mmol) and then (R)-methyl 2-hydroxypropanoate (2.94 mL, 31 mmol). And then DIAD (8.2 mL, 42 mmol) was added dropwise to the above cole solution. The mixture was stirred at room temperature for 16 hr. The solvent was removed and the residue was purified by silica gel to obtain the title compound.

Step 2: (2S)-methyl 2-(3-(1-bromoethyl)phenoxy)propanoate

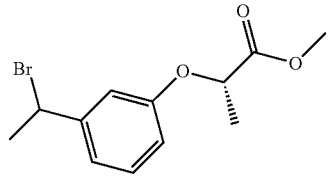 [SMILES: COC(=O)[C@H](C)Oc1cccc(C(C)Br)c1]

The title compound was prepared following the same general protocol as described in Step 2, Example 35, using (S)-methyl 2-(3-ethylphenoxy)propanoate.

Step 3: Allyl 1-(1-(3-(((S)-1-methoxy-1-oxopropan-2-yl)oxy)phenyl)ethyl)-2,3-dimethyl-1H-indole-5-carboxylate

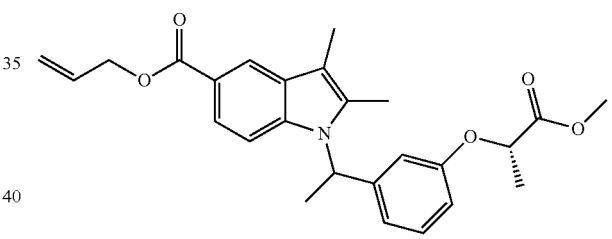

The title compound was prepared following the same general protocol as described in Step 2, Example 1, using (2S)-methyl 2-(3-(1-bromoethyl)phenoxy)propanoate and allyl 2,3-dimethyl-1H-indole-5-carboxylate. ESI-MS (m/z): 436 [M+H]$^+$.

Step 4: 1-(1-(3-(((S)-1-methoxy-1-oxopropan-2-yl)oxy)phenyl)ethyl)-2,3-dimethyl-1H-indole-5-carboxylic acid

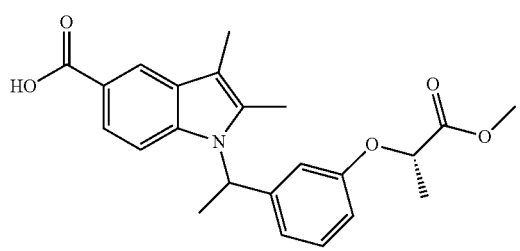 [SMILES: COC(=O)[C@H](C)Oc1cccc(C(C)n2c(C)c(C)c3cc(C(=O)O)ccc32)c1]

The title compound was prepared following the same general protocol as described in Step 4. Example 36, using allyl 1-(1-(3-(((S)-1-methoxy-1-oxopropan-2-yl)oxy)phenyl)ethyl)-2,3-dimethyl-1H-indole-5-carboxylate. ESI-MS (m/z): 396 [M+H]⁺.

Step 5: (2S)-methyl 2-(3-(1-(5-(((S)-1-(3-cyclopropylphenyl)ethyl)carbamoyl)-2,3-dimethyl-1H-indol-1-yl)ethyl)phenoxy)propanoate

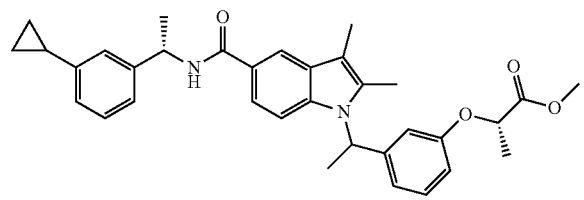 [SMILES: COC(=O)[C@H](C)Oc1cccc(C(C)n2c(C)c(C)c3cc(C(=O)N[C@@H](C)c4cccc(C5CC5)c4)ccc32)c1]

The title compound was prepared following the same general protocol as described in Step 4, Example 1, using (S)-1-(3-cyclopropylphenyl)ethanamine hydrochloride and 1-(3-(2-cyanopropan-2-yl)benzyl)-2,3-dimethyl-1H-indole-5-carboxylic acid. ESI-MS (m/z): 539 [M+H]⁺.

Step 6: (2S)-2-(3-(1-(5-(((S)-1-(3-cyclopropylphenyl)ethyl)carbamoyl)-2,3-dimethyl-1H-indol-1-yl)ethyl)phenoxy)propanoic acid NaOH (2 N, 0.1 mL, 0.2 mmol) was added to (2S)-methyl 2-(3-(1-(5-(((S)-1-(3-cclopropylphenyl)ethyl)carbamoyl)-2,3-dimethyl-1H-indol-1-yl)ethyl)phenoxy)propanoate (0.03 g, 0.06 mmol) in Methanol (0.5 mL). The reaction mixture was acidified to pH 4. The solvent was removed and the residue was purified by preparative-HPLC to obtain the title compound. ESI-MS (m/z): 525 [M+H]⁺.

Example 104: (2S)-2-(3-(1-(5-(((S)-1-(4-(tert-butyl)phenyl)ethyl)carbamoyl)-2,3-dimethyl-1H-indol-1-yl)ethyl)phenoxy)propanoic acid

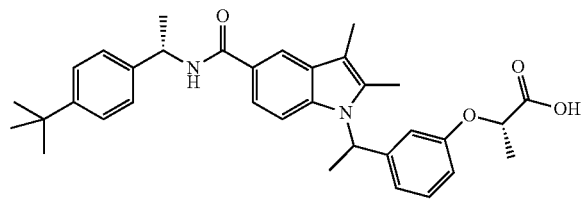 [SMILES: Cc1c(C)n(C(C)c2cccc(O[C@@H](C)C(=O)O)c2)c2ccc(C(=O)N[C@@H](C)c3ccc(C(C)(C)C)cc3)cc12]

The title compound was prepared following the same general protocol as described in Step 5-6. Example 103, using (S)-1-(4-(tert-butyl)phenyl)ethanamine hydrochloride. ESI-MS (m/z): 541 [M+H]⁺.

Example 105: (S)-2-(3-((5-(((S)-1-(3-isopropoxyphenyl)ethyl)carbamoyl)-2,3-dimethyl-1H-indol-1-yl)methyl)phenoxy)propanoic acid

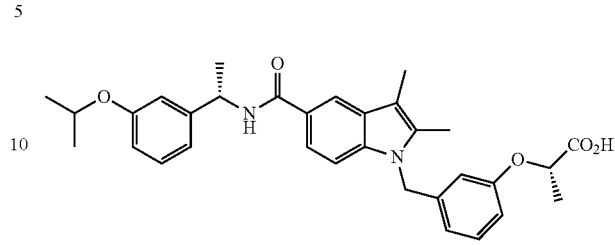

Step 1: (S)-methyl 2-(m-tolyloxy)propanoate

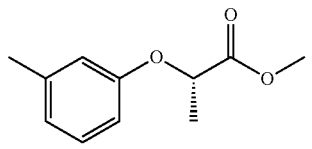

To a solution of m-cresol (5.0 g, 46 mmol, 1 equiv), methyl-D(+) lactate (4.8 g, 46 mmol, 1 equiv) and PPh₃ (14.5 g, 55.2 mmol, 1.2 equiv) in anhydrous THF (200 mL) under argon and at 0° C., was added dropwise DIAD (9.96 g, 48.2 mmol, 1.5 equiv). The reaction mixture was stirred at 0° C. until room temperature overnight. The crude mixture was dissolved in AcOEt (200 mL) and washed with a 0.5 N HCl aqueous solution (×2), a saturated NaHCO₃ solution (×2), brine and then dried over Na₂SO₄. After filtration, solvent was evaporated. The crude product was purified by flash chromatography on silica gel (AcOEt/hexane 0->60%) to obtain the title compound.

Step 2: (S)-methyl 2-(3-(bromomethyl)phenoxy)propanoate

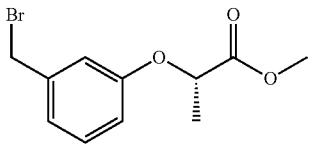

To a 250 mL round-bottom flask was (S)-methyl 2-(m-tolyloxy)propanoate (2.0 g, 10.3 mmol, 1 equiv), NBS (1.83 g, 10.3 mmol, 1 equiv), AIBN (169 mg, 1.03 mmol, 0.1 equiv) and CCl₄ (100 mL). The reaction mixture was refluxed for 16 h at 80° C. The completion of the reaction was monitored by analytical HPLC. The reaction mixture was allowed to cool to room temperature. The crude mixture was dissolved in AcOEt (100 mL) and washed with a 0.5N HCl aqueous solution (×2), a saturated NaHCO₃ solution (×2) and brine, dried over Na₂SO₄. The filtrate was concentrated to obtain the crude product which was purified by flash chromatography (AcOEt/Hexane 0->60%) to obtain the title compound.

Step 3: (S)-allyl 1-(3-((1-methoxy-1-oxopropan-2-yl)oxy)benzyl)-2,3-dimethyl-1H-indole-5-carboxylate

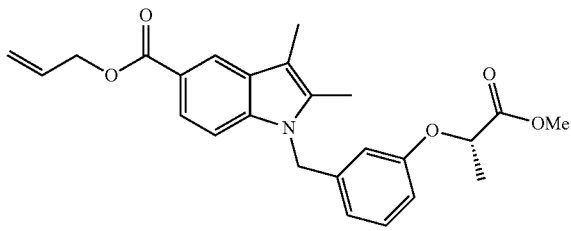 [SMILES: C=CCOC(=O)c1ccc2c(c1)c(C)c(C)n2Cc1cccc(O[C@@H](C)C(=O)OC)c1]

To a solution of allyl 2,3-dimethyl-1H-indole-5-carboxylate (1.0 g, 4.4 mmol, 1 equiv) and (S)-methyl 2-(3-(bromomethyl)phenoxy)propanoate (1.30 g, 4.84 mmol, 1.1 equiv) in anhydrous DMF (30 mL) under argon atmosphere was added sodium hydride (211 mg, 8.8 mmol, 2 equiv) in small portions. The mixture was stirred 2 h at room temperature. The reaction mixture was then quenched slowly with a solution of HCl 0.5 N. The residue was dissolved in AcOEt, washed with a saturated NaHCO₃ solution and brine, dried over MgSO₄. The crude was purified by flash chromatography (AcOEt/Hexane 0->60%) to afford the title compound.

Step 4: (S)-1-(3-(1-methoxy-1-oxopropan-2-yl)oxy)benzyl)-2,3-dimethyl-1H-indole-5-carboxylic acid

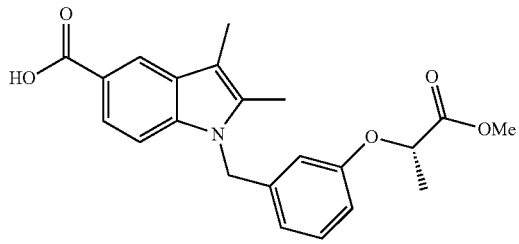 [SMILES: COC(=O)[C@H](C)Oc1cccc(Cn2c(C)c(C)c3cc(C(=O)O)ccc32)c1]

A mixture of (S)-allyl 1-(3-((1-methoxy-1-oxopropan-2-yl)oxy)benzyl)-2,3-dimethyl-1H-indole-5-carboxylate (1.0 g, 2.37 mmol, 1 equiv), Pd(PPh₃)₄ (277 mg, 0.24 mmol, 0.1 equiv), and morpholine (2 mL, 23.7 mmol, 10 equiv) in anhydrous THF (30 mL) was stirred at room temperature under argon atmosphere for 16 h. The completion of the reaction was monitored by anal. HPLC. The crude mixture was dissolved in AcOEt (100 mL) and washed with a 0.5N HCl aqueous solution (×2) and brine, then dried over Na₂SO₄. The filtrate was concentrated to obtain the crude product which was purified by flash chromatography (AcOEt/Hexane 0->60%) to obtain the title compound.

Step 5: (S)-methyl 2-(3-((5-(O)-1-(3-isopropoxyphenyl)ethyl)carbamoyl)-2,3-dimethyl-1H-indol-1-yl)methyl)phenoxy)propanoate

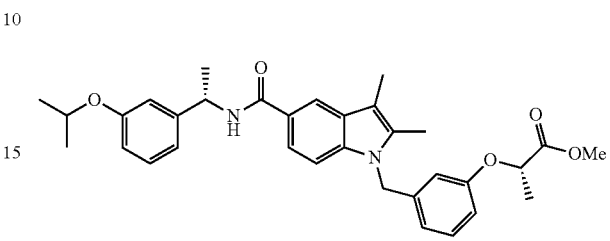

To a solution of (S)-1-(3-((1-methoxy-1-oxopropan-2-yl)oxy)benzyl)-2,3-dimethyl-1H-indole-5-carboxylic acid (50 mg, 0.13 mmol, 1 equiv) in DCM (2 mL) was added (S)-1-(3-isopropoxyphenyl)ethanamine (34 mg, 0.16 mmol, 1.2 equiv), DIEA (70 µL, 0.39 mmol, 3 equiv) and HATU (50 mg, 0.13 mmol, 1 equiv). The reaction mixture was stirred 2 h at room temperature. The solvent was removed in vacuo. The residue was dissolved in AcOEt and washed with a 0.5N HCl aqueous solution, a saturated NaHCO₃ solution and brine, dried over MgSO₄. The filtrate was concentrated to obtain the crude product which was purified by flash chromatography (AcOEt/Hexane 0->50%) to obtain the title compound.

Step 6: (S)-2-(3-((5-(((S)-1-(3-isopropoxyphenyl)ethyl)carbamoyl)-2,3-dimethyl-1H-indol-1-yl)methyl)phenoxy)propanoic acid

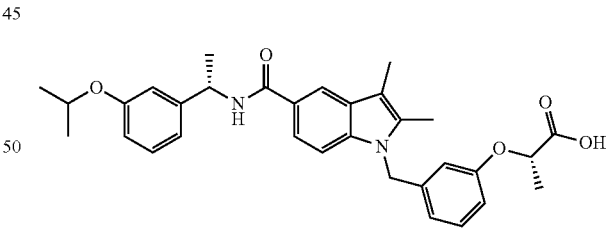

To a solution of (S)-methyl 2-(3-((5-(O)-1-(3-isopropoxyphenyl)ethyl) carbamoyl)-2,3-dimethyl-1H-indol-1-yl) methyl)phenoxy)propanoate (70 mg, 0.13 mmol, 1 equiv) in THF (2 mL) was added a 1 N LiOH aqueous solution of (1 mL). The reaction mixture was stirred 6 h at room temperature, then acidified with a 0.5 N HCl aqueous solution. The mixture was filtered and the precipitate was dissolved in methanol and concentrated to obtain the crude product which was purified by prep. HPLC (MeOH/Acetonitrile/water 0.1% TFA) to obtain the title compound. ESI-MS (m/z): 529 [M+H]⁺.

Example 106: (S)-2-(3-((5-(((S)-1-(3-(tert-butyl)phenyl)ethyl)carbamoyl)-2,3-dimethyl-1H-indol-1-yl)methyl)phenoxy)propanoic acid

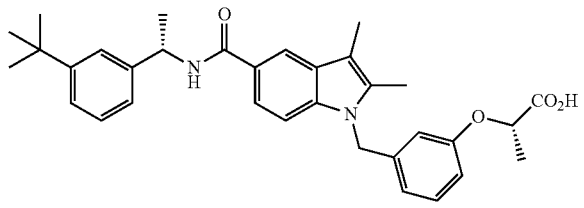 [SMILES: Cc1c(C)n(Cc2cccc(O[C@@H](C)C(=O)O)c2)c2ccc(C(=O)N[C@@H](C)c3cccc(C(C)(C)C)c3)cc12]

The title compound was prepared following the same protocol as described in Steps 4-6, Example 105, using (S)-1-(3-(tert-butyl)phenyl)ethanamine instead of the (S)-1-(3-isopropoxyphenyl)ethanamine. ESI-MS (m/z): 527 [M+H]$^+$.

Example 107: (S)-2-(3-((5-(((S)-1-(4-bromophenyl)ethyl)carbamoyl)-2,3-dimethyl-1H-indol-1-yl)methyl)phenoxy)propanoic acid

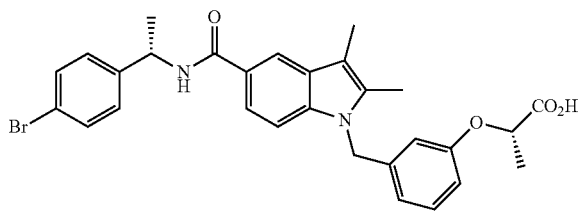 [SMILES: Cc1c(C)n(Cc2cccc(O[C@@H](C)C(=O)O)c2)c2ccc(C(=O)N[C@@H](C)c3ccc(Br)cc3)cc12]

The title compound was prepared following the same protocol as described in Steps 4-6, Example 105, using (S)-1-(4-bromophenyl)ethanamine instead of the (S)-1-(3-isopropoxyphenyl)ethanamine. ESI-MS (m/z): 549 [M+H]$^+$.

Example 108: (S)-2-(3-((2,3-dimethyl-5-(((S)-1-(4-(trifluoromethyl)phenyl)ethyl)carbamoyl)-1H-indol-1-yl)methyl)phenoxy)propanoic acid

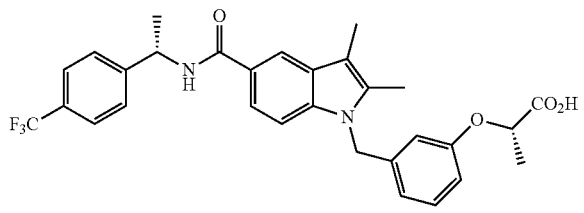 [SMILES: Cc1c(C)n(Cc2cccc(O[C@@H](C)C(=O)O)c2)c2ccc(C(=O)N[C@@H](C)c3ccc(C(F)(F)F)cc3)cc12]

The title compound was prepared following the same protocol as described in Steps 4-6, Example 105, using (S)-1-(3-(trifluoromethyl)phenyl)ethanamine instead of the (S)-1-(3-isopropoxyphenyl)ethanamine. ESI-MS (m/z): 539 [M+H]$^+$.

Example 109: (S)-2-(3-((5-(((S)-1-(3-chlorophenyl)ethyl)carbamoyl)-2,3-dimethyl-1H-indol-1-yl)methyl)phenoxy)propanoic acid

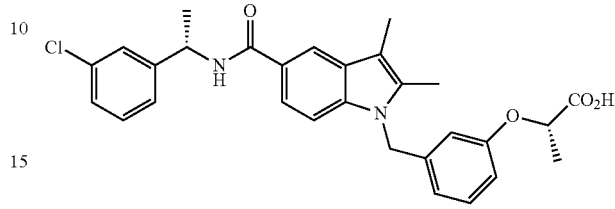

The title compound was prepared following the same protocol as described in Steps 4-6, Example 105, using (S)-1-(3-chlorophenyl)ethanamine instead of the (S)-1-(3-isopropoxyphenyl)ethanamine. ESI-MS (m/z): 505 [M+H]$^+$.

Example 110: (S)-2-(3-((5-(((S)-1-(4-chlorophenyl)ethyl)carbamoyl)-2,3-dimethyl-1H-indol-1-yl)methyl)phenoxy)propanoic acid

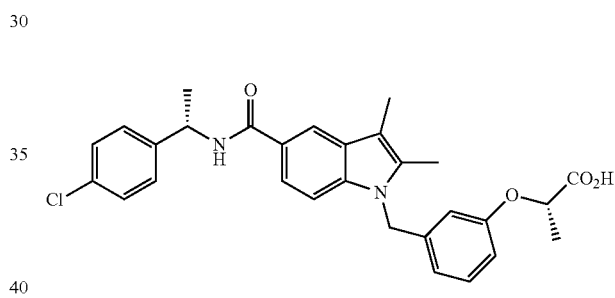

The title compound was prepared following the same protocol as described in Steps 4-6, Example 105, using (S)-1-(4-chlorophenyl)ethanamine instead of the (S)-1-(3-isopropoxyphenyl)ethanamine. ESI-MS (m/z): 505 [M+H]$^+$.

Example 111: (S)-2-(3-((5-(((S)-1-(2-chlorophenyl)ethyl)carbamoyl)-2,3-dimethyl-1H-indol-1-yl)methyl)phenoxy)propanoic acid

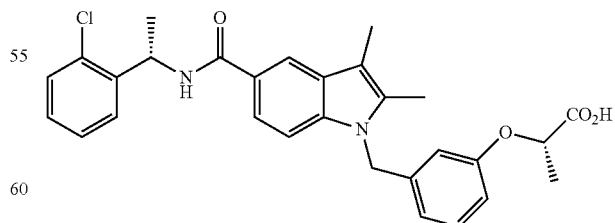

The title compound was prepared following the same protocol as described in Steps 4-6, Example 105, using (S)-1-(2-chlorophenyl)ethanamine instead of the (S)-1-(3-isopropoxyphenyl)ethanamine. ESI-MS (m/z): 505 [M+H]$^+$.

Example 112: (S)-2-(5-((5-(((S)-1-(4-(tert-butyl)phenyl)ethyl)carbamoyl)-2,3-dimethyl-1H-indol-1-yl)methyl)-2-methoxyphenoxy)propanoic acid

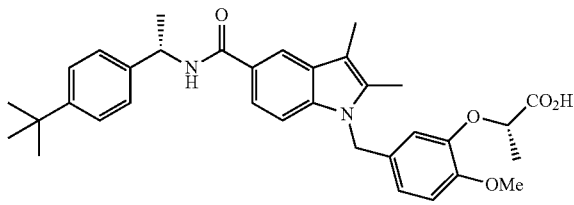 [SMILES: COc1ccc(Cn2c(C)c(C)c3cc(C(=O)N[C@@H](C)c4ccc(C(C)(C)C)cc4)ccc32)cc1O[C@@H](C)C(=O)O]

The title compound was prepared following the same protocol as described in Steps 4-6, Example 105, using (S)-1-(4-(tert-butyl)phenyl)ethanamine instead of the (S)-1-(3-isopropoxyphenyl)ethanamine. ESI-MS (m/z): 557 [M+H]+.

Example 113: (S)-2-(5-((5-(((S)-1-(3-cyclopropylphenyl)ethyl)carbamoyl)-2,3-dimethyl-1H-indol-1-yl)methyl)-2-methoxyphenoxy)propanoic acid

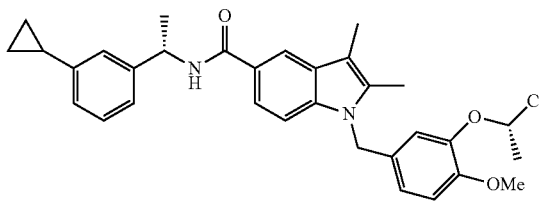

The title compound was prepared following the same protocol as described in Steps 4-6, Example 105, using (S)-1-(3-cyclopropylphenyl)ethanamine instead of the (S)-1-(3-isopropoxyphenyl)ethanamine. ESI-MS (m/z): 541 [M+H]+.

Example 114: (S)-2-(3-((5-(((S)-1-(4-(tert-butyl)phenyl)ethyl)carbamoyl)-2,3-dimethyl-1H-indol-1-yl)methyl)-4-fluorophenoxy)propanoic acid

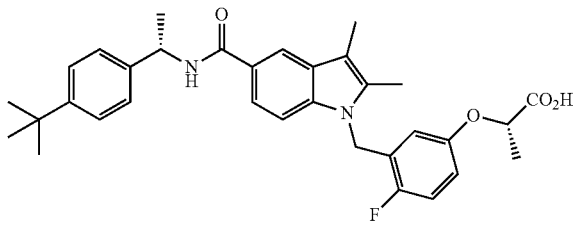 [SMILES: Cc1c(C)n(Cc2cc(O[C@@H](C)C(=O)O)ccc2F)c2ccc(C(=O)N[C@@H](C)c3ccc(C(C)(C)C)cc3)cc12]

The title compound was prepared following the same protocol as described in Steps 4-6, Example 105, using (S)-1-(4-(tert-butyl)phenyl)ethanamine instead of the (S)-1-(3-isopropoxyphenyl)ethanamine. ESI-MS (m/z): 545 [M+H]+.

Example 115: (S)-2-(5-((5-(((S)-1-(4-(tert-butyl)phenyl)ethyl)carbamoyl)-2,3-dimethyl-1H-indol-1-yl)methyl)-2-fluorophenoxy)propanoic acid

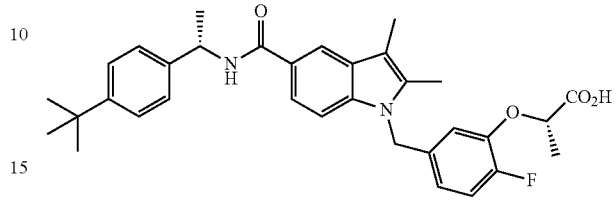

The title compound was prepared following the same protocol as described in Steps 4-6, Example 105, using (S)-1-(4-(tert-butyl)phenyl)ethanamine instead of the (S)-1-(3-isopropoxyphenyl)ethanamine. ESI-MS (m/z): 545 [M+H]+.

Example 116: (S)-2-(5-((5-(((S)-1-(3-cyclopropylphenyl)ethyl)carbamoyl)-2,3-dimethyl-1H-indol-1-yl)methyl)-2-fluorophenoxy)propanoic acid

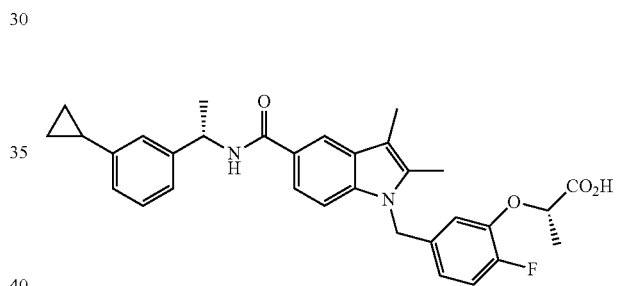

The title compound was prepared following the same protocol as described in Steps 4-6, Example 105, using (S)-1-(3-cyclopropylphenyl)ethanamine instead of the (S)-1-(3-isopropoxyphenyl)ethanamine. ESI-MS (m/z): 529 [M+H]+.

Example 117: (S)-2-(3-((5-(((S)-1-(4-methoxyphenyl)ethyl)carbamoyl)-2,3-dimethyl-1H-indol-1-yl)methyl)phenoxy)propanoic acid

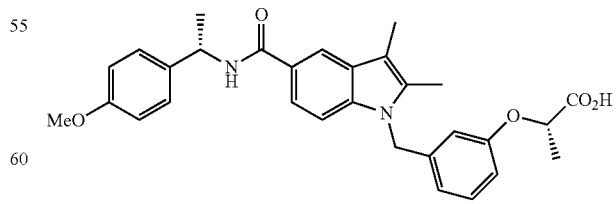

The title compound was prepared following the same protocol as described in Steps 4-6, Example 105, using (S)-1-(4-methoxyphenyl)ethanamine instead of the (S)-1-(3-isopropoxyphenyl)ethanamine. ESI-MS (m/z): 501 [M+H]+.

Example 118: (2S)-2-(4-(1-(5-(((S)-1-(4-(tert-butyl)phenyl)ethyl)carbamoyl)-2,3-dimethyl-1H-indol-1-yl)ethyl)phenoxy)propanoic acid

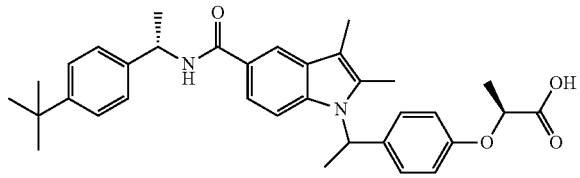 [SMILES: Cc1c(C)n(C(C)c2ccc(O[C@@H](C)C(=O)O)cc2)c2ccc(C(=O)N[C@@H](C)c3ccc(C(C)(C)C)cc3)cc12]

Step 1: 4-Ethylphenyl acetate

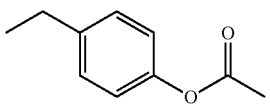

To a stirred solution of 4-ethylphenol (3.38 g, 27.67 mmol) in DCM (50 mL) in an ice bath was added TEA (7.2 mL, 55.34 mmol), followed by the dropwise addition of acetyl chloride (2.2 mL, 30.44 mmol). The mixture was stirred at room temperature for 30 min. The reaction mixture was quenched with water (40 mL) and extracted with DCM (3×50 mL). The combined organic layers were washed with brine, dried over Na$_2$SO$_4$, filtered and concentrated under reduced pressure and purified by silica gel chromatography to obtain the title compound.

Step 2: 4-(1-Bromoethyl)phenyl acetate

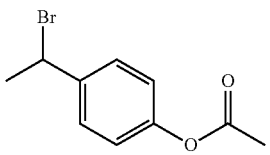

The title compound was prepared following the same general protocol as described in Step 2, Example 35, using 4-ethylphenyl acetate.

$^1$H NMR (400 MHz, CDCl$_3$) δ 7.45 (d, J=8.8 Hz, 2H), 7.06 (d, J=8.8 Hz, 2H), 5.21 (q, J=7.2 Hz, 1H), 2.99 (s, 3H), 2.04 (d, J=6.8 Hz, 3H).

Step 3: Allyl 1-(1-(4-hydroxyphenyl)ethyl)-2,3-dimethyl-1H-indole-5-carboxylate

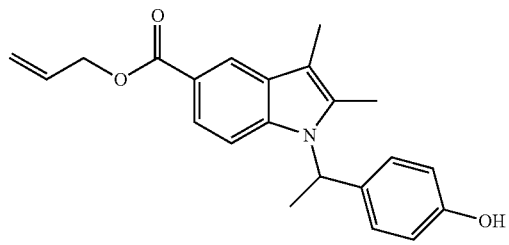 [SMILES: C=CCOC(=O)c1ccc2c(c1)c(C)c(C)n2C(C)c1ccc(O)cc1]

The title compound was prepared following the same general protocol as described in Step 2, Example 1, using 4-(1-bromoethyl)phenyl acetate and allyl 2,3-dimethyl-1H-indole-5-carboxylate.

To the above reaction mixture was added saturated Na$_2$CO$_3$ solution (20 mL) and the mixture was stirred at room temperature for 1 h. The mixture was diluted with EtOAc, followed by the addition of a saturated NH$_4$C$_1$ solution. The aqueous layer was removed and the organic layer was washed with water and then brine and dried over Na$_2$SO$_4$. The solvent was removed under reduced pressure and the residue was purified by silica gel chromatography to obtain the title compound. ESI-MS (m/z): 350 [M+H]$^+$.

Step 4: Allyl 1-(1-(4-(((S)-1-methoxy-1-oxopropan-2-yl)oxy)phenyl)ethyl)-2,3-dimethyl-1H-indole-5-carboxylate

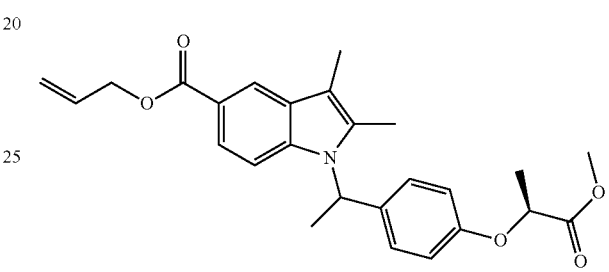

To allyl 1-(1-(4-hydroxyphenyl)ethyl)-2,3-dimethyl-1H-indole-5-carboxylate (0.286 g, 0.82 mmol) in THF (0.8 mL) in an ice bath was added triphenylphosphine (0.28 g, 1.07 mmol) and then (R)-methyl 2-hydroxypropanoate (0.093 mL, 0.98 mmol). DIAD (0.24 mL, 1.23 mmol) was added dropwise to the cold solution. The mixture was stirred at room temperature for 16 hr. The solvent was removed and the residue was purified by silica gel chromatography to obtain the title compound. ESI-MS (m/z): 436 [M+H]$^+$.

Step 5: 1-(1-(4-(((S)-1-Methoxy-1-oxopropan-2-yl)oxy)phenyl)ethyl)-2,3-dimethyl-1H-indole-5-carboxylic acid

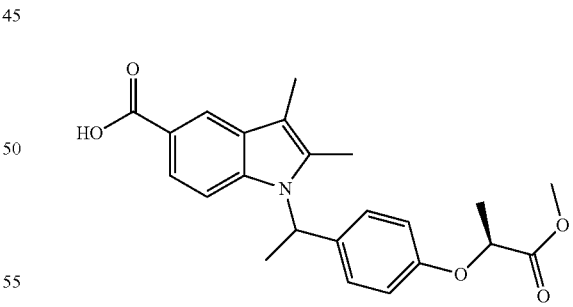

The mixture of allyl 1-(1-(4-(((S)-1-methoxy-1-oxopropan-2-yl)oxy)phenyl)ethyl)-2,3-dimethyl-1H-indole-5-carboxylate (0.55 g, 1.26 mmol) and morpholine (1.0 mL, 12.6 mmol) in THF (5 mL) was degassed and then Pd(PPh$_3$)$_4$ (0.15 g, 0.13 mmol) was added. The mixture was stirred at room temperature for 1 h. The solvent was removed and the residue was dissolved in Methanol and acidified to pH 4. The solvent was removed and the residue was purified by silica gel chromatography to obtain the title compound. ESI-MS (m/z): 396 [M+H]$^+$.

Step 6: (2S)-Methyl 2-(4-(1-(5-(((S)-1-(4-(tert-bu-tyl)phenyl)ethyl)carbamoyl)-2,3-dimethyl-1H-indol-1-yl)ethyl)phenoxy)propanoate

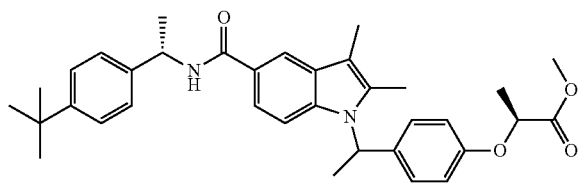 [SMILES: COC(=O)[C@H](C)Oc1ccc(C(C)n2c(C)c(C)c3cc(C(=O)N[C@@H](C)c4ccc(C(C)(C)C)cc4)ccc32)cc1]

The title compound was prepared following the same general protocol as described in Step 5, Example 35, using (S)-1-(4-(tert-butyl)phenyl)ethanamine instead of (S)-1-(3-bromophenyl)ethylamine and 1-(1-(4-(((S)-1-methoxy-1-oxopropan-2-yl)oxy)phenyl)ethyl)-2,3-dimethyl-1H-indole-5-carboxylic acid instead of 1-(4-(1-(methoxycarbonyl)cyclopropyl)benzyl)-2,3-dimethyl-1H-indole-5-carboxylic acid'

Step 7: (2S)-2-(4-(1-(5-(((S)-1-(4-(tert-butyl)phenyl)ethyl)carbamoyl)-2,3-dimethyl-1H-indol-1-yl)ethyl)phenoxy)propanoic acid

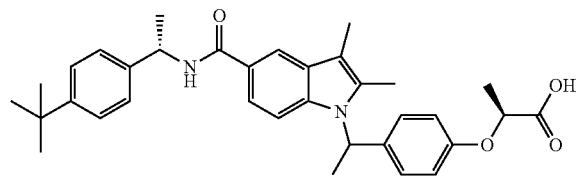 [SMILES: Cc1c(C)n(C(C)c2ccc(O[C@@H](C)C(=O)O)cc2)c2ccc(C(=O)N[C@@H](C)c3ccc(C(C)(C)C)cc3)cc12]

A solution of (2S)-methyl 2-(4-(1-(5-(((S)-1-(4-(tert-butyl)phenyl)ethyl)carbamoyl)-2,3-dimethyl-1H-indol-1-yl)ethyl)phenoxy)propanoate (~0.07 mmol) and NaOH (2 M, 0.2 mL) in MeOH (2 mL) and DMF (1 mL) was stirred at rt for 5 h. It was neutralized and purified by preparative HPLC to yield the title compound as a white solid. ESI-MS (m/z): 541 [M+H]+.

Example 119: (2S)-2-(4-(1-(5-(((S)-1-(3-Cyclopropylphenyl)ethyl)carbamoyl)-2,3-dimethyl-1H-indol-1-yl)ethyl)phenoxy)propanoic acid

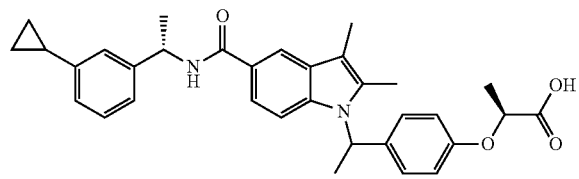 [SMILES: Cc1c(C)n(C(C)c2ccc(O[C@@H](C)C(=O)O)cc2)c2ccc(C(=O)N[C@@H](C)c3cccc(C4CC4)c3)cc12]

The title compound was prepared following the same general protocol as described in the previous example. ESI-MS (m/z): 525 [M+H]+.

Example 120: (S)-1-(3-((5-((1-(3-Cyclopropylphenyl)ethyl)carbamoyl)-2,3-dimethyl-1H-indol-1-yl)methyl)phenyl)cyclopropanecarboxylic acid

Step 1: 1-(m-Tolyl)cyclopropanecarbonitrile

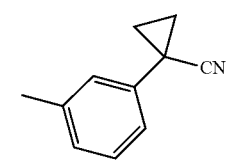

To a stirred solution of 2-(m-tolyl)acetonitrile (4.2 g, 32 mmol) in toluene (15 mL) was added sodium hydroxide (30 mL, 50% w/w in water, 375 mmol), 1-bromo-2-chloroethane (9.3 mL, 112 mmol) and (n-Bu)$_4$Br (0.5 g, 1.55 mmol). The mixture was heated at 60° C. overnight. After cooling to room temperature, the reaction mixture was diluted with water (40 mL) and extracted with EtOAc (3×50 mL). The combined organic layers were washed with brine, dried over Na$_2$SO$_4$, filtered and concentrated under reduced pressure and purified by silica gel chromatography to obtain the title compound.

$^1$H NMR (400 MHz, CDCl$_3$) δ 7.26-7.22 (m, 1H), 7.13-7.05 (m, 3H), 2.36 (s, 3H), 1.72-1.68 (m, 2H), 1.41-1.38 (m, 2H).

Step 2: 1-(3-(Bromomethyl)phenyl)cyclopropanecarbonitrile

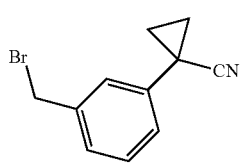 [SMILES: N#CC1(c2cccc(CBr)c2)CC1]

The title compound was prepared following the same general protocol as described in Step 2, Example 35, using 1-(m-tolyl)cyclopropanecarbonitrile.

Step 3: Allyl 1-(3-(1-cyanocyclopropyl)benzyl)-2,3-dimethyl-1H-indole-5-carboxylate

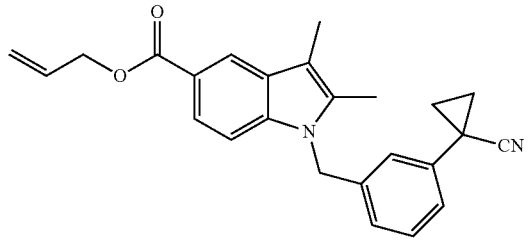 [SMILES: C=CCOC(=O)c1ccc2c(c1)c(C)c(C)n2Cc1cccc(C2(C#N)CC2)c1]

The title compound was prepared following the same general protocol as described in Step 2, Example 1, using 1-(3-(bromomethyl)phenyl)cyclopropanecarbonitrile and allyl 2,3-dimethyl-1H-indole-5-carboxylate.

Step 4: 1-(3-(1-Cyanocyclopropyl)benzyl)-2,3-dimethyl-1H-indole-5-carboxylic acid

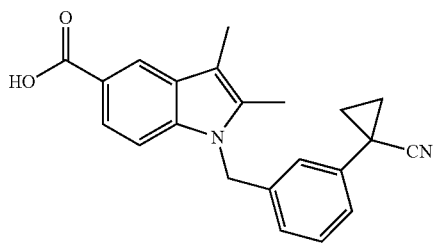 [SMILES: Cc1c(C)n(Cc2cccc(C3(C#N)CC3)c2)c2ccc(C(=O)O)cc12]

The mixture of allyl 1-(3-(1-cyanocyclopropyl)benzyl)-2,3-dimethyl-1H-indole-5-carboxylate (375 mg, 0.98 mmol) and morpholine (0.8 mL, 9.2 mmol) in THF (8 mL) was degassed and then Pd(PPh$_3$)$_4$ (117 mg, 0.10 mmol) was added. The mixture was stirred at room temperature for 1 h. The solvent was removed and the residue was dissolved in Methanol and acidified to pH 4. The precipitate was collected and washed with water to obtain the title compound.

Step 5: (S)-1-(3-(1-Cyanocyclopropyl)benzyl)-N-(1-(3-cyclopropylphenyl)ethyl)-2,3-dimethyl-1H-indole-5-carboxamide

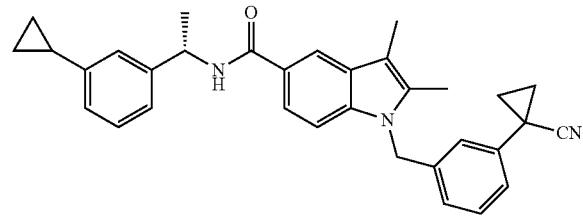 [SMILES: Cc1c(C)n(Cc2cccc(C3(C#N)CC3)c2)c2ccc(C(=O)N[C@@H](C)c3cccc(C4CC4)c3)cc12]

The title compound was prepared following the same general protocol as described in Step 5, Example 35, using 1-(3-(1-cyanocyclopropyl)benzyl)-2,3-dimethyl-1H-indole-5-carboxylic acid and (S)-1-(3-cyclopropylphenyl)ethanamine.

Step 6: (S)-1-(3-((5-((1-(3-Cyclopropylphenyl)ethyl)carbamoyl)-2,3-dimethyl-1H-indol-1-yl)methyl)phenyl)cyclopropanecarboxylic acid

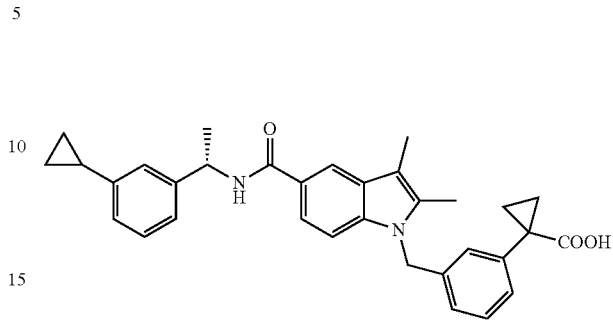

To a solution of (S)-1-(3-(1-Cyanocyclopropyl)benzyl)-N-(1-(3-cyclopropylphenyl)ethyl)-2,3-dimethyl-1H-indole-5-carboxamide (~0.2 mmol) in Ethanol was added NaOH (5 N, 1 mL). The mixture was heated at 130° C. in an oil bath for 14 days. The mixture was cooled to room temperature and acidified to pH 4. The solvent was removed and the residue was purified by preparative-HPLC to obtain the title compound. ESI-MS (m/z): 507 [M+H]$^+$.

Example 121: ((S)-3-((5-((1-(3-Cyclopropylphenyl)ethyl)carbamoyl)-2,3-dimethyl-1H-indol-1-yl)methyl)benzoic acid

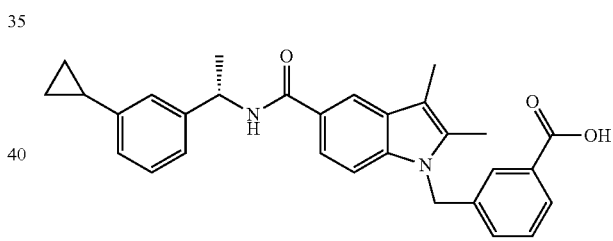

Step 1: Allyl 1-(3-(methoxycarbonyl)benzyl)-2,3-dimethyl-1H-indole-5-carboxylate

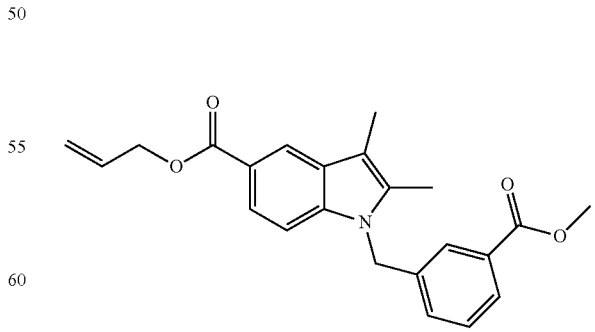

The title compound was prepared following the same general protocol as described in Step 2, Example 1, using methyl 3-(bromomethyl)benzoate and allyl 2,3-dimethyl-1H-indole-5-carboxylate.

Step 4: 1-(3-(Methoxycarbonyl)benzyl)-2,3-dimethyl-1H-indole-5-carboxylic acid

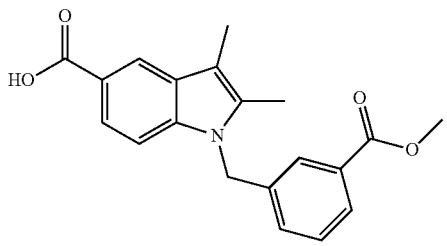 [SMILES: COC(=O)c1cccc(Cn2c(C)c(C)c3cc(C(=O)O)ccc32)c1]

The mixture of allyl 1-(3-(methoxycarbonyl)benzyl)-2,3-dimethyl-1H-indole-5-carboxylate (133 mg, 0.35 mmol) and morpholine (0.3 mL, 3.4 mmol) in THF (4 mL) was degassed and then Pd(PPh$_3$)$_4$ (41 mg, 0.035 mmol) was added. The mixture was stirred at room temperature for 1 h. The solvent was removed and the residue was dissolved in Methanol and acidified to pH 4. The precipitate was collected and washed with water to obtain the title compound.

Step 5: (S)-Methyl 3-((5-((1-(3-cyclopropylphenyl)ethyl)carbamoyl)-2,3-dimethyl-1H-indol-1-yl)methyl)benzoate

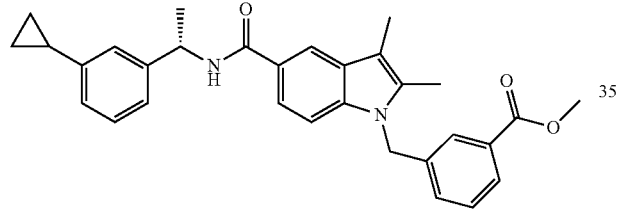

The title compound was prepared following the same general protocol as described in Step 5, Example 35, using 1-(3-(methoxycarbonyl)benzyl)-2,3-dimethyl-1H-indole-5-carboxylic acid and (S)-1-(3-cyclopropylphenyl)ethanamine.

Step 6: ((S)-3-((5-((1-(3-Cyclopropylphenyl)ethyl)carbamoyl)-2,3-dimethyl-1H-indol-1-yl)methyl)benzoic acid

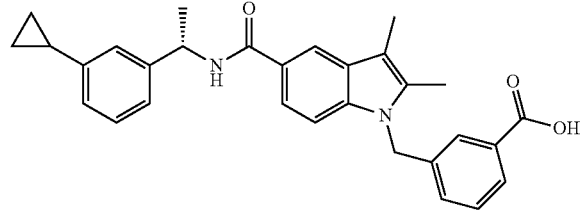 [SMILES: Cc1c(C)n(Cc2cccc(C(=O)O)c2)c2ccc(C(=O)N[C@@H](C)c3cccc(C4CC4)c3)cc12]

A solution of (S)-Methyl 3-((5-((1-(3-cyclopropylphenyl)ethyl)carbamoyl)-2,3-dimethyl-1H-indol-1-yl)methyl)benzoate (~0.07 mmol) and NaOH (2 M, 0.5 mL) in MeOH (2 mL) and DMSO (1 mL) was stirred at rt for 15 h. It was neutralized and purified by preparative HPLC to yield the title compound as a white solid. ESI-MS (m/z): 467 [M+H]$^+$.

Example 122: (S)-1-(3-Carbamoylbenzyl)-N-(1-(3-cyclopropylphenyl)ethyl)-2,3-dimethyl-1H-indole-5-carboxamide

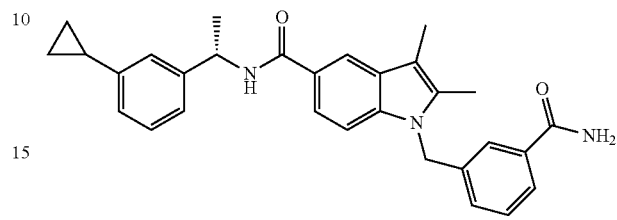

The title compound was prepared following the same general protocol as described in Step 5, Example 35. ESI-MS (m/z): 466 [M+H]$^+$.

Example 123: (S)-2-(5-((5-(((S)-1-(3-isopropylphenyl)ethyl)carbamoyl)-2,3-dimethyl-1H-indol-1-yl)methyl)-2-methoxyphenoxy)propanoic acid

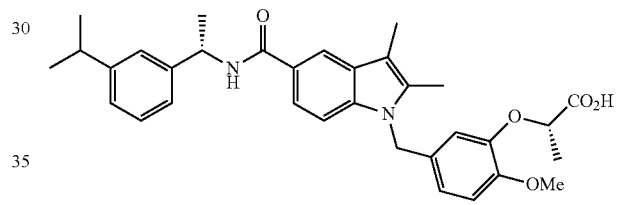

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride, followed by an ester hydrolysis step as outlined in Step 6, example 36.

Example 124: (S)-2-(2-fluoro-5-((5-(((S)-1-(3-isopropylphenyl)ethyl)carbamoyl)-2,3-dimethyl-1H-indol-1-yl)methyl)phenoxy)propanoic acid

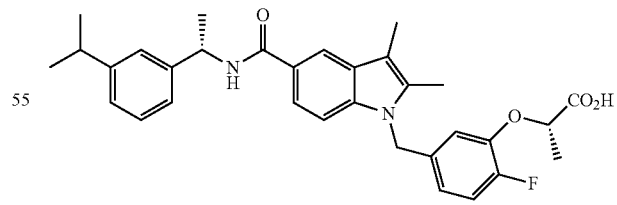

The title compound was prepared following the same protocol as described in Step 5, Example 36, using the (S)-1-(3-isopropylphenyl)ethanamine hydrochloride instead of the (S)-1-(3-cyclopropylphenyl)ethanamine hydrochloride and (S)-1-(4-fluoro-3-((1-methoxy-1-oxopropan-2-yl)oxy)benzyl)-2,3-dimethyl-1H-indole-5-carboxylic acid instead of the 1-(4-(2-methoxy-2-oxoethoxy)benzyl)-2,3-dimethyl-1H-indole-5-carboxylic acid, followed by an ester hydrolysis step as outlined in Step 6, example 36.

Synthetic Examples

Compounds of Formula (IB)

Example 1: (S)-4'-((5-(1-(4-Bromophenyl)ethylcarbamoyl)-2,3-dimethyl-1H-indol-1-yl)methyl)biphenyl-2-carboxylic acid

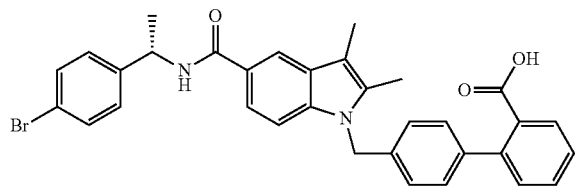

Step 1: tert-Butyl 2-bromobenzoate

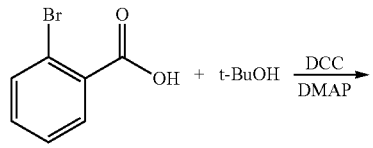

To a solution of 2-bromobenzoic acid (8.08 g, 40.2 mmol), DMAP (0.492 g, 8.0 mmol) and t-BuOH (9.3 mL, 80.4 mmol) in dry DCM (300 mL) under argon, was added DCC (9.96 g, 48.2 mmol). The reaction mixture was stirred at room temperature for 20 h. The resulting mixture was filtered and the filtrate was evaporated in vacuo. The crude mixture was dissolved in AcOEt (300 mL) and washed with saturated aqueous NaHCO$_3$ (261), brine and then dried over Na$_2$SO$_4$. After filtration, solvent was evaporated. The crude product was purified by flash chromatography on silica gel (AcOEt/hexane 0->30%) to obtain the title compound.

Step 2: tert-Butyl 4'-methylbiphenyl-2-carboxylate

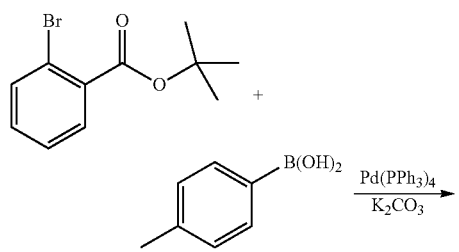

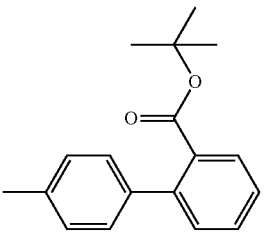

To a 350 mL high-pressure vial was added tert-butyl 2-bromobenzoate (5.142 g, 20.0 mmol), p-tolylboronic acid (4.08 g, 30.0 mmol), Pd(PPh$_3$)$_4$ (3.47 g, 3.0 mmol), potassium carbonate (8.29 g, 60.0 mmol) and dioxane with water (4:1, 200 mL). The mixture was degassed for 5 min and sealed. The mixture was heated at 100° C. for 40 min wherein analytical HPLC analysis indicated the completion of the reaction. The mixture was filtered through Celite and MeOH was used to wash the Celite pad. The solvent was removed and the crude was purified by flash chromatography (AcOEt/Hexane 0->30%) to obtain the title compound.

Step 3: tert-butyl 4'-(bromomethyl)biphenyl-2-carboxylate

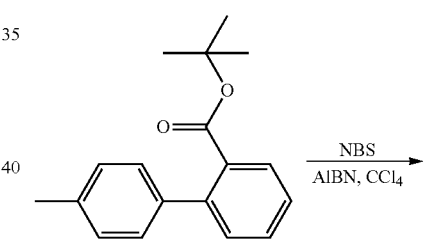

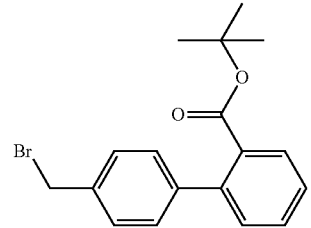

To a 500 mL round-bottom flask was added tert-butyl 4'-methylbiphenyl-2-carboxylate (7.04 g, 26.23 mmol), NBS (5.14 g, 28.85 mmol), AIBN (0.43 g, 2.62 mmol) and CCl$_4$ (200 mL). The reaction mixture was refluxed for 2 h at 100° C. The completion of the reaction was monitored by analytical HPLC. The reaction mixture was allowed to cool to room temperature and filtered. The filtrate was concentrated to obtain the crude product which was purified by flash chromatography (AcOEt/Hexane 0->30%) to obtain the title compound.

Step 4: tert-Butyl 1-(4-(ethoxycarbonyl)phenyl)hydrazinecarboxylate

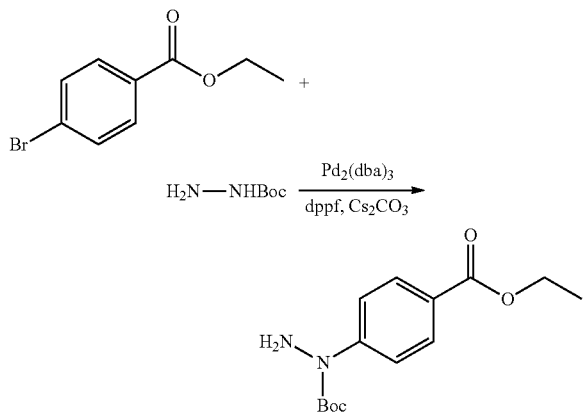

To a 350 mL high-pressure vial was added ethyl 4-bromobenzoate (12.92 g, 56.4 mmol), t-butyl carbazate (14.91 g, 112.8 mmol), Pd$_2$(dba)$_3$ (0.516 g, 0.56 mmol), dppf (0.938 g, 1.69 mmol), Cs$_2$CO$_3$ (18.4 g, 56.4 mmol), and dry toluene (113 mL). The reaction mixture was degassed for 5 min, sealed and heated to 100° C. for 16 h. The completion of the reaction was monitored by analytical HPLC. The reaction mixture was allowed to cool to room temperature, diluted with DCM, filtered and the filtrate was concentrated. The crude was then purified by flash chromatography (AcOEt/Hexane (0->30%) to afford the desired product. ESI-MS (m/z): 265 [M+H–NH$_3$]$^+$, 225 [M+H–tBu]$^+$, 181 [M+H–Boc]$^+$. $^1$H NMR (400 MHz, DMSO-d$_6$): δ (ppm) 1.31 (t, J=7.1 Hz, 3H, CH$_3$ ethyl), 1.50 (s, 9H, CH$_3$ Boc), 4.28 (q, J=7.1 Hz, 2H, CH$_2$ ethyl), 5.14 (s, 2H, NH$_2$), 7.70 (dt, J=8.8, 2.2 Hz, 2H, H$_2$ and H$_6$ phenyl), 7.87 (dt, J=8.8, 2.2 Hz, 2H, H$_3$ and H$_5$ phenyl).

Step 5: Ethyl 2,3-dimethyl-1H-indole-5-carboxylate

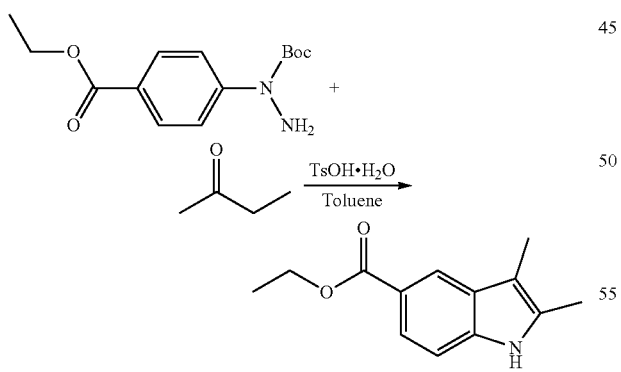

A mixture of tert-butyl 1-(4-(ethoxycarbonyl)phenyl)hydrazinecarboxylate (5.27 g, 18.8 mmol), butan-2-one (2.53 mL, 28.2 mmol), and TsOH monohydrate (21.5 g, 112.8 mmol) in toluene (300 mL) was heated at 80° C. for 2 h. The reaction mixture was allowed to cool to room temperature and filtered. The filtrate was concentrated and then purified by flash chromatography (AcOEt/Hexane 5%) to obtain the title compound. ESI-MS (m/z): 218 [M+H]$^+$. $^1$H NMR (400 MHz, DMSO-d$_6$): δ (ppm) 1.33 (t, J=7.2 Hz, 3H, CH$_3$ ethyl), 2.18 (s, 3H, CH$_3$), 2.32 (s, 3H, CH$_3$), 4.29 (q, J=7.2 Hz, 2H, CH$_2$ ethyl), 7.28 (dd, J=8.4, 0.4 Hz, 1H, H$_7$ indole), 7.64 (dd, J=8.4, 1.6 Hz, 1H, H$_6$ indole), 8.05 (m, 1H, H$_4$ indole).

Step 6: Ethyl 1-((2'-(tert-butoxycarbonyl)biphenyl-4-yl)methyl)-2,3-dimethyl-1H-indole-5-carboxylate

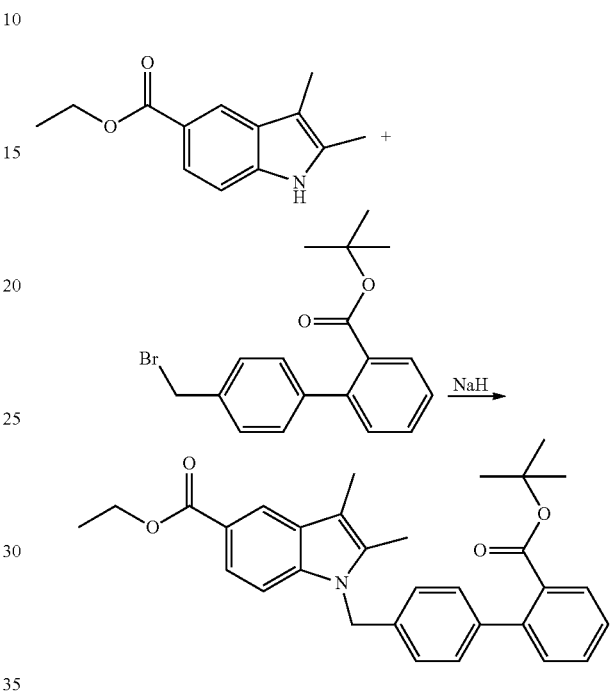

To a mixture of ethyl 2,3-dimethyl-1H-indole-5-carboxylate (1.493 g, 6.87 mmol) in dry DMF (10 mL) at 0° C. under argon was added NaH (0.3 g, 60% dispersion in mineral oil, 7.56 mmol) in portions. The reaction mixture was stirred at rt for 30 min and then re-cooled to 0° C. Tert-butyl 4'-(bromomethyl)biphenyl-2-carboxylate (2.62 g, 7.56 mmol) in DMF (2 mL) was slowly added. The reaction mixture was stirred at rt for another 1 h. The completion of the reaction was monitored by anal. HPLC. The reaction was quenched with MeOH, and then the solvent was removed in vacuo. The crude was dissolved in AcOEt, washed with saturated aqueous NaHCO$_3$, brine and dried over Na$_2$SO$_4$ and filtered. The filtrate was evaporated in vacuo to obtain the crude which was purified by flash chromatography (AcOEt/Hex 10->100%) to obtain the title compound. ESI-MS (m/z): 484 [M+H]$^+$.

Step 7: 1-((2'-(tert-Butoxycarbonyl)biphenyl-4-yl)methyl)-2,3-dimethyl-1H-indole-5-carboxylic acid

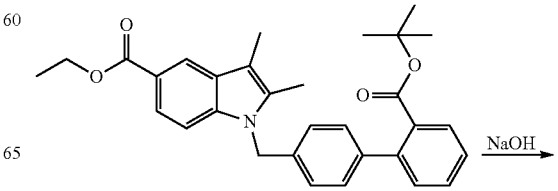

253

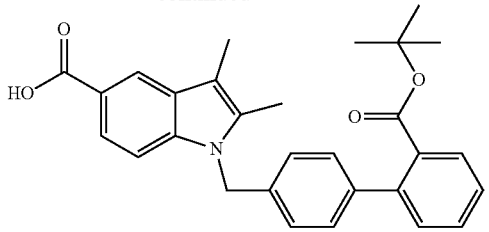

A mixture of ethyl 1-((2'-(tert-butoxycarbonyl)biphenyl-4-yl)methyl)-2,3-dimethyl-1H-indole-5-carboxylate (3.72 g, 7.69 mmol) and NaOH (7.7 mL, 2 N, 15.4 mmol) in EtOH (30 mL) was refluxed at 100° C. for 2 h. The completion of the reaction was monitored by anal. HPLC. The reaction mixture was cooled to rt, then acidified to pH-4 with 2 N HCl solution. The mixture was evaporated in vacuo to obtain the crude, which was precipitated from water and filtered to obtain the title compound. ESI-MS (m/z): 456 [M+H]$^+$. $^1$H NMR (400 MHz, DMSO-d$_6$): δ (ppm) 1.13 (s, 9H, CH$_3$ tBu), 2.26 (s, 3H, CH$_3$ indole), 2.33 (s, 3H, CH$_3$ indole), 5.49 (s, 2H, CH$_2$-biphenyl), 7.01 (d, J=8 Hz, 2H, H$_7$ and H$_9$ biphenyl), 7.19 (d, J=8 Hz, 2H, H$_6$ and H$_{10}$ biphenyl), 7.30 (d, J=7.6 Hz, 1H, H$_7$ indole), 7.40-7.47 (m, 2H, H$_2$ and H$_4$ biphenyl), 7.53 (dt, J=1.2, 7.6 Hz, 1H, H$_3$ biphenyl), 7.63-7.69 (m, 2H H$_6$ indole and H$_5$ biphenyl), 8.13 (d, J=1.2 Hz, 1H, H$_4$ indole).

Step 8: (S)-tert-Butyl 4'-((5-(1-(4-bromophenyl)ethylcarbamoyl)-2,3-dimethyl-1H-indol-1-yl)methyl)biphenyl-2-carboxylate

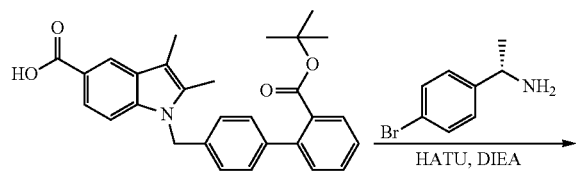

254

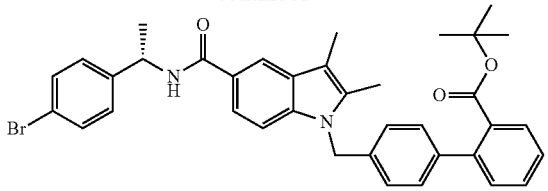

To a mixture of 1-((2'-(tert-butoxycarbonyl)biphenyl-4-yl)methyl)-2,3-dimethyl-1H-indole-5-carboxylic acid (46 mg, 0.1 mmol) in DMF (1 mL) was added DIEA (26 mg, 0.2 mmol) and HATU (46 mg, 0.12 mmol). The mixture was stirred for 5 min, and then (S)-1-(4-bromophenyl)ethanamine (20 mg, 0.13 mmol) was added. The reaction mixture was stirred at rt for 30 min. The completion of the reaction was monitored by anal. HPLC. The solvent was removed in vacuo to obtain the crude which was purified by flash chromatography (AcOEt/Hex 10->100%) to obtain the title compound. ESI-MS (m/z): 637/639 [M+H]$^+$.

Step 9: (S)-4'-((5-(1-(4-Bromophenyl)ethylcarbamoyl)-2,3-dimethyl-1H-indol-1-yl)methyl)biphenyl-2-carboxylic acid

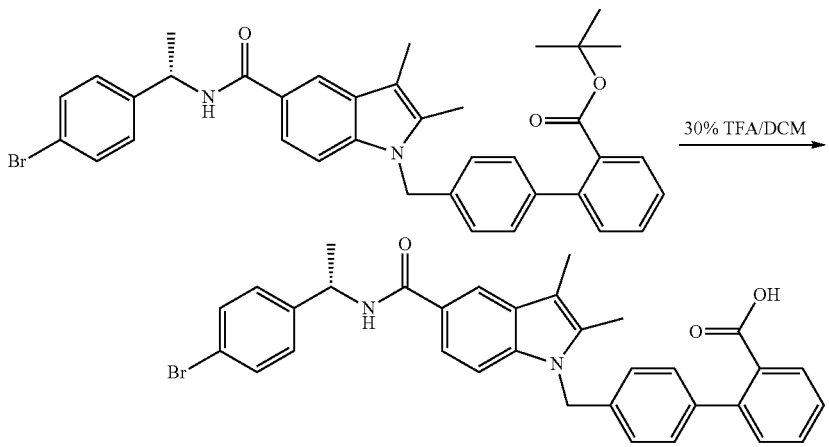

A mixture of (S)-tert-butyl 4'-((5-(1-(4-bromophenyl)ethylcarbamoyl)-2,3-dimethyl-1H-indol-1-yl)methyl)biphenyl-2-carboxylate (20 mg, 0.03 mmol) in TFA/DCM (1 mL, 30%) was stirred at rt for 2 h. The completion of the reaction was monitored by anal. HPLC. The solvent was removed to obtain the crude which was purified by reverse phase prep-HPLC (MeOH/Acetonitrile/water) to obtain the title compound. ESI-MS (m/z): 581/583 [M+H]$^+$. $^1$H NMR (400 MHz, DMSO-d$_6$): δ (ppm) 1.48 (d, J=6.8 Hz, 3H, CH$_3$ (4-bromophenyl)ethylcarbamoyl), 2.28 (s, 3H, CH$_3$ indole), 2.32 (s, 3H, CH$_3$ indole), 5.17 (quintuplet, J=7.6 Hz, 1H, CH (4-bromophenyl)ethylcarbamoyl), 5.47 (s, 2H, CH$_2$-biphenyl), 6.99 (d, J=8 Hz, 2H, H$_7$ and H$_9$ biphenyl), 7.24 (d, J=8 Hz, 2H, H$_6$ and H$_{10}$ biphenyl), 7.31 (d, J=7.6 Hz, 1H, H$_7$ indole), 7.36-7.55 (m, 7H, H$_2$, H$_3$ and H$_4$ biphenyl, H$_6$ indole and H 4-bromophenyl), 8.10 (d, J=1.6 Hz, 1H, H$_4$ indole), 8.65 (d, J=8 Hz, 1H, NH amide).

Example 2: (S)-4'-((5-((1-(4-(tert-butyl)phenyl)ethyl)carbamoyl)-2,3-dimethyl-1H-indol-1-yl)methyl)-[1,1'-biphenyl]-2-carboxylic acid

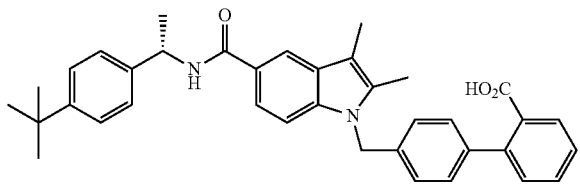 [SMILES: Cc1c(C)n(Cc2ccc(-c3ccccc3C(=O)O)cc2)c2ccc(C(=O)N[C@@H](C)c3ccc(C(C)(C)C)cc3)cc12]

Step 1: (R)—N—((S)-1-(4-(tert-butyl)phenyl)ethyl)-2-methylpropane-2-sulfinamide

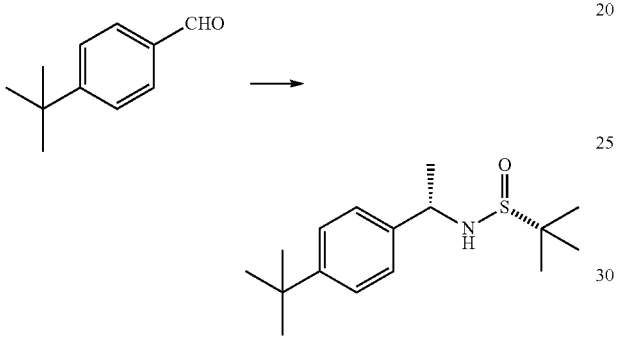

To a solution of 4-t-butylbenzaldehyde (753 µL) in THF (8 mL) was added (R)-2-methylpropane-2-sulfinamide (500 mg) followed by Ti(OiPr)$_4$ (2.5 mL). The resulting solution was allowed to stir at room temperature for 18 h, and then quenched with saturated aqueous NH$_4$C$_1$ and diluted with EtOAc. The mixture was filtered through a pad of celite, and washed with EtOAc. The layers were separated, and the organic phase was washed with brine (2×), dried (MgSO$_4$) and concentrated to give the imine as a light yellow oil (1.20 g) which was used without further purification.

To a solution of the crude imine in CH$_2$C$_{12}$ (10 mL) at −50° C. was added MeMgBr (2.7 mL, 3.0 M in Et$_2$O). The reaction was maintained at −50° C. for 6 h, and then allowed to warm to room temperature overnight. After 16 h, the reaction was quenched with brine and diluted with EtOAc and the layers were separated. The organic layer was washed with brine (2×), dried (MgSO$_4$) and concentrated. The crude residue was purified by chromatography on silica gel (EtOAc/hex) to afford the title compound as a colorless solid (1.01 g). ESI-MS (m/z): 282 [MH]$^+$ Step 2: (S)-1-(4-(tert-butyl)phenyl)ethanaminium chloride

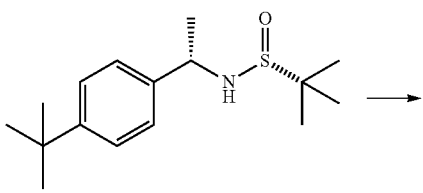

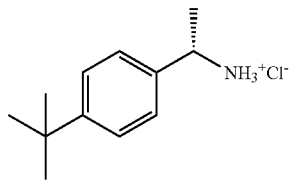

To a solution of (R)—N—((S)-1-(4-(tert-butyl)phenyl)ethyl)-2-methylpropane-2-sulfinamide (977 mg) in MeOH (1.75 mL) was added conc. HCl (1.75 mL). The reaction was aged at room temperature monitoring disappearance of starting material by analytical reverse-phase HPLC. When the starting material was consumed, the reaction was concentrated in vacuo. The crude residue was resuspended in MeOH (1 mL) and crashed out of solution by the addition of Et$_2$O. Filtration afforded the title compound as a colorless solid (559 mg). ESI-MS (m/z): 161 [M+H−NH$_3$]$^+$, 338 [2M+H−NH$_3$]$^+$ Step 3: (S)-tert-butyl 4'-((5-((1-(4-(tert-butyl)phenyl)ethyl)carbamoyl)-2,3-dimethyl-1H-indol-1-yl)methyl)-[1,1'-biphenyl]-2-carboxylate

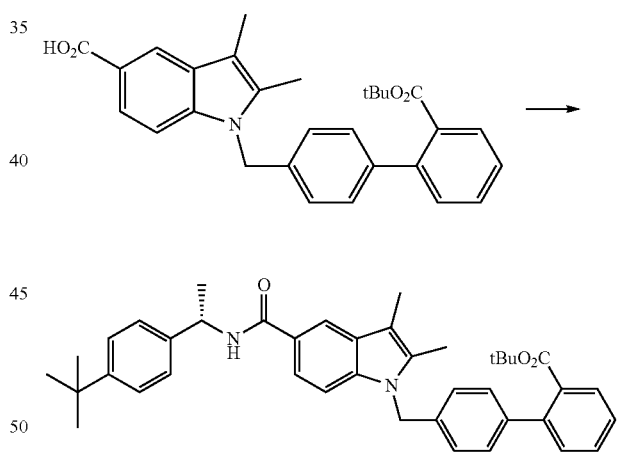

To a mixture of 1-((2'-(tert-butoxycarbonyl)biphenyl-4-yl)methyl)-2,3-dimethyl-1H-indole-5-carboxylic acid (100 mg) in DMF (2 mL) was added DIEA (116 µL) and HATU (88 mg). The mixture was stirred for 5 min, and then (S)-1-(4-(tert-butyl)phenyl)ethanaminium chloride (49 mg) was added. The reaction mixture was stirred at rt for 30 min. The completion of the reaction was monitored by anal. HPLC. The solvent was removed in vacuo to obtain the crude which was purified by flash chromatography (AcOEt/Hex 10->100%) to obtain the title compound (120 mg). ESI-MS (m/z): 559 [M+H−tBu]$^+$, 615 [M+H]$^+$, 637 [M+Na]$^+$ Step 4: (S)-4'-((5-(1-(4-Bromophenyl)ethylcarbamoyl)-2,3-dimethyl-1H-indol-1-yl)methyl)biphenyl-2-carboxylic acid

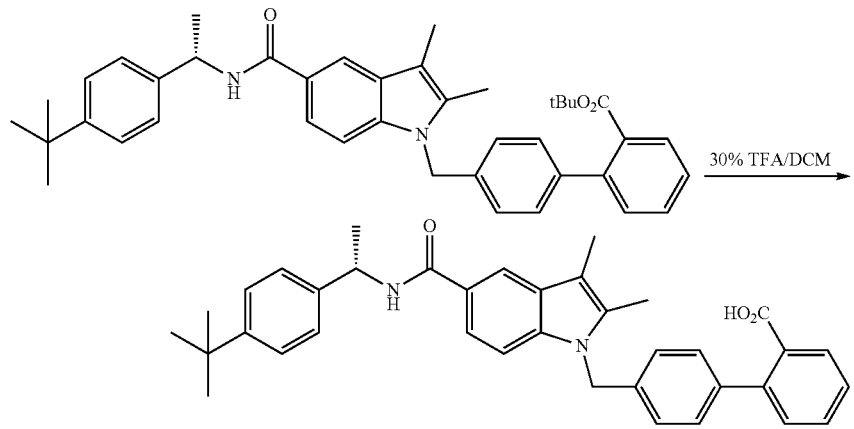

A mixture of (S)-tert-butyl 4'-((5-((1-(4-(tert-butyl)phenyl)ethyl)carbamoyl)-2,3-dimethyl-1H-indol-1-yl)methyl)-[1,1'-biphenyl]-2-carboxylate (120 mg) in TFA/DCM (1 mL, 30%) was stirred at rt for 2 h. The completion of the reaction was monitored by anal. HPLC. The solvent was removed to obtain the crude which was purified by reverse phase prep-HPLC (MeOH/Acetonitrile/water) to obtain the title compound (70 mg). ESI-MS (m/z): 559 [M+H]$^+$ $^1$H NMR (400 MHz, DMSO-d$_6$): δ (ppm) 1.26 (s, 9H), 1.49 (d, J=7.2 Hz, 3H), 2.28 (s, 3H), 2.32 (s, 3H), 5.19 (quintuplet, 1H), 5.47 (s, 2H), 6.99 (d, J=8.0 Hz, 2H), 7.24 (d, J=8.0 Hz, 2H), 7.29-7.39 (m, 5H), 7.39-7.49 (m, 2H), 7.53 (t, J=7.2 Hz, 1H), 7.65 (d, J=8.4 Hz, 1H), 7.69 (d, J=7.6 Hz, 1H), 8.1 (s, 1H), 8.58 (d, J=8.0 Hz, 1H).

Example 3: 4'-((5-(Benzyl(methyl)carbamoyl)-2,3-dimethyl-1H-indol-1-yl)methyl)biphenyl-2-carboxylic acid Step 1: tert-Butyl 4'-((5-(benzyl(methyl)carbamoyl)-2,3-dimethyl-1H-indol-1-yl)methyl)biphenyl-2-carboxylate The title compound was prepared following the same general protocol as described in Step 8, Example 1, using N-methyl-1-phenylmethanamine instead of (S)-1-(4-bromophenyl)ethanamine. ESI-MS (m/z): 559 [M+H]$^+$.

Step 2: 4'-((5-(Benzyl(methyl)carbamoyl)-2,3-dimethyl-1H-indol-1-yl)methyl)biphenyl-2-carboxylic acid The title compound was prepared following the same general protocol as described in Step 9, Example 1. ESI-MS (m/z): 503 [M+H]$^+$.

Example 4: 4'-((2,3-Dimethyl-5-(3-(methylsulfonyl) benzylcarbamoyl)-1H-indol-1-yl)methyl)biphenyl-2-carboxylic acid

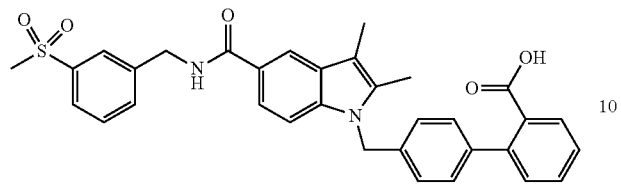

Step 1: tert-Butyl 4'-((2,3-dimethyl-5-(3-(methylsulfonyl)benzylcarbamoyl)-1H-indol-1-yl)methyl)biphenyl-2-carboxylate

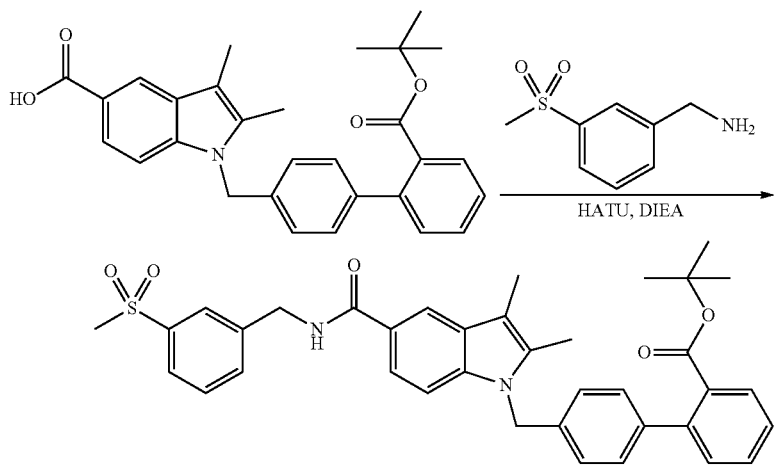

The title compound was prepared following the same general protocol as described in Step 8, Example 1, using (3-(methylsulfonyl)phenyl)methanamine instead of (S)-1-(4-bromophenyl)ethanamine. ESI-MS (m/z): 567 [M+H]$^+$-tert-butyl.

Step 2: 4'-((2,3-Dimethyl-5-(3-(methylsulfonyl)benzylcarbamoyl)-1H-indol-1-yl)methyl)biphenyl-2-carboxylic acid

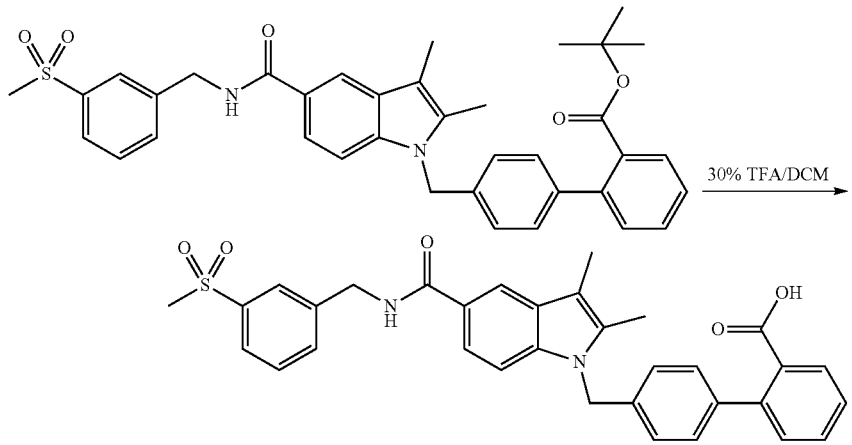

The title compound was prepared following the same general protocol as described in Step 9, Example 1. ESI-MS (m/z): 567 [M+H]$^+$.

Example 5: 4'-((2,3-Dimethyl-5-(3-(trifluoromethoxy)benzylcarbamoyl)-1H-indol-1-yl)methyl)biphenyl-2-carboxylic acid

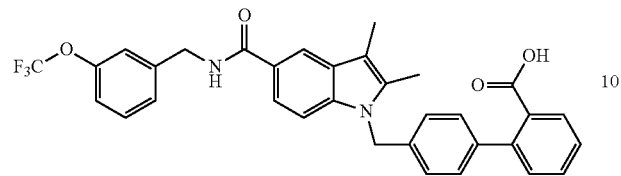

Step 1: tert-Butyl 4'-((2,3-dimethyl-5-(3-(trifluoromethoxy)benzylcarbamoyl)-1H-indol-1-yl)methyl)biphenyl-2-carboxylate

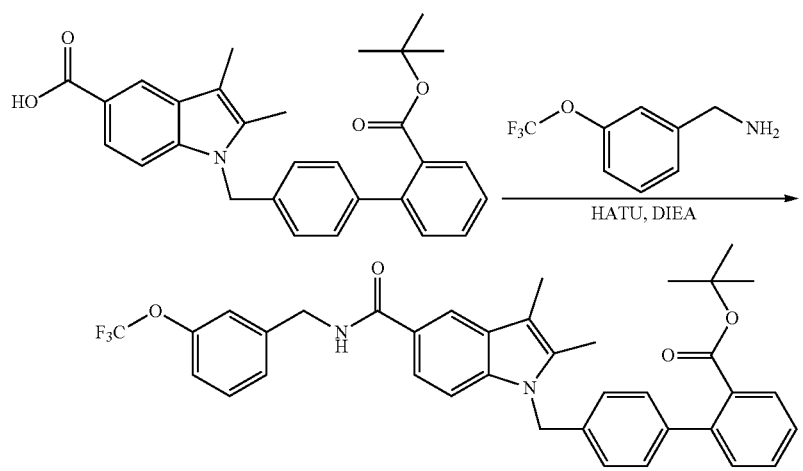

The title compound was prepared following the same general protocol as described in Step 8, Example 1, using (3-(trifluoromethoxy)phenyl)methanamine instead of (S)-1-(4-bromophenyl)ethanamine. ESI-MS (m/z): 629 [M+H]$^+$.

Step 2: 4'-((2,3-Dimethyl-5-(3-(trifluoromethoxy)benzylcarbamoyl)-1H-indol-1-yl)methyl)biphenyl-2-carboxylic acid

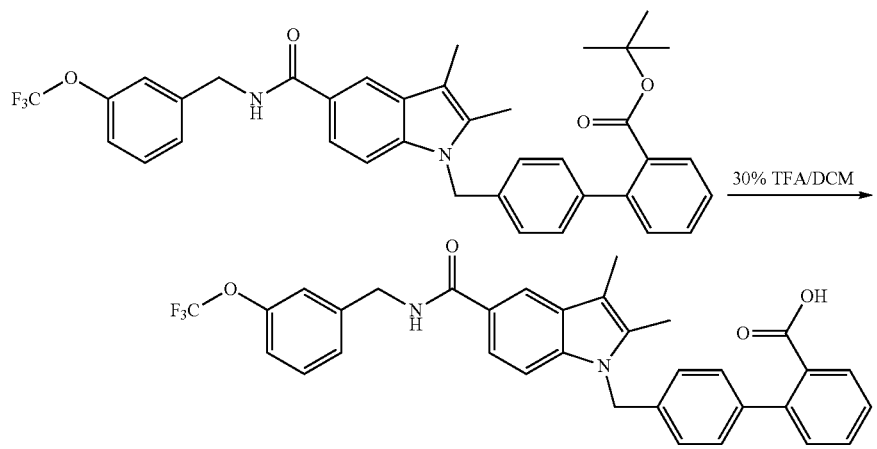

The title compound was prepared following the same general protocol as described in Step 9, Example 1. ESI-MS (m/z): 573 [M+H]⁺.

Example 6: (R)-4'-((5-(1-(4-Bromophenyl)ethylcarbamoyl)-2,3-dimethyl-1H-indol-1-yl)methyl)biphenyl-2-carboxylic acid

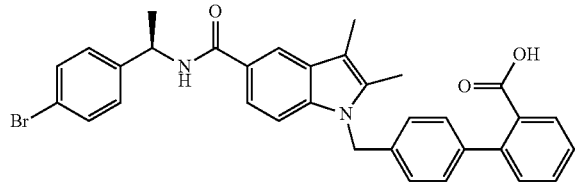

Step 1: (R)-tert-Butyl 4'-((5-(1-(4-bromophenyl)ethylcarbamoyl)-2,3-dimethyl-1H-indol-1-yl)methyl)biphenyl-2-carboxylate

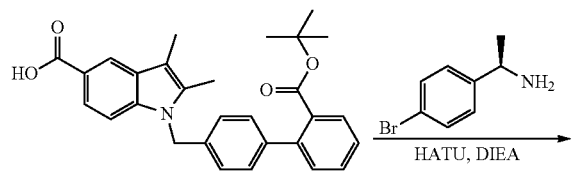

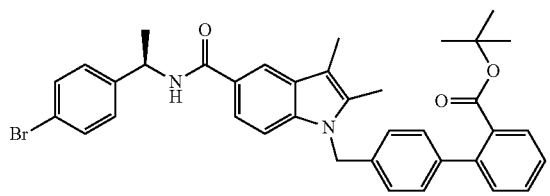

The title compound was prepared following the same general protocol as described in Step 8, Example 1, using (R)-1-(4-bromophenyl)ethanamine instead of (S)-1-(4-bromophenyl)ethanamine. ESI-MS (m/z): 637/639 [M+H]⁺.

Step 2: (R)-4'-((5-(1-(4-Bromophenyl)ethylcarbamoyl)-2,3-dimethyl-1H-indol-1-yl)methyl)biphenyl-2-carboxylic acid

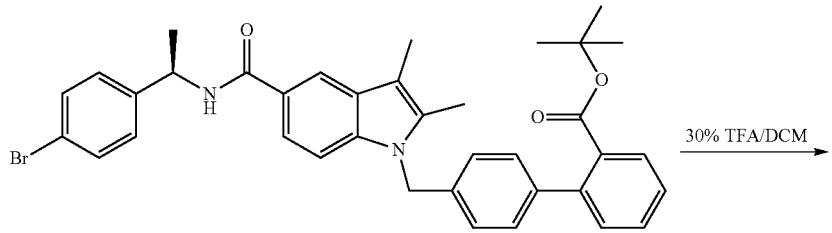

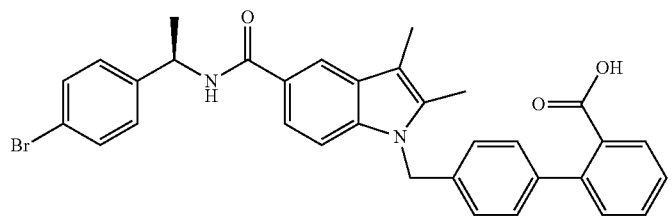

The title compound was prepared following the same general protocol as described in Step 9, Example 1. ESI-MS (m/z): 581/583 [M+H]$^+$.

Example 7: 4'-((5-(4-Iodobenzylcarbamoyl)-2,3-dimethyl-1H-indol-1-yl)methyl)biphenyl-2-carboxylic acid

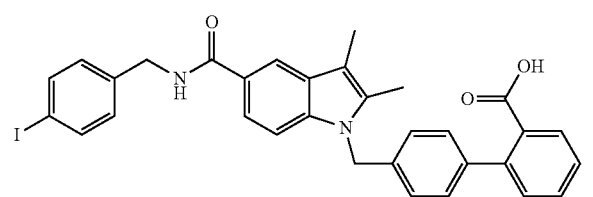 [SMILES: Cc1c(C)n(Cc2ccc(-c3ccccc3C(=O)O)cc2)c2ccc(C(=O)NCc3ccc(I)cc3)cc12]

Step 1: tert-Butyl 4'-((5-(4-iodobenzylcarbamoyl)-2,3-dimethyl-1H-indol-1-yl)methyl)biphenyl-2-carboxylate

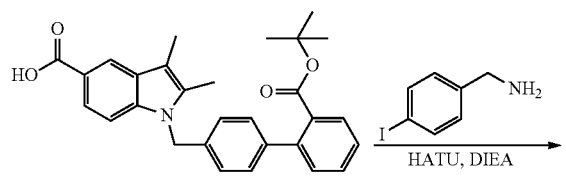

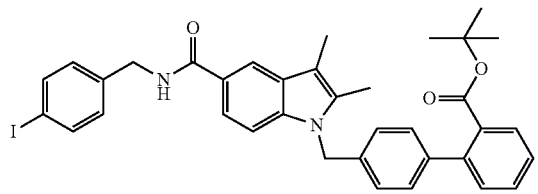

The title compound was prepared following the same general protocol as described in Step 8, Example 1, using (4-iodophenyl)methanamine instead of (S)-1-(4-bromophenyl)ethanamine. ESI-MS (m/z): 671 [M+H]$^+$.

Step 2: 4'-((5-(4-Iodobenzylcarbamoyl)-2,3-dimethyl-1H-indol-1-yl)methyl)biphenyl-2-carboxylic acid

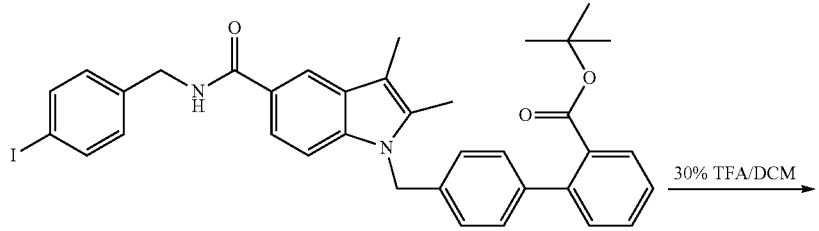

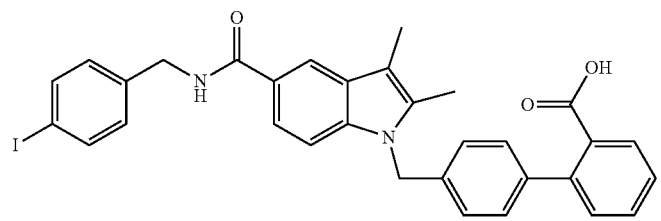

The title compound was prepared following the same general protocol as described in Step 9, Example 1. ESI-MS (m/z): 615 [M+H]$^+$.

Example 8: 4'-((5-(4-Cyanobenzylcarbamoyl)-2,3-dimethyl-1H-indol-1-yl)methyl)biphenyl-2-carboxylic acid

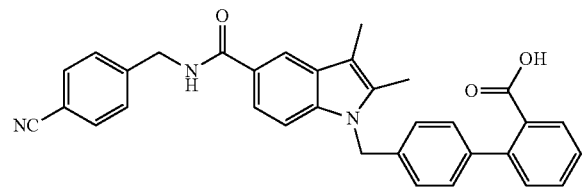 [SMILES: Cc1c(C)n(Cc2ccc(-c3ccccc3C(=O)O)cc2)c2ccc(C(=O)NCc3ccc(C#N)cc3)cc12]

Step 1: tert-Butyl 4'-((5-(4-cyanobenzylcarbamoyl)-2,3-dimethyl-1H-indol-1-yl)methyl)biphenyl-2-carboxylate

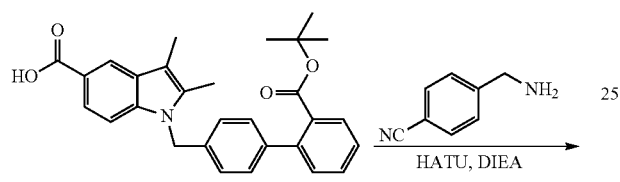

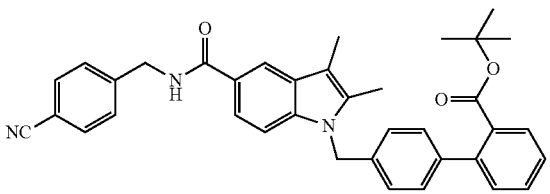

The title compound was prepared following the same general protocol as described in Step 8, Example 1, using 4-(aminomethyl)benzonitrile instead of (S)-1-(4-bromophenyl)ethanamine. ESI-MS (m/z): 514 [M+H]$^+$-tert-butyl.

Step 2: 4'-((5-(4-Cyanobenzylcarbamoyl)-2,3-dimethyl-1H-indol-1-yl)methyl)biphenyl-2-carboxylic acid

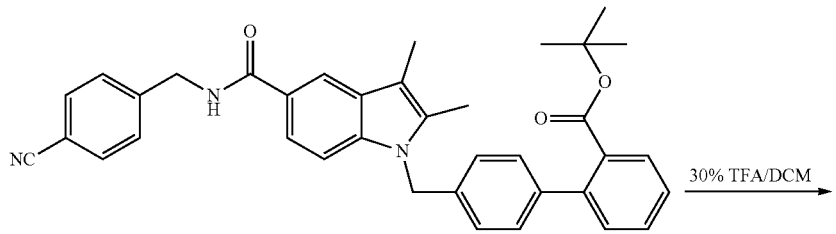

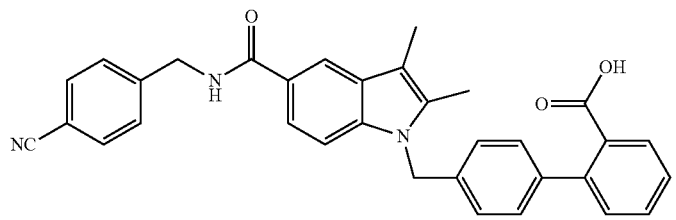 [SMILES: Cc1c(C)n(Cc2ccc(-c3ccccc3C(=O)O)cc2)c2ccc(C(=O)NCc3ccc(Cl)cc3)cc12]

The title compound was prepared following the same general protocol as described in Step 9, Example 1. ESI-MS (m/z): 514 [M+H]+.

Example 9: 4'-((5-(4-Isopropylbenzylcarbamoyl)-2,3-dimethyl-1H-indol-1-yl)methyl)biphenyl-2-carboxylic acid

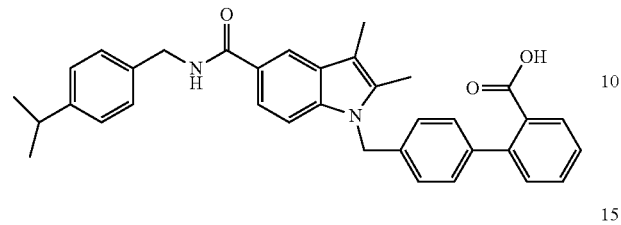

Step 1: tert-Butyl 4'-((5-(4-isopropylbenzylcarbamoyl)-2,3-dimethyl-1H-indol-1-yl)methyl)biphenyl-2-carboxylate

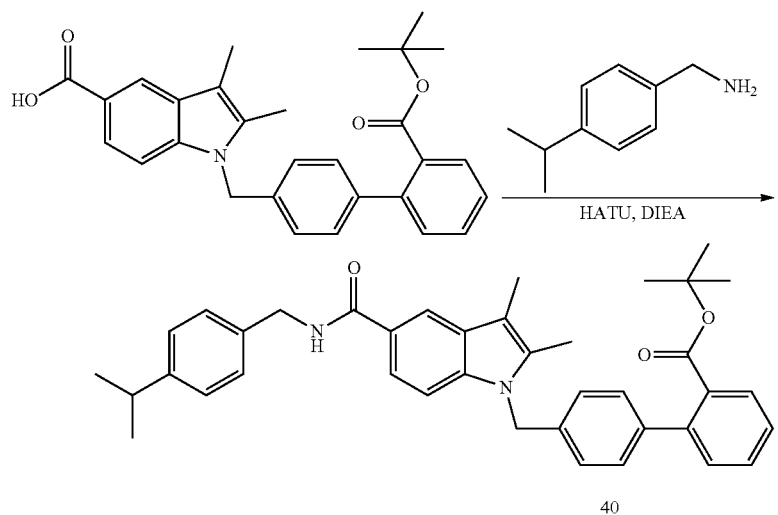

The title compound was prepared following the same general protocol as described in Step 8, Example 1, using (4-isopropylphenyl)methanamine instead of (S)-1-(4-bromophenyl)ethanamine. ESI-MS (m/z): 587 [M+H]+.

Step 2: 4'-((5-(4-Isopropylbenzylcarbamoyl)-2,3-dimethyl-1H-indol-1-yl)methyl)biphenyl-2-carboxylic acid

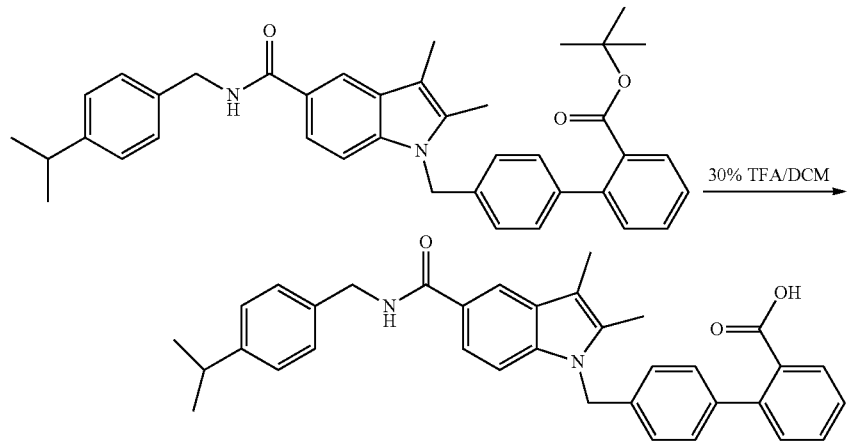

The title compound was prepared following the same general protocol as described in Step 9, Example 1. ESI-MS (m/z): 531 [M+H]+.

Example 10: 4'-((2,3-Dimethyl-5-(4-(methylsulfonyl)benzylcarbamoyl)-1H-indol-1-yl)methyl)biphenyl-2-carboxylic acid

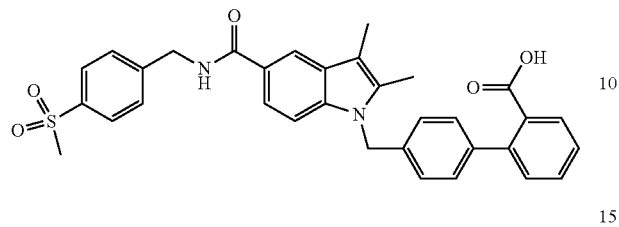

Step 1: tert-Butyl 4'-((2,3-dimethyl-5-(4-(methylsulfonyl)benzylcarbamoyl)-1H-indol-1-yl)methyl)biphenyl-2-carboxylate

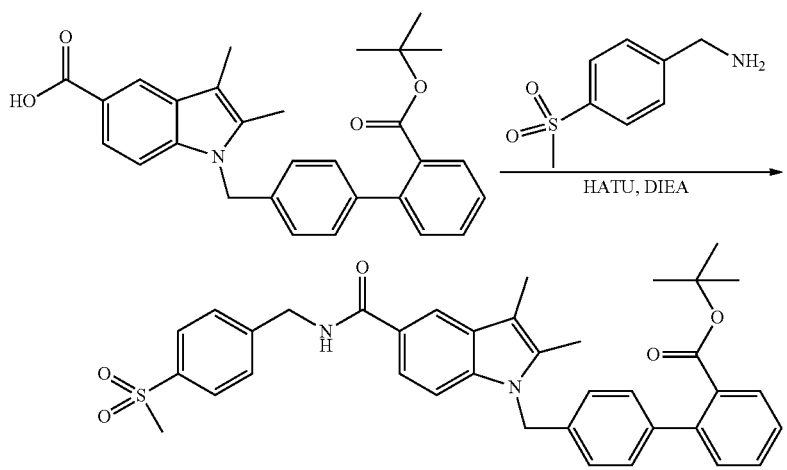

The title compound was prepared following the same general protocol as described in Step 8, Example 1, using (4-(methylsulfonyl)phenyl)methanamine instead of (S)-1-(4-bromophenyl)ethanamine. ESI-MS (m/z): 567 [M+H]+-tert-butyl.

Step 2: 4'-((2,3-Dimethyl-5-(4-(methylsulfonyl)benzylcarbamoyl)-1H-indol-1-yl)methyl)biphenyl-2-carboxylic acid

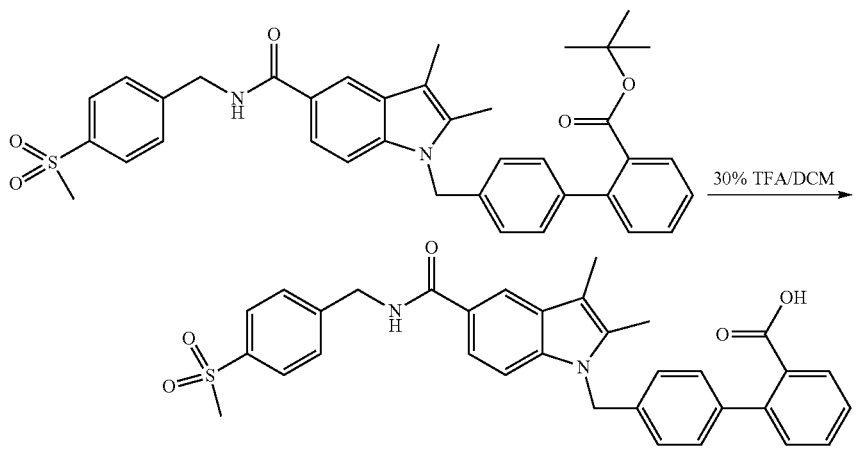

The title compound was prepared following the same general protocol as described in Step 9, Example 1. ESI-MS (m/z): 567 [M+H]$^+$.

Example 11: 4'-((5-(4-(Dimethylamino)benzylcarbamoyl)-2,3-dimethyl-1H-indol-1-yl)methyl)biphenyl-2-carboxylic acid

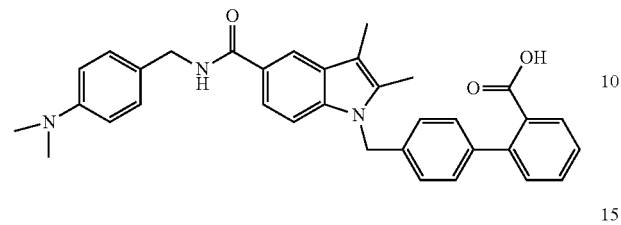

Step 1: tert-Butyl 4'-((5-(4-(dimethylamino)benzylcarbamoyl)-2,3-dimethyl-1H-indol-1-yl)methyl)biphenyl-2-carboxylate

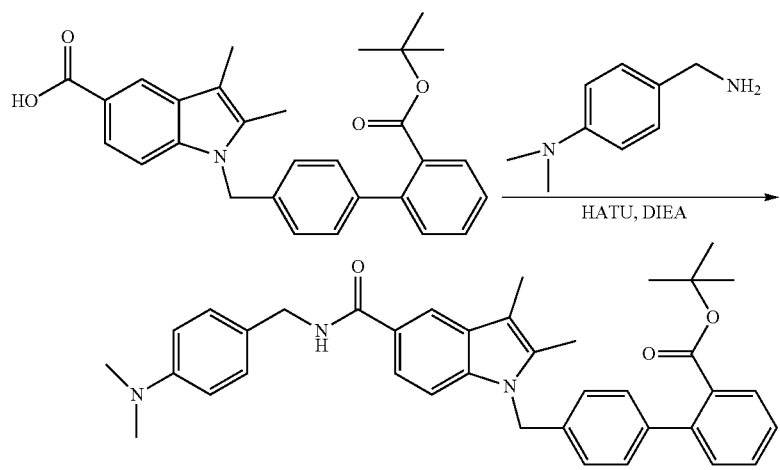

The title compound was prepared following the same general protocol as described in Step 8, Example 1, using 4-(aminomethyl)-N,N-dimethylaniline instead of (S)-1-(4-bromophenyl)ethanamine. ESI-MS (m/z): 588 [M+H]$^+$.

Step 2: 4'-((5-(4-(Dimethylamino)benzylcarbamoyl)-2,3-dimethyl-1H-indol-1-yl)methyl)biphenyl-2-carboxylic acid

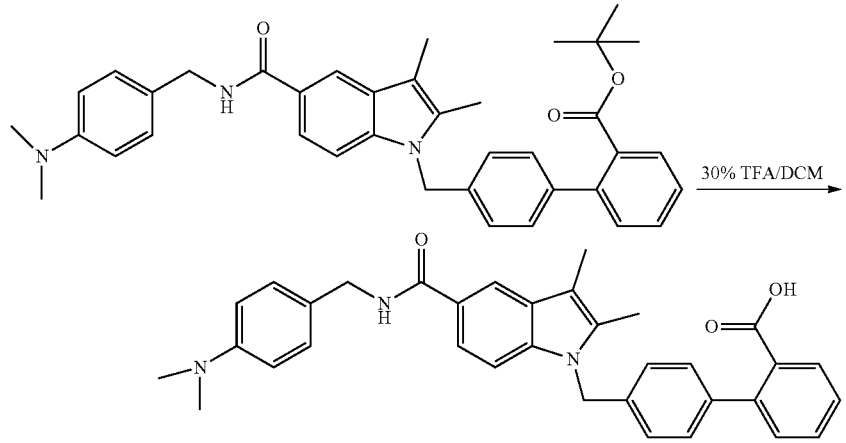

The title compound was prepared following the same general protocol as described in Step 9, Example 1. ESI-MS (m/z): 532 [M+H]$^+$.

Example 12: 4'-((5-(4-Bromobenzylcarbamoyl)-2,3-dimethyl-1H-indol-1-yl)methyl)biphenyl-2-carboxylic acid

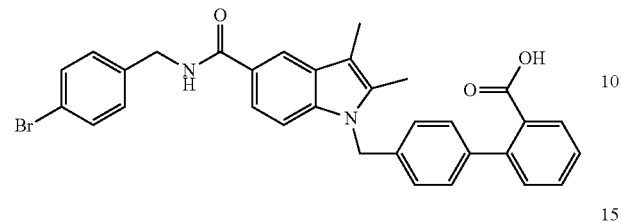

Step 1: tert-Butyl 4'-((5-(4-bromobenzylcarbamoyl)-2,3-dimethyl-1H-indol-1-yl)methyl)biphenyl-2-carboxylate

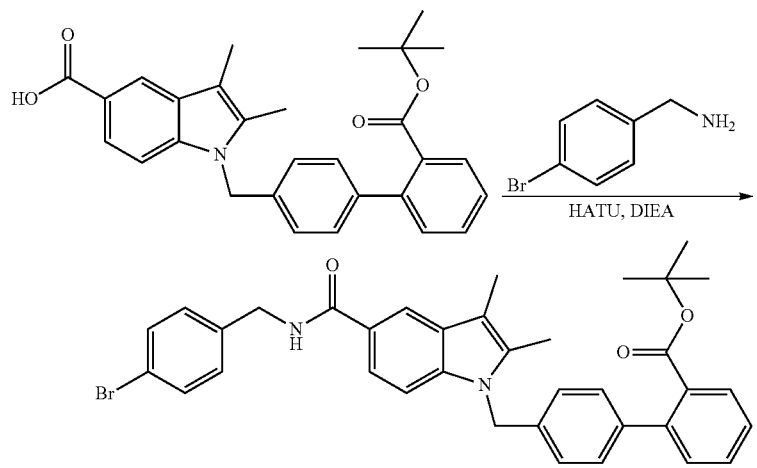

The title compound was prepared following the same general protocol as described in Step 8, Example 1, using (4-bromophenyl)methanamine instead of (S)-1-(4-bromophenyl)ethanamine. ESI-MS (m/z): 567/569, [M+H]$^+$-tert-butyl.

Step 2: 4'-((5-(4-Bromobenzylcarbamoyl)-2,3-dimethyl-1H-indol-1-yl)methyl)biphenyl-2-carboxylic acid

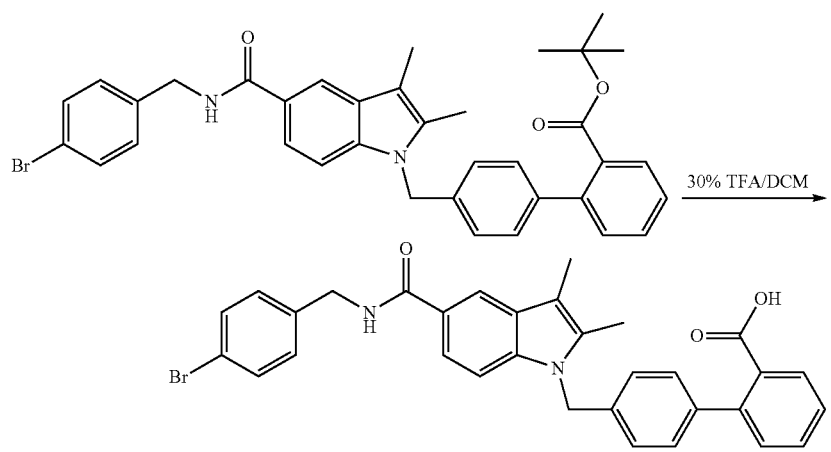

The title compound was prepared following the same general protocol as described in Step 9, Example 1. ESI-MS (m/z): 567/569 [M+H]$^+$.

Example 13: 4'-((5-(4-tert-Butylbenzylcarbamoyl)-2,3-dimethyl-1H-indol-1-yl)methyl)biphenyl-2-carboxylic acid

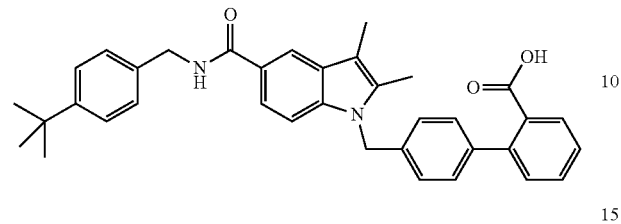

Step 1: tert-Butyl 4'-((5-(4-tert-butylbenzylcarbamoyl)-2,3-dimethyl-1H-indol-1-yl)methyl)biphenyl-2-carboxylate

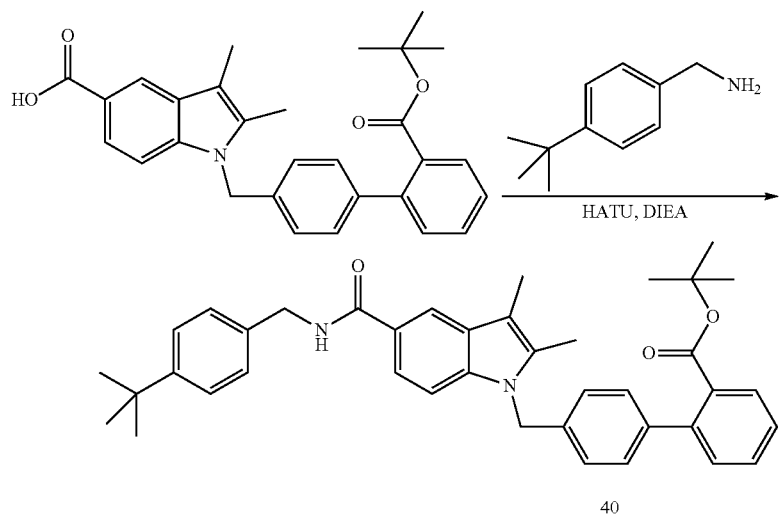

The title compound was prepared following the same general protocol as described in Step 8, Example 1, using (4-tert-butylphenyl)methanamine instead of (S)-1-(4-bromophenyl)ethanamine. ESI-MS (m/z): 601 [M+H]$^+$.

Step 2: 4'-((5-(4-tert-Butylbenzylcarbamoyl)-2,3-dimethyl-1H-indol-1-yl)methyl)biphenyl-2-carboxylic acid

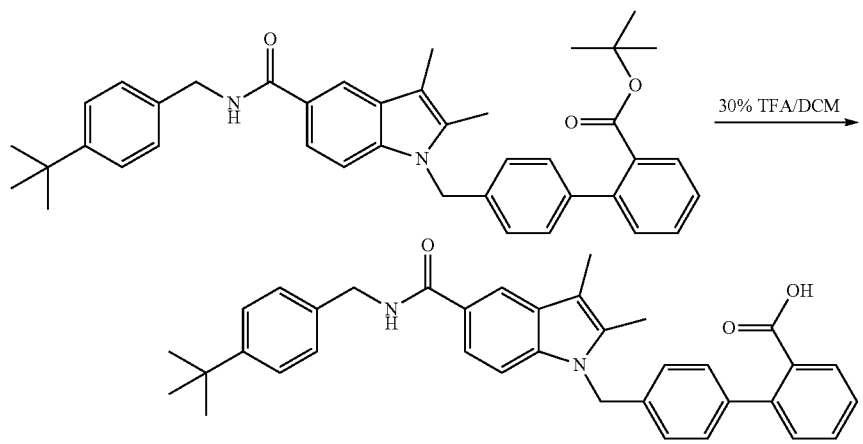

The title compound was prepared following the same general protocol as described in Step 9, Example 1. ESI-MS (m/z): 545 [M+H]+.

Example 14: 4'-((5-(4-Chlorobenzylcarbamoyl)-2,3-dimethyl-1H-indol-1-yl)methyl)biphenyl-2-carboxylic acid

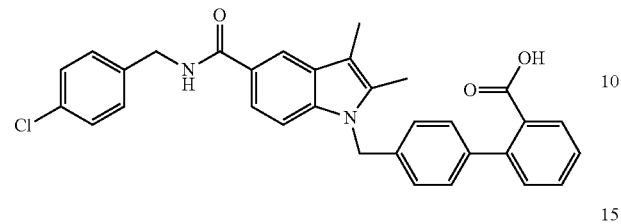

Step 1: tert-Butyl 4'-((5-(4-chlorobenzylcarbamoyl)-2,3-dimethyl-1H-indol-1-yl)methyl)biphenyl-2-carboxylate

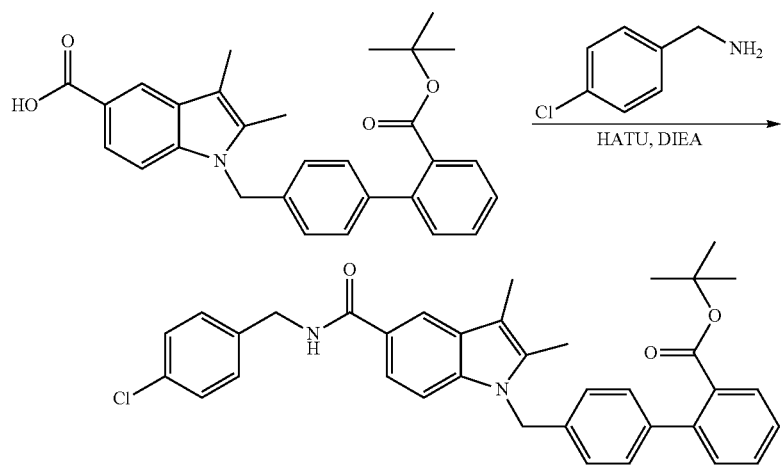

The title compound was prepared following the same general protocol as described in Step 8, Example 1, using (4-chlorophenyl)methanamine instead of (S)-1-(4-bromophenyl)ethanamine. ESI-MS (m/z): 523 [M+H]+-tert-butyl.

Step 2: 4'-((5-(4-Chlorobenzylcarbamoyl)-2,3-dimethyl-1H-indol-1-yl)methyl)biphenyl-2-carboxylic acid

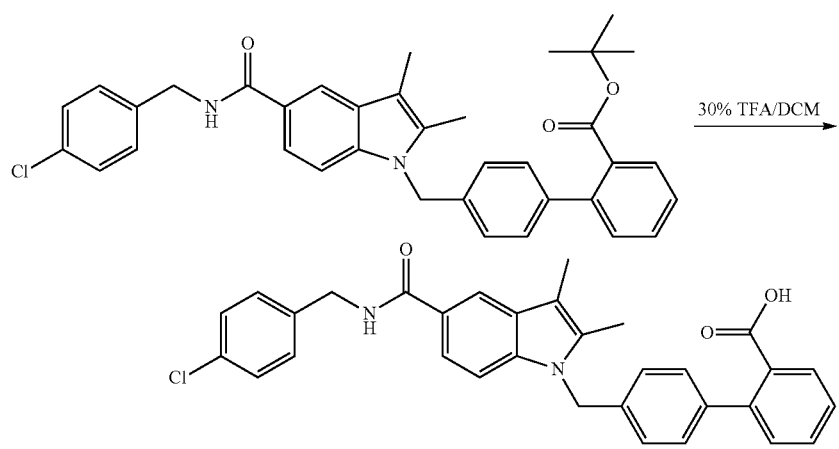

The title compound was prepared following the same general protocol as described in Step 9, Example 1. ESI-MS (m/z): 523 [M+H]$^+$.

Example 15: 4'-((2,3-Dimethyl-5-(4-(trifluoromethoxy)benzylcarbamoyl)-1H-indol-1-yl)methyl)biphenyl-2-carboxylic acid

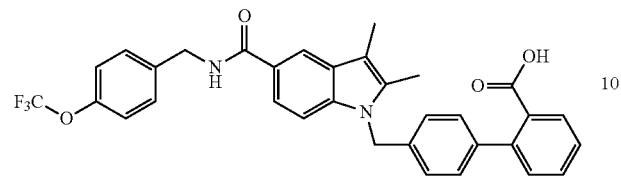

Step 1: tert-Butyl 4'-((2,3-dimethyl-5-(4-(trifluoromethoxy)benzylcarbamoyl)-1H-indol-1-yl)methyl)biphenyl-2-carboxylate

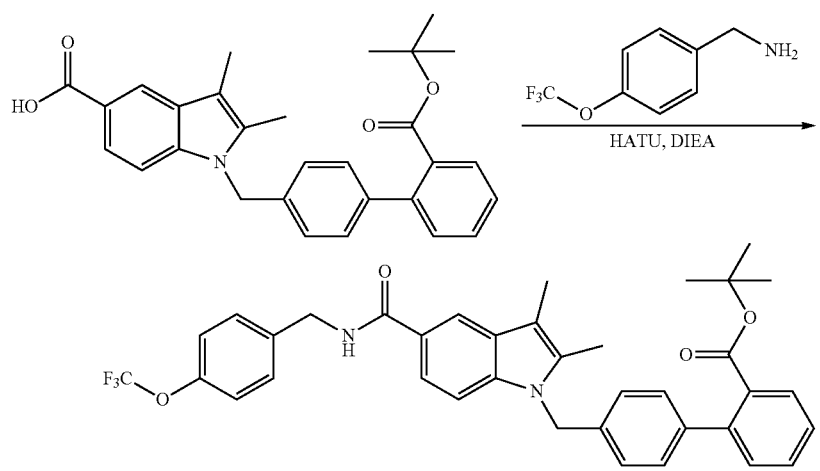

The title compound was prepared following the same general protocol as described in Step 8, Example 1, using (4-(trifluoromethoxy)phenyl)methanamine instead of (S)-1-(4-bromophenyl)ethanamine. ESI-MS (m/z): 573 [M+H]$^+$-tert-butyl.

Step 2: 4'-((2,3-Dimethyl-5-(4-(trifluoromethoxy)benzylcarbamoyl)-1H-indol-1-yl)methyl)biphenyl-2-carboxylic acid

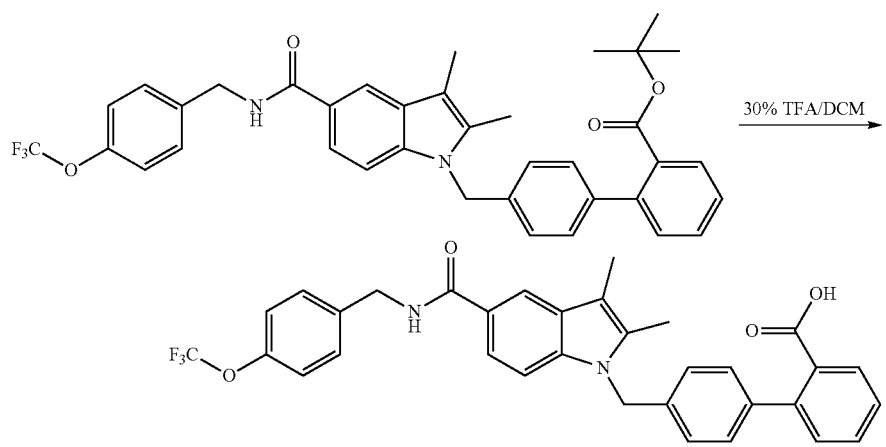

The title compound was prepared following the same general protocol as described in Step 9, Example 1. ESI-MS (m/z): 573 [M+H]$^+$.

Example 16: 4'-((5-(4-(Methoxycarbonyl)benzylcarbamoyl)-2,3-dimethyl-1H-indol-1-yl)methyl)biphenyl-2-carboxylic acid

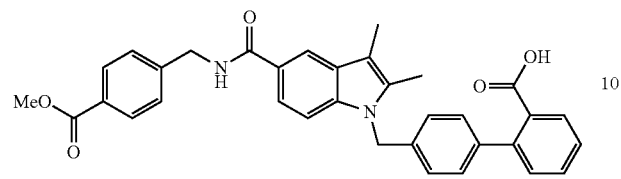

Step 1: tert-Butyl 4'-((5-(4-(methoxycarbonyl)benzylcarbamoyl)-2,3-dimethyl-1H-indol-1-yl)methyl)biphenyl-2-carboxylate

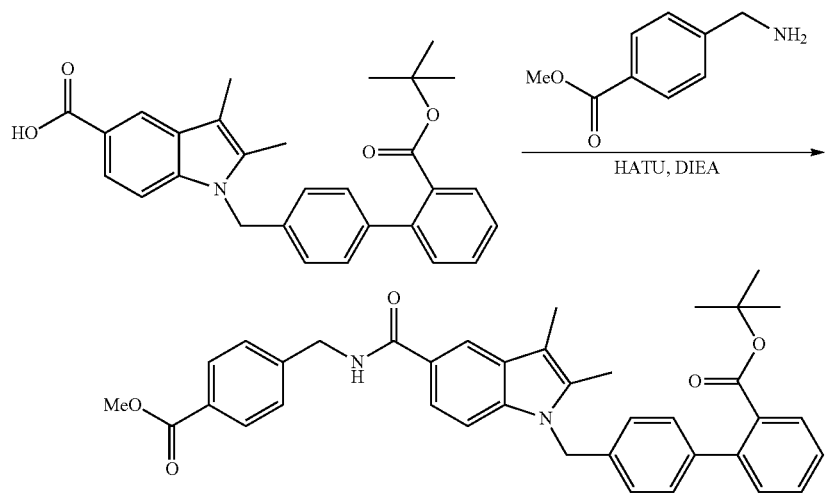

The title compound was prepared following the same general protocol as described in Step 8, Example 1, using methyl 4-(aminomethyl)benzoate instead of (S)-1-(4-bromophenyl)ethanamine. ESI-MS (m/z): 547 [M+H]$^+$-tert-butyl.

Step 2: 4'-((5-(4-(Methoxycarbonyl)benzylcarbamoyl)-2,3-dimethyl-1H-indol-1-yl)methyl)biphenyl-2-carboxylic acid

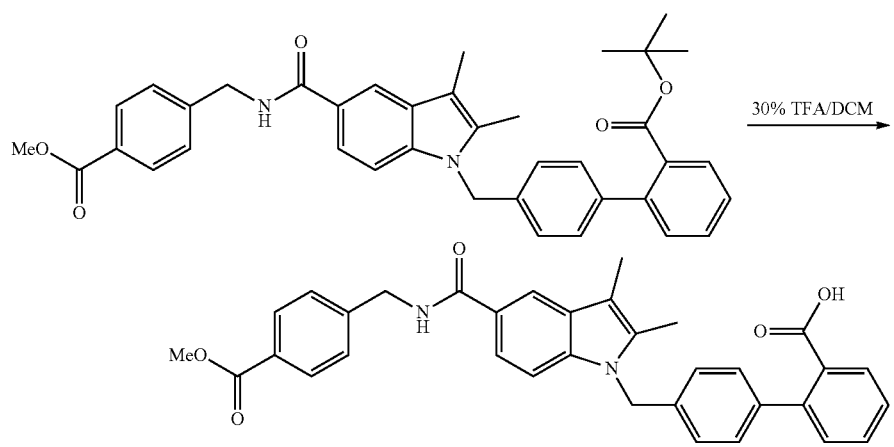

The title compound was prepared following the same general protocol as described in Step 9, Example 1. ESI-MS (m/z): 547 [M+H]$^+$.

Example 17: 4'-((2,3-Dimethyl-5-(4-sulfamoylbenzylcarbamoyl)-1H-indol-1-yl)methyl)biphenyl-2-carboxylic acid

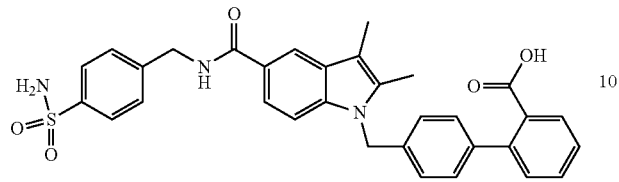

Step 1: tert-Butyl 4'-((2,3-dimethyl-5-(4-sulfamoylbenzylcarbamoyl)-1H-indol-1-yl)methyl)biphenyl-2-carboxylate

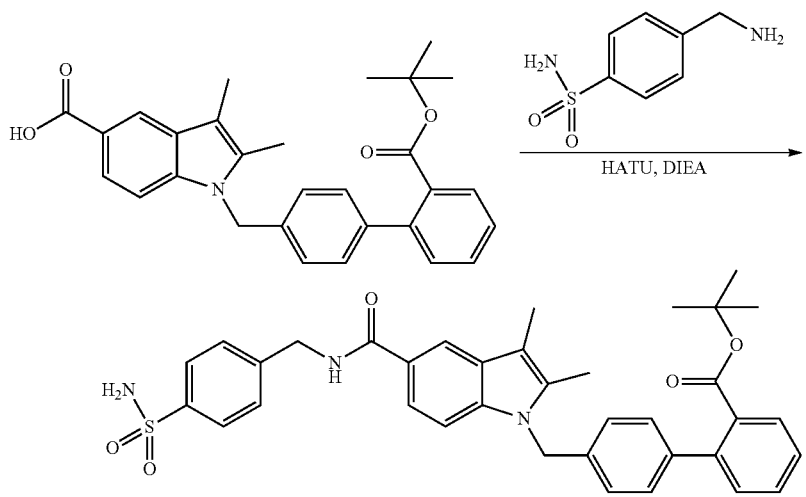

The title compound was prepared following the same general protocol as described in Step 8, Example 1, using 4-(aminomethyl)benzenesulfonamide instead of (S)-1-(4-bromophenyl)ethanamine. ESI-MS (m/z): 568 [M+H]$^+$-tert-butyl.

Step 2: 4'-((2,3-Dimethyl-5-(4-sulfamoylbenzylcarbamoyl)-1H-indol-1-yl)methyl)biphenyl-2-carboxylic acid

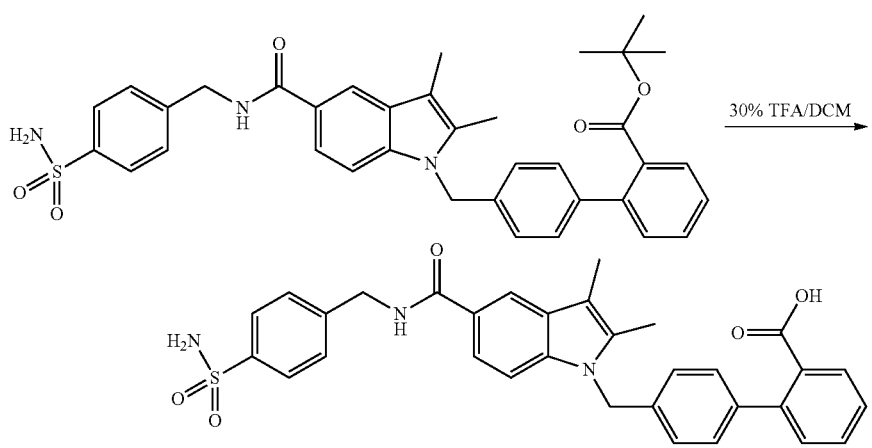

The title compound was prepared following the same general protocol as described in Step 9, Example 1. ESI-MS (m/z): 568 [M+H]+.

Example 18: 4'-((2,3-Dimethyl-5-(4-(methylthio)benzylcarbamoyl)-1H-indol-1-yl)methyl)biphenyl-2-carboxylic acid

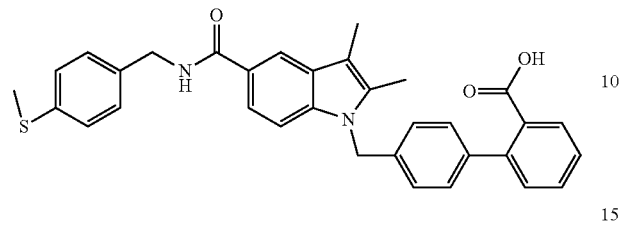

Step 1: tert-Butyl 4'-((2,3-dimethyl-5-(4-(methylthio)benzylcarbamoyl)-1H-indol-1-yl)methyl)biphenyl-2-carboxylate

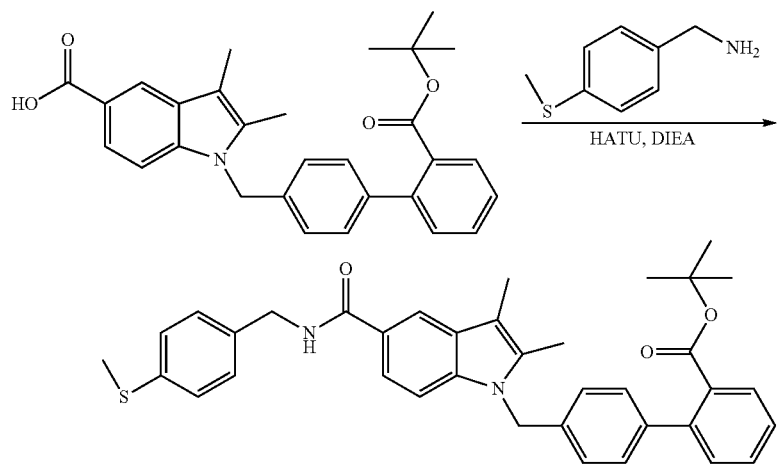

The title compound was prepared following the same general protocol as described in Step 8, Example 1, using (4-(methylthio)phenyl)methanamine instead of (S)-1-(4-bromophenyl)ethanamine. ESI-MS (m/z): 591 [M+H]+.

Step 2: 4'-((2,3-Dimethyl-5-(4-(methylthio)benzylcarbamoyl)-1H-indol-1-yl)methyl)biphenyl-2-carboxylic acid

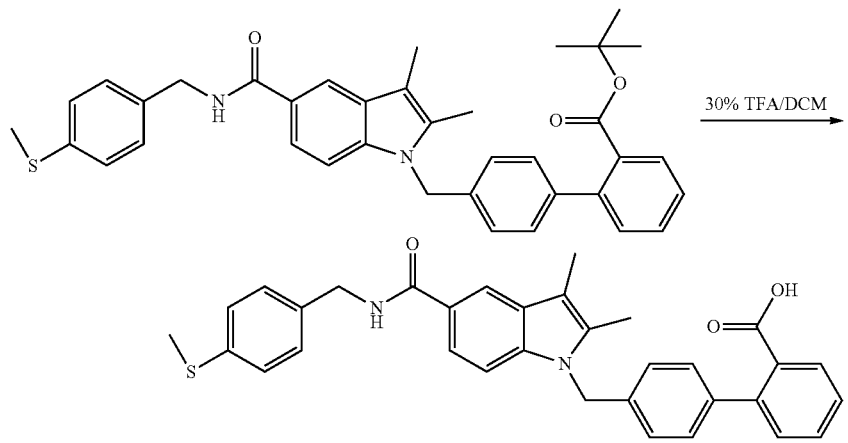

The title compound was prepared following the same general protocol as described in Step 9, Example 1. ESI-MS (m/z): 535 [M+H]⁺.

Example 19: (S)-4'-((5-(1-(4-Methoxyphenyl)ethylcarbamoyl)-2,3-dimethyl-1H-indol-1-yl)methyl)biphenyl-2-carboxylic acid

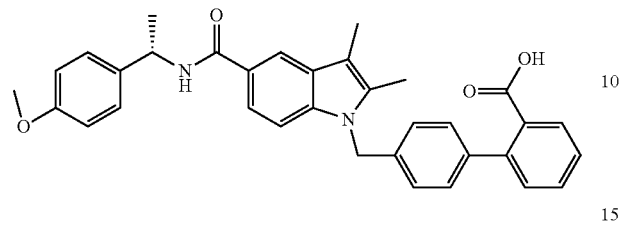

Step 1: (S)-tert-Butyl 4'-((5-(1-(4-methoxyphenyl)ethylcarbamoyl)-2,3-dimethyl-1H-indol-1-yl)methyl)biphenyl-2-carboxylate

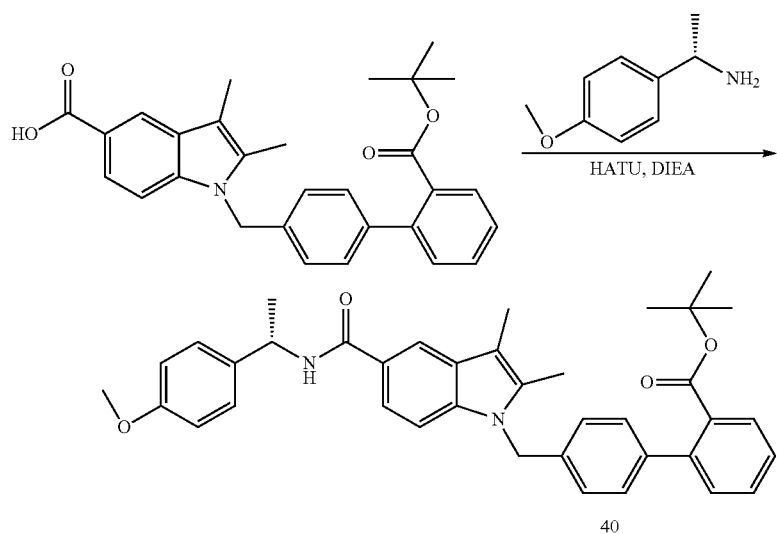

The title compound was prepared following the same general protocol as described in Step 8, Example 1, using (S)-1-(4-methoxyphenyl)ethanamine instead of (S)-1-(4-bromophenyl)ethanamine. ESI-MS (m/z): 589 [M+H]⁺.

Step 2: (S)-4'-((5-(1-(4-Methoxyphenyl)ethylcarbamoyl)-2,3-dimethyl-1H-indol-1-yl)methyl)biphenyl-2-carboxylic acid

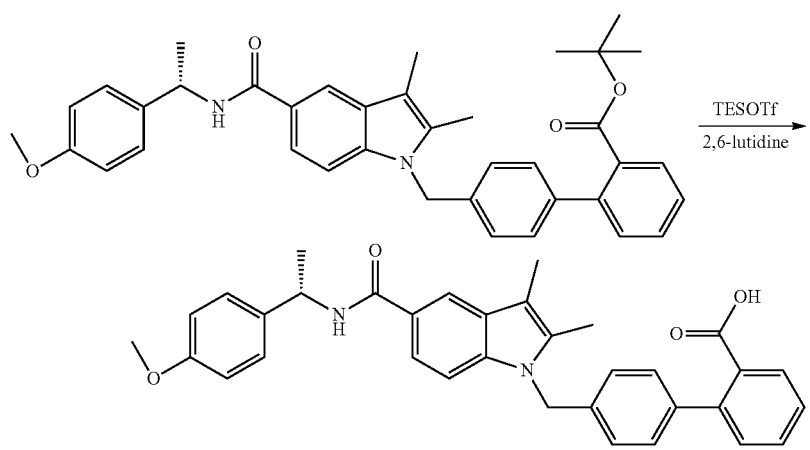

To a mixture of (S)-tert-butyl 4'-((5-(1-(4-methoxyphenyl)ethylcarbamoyl)-2,3-dimethyl-1H-indol-1-yl)methyl)biphenyl-2-carboxylate (58.9 mg, 0.1 mmol) and 2,6-lutidine (0.13 mL, 1.15 mmol) in DCM (1 mL) at 0° C. was added TESOTf (0.17 mL, 0.75 mmol). The reaction mixture was stirred at rt for 2 h. The completion of the reaction was monitored by anal. HPLC. The mixture was evaporated in vacuo to obtain the crude which was purified by prep. HPLC (MeOH/Acetonitrile/water) to obtain the title compound. ESI-MS (m/z): 533 [M+H]$^+$.

Example 20: 4'-((5-(2,4-Dimethoxybenzylcarbamoyl)-2,3-dimethyl-1H-indol-1-yl)methyl)biphenyl-2-carboxylic acid

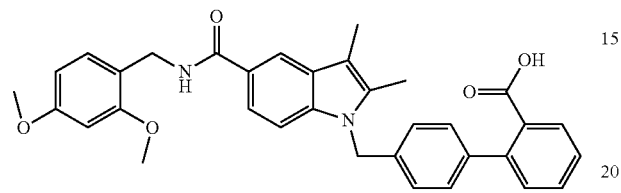

Step 1: tert-Butyl 4'-((5-(2,4-dimethoxybenzylcarbamoyl)-2,3-dimethyl-1H-indol-1-yl)methyl)biphenyl-2-carboxylate

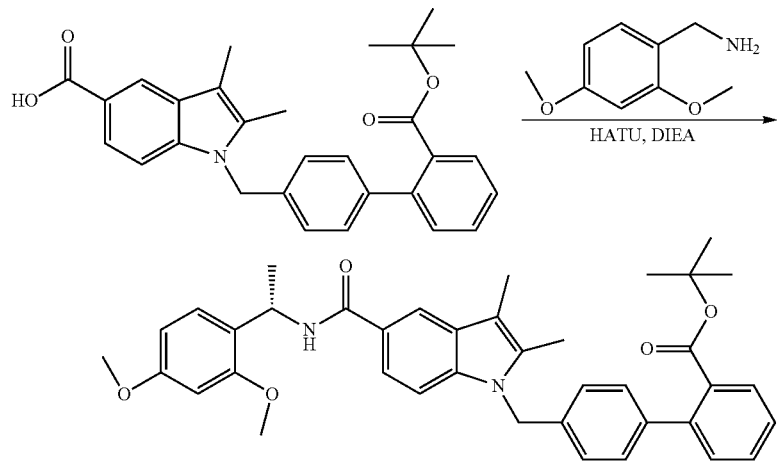

The title compound was prepared following the same general protocol as described in Step 8, Example 1, using (2,4-dimethoxyphenyl)methanamine instead of (S)-1-(4-bromophenyl)ethanamine. ESI-MS (m/z): 605 [M+H]$^+$.

Step 2: 4'-((5-(2,4-Dimethoxybenzylcarbamoyl)-2,3-dimethyl-1H-indol-1-yl)methyl)biphenyl-2-carboxylic acid

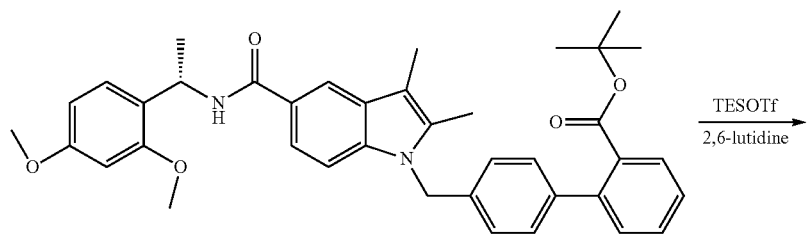

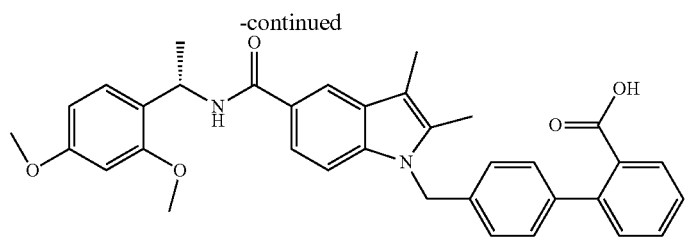

The title compound was prepared following the same general protocol as described in Step 2, Example 19. ESI-MS (m/z): 549 [M+H]⁺.

Example 21: (S)-4'-((5-(1-(3-Methoxyphenyl)ethylcarbamoyl)-2,3-dimethyl-1H-indol-1-yl)methyl)biphenyl-2-carboxylic acid

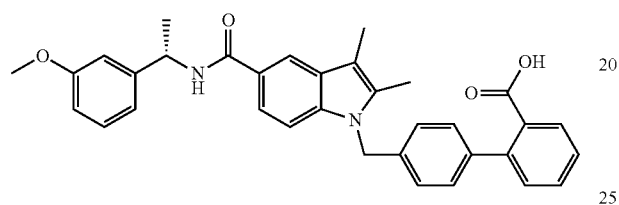

Step 1: (S)-tert-Butyl 4'-((5-(1-(3-methoxyphenyl)ethylcarbamoyl)-2,3-dimethyl-1H-indol-1-yl)methyl)biphenyl-2-carboxylate

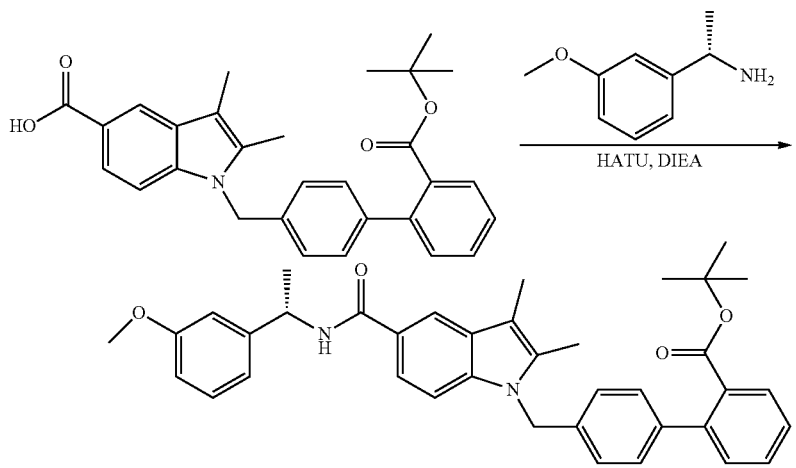

The title compound was prepared following the same general protocol as described in Step 8, Example 1, using (S)-1-(3-methoxyphenyl)ethanamine instead of (S)-1-(4-bromophenyl)ethanamine. ESI-MS (m/z): 589 [M+H]⁺.

Step 2: (S)-4'-((5-(1-(3-Methoxyphenyl)ethylcarbamoyl)-2,3-dimethyl-1H-indol-1-yl)methyl)biphenyl-2-carboxylic acid

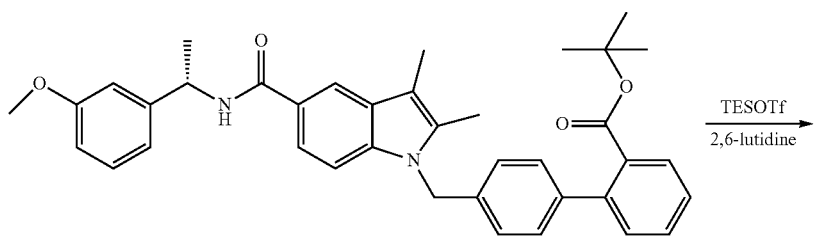

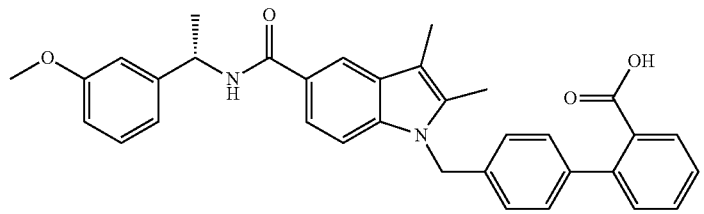
The title compound was prepared following the same general protocol as described in Step 2, Example 19. ESI-MS (m/z): 533 [M+H]+.
Example 22: 4'-((5-(3,5-Dimethoxybenzylcarbamoyl)-2,3-dimethyl-1H-indol-1-yl)methyl)biphenyl-2-carboxylic acid
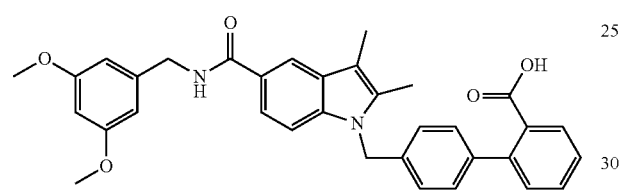
Step 1: tert-Butyl 4'-((5-(3,5-dimethoxybenzylcarbamoyl)-2,3-dimethyl-1H-indol-1-yl)methyl)biphenyl-2-carboxylate
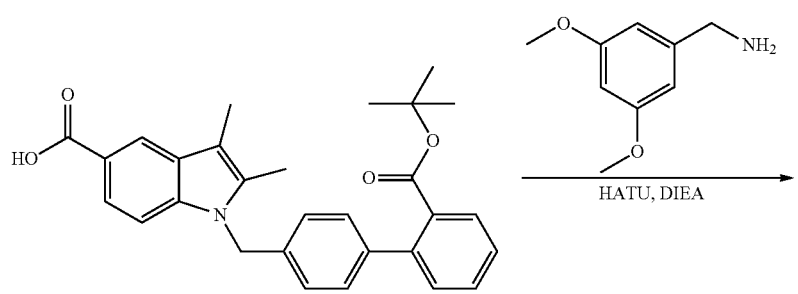
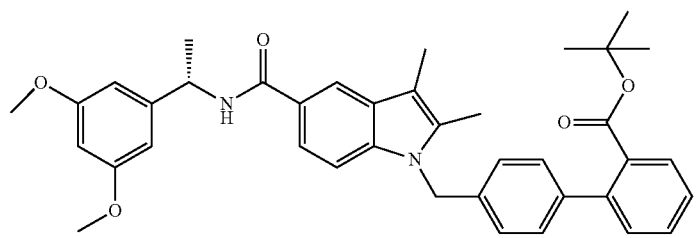

The title compound was prepared following the same general protocol as described in Step 8, Example 1, using (3,5-dimethoxyphenyl)methanamine instead of (S)-1-(4-bromophenyl)ethanamine. ESI-MS (m/z): 605 [M+H]$^+$.

Step 2: 4'-((5-(3,5-Dimethoxybenzylcarbamoyl)-2,3-dimethyl-1H-indol-1-yl)methyl)biphenyl-2-carboxylic acid

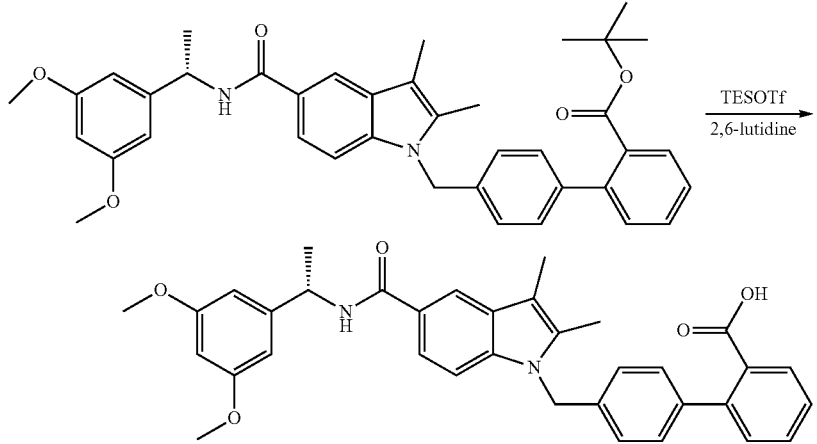

The title compound was prepared following the same general protocol as described in Step 2, Example 19. ESI-MS (m/z): 549 [M+H]$^+$.

Example 23: (R)-4'-((5-(1-(4-Methoxyphenyl)ethylcarbamoyl)-2,3-dimethyl-1H-indol-1-yl)methyl)biphenyl-2-carboxylic acid

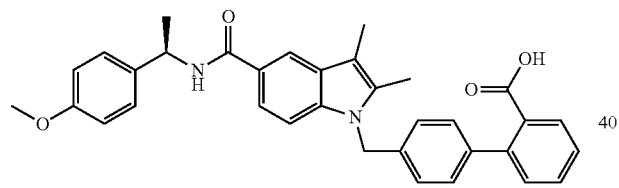

Step 1: (R)-tert-Butyl 4'-((5-(1-(4-methoxyphenyl)ethylcarbamoyl)-2,3-dimethyl-1H-indol-1-yl)methyl)biphenyl-2-carboxylate

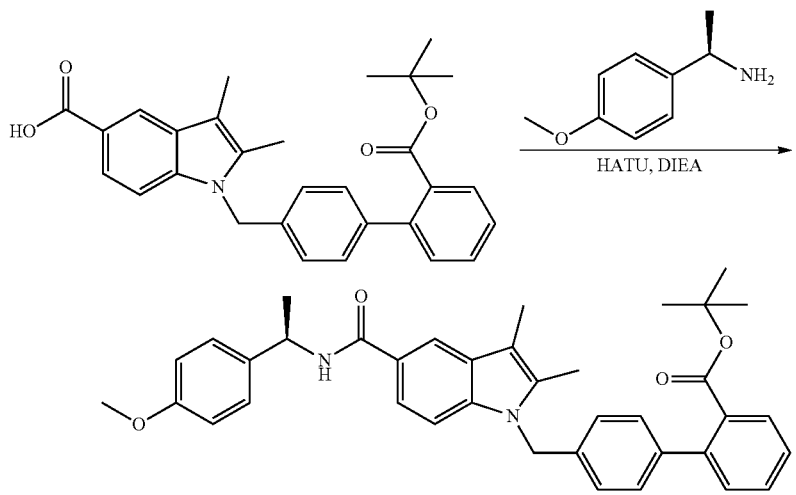

The title compound was prepared following the same general protocol as described in Step 8, Example 1, using (R)-1-(4-methoxyphenyl)ethanamine instead of (S)-1-(4-bromophenyl)ethanamine. ESI-MS (m/z): 589 [M+H]⁺.

Step 2: (R)-4'-((5-(1-(4-Methoxyphenyl)ethylcarbamoyl)-2,3-dimethyl-1H-indol-1-yl)methyl)biphenyl-2-carboxylic acid

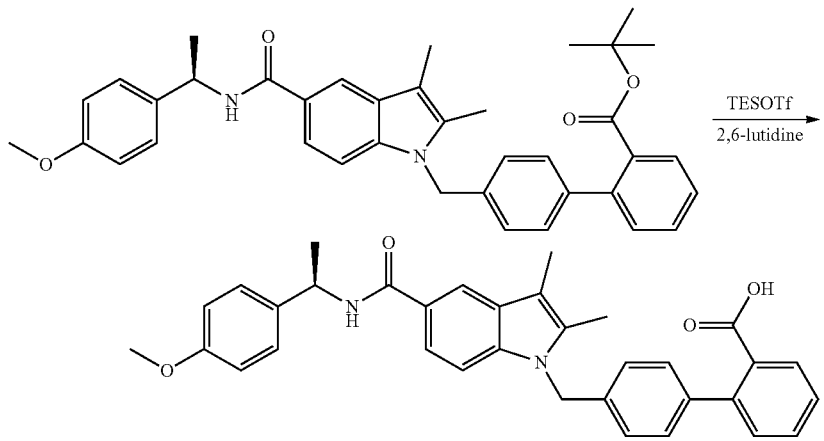

The title compound was prepared following the same general protocol as described in Step 2, Example 19. ESI-MS (m/z): 533 [M+H]⁺.

Example 24: 4'-((5-(3,4-Dimethoxybenzylcarbamoyl)-2,3-dimethyl-1H-indol-1-yl)methyl)biphenyl-2-carboxylic acid

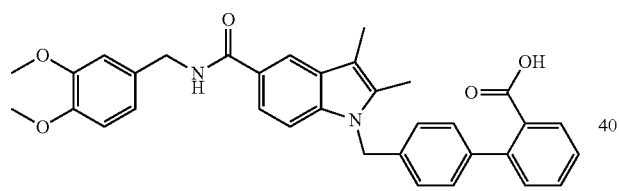

Step 1: tert-Butyl 4'-((5-(3,4-dimethoxybenzylcarbamoyl)-2,3-dimethyl-1H-indol-1-yl)methyl)biphenyl-2-carboxylate

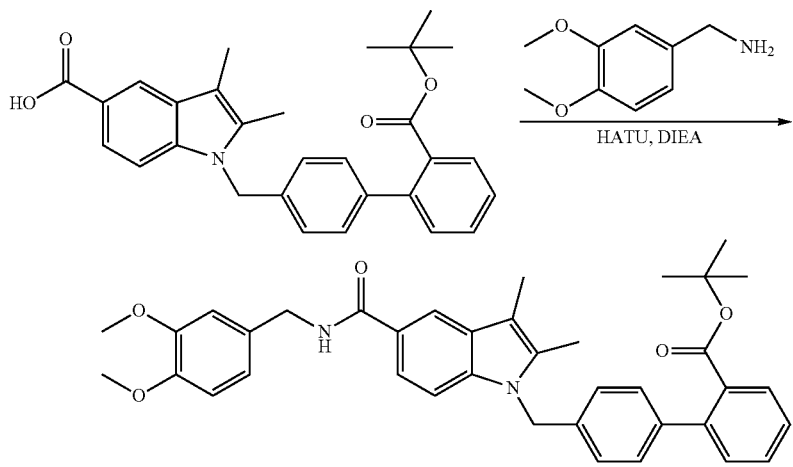

The title compound was prepared following the same general protocol as described in Step 8, Example 1, using (3,4-dimethoxyphenyl)methanamine instead of (S)-1-(4-bromophenyl)ethanamine. ESI-MS (m/z): 605 [M+H]$^+$.

Step 2: 4'-((5-(3,4-Dimethoxybenzylcarbamoyl)-2,3-dimethyl-1H-indol-1-yl)methyl)biphenyl-2-carboxylic acid

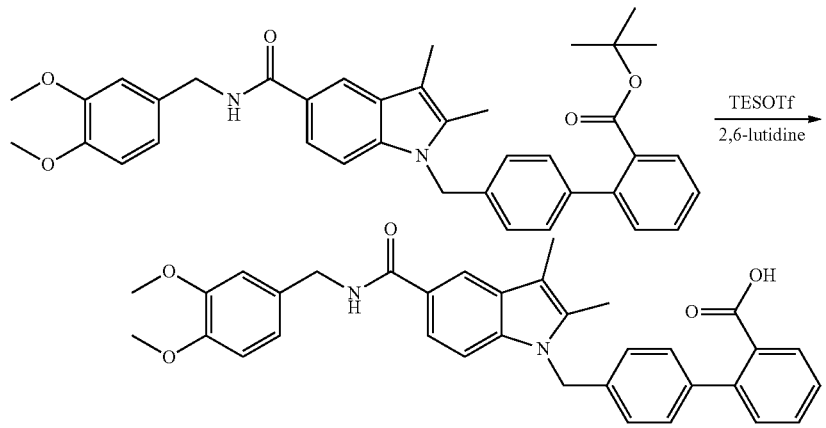

The title compound was prepared following the same general protocol as described in Step 2, Example 19. ESI-MS (m/z): 549 [M+H]$^+$.

Example 25: 4'-((2,3-Dimethyl-5-((2-phenylpropan-2-yl)carbamoyl)-1H-indol-1-yl)methyl)-[1,1'-biphenyl]-2-carboxylic acid

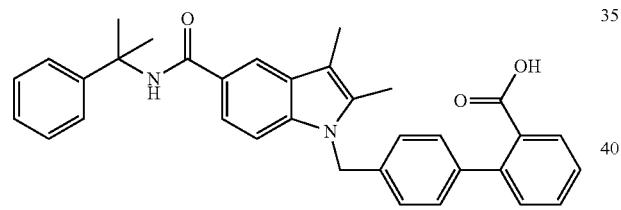

Step 1: tert-Butyl 4'-((2,3-dimethyl-5-((2-phenylpropan-2-yl)carbamoyl)-1H-indol-1-yl)methyl)-[1,1'-biphenyl]-2-carboxylate

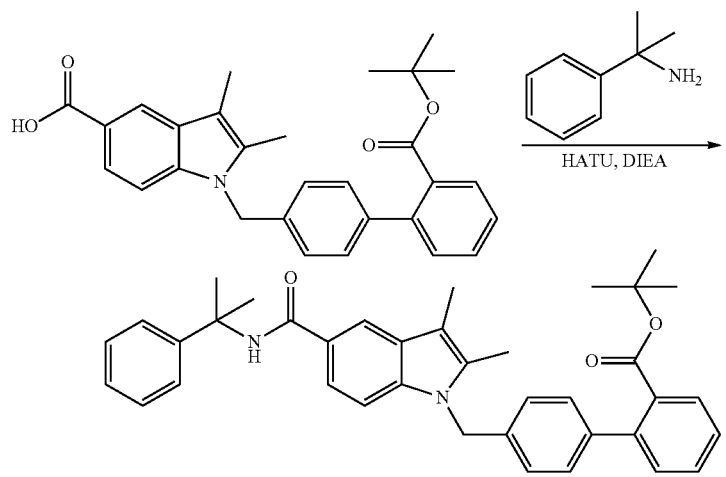

The title compound was prepared following the same general protocol as described in Step 8, Example 1, using 2-phenylpropan-2-amine instead of (S)-1-(4-bromophenyl)ethanamine. ESI-MS (m/z): 573 [M+H]+.

Step 2: 4'-((2,3-Dimethyl-5-((2-phenylpropan-2-yl)carbamoyl)-1H-indol-1-yl)methyl)-[1,1'-biphenyl]-2-carboxylic acid

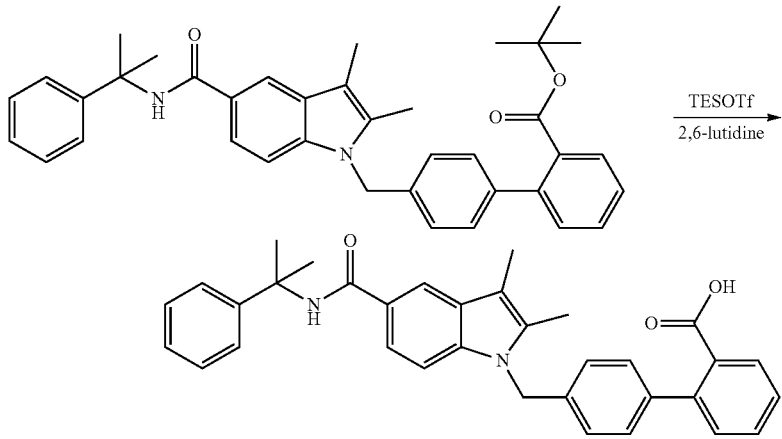

The title compound was prepared following the same general protocol as described in Step 2, Example 19. ESI-MS (m/z): 517 [M+H]+.

Example 26: (S)-4'-((2,3-Dimethyl-5-((1-(naphthalen-2-yl)ethyl)carbamoyl)-1H-indol-1-yl)methyl)-[1,1'-biphenyl]-2-carboxylic acid

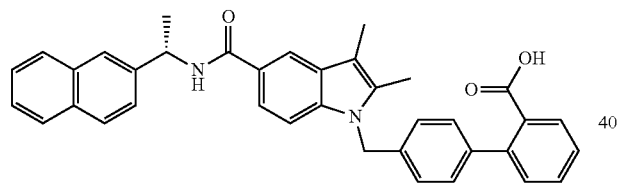

Step 1: (S)-tert-Butyl 4'-((2,3-dimethyl-5-((1-(naphthalen-2-yl)ethyl)carbamoyl)-1H-indol-1-yl)methyl)-[1,1'-biphenyl]-2-carboxylate

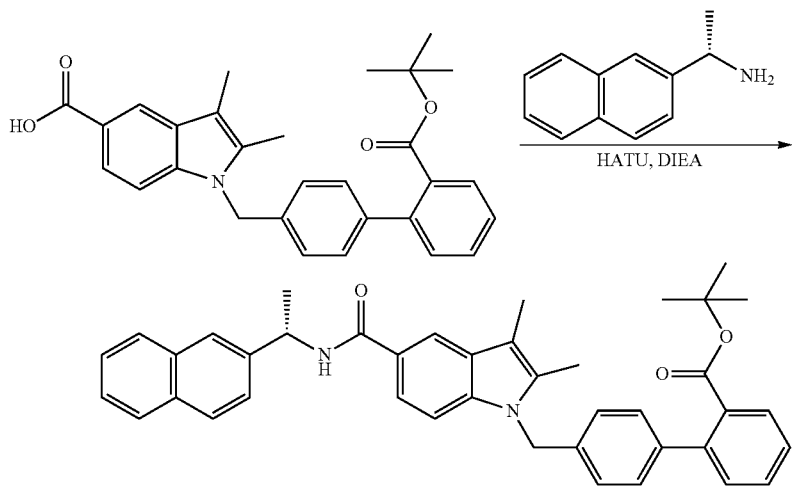

The title compound was prepared following the same general protocol as described in Step 8, Example 1, using (S)-1-(naphthalen-2-yl)ethanamine instead of (S)-1-(4-bromophenyl)ethanamine. ESI-MS (m/z): 609 [M+H]$^+$ Step 2: (S)-4'-((2,3-Dimethyl-5-((1-(naphthalen-2-yl)ethyl)carbamoyl)-1H-indol-1-yl)methyl)-[1,1'-biphenyl]-2-carboxylic acid

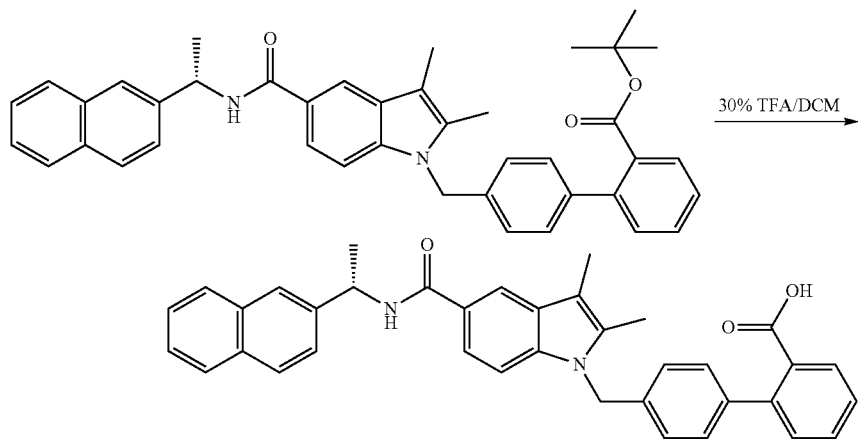

The title compound was prepared following the same general protocol as described in Step 9, Example 1. ESI-MS (m/z): 553 [M+H]$^+$.

Example 27: (S)-4'-((5-((1-(4-Chlorophenyl)ethyl)carbamoyl)-2,3-dimethyl-1H-indol-1-yl)methyl)-[1,1'-biphenyl]-2-carboxylic acid

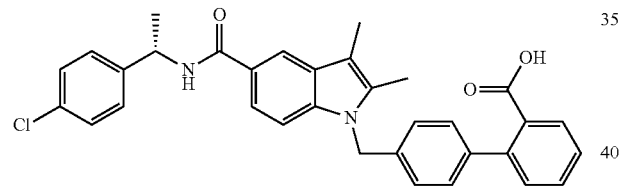

Step 1: (S)-tert-Butyl 4'-((5-((1-(4-chlorophenyl)ethyl)carbamoyl)-2,3-dimethyl-1H-indol-1-yl)methyl)-[1,1'-biphenyl]-2-carboxylate

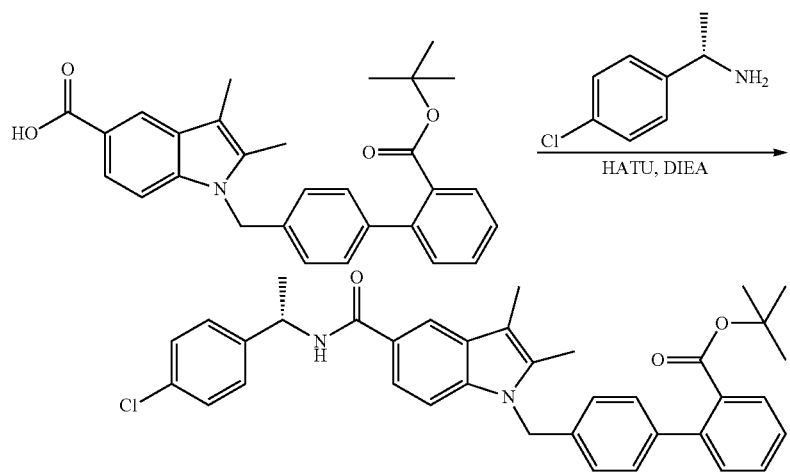

The title compound was prepared following the same general protocol as described in Step 8, Example 1, using (S)-1-(4-chlorophenyl)ethanamine instead of (S)-1-(4-bromophenyl)ethanamine. ESI-MS (m/z): 537 [M+H]$^+$-tert-butyl Step 2: (S)-4'-((5-((1-(4-Chlorophenyl)ethyl)carbamoyl)-2,3-dimethyl-1H-indol-1-yl)methyl)-[1,1'-biphenyl]-2-carboxylic acid

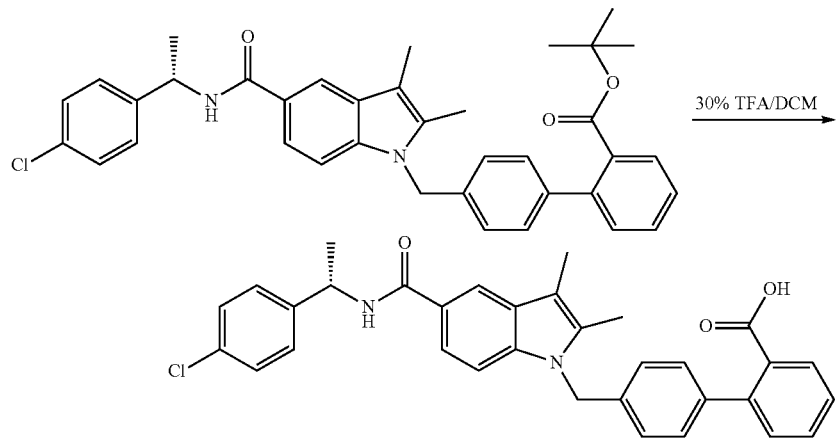

The title compound was prepared following the same general protocol as described in Step 9, Example 1. ESI-MS (m/z): 537 [M+H]$^+$.

Example 30: (S)-4'-((5-((1-(3-Bromophenyl)ethyl)carbamoyl)-2,3-dimethyl-1H-indol-1-yl)methyl)-[1,1'-biphenyl]-2-carboxylic acid

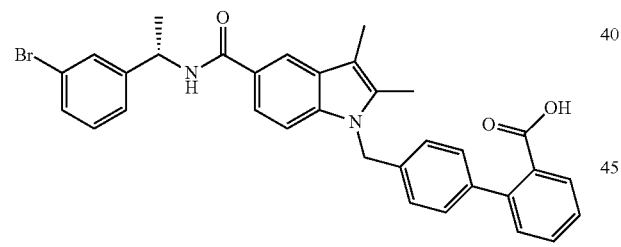

Step 1: (S)-tert-Butyl 4'-((5-((1-(3-bromophenyl)ethyl)carbamoyl)-2,3-dimethyl-1H-indol-1-yl)methyl)-[1,1'-biphenyl]-2-carboxylate

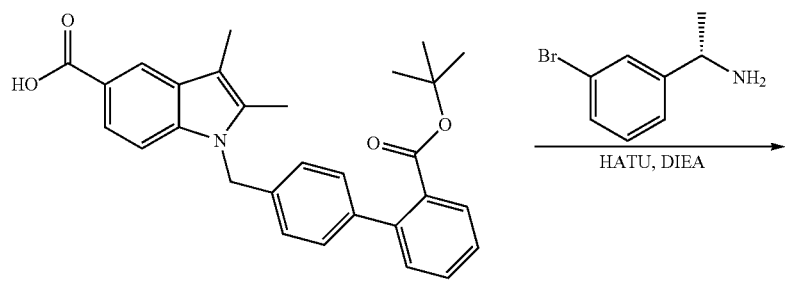

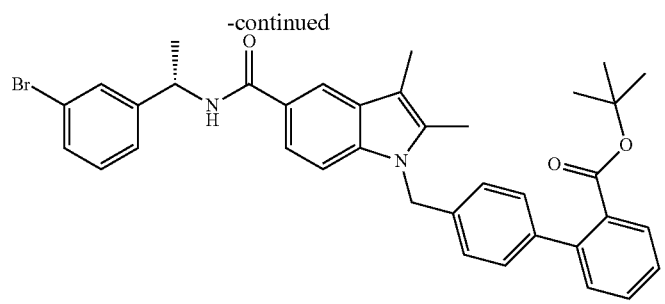

The title compound was prepared following the same general protocol as described in Step 8, Example 1, using (S)-1-(3-bromophenyl)ethanamine was used instead of (S)-1-(4-bromophenyl)ethanamine. ESI-MS (m/z): 659/661 [M+H]$^+$.

Step 2: (S)-4'-((5-((1-(3-Bromophenyl)ethyl)carbamoyl)-2,3-dimethyl-1H-indol-1-yl)methyl)-[1,1'-biphenyl]-2-carboxylic acid

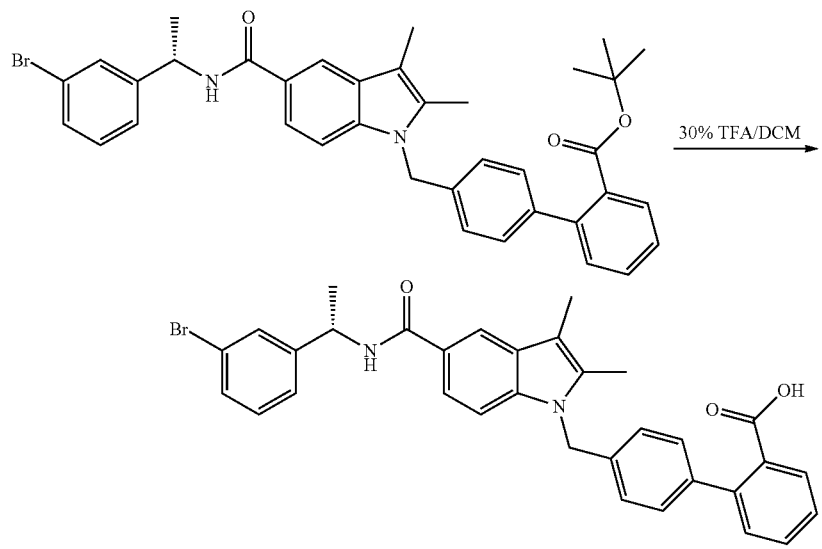

The title compound was prepared following the same general protocol as described in Step 9, Example 1. ESI-MS (m/z): 581/583 [M+H]$^+$.

Example 31: 4'-((2,3-Dimethyl-5-((2-oxo-2-phenylethyl)carbamoyl)-1H-indol-1-yl)methyl)-[1,1'-biphenyl]-2-carboxylic acid

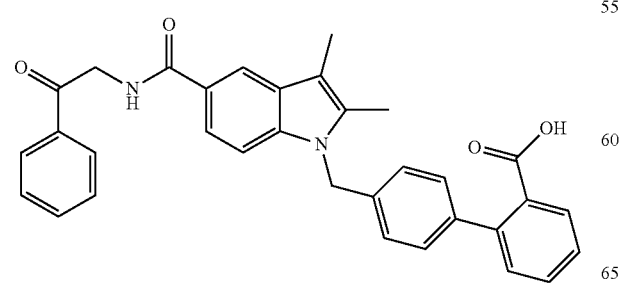

311

Step 1: tert-Butyl 4'-((2,3-dimethyl-5-((2-oxo-2-phenylethyl)carbamoyl)-1H-indol-1-yl)methyl)-[1,1'-biphenyl]-2-carboxylate

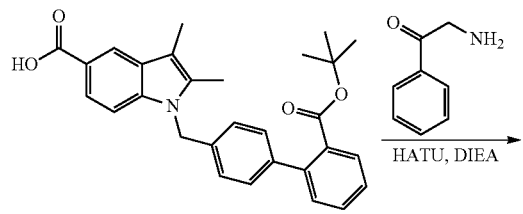

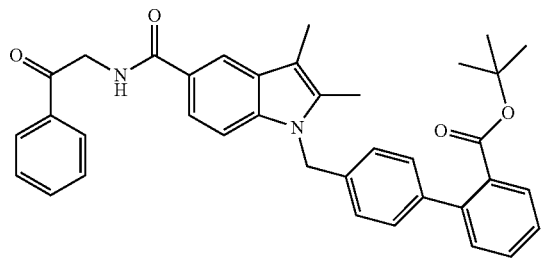

The title compound was prepared following the same general protocol as described in Step 8, Example 1, using 2-amino-1-phenylethanone instead of (S)-1-(4-bromophenyl)ethanamine. ESI-MS (m/z): 573 [M+H]$^+$.

Step 2: 4'-((2,3-Dimethyl-5-((2-oxo-2-phenylethyl)carbamoyl)-1H-indol-1-yl)methyl)-[1,1'-biphenyl]-2-carboxylic acid

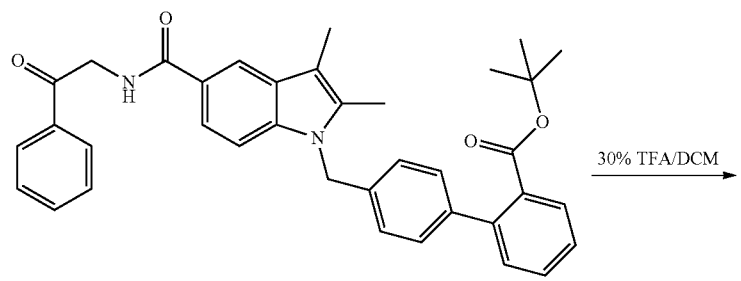

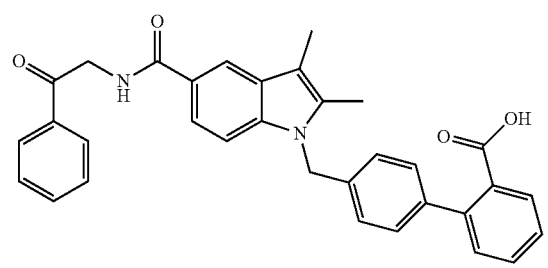 [SMILES: Cc1c(C)n(Cc2ccc(-c3ccccc3C(=O)O)cc2)c2ccc(C(=O)NCC(=O)c3ccccc3)cc12]

312

The title compound was prepared following the same general protocol as described in Step 9, Example 1. ESI-MS (m/z): 517 [M+H]$^+$.

Example 34: 1-((2'-Cyano-[1,1'-biphenyl]-4-yl)methyl)-2,3-dimethyl-N-(1-phenylpropyl)-1H-indole-5-carboxamide

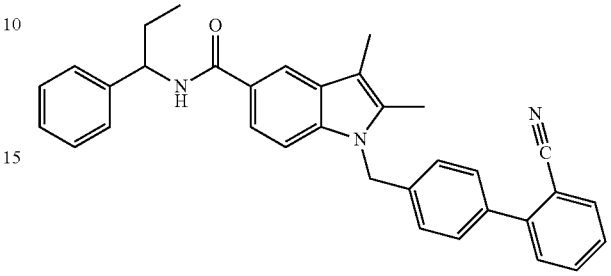

Step 1: 4'-Methyl-[1,1'-biphenyl]-2-carbonitrile

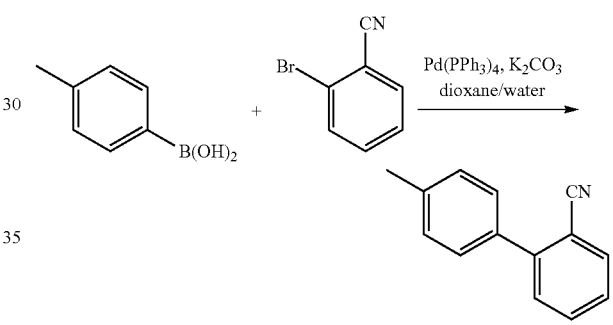

The title compound was prepared following the same protocol as described in Step 2, Example 1, using 2-bromobenzonitrile instead of the tert-butyl 2-bromobenzoate. $^1$H NMR (400 MHz, DMSO-d$_6$): δ (ppm) 2.38 (s, 3H, CH$_3$), 7.34 (d, J=8 Hz, 2H, H$_7$ and H$_5$ biphenyl), 7.47 (d, J=8 Hz, 2H, H$_5$ and H$_6$ biphenyl), 7.55 (dt, J=1.2, 7.6 Hz, 1H, H$_4$ biphenyl), 7.59 (m, 1H, H$_2$ biphenyl), 7.77 (dt, J=1.2, 7.6 Hz, 1H, H$_3$ biphenyl), 7.93 (m, 1H, H$_5$ biphenyl).

Step 2: 4'-(Bromomethyl)-[1,1'-biphenyl]-2-carbonitrile

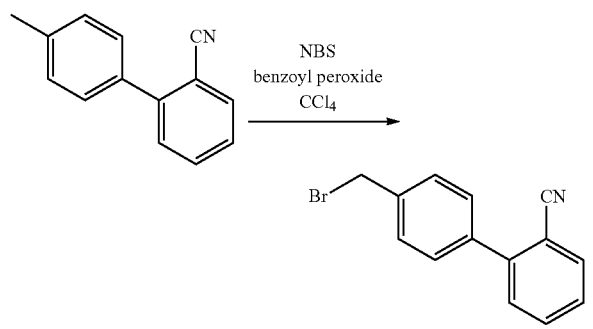

The title compound was prepared following the same protocol as described in Step 3, Example 1, using 4'-methyl-[1,1'-biphenyl]-2-carbonitrile instead of the tert-butyl 4'-methylbiphenyl-2-carboxylate and benzoyl peroxide instead of AIBN. $^1$H NMR (400 MHz, DMSO-d$_6$): δ (ppm) 4.79 (s, 2H, CH$_2$), 7.55-7.68 (m, 6H, H$_2$, H$_4$, H$_5$, H$_6$, H$_7$ and H$_5$ biphenyl), 7.77 (t, J=7.2 Hz, 1H, H$_3$ biphenyl), 7.93 (d, J=7.2 Hz, 1H, H$_5$ biphenyl).

Step 3: Ethyl 1-((2'-cyano-[1,1'-biphenyl]-4-yl)methyl)-2,3-dimethyl-1H-indole-5-carboxylate

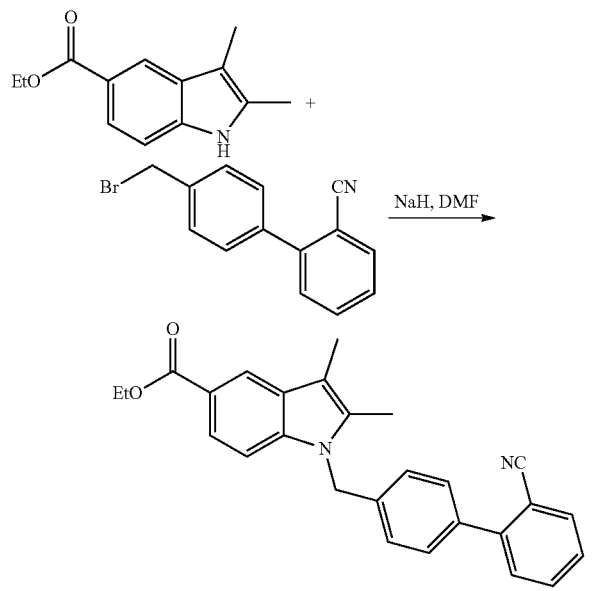

The title compound was prepared following the same protocol as described in Step 6, Example 1, using 4'-(Bromomethyl)-[1,1'-biphenyl]-2-carbonitrile instead of the tert-butyl 4'-(bromomethyl)biphenyl-2-carboxylate. ESI-MS (m/z): 409 [M+H]$^+$.

Step 4: 1-((2'-Cyano-[1,1'-biphenyl]-4-yl)methyl)-2,3-dimethyl-1H-indole-5-carboxylic acid

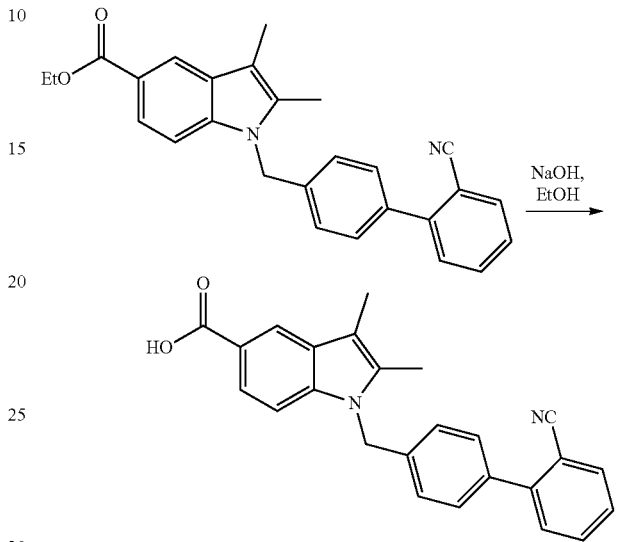

The title compound was prepared following the same protocol as described in Step 7, Example 1, using ethyl 1-((2'-cyano-[1,1'-biphenyl]-4-yl)methyl)-2,3-dimethyl-1H-indole-5-carboxylate instead of the ethyl 1-((2'-(tert-butoxycarbonyl)biphenyl-4-yl)methyl)-2,3-dimethyl-1H-indole-5-carboxylate. ESI-MS (m/z): 381 [M+H]$^+$.

Step 5: 1-((2'-Cyano-[1,1'-biphenyl]-4-yl)methyl)-2,3-dimethyl-N-(1-phenylpropyl)-1H-indole-5-carboxamide

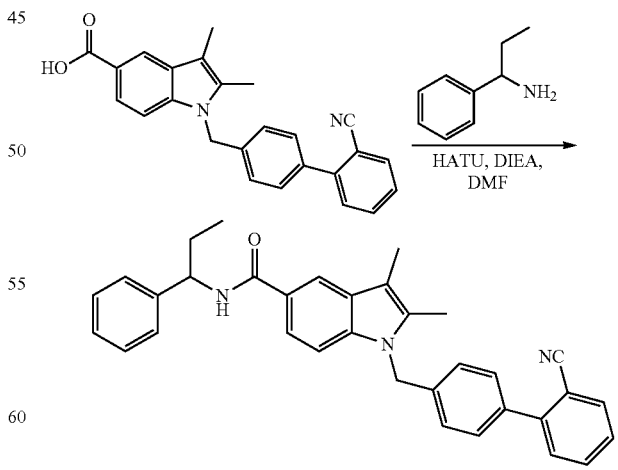

The title compound was prepared following the same protocol as described in Step 8, Example 1, using 1-((2'-cyano-[1,1'-biphenyl]-4-yl)methyl)-2,3-dimethyl-1H-indole-5-carboxylic acid instead of the 1-((2'-(tert-butoxycarbonyl)biphenyl-4-yl)methyl)-2,3-dimethyl-1H-indole-5-carboxylic acid, and 1-phenylpropan-1-amine instead of the (S)-1-(4-bromophenyl)ethanamine. ESI-MS (m/z): 498 [M+H]⁺.

Example 35: (S)—N-(1-(4-Bromophenyl)ethyl)-1-((2'-cyano-[1,1'-biphenyl]-4-yl)methyl)-2,3-dimethyl-1H-indole-5-carboxamide

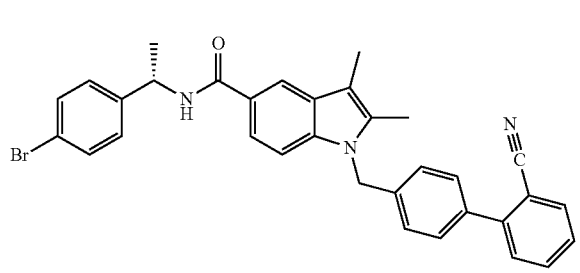

The title compound was prepared following the same protocol as described in Step 5, Example 34, using (S)-1-(4-bromophenyl)ethanamine instead of the 1-phenylpropan-1-amine. ESI-MS (m/z): 562/564 [M+H]⁺.

Example 36: 1-((2'-(1H-Tetrazol-5-yl)-[1,1'-biphenyl]-4-yl)methyl)-2,3-dimethyl-N-(1-phenylpropyl)-1H-indole-5-carboxamide

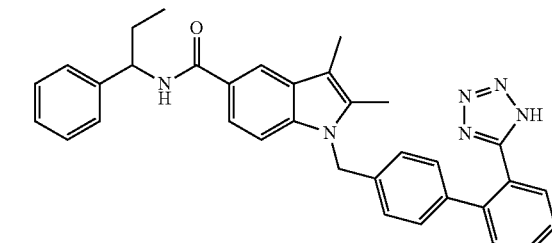

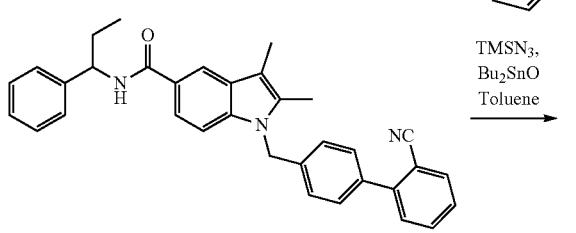

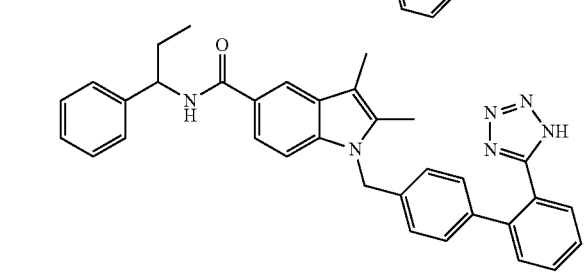

To a solution of 1-((2'-cyano-[1,1'-biphenyl]-4-yl)methyl)-2,3-dimethyl-N-(1-phenylpropyl)-1H-indole-5-carboxamide (27 mg, 0.05 mmol, 1 equiv) in toluene (0.6 mL) in a high-pressure vial were added TMSN₃ (14 μL, 0.05 mmol, 2 equiv) and Bu₂SnO (2 mg, 0.005 mmol, 0.1 equiv). The vial was sealed and the reaction mixture was heated at reflux for 2 h. After concentration, the residue was purified by preparative HPLC to afford a beige powder. ESI-MS (m/z): 541 [M+H]⁺.

Example 37: (S)-1-((2'-(1H-tetrazol-5-yl)-[1,1'-biphenyl]-4-yl)methyl)-N-(1-(4-bromophenyl)ethyl)-2,3-dimethyl-1H-indole-5-carboxamide

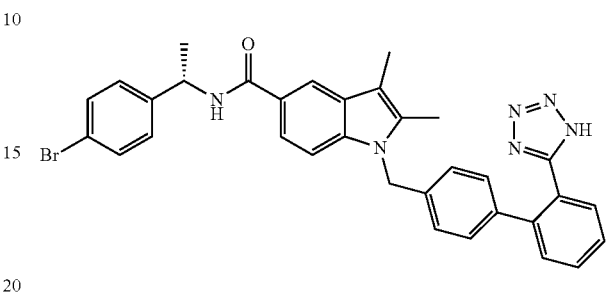

The title compound was prepared following the same protocol as described in Example 36, using (S)—N-(1-(4-bromophenyl)ethyl)-1-((2'-cyano-[1,1'-biphenyl]-4-yl)methyl)-2,3-dimethyl-1H-indole-5-carboxamide instead of the 1-((2'-cyano-[1,1'-biphenyl]-4-yl)methyl)-2,3-dimethyl-N-(1-phenylpropyl)-1H-indole-5-carboxamide. ESI-MS (m/z): 605/607 [M+H]⁺.

Example 38: (S)-1-([1,1'-Biphenyl]-4-ylmethyl)-N-(1-(4-nitrophenyl)ethyl)-1H-indole-5-carboxamide

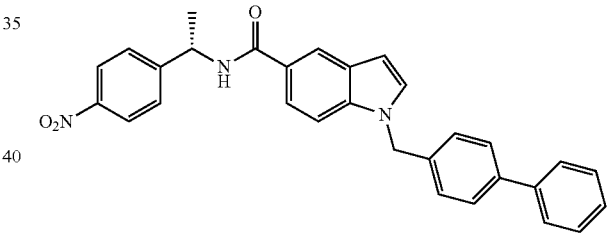

Step 1: Methyl 1H-indole-5-carboxylate

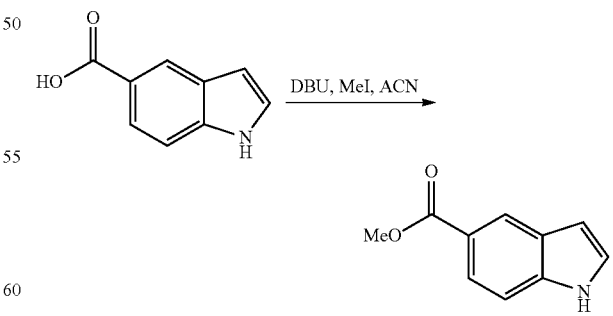

To a solution of 1H-indole-5-carboxylic acid (1 g, 6.2 mmol, 1.0 equiv) in acetonitrile (40 mL) were added 1,8-Diazabicyclo[5.4.0]undec-7-ene (1.1 mL, 7.4 mmol, 1.2 equiv) and iodomethane (2.3 mL, 37.2 mmol, 6 equiv). The solution was stirred under reflux overnight. The reaction mixture was concentrated in vacuo. The residue was dissolved in AcOEt, washed with a 0.5 N HCl aqueous solution, a saturated NaHCO₃ solution and brine, dried over MgSO₄ and concentrated in vacuo. The obtained oil was used in the next step without further purification.

Step 2: Methyl 1-(4-bromobenzyl)-1H-indole-5-carboxylate

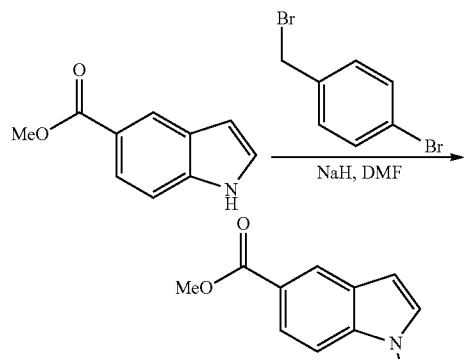

To a solution of methyl 1H-indole-5-carboxylate (1.09 g, 6.2 mmol, 1 equiv) and 1-(bromomethyl)-4-bromobenzene (1.70 g, 6.82 mmol, 1.1 equiv) in anhydrous DMF (30 mL) under argon atmosphere was added sodium hydride (500 mg, 12.4 mmol, 2 equiv) in small portions. The mixture was stirred 2 h at room temperature. The reaction mixture was then neutralized by addition of methanol and concentrated in vacuo. The residue was dissolved in AcOEt, washed with brine and dried over MgSO₄. The crude was purified by flash chromatography (Hexane/AcOEt 7.5/2.5) to afford the title compound as a white powder (1.09 g, 3.2 mmol, 52%). ESI-MS (m/z): 344/346 [M+H]⁺.

Step 3: 1-(4-Bromobenzyl)-1H-indole-5-carboxylic acid

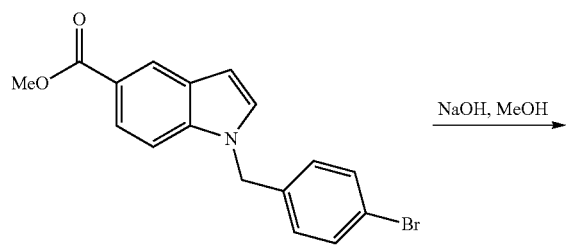

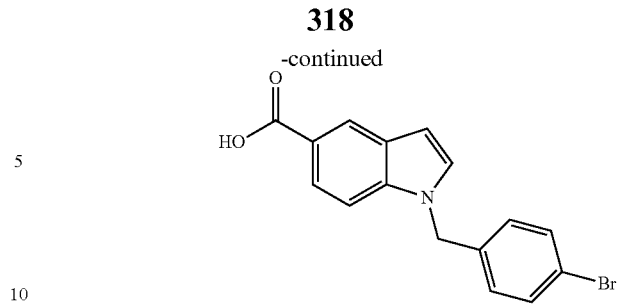

To a solution of methyl 1-(4-bromobenzyl)-1H-indole-5-carboxylate (1.09 g, 3.2 mmol, 1 equiv) in methanol (30 mL) was added a 5 N NaOH solution (6.3 mL, 32 mmol, 10 equiv). The reaction mixture was stirred 2 h at 40° C. The mixture was then acidified and extracted with DCM. After concentration in vacuo, the title compound was precipitated in Et₂O to afford a white powder (1.03 g, 3.1 mmol, 99%). ESI-MS (m/z): 330/332 [M+H]⁺.

Step 4: (S)-1-(4-Bromobenzyl)-N-(1-(4-nitrophenyl)ethyl)-1H-indole-5-carboxamide

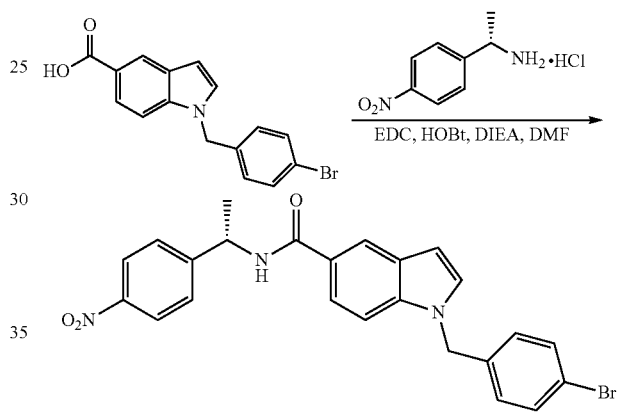

To a solution of 1-(4-bromobenzyl)-1H-indole-5-carboxylic acid (1.03 g, 3.1 mmol, 1 equiv) in DMF (30 mL) were added the (S)-1-(4-nitrophenyl)ethanamine hydrochloride (695 mg, 3.4 mmol, 1.1 equiv), DIEA (600 μL, 3.4 mmol, 1.1 equiv), HOBt (525 mg, 3.4 mmol, 1.1 equiv) and EDC (658 mg, 3.4 mmol, 1.1 equiv). After stirring 4 h at room temperature, the mixture was diluted with AcOEt and washed with a 0.5 N HCl aqueous solution, a saturated NaHCO₃ solution and brine, dried over MgSO₄ and concentrated in vacuo. The crude was purified by flash chromatography (Hexane/AcOEt 1/1) to afford a yellow powder (1.3 g, 2.7 mmol, 87%). ESI-MS (m/z): 478/480 [M+H]⁺.

Step 5: (S)-1-([1,1'-Biphenyl]-4-ylmethyl)-N-(1-(4-nitrophenyl)ethyl)-1H-indole-5-carboxamide

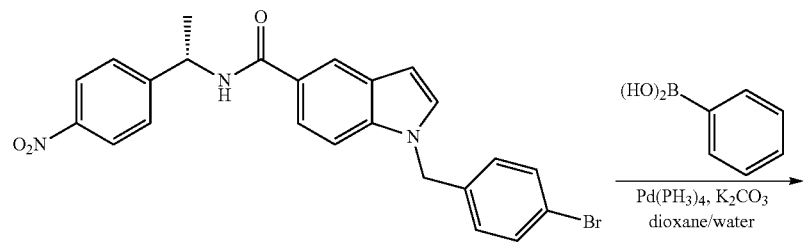

-continued

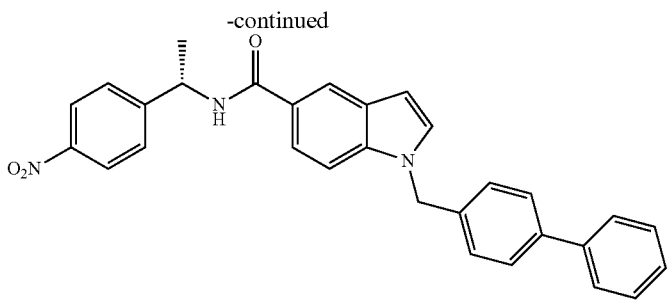

A high-pressure vial was filled with the (S)-1-(4-bromobenzyl)-N-(1-(4-nitrophenyl)ethyl)-1H-indole-5-carboxamide (50 mg, 0.1 mmol, 1 equiv), the phenylboronic acid (19 mg, 0.15 mmol, 1.5 equiv), $K_2CO_3$ (29 mg, 0.2 mmol, 2 equiv), $Pd(PPh_3)_4$ (12 mg, 0.01 mmol, 0.1 equiv), dioxane (1.5 mL) and water (0.3 mL). The mixture was degassed for 5 min under argon atmosphere and the vial was sealed. The reaction mixture was heated at 100° C. for 30 min under microwaves. The solution was then concentrated in vacuo, filtered and purified by preparative HPLC to afford a beige powder (50 mg, 0.1 mmol, 100%). ESI-MS (m/z): 476 [M+H]$^+$.

Example 39: (S)-1-((2'-Methoxy-[1,1'-biphenyl]-4-yl)methyl)-N-(1-(4-nitrophenyl)ethyl)-1H-indole-5-carboxamide

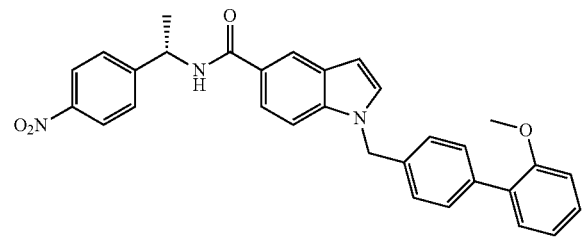 [SMILES: COc1ccccc1-c1ccc(Cn2ccc3cc(C(=O)N[C@@H](C)c4ccc([N+](=O)[O-])cc4)ccc32)cc1]

The title compound was prepared following the same general protocol as described in Step 5, Example 38, using (2-methoxyphenyl)boronic acid instead of the phenylboronic acid. A yellow powder was obtained (32 mg, 0.06 mmol, 61%). ESI-MS (m/z): 506 [M+H]$^+$.

Example 40: (S)-1-((2'-Hydroxy-[1,1'-biphenyl]-4-yl)methyl)-N-(1-(4-nitrophenyl)ethyl)-1H-indole-5-carboxamide

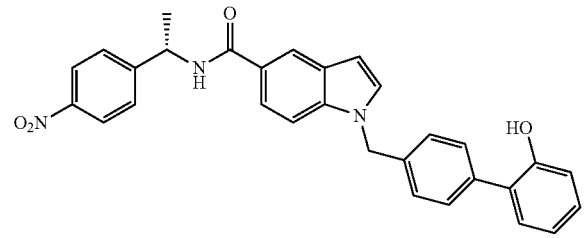 [SMILES: C[C@H](NC(=O)c1ccc2c(ccn2Cc2ccc(-c3ccccc3O)cc2)c1)c1ccc([N+](=O)[O-])cc1]

The title compound was prepared following the same general protocol as described in Step 5, Example 38, using (2-hydroxyphenyl)boronic acid instead of the phenylboronic acid. A yellow powder was obtained (39 mg, 0.08 mmol, 76%). ESI-MS (m/z): 492 [M+H]$^+$.

Example 41: (S)-1-((2'-(Methylsulfonyl)-[1,1'-biphenyl]-4-yl)methyl)-N-(1-(4-nitrophenyl)ethyl)-1H-indole-5-carboxamide

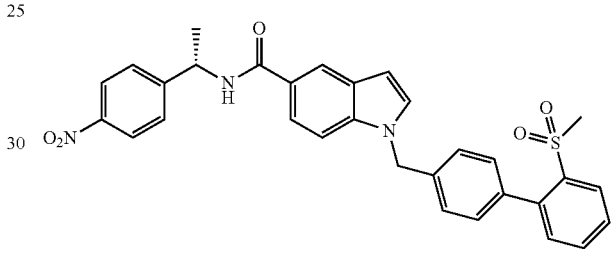

The title compound was prepared following the same general protocol as described in Step 5, Example 38, using (2-(methylsulfonyl)phenyl)boronic acid instead of the phenylboronic acid. A beige powder was obtained (46 mg, 0.08 mmol, 80%). ESI-MS (m/z): 554 [M+H]$^+$.

Example 42: (S)-1-((2'-Methyl-[1,1'-biphenyl]-4-yl)methyl)-N-(1-(4-nitrophenyl)ethyl)-1H-indole-5-carboxamide

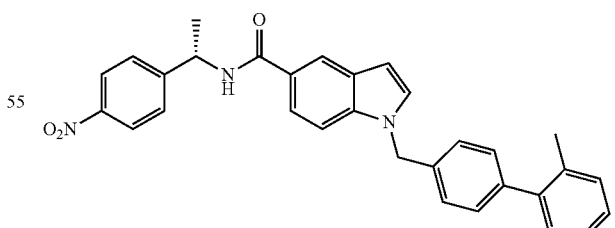

The title compound was prepared following the same general protocol as described in Step 5, Example 38, using o-tolylboronic acid instead of the phenylboronic acid. A yellow powder was obtained (35 mg, 0.07 mmol, 69%). ESI-MS (m/z): 490 [M+H]$^+$.

Example 43: (S)-Ethyl 4'-((5-((1-(4-nitrophenyl)ethyl)carbamoyl)-1H-indol-1-yl)methyl)-[1,1'-biphenyl]-4-carboxylate

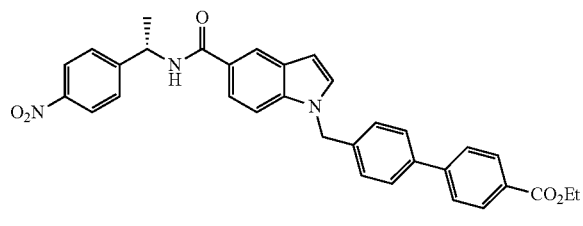 [SMILES: CCOC(=O)c1ccc(-c2ccc(Cn3ccc4cc(C(=O)N[C@@H](C)c5ccc([N+](=O)[O-])cc5)ccc43)cc2)cc1]

The title compound was prepared following the same general protocol as described in Step 5, Example 38, using (4-(ethoxycarbonyl)phenyl)boronic acid instead of the phenylboronic acid. A yellow powder was obtained (41 mg, 0.07 mmol, 72%). ESI-MS (m/z): 548 [M+H]$^+$.

Example 44: (S)-1-((3'-Methoxy-[1,1'-biphenyl]-4-yl)methyl)-N-(1-(4-nitrophenyl)ethyl)-1H-indole-5-carboxamide

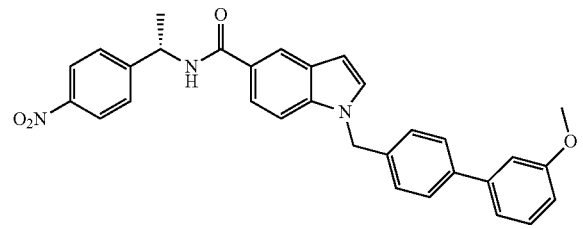 [SMILES: COc1cccc(-c2ccc(Cn3ccc4cc(C(=O)N[C@@H](C)c5ccc([N+](=O)[O-])cc5)ccc43)cc2)c1]

The title compound was prepared following the same general protocol as described in Step 5, Example 38, using (3-methoxyphenyl)boronic acid instead of the phenylboronic acid. A yellow powder was obtained (44 mg, 0.09 mmol, 84%). ESI-MS (m/z): 506 [M+H]$^+$.

Example 45: (S)-1-((3'-(Methylsulfonyl)-[1,1'-biphenyl]-4-yl)methyl)-N-(1-(4-nitrophenyl)ethyl)-1H-indole-5-carboxamide

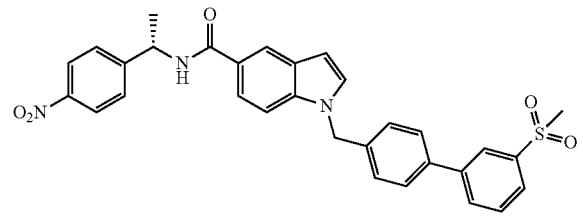 [SMILES: C[C@H](NC(=O)c1ccc2c(ccn2Cc2ccc(-c3cccc(S(C)(=O)=O)c3)cc2)c1)c1ccc([N+](=O)[O-])cc1]

The title compound was prepared following the same general protocol as described in Step 5, Example 38, using (3-(methylsulfonyl)phenyl)boronic acid instead of the phenylboronic acid. A yellow powder was obtained (49 mg, 0.09 mmol, 85%). ESI-MS (m/z): 554 [M+H]$^+$.

Example 46: (S)-1-((2'-Chloro-[1,1'-biphenyl]-4-yl)methyl)-N-(1-(4-nitrophenyl)ethyl)-1H-indole-5-carboxamide

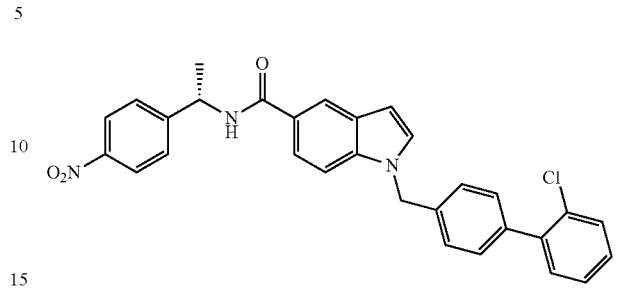

The title compound was prepared following the same general protocol as described in Step 5, Example 38, using (2-chlorophenyl)boronic acid instead of the phenylboronic acid. A beige powder was obtained (39 mg, 0.08 mmol, 74%). ESI-MS (m/z): 510 [M+H]$^+$.

Example 47: (S)-1-((4'-Hydroxy-[1,1'-biphenyl]-4-yl)methyl)-N-(1-(4-nitrophenyl)ethyl)-1H-indole-5-carboxamide

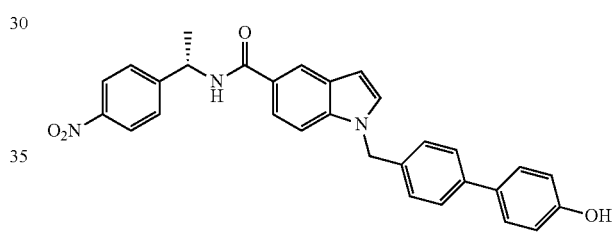

The title compound was prepared following the same general protocol as described in Step 5, Example 38, using (4-hydroxyphenyl)boronic acid instead of the phenylboronic acid. A yellow powder was obtained (37 mg, 0.08 mmol, 72%). ESI-MS (m/z): 492 [M+H]$^+$.

Example 48: (S)-Ethyl 4'-((5-((1-(4-nitrophenyl)ethyl)carbamoyl)-1H-indol-1-yl)methyl)-[1,1'-biphenyl]-3-carboxylate

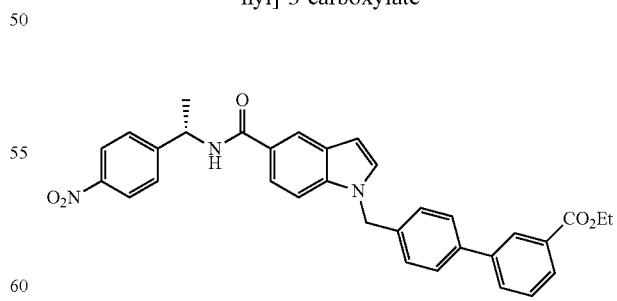

The title compound was prepared following the same general protocol as described in Step 5, Example 38, using (3-(ethoxycarbonyl)phenyl)boronic acid instead of the phenylboronic acid. A yellow powder was obtained (48 mg, 0.09 mmol, 84%). ESI-MS (m/z): 548 [M+H]$^+$.

Example 49: (S)-1-((3'-Methyl-[1,1'-biphenyl]-4-yl)methyl)-N-(1-(4-nitrophenyl)ethyl)-1H-indole-5-carboxamide

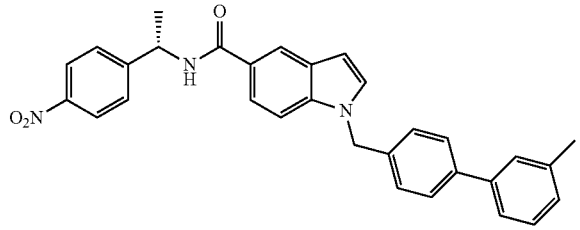 [SMILES: Cc1cccc(-c2ccc(Cn3ccc4cc(C(=O)N[C@@H](C)c5ccc([N+](=O)[O-])cc5)ccc43)cc2)c1]

The title compound was prepared following the same general protocol as described in Step 5, Example 38, using m-tolylboronic acid instead of the phenylboronic acid. A yellow powder was obtained (38 mg, 0.08 mmol, 75%). ESI-MS (m/z): 490 [M+H]$^+$.

Example 50: (S)-1-((4'-(Methylsulfonyl)-[1,1'-biphenyl]-4-yl)methyl)-N-(1-(4-nitrophenyl)ethyl)-1H-indole-5-carboxamide

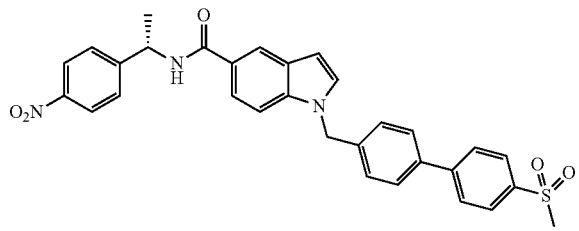 [SMILES: C[C@H](NC(=O)c1ccc2c(ccn2Cc2ccc(-c3ccc(S(C)(=O)=O)cc3)cc2)c1)c1ccc([N+](=O)[O-])cc1]

The title compound was prepared following the same general protocol as described in Step 5, Example 38, using (4-(methylsulfonyl)phenyl)boronic acid instead of the phenylboronic acid. A beige powder was obtained (46 mg, 0.08 mmol, 80%). ESI-MS (m/z): 554 [M+H]$^+$.

Example 51: (S)-1-((4'-(Methylthio)-[1,1'-biphenyl]-4-yl)methyl)-N-(1-(4-nitrophenyl)ethyl)-1H-indole-5-carboxamide

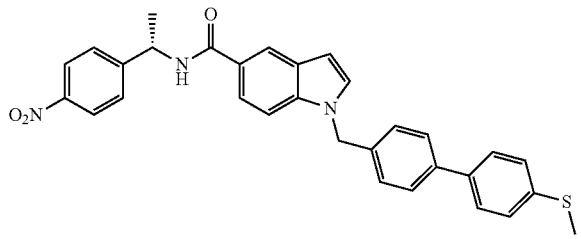 [SMILES: CSc1ccc(-c2ccc(Cn3ccc4cc(C(=O)N[C@@H](C)c5ccc([N+](=O)[O-])cc5)ccc43)cc2)cc1]

The title compound was prepared following the same general protocol as described in Step 5, Example 38, using (4-(methylthio)phenyl)boronic acid instead of the phenylboronic acid. A yellow powder was obtained (29 mg, 0.06 mmol, 53%). ESI-MS (m/z): 522 [M+H]$^+$.

Example 52: (S)-1-((3'-Amino-[1,1'-biphenyl]-4-yl)methyl)-N-(1-(4-nitrophenyl)ethyl)-1H-indole-5-carboxamide

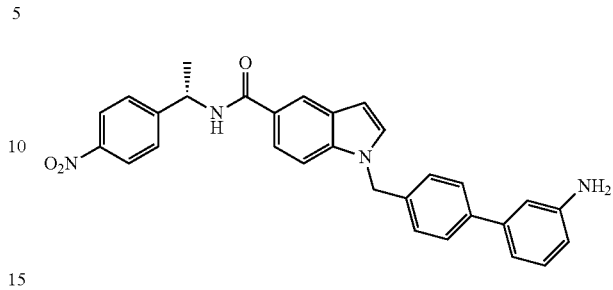

The title compound was prepared following the same general protocol as described in Step 5, Example 38, using (3-aminophenyl)boronic acid instead of the phenylboronic acid. A beige powder was obtained (40 mg, 0.08 mmol, 78%). ESI-MS (m/z): 491 [M+H]$^+$.

Example 53: (S)-1-((3'-(Aminomethyl)-[1,1'-biphenyl]-4-yl)methyl)-N-(1-(4-nitrophenyl)ethyl)-1H-indole-5-carboxamide

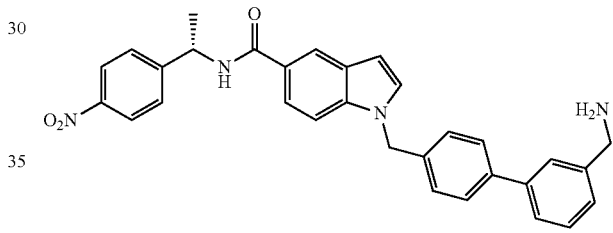

The title compound was prepared following the same general protocol as described in Step 5, Example 38, using (3-(aminomethyl)phenyl)boronic acid instead of the phenylboronic acid. A beige powder was obtained (47 mg, 0.09 mmol, 90%). ESI-MS (m/z): 505 [M+H]$^+$.

Example 54: (S)-1-((2'-(Hydroxymethyl)-[1,1'-biphenyl]-4-yl)methyl)-N-(1-(4-nitrophenyl)ethyl)-1H-indole-5-carboxamide

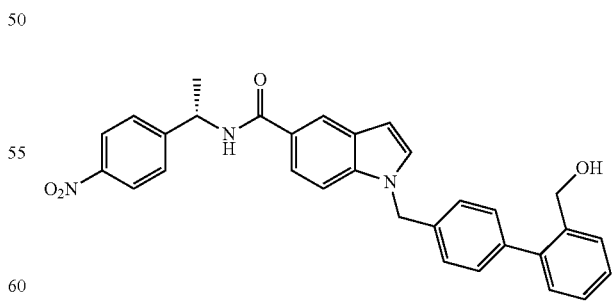

The title compound was prepared following the same general protocol as described in Step 5, Example 38, using (2-(hydroxymethyl)phenyl)boronic acid instead of the phenylboronic acid. A beige powder was obtained (17 mg, 0.03 mmol, 32%). ESI-MS (m/z): 506 [M+H]$^+$.

Example 55: (S)-tert-Butyl 4'-((5-((1-(4-nitrophenyl)ethyl)carbamoyl)-1H-indol-1-yl)methyl)-[1,1'-biphenyl]-2-carboxylate

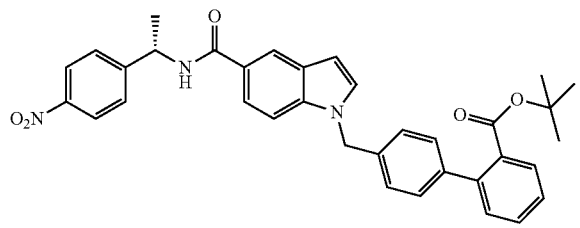 [SMILES: C[C@H](NC(=O)c1ccc2c(ccn2Cc2ccc(-c3ccccc3C(=O)OC(C)(C)C)cc2)c1)c1ccc([N+](=O)[O-])cc1]

The title compound was prepared following the same general protocol as described in Step 5, Example 38, using (2-(tert-butoxycarbonyl)phenyl)boronic acid instead of the phenylboronic acid. A yellow powder was obtained (47 mg, 0.08 mmol, 79%). ESI-MS (m/z): 576 [M+H]+.

Example 56: (S)-tert-Butyl 4'-((5-((1-(4-nitrophenyl)ethyl)carbamoyl)-1H-indol-1-yl)methyl)-[1,1'-biphenyl]-3-carboxylate

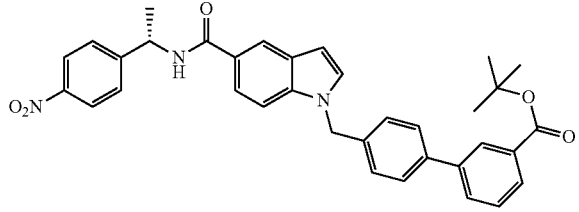 [SMILES: C[C@H](NC(=O)c1ccc2c(ccn2Cc2ccc(-c3cccc(C(=O)OC(C)(C)C)c3)cc2)c1)c1ccc([N+](=O)[O-])cc1]

The title compound was prepared following the same general protocol as described in Step 5, Example 38, using (3-(tert-butoxycarbonyl)phenyl)boronic acid instead of the phenylboronic acid. A yellow powder was obtained (43 mg, 0.07 mmol, 72%). ESI-MS (m/z): 576 [M+H]+.

Example 57: (S)-1-((4'-Methyl-[1,1'-biphenyl]-4-yl)methyl)-N-(1-(4-nitrophenyl)ethyl)-1H-indole-5-carboxamide

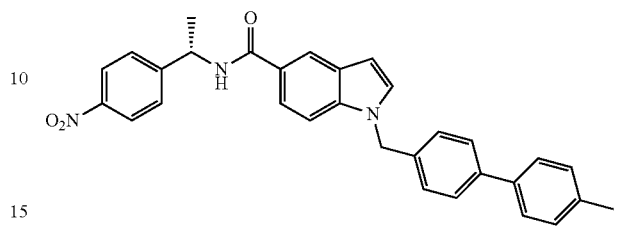

The title compound was prepared following the same general protocol as described in Step 5, Example 38, using p-tolylboronic acid instead of the phenylboronic acid. A beige powder was obtained (13 mg, 0.03 mmol, 26%). ESI-MS (m/z): 490 [M+H]+.

Example 58: (S)-1-((3'-Chloro-[1,1'-biphenyl]-4-yl)methyl)-N-(1-(4-nitrophenyl)ethyl)-1H-indole-5-carboxamide

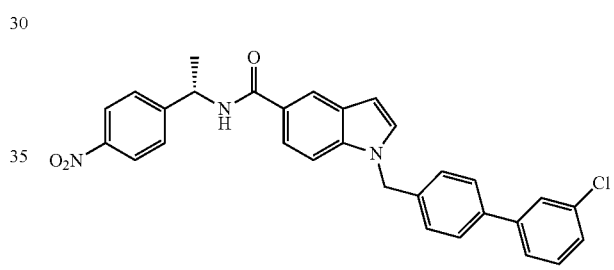

The title compound was prepared following the same general protocol as described in Step 5, Example 38, using (3-chlorophenyl)boronic acid instead of the phenylboronic acid. A beige powder was obtained (18 mg, 0.04 mmol, 34%). ESI-MS (m/z): 510 [M+H]+.

Example 59: (S)-4'-((5-((1-(4-Nitrophenyl)ethyl)carbamoyl)-1H-indol-1-yl)methyl)-[1,1'-biphenyl]-4-carboxylic acid

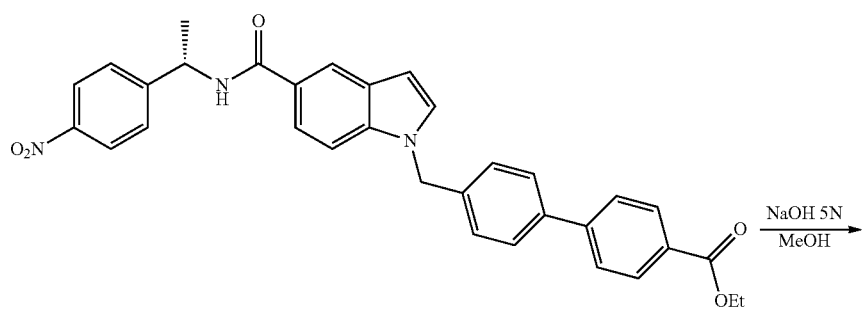

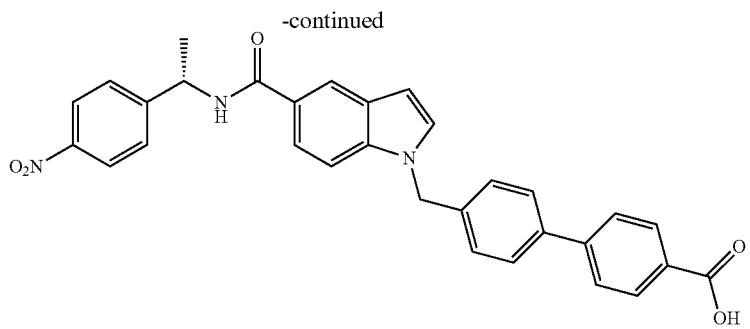

To a solution of (S)-ethyl 4'-((5-((1-(4-nitrophenyl)ethyl)carbamoyl)-1H-indol-1-yl)methyl)-[1,1'-biphenyl]-4-carboxylate (23 mg, 0.04 mmol, 1 equiv) in MeOH (1 mL) was added 100 µL of a 5 N NaOH solution. The mixture is stirred at room temperature overnight and then hydrolyzed by addition of a 1 N HCl solution. After concentration, the crude is purified by preparative HPLC to afford a beige powder (9 mg, 0.02 mmol, 43%). ESI-MS (m/z): 520 [M+H]$^+$.

Example 60: (S)-4'-((5-((1-(4-Nitrophenyl)ethyl)carbamoyl)-1H-indol-1-yl)methyl)-[1,1'-biphenyl]-3-carboxylic acid

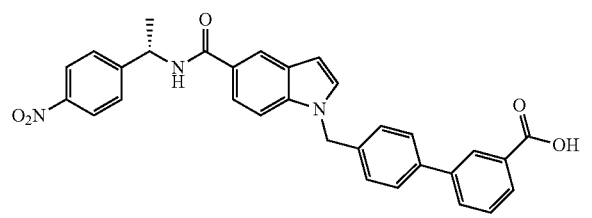 [SMILES: C[C@H](NC(=O)c1ccc2c(ccn2Cc2ccc(-c3cccc(C(=O)O)c3)cc2)c1)c1ccc([N+](=O)[O-])cc1]

The title compound was prepared following the same general protocol as described in Example 59, using (S)-ethyl 4'-((5-((1-(4-nitrophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. A beige powder was obtained (18 mg, 0.04 mmol, 34%). ESI-MS (m/z): 520 [M+H]$^+$.

Example 61: (S)-4'-((5-((1-(4-Nitrophenyl)ethyl)carbamoyl)-1H-indol-1-yl)methyl)-[1,1'-biphenyl]-2-carboxylic acid

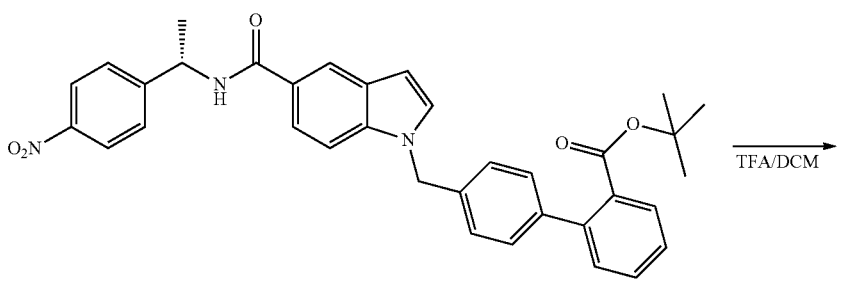

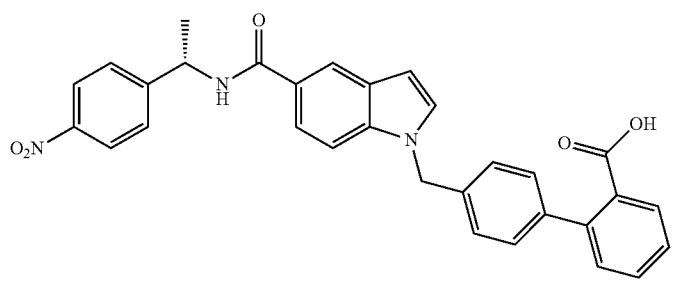

A solution of (S)-tert-butyl 4'-((5-((1-(4-nitrophenyl)ethyl)carbamoyl)-1H-indol-1-yl)methyl)-[1,1'-biphenyl]-2-carboxylate (23 mg, 0.04 mmol, 1 equiv) in DCM/TFA 1/1 was stirred for 30 min at room temperature. The reaction mixture was neutralized by addition of DIEA, concentrated and purified by preparative HPLC to afford a beige powder (9 mg, 0.02 mmol, 43%). ESI-MS (m/z): 520 [M+H]$^+$.

Example 62: (S)-2,3-Dimethyl-N-(1-(4-nitrophenyl)ethyl)-1-(4-(pyridin-3-yl)benzyl)-1H-indole-5-carboxamide

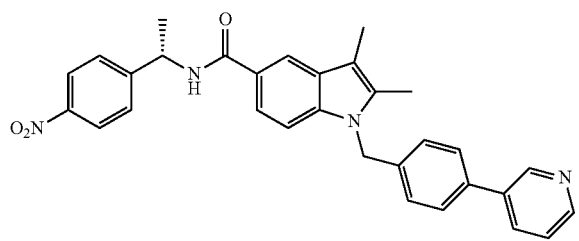 [SMILES: Cc1c(C)n(Cc2ccc(-c3cccnc3)cc2)c2ccc(C(=O)N[C@@H](C)c3ccc([N+](=O)[O-])cc3)cc12]

The title compound was prepared following the same general protocol as described in Step 5, Example 38, using pyridin-3-ylboronic acid instead of the phenylboronic acid. A beige powder was obtained (34 mg, 0.07 mmol, 69%). ESI-MS (m/z): 477 [M+H]$^+$.

Example 63: (S)-2,3-Dimethyl-N-(1-(4-nitrophenyl)ethyl)-1-(4-(pyridin-4-yl)benzyl)-1H-indole-5-carboxamide

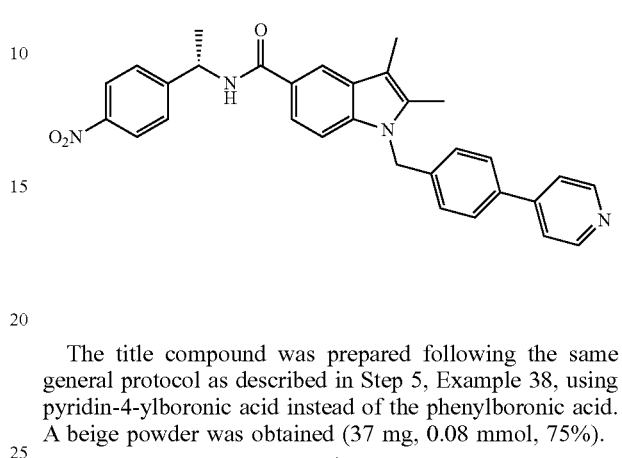

The title compound was prepared following the same general protocol as described in Step 5, Example 38, using pyridin-4-ylboronic acid instead of the phenylboronic acid. A beige powder was obtained (37 mg, 0.08 mmol, 75%).

ESI-MS (m/z): 477 [M+H]$^+$

Example 64: (S)-2,3-Dimethyl-N-(1-(4-nitrophenyl)ethyl)-1-(4-(pyridin-2-yl)benzyl)-1H-indole-5-carboxamide

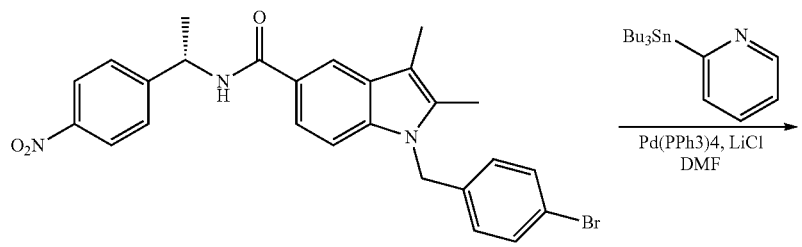

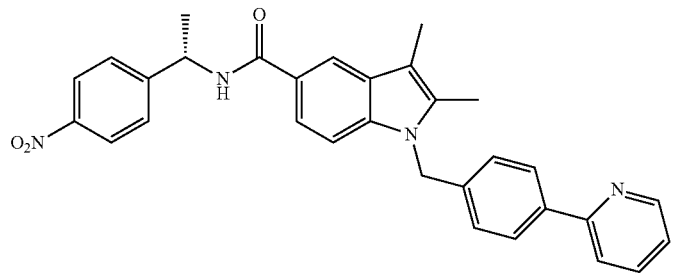

A high-pressure vial was filled with the (S)-1-(4-bromobenzyl)-N-(1-(4-nitrophenyl)ethyl)-1H-indole-5-carboxamide (37 mg, 0.08 mmol, 1 equiv), 2-(tributylstannyl)pyridine (28 µL, 0.09 mmol, 1.1 equiv), LiCl (10 mg, 0.24 mmol, 3 equiv), Pd(PPh$_3$)$_4$ (9 mg, 0.008 mmol, 0.1 equiv), and anhydrous DMF (1 mL). The mixture was degassed for 5 min under argon atmosphere and the vial was sealed. The reaction mixture was heated at 120° C. for 1 h under microwaves. The solution was then concentrated in vacuo, filtered and purified by preparative HPLC to afford a beige powder (18 mg, 0.4 mmol, 50%). ESI-MS (m/z): 477 [M+H]$^+$.

Example 65: 3'-((5-((1-phenylpropyl)carbamoyl)-1H-indol-1-yl)methyl)-[1,1'-biphenyl]-2-carboxylic acid

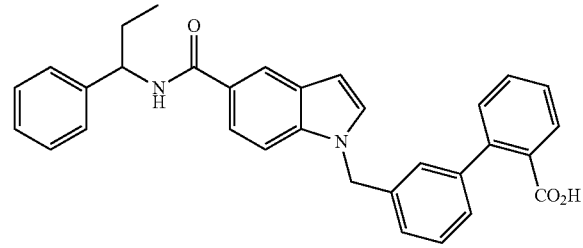 [SMILES: CCC(NC(=O)c1ccc2c(ccn2Cc2cccc(-c3ccccc3C(=O)O)c2)c1)c1ccccc1]

Step 1: 1-(3-Bromobenzyl)-2,3-dimethyl-1H-indole-5-carboxylic acid

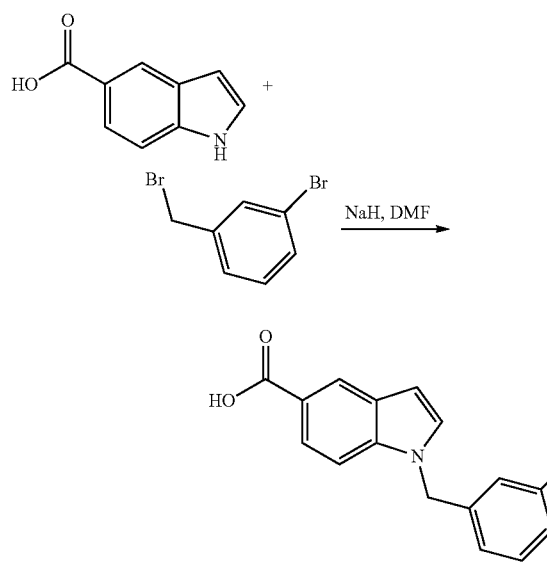

The title compound is prepared following the same protocol as described in Step 2, Example 38, using 1H-indole-5-carboxylic acid instead of the methyl 1H-indole-5-carboxylate, and 1-bromo-3-(bromomethyl)benzene instead of the 1-bromo-4-(bromomethyl)benzene. ESI-MS (m/z): 331 [M+H]$^+$.

Step 2: 1-(3-Bromobenzyl)-N-(1-phenylpropyl)-1H-indole-5-carboxamide

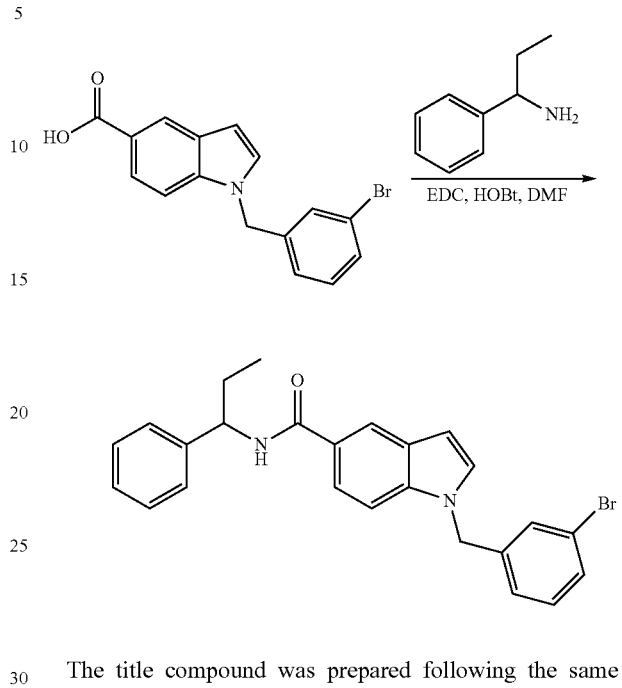

The title compound was prepared following the same protocol as described in Step 4, Example 38, using 1-phenylpropan-1-amine instead of the (S)-1-(4-nitrophenyl)ethanamine hydrochloride, and 1-(2-Bromobenzyl)-2,3-dimethyl-1H-indole-5-carboxylic acid instead of the 1-(4-bromobenzyl)-1H-indole-5-carboxylic acid. ESI-MS (m/z): 447/449 [M+H]$^+$.

Step 3: tert-Butyl 3'-((5-((1-phenylpropyl)carbamoyl)-1H-indol-1-yl)methyl)-[1,1'-biphenyl]-2-carboxylate

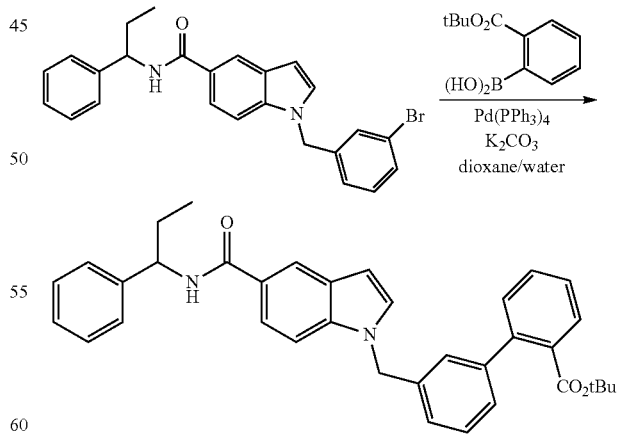

The title compound was prepared following the same protocol as described in Example 55, using 1-(3-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 4: 3'-((5-(1-Phenylpropyl)carbamoyl)-1H-indol-1-yl)methyl)-[1,1'-biphenyl]-2-carboxylic acid

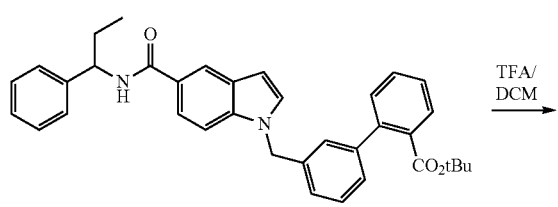

TFA/DCM

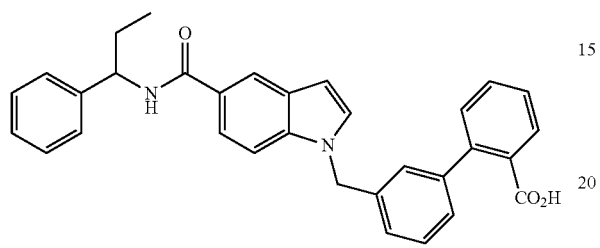

The title compound was prepared following the same protocol as described in Example 61, using tert-butyl 3'-((5-((1-phenylpropyl)carbamoyl)-1H-indol-1-yl)methyl)-[1,1'-biphenyl]-2-carboxylate instead of the (S)-tert-butyl 4'-((5-((1-(4-nitrophenyl)ethyl)carbamoyl)-1H-indol-1-yl)methyl)-[1,1'-biphenyl]-2-carboxylate. ESI-MS (m/z): 489 [M+H]+.

Example 66: 3'-((5-((1-Phenylpropyl)carbamoyl)-1H-indol-1-yl)methyl)-[1,1'-biphenyl]-3-carboxylic acid

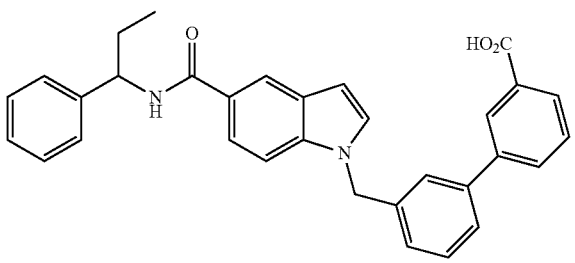 [SMILES: CCC(NC(=O)c1ccc2c(ccn2Cc2cccc(-c3cccc(C(=O)O)c3)c2)c1)c1ccccc1]

Step 1: tert-Butyl 3'-((5-((1-phenylpropyl)carbamoyl)-1H-indol-1-yl)methyl)-[1,1'-biphenyl]-3-carboxylate

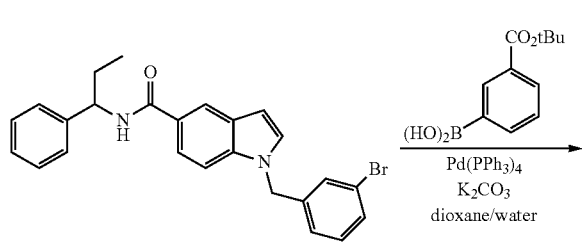

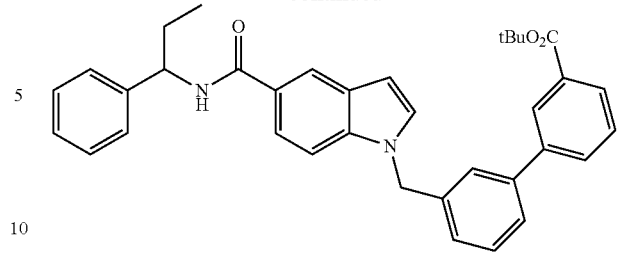

The title compound was prepared following the same protocol as described in Example 56, using 1-(3-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 3'-((5-(1-Phenylpropyl)carbamoyl)-1H-indol-1-yl)methyl)-[1,1'-biphenyl]-3-carboxylic acid

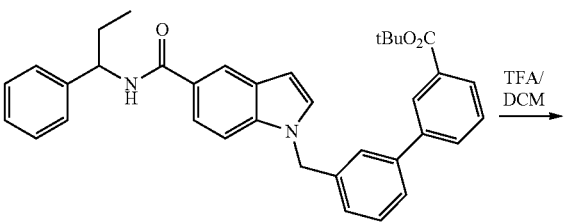

TFA/DCM

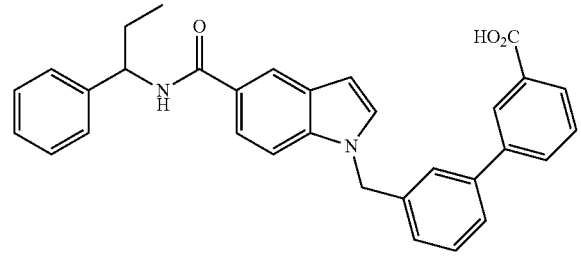

The title compound was prepared following the same protocol as described in Example 60, using tert-butyl 3'-((5-((1-phenylpropyl)carbamoyl)-1H-indol-1-yl)methyl)-[1,1'-biphenyl]-3-carboxylate instead of the (S)-tert-butyl 4'-((5-((1-(4-nitrophenyl)ethyl)carbamoyl)-1H-indol-1-yl)methyl)-[1,1'-biphenyl]-3-carboxylate. ESI-MS (m/z): 489 [M+H]+.

Example 67: 3'-((5-((1-Phenylpropyl)carbamoyl)-1H-indol-1-yl)methyl)-[1,1'-biphenyl]-4-carboxylic acid

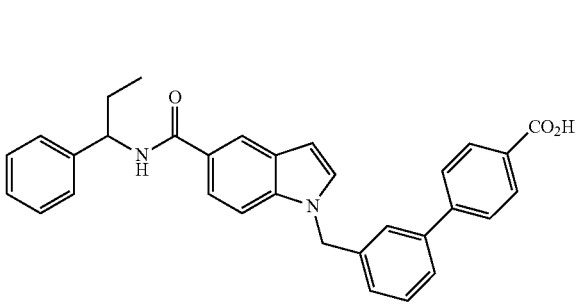 [SMILES: CCC(NC(=O)c1ccc2c(ccn2Cc2cccc(-c3ccc(C(=O)O)cc3)c2)c1)c1ccccc1]

Step 1: Ethyl 3'-((5-((1-phenylpropyl)carbamoyl)-1H-indol-1-yl)methyl)-[1,1'-biphenyl]-4-carboxylate

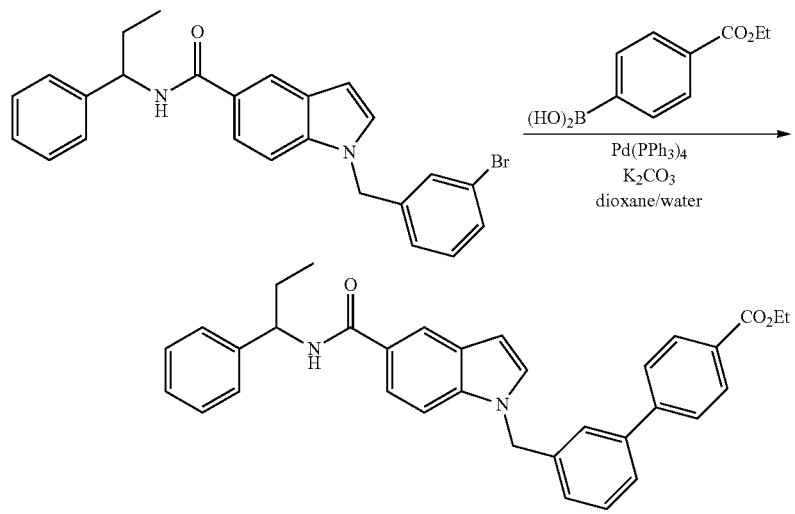

The title compound was prepared following the same protocol as described in Example 43, using 1-(3-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 3'-((5-(1-Phenylpropyl)carbamoyl)-1H-indol-1-yl)methyl)-[1,1'-biphenyl]-4-carboxylic acid The title compound was prepared following the same protocol as described in Example 59, using ethyl 3'-((5-((1-phenylpropyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 489 [M+H]+.

Example 68: 2'-((5-((1-phenylpropyl)carbamoyl)-1H-indol-1-yl)methyl)-[1,1'-biphenyl]-2-carboxylic acid Step 1: 1-(2-Bromobenzyl)-2,3-dimethyl-1H-indole-5-carboxylic acid

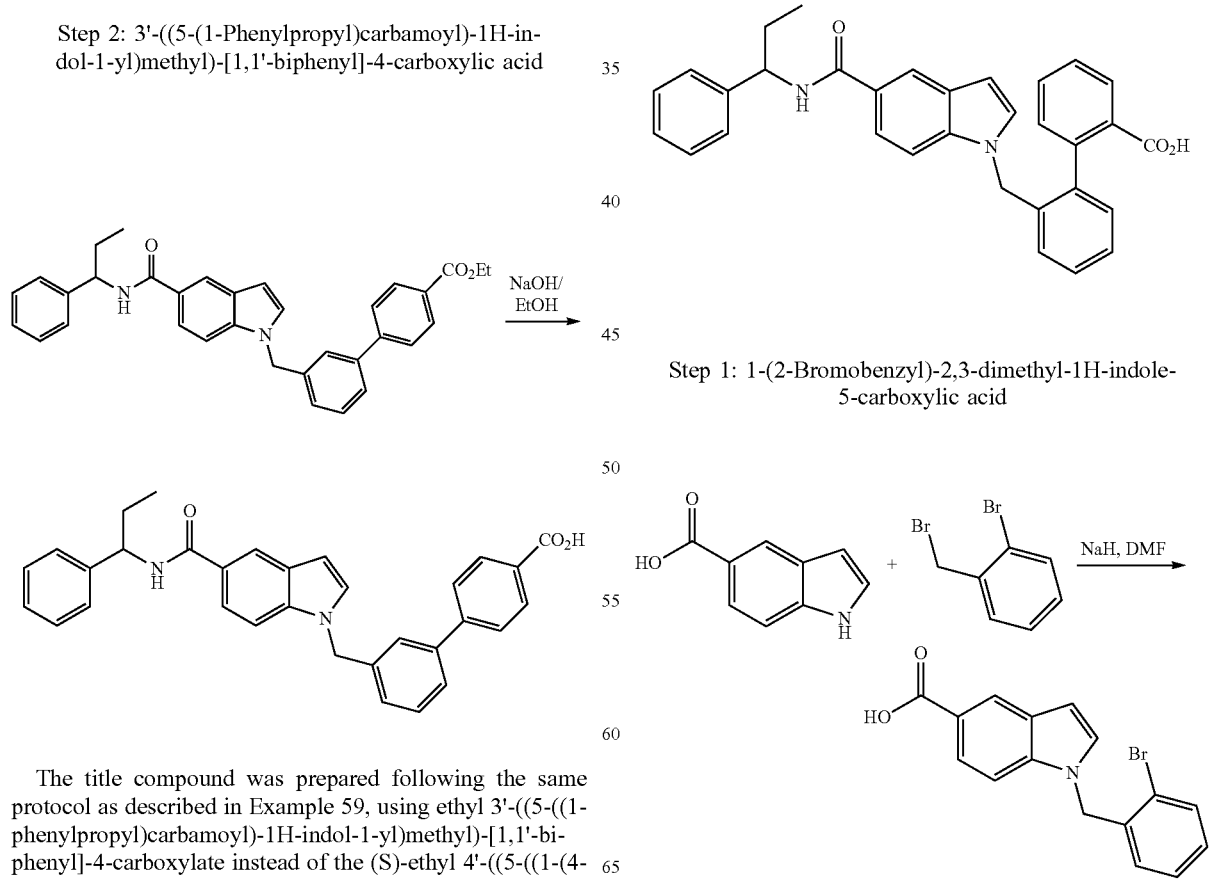

The title compound was prepared following the same protocol as described in Step 2, Example 38, using 1H-indole-5-carboxylic acid instead of the methyl 1H-indole-5-carboxylate, and 1-bromo-2-(bromomethyl)benzene instead of the 1-bromo-4-(bromomethyl)benzene.
ESI-MS (m/z): 331 [M+H]$^+$ Step 2: 1-(2-Bromobenzyl)-N-(1-phenylpropyl)-1H-indole-5-carboxamide

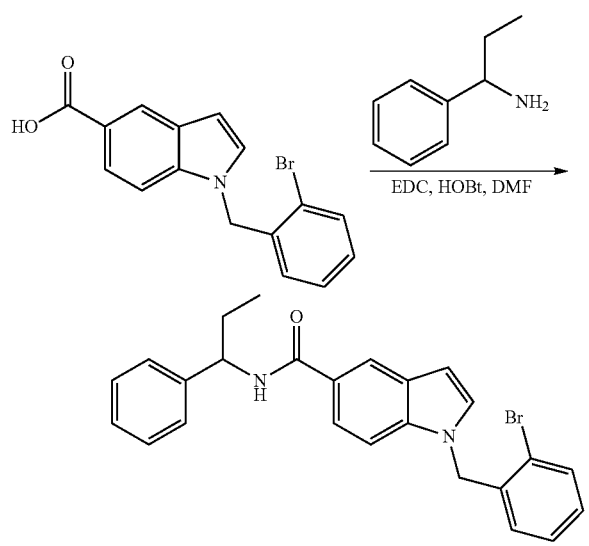

The title compound was prepared following the same protocol as described in Step 4, Example 38, using 1-phenylpropan-1-amine instead of the (S)-1-(4-nitrophenyl) ethanamine hydrochloride, and 1-(2-Bromobenzyl)-2,3-dimethyl-1H-indole-5-carboxylic acid instead of the 1-(4-bromobenzyl)-1H-indole-5-carboxylic acid. ESI-MS (m/z): 447/449 [M+H]$^+$.

Step 3: tert-Butyl 2'-((5-(((1-phenylpropyl)carbamoyl)-1H-indol-1-yl)methyl)-[1,1'-biphenyl]-2-carboxylate

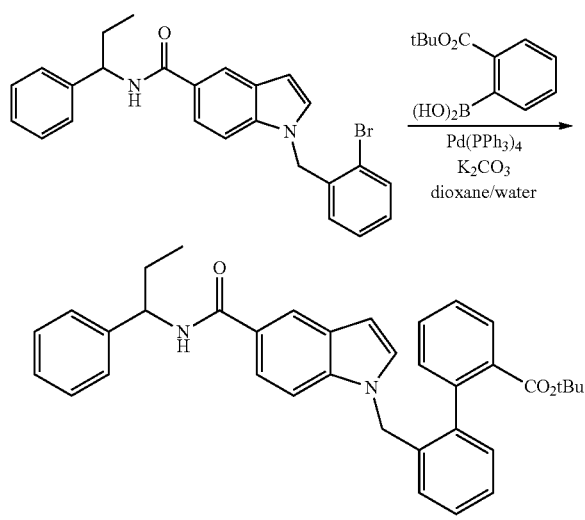

The title compound was prepared following the same protocol as described in Example 55, using 1-(2-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 4: 2'-((5-(1-Phenylpropyl)carbamoyl)-1H-indol-1-yl)methyl)-[1,1'-biphenyl]-2-carboxylic acid

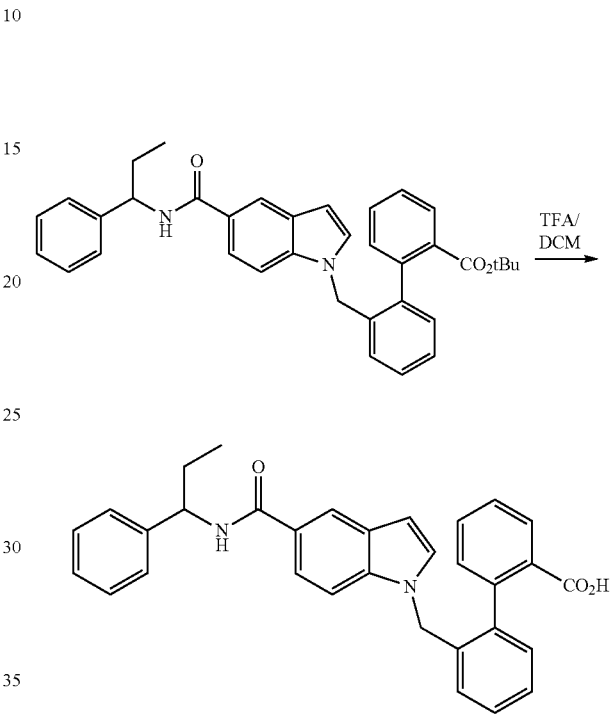

The title compound was prepared following the same protocol as described in Example 61, using tert-butyl 2'-((5-(1-phenylpropyl)carbamoyl)-1H-indol-1-yl)methyl)-[1,1'-biphenyl]-2-carboxylate instead of the (S)-tert-butyl 4'-((5-(((1-(4-nitrophenyl)ethyl)carbamoyl)-1H-indol-1-yl)methyl)-[1,1'-biphenyl]-2-carboxylate. ESI-MS (m/z): 489 [M+H]$^+$.

Example 69: 2'-((5-(((1-Phenylpropyl)carbamoyl)-1H-indol-1-yl)methyl)-[1,1'-biphenyl]-3-carboxylic acid

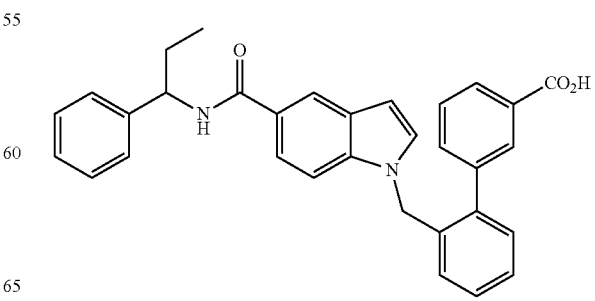

339

Step 1: tert-Butyl 2'-((5-((1-phenylpropyl)carbamoyl)-1H-indol-1-yl)methyl)-[1,1'-biphenyl]-3-carboxylate

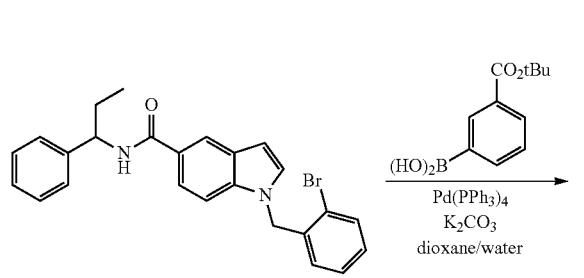

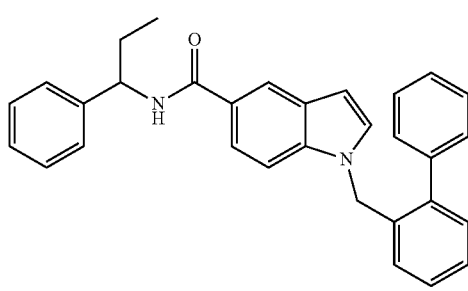

The title compound was prepared following the same protocol as described in Example 56, using 1-(2-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 2'-((5-(1-Phenylpropyl)carbamoyl)-1H-indol-1-yl)methyl)-[1,1'-biphenyl]-3-carboxylic acid

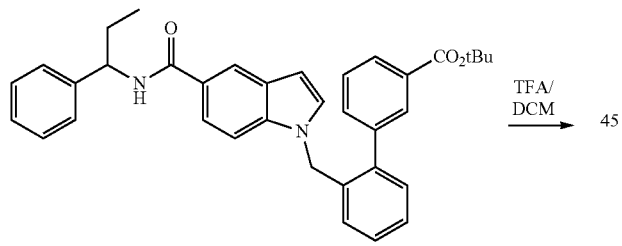

340

-continued

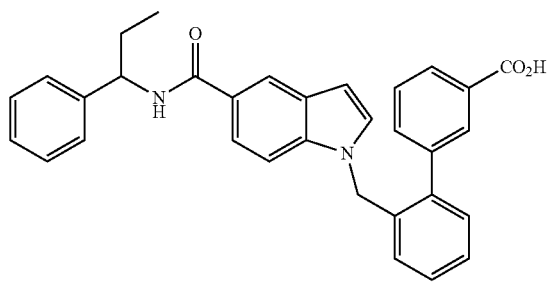 [SMILES: CCC(NC(=O)c1ccc2c(ccn2Cc2ccccc2-c2cccc(C(=O)O)c2)c1)c1ccccc1]

The title compound was prepared following the same protocol as described in Example 60, using tert-butyl 2'-((5-(1-phenylpropyl)carbamoyl)-1H-indol-1-yl)methyl)-[1,1'-biphenyl]-3-carboxylate instead of the (S)-tert-butyl 4'-((5-((1-(4-nitrophenyl)ethyl)carbamoyl)-1H-indol-1-yl)methyl)-[1,1'-biphenyl]-3-carboxylate. ESI-MS (m/z): 489 [M+H]$^+$.

Example 70: 2'-((5-((1-Phenylpropyl)carbamoyl)-1H-indol-1-yl)methyl)-[1,1'-biphenyl]-4-carboxylic acid

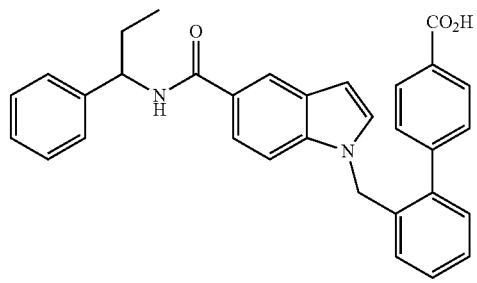 [SMILES: CCC(NC(=O)c1ccc2c(ccn2Cc2ccccc2-c2ccc(C(=O)O)cc2)c1)c1ccccc1]

Step 1: Ethyl 2'-((5-((1-phenylpropyl)carbamoyl)-1H-indol-1-yl)methyl)-[1,1'-biphenyl]-4-carboxylate

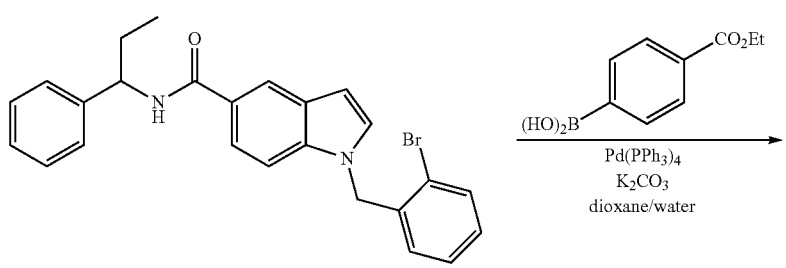

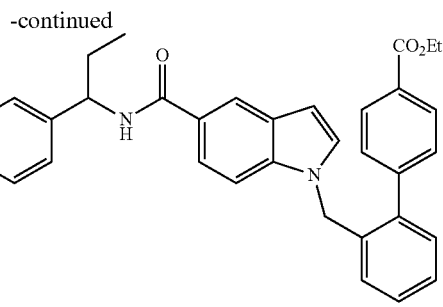

The title compound was prepared following the same protocol as described in Example 43, using 1-(2-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 2'-((5-(1-Phenylpropyl)carbamoyl)-1H-indol-1-yl)methyl)-[1,1'-biphenyl]-4-carboxylic acid

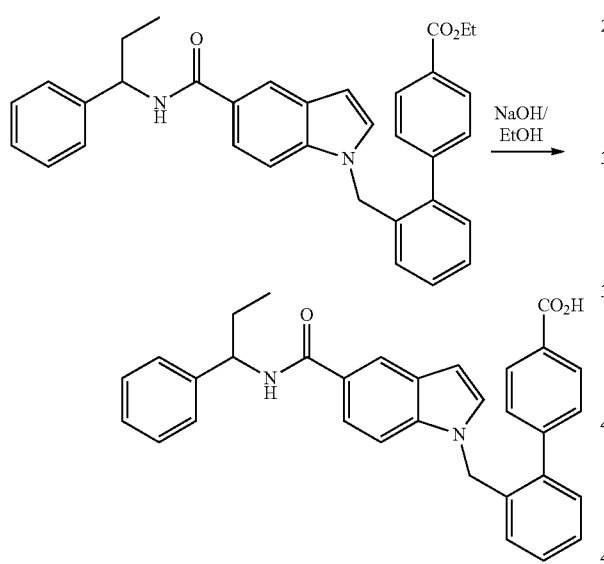

The title compound was prepared following the same protocol as described in Example 59, using ethyl 2'-((5-((1-phenylpropyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 489 [M+H]+

Example 72: (R)-4'-((2,3-dimethyl-5-(1-(4-nitrophenyl)ethylcarbamoyl)-1H-indol-1-yl)methyl)biphenyl-2-carboxylic acid

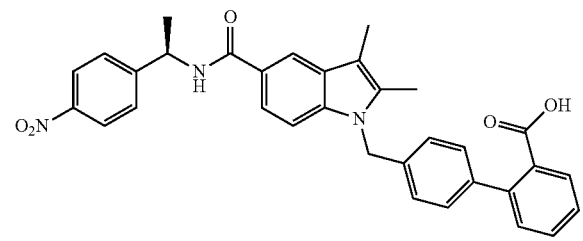 [SMILES: Cc1c(C)n(Cc2ccc(-c3ccccc3C(=O)O)cc2)c2ccc(C(=O)N[C@H](C)c3ccc([N+](=O)[O-])cc3)cc12]

The title compound was prepared following the same general protocol as described in Steps 8-9, Example 1, using (R)-α-methyl-4-nitrobenzylamine and 1-((2'-(tert-butoxycarbonyl)biphenyl-4-yl)methyl)-2,3-dimethyl-1H-indole-5-carboxylic acid. LC-MS 548 (M+H).

Example 73: (S)-4'-((2,3-dimethyl-5-(1-(4-nitrophenyl)ethylcarbamoyl)-1H-indol-1-yl)methyl)biphenyl-2-carboxylic acid

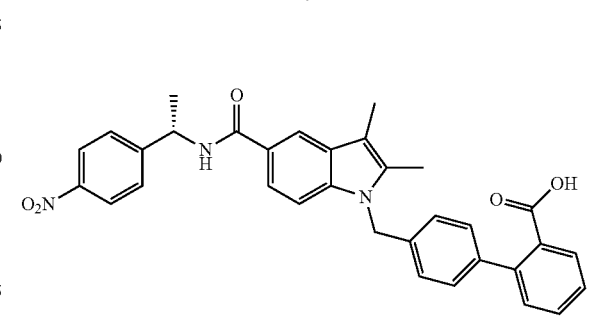

The title compound was prepared following the same general protocol as described in Steps 8-9, Example 1, using (S)-α-methyl-4-nitrobenzylamine and 1-((2'-(tert-butoxycarbonyl)biphenyl-4-yl)methyl)-2,3-dimethyl-1H-indole-5-carboxylic acid. LC-MS 548 (M+H).

Example 74: (R)-4'-((2,3-dimethyl-5-(2-phenylpropylcarbamoyl)-1H-indol-1-yl)methyl)biphenyl-2-carboxylic acid

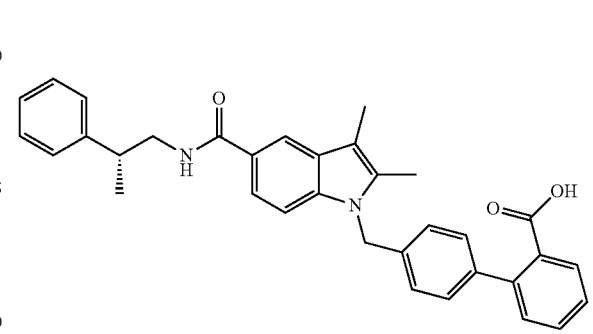

The title compound was prepared following the same general protocol as described in Steps 8-9, Example 1, using (R)-2-phenylpropan-1-amine and 1-((2'-(tert-butoxycarbonyl)biphenyl-4-yl)methyl)-2,3-dimethyl-1H-indole-5-carboxylic acid. LC-MS 517 (M+H).

Example 75: 4'-((5-(benzhydrylcarbamoyl)-2,3-dimethyl-1H-indol-1-yl)methyl)biphenyl-2-carboxylic acid

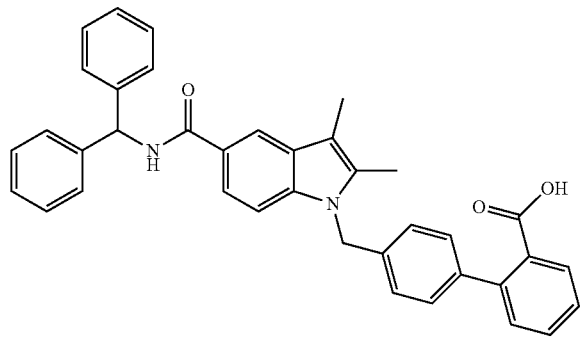 [SMILES: Cc1c(C)n(Cc2ccc(-c3ccccc3C(=O)O)cc2)c2ccc(C(=O)NC(c3ccccc3)c3ccccc3)cc12]

The title compound was prepared following the same general protocol as described in Steps 8-9, Example 1, using diphenylmethanamine and 1-((2'-(tert-butoxycarbonyl)biphenyl-4-yl)methyl)-2,3-dimethyl-1H-indole-5-carboxylic acid. LC-MS 515 (M+H).

Example 76: 4'-((5-(4-fluorobenzylcarbamoyl)-2,3-dimethyl-1H-indol-1-yl)methyl)biphenyl-2-carboxylic acid

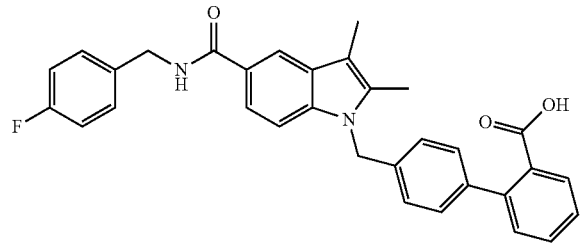 [SMILES: Cc1c(C)n(Cc2ccc(-c3ccccc3C(=O)O)cc2)c2ccc(C(=O)NCc3ccc(F)cc3)cc12]

The title compound was prepared following the same general protocol as described in Steps 8-9, Example 1, using 4-fluorobenzylamine and 1-((2'-(tert-butoxycarbonyl)biphenyl-4-yl)methyl)-2,3-dimethyl-1H-indole-5-carboxylic acid. LC-MS 507 (M+H).

Example 77: 4'-((5-(3,4-difluorobenzylcarbamoyl)-2,3-dimethyl-1H-indol-1-yl)methyl)biphenyl-2-carboxylic acid

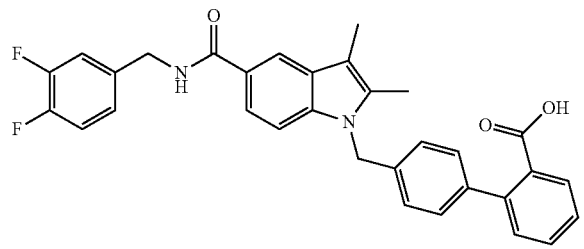 [SMILES: Cc1c(C)n(Cc2ccc(-c3ccccc3C(=O)O)cc2)c2ccc(C(=O)NCc3ccc(F)c(F)c3)cc12]

The title compound was prepared following the same general protocol as described in Steps 8-9, Example 1, using 3,4-fluorobenzylamine and 1-((2'-(tert-butoxycarbonyl)biphenyl-4-yl)methyl)-2,3-dimethyl-1H-indole-5-carboxylic acid. LC-MS 524 (M+H).

Example 78: 4'-((5-(benzo[d][1,3]dioxol-5-ylmethylcarbamoyl)-2,3-dimethyl-1H-indol-1-yl)methyl)biphenyl-2-carboxylic acid

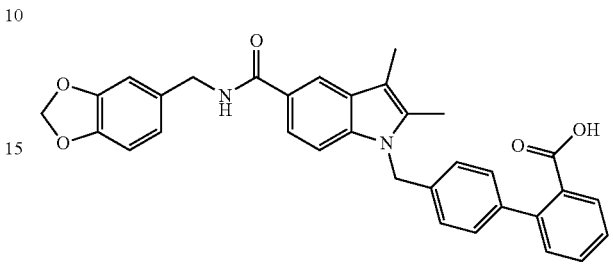

The title compound was prepared following the same general protocol as described in Steps 8-9, Example 1, using benzo[d][1,3]dioxol-5-ylmethanamine and 1-((2'-(tert-butoxycarbonyl)biphenyl-4-yl)methyl)-2,3-dimethyl-1H-indole-5-carboxylic acid. LC-MS 533 (M+H).

Example 79: (R)-4'-((5-(2-hydroxy-1-phenylethylcarbamoyl)-2,3-dimethyl-1H-indol-1-yl)methyl)biphenyl-2-carboxylic acid

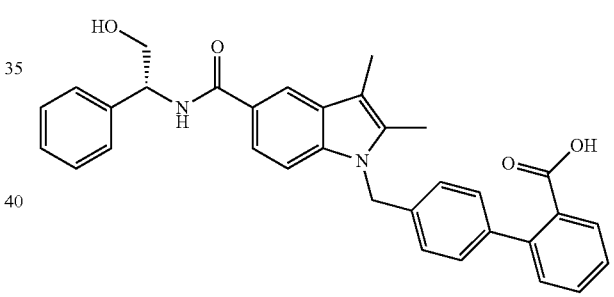

The title compound was prepared following the same general protocol as described in Steps 8-9, Example 1, using (R)-2-amino-2-phenylethanol and 1-((2'-(tert-butoxycarbonyl)biphenyl-4-yl)methyl)-2,3-dimethyl-1H-indole-5-carboxylic acid. LC-MS 519 (M+H).

Example 80: 4'-((5-(3-aminobenzylcarbamoyl)-2,3-dimethyl-1H-indol-1-yl)methyl)biphenyl-2-carboxylic acid

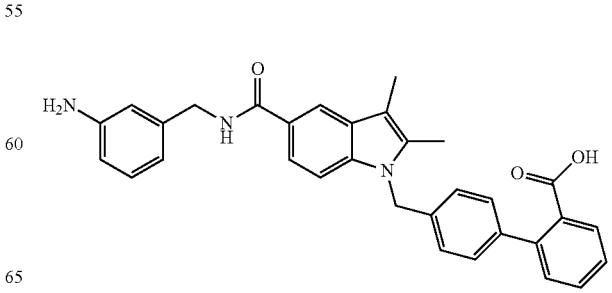

The title compound was prepared following the same general protocol as described in Steps 8-9, Example 1, using 3-aminobenzylamine and 1-((2'-(tert-butoxycarbonyl)biphenyl-4-yl)methyl)-2,3-dimethyl-1H-indole-5-carboxylic acid. LC-MS 504 (M+H).

Example 81: 4'-((5-(cyclohexylmethylcarbamoyl)-2,3-dimethyl-1H-indol-1-yl)methyl)biphenyl-2-carboxylic acid

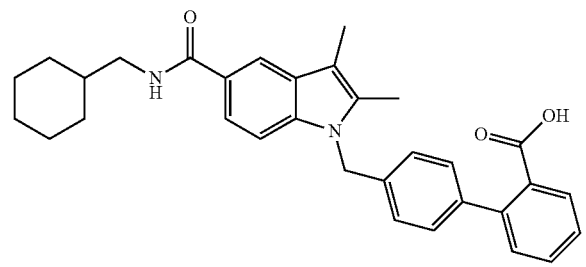 [SMILES: Cc1c(C)n(Cc2ccc(-c3ccccc3C(=O)O)cc2)c2ccc(C(=O)NCC3CCCCC3)cc12]

The title compound was prepared following the same general protocol as described in Steps 8-9, Example 1, using cyclohexylmethylamine and 1-((2'-(tert-butoxycarbonyl)biphenyl-4-yl)methyl)-2,3-dimethyl-1H-indole-5-carboxylic acid. LC-MS 495 (M+H).

Example 82: 4'-((5-(3-(aminomethyl)benzylcarbamoyl)-2,3-dimethyl-1H-indol-1-yl)methyl)biphenyl-2-carboxylic acid

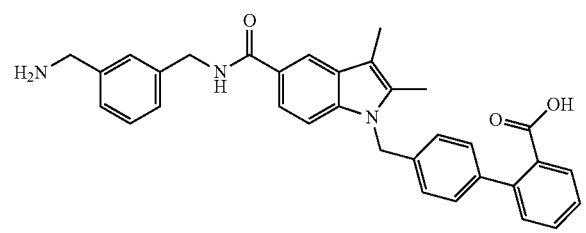 [SMILES: Cc1c(C)n(Cc2ccc(-c3ccccc3C(=O)O)cc2)c2ccc(C(=O)NCc3cccc(CN)c3)cc12]

The title compound was prepared following the same general protocol as described in Steps 8-9, Example 1, using tert-butyl 3-(aminomethyl)benzylcarbamate and 1-((2'-(tert-butoxycarbonyl)biphenyl-4-yl)methyl)-2,3-dimethyl-1H-indole-5-carboxylic acid. LC-MS 518 (M+H).

Example 83: 4'-((2,3-dimethyl-5-(thiophen-2-ylmethylcarbamoyl)-1H-indol-1-yl)methyl)biphenyl-2-carboxylic acid

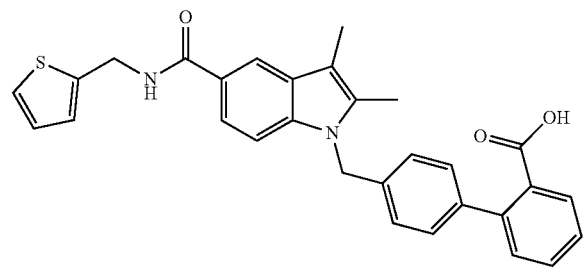 [SMILES: Cc1c(C)n(Cc2ccc(-c3ccccc3C(=O)O)cc2)c2ccc(C(=O)NCc3cccs3)cc12]

The title compound was prepared following the same general protocol as described in Steps 8-9, Example 1, using 2-thiophenemethylamine and 1-((2'-(tert-butoxycarbonyl)biphenyl-4-yl)methyl)-2,3-dimethyl-1H-indole-5-carboxylic acid. LC-MS 495 (M+H).

Example 84: 4'-((2,3-dimethyl-5-((5-methylfuran-2-yl)methylcarbamoyl)-1H-indol-1-yl)methyl)biphenyl-2-carboxylic acid

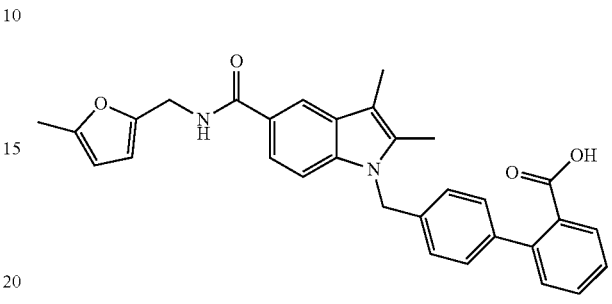

The title compound was prepared following the same general protocol as described in Steps 8-9, Example 1, using 5-methyl-2-furanylmethylamine and 1-((2'-(tert-butoxycarbonyl)biphenyl-4-yl)methyl)-2,3-dimethyl-1H-indole-5-carboxylic acid. LC-MS 493 (M+H).

Example 85: 4'-((2,3-dimethyl-5-(2-morpholinoethylcarbamoyl)-1H-indol-1-yl)methyl)biphenyl-2-carboxylic acid

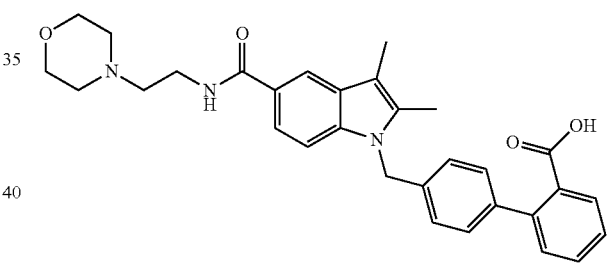

The title compound was prepared following the same general protocol as described in Steps 8-9, Example 1, using 2-morphorinethylamine and 1-((2'-(tert-butoxycarbonyl)biphenyl-4-yl)methyl)-2,3-dimethyl-1H-indole-5-carboxylic acid. LC-MS 512 (M+H).

Example 86: 4'-((5-(chroman-3-ylcarbamoyl)-2,3-dimethyl-1H-indol-1-yl)methyl)biphenyl-2-carboxylic acid

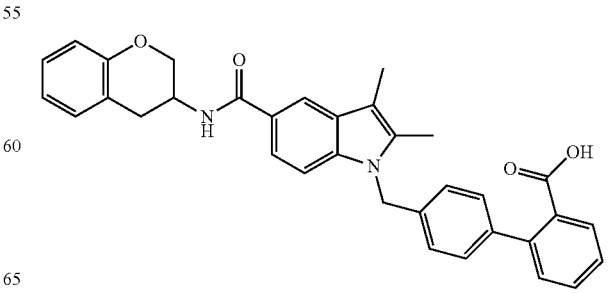

The title compound was prepared following the same general protocol as described in Steps 8-9, Example 1, using chroman-3-amine and 1-((2'-(tert-butoxycarbonyl)biphenyl-4-yl)methyl)-2,3-dimethyl-1H-indole-5-carboxylic acid. LC-MS 531 (M+H).

Example 87: 4'-((5-(chroman-3-ylmethylcarbamoyl)-2,3-dimethyl-1H-indol-1-yl)methyl)biphenyl-2-carboxylic acid

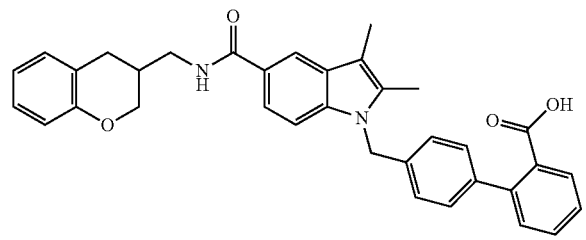 [SMILES: Cc1c(C)n(Cc2ccc(-c3ccccc3C(=O)O)cc2)c2ccc(C(=O)NCC3COc4ccccc4C3)cc12]

The title compound was prepared following the same general protocol as described in Steps 8-9, Example 1, using chroman-3-ylmethanamine and 1-((2'-(tert-butoxycarbonyl)biphenyl-4-yl)methyl)-2,3-dimethyl-1H-indole-5-carboxylic acid. LC-MS 545 (M+H).

Example 88: 4'-((5-((2,3-dihydrobenzo[b][1,4]dioxin-2-yl)methylcarbamoyl)-2,3-dimethyl-1H-indol-1-yl)methyl)biphenyl-2-carboxylic acid

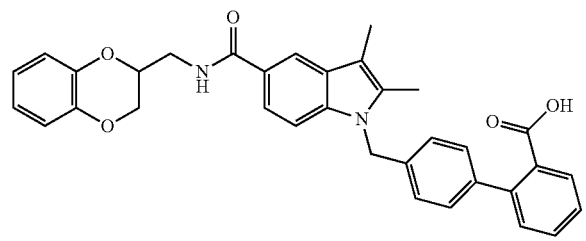 [SMILES: Cc1c(C)n(Cc2ccc(-c3ccccc3C(=O)O)cc2)c2ccc(C(=O)NCC3COc4ccccc4O3)cc12]

The title compound was prepared following the same general protocol as described in Steps 8-9, Example 1, using (2,3-dihydrobenzo[b][1,4]dioxin-2-yl)methanamine and 1-((2'-(tert-butoxycarbonyl)biphenyl-4-yl)methyl)-2,3-dimethyl-1H-indole-5-carboxylic acid. LC-MS 547 (M+H).

Example 89: 4'-((5-(cyclobutylcarbamoyl)-2,3-dimethyl-1H-indol-1-yl)methyl)biphenyl-2-carboxylic acid

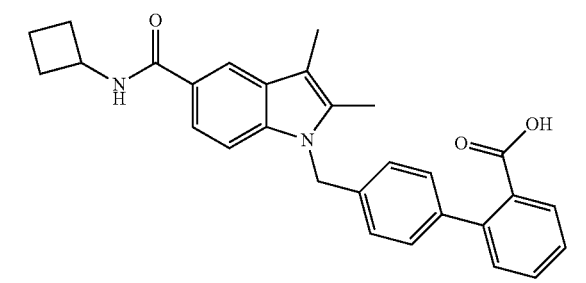 [SMILES: Cc1c(C)n(Cc2ccc(-c3ccccc3C(=O)O)cc2)c2ccc(C(=O)NC3CCC3)cc12]

The title compound was prepared following the same general protocol as described in Steps 8-9, Example 1, using cyclobutylamine and 1-((2'-(tert-butoxycarbonyl)biphenyl-4-yl)methyl)-2,3-dimethyl-1H-indole-5-carboxylic acid. LC-MS 453 (M+H).

Example 90: 4'-((5-(cyclopentylcarbamoyl)-2,3-dimethyl-1H-indol-1-yl)methyl)biphenyl-2-carboxylic acid

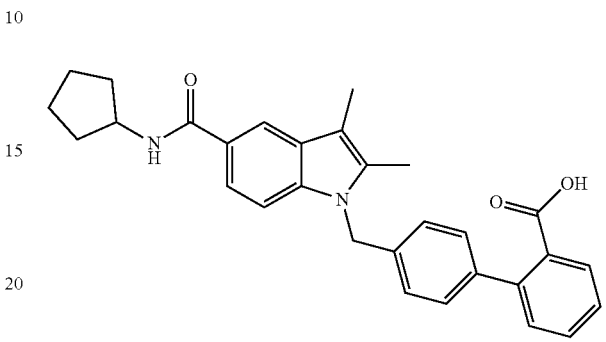

The title compound was prepared following the same general protocol as described in Steps 8-9, Example 1, using cyclopentylamine and 1-((2'-(tert-butoxycarbonyl)biphenyl-4-yl)methyl)-2,3-dimethyl-1H-indole-5-carboxylic acid. LC-MS 467 (M+H).

Example 91: 4'-((5-(3-aminocyclohexylcarbamoyl)-2,3-dimethyl-1H-indol-1-yl)methyl)biphenyl-2-carboxylic acid

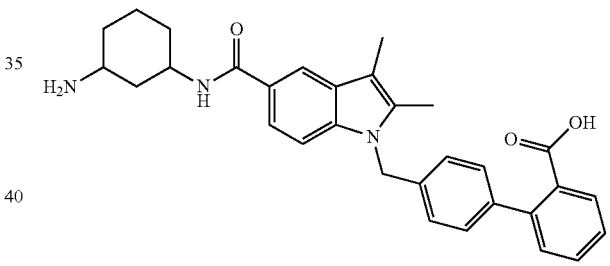

The title compound was prepared following the same general protocol as described in Steps 8-9, Example 1, using tert-butyl 3-aminocyclohexylcarbamate and 1-((2'-(tert-butoxycarbonyl)biphenyl-4-yl)methyl)-2,3-dimethyl-1H-indole-5-carboxylic acid. LC-MS 496 (M+H).

Example 92: 4'-((5-(2-methoxyethylcarbamoyl)-2,3-dimethyl-1H-indol-1-yl)methyl)biphenyl-2-carboxylic acid

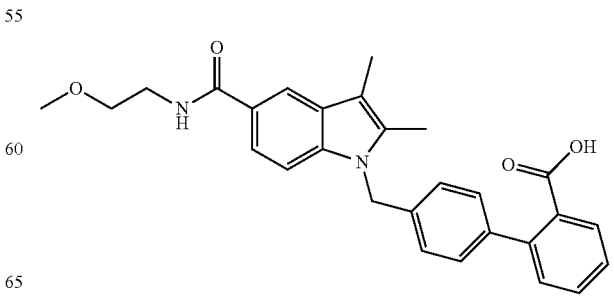

The title compound was prepared following the same general protocol as described in Steps 8-9, Example 1, using 2-methoxyethyleneamine and 1-((2'-(tert-butoxycarbonyl)biphenyl-4-yl)methyl)-2,3-dimethyl-1H-indole-5-carboxylic acid. LC-MS 457 (M+H).

Example 93: 4'-((5-(benzylcarbamoyl)-2,3-dimethyl-1H-indol-1-yl)methyl)biphenyl-2-carboxylic acid

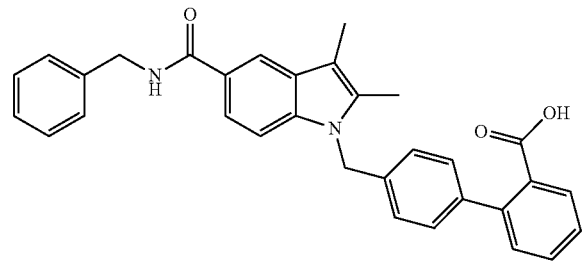 [SMILES: Cc1c(C)n(Cc2ccc(-c3ccccc3C(=O)O)cc2)c2ccc(C(=O)NCc3ccccc3)cc12]

The title compound was prepared following the same general protocol as described in Steps 8-9, Example 1, using benzylamine and 1-((2'-(tert-butoxycarbonyl)biphenyl-4-yl)methyl)-2,3-dimethyl-1H-indole-5-carboxylic acid. LC-MS 489 (M+H).

Example 94: 4'-((5-(2-aminobenzylcarbamoyl)-2,3-dimethyl-1H-indol-1-yl)methyl)biphenyl-2-carboxylic acid

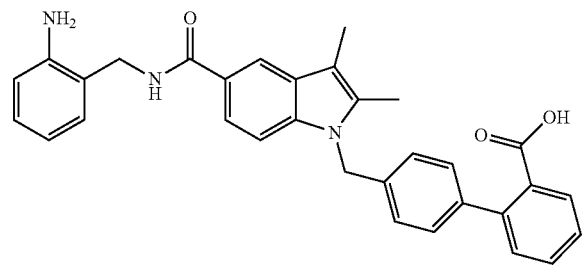 [SMILES: Cc1c(C)n(Cc2ccc(-c3ccccc3C(=O)O)cc2)c2ccc(C(=O)NCc3ccccc3N)cc12]

The title compound was prepared following the same general protocol as described in Steps 8-9, Example 1, using 2-aminobenzylamine and 1-((2'-(tert-butoxycarbonyl)biphenyl-4-yl)methyl)-2,3-dimethyl-1H-indole-5-carboxylic acid. LC-MS 504 (M+H).

Example 95: 4'-((5-(4-aminobenzylcarbamoyl)-2,3-dimethyl-1H-indol-1-yl)methyl)biphenyl-2-carboxylic acid

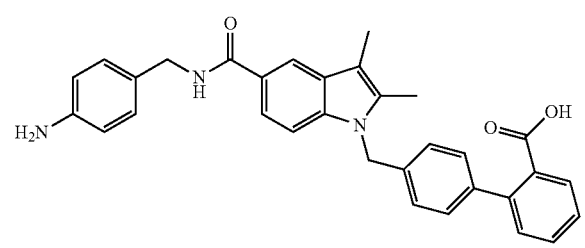 [SMILES: Cc1c(C)n(Cc2ccc(-c3ccccc3C(=O)O)cc2)c2ccc(C(=O)NCc3ccc([N+](=O)[O-])cc3)cc12]

The title compound was prepared following the same general protocol as described in Steps 8-9, Example 1, using 4-aminobenzylamine and 1-(((2'-(tert-butoxycarbonyl)biphenyl-4-yl)methyl)-2,3-dimethyl-1H-indole-5-carboxylic acid. LC-MS 504 (M+H).

Example 96: 4'-((2,3-dimethyl-5-(4-nitrobenzylcarbamoyl)-1H-indol-1-yl)methyl)biphenyl-2-carboxylic acid

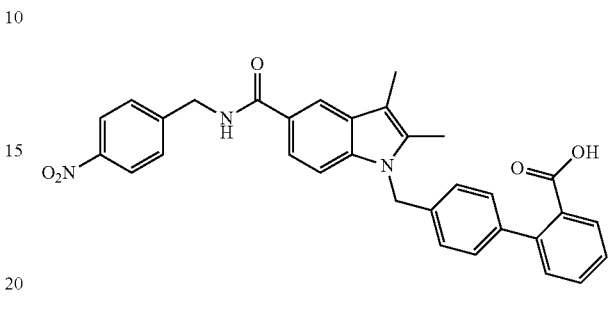

The title compound was prepared following the same general protocol as described in Steps 8-9, Example 1, using 4-nitrobenzylamine and 1-((2'-(tert-butoxycarbonyl)biphenyl-4-yl)methyl)-2,3-dimethyl-1H-indole-5-carboxylic acid. LC-MS 534 (M+H).

Example 97: (R)-4'-((2,3-dimethyl-5-(1-phenylpropylcarbamoyl)-1H-indol-1-yl)methyl)biphenyl-2-carboxylic acid

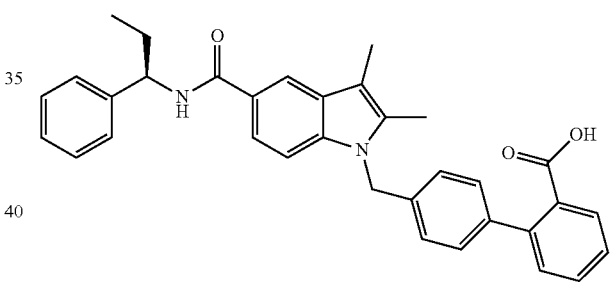

The title compound was prepared following the same general protocol as described in Steps 8-9, Example 1, using (R)-α-ethylbenzylamine and 1-((2'-(tert-butoxycarbonyl)biphenyl-4-yl)methyl)-2,3-dimethyl-1H-indole-5-carboxylic acid. LC-MS 517 (M+H).

Example 98: (S)-4'-((2,3-dimethyl-5-(1-phenylpropylcarbamoyl)-1H-indol-1-yl)methyl)biphenyl-2-carboxylic acid

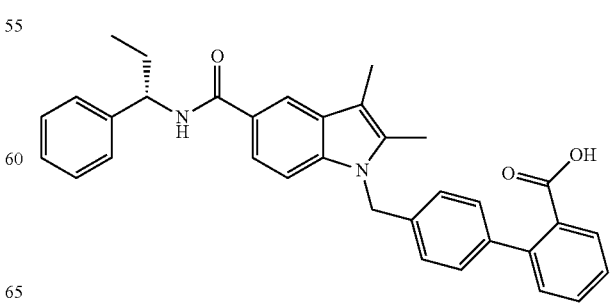

The title compound was prepared following the same general protocol as described in Steps 8-9, Example 1, using (S)-α-ethylbenzylamine and 1-((2'-(tert-butoxycarbonyl)biphenyl-4-yl)methyl)-2,3-dimethyl-1H-indole-5-carboxylic acid. LC-MS 517 (M+H).

Example 99: (S)-4'-((5-(1-(4-aminophenyl)ethylcarbamoyl)-2,3-dimethyl-1H-indol-1-yl)methyl)biphenyl-2-carboxylic acid

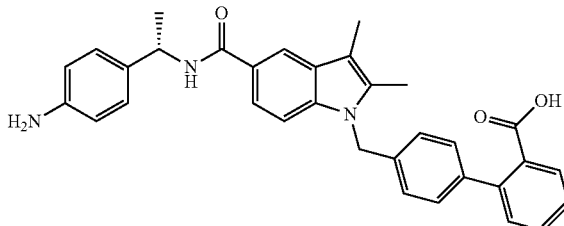

The title compound was prepared following the same general protocol as described in Steps 8-9, Example 1, using 4-amino-(S)-α-methylbenzylamine and 1-((2'-(tert-butoxycarbonyl)biphenyl-4-yl)methyl)-2,3-dimethyl-1H-indole-5-carboxylic acid. LC-MS 518 (M+H).

Example 100: 4'-((2,3-dimethyl-5-(3-(trifluoromethyl)benzylcarbamoyl)-1H-indol-1-yl)methyl)biphenyl-2-carboxylic acid

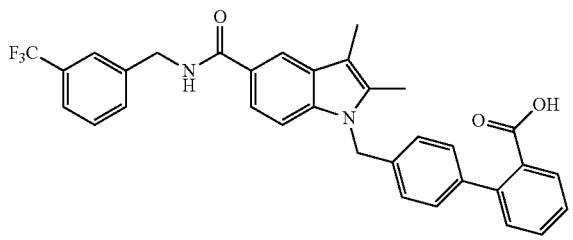 [SMILES: Cc1c(C)n(Cc2ccc(-c3ccccc3C(=O)O)cc2)c2ccc(C(=O)NCc3cccc(C(F)(F)F)c3)cc12]

The title compound was prepared following the same general protocol as described in Steps 8-9, Example 1, using 3-trifluoromethylbenzylamine and 1-((2'-(tert-butoxycarbonyl)biphenyl-4-yl)methyl)-2,3-dimethyl-1H-indole-5-carboxylic acid. LC-MS 557 (M+H).

Example 101: 4'-((2,3-dimethyl-5-(4-(trifluoromethyl)benzylcarbamoyl)-1H-indol-1-yl)methyl)biphenyl-2-carboxylic acid

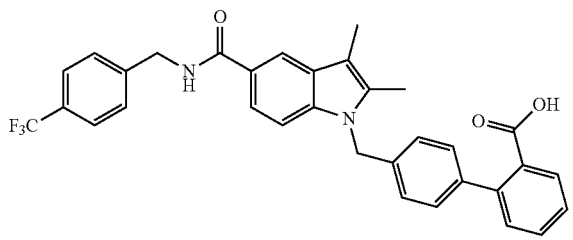 [SMILES: Cc1c(C)n(Cc2ccc(-c3ccccc3C(=O)O)cc2)c2ccc(C(=O)NCc3ccc(C(F)(F)F)cc3)cc12]

The title compound was prepared following the same general protocol as described in Steps 8-9, Example 1, using 4-trifluoromethylbenzylamine and 1-((2'-(tert-butoxycarbonyl)biphenyl-4-yl)methyl)-2,3-dimethyl-1H-indole-5-carboxylic acid. LC-MS 557 (M+H).

Example 102: 4'-((5-(biphenyl-4-ylmethylcarbamoyl)-2,3-dimethyl-1H-indol-1-yl)methyl)biphenyl-2-carboxylic acid

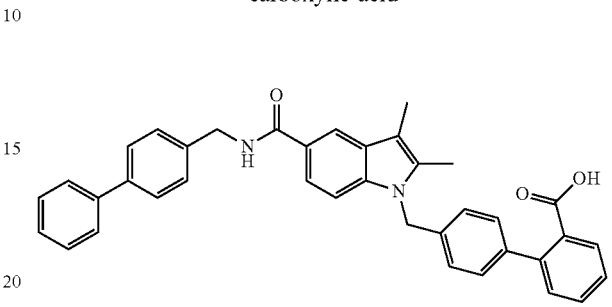

The title compound was prepared following the same general protocol as described in Steps 8-9, Example 1, using 4-phenylbenzylamine and 1-((2'-(tert-butoxycarbonyl)biphenyl-4-yl)methyl)-2,3-dimethyl-1H-indole-5-carboxylic acid. LC-MS 565 (M+H).

Example 103: 4'-((5-(3-methoxybenzylcarbamoyl)-2,3-dimethyl-1H-indol-1-yl)methyl)biphenyl-2-carboxylic acid

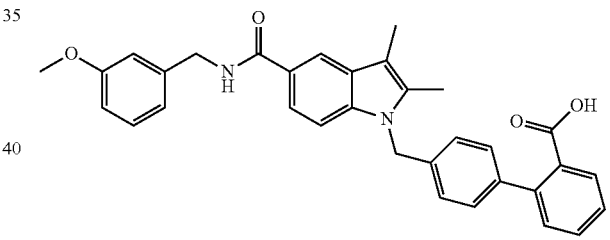

The title compound was prepared following the same general protocol as described in Steps 8-9, Example 1, using 3-methoxylbenzylamine and 1-((2'-(tert-butoxycarbonyl)biphenyl-4-yl)methyl)-2,3-dimethyl-1H-indole-5-carboxylic acid. LC-MS 519 (M+H).

Example 104: 4'-((5-(4-methoxybenzylcarbamoyl)-2,3-dimethyl-1H-indol-1-yl)methyl)biphenyl-2-carboxylic acid

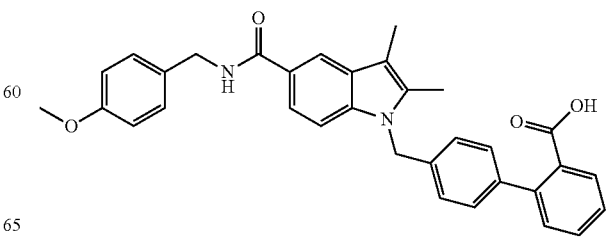

The title compound was prepared following the same general protocol as described in Steps 8-9, Example 1, using 4-methoxylbenzylamine and 1-((2'-(tert-butoxycarbonyl)biphenyl-4-yl)methyl)-2,3-dimethyl-1H-indole-5-carboxylic acid. LC-MS 519 (M+H).

Example 105: 4'-((2,3-dimethyl-5-(3-methylbenzylcarbamoyl)-1H-indol-1-yl)methyl)biphenyl-2-carboxylic acid

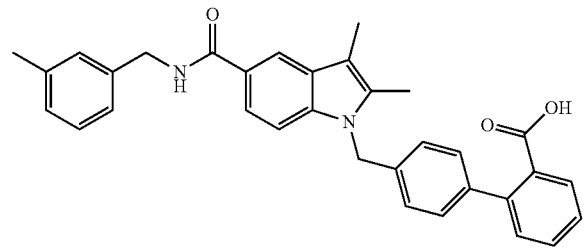 [SMILES: Cc1cccc(CNC(=O)c2ccc3c(c2)c(C)c(C)n3Cc2ccc(-c3ccccc3C(=O)O)cc2)c1]

The title compound was prepared following the same general protocol as described in Steps 8-9, Example 1, using 3-methylbenzylamine and 1-((2'-(tert-butoxycarbonyl)biphenyl-4-yl)methyl)-2,3-dimethyl-1H-indole-5-carboxylic acid. LC-MS 503 (M+H).

Example 106: 4'-((2,3-dimethyl-5-(4-methylbenzylcarbamoyl)-1H-indol-1-yl)methyl)biphenyl-2-carboxylic acid

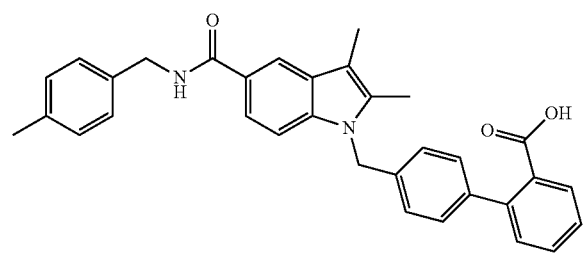 [SMILES: Cc1ccc(CNC(=O)c2ccc3c(c2)c(C)c(C)n3Cc2ccc(-c3ccccc3C(=O)O)cc2)cc1]

The title compound was prepared following the same general protocol as described in Steps 8-9, Example 1, using 4-methylbenzylamine and 1-((2'-(tert-butoxycarbonyl)biphenyl-4-yl)methyl)-2,3-dimethyl-1H-indole-5-carboxylic acid. LC-MS 503 (M+H).

Example 107: 4'-((2,3-dimethyl-5-(2-methylbenzylcarbamoyl)-1H-indol-1-yl)methyl)biphenyl-2-carboxylic acid

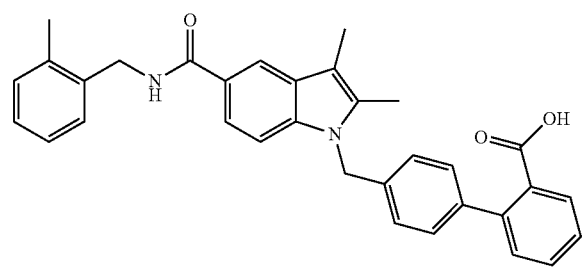 [SMILES: Cc1ccccc1CNC(=O)c1ccc2c(c1)c(C)c(C)n2Cc1ccc(-c2ccccc2C(=O)O)cc1]

The title compound was prepared following the same general protocol as described in Steps 8-9, Example 1, using 2-methylbenzylamine and 1-((2'-(tert-butoxycarbonyl)biphenyl-4-yl)methyl)-2,3-dimethyl-1H-indole-5-carboxylic acid. LC-MS 503 (M+H).

Example 108: 4'-((5-(2-chlorobenzylcarbamoyl)-2,3-dimethyl-1H-indol-1-yl)methyl)biphenyl-2-carboxylic acid

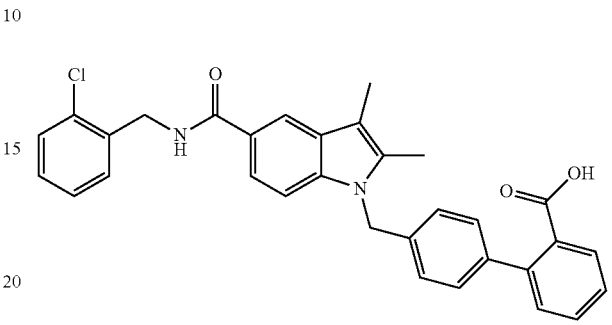

The title compound was prepared following the same general protocol as described in Steps 8-9, Example 1, using 2-chlorobenzylamine and 1-((2'-(tert-butoxycarbonyl)biphenyl-4-yl)methyl)-2,3-dimethyl-1H-indole-5-carboxylic acid. LC-MS 523 (M+H).

Example 109: 4'-((5-(3-chlorobenzylcarbamoyl)-2,3-dimethyl-1H-indol-1-yl)methyl)biphenyl-2-carboxylic acid

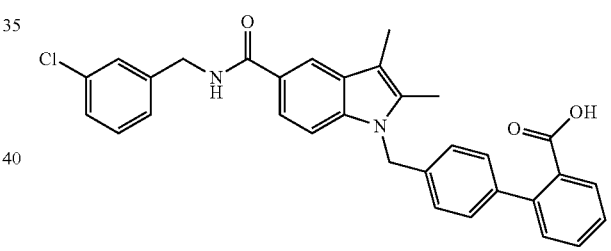

The title compound was prepared following the same general protocol as described in Steps 8-9, Example 1, using 3-chlorobenzylamine and 1-((2'-(tert-butoxycarbonyl)biphenyl-4-yl)methyl)-2,3-dimethyl-1H-indole-5-carboxylic acid. LC-MS 523 (M+H).

Example 110: 4'-((2,3-dimethyl-5-(3-nitrobenzylcarbamoyl)-1H-indol-1-yl)methyl)biphenyl-2-carboxylic acid

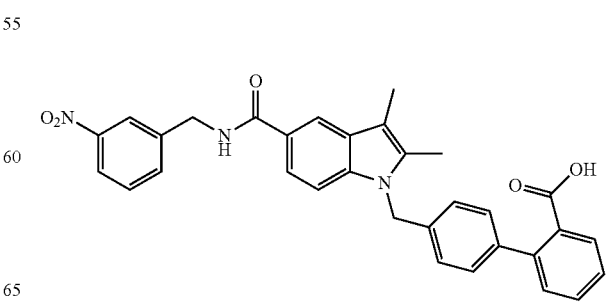

The title compound was prepared following the same general protocol as described in Steps 8-9, Example 1, using 3-nitrobenzylamine and 1-((2'-(tert-butoxycarbonyl)biphenyl-4-yl)methyl)-2,3-dimethyl-1H-indole-5-carboxylic acid. LC-MS 534 (M+H).

Example 111: 4'-((5-(3-fluoro-4-methoxybenzylcarbamoyl)-2,3-dimethyl-1H-indol-1-yl)methyl)biphenyl-2-carboxylic acid

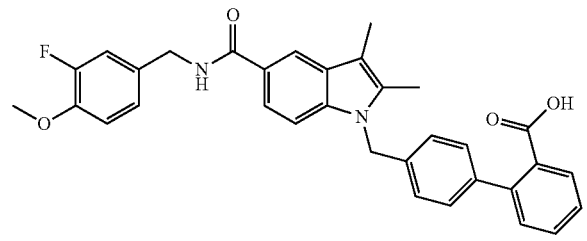 [SMILES: COc1ccc(CNC(=O)c2ccc3c(c2)c(C)c(C)n3Cc2ccc(-c3ccccc3C(=O)O)cc2)cc1F]

The title compound was prepared following the same general protocol as described in Steps 8-9, Example 1, using 3-fluoro-4-methoxybenzylamine and 1-((2'-(tert-butoxycarbonyl)biphenyl-4-yl)methyl)-2,3-dimethyl-1H-indole-5-carboxylic acid. LC-MS 537 (M+H).

Example 112: (S)-4'-((5-(1-(4-fluorophenyl)ethylcarbamoyl)-2,3-dimethyl-1H-indol-1-yl)methyl)biphenyl-2-carboxylic acid

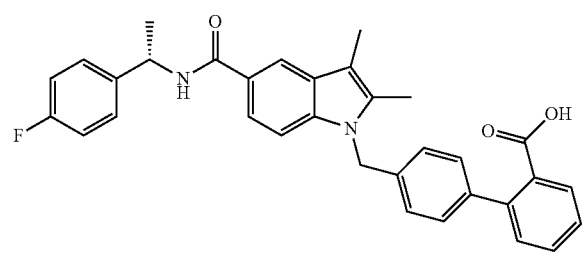 [SMILES: Cc1c(C)n(Cc2ccc(-c3ccccc3C(=O)O)cc2)c2ccc(C(=O)N[C@@H](C)c3ccc(F)cc3)cc12]

The title compound was prepared following the same general protocol as described in Steps 8-9, Example 1, using 4-fluoro-α-(S)-methylbenzylamine and 1-((2'-(tert-butoxycarbonyl)biphenyl-4-yl)methyl)-2,3-dimethyl-1H-indole-5-carboxylic acid. LC-MS 521 (M+H).

Example 113: (R)-4'-((5-(1-(4-fluorophenyl)ethylcarbamoyl)-2,3-dimethyl-1H-indol-1-yl)methyl)biphenyl-2-carboxylic acid

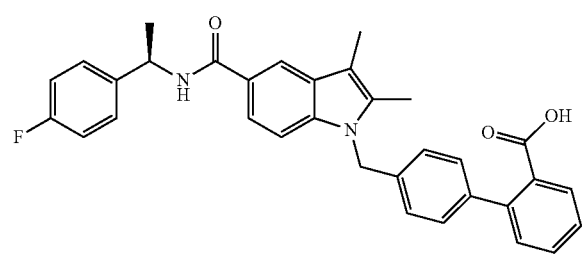 [SMILES: Cc1c(C)n(Cc2ccc(-c3ccccc3C(=O)O)cc2)c2ccc(C(=O)N[C@H](C)c3ccc(F)cc3)cc12]

The title compound was prepared following the same general protocol as described in Steps 8-9, Example 1, using 4-fluoro-α-(R)-methylbenzylamine and 1-((2'-(tert-butoxycarbonyl)biphenyl-4-yl)methyl)-2,3-dimethyl-1H-indole-5-carboxylic acid. LC-MS 521 (M+H).

Example 114: (S)-4'-((2,3-dimethyl-5-(1-phenylbutylcarbamoyl)-1H-indol-1-yl)methyl)biphenyl-2-carboxylic acid

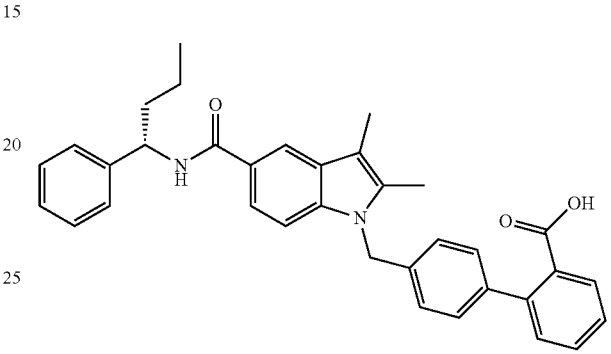

The title compound was prepared following the same general protocol as described in Steps 8-9, Example 1, using α-(S)-ethylbenzylamine and 1-((2'-(tert-butoxycarbonyl)biphenyl-4-yl)methyl)-2,3-dimethyl-1H-indole-5-carboxylic acid. LC-MS 531 (M+H).

Example 115: 4'-((2,3-dimethyl-5-(naphthalen-1-ylmethylcarbamoyl)-1H-indol-1-yl)methyl)biphenyl-2-carboxylic acid

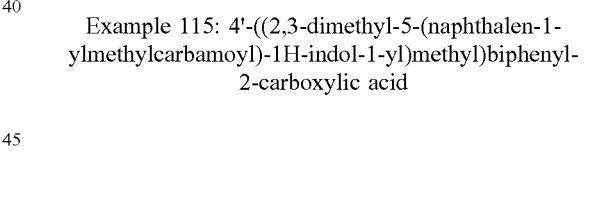

The title compound was prepared following the same general protocol as described in Steps 8-9, Example 1, using 1-naphthylmethylamine and 1-((2'-(tert-butoxycarbonyl)biphenyl-4-yl)methyl)-2,3-dimethyl-1H-indole-5-carboxylic acid. LC-MS 539 (M+H).

Example 116: 4'-((2,3-dimethyl-5-(1-(naphthalen-1-yl)ethylcarbamoyl)-1H-indol-1-yl)methyl)biphenyl-2-carboxylic acid

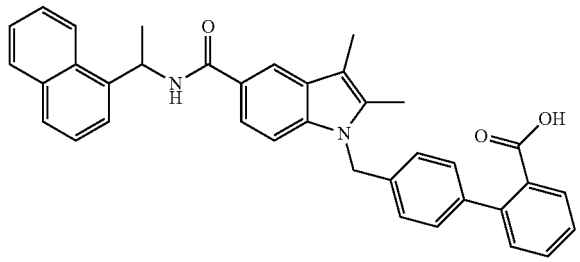 [SMILES: Cc1c(C)n(Cc2ccc(-c3ccccc3C(=O)O)cc2)c2ccc(C(=O)NC(C)c3cccc4ccccc34)cc12]

The title compound was prepared following the same general protocol as described in Steps 8-9, Example 1, using 1-(naphthalen-1-yl)ethanamine and 1-((2'-(tert-butoxycarbonyl)biphenyl-4-yl)methyl)-2,3-dimethyl-1H-indole-5-carboxylic acid. LC-MS 553 (M+H).

Example 117: 4'-((2,3-dimethyl-5-(4-phenylbutan-2-ylcarbamoyl)-1H-indol-1-yl)methyl)biphenyl-2-carboxylic acid

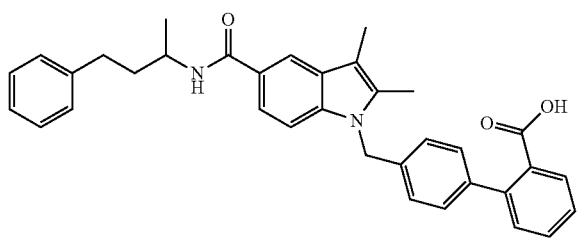 [SMILES: Cc1c(C)n(Cc2ccc(-c3ccccc3C(=O)O)cc2)c2ccc(C(=O)NC(C)CCc3ccccc3)cc12]

The title compound was prepared following the same general protocol as described in Steps 8-9, Example 1, using 4-phenylbutan-2-amine and 1-((2'-(tert-butoxycarbonyl)biphenyl-4-yl)methyl)-2,3-dimethyl-1H-indole-5-carboxylic acid. LC-MS 531 (M+H).

Example 118: 4'-((5-((2-Bromobenzyl)carbamoyl)-2,3-dimethyl-1H-indol-1-yl)methyl)-[1,1'-biphenyl]-2-carboxylic acid (SR-3-2223)

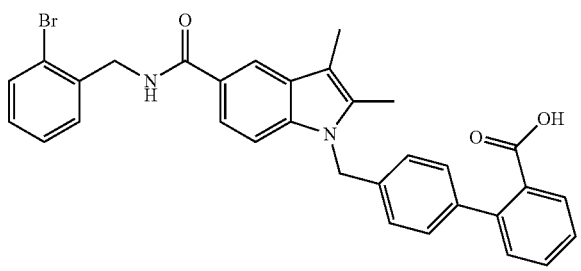

Step 1: tert-Butyl 4'-((5-((2-bromobenzyl)carbamoyl)-2,3-dimethyl-1H-indol-1-yl)methyl)-[1,1'-biphenyl]-2-carboxylate

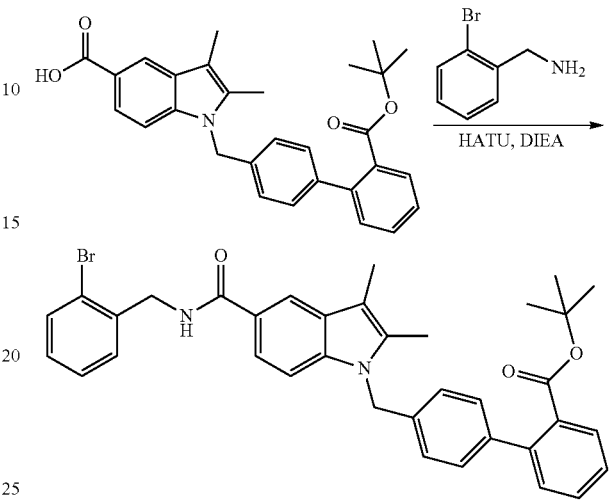

The title compound was prepared following the same general protocol as described in Step 8, Example 1, the (2-bromophenyl)methanamine was used instead of the (S)-1-(4-bromophenyl)ethanamine.

ESI-MS (m/z): 623/625 [M+H]$^+$.

Step 2: 4'-((5-(2-Bromobenzyl)carbamoyl)-2,3-dimethyl-1H-indol-1-yl)methyl)-[1,1'-biphenyl]-2-carboxylic acid

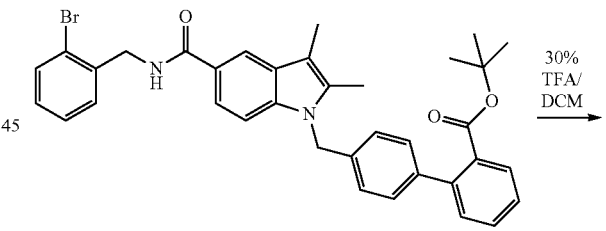

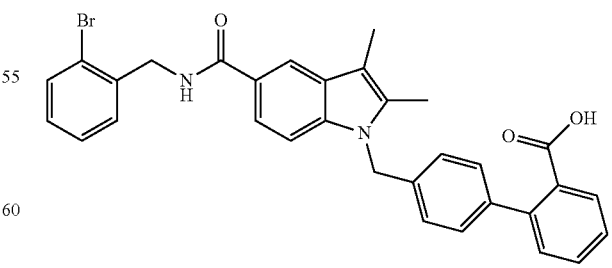

The title compound was prepared following the same general protocol as described in Step 9, Example 1.

ESI-MS (m/z): 567/569 [M+H]$^+$.

Example 119: 4'-((5-((2-Nitrobenzyl)carbamoyl)-2,3-dimethyl-1H-indol-1-yl)methyl)-[1,1'-biphenyl]-2-carboxylic acid (SR-3-2224)

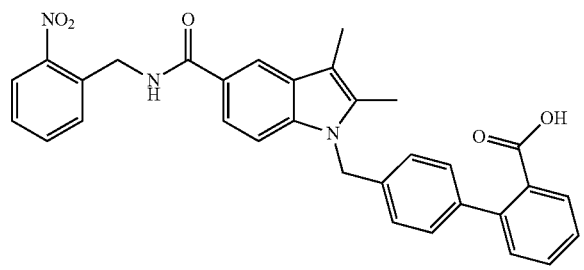

Step 1: tert-Butyl 4'-((5-((2-nitrobenzyl)carbamoyl)-2,3-dimethyl-1H-indol-1-yl)methyl)-[1,1'-biphenyl]-2-carboxylate

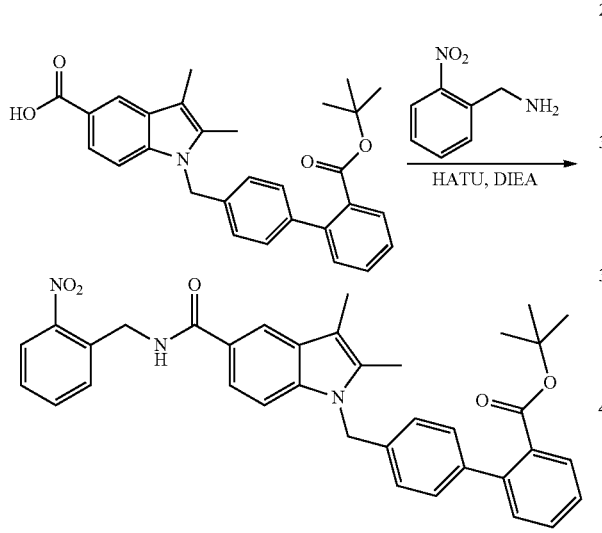

The title compound was prepared following the same general protocol as described in Step 8, Example 1, the (2-nitrophenyl)methanamine was used instead of the (S)-1-(4-bromophenyl)ethanamine.
ESI-MS (m/z): 590 [M+H]$^+$.

Step 2: 4'-((5-((2-Nitrobenzyl)carbamoyl)-2,3-dimethyl-1H-indol-1-yl)methyl)-[1,1'-biphenyl]-2-carboxylic acid

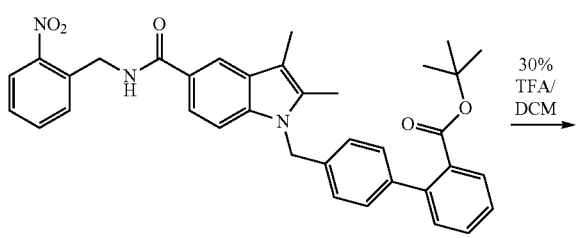

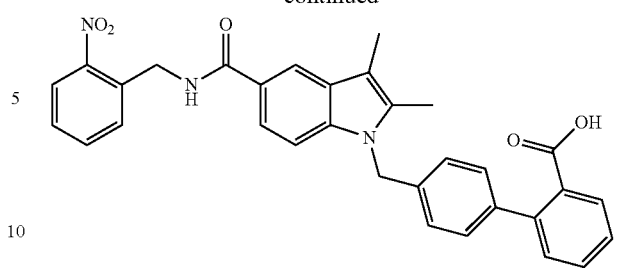

The title compound was prepared following the same general protocol as described in Step 9, Example 1.
ESI-MS (m/z): 534 [M+H]$^+$.

Example 120: (S)-2'-((5-((1-(4-Bromophenyl)ethyl)carbamoyl)-1H-indol-1-yl)methyl)-[1,1'-biphenyl]-4-carboxylic acid

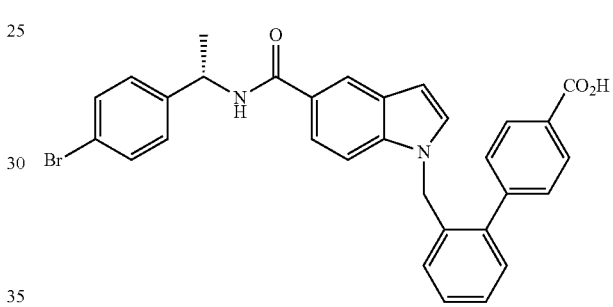

Step 1: 1-(3-Bromobenzyl)-2,3-dimethyl-1H-indole-5-carboxylic acid

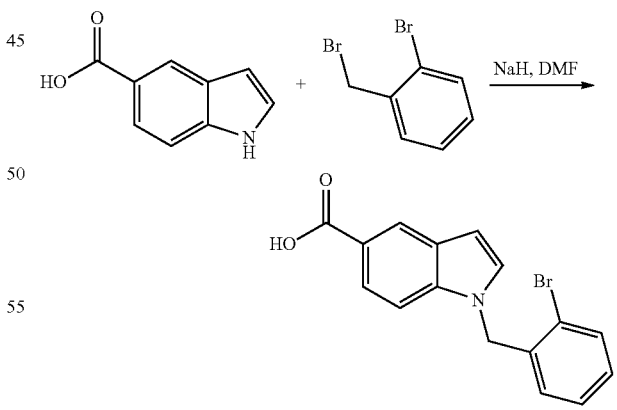

The title compound was prepared following the same protocol as described in Step 2, Example 38, using 1H-indole-5-carboxylic acid instead of the methyl 1H-indole-5-carboxylate, and 1-bromo-2-(bromomethyl)benzene instead of the 1-bromo-4-(bromomethyl)benzene. ESI-MS (m/z): 330/332 [M+H]$^+$.

Step 2: 1-((4'-(Ethoxycarbonyl)-[1,1'-biphenyl]-2-yl)methyl)-1H-indole-5-carboxylic acid

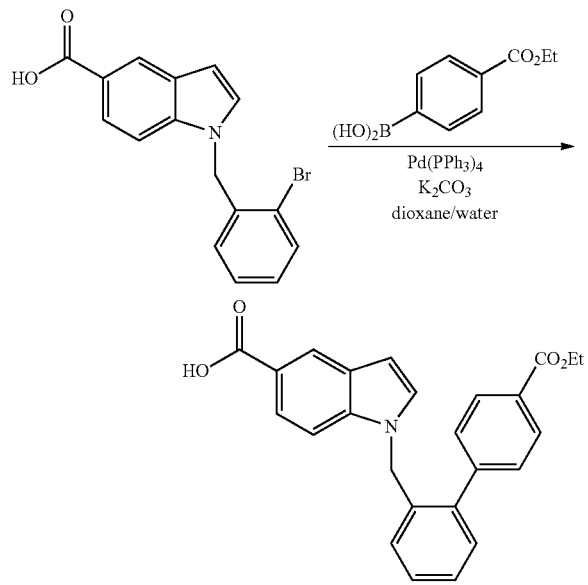

The title compound was prepared following the same protocol as described in Step 5, Example 38, using 1-(2-bromobenzyl)-1H-indole-5-carboxylic acid instead of the (S)-1-(4-bromobenzyl)-N-(1-(4-nitrophenyl)ethyl)-1H-indole-5-carboxamide and the (4-(ethoxycarbonyl)phenyl)boronic acid instead of the phenylboronic acid. ESI-MS (m/z): 400 [M+H]$^+$.

Step 3: (S)-Ethyl 2'-((5-((1-(4-bromophenyl)ethyl)carbamoyl)-1H-indol-1-yl)methyl)-[1,1'-biphenyl]-4-carboxylate

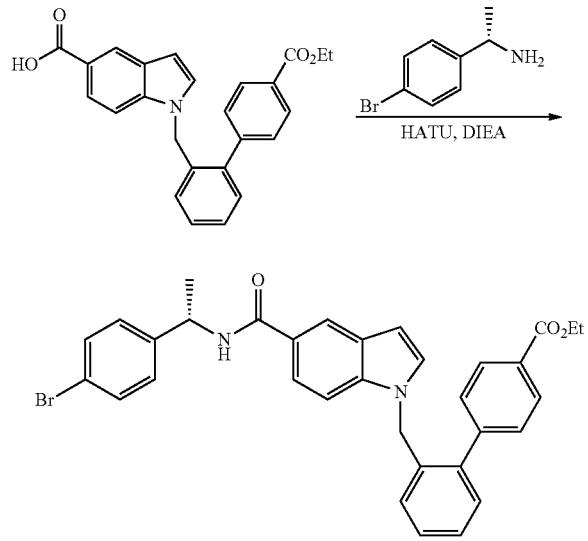

The title compound was prepared following the same protocol as described in Step 8, Example 1, using the 1-((4'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid.

Step 4: (S)-2'-((5-((1-(4-Bromophenyl)ethyl)carbamoyl)-1H-indol-1-yl)methyl)-[1,1'-biphenyl]-4-carboxylic acid

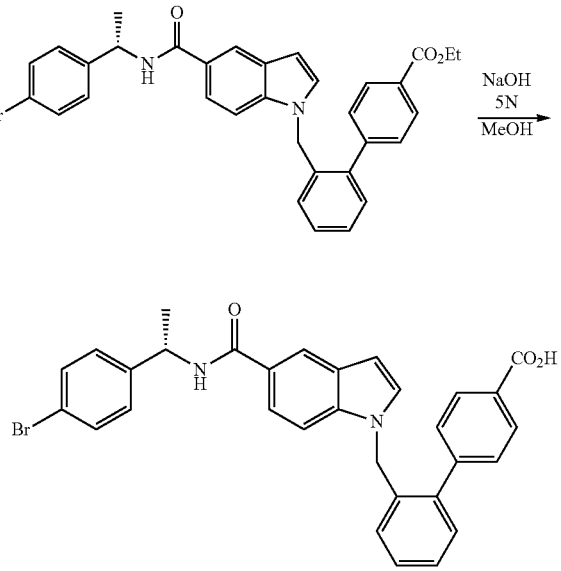

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 553/555 [M+H]$^+$.

Example 121: (S)-2'-((5-((1-(4-Nitrophenyl)ethyl)carbamoyl)-1H-indol-1-yl)methyl)-[1,1'-biphenyl]-4-carboxylic acid

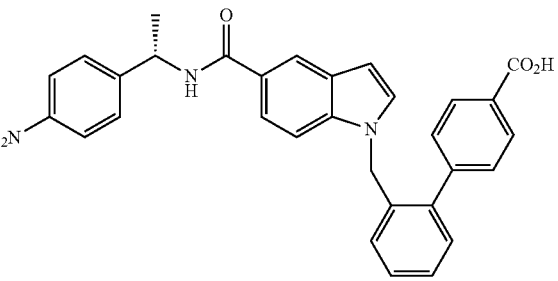

Step 1: (S)-Ethyl 2'-((5-((1-(4-nitrophenyl)ethyl)carbamoyl)-1H-indol-1-yl)methyl)-[1,1'-biphenyl]-4-carboxylate

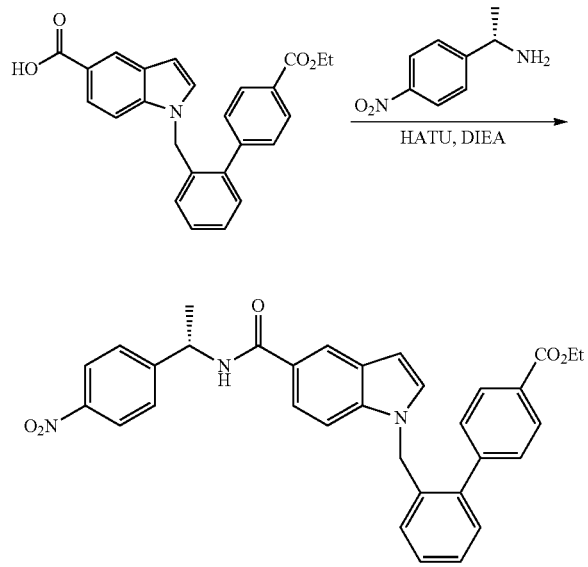 [SMILES: CCOC(=O)c1ccc(-c2ccccc2Cn2ccc3cc(C(=O)O)ccc32)cc1 ; C[C@H](N)c1ccc([N+](=O)[O-])cc1 ; CCOC(=O)c1ccc(-c2ccccc2Cn2ccc3cc(C(=O)N[C@@H](C)c4ccc([N+](=O)[O-])cc4)ccc32)cc1]

The title compound was prepared following the same protocol as described in Step 8, Example 1, using the 1-((4'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((5-((1-(4-Nitrophenyl)ethyl)carbamoyl)-1H-indol-1-yl)methyl)-[1,1'-biphenyl]-4-carboxylic acid

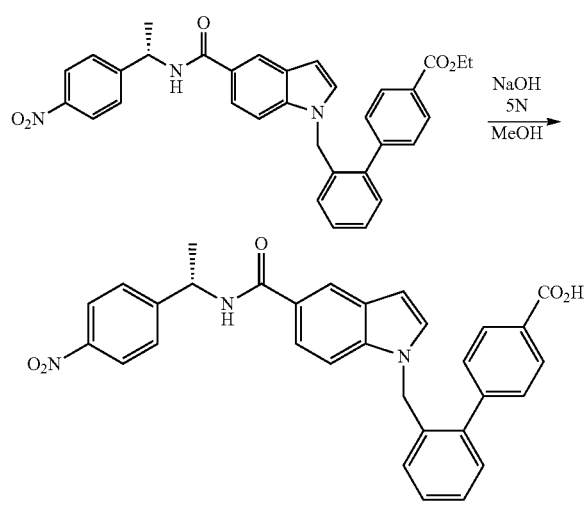

The title compound was prepared following the same protocol as described in Example 59, using (S)-ethyl 2'-((5-((1-(4-nitrophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 520 [M+H]$^+$.

Example 122: (S)-2'-((5-((1-(4-Bromophenyl)ethyl)carbamoyl)-1H-indol-1-yl)methyl)-[1,1'-biphenyl]-3-carboxylic acid

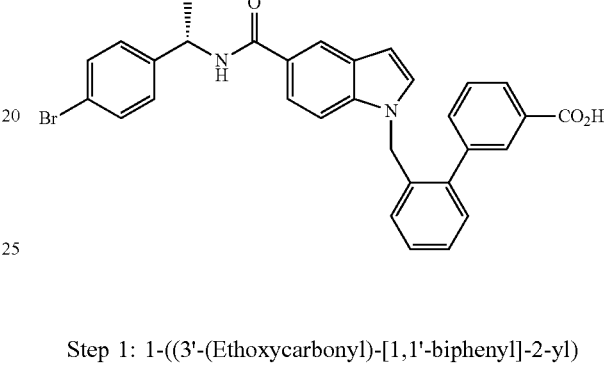

Step 1: 1-((3'-(Ethoxycarbonyl)-[1,1'-biphenyl]-2-yl)methyl)-1H-indole-5-carboxylic acid

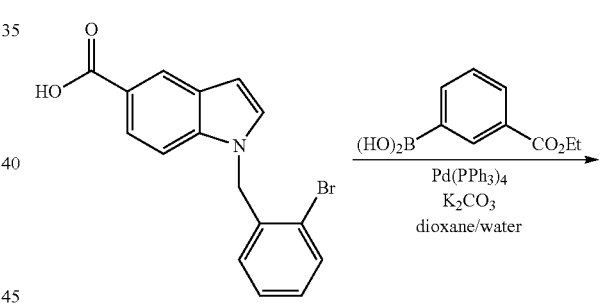

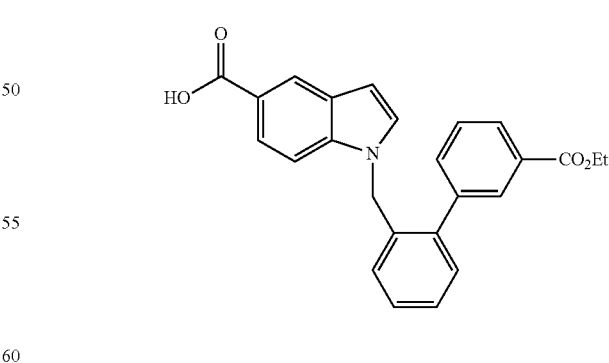

The title compound was prepared following the same protocol as described in Step 5, Example 38, using 1-(2-bromobenzyl)-1H-indole-5-carboxylic acid instead of the (S)-1-(4-bromobenzyl)-N-(1-(4-nitrophenyl)ethyl)-1H-indole-5-carboxamide and the (3-(ethoxycarbonyl)phenyl)boronic acid instead of the phenylboronic acid. ESI-MS (m/z): 400 [M+H]$^+$.

365

Step 2: (S)-Ethyl 2'-((5-((1-(4-bromophenyl)ethyl)carbamoyl)-1H-indol-1-yl)methyl)-[1,1'-biphenyl]-3-carboxylate

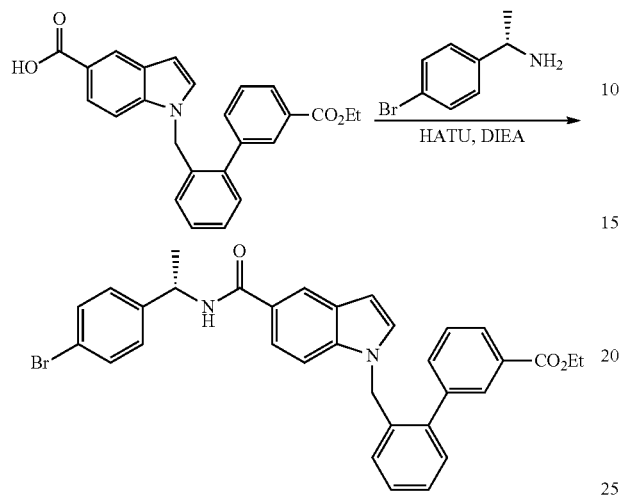

The title compound was prepared following the same protocol as described in Step 8, Example 1, using the 1-((3'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid.

Step 3: (S)-2'-((5-((1-(4-Bromophenyl)ethyl)carbamoyl)-1H-indol-1-yl)methyl)-[1,1'-biphenyl]-3-carboxylic acid

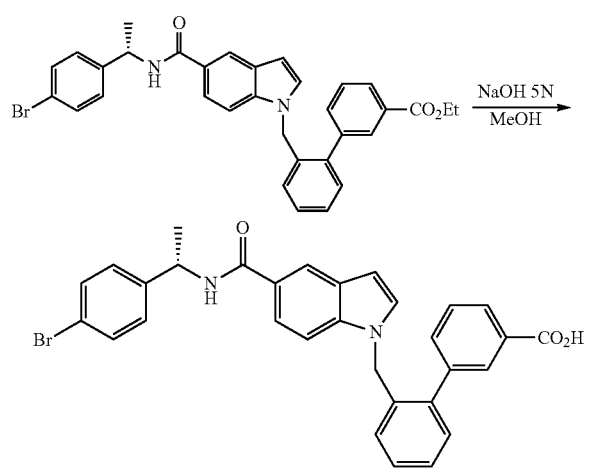

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 553/555 [M+H]$^+$.

366

Example 123: (S)-2'-((5-((1-(4-Nitrophenyl)ethyl)carbamoyl)-1H-indol-1-yl)methyl)-[1,1'-biphenyl]-3-carboxylic acid

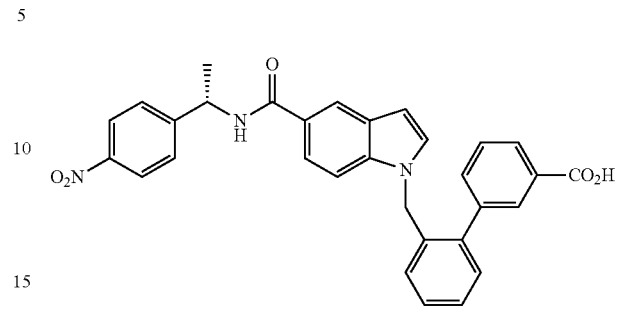

Step 1: (S)-Ethyl 2'-((5-((1-(4-nitrophenyl)ethyl)carbamoyl)-1H-indol-1-yl)methyl)-[1,1'-biphenyl]-3-carboxylate

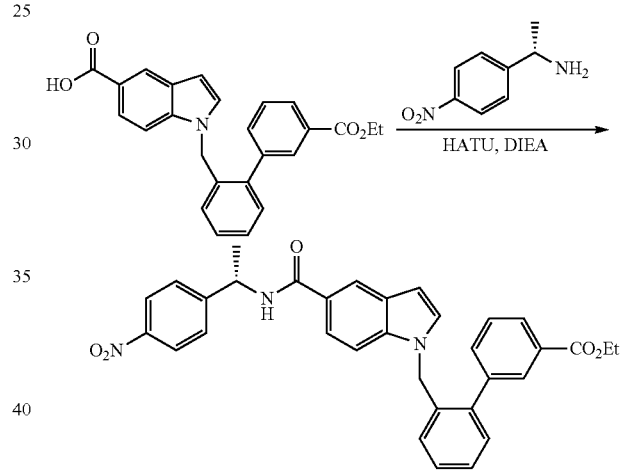

The title compound was prepared following the same protocol as described in Step 8, Example 1, using the 1-((3'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((5-((1-(4-Nitrophenyl)ethyl)carbamoyl)-1H-indol-1-yl)methyl)-[1,1'-biphenyl]-3-carboxylic acid

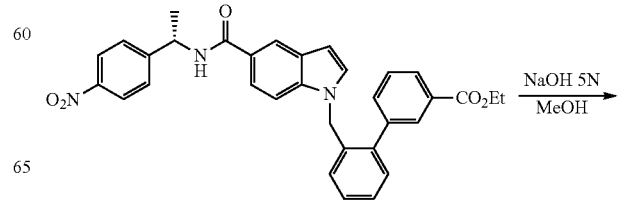

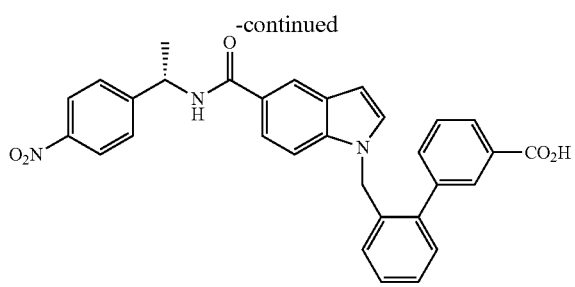

The title compound was prepared following the same protocol as described in Example 59, using (S)-ethyl 2'-((5-((1-(4-nitrophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 520 [M+H]⁺.

Example 124: (S)-2'-((5-((1-(4-Bromophenyl)ethyl)carbamoyl)-2,3-dimethyl-1H-indol-1-yl)methyl)-[1,1'-biphenyl]-3-carboxylic acid

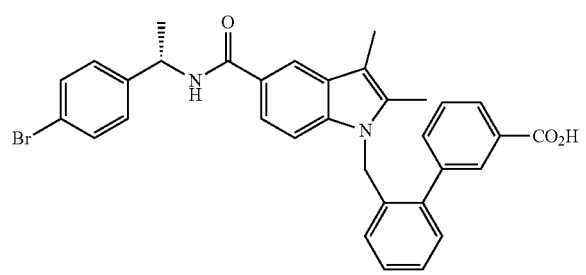 [SMILES: Cc1c(C)n(Cc2ccccc2-c2cccc(C(=O)O)c2)c2ccc(C(=O)N[C@@H](C)c3ccc(Br)cc3)cc12]

Step 1: Ethyl 1-(2-bromobenzyl)-2,3-dimethyl-1H-indole-5-carboxylate

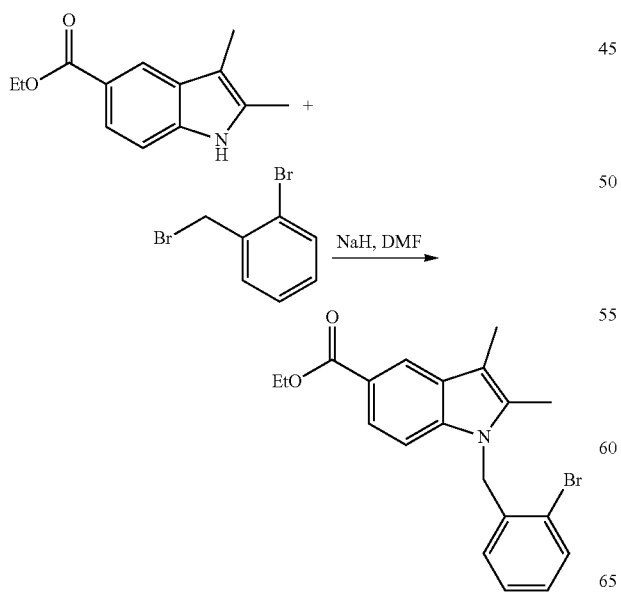

The title compound was prepared following the same protocol as described in Step 6, Example 1, using the 1-bromo-2-(bromomethyl)benzene instead of the tert-butyl 4'-(bromomethyl)biphenyl-2-carboxylate. ESI-MS (m/z): 386/388 [M+H]⁺.

Step 2: 1-(2-Bromobenzyl)-2,3-dimethyl-1H-indole-5-carboxylic acid

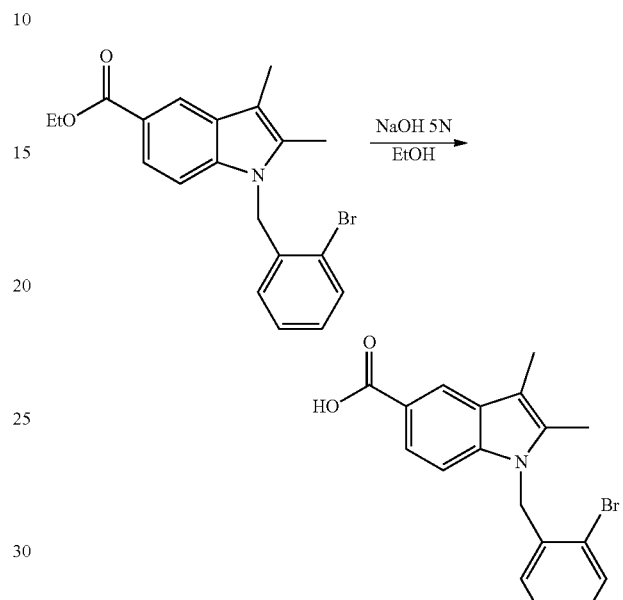

The title compound was prepared following the same protocol as described in Step 7, Example 1, using the ethyl 1-(2-bromobenzyl)-2,3-dimethyl-1H-indole-5-carboxylate instead of the ethyl 1-((2'-(tert-butoxycarbonyl)biphenyl-4-yl)methyl)-2,3-dimethyl-1H-indole-5-carboxylate. ESI-MS (m/z): 358/360 [M+H]⁺.

Step 3: 1-((3'-(Ethoxycarbonyl)-[1,1'-biphenyl]-2-yl)methyl)-2,3-dimethyl-1H-indole-5-carboxylic acid

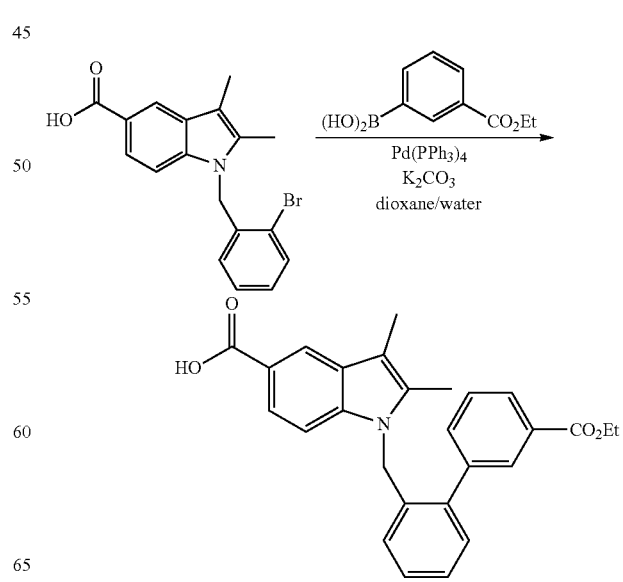

The title compound was prepared following the same protocol as described in Step 5, Example 38, using 1-(2-bromobenzyl)-2,3-dimethyl-1H-indole-5-carboxylic acid instead of the (S)-1-(4-bromobenzyl)-N-(1-(4-nitrophenyl)ethyl)-1H-indole-5-carboxamide and the (3-(ethoxycarbonyl)phenyl)boronic acid instead of the phenylboronic acid. ESI-MS (m/z): 428 [M+H]$^+$.

Step 4: (S)-Ethyl 2'-((5-((1-(4-bromophenyl)ethyl)carbamoyl)-2,3-dimethyl-1H-indol-1-yl)methyl)-[1,1'-biphenyl]-3-carboxylate

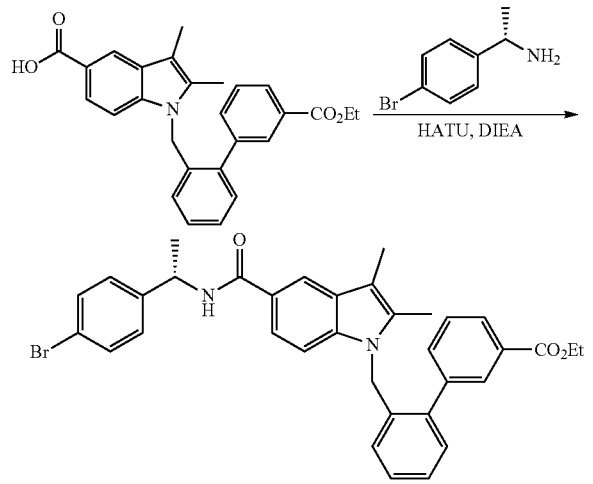

The title compound was prepared following the same protocol as described in Step 8, Example 1, using the 1-((3'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid.

Step 5: (S)-2'-((5-((1-(4-Bromophenyl)ethyl)carbamoyl)-2,3-dimethyl-1H-indol-1-yl)methyl)-[1,1'-biphenyl]-3-carboxylic acid

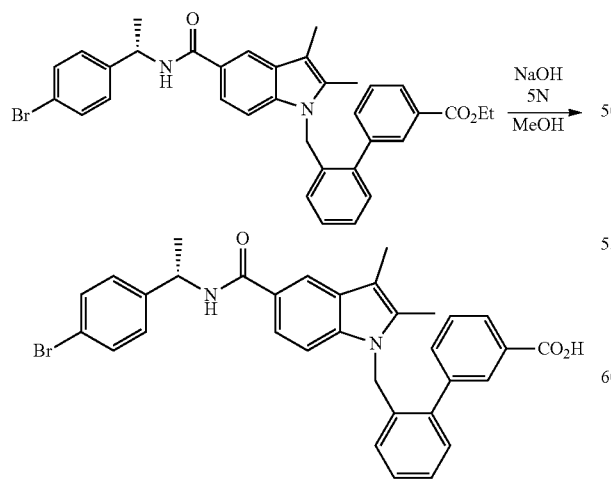

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 581/583 [M+H]$^+$.

Example 125: (S)-2'-((2,3-Dimethyl-5-((1-(4-nitrophenyl)ethyl)carbamoyl)-1H-indol-1-yl)methyl)-[1,1'-biphenyl]-3-carboxylic acid

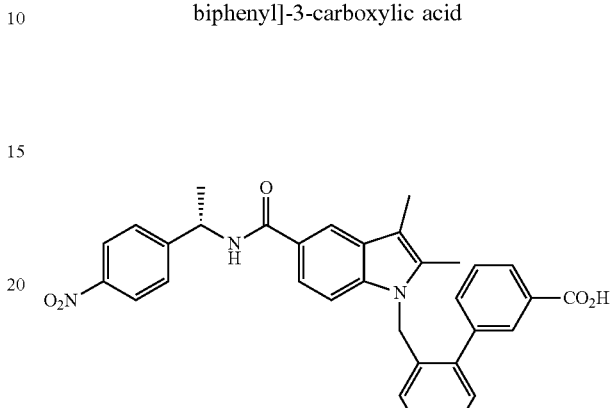

Step 1: (S)-Ethyl 2'-((2,3-dimethyl-5-((1-(4-nitrophenyl)ethyl)carbamoyl)-1H-indol-1-yl)methyl)-[1,1'-biphenyl]-3-carboxylate

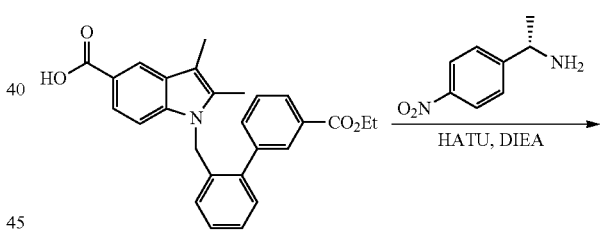

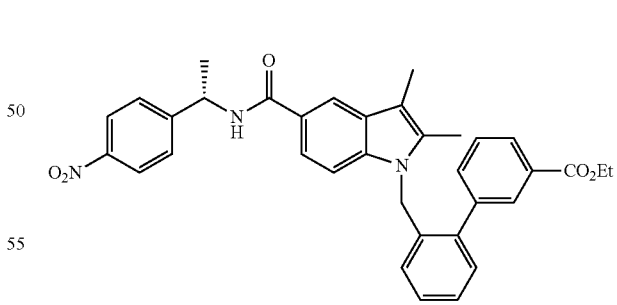

The title compound was prepared following the same protocol as described in Step 8, Example 1, using the 1-((3'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((2,3-Dimethyl-5-((1-(4-nitrophenyl)ethyl)carbamoyl)-1H-indol-1-yl)methyl)-[1,1'-biphenyl]-3-carboxylic acid

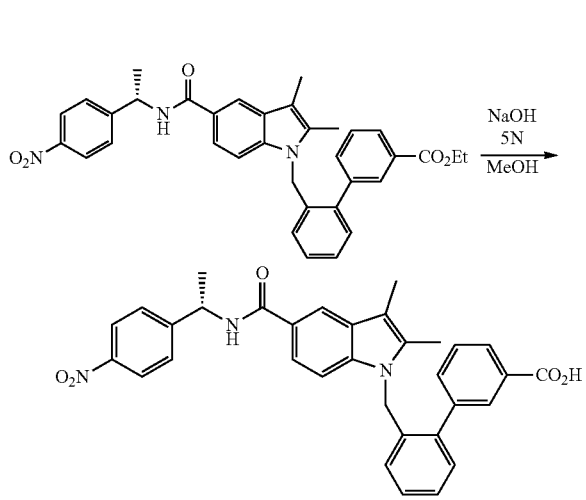

The title compound was prepared following the same protocol as described in Example 59, using (5)-ethyl 2'-((2,3-dimethyl-5-((1-(4-nitrophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 548 [M+H]+.

Example 126: 2'-((2,3-Dimethyl-5-((1-phenylpropyl)carbamoyl)-1H-indol-1-yl)methyl)-[1,1'-biphenyl]-3-carboxylic acid

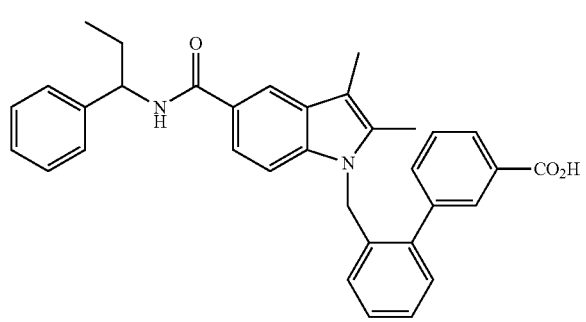

Step 1: Ethyl 2'-((2,3-dimethyl-5-((1-phenylpropyl)carbamoyl)-1H-indol-1-yl)methyl)-[1,1'-biphenyl]-3-carboxylate

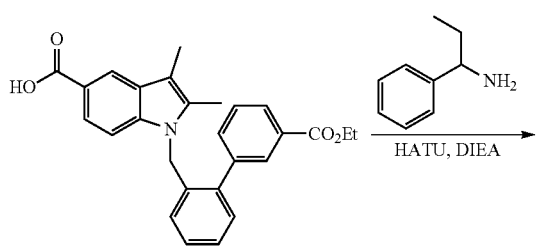

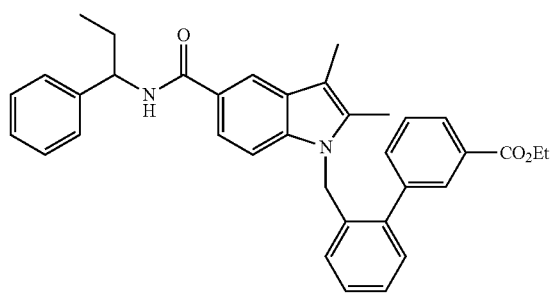

The title compound was prepared following the same protocol as described in Step 8, Example 1, using the 1-((3'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 2'-((2,3-Dimethyl-5-(1-phenylpropyl)carbamoyl)-1H-indol-1-yl)methyl)-[1,1'-biphenyl]-3-carboxylic acid

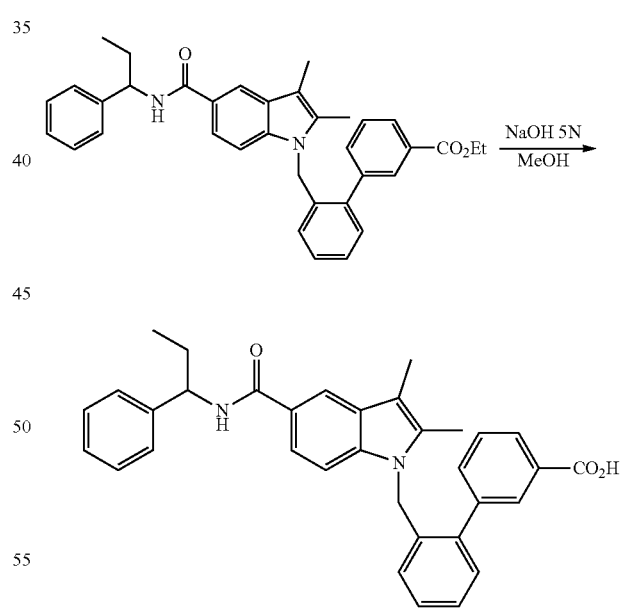

The title compound was prepared following the same protocol as described in Example 59, using ethyl 2'-((2,3-dimethyl-5-(1-phenylpropyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 517 [M+H]+.

Example 127: (S)-2'-((5-(((1-(4-bromophenyl)ethyl)carbamoyl)-2,3-dimethyl-1H-indol-1-yl)methyl)-[1,1'-biphenyl]-4-carboxylic acid

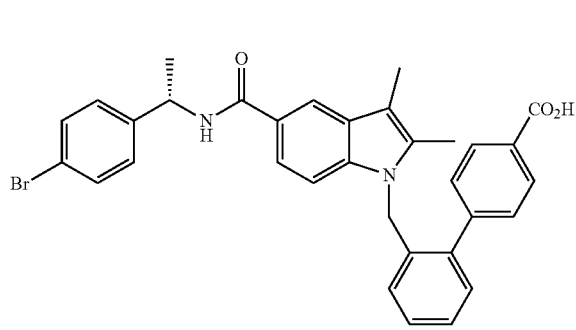 [SMILES: Cc1c(C)n(Cc2ccccc2-c2ccc(C(=O)O)cc2)c2ccc(C(=O)N[C@@H](C)c3ccc(Br)cc3)cc12]

Step 1: 1-((4'-(Ethoxycarbonyl)-[1,1'-biphenyl]-2-yl)methyl)-2,3-dimethyl-1H-indole-5-carboxylic acid

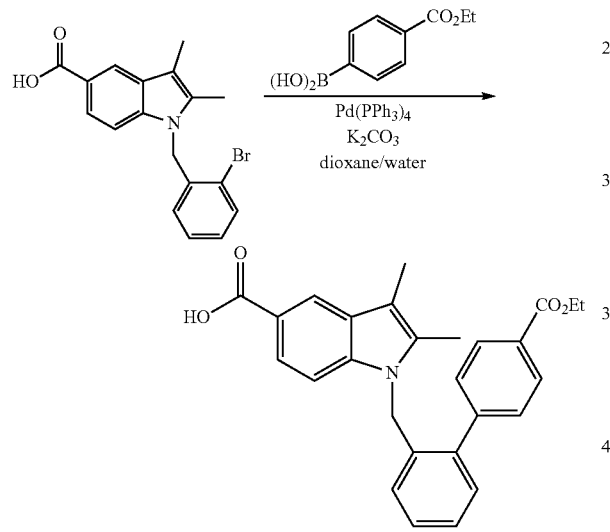

The title compound was prepared following the same protocol as described in Step 5, Example 38, using 1-(2-bromobenzyl)-2,3-dimethyl-1H-indole-5-carboxylic acid instead of the (S)-1-(4-bromobenzyl)-N-(1-(4-nitrophenyl)ethyl)-1H-indole-5-carboxamide and the (4-(ethoxycarbonyl)phenyl)boronic acid instead of the phenylboronic acid. ESI-MS (m/z): 428 [M+H]⁺.

Step 2: (S)-Ethyl 2'-((5-(((1-(4-bromophenyl)ethyl)carbamoyl)-2,3-dimethyl-1H-indol-1-yl)methyl)-[1,1'-biphenyl]-4-carboxylate

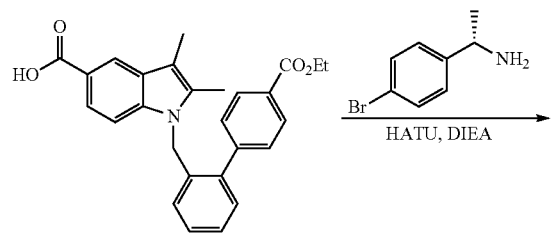

-continued

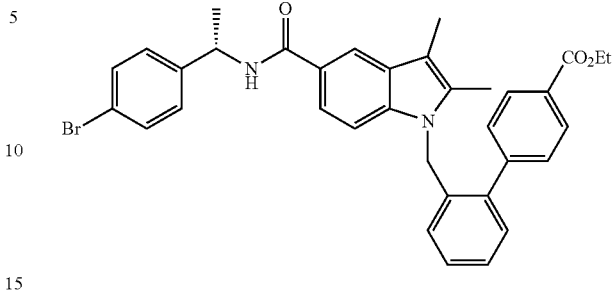

The title compound was prepared following the same protocol as described in Step 8, Example 1, using the 1-((4'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid.

Step 3: (S)-2'-((5-(((1-(4-Bromophenyl)ethyl)carbamoyl)-2,3-dimethyl-1H-indol-1-yl)methyl)-[1,1'-biphenyl]-4-carboxylic acid

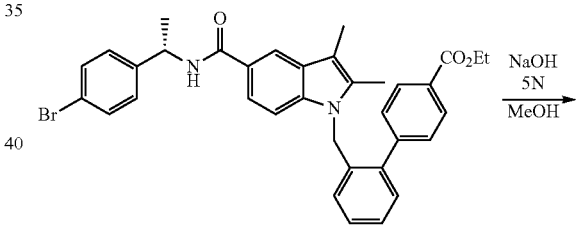

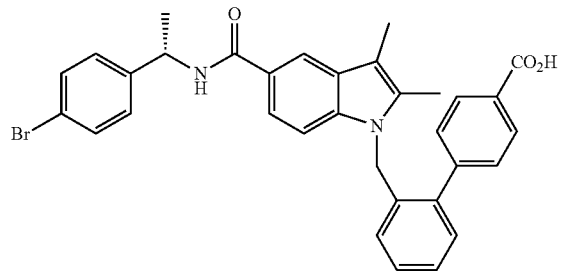

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-4-carboxylate instead of the (S)-ethyl 4'-((5-(((1-(4-nitrophenyl)ethyl)carbamoyl)-1H-indol-1-yl)methyl)-[1,1'-biphenyl]-4-carboxylate. ESI-MS (m/z): 581/583 [M+H]⁺.

Example 128: (S)-2'-((2,3-Dimethyl-5-((1-(4-nitrophenyl)ethyl)carbamoyl)-1H-indol-1-yl)methyl)-[1,1'-biphenyl]-4-carboxylic acid

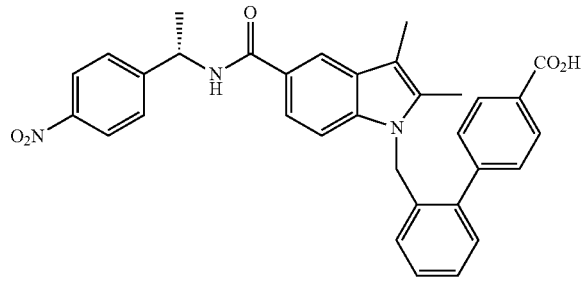 [SMILES: Cc1c(C)n(Cc2ccccc2-c2ccc(C(=O)O)cc2)c2ccc(C(=O)N[C@@H](C)c3ccc([N+](=O)[O-])cc3)cc12]

Step 1: (S)-Ethyl 2'-((2,3-dimethyl-5-((1-(4-nitrophenyl)ethyl)carbamoyl)-1H-indol-1-yl)methyl)-[1,1'-biphenyl]-4-carboxylate

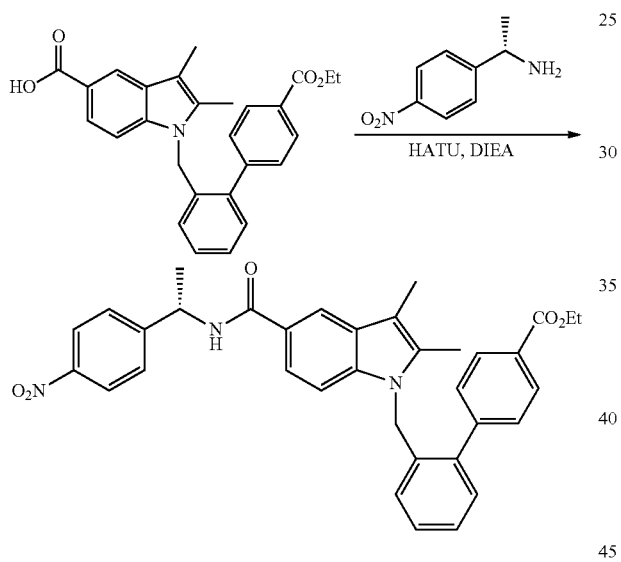

The title compound was prepared following the same protocol as described in Step 8, Example 1, using the 1-((4'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((2,3-Dimethyl-5-((1-(4-nitrophenyl)ethyl)carbamoyl)-1H-indol-1-yl)methyl)-[1,1'-biphenyl]-4-carboxylic acid

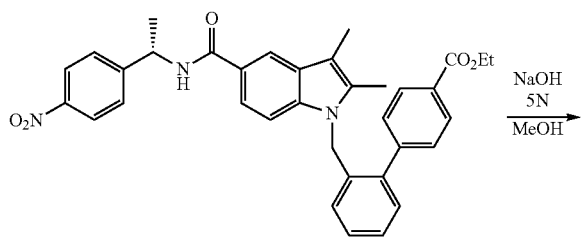

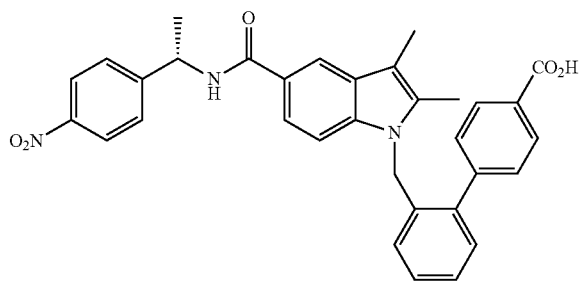

The title compound was prepared following the same protocol as described in Example 59, using (S)-ethyl 2'-((2,3-dimethyl-5-((1-(4-nitrophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 548 [M+H]$^+$.

Example 129: 2'-((2,3-Dimethyl-5-((1-phenylpropyl)carbamoyl)-1H-indol-1-yl)methyl)-[1,1'-biphenyl]-4-carboxylic acid

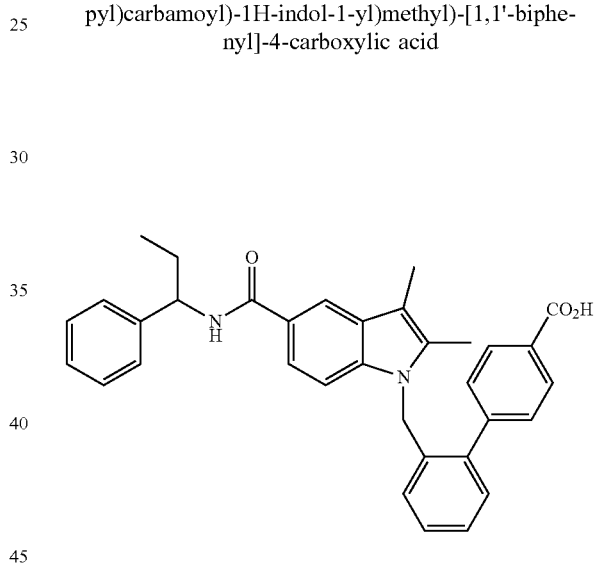

Step 1: Ethyl 2'-((2,3-dimethyl-5-((1-phenylpropyl)carbamoyl)-1H-indol-1-yl)methyl)-[1,1'-biphenyl]-4-carboxylate

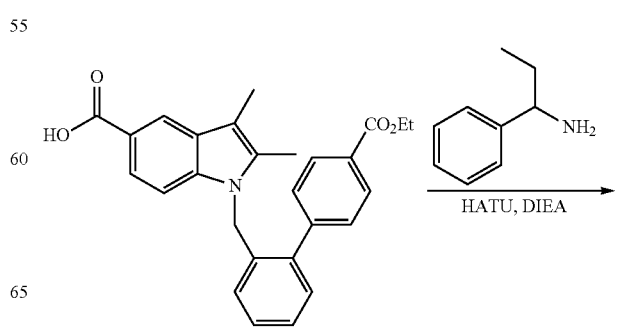

-continued

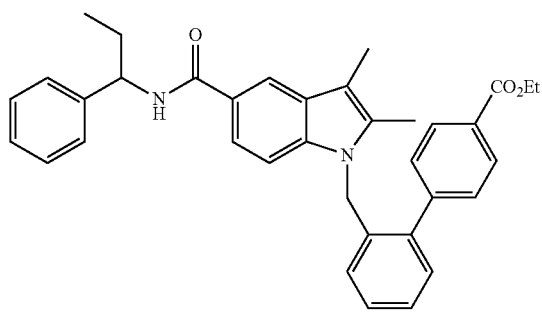

The title compound was prepared following the same protocol as described in Step 8, Example 1, using the 1-((4'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 2'-((2,3-Dimethyl-5-(1-phenylpropyl)carbamoyl)-1H-indol-1-yl)methyl)-[1,1'-biphenyl]-4-carboxylic acid

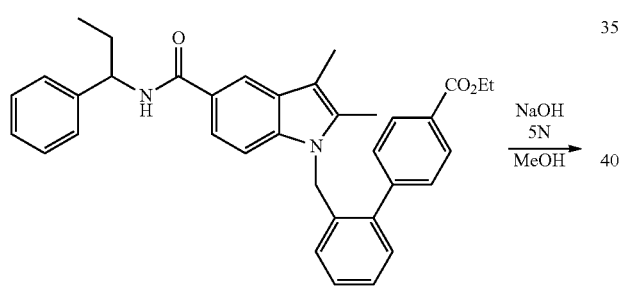

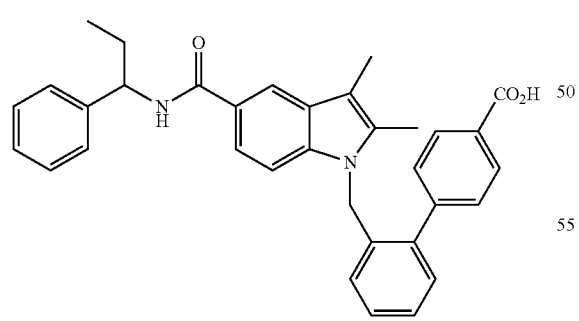

The title compound was prepared following the same protocol as described in Example 59, using ethyl 2'-((2,3-dimethyl-5-(1-phenylpropyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 517 [M+H]$^+$.

Example 130: (S)-4'-((5-((1-(4-Bromophenyl)ethyl)carbamoyl)-1H-indol-1-yl)methyl)-[1,1'-biphenyl]-2-carboxylic acid

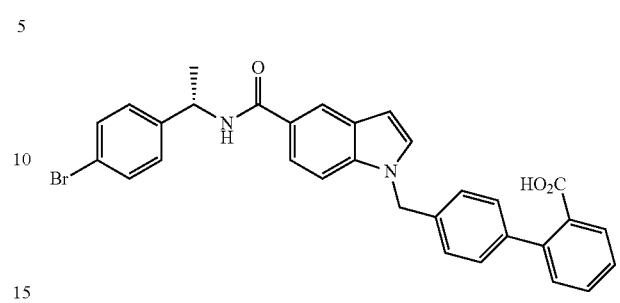

Step 1: 1-((2'-(tert-Butoxycarbonyl)-[1,1'-biphenyl]-4-yl)methyl)-1H-indole-5-carboxylic acid

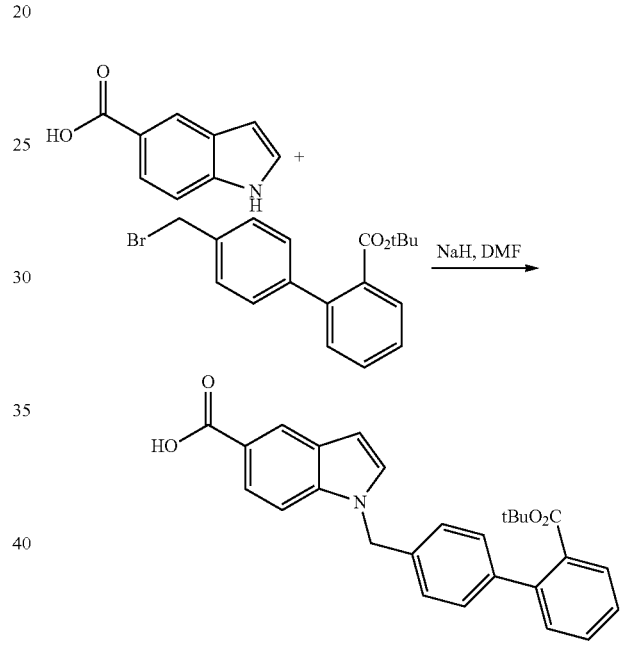

The title compound was prepared following the same protocol as described in Step 2, Example 38, using 1H-indole-5-carboxylic acid instead of the methyl 1H-indole-5-carboxylate, and the tert-butyl 4'-(bromomethyl)biphenyl-2-carboxylate instead of the 1-bromo-4-(bromomethyl)benzene. ESI-MS (m/z): 428 [M+H]$^+$.

Step 2: (S)-tert-Butyl 4'-((5-((1-(4-bromophenyl)ethyl)carbamoyl)-1H-indol-1-yl)methyl)-[1,1'-biphenyl]-2-carboxylate

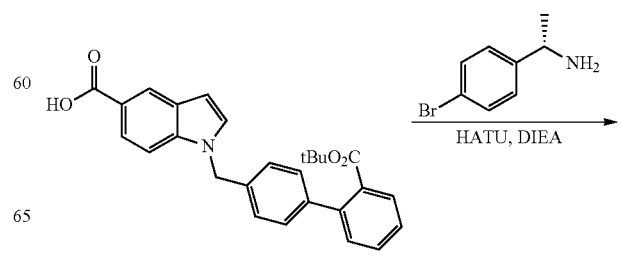

379

-continued

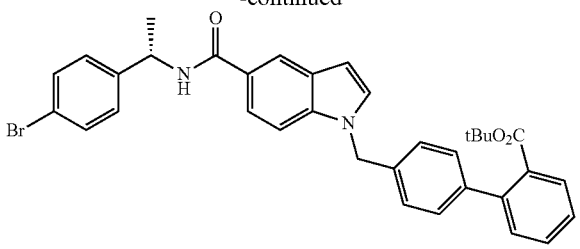

The title compound was prepared following the same protocol as described in Step 8, Example 1, using the 1-((2'-(tert-butoxycarbonyl)-[1,1'-biphenyl]-4-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid.

Step 3: (S)-4'-((5-((1-(4-Bromophenyl)ethyl)carbamoyl)-1H-indol-1-yl)methyl)-[1,1'-biphenyl]-2-carboxylic acid

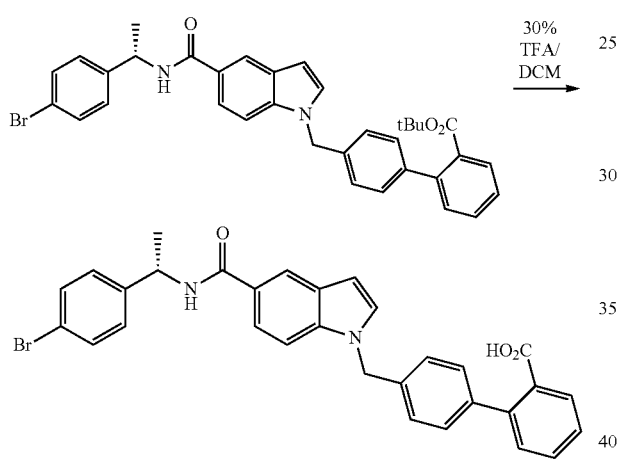

The title compound was prepared following the same protocol as described in Step 9, Example 1, using (S)-tert-Butyl 4'-((5-((1-(4-bromophenyl)ethyl)carbamoyl)-1H-indol-1-yl)methyl)-[1,1'-biphenyl]-2-carboxylate instead of the (S)-tert-Butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 553/555 [M+H]$^+$.

Example 131: 4'-((5-((1-Phenylpropyl)carbamoyl)-1H-indol-1-yl)methyl)-[1,1'-biphenyl]-2-carboxylic acid

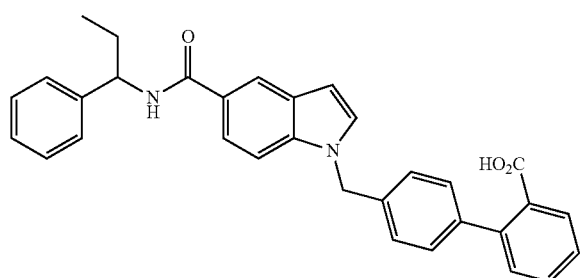

380

Step 1: tert-Butyl 4'-((5-((1-phenylpropyl)carbamoyl)-1H-indol-1-yl)methyl)-[1,1'-biphenyl]-2-carboxylate

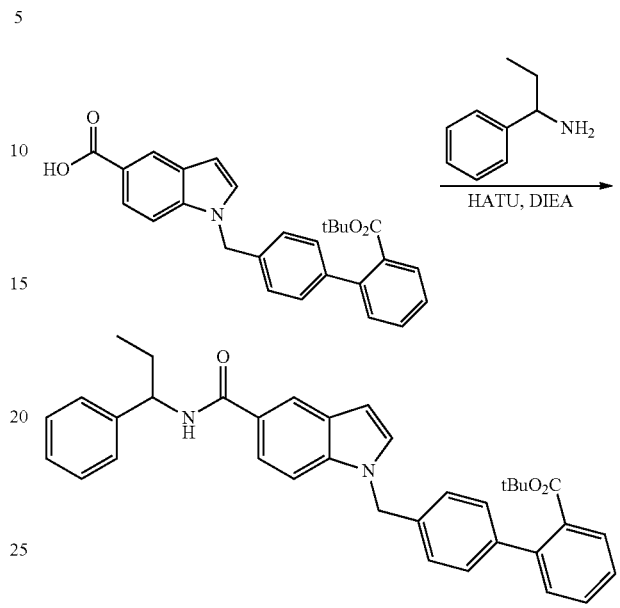

The title compound was prepared following the same protocol as described in Step 8, Example 1, using the 1-((2'-(tert-butoxycarbonyl)-[1,1'-biphenyl]-4-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 4'-((5-(1-Phenylpropyl)carbamoyl)-1H-indol-1-yl)methyl)-[1,1'-biphenyl]-2-carboxylic acid

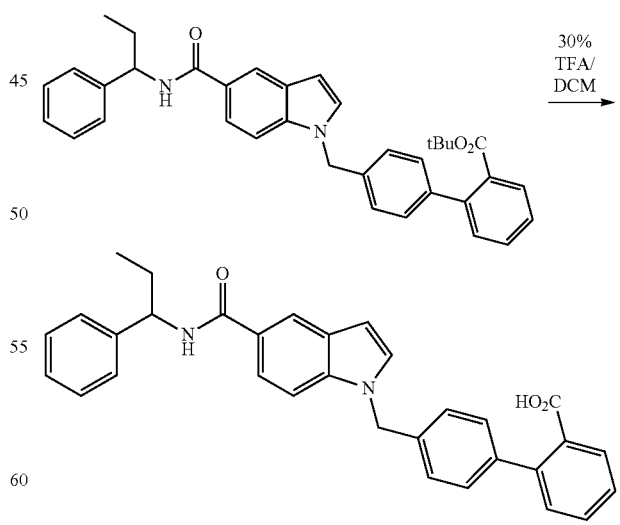

The title compound was prepared following the same protocol as described in Step 9, Example 1, using tert-butyl 4'-((5-(1-phenylpropyl)carbamoyl)-1H-indol-1-yl)methyl)-[1,1'-biphenyl]-2-carboxylate instead of the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 489 [M+H]+.

Example 132: (S)-4'-((5-((1-(4-Bromophenyl)ethyl)carbamoyl)-3-methyl-1H-indol-1-yl)methyl)-[1,1'-biphenyl]-2-carboxylic acid

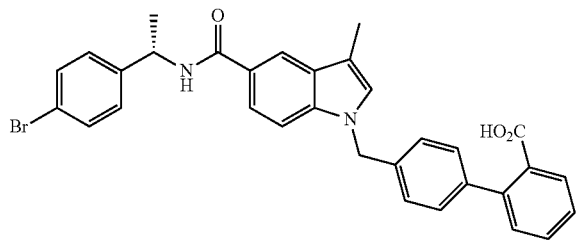 [SMILES: Cc1cn(Cc2ccc(-c3ccccc3C(=O)O)cc2)c2ccc(C(=O)N[C@@H](C)c3ccc(Br)cc3)cc12]

Step 1: Methyl 3-formyl-1H-indole-5-carboxylate

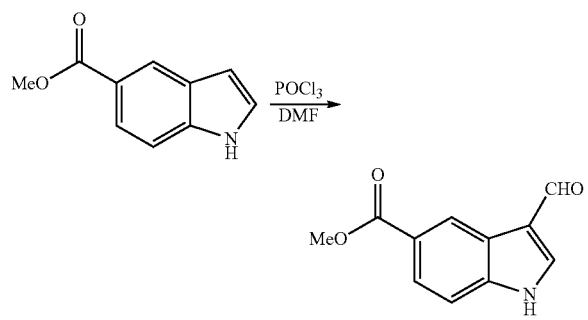

To a solution of anhydrous DMF (12 mL) under argon at 0° C. was added POCl₃ (446 µL, 4.9 mmol). The reaction mixture has been stirred at 0° C. for 5 min. The methyl 1H-indole-5-carboxylate (854 mg, 4.9 mmol) in solution in DMF was added dropwise. The resulting mixture has been heated at 120° C. for 1 h. Then, it is quenched by addition of a saturated solution of NaHCO₃ (2 mL). The mixture is diluted with DCM, washed with brine, dried over MgSO₄ and concentrated. The product is precipitated in hexane/diethyl ether (1/1) to yield a red powder (896 mg, 4.4 mmol, 91%). ESI-MS (m/z): 204 [M+H]+.

Step 2: Methyl 3-methyl-1H-indole-5-carboxylate

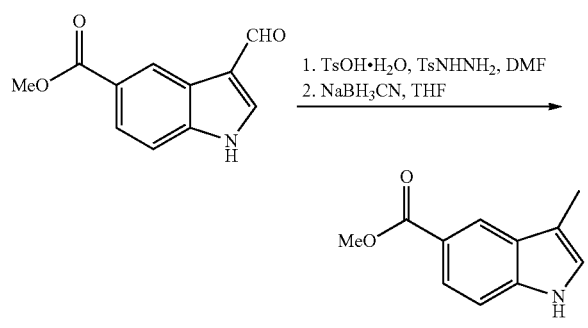

To a solution of the methyl 3-formyl-1H-indole-5-carboxylate (893 mg, 4.4 mmol) in DMF (20 mL) was added the p-toluenesulfonic acid monohydrate (125 mg, 0.7 mmol) and the p-toluenesulfonyl hydrazide (982 mg, 5.3 mmol). The solution has been heated for 20 min at 100° C. The resulting mixture was diluted with ethyl acetate, washed with brine, dried over MgSO₄ and concentrated. The crude product is dissolved in THF (40 mL) and NaBH₃CN (1.1 g, 17.6 mmol) was added. The solution has been heated for 8 h at 75° C. The resulting mixture was diluted with ethyl acetate, washed with a solution of 0.5 N HCl, a saturated solution of NaHCO₃ and brine, dried over MgSO₄ and concentrated. The crude product was purified by flash chromatography (Hexane/AcOEt, from 0 to 30%) to yield a white powder (500 mg, 2.6 mmol, 60%). ESI-MS (m/z): 190 [M+H]+.

Step 3: Methyl 1-((2'-(tert-butoxycarbonyl)-[1,1'-biphenyl]-4-yl)methyl)-3-methyl-1H-indole-5-carboxylate

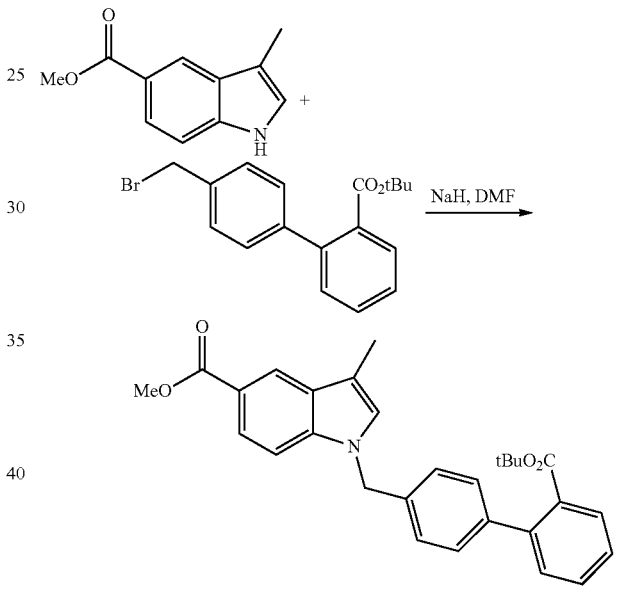

The title compound was prepared following the same protocol as described in Step 2, Example 38, using the methyl 3-methyl-1H-indole-5-carboxylate instead of the methyl 1H-indole-5-carboxylate, and the tert-butyl 4'-(bromomethyl)biphenyl-2-carboxylate instead of the 1-bromo-4-(bromomethyl)benzene. ESI-MS (m/z): 456 [M+H]+.

Step 4: 1-((2'-(tert-Butoxycarbonyl)-[1,1'-biphenyl]-4-yl)methyl)-3-methyl-1H-indole-5-carboxylic acid

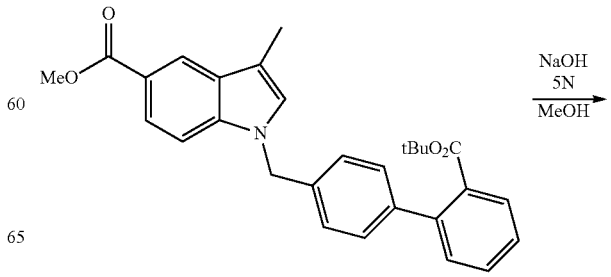

383

-continued

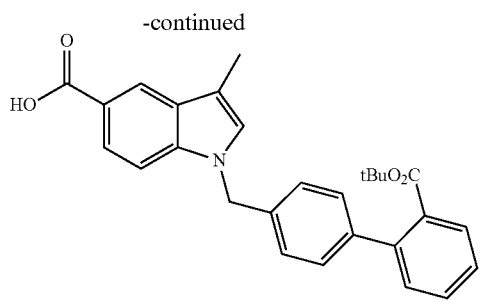

The title compound was prepared following the same protocol as described in Step 3, Example 38, using the methyl 1-((2'-(tert-butoxycarbonyl)-[1,1'-biphenyl]-4-yl)methyl)-3-methyl-1H-indole-5-carboxylate instead of the methyl 1-(4-bromobenzyl)-1H-indole-5-carboxylate. ESI-MS (m/z): 442 [M+H]+.

Step 5: (S)-tert-Butyl 4'-((5-((1-(4-bromophenyl)ethyl)carbamoyl)-3-methyl-1H-indol-1-yl)methyl)-[1,1'-biphenyl]-2-carboxylate

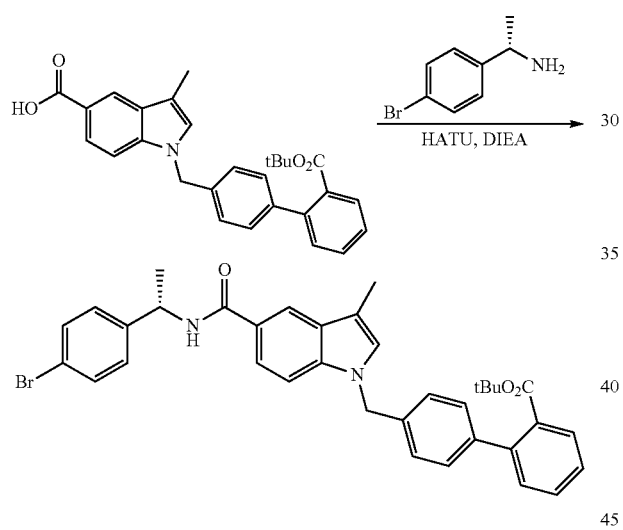

The title compound was prepared following the same protocol as described in Step 8, Example 1, using the 1-((2'-(tert-butoxycarbonyl)-[1,1'-biphenyl]-4-yl)methyl)-3-methyl-1H-indole-5-carboxylic acid instead of the 1-((2'-(tert-Butoxycarbonyl)biphenyl-4-yl)methyl)-2,3-dimethyl-1H-indole-5-carboxylic acid.

Step 6: (S)-4'-((5-((1-(4-Bromophenyl)ethyl)carbamoyl)-3-methyl-1H-indol-1-yl)methyl)-[1,1'-biphenyl]-2-carboxylic acid

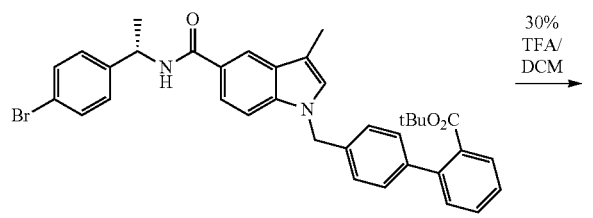

384

-continued

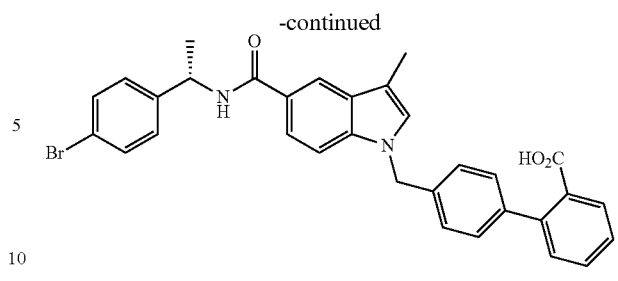

The title compound was prepared following the same protocol as described in Step 9, Example 1, using the (S)-tert-Butyl 4'-((5-((1-(4-bromophenyl)ethyl)carbamoyl)-3-methyl-1H-indol-1-yl)methyl)-[1,1'-biphenyl]-2-carboxylate instead of the (S)-tert-Butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 566/568 [M+H]+.

Example 133: 4'-((3-Methyl-5-((1-phenylpropyl)carbamoyl)-1H-indol-1-yl)methyl)-[1,1'-biphenyl]-2-carboxylic acid

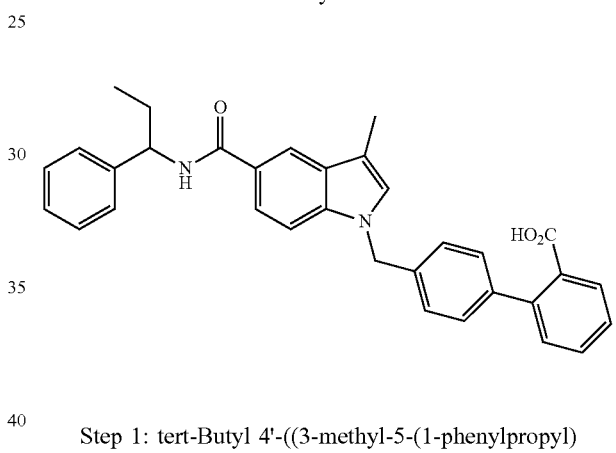

Step 1: tert-Butyl 4'-((3-methyl-5-(1-phenylpropyl)carbamoyl)-1H-indol-1-yl)methyl)-[1,1'-biphenyl]-2-carboxylate

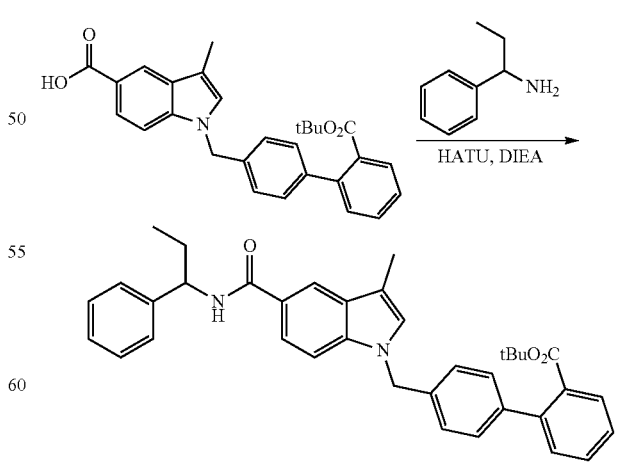

The title compound was prepared following the same protocol as described in Step 8, Example 1, using the 1-((2'-(tert-Butoxycarbonyl)biphenyl-4-yl)methyl)-3- methyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 4'-((3-Methyl-5-((1-phenylpropyl)carbamoyl)-1H-indol-1-yl)methyl)-[1,1'-biphenyl]-2-carboxylic acid The title compound was prepared following the same protocol as described in Step 9, Example 1, using the tert-Butyl 4'-((3-methyl-5-(1-phenylpropyl)carbamoyl)-1H-indol-1-yl)methyl)-[1,1'-biphenyl]-2-carboxylate instead of the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 559 [M+H]⁺.

Example 134: (S)-4'-((3-Methyl-5-((1-(4-nitrophenyl)ethyl)carbamoyl)-1H-indol-1-yl)methyl)-[1,1'-biphenyl]-2-carboxylic acid

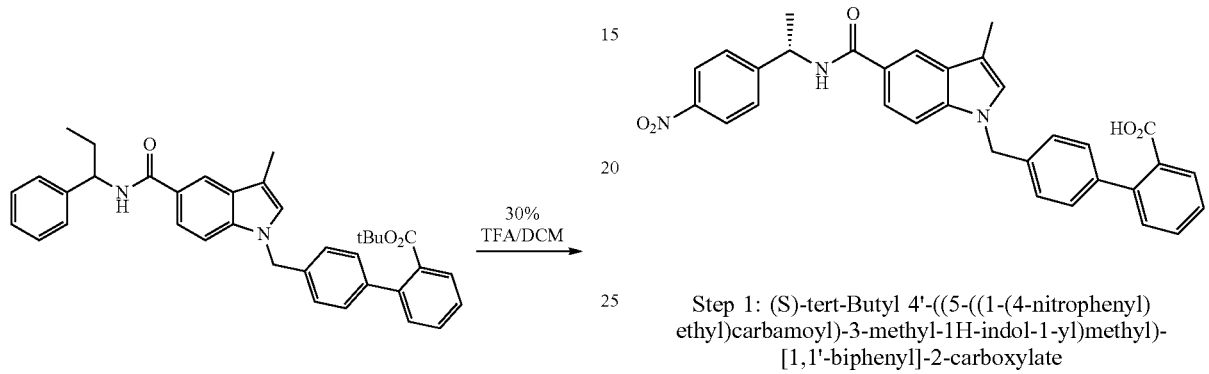

Step 1: (S)-tert-Butyl 4'-((5-((1-(4-nitrophenyl)ethyl)carbamoyl)-3-methyl-1H-indol-1-yl)methyl)-[1,1'-biphenyl]-2-carboxylate

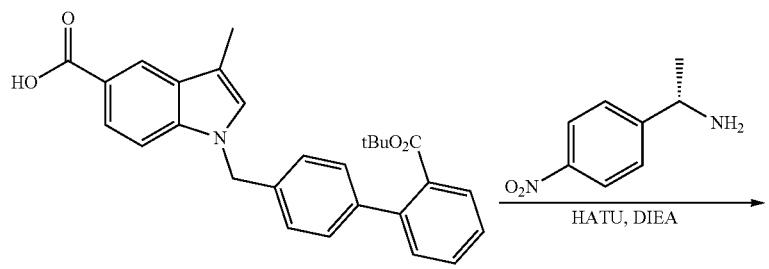

-continued

The title compound was prepared following the same protocol as described in Step 8, Example 1, using the 1-((2'-(tert-butoxycarbonyl)-[1,1'-biphenyl]-4-yl)methyl)-3-methyl-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-4'-((3-methyl-5-((1-(4-nitrophenyl)ethyl)carbamoyl)-1H-indol-1-yl)methyl)-[1,1'-biphenyl]-2-carboxylic acid

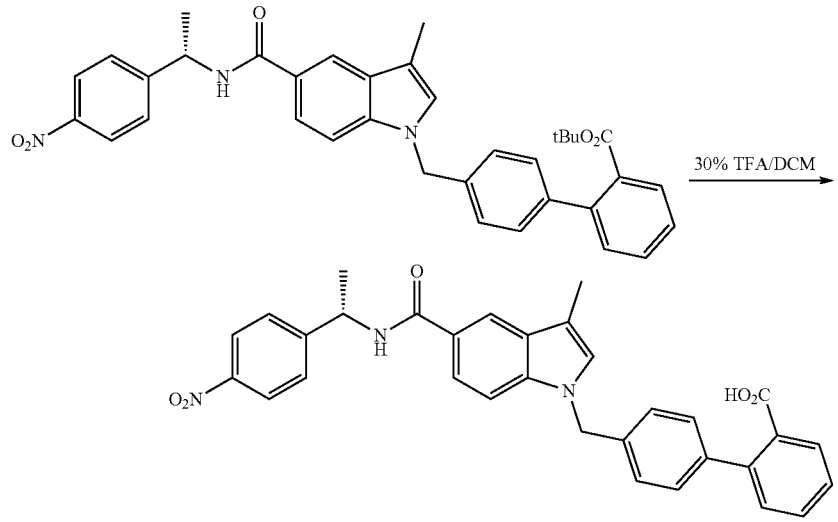

The title compound was prepared following the same protocol as described in Step 9, Example 1, using the (S)-tert-Butyl 4'-((5-((1-(4-nitrophenyl)ethyl)carbamoyl)-3-methyl-1H-indol-1-yl)methyl)-[1,1'-biphenyl]-2-carboxylate instead of the (S)-tert-Butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 533 [M+H]$^+$.

Example 135: (S)-4'-((5-((1-(4-Bromophenyl)ethyl)carbamoyl)-2-methyl-1H-indol-1-yl)methyl)-[1,1'-biphenyl]-2-carboxylic acid

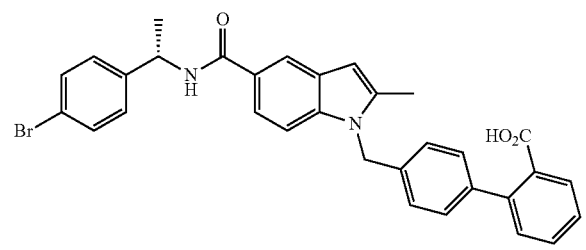 [SMILES: Cc1cc2cc(C(=O)N[C@@H](C)c3ccc(Br)cc3)ccc2n1Cc1ccc(-c2ccccc2C(=O)O)cc1]

Step 1: Methyl 1-((2'-(tert-butoxycarbonyl)-[1,1'-biphenyl]-4-yl)methyl)-2-methyl-1H-indole-5-carboxylate

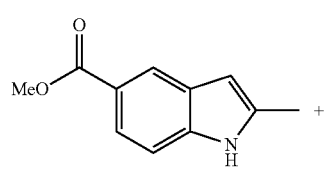 +

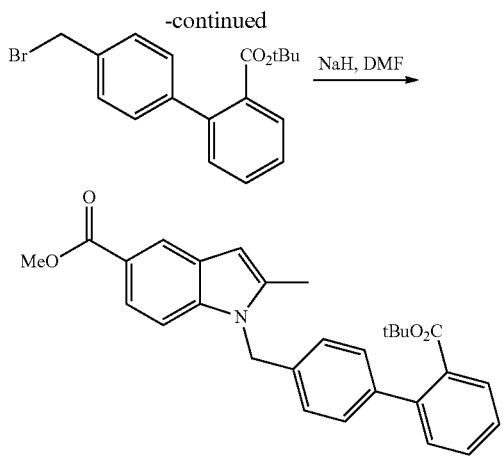

The title compound was prepared following the same protocol as described in Step 2, Example 38, using the methyl 2-methyl-1H-indole-5-carboxylate instead of the methyl 1H-indole-5-carboxylate, and the tert-butyl 4'-(bromomethyl)biphenyl-2-carboxylate instead of the 1-bromo-4-(bromomethyl)benzene. ESI-MS (m/z): 456 [M+H]$^+$.

Step 2: 1-((2'-(tert-Butoxycarbonyl)-[1,1'-biphenyl]-4-yl)methyl)-2-methyl-1H-indole-5-carboxylic acid

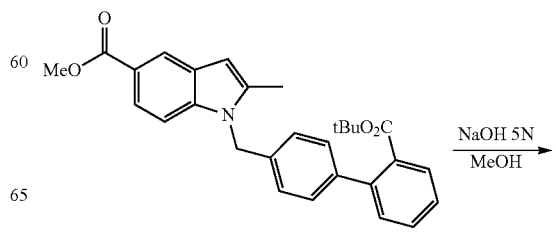

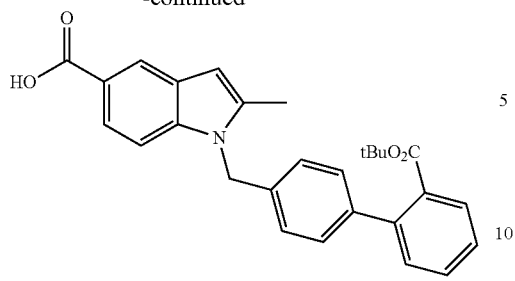

The title compound was prepared following the same protocol as described in Step 3, Example 38, using the methyl 1-((2'-(tert-butoxycarbonyl)-[1,1'-biphenyl]-4-yl)methyl)-2-methyl-1H-indole-5-carboxylate instead of the methyl 1-(4-bromobenzyl)-1H-indole-5-carboxylate. ESI-MS (m/z): 442 [M+H]$^+$.

Step 3: (S)-tert-Butyl 4'-((5-((1-(4-bromophenyl)ethyl)carbamoyl)-2-methyl-1H-indol-1-yl)methyl)-[1,1'-biphenyl]-2-carboxylate

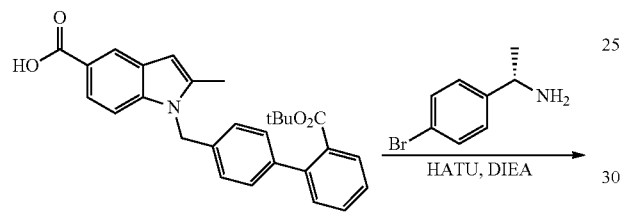

The title compound was prepared following the same protocol as described in Step 8, Example 1, using the 1-((2'-(tert-butoxycarbonyl)-[1,1'-biphenyl]-4-yl)methyl)-2-methyl-1H-indole-5-carboxylic acid instead of the 1-((2'-(tert-Butoxycarbonyl)biphenyl-4-yl)methyl)-2,3-dimethyl-1H-indole-5-carboxylic acid.

Step 4: (S)-4'-((5-((1-(4-Bromophenyl)ethyl)carbamoyl)-2-methyl-1H-indol-1-yl)methyl)-[1,1'-biphenyl]-2-carboxylic acid

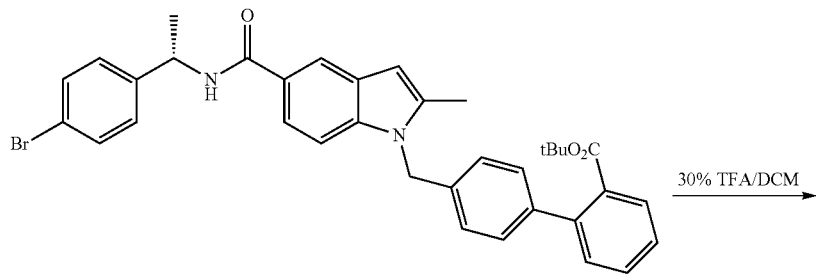

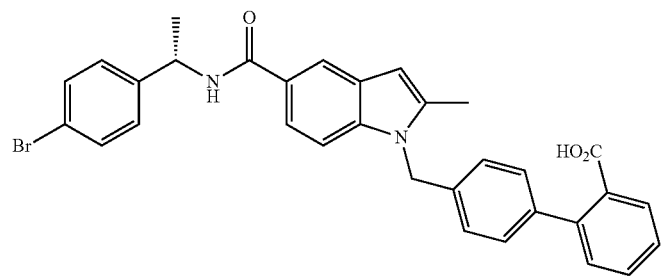

The title compound was prepared following the same protocol as described in Step 9, Example 1, using the (S)-tert-Butyl 4'-((5-((1-(4-bromophenyl)ethyl)carbamoyl)-2-methyl-1H-indol-1-yl)methyl)-[1,1'-biphenyl]-2-carboxylate instead of the (S)-tert-Butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 566/568 [M+H]+.

Example 136: 4'-((2-Methyl-5-((1-phenylpropyl)carbamoyl)-1H-indol-1-yl)methyl)-[1,1'-biphenyl]-2-carboxylic acid Step 1: tert-Butyl 4'-((2-methyl-5-(1-phenylpropyl)carbamoyl)-1H-indol-1-yl)methyl)-[1,1'-biphenyl]-2-carboxylate

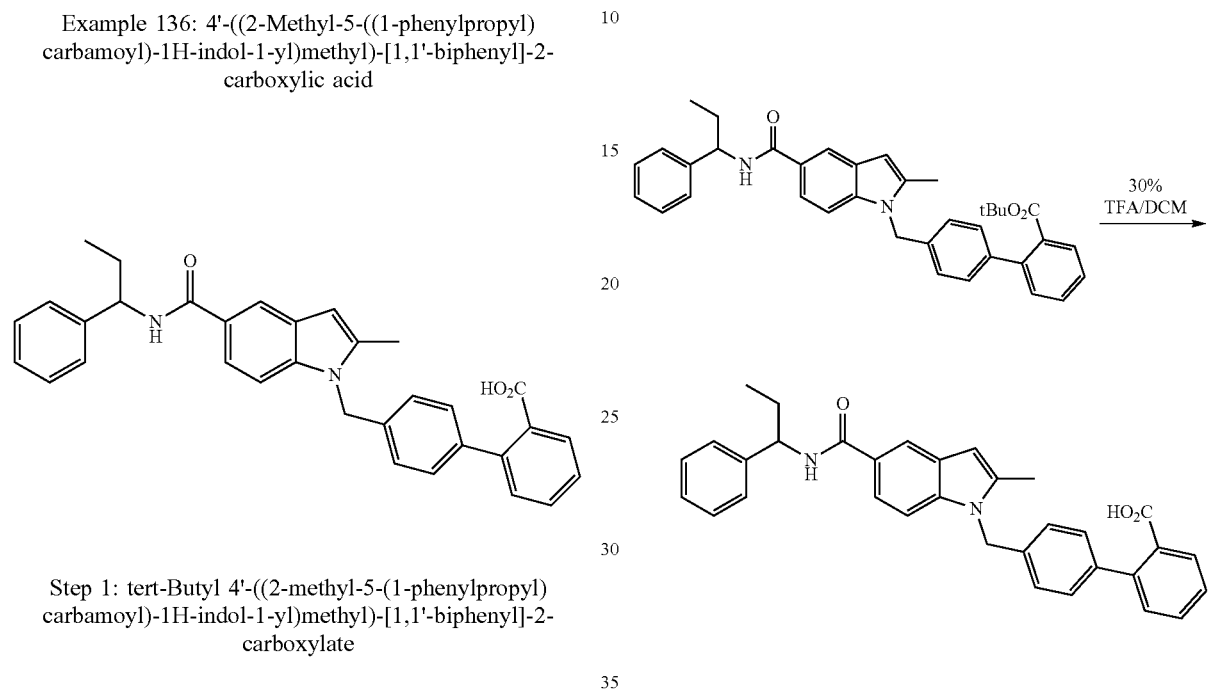

The title compound was prepared following the same protocol as described in Step 8, Example 1, using the 1-((2'-(tert-Butoxycarbonyl)biphenyl-4-yl)methyl)-2-methyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 4'-((2-Methyl-5-((1-phenylpropyl)carbamoyl)-1H-indol-1-yl)methyl)-[1,1'-biphenyl]-2-carboxylic acid

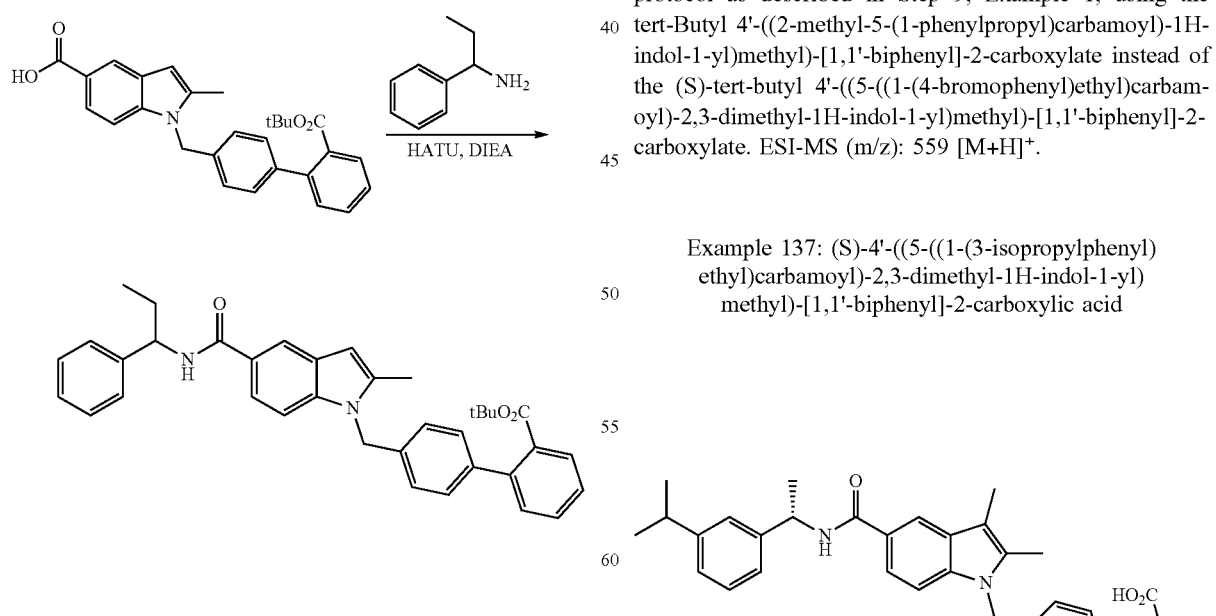

The title compound was prepared following the same protocol as described in Step 9, Example 1, using the tert-Butyl 4'-((2-methyl-5-(1-phenylpropyl)carbamoyl)-1H-indol-1-yl)methyl)-[1,1'-biphenyl]-2-carboxylate instead of the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 559 [M+H]+.

Example 137: (S)-4'-((5-((1-(3-isopropylphenyl)ethyl)carbamoyl)-2,3-dimethyl-1H-indol-1-yl)methyl)-[1,1'-biphenyl]-2-carboxylic acid Step 1: (S)-tert-butyl 4'-((2,3-dimethyl-5-((1-(3-(prop-1-en-2-yl)phenyl)ethyl)carbamoyl)-1H-indol-1-yl)methyl)-[1,1'-biphenyl]-2-carboxylate

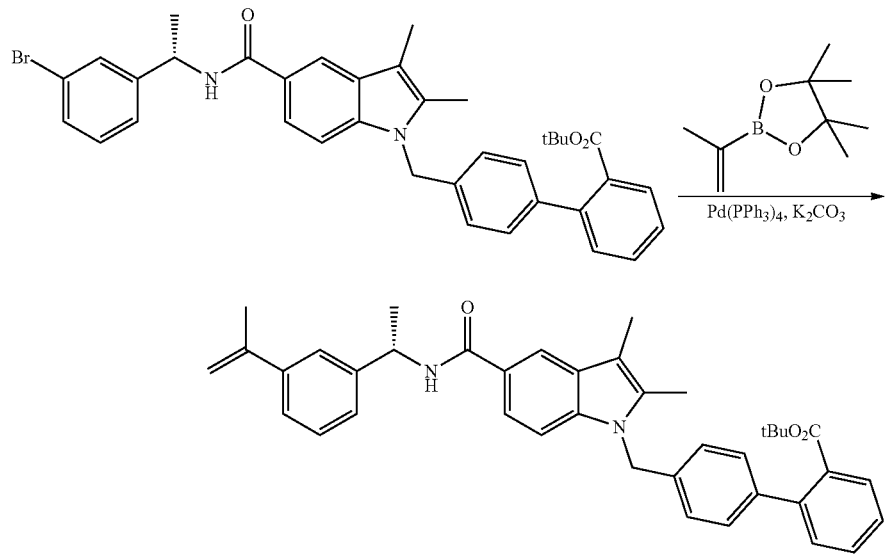

A solution of (S)-tert-butyl 4'-((5-((1-(3-bromophenyl)ethyl)carbamoyl)-2,3-dimethyl-1H-indol-1-yl)methyl)-[1,1'-biphenyl]-2-carboxylate (83 mg, 0.13 mmol, 1 equiv.), K$_2$CO$_3$ (36 mg, 0.26 mmol, 2 equiv.) and Pd(PPh$_3$)$_4$ (15 mg, 0.013 mmol, 0.1 equiv.) in dioxane/water (1.2 mL/0.3 mL) was degassed with argon. The isopropenylboronic acid pinacol ester (49 µL, 0.26 mmol, 2 equiv.) was added and the solution was heated at 100° C. for 1 h under microwave irradiation. The resulting solution was diluted with ethyl acetate, washed with a 0.5 N HCl solution, saturated aqueous NaHCO$_3$ and brine, and then dried over Na$_2$SO$_4$. The obtained oil was used without further purification. ESI-MS (m/z): 599 [M+H]$^+$.

Step 2: (S)-tert-butyl 4'-((5-((1-(3-isopropylphenyl)ethyl)carbamoyl)-2,3-dimethyl-1H-indol-1-yl)methyl)-[1,1'-biphenyl]-2-carboxylate

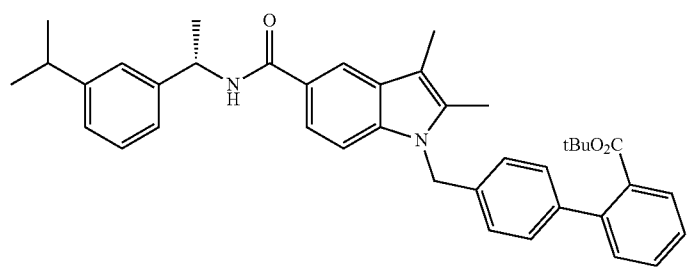

A solution of (S)-tert-butyl 4'-((2,3-dimethyl-5-((1-(3-(prop-1-en-2-yl)phenyl)ethyl)carbamoyl)-1H-indol-1-yl)methyl)-[1,1'-biphenyl]-2-carboxylate (0.13 mmol, 1 equiv.) in ethanol (5 mL) was degassed with argon. A hint of Pd/C 10% was added to the solution. The suspension was stirred at rt for 5 h under H$_2$ bubbling. The resulting mixture was then filtered and concentrated. The obtained oil was used without further purification. ESI-MS (m/z): 601 [M+H]$^+$.

Step 3: (S)-4'-((5-((1-(3-isopropylphenyl)ethyl)carbamoyl)-2,3-dimethyl-1H-indol-1-yl)methyl)-[1,1'-biphenyl]-2-carboxylic acid

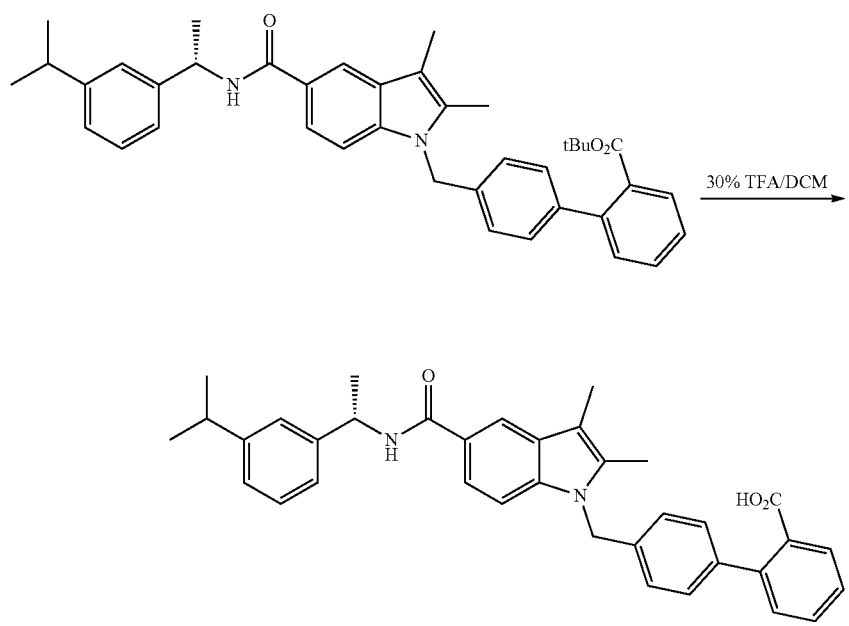

The title compound was prepared following the same general protocol as described in Step 9, Example 1. ESI-MS (m/z): 545 [M+H]$^+$.

Example 138: (S)-4'-((5-((1-(3-(tert-butyl)phenyl)ethyl)carbamoyl)-2,3-dimethyl-1H-indol-1-yl)methyl)-[1,1'-biphenyl]-2-carboxylic acid

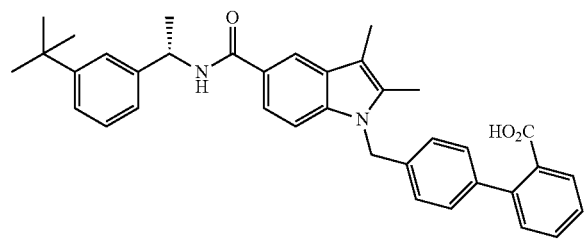

Step 1: (S)-1-(3-(tert-butyl)phenyl)ethanaminium chloride

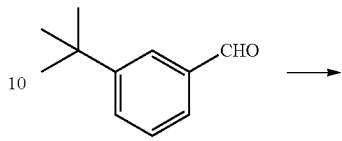

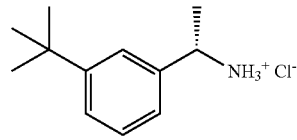

The title compound was prepared following the same general synthetic procedure as described in Steps 1-2, Example 2, using 3-(tert-butyl)benzaldehyde instead of 4-(tert-butyl)benzaldehyde.

Step 2: (S)-4'-((5-((1-(3-(tert-butyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (S)-1-(3-(tert-butyl)phenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 559 [M+H]$^+$.

Example 139: (R)-4'-((2,3-dimethyl-5-((2,2,2-trifluoro-1-(3-isopropylphenyl)ethyl)carbamoyl)-1H-indol-1-yl)methyl)-[1,1'-biphenyl]-2-carboxylic acid

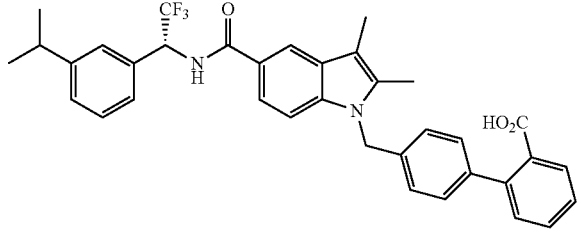 [SMILES: Cc1c(C)n(Cc2ccc(-c3ccccc3C(=O)O)cc2)c2ccc(C(=O)N[C@@H](C)c3cccc(C(C)C)c3)cc12]

Step 1: (S,E)-N-(3-isopropylbenzylidene)-2-methyl-propane-2-sulfinamide

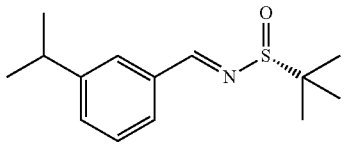 [SMILES: CC(C)c1cccc(/C=N/[S@](=O)C(C)(C)C)c1]

To a solution of 3-isopropylbenzaldehyde (0.711 g, 4.75 mmol) in THF (5 mL) was added (S)-2-methyl-2-propane-sulfinamide (0.534 g, 4.32 mmol) and Ti(OiPr)$_4$ (2.75 mL, 8.64 mmol). The resulting mixture was allowed to stir over night at rt where it was then quenched with aqueous NH$_4$C$_1$ (5 mL) and diluted with EtOAc (100 mL). The mixture was then filtered through celite using excess EtOAc to rinse, concentrated to an oil crude and separated by silica gel (EtOAc:Hexanes) to isolate the title compound.

Step 2: (S)-2-methyl-N—((R)-2,2,2-trifluoro-1-(3-isopropylphenyl)ethyl)propane-2-sulfinamide

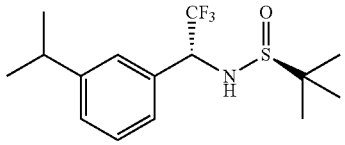 [SMILES: CC(C)c1cccc([C@@H](N[S@@](=O)C(C)(C)C)C(F)(F)F)c1]

Tetra-n-butylammonium difluorotriphenylsilicate (TBAT) (1.19 g, 2.13 mmol) and (trifluoromethyl)trimethylsilane (TMS-CF$_3$) (0.371 mL, 2.33 mmol) was added to a solution of (S,E)-N-(3-isopropylbenzylidene)-2-methylpropane-2-sulfinamide (0.487 g, 1.937 mmol) in anhydrous THF (16 mL) at −20° C. under argon. The reaction was allowed to proceed for ~2 h where the starting material appeared to have been consumed as determined by analytical-HPLC. A saturated solution of NH$_4$C$_1$ (20 mL) was added to quench and the mixture was extracted with EtOAc (100 mL×3) and dried over Na$_2$SO$_4$. The organic partition was then concentrated to an oil and the title compound was isolated by flash chromatography using silica gel (EtOAc:Hexanes). ESI-MS (m/z): 321 [M+1]$^+$.

Step 3: (R)-2,2,2-trifluoro-1-(3-isopropylphenyl) ethanaminium chloride

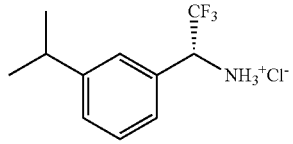

The title compound was prepared following the same general synthetic procedure as described in Step 2, Example 2, using (S)-2-methyl-N—((R)-2,2,2-trifluoro-1-(3-isopropylphenyl)ethyl)propane-2-sulfinamide instead of 4-(tert-butyl)benzaldehyde.

Step 4: (R)-4'-((2,3-dimethyl-5-((2,2,2-trifluoro-1-(3-isopropylphenyl)ethyl)carbamoyl)-1H-indol-1-yl) methyl)-[1,1'-biphenyl]-2-carboxylic acid The title compound was prepared following the same general protocol as described in Step 8-9, Example 1, using (R)-2,2,2-trifluoro-1-(3-isopropylphenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 599 [M+H]$^+$.

Example 140: (S)-4'-((5-((cyclopropyl(3-isopropylphenyl)methyl)carbamoyl)-2,3-dimethyl-1H-indol-1-yl)methyl)-[1,1'-biphenyl]-2-carboxylic acid

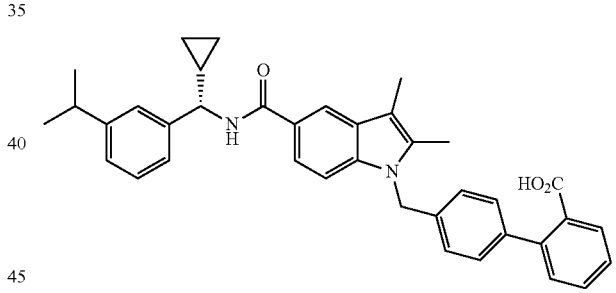

Step 1: (S)-cyclopropyl(3-isopropylphenyl)methanaminium chloride

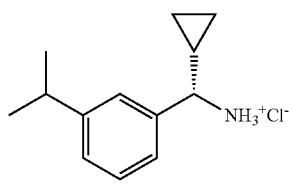

The title compound was prepared following the same general synthetic procedure as described in Steps 1-2, Example 2, using 3-isopropylbenzaldehyde and cyclopropylmagnesium bromide instead of 4-(tert-butyl)benzaldehyde and methylmagnesium bromide.

Step 2: Example: (S)-4'-((5-(((cyclopropyl(3-isopropylphenyl)methyl)carbamoyl)-2,3-dimethyl-1H-indol-1-yl)methyl)-[1,1'-biphenyl]-2-carboxylic acid The title compound was prepared following the same general protocol as described in Step 1-2, Example 19, using (S)-cyclopropyl(3-isopropylphenyl)methanamine and 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]⁺.

Example 141: (R)-4'-((5-((1-(2,6-dichlorophenyl)ethyl)carbamoyl)-2,3-dimethyl-1H-indol-1-yl)methyl)-[1,1'-biphenyl]-2-carboxylic acid

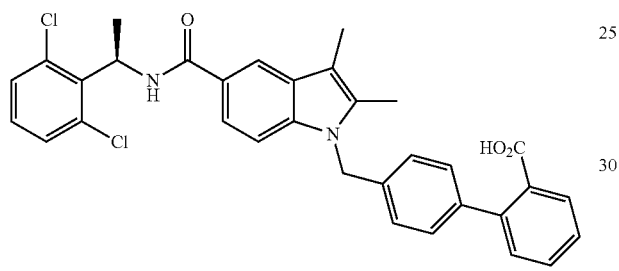

Step 1: (R)-1-(2,6-dichlorophenyl)ethanamine

The title compound was prepared following the same general protocol as described in Step 1-2, Example 2, using 2,6-dichlorobenzaldehyde.

Step 2: (R)-4'-((5-((1-(2,6-dichlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (R)-1-(2,6-dichlorophenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]⁺.

Example 142: (S)-4'-((5-((1-(2,6-dichlorophenyl)ethyl)carbamoyl)-2,3-dimethyl-1H-indol-1-yl)methyl)-[1,1'-biphenyl]-2-carboxylic acid

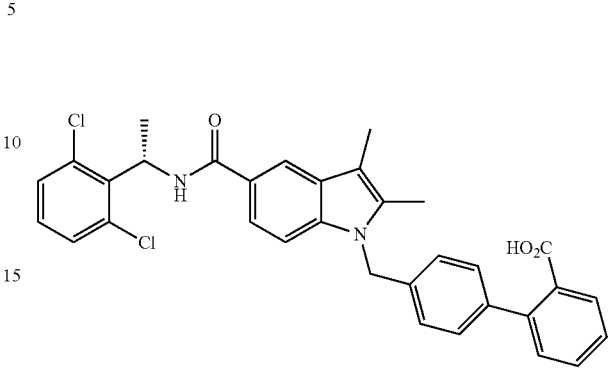

Step 1: (S)-1-(2,6-dichlorophenyl)ethanamine

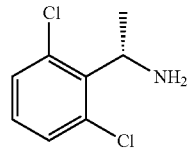

The title compound was prepared following the same general protocol as described in Step 1-2, Example 2, using 2,6-dichlorobenzaldehyde.

Step 2: (S)-4'-((5-((1-(2,6-dichlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (S)-1-(2,6-dichlorophenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]⁺.

Example 143: (S)-4'-((5-((1-(benzo[d][1,3]dioxol-4-yl)ethyl)carbamoyl)-2,3-dimethyl-1H-indol-1-yl)methyl)-[1,1'-biphenyl]-2-carboxylic acid

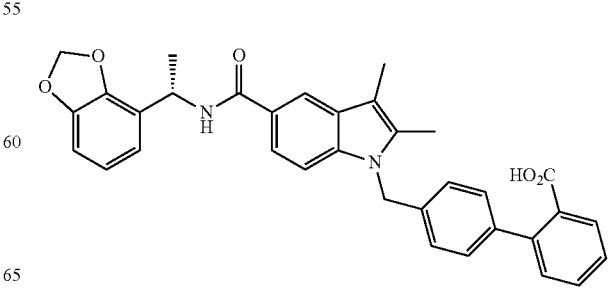

Step 1: (S)-1-(benzo[d][1,3]dioxol-4-yl)ethanamine

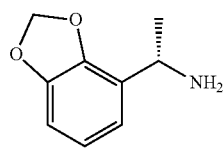

The title compound was prepared following the same general protocol as described in Step 1-2, Example 2, using benzo[d][1,3]dioxole-4-carbaldehyde.

Step 2: (S)-4'-((5-((1-(benzo[d][1,3]dioxol-4-yl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (S)-1-(benzo[d][1,3]dioxol-4-yl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 547 [M+H]⁺.

Example 144: (S)-4'-((2,3-dimethyl-5-((1-(pyridin-2-yl)ethyl)carbamoyl)-1H-indol-1-yl)methyl)-[1,1'-biphenyl]-2-carboxylic acid

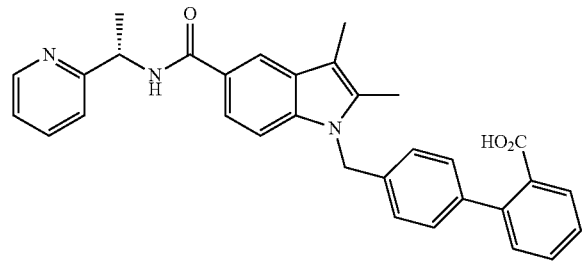 [SMILES: Cc1c(C)n(Cc2ccc(-c3ccccc3C(=O)O)cc2)c2ccc(C(=O)N[C@@H](C)c3ccccn3)cc12]

Step 1: (S)-1-(pyridin-2-yl)ethanamine

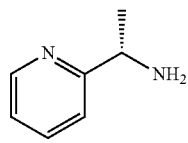

The title compound was prepared following the same general protocol as described in Step 1-2, Example 2, using the picolinaldehyde.

Step 2: (S)-4'-((2,3-dimethyl-5-((1-(pyridin-2-yl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(pyridin-2-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 504 [M+H]⁺.

Example 145: (S)-4'-((5-((1-(3-fluoro-2-methylphenyl)ethyl)carbamoyl)-2,3-dimethyl-1H-indol-1-yl)methyl)-[1,1'-biphenyl]-2-carboxylic acid

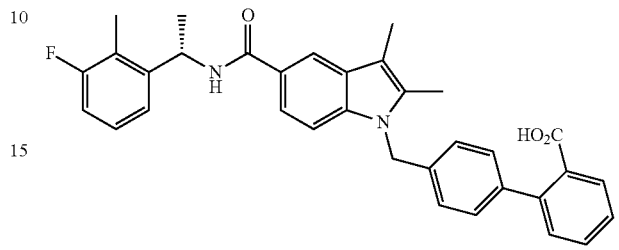

Step 1: (S)-1-(3-fluoro-2-methylphenyl)ethanaminium chloride

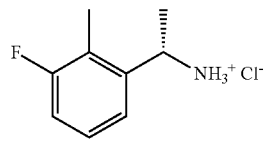

The title compound was prepared following the same general synthetic procedure as described in Steps 1-2, Example 2, using 3-fluoro-2-methylbenzaldehyde instead of 4-(tert-butyl)benzaldehyde.

Step 2: (S)-4'-((5-((1-(3-fluoro-2-methylphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-fluoro-2-methylphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 535 [M+H]⁺.

Example 146: (S)-4'-((5-((1-(3-fluoro-5-methoxyphenyl)ethyl)carbamoyl)-2,3-dimethyl-1H-indol-1-yl)methyl)-[1,1'-biphenyl]-2-carboxylic acid

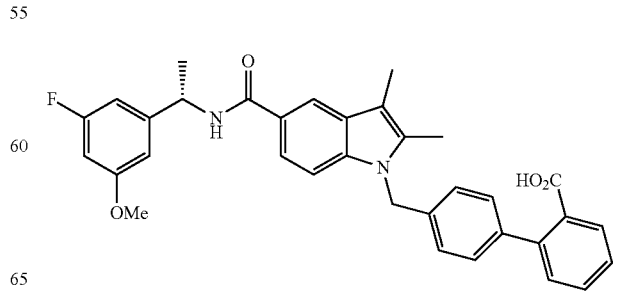

Step 1: (S)-1-(3-fluoro-5-methoxyphenyl)ethanaminium chloride

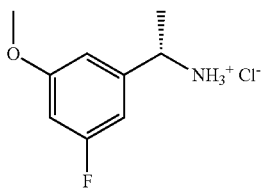

The title compound was prepared following the same general synthetic procedure as described in Steps 1-2, Example 2, using 3-fluoro-5-methoxybenzaldehyde instead of 4-(tert-butyl)benzaldehyde.

Step 2: (S)-4'-((5-((1-(3-fluoro-5-methoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-fluoro-5-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 551 [M+H]$^+$.

Example 147: (S)-4'-((5-((1-(3,5-dimethoxyphenyl)ethyl)carbamoyl)-2,3-dimethyl-1H-indol-1-yl)methyl)-[1,1'-biphenyl]-2-carboxylic acid

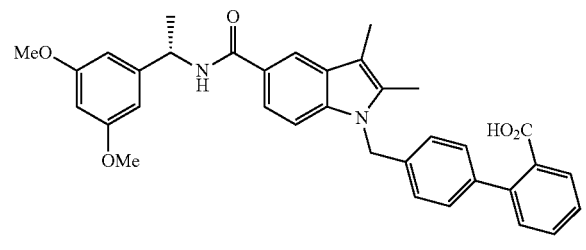 [SMILES: COc1cc(OC)cc([C@H](C)NC(=O)c2ccc3c(c2)c(C)c(C)n3Cc2ccc(-c3ccccc3C(=O)O)cc2)c1]

Step 1: (S)-1-(3,5-dimethoxyphenyl)ethanaminium chloride

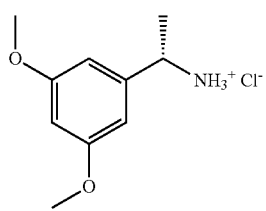

The title compound was prepared following the same general synthetic procedure as described in Steps 1-2, Example 2, using 3,5-dimethoxybenzaldehyde instead of 4-(tert-butyl)benzaldehyde.

Step 2: (S)-4'-((5-((1-(3,5-dimethoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3,5-dimethoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 563 [M+H]$^+$.

Example 148: (S)-4'-((5-((1-(3-chloropyridin-4-yl)ethyl)carbamoyl)-2,3-dimethyl-1H-indol-1-yl)methyl)-[1,1'-biphenyl]-2-carboxylic acid

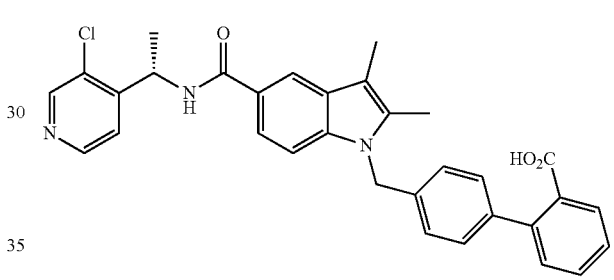

Step 1: (S)-1-(3-chloropyridin-4-yl)ethanamine

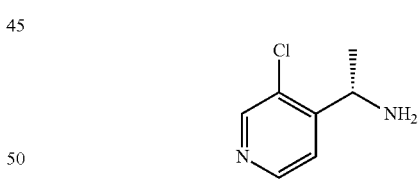

The title compound was prepared following the same general protocol as described in Step 1-2, Example 2, using the 3-chloroisonicotinaldehyde.

Step 2: (S)-4'-((5-((1-(3-chloropyridin-4-yl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-chloropyridin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 538/539/540 [M+H]$^+$.

Example 149: (S)-4'-((2,3-dimethyl-5-((1-(quinolin-4-yl)ethyl)carbamoyl)-1H-indol-1-yl)methyl)-[1,1'-biphenyl]-2-carboxylic acid

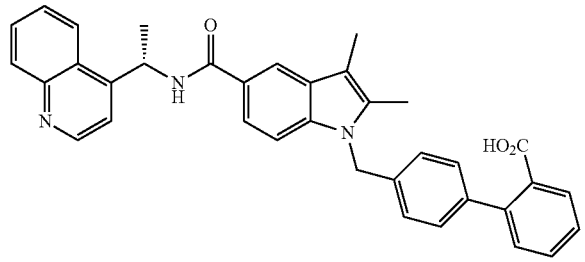 [SMILES: Cc1c(C)n(Cc2ccc(-c3ccccc3C(=O)O)cc2)c2ccc(C(=O)N[C@@H](C)c3ccnc4ccccc34)cc12]

Step 1: (S)-1-(quinolin-4-yl)ethanamine

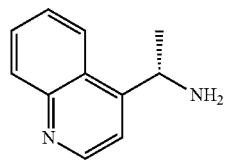

The title compound was prepared following the same general protocol as described in Step 1-2, Example 2, using the quinoline-4-carbaldehyde.

Step 2: (S)-4'-((2,3-dimethyl-5-((1-(quinolin-4-yl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(quinolin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 554 [M+H]$^+$.

Example 150: (S)-4'-((5-((1-(2,4-difluorophenyl)ethyl)carbamoyl)-2,3-dimethyl-1H-indol-1-yl)methyl)-[1,1'-biphenyl]-2-carboxylic acid

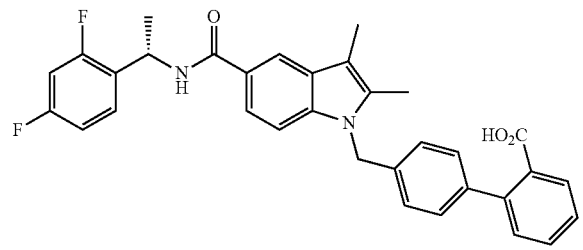 [SMILES: Cc1c(C)n(Cc2ccc(-c3ccccc3C(=O)O)cc2)c2ccc(C(=O)N[C@@H](C)c3ccc(F)cc3F)cc12]

Step 1: (S)-1-(2,4-difluorophenyl)ethanaminium chloride

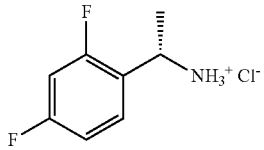

The title compound was prepared following the same general synthetic procedure as described in Steps 1-2, Example 2, using 2,4-difluorobenzaldehyde instead of 4-(tert-butyl)benzaldehyde.

Step 2: (S)-4'-((5-((1-(2,4-difluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2,4-difluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 539 [M+H]$^+$.

Example 151: (S)-4'-((5-((1-(3-ethoxyphenyl)ethyl)carbamoyl)-2,3-dimethyl-1H-indol-1-yl)methyl)-[1,1'-biphenyl]-2-carboxylic acid

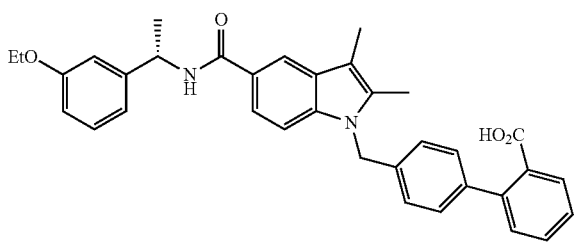 [SMILES: CCOc1cccc([C@H](C)NC(=O)c2ccc3c(c2)c(C)c(C)n3Cc2ccc(-c3ccccc3C(=O)O)cc2)c1]

Step 1: (S)-(3-ethoxyphenyl)ethanamine

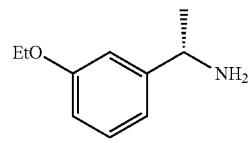

The title compound was prepared following the same general protocol as described in Step 1-2, Example 2, using the 3-ethoxybenzaldehyde.

Step 2: (S)-4'-((5-((1-(3-ethoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-ethoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 545 [M+H]⁺.

Example 152: (S)-4'-((2,3-dimethyl-5-((1-(naphthalen-1-yl)ethyl)carbamoyl)-1H-indol-1-yl)methyl)-[1,1'-biphenyl]-2-carboxylic acid

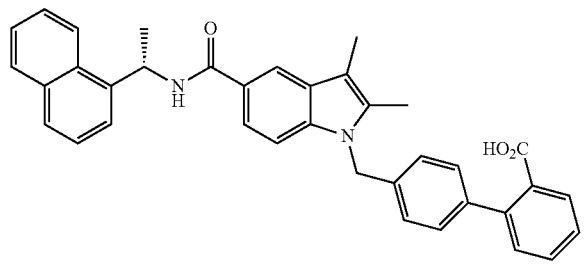 [SMILES: Cc1c(C)n(Cc2ccc(-c3ccccc3C(=O)O)cc2)c2ccc(C(=O)N[C@@H](C)c3cccc4ccccc34)cc12]

Step 1: (S)-1-(naphthalen-1-yl)ethanamine

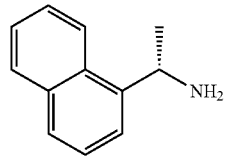

The title compound was prepared following the same general protocol as described in Step 1-2, Example 2, using the 1-naphthaldehyde.

Step 2: (S)-4'-((2,3-dimethyl-5-((1-(naphthalen-1-yl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(naphthalen-1-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 553 [M+H]⁺.

Example 153: (S)-4'-((2,3-dimethyl-5-((1-(4-(trifluoromethoxy)phenyl)ethyl)carbamoyl)-1H-indol-1-yl)methyl)-[1,1'-biphenyl]-2-carboxylic acid

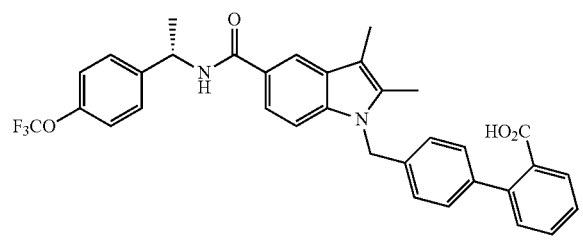 [SMILES: Cc1c(C)n(Cc2ccc(-c3ccccc3C(=O)O)cc2)c2ccc(C(=O)N[C@@H](C)c3ccc(OC(F)(F)F)cc3)cc12]

Step 1: (S)-1-(4-(trifluoromethoxy)phenyl)ethanaminium chloride

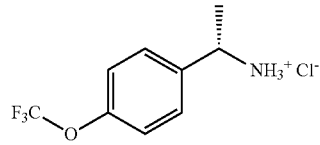

The title compound was prepared following the same general synthetic procedure as described in Steps 1-2, Example 2, using 4-(trifluoromethoxy)benzaldehyde instead of 4-(tert-butyl)benzaldehyde.

Step 2: (S)-4'-((2,3-dimethyl-5-((1-(4-(trifluoromethoxy)phenyl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(4-(trifluoromethoxy)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]⁺.

Example 154: (S)-4'-((2,3-dimethyl-5-((1-(4-(trifluoromethyl)phenyl)ethyl)carbamoyl)-1H-indol-1-yl)methyl)-[1,1'-biphenyl]-2-carboxylic acid

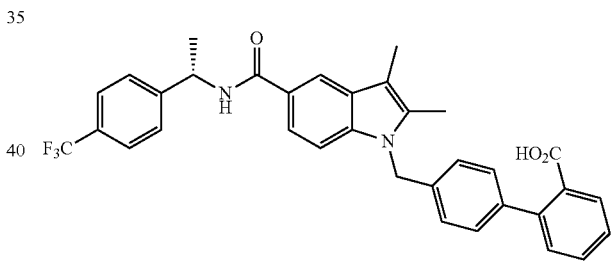

Step 1: (S)-1-(4-(trifluoromethyl)phenyl)ethanamine

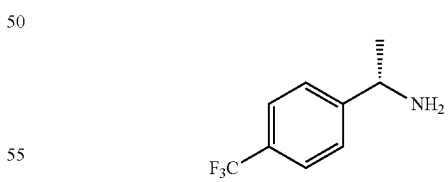

The title compound was prepared following the same general protocol as described in Step 1-2, Example 2, using the 4-trifluoromethylbenzaldehyde.

Step 2: (S)-4'-((2,3-dimethyl-5-((1-(4-(trifluoromethyl)phenyl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(4-(trifluoromethyl)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]$^+$.

Example 155: (S)-4'-((5-((1-(3-isopropylphenyl)-3-methylbutyl)carbamoyl)-2,3-dimethyl-1H-indol-1-yl)methyl)-[1,1'-biphenyl]-2-carboxylic acid

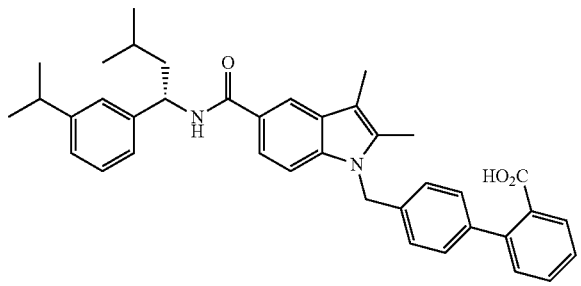 [SMILES: Cc1c(C)n(Cc2ccc(-c3ccccc3C(=O)O)cc2)c2ccc(C(=O)N[C@@H](CC(C)C)c3cccc(C(C)C)c3)cc12]

Step 1: (S)-1-(3-isopropylphenyl)-3-methylbutan-1-amine

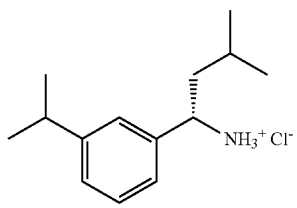

The title compound was prepared following the same general synthetic procedure as described in Steps 1-2, Example 2, using 3-isopropylbenzaldehyde and isobutylmagnesium chloride instead of 4-(tert-butyl)benzaldehyde and methylmagnesium bromide.

Step 2: (S)-4'-((5-((1-(3-isopropylphenyl)-3-methylbutyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)-3-methylbutan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]$^+$.

Example 156: (R)-4'-((5-((1-(3-isopropylphenyl)-2-methylpropyl)carbamoyl)-2,3-dimethyl-1H-indol-1-yl)methyl)-[1,1'-biphenyl]-2-carboxylic acid

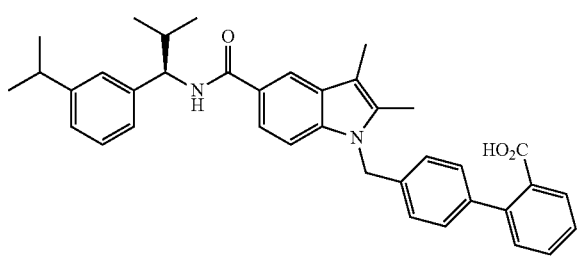 [SMILES: Cc1c(C)n(Cc2ccc(-c3ccccc3C(=O)O)cc2)c2ccc(C(=O)N[C@@H](c3cccc(C(C)C)c3)C(C)C)cc12]

Step 1: (R)-1-(3-isopropylphenyl)-2-methylpropan-1-aminium chloride

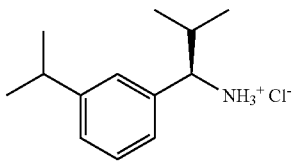

The title compound was prepared following the same general synthetic procedure as described in Steps 1-2, Example 2, using 3-isopropylbenzaldehyde and 2-propylmagnesium chloride instead of 4-(tert-butyl)benzaldehyde and methylmagnesium bromide.

Step 2: (R)-4'-((5-((1-(3-isopropylphenyl)-2-methylpropyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (R)-1-(3-isopropylphenyl)-2-methylpropan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 573 [M+H]$^+$.

Example 157: (S)-4'-((5-((1-(3-isopropylphenyl)-2-methylpropyl)carbamoyl)-2,3-dimethyl-1H-indol-1-yl)methyl)-[1,1'-biphenyl]-2-carboxylic acid

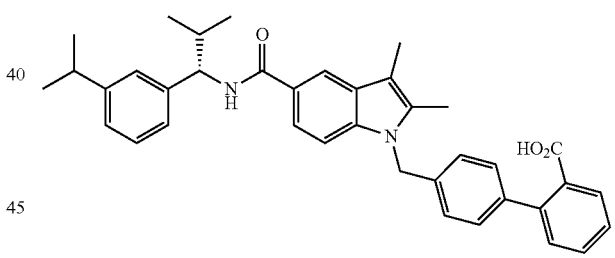

Step 1: (R)-1-(3-isopropylphenyl)-2-methylpropan-1-aminium chloride

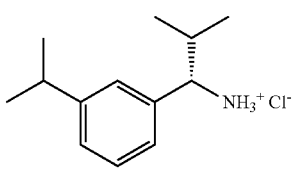

The title compound was prepared following the same general synthetic procedure as described in Steps 1-2, Example 2, using 3-isopropylbenzaldehyde and 2-propylmagnesium chloride instead of 4-(tert-butyl)benzaldehyde and methylmagnesium bromide.

Step 2: (S)-4'-((5-((1-(3-isopropylphenyl)-2-methyl-propyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)-2-methylpropan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 573 [M+H]⁺.

Example 158: (S)-4'-((5-((1-(3-fluorophenyl)ethyl)carbamoyl)-2,3-dimethyl-1H-indol-1-yl)methyl)-[1,1'-biphenyl]-2-carboxylic acid

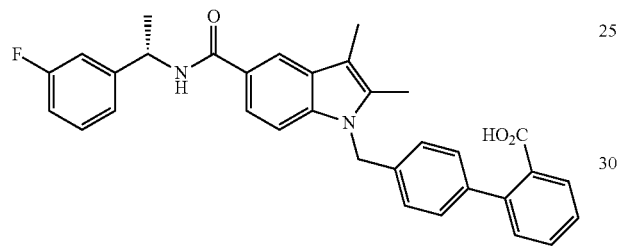

Step 1: (S)-1-(3-fluorophenyl)ethanamine

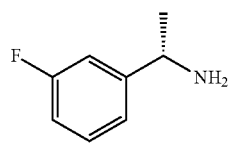

The title compound was prepared following the same general protocol as described in Step 1-2, Example 2, using the 3-fluorobenzaldehyde.

Step 2: (S)-4'-((5-((1-(3-fluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-fluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 521 [M+H]⁺.

Example 159: (S)-4'-((5-((1-(2-chlorophenyl)ethyl)carbamoyl)-2,3-dimethyl-1H-indol-1-yl)methyl)-[1,1'-biphenyl]-2-carboxylic acid

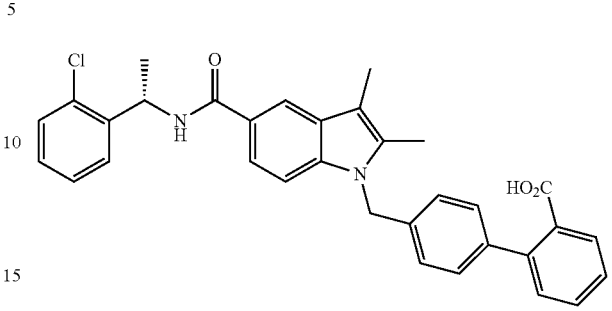

Step 1: (S)-1-(2-chlorophenyl)ethanamine

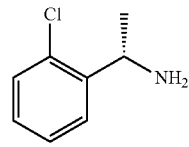

The title compound was prepared following the same general protocol as described in Step 1-2, Example 2, using the 2-chlorobenzaldehyde.

Step 2: (S)-4'-((5-((1-(2-chlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2-chlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 537/538/539 [M+H]⁺.

Example 160: (S)-4'-((5-((1-(2-fluorophenyl)ethyl)carbamoyl)-2,3-dimethyl-1H-indol-1-yl)methyl)-[1,1'-biphenyl]-2-carboxylic acid

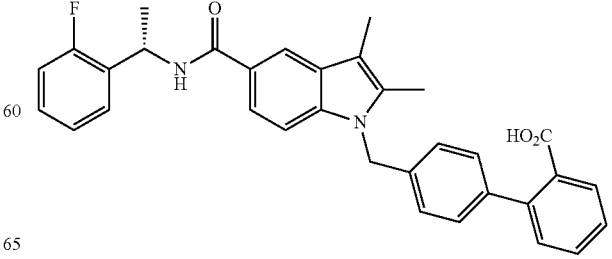

Step 1: (S)-1-(2-fluorophenyl)ethanamine

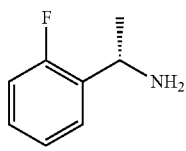

The title compound was prepared following the same general protocol as described in Step 1-2, Example 2, using the 2-fluorobenzaldehyde.

Step 2: (S)-4'-((5-((1-(2-fluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2-fluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 521 [M+H]$^+$.

Example 161: (R)-4'-((5-((1-(3-methoxyphenyl)ethyl)carbamoyl)-2,3-dimethyl-1H-indol-1-yl)methyl)-[1,1'-biphenyl]-2-carboxylic acid

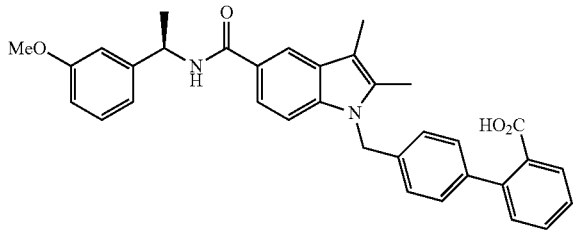

The title compound was prepared following the same general protocol as described in Step 8-9, Example 1, using the (R)-1-(3-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 533 [M+H]$^+$.

Example 162: (R)-4'-((5-((1-(3-chlorophenyl)ethyl)carbamoyl)-2,3-dimethyl-1H-indol-1-yl)methyl)-[1,1'-biphenyl]-2-carboxylic acid

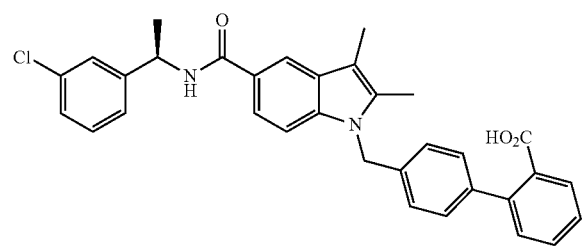 [SMILES: Cc1c(C)n(Cc2ccc(-c3ccccc3C(=O)O)cc2)c2ccc(C(=O)N[C@H](C)c3cccc(Cl)c3)cc12]

The title compound was prepared following the same general protocol as described in Step 8-9, Example 1, using the (R)-1-(3-chlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 537/538/539 [M+H]$^+$.

Example 163: (S)-4'-((5-((1-(4-isopropylphenyl)ethyl)carbamoyl)-2,3-dimethyl-1H-indol-1-yl)methyl)-[1,1'-biphenyl]-2-carboxylic acid

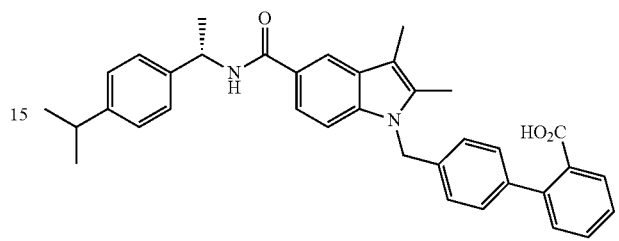

The title compound was prepared following the same general protocol as described in Step 1-2-3, Example 137, using the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 545 [M+H]$^+$.

Example 164: 4'-((5-((2,4-difluorobenzyl)carbamoyl)-2,3-dimethyl-1H-indol-1-yl)methyl)-[1,1'-biphenyl]-2-carboxylic acid

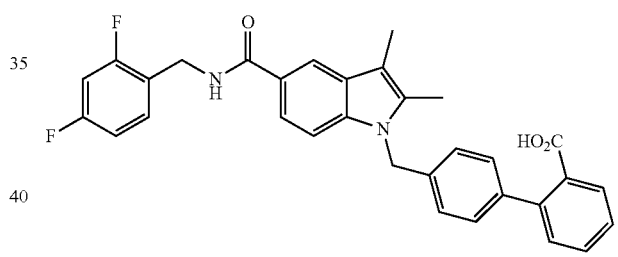

The title compound was prepared following the same general protocol as described in Step 8-9, Example 1, using the (2,4-difluorophenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 525 [M+H]$^+$.

Example 165: 4'-((5-((4-chloro-2-(trifluoromethyl)benzyl)carbamoyl)-2,3-dimethyl-1H-indol-1-yl)methyl)-[1,1'-biphenyl]-2-carboxylic acid

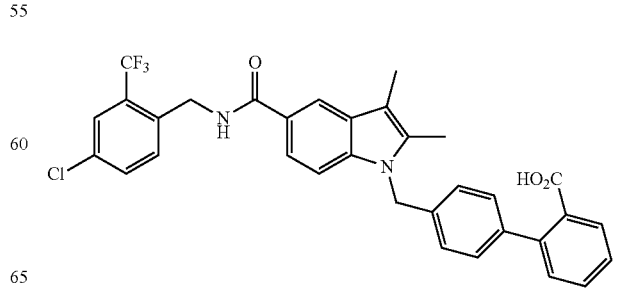

The title compound was prepared following the same general protocol as described in Step 8-9, Example 1, using the (4-chloro-2-(trifluoromethyl)phenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 591 [M+H]⁺.

Example 166: (R)-4'-((5-((1-(3-isopropylphenyl)ethyl)carbamoyl)-2,3-dimethyl-1H-indol-1-yl)methyl)-[1,1'-biphenyl]-2-carboxylic acid

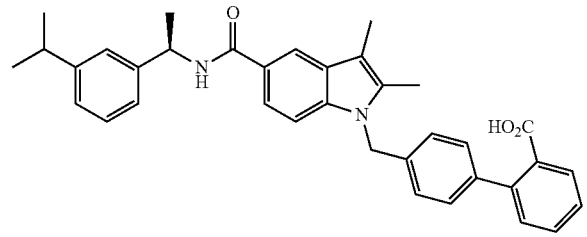 [SMILES: Cc1c(C)n(Cc2ccc(-c3ccccc3C(=O)O)cc2)c2ccc(C(=O)N[C@H](C)c3cccc(C(C)C)c3)cc12]

The title compound was prepared following the same general protocol as described in Step 1-2-3, Example 137, using the (R)-tert-butyl 4'-((5-((1-(3-bromophenyl)ethyl)carbamoyl)-2,3-dimethyl-1H-indol-1-yl)methyl)-[1,1'-biphenyl]-2-carboxylate. ESI-MS (m/z): 545 [M+H]⁺.

Example 167: 4'-((5-((2-fluoro-4-(trifluoromethyl)benzyl)carbamoyl)-2,3-dimethyl-1H-indol-1-yl)methyl)-[1,1'-biphenyl]-2-carboxylic acid

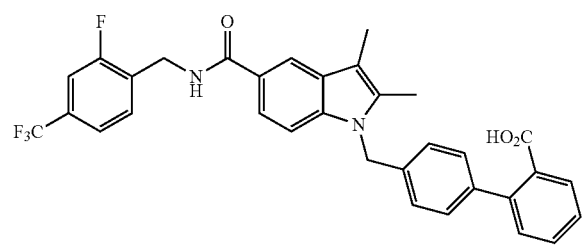 [SMILES: Cc1c(C)n(Cc2ccc(-c3ccccc3C(=O)O)cc2)c2ccc(C(=O)NCc3ccc(C(F)(F)F)cc3F)cc12]

The title compound was prepared following the same general protocol as described in Step 8-9, Example 1, using the (2-fluoro-4-(trifluoromethyl)phenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 575 [M+H]⁺.

Example 168: 4'-((5-((2,4-dichlorobenzyl)carbamoyl)-2,3-dimethyl-1H-indol-1-yl)methyl)-[1,1'-biphenyl]-2-carboxylic acid

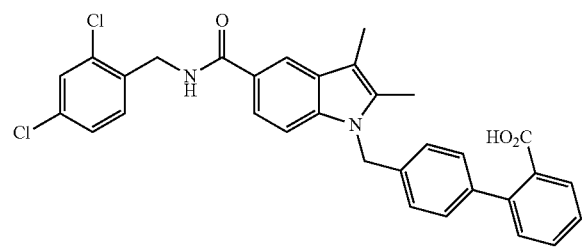 [SMILES: Cc1c(C)n(Cc2ccc(-c3ccccc3C(=O)O)cc2)c2ccc(C(=O)NCc3ccc(Cl)cc3Cl)cc12]

The title compound was prepared following the same general protocol as described in Step 8-9, Example 1, using the (2,4-dichlorophenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 557/559 [M+H]⁺.

Example 169: (R)-4'-((2,3-dimethyl-5-((1-(pyridin-4-yl)ethyl)carbamoyl)-1H-indol-1-yl)methyl)-[1,1'-biphenyl]-2-carboxylic acid

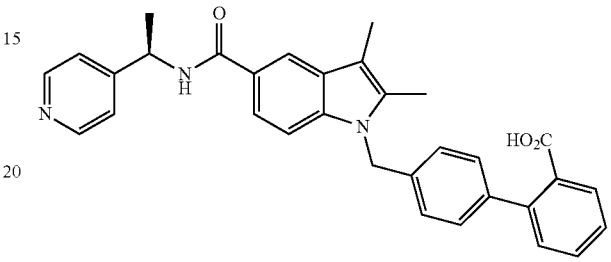

Step 1: (R)-1-(pyridin-4-yl)ethanamine

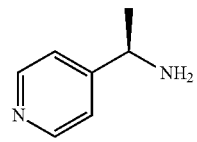

The title compound was prepared following the same general protocol as described in Step 1-2, Example 2, using the isonicotinaldehyde.

Step 2: (R)-4'-((2,3-dimethyl-5-((1-(pyridin-4-yl)ethyl)carbamoyl)-1H-indol-1-yl)methyl)-[1,1'-biphenyl]-2-carboxylic acid The title compound was prepared following the same general protocol as described in Step 8-9, Example 1, using the (R)-1-(pyridin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 504 [M+H]⁺.

Example 170: (S)-4'-((5-((1-(2-chloro-3-fluorophenyl)ethyl)carbamoyl)-2,3-dimethyl-1H-indol-1-yl)methyl)-[1,1'-biphenyl]-2-carboxylic acid

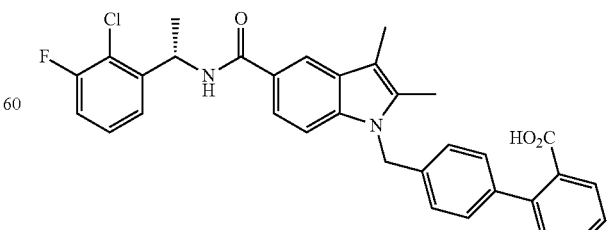

Step 1: (S)-1-(2-chloro-3-fluorophenyl)ethanamine

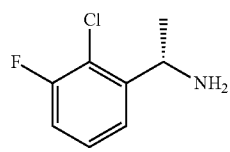

The title compound was prepared following the same general protocol as described in Step 1-2, Example 2, using the 2-chloro-3-fluorobenzaldehyde.

Step 2: (S)-4'-((5-(((1-(2-chloro-3-fluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2-chloro-3-fluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 504 [M+H]$^+$.

Example 171: (R)-4'-((5-(((1-(2,3-dichlorophenyl)ethyl)carbamoyl)-2,3-dimethyl-1H-indol-1-yl)methyl)-[1,1'-biphenyl]-2-carboxylic acid

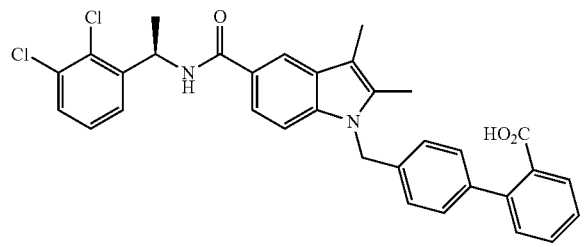 [SMILES: Cc1c(C)n(Cc2ccc(-c3ccccc3C(=O)O)cc2)c2ccc(C(=O)N[C@H](C)c3cccc(Cl)c3Cl)cc12]

Step 1: (R)-1-(2,3-dichlorophenyl)ethanamine

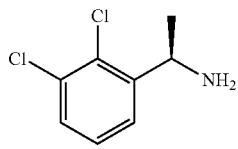

The title compound was prepared following the same general protocol as described in Step 1-2, Example 2, using the 2,3-dichlorobenzaldehyde.

Step 2: (R)-4'-((5-(((1-(2,3-dichlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (R)-1-(2,3-dichlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]$^+$.

Example 172: (S)-4'-((5-(((1-(2,5-bis(trifluoromethyl)phenyl)ethyl)carbamoyl)-2,3-dimethyl-1H-indol-1-yl)methyl)-[1,1'-biphenyl]-2-carboxylic acid

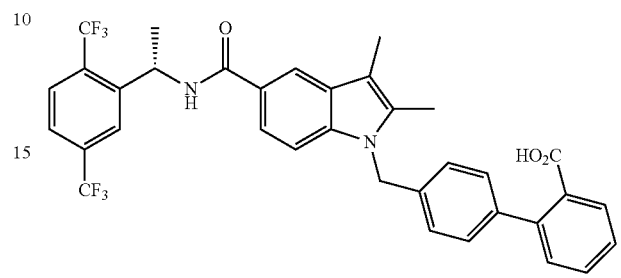

Step 1: (S)-1-(2,5-bis(trifluoromethyl)phenyl)ethanamine

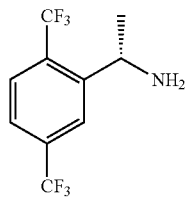

The title compound was prepared following the same general protocol as described in Step 1-2, Example 2, using the 2,5-bis(trifluoromethyl)benzaldehyde.

Step 2: (S)-4'-((5-(((1-(2,5-bis(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2,5-bis(trifluoromethyl)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 639 [M+H]$^+$.

Example 173: (R)-4'-((5-(((1-(2,5-bis(trifluoromethyl)phenyl)ethyl)carbamoyl)-2,3-dimethyl-1H-indol-1-yl)methyl)-[1,1'-biphenyl]-2-carboxylic acid

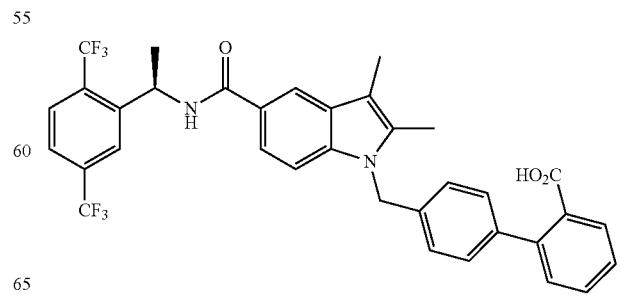

Step 1:
(R)-1-(2,5-bis(trifluoromethyl)phenyl)ethanamine

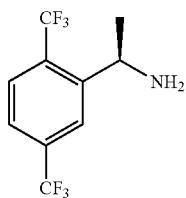 [SMILES: C[C@@H](N)c1cc(C(F)(F)F)ccc1C(F)(F)F]

The title compound was prepared following the same general protocol as described in Step 1-2, Example 2, using the 2,5-bis(trifluoromethyl)benzaldehyde.

Step 2: (R)-4'-((5-((1-(2,5-bis(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (R)-1-(2,5-bis(trifluoromethyl)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 639 [M+H]$^+$.

Example 174: (S)-4'-((5-((1-(3-chlorophenyl)ethyl)carbamoyl)-2,3-dimethyl-1H-indol-1-yl)methyl)-[1,1'-biphenyl]-2-carboxylic acid

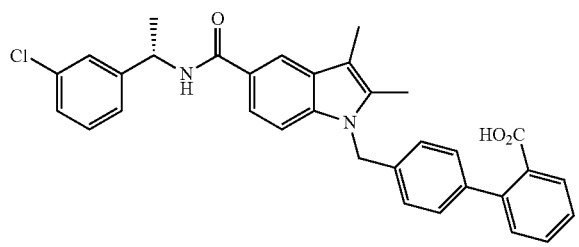 [SMILES: Cc1c(C)n(Cc2ccc(-c3ccccc3C(=O)O)cc2)c2ccc(C(=O)N[C@@H](C)c3cccc(Cl)c3)cc12]

The title compound was prepared following the same general protocol as described in Step 8-9, Example 1, using the (S)-1-(3-chlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 537/538/539 [M+H]$^+$.

Example 175: (S)-4'-((5-((1-(2-methoxyphenyl)ethyl)carbamoyl)-2,3-dimethyl-1H-indol-1-yl)methyl)-[1,1'-biphenyl]-2-carboxylic acid

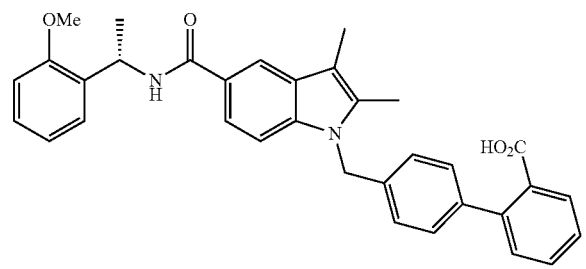 [SMILES: COc1ccccc1[C@H](C)NC(=O)c1ccc2c(c1)c(C)c(C)n2Cc1ccc(-c2ccccc2C(=O)O)cc1]

The title compound was prepared following the same general protocol as described in Step 8-9, Example 1, using the (S)-1-(2-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 533 [M+H]$^+$.

Example 176: (S)-4'-((2,3-dimethyl-5-((1-(3-(trifluoromethyl)phenyl)ethyl)carbamoyl)-1H-indol-1-yl)methyl)-[1,1'-biphenyl]-2-carboxylic acid

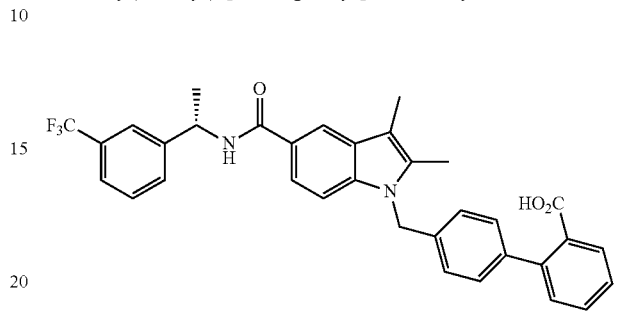

Step 1:
(S)-1-(3-(trifluoromethyl)phenyl)ethanaminium chloride

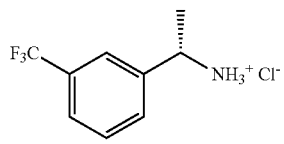

The title compound was prepared following the same general synthetic procedure as described in Steps 1-2, Example 2, using 3-(trifluoromethyl)benzaldehyde instead of 4-(tert-butyl)benzaldehyde.

Step 2: (S)-4'-((2,3-dimethyl-5-((1-(3-(trifluoromethyl)phenyl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(3-(trifluoromethyl)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]$^+$.

Example 177: (S)-4'-((5-((1-(3-fluoro-2-methoxyphenyl)ethyl)carbamoyl)-2,3-dimethyl-1H-indol-1-yl)methyl)-[1,1'-biphenyl]-2-carboxylic acid

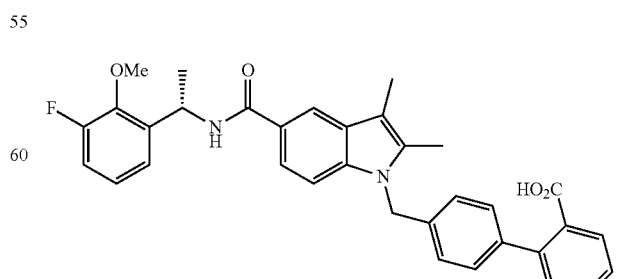

Step 1: (S)-1-(3-fluoro-2-methoxyphenyl)ethanamine

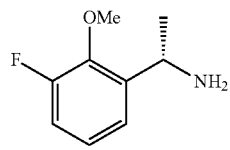

The title compound was prepared following the same general protocol as described in Step 1-2, Example 2, using the 3-fluoro-2-methoxybenzaldehyde.

Step 2: (S)-4'-((5-((1-(3-fluoro-2-methoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 1-2, Example 2, using the (S)-1-(3-fluoro-2-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 551 [M+H]$^+$.

Example 178: (S)-4'-((5-((1-(3-isopropylphenyl)pentyl)carbamoyl)-2,3-dimethyl-1H-indol-1-yl)methyl)-[1,1'-biphenyl]-2-carboxylic acid

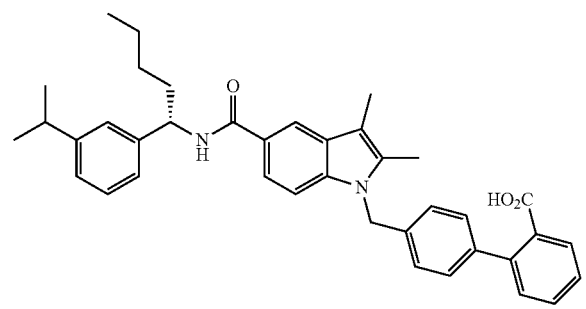 [SMILES: CCCC[C@H](NC(=O)c1ccc2c(c1)c(C)c(C)n2Cc1ccc(-c2ccccc2C(=O)O)cc1)c1cccc(C(C)C)c1]

Step 1: (S)-1-(3-isopropylphenyl)pentan-1-aminium chloride

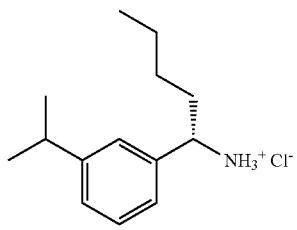

The title compound was prepared following the same general synthetic procedure as described in Steps 1-2, Example 2, using 3-isopropylbenzaldehyde and n-butylmagnesium bromide instead of 4-(tert-butyl)benzaldehyde and methylmagnesium bromide.

Step 2: (S)-4'-((5-((1-(3-isopropylphenyl)pentyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)pentan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]$^+$.

Example 179: (S)-4'-((2,3-dimethyl-5-((1-(p-tolyl)ethyl)carbamoyl)-1H-indol-1-yl)methyl)-[1,1'-biphenyl]-2-carboxylic acid

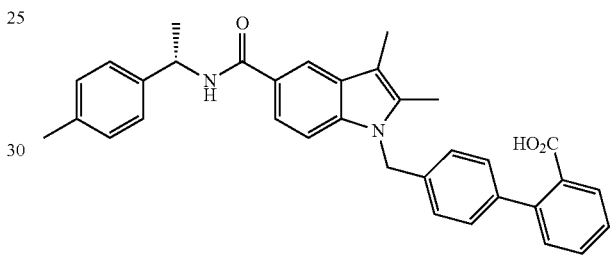

The title compound was prepared following the same general protocol as described in Step 8-9, Example 1, using the (S)-1-(p-tolyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 517 [M+H]$^+$.

Example 180: 4'-((5-((2-(4-bromophenyl)propan-2-yl)carbamoyl)-2,3-dimethyl-1H-indol-1-yl)methyl)-[1,1'-biphenyl]-2-carboxylic acid

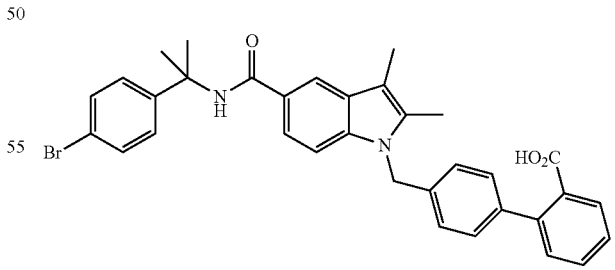

The title compound was prepared following the same general protocol as described in Step 8-9, Example 1, using the 2-(4-bromophenyl)propan-2-amine and the 1-((2'-(tert-butoxycarbonyl)-[1,1'-biphenyl]-4-yl)methyl)-2,3-dimethyl-1H-indole-5-carboxylic acid. ESI-MS (m/z): 595/597 [M+H]$^+$.

Example 181: (R)-4'-((2,3-dimethyl-5-((1-(quinolin-4-yl)ethyl)carbamoyl)-1H-indol-1-yl)methyl)-[1,1'-biphenyl]-2-carboxylic acid

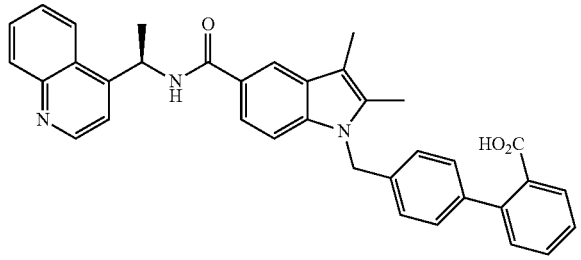 [SMILES: Cc1c(C)n(Cc2ccc(-c3ccccc3C(=O)O)cc2)c2ccc(C(=O)N[C@H](C)c3ccnc4ccccc34)cc12]

Step 1: (R)-1-(quinolin-4-yl)ethanamine

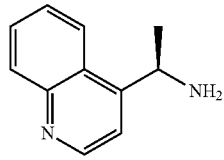

The title compound was prepared following the same general protocol as described in Step 1-2, Example 2, using the quinoline-4-carbaldehyde.

Step 2: (R)-4'-((2,3-dimethyl-5-((1-(quinolin-4-yl)ethyl)carbamoyl)-1H-indol-1-yl)methyl)-[1,1'-biphenyl]-2-carboxylic acid The title compound was prepared following the same general protocol as described in Step 8-9, Example 1, using the (R)-1-(quinolin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 554 [M+H]$^+$.

Example 182: 4'-((5-((3-isopropylbenzyl)carbamoyl)-2,3-dimethyl-1H-indol-1-yl)methyl)-[1,1'-biphenyl]-2-carboxylic acid

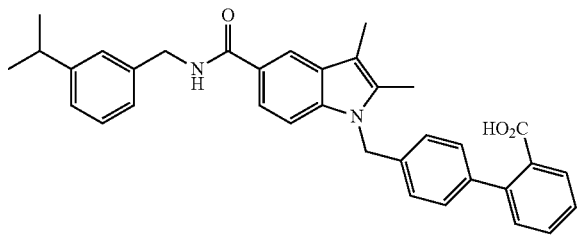 [SMILES: Cc1c(C)n(Cc2ccc(-c3ccccc3C(=O)O)cc2)c2ccc(C(=O)NCc3cccc(C(C)C)c3)cc12]

The title compound was prepared following the same general protocol as described in Step 8-9, Example 1, using the (3-isopropylphenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 531 [M+H]$^+$.

Example 183: (S)-4'-((5-((1-(3-isopropylphenyl)-2-phenylethyl)carbamoyl)-2,3-dimethyl-1H-indol-1-yl)methyl)-[1,1'-biphenyl]-2-carboxylic acid

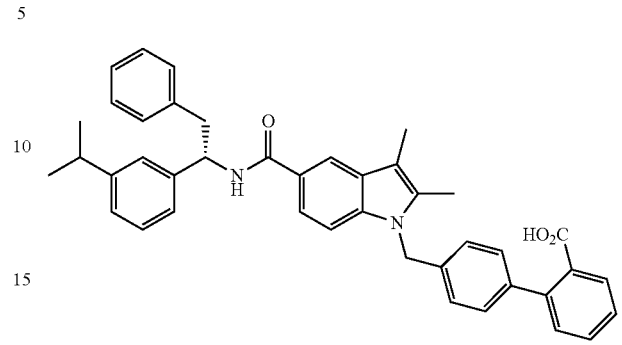

Step 1: (S)-1-(3-isopropylphenyl)-2-phenylethanaminium chloride

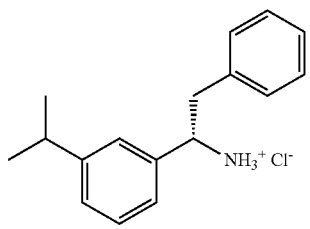

The title compound was prepared following the same general synthetic procedure as described in Steps 1-2, Example 2, using 3-isopropylbenzaldehyde and benzylmagnesium bromide instead of 4-(tert-butyl)benzaldehyde and methylmagnesium bromide.

Step 2: (S)-4'-((5-((1-(3-isopropylphenyl)-2-phenylethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)-2-phenylethanamine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]$^+$.

Example 184: (S)—N-(1-(4-(tert-butyl)phenyl)ethyl)-1-((2'-cyano-[1,1'-biphenyl]-4-yl)methyl)-2,3-dimethyl-1H-indole-5-carboxamide

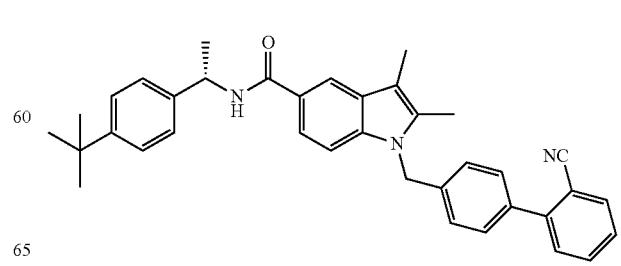

The title compound was prepared following the same general protocol as described in Step 5, Example 34, using the (S)-1-(4-(tert-butyl)phenyl)ethanamine instead of the 1-phenylpropan-1-amine. ESI-MS (m/z): 540 [M+H]⁺.

Example 185: (S)—N-(1-(3-(tert-butyl)phenyl)ethyl)-1-((2'-cyano-[1,1'-biphenyl]-4-yl)methyl)-2,3-dimethyl-1H-indole-5-carboxamide

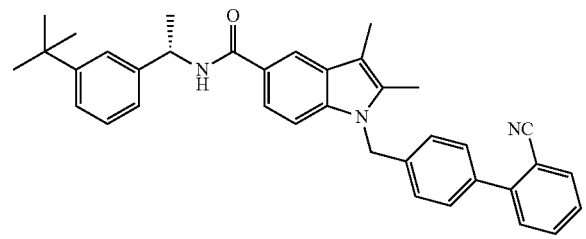 [SMILES: Cc1c(C)n(Cc2ccc(-c3ccccc3C#N)cc2)c2ccc(C(=O)N[C@@H](C)c3cccc(C(C)(C)C)c3)cc12]

The title compound was prepared following the same general protocol as described in Step 5, Example 34, using the (S)-1-(3-(tert-butyl)phenyl)ethanamine instead of the 1-phenylpropan-1-amine. ESI-MS (m/z): 540 [M+H]⁺.

Example 186: (S)-1-((2'-cyano-[1,1'-biphenyl]-4-yl)methyl)-N-(1-(4-isopropylphenyl)ethyl)-2,3-dimethyl-1H-indole-5-carboxamide

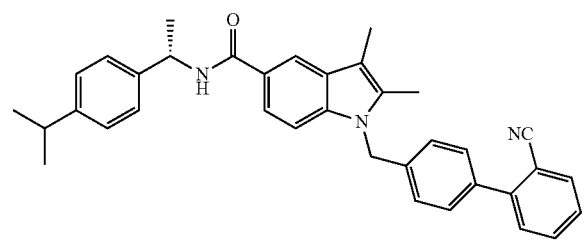 [SMILES: Cc1c(C)n(Cc2ccc(-c3ccccc3C#N)cc2)c2ccc(C(=O)N[C@@H](C)c3ccc(C(C)C)cc3)cc12]

The title compound was prepared following the same general protocol as described in Step 1-2-3, Example 137, using the (S)—N-(1-(4-bromophenyl)ethyl)-1-((2'-cyano-[1,1'-biphenyl]-4-yl)methyl)-2,3-dimethyl-1H-indole-5-carboxamide. ESI-MS (m/z): 526 [M+H]⁺.

Example 187: (R)-1-((2'-(1H-tetrazol-5-yl)-[1,1'-biphenyl]-4-yl)methyl)-N-(1-(3-bromophenyl)ethyl)-2,3-dimethyl-1H-indole-5-carboxamide

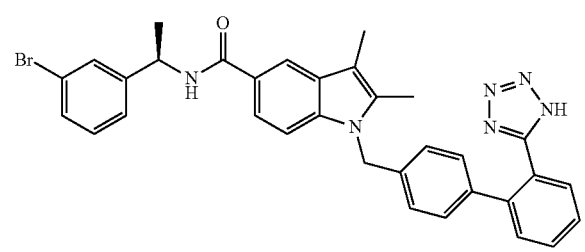 [SMILES: Cc1c(C)n(Cc2ccc(-c3ccccc3-c3nnn[nH]3)cc2)c2ccc(C(=O)N[C@H](C)c3cccc(Br)c3)cc12]

Step 1: (R)—N-(1-(3-bromophenyl)ethyl)-1-((2'-cyano-[1,1'-biphenyl]-4-yl)methyl)-2,3-dimethyl-1H-indole-5-carboxamide

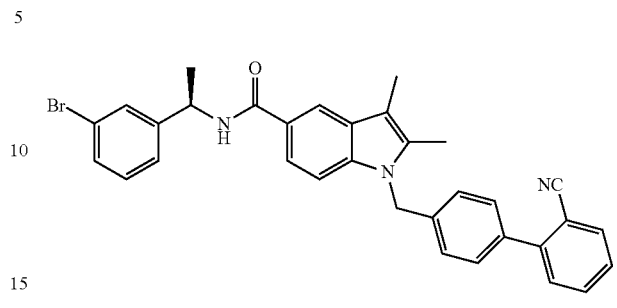

The title compound was prepared following the same general protocol as described in Step 5, Example 34, using the (R)-1-(3-bromophenyl)ethanamine instead of the 1-phenylpropan-1-amine.

Step 2: (R)-1-((2'-(1H-tetrazol-5-yl)-[1,1'-biphenyl]-4-yl)methyl)-N-(1-(3-bromophenyl)ethyl)-2,3-dimethyl-1H-indole-5-carboxamide The title compound was prepared following the same general protocol as described in Example 36, using the (R)—N-(1-(3-bromophenyl)ethyl)-1-((2'-cyano-[1,1'-biphenyl]-4-yl)methyl)-2,3-dimethyl-1H-indole-5-carboxamide. ESI-MS (m/z): 605/607 [M+H]⁺.

Example 188: (S)-1-((2'-(1H-tetrazol-5-yl)-[1,1'-biphenyl]-4-yl)methyl)-N-(1-(3-cyclopropylphenyl)ethyl)-2,3-dimethyl-1H-indole-5-carboxamide

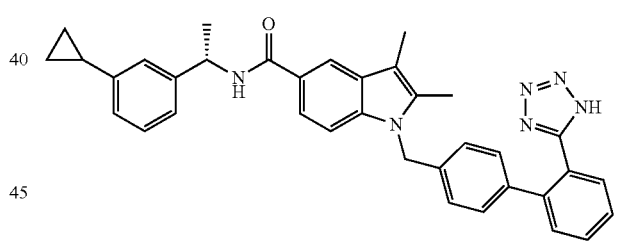

Step 1: (S)-1-((2'-cyano-[1,1'-biphenyl]-4-yl)methyl)-N-(1-(3-cyclopropylphenyl)ethyl)-2,3-dimethyl-1H-indole-5-carboxamide

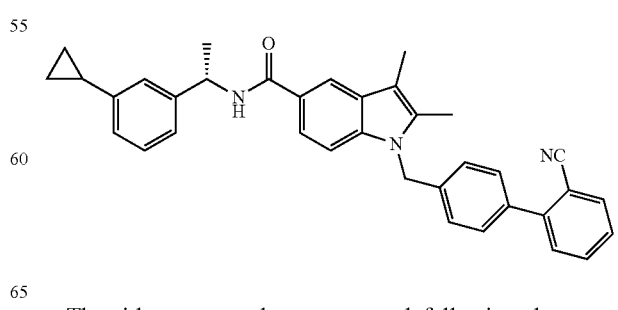

The title compound was prepared following the same general protocol as described in Step 5, Example 34, using the (S)-1-(3-cyclopropylphenyl)ethanamine instead of the 1-phenylpropan-1-amine. ESI-MS (m/z): 524 [M+H]+.

Step 2: (S)-1-((2'-(1H-tetrazol-5-yl)-[1,1'-biphenyl]-4-yl)methyl)-N-(1-(3-cyclopropylphenyl)ethyl)-2,3-dimethyl-1H-indole-5-carboxamide The title compound was prepared following the same general protocol as described in Example 36, using the (S)-1-((2'-cyano-[1,1'-biphenyl]-4-yl)methyl)-N-(1-(3-cyclopropylphenyl)ethyl)-2,3-dimethyl-1H-indole-5-carboxamide. ESI-MS (m/z): 567 [M+H]+.

Example 189: (S)-2'-((5-((1-phenylpropyl)carbamoyl)-1H-indol-1-yl)methyl)-[1,1'-biphenyl]-4-carboxylic acid

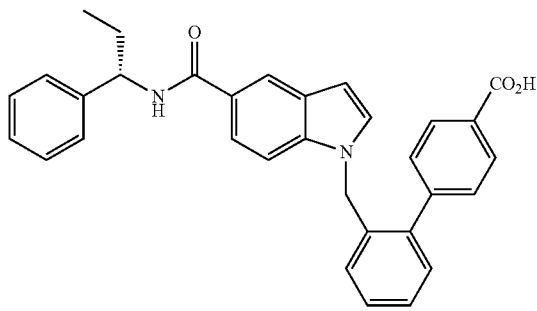 [SMILES: CC[C@H](NC(=O)c1ccc2c(ccn2Cc2ccccc2-c2ccc(C(=O)O)cc2)c1)c1ccccc1]

The title compound was prepared following the same protocol as described in Step 3-4, Example 120 using the (S)-1-phenylpropylamine instead of the (S)-1-(4-bromophenyl)ethanamine. ESI-MS (m/z): 489 [M+H]+.

Example 190: (R)-2'-((5-((1-phenylpropyl)carbamoyl)-1H-indol-1-yl)methyl)-[1,1'-biphenyl]-4-carboxylic acid

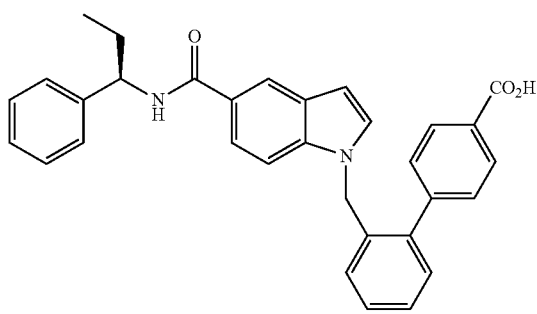 [SMILES: CC[C@@H](NC(=O)c1ccc2c(ccn2Cc2ccccc2-c2ccc(C(=O)O)cc2)c1)c1ccccc1]

The title compound was prepared following the same protocol as described in Step 3-4, Example 120 using the (R)-1-phenylpropylamine instead of the (S)-1-(4-bromophenyl)ethanamine. ESI-MS (m/z): 489 [M+H]+.

Example 191: (S)-2'-((5-((1-phenylpropyl)carbamoyl)-1H-indol-1-yl)methyl)-[1,1'-biphenyl]-3-carboxylic acid

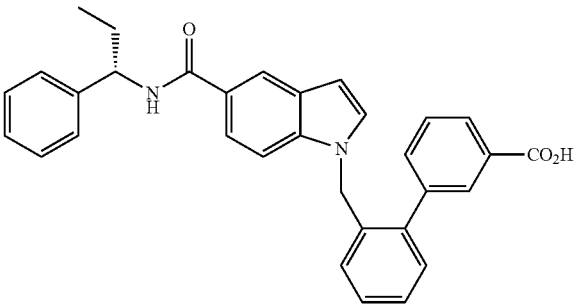 [SMILES: CC[C@H](NC(=O)c1ccc2c(ccn2Cc2ccccc2-c2cccc(C(=O)O)c2)c1)c1ccccc1]

The title compound was prepared following the same protocol as described in Step 3-4, Example 122 using the (S)-1-phenylpropylamine instead of the (S)-1-(4-bromophenyl)ethanamine. ESI-MS (m/z): 489 [M+H]+.

Example 192: (R)-2'-((5-((1-phenylpropyl)carbamoyl)-1H-indol-1-yl)methyl)-[1,1'-biphenyl]-3-carboxylic acid

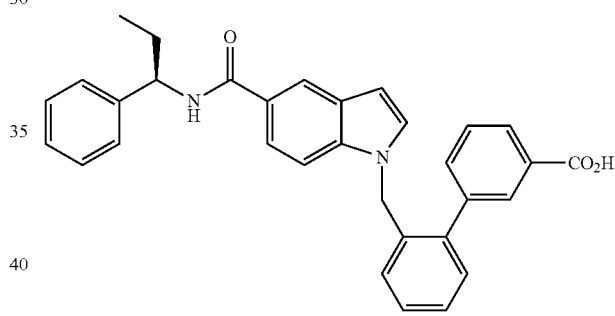

The title compound was prepared following the same protocol as described in Step 2-3, Example 122 using the (R)-1-phenylpropylamine instead of the (S)-1-(4-bromophenyl)ethanamine. ESI-MS (m/z): 489 [M+H]+.

Example 193: (R)-2'-((2,3-dimethyl-5-((1-phenylpropyl)carbamoyl)-1H-indol-1-yl)methyl)-[1,1'-biphenyl]-3-carboxylic acid

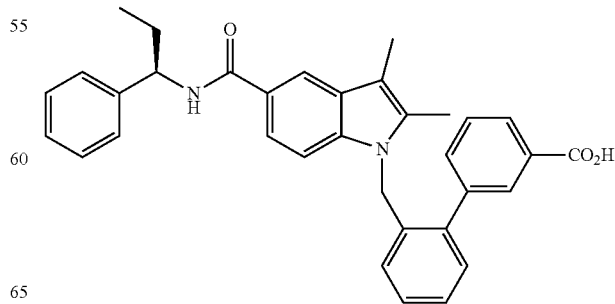

The title compound was prepared following the same protocol as described in Step 4-5, Example 124 using the (R)-1-phenylpropylamine instead of the (S)-1-(4-bromophenyl)ethanamine. ESI-MS (m/z): 489 [M+H]$^+$.

Example 194: (S)-2'-((2,3-dimethyl-5-((1-phenylpropyl)carbamoyl)-1H-indol-1-yl)methyl)-[1,1'-biphenyl]-3-carboxylic acid

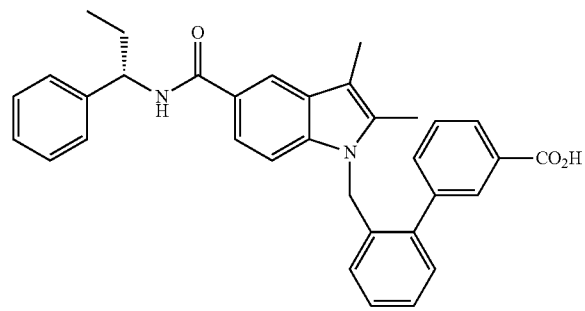 [SMILES: CC[C@H](NC(=O)c1ccc2c(c1)c(C)c(C)n2Cc1ccccc1-c1cccc(C(=O)O)c1)c1ccccc1]

The title compound was prepared following the same protocol as described in Step 4-5, Example 124 using the (S)-1-phenylpropylamine instead of the (S)-1-(4-bromophenyl)ethanamine. ESI-MS (m/z): 489 [M+H]$^+$.

Example 195: (R)-2'-((2,3-dimethyl-5-((1-phenylpropyl)carbamoyl)-1H-indol-1-yl)methyl)-[1,1'-biphenyl]-4-carboxylic acid

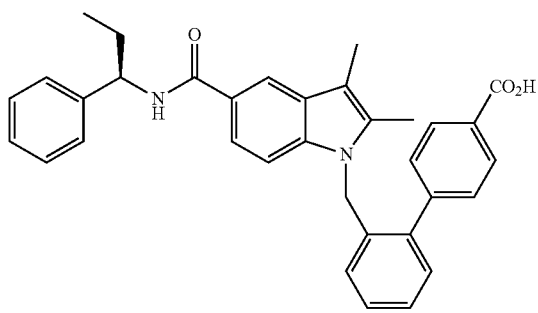 [SMILES: CC[C@@H](NC(=O)c1ccc2c(c1)c(C)c(C)n2Cc1ccccc1-c1ccc(C(=O)O)cc1)c1ccccc1]

The title compound was prepared following the same protocol as described in Step 2-3, Example 127 using the (R)-1-phenylpropylamine instead of the (S)-1-(4-bromophenyl)ethanamine. ESI-MS (m/z): 489 [M+H]$^+$.

Example 196: (S)-2'-((2,3-dimethyl-5-((1-phenylpropyl)carbamoyl)-1H-indol-1-yl)methyl)-[1,1'-biphenyl]-4-carboxylic acid

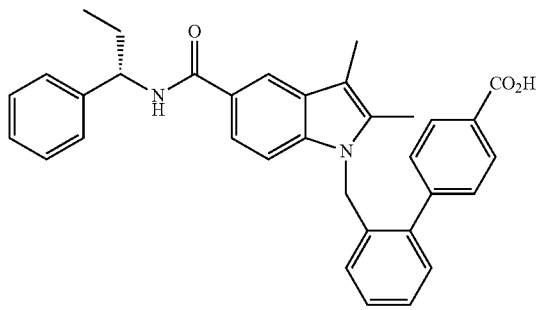 [SMILES: CC[C@H](NC(=O)c1ccc2c(c1)c(C)c(C)n2Cc1ccccc1-c1ccc(C(=O)O)cc1)c1ccccc1]

The title compound was prepared following the same protocol as described in Step 2-3, Example 127 using the (S)-1-phenylpropylamine instead of the (S)-1-(4-bromophenyl)ethanamine. ESI-MS (m/z): 489 [M+H]$^+$.

Example 197: (S)-4'-((5-((1-(3-chloro-4-methoxyphenyl)ethyl)carbamoyl)-2,3-dimethyl-1H-indol-1-yl)methyl)-[1,1'-biphenyl]-2-carboxylic acid

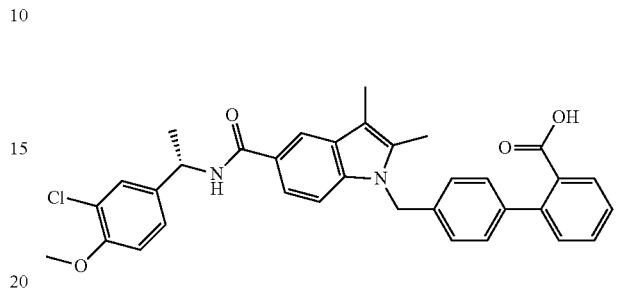

Step 1: (S)-1-(3-chloro-4-methoxyphenyl)ethanaminium chloride

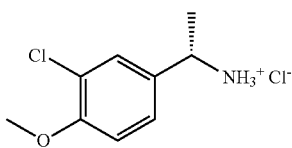

The title compound was prepared following the same general synthetic procedure as described in Steps 1-2, Example 2, using 3-chloro-4-methoxybenzaldehyde instead of 4-(tert-butyl)benzaldehyde.

Step 2: (S)-4'-((5-((1-(3-chloro-4-methoxyphenyl)ethyl)carbamoyl)-2,3-dimethyl-1H-indol-1-yl)methyl)-[1,1'-biphenyl]-2-carboxylic acid

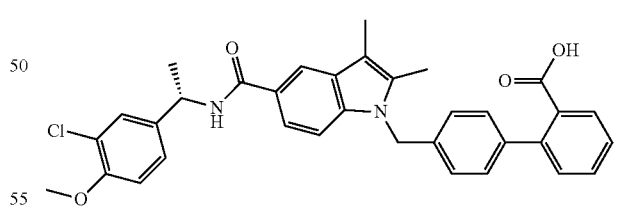

The title compound was prepared following the same general synthetic procedure as described in Steps 3-4, Example 2, starting with (S)-1-(3-chloro-4-methoxyphenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 567 [M+1]$^+$.

Example 198: (S)-4'-((5-((1-(3-isopropylphenyl) propyl)carbamoyl)-2,3-dimethyl-1H-indol-1-yl) methyl)-[1,1'-biphenyl]-2-carboxylic acid

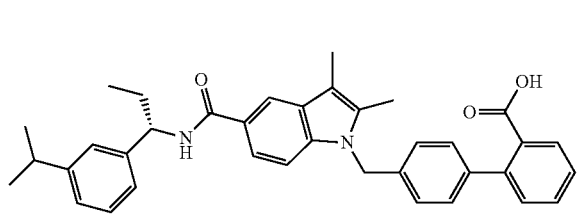 [SMILES: CC[C@H](NC(=O)c1ccc2c(c1)c(C)c(C)n2Cc1ccc(-c2ccccc2C(=O)O)cc1)c1cccc(C(C)C)c1]

Step 1: (S)-1-(3-isopropylphenyl)propan-1-aminium chloride

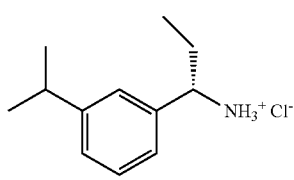

The title compound was prepared following the same general synthetic procedure as described in Steps 1-2, Example 2, using 3-isopropylbenzaldehyde and ethylmagnesium bromide instead of 4-(tert-butyl)benzaldehyde and methylmagnesium bromide.

Step 2: (S)-4'-((5-((1-(3-isopropylphenyl)propyl) carbamoyl)-2,3-dimethyl-1H-indol-1-yl)methyl)-[1, 1'-biphenyl]-2-carboxylic acid

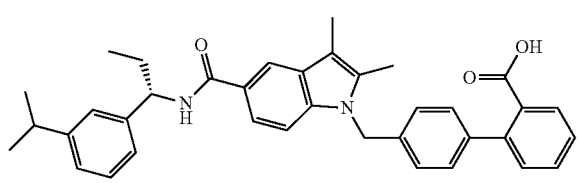 [SMILES: CC[C@H](NC(=O)c1ccc2c(c1)c(C)c(C)n2Cc1ccc(-c2ccccc2C(=O)O)cc1)c1cccc(C(C)C)c1]

The title compound was prepared following the same general synthetic procedure as described in Steps 3-4, Example 2, starting with (S)-1-(3-isopropylphenyl)propan-1-aminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 558 [M+1]$^+$.

Example 199: (S)-4'-((5-((1-(3-isopropoxyphenyl) ethyl)carbamoyl)-2,3-dimethyl-1H-indol-1-yl) methyl)-[1,1'-biphenyl]-2-carboxylic acid

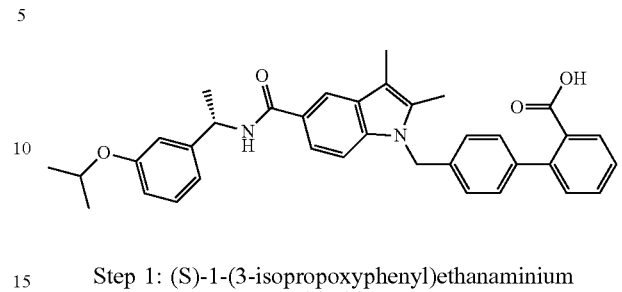

Step 1: (S)-1-(3-isopropoxyphenyl)ethanaminium chloride

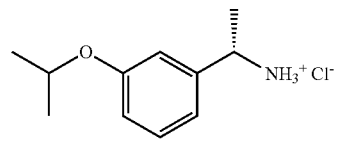

The title compound was prepared following the same general synthetic procedure as described in Steps 1-2, Example 2, using 3-isopropoxybenzaldehyde instead of 4-(tert-butyl)benzaldehyde.

Step 2: (S)-4'-((5-((1-(3-isopropoxyphenyl)ethyl) carbamoyl)-2,3-dimethyl-1H-indol-1-yl)methyl)-[1, 1'-biphenyl]-2-carboxylic acid

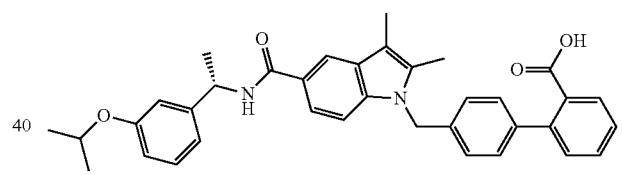

The title compound was prepared following the same general synthetic procedure as described in Steps 3-4, Example 2, starting with (S)-1-(3-isopropoxyphenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 560 [M+1]$^+$.

Example 200: (S)-4'-((5-((1-(4-(tert-butoxy)phenyl) ethyl)carbamoyl)-2,3-dimethyl-1H-indol-1-yl) methyl)-[1,1'-biphenyl]-2-carboxylic acid

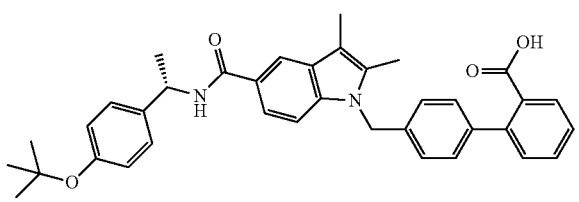 [SMILES: Cc1c(C)n(Cc2ccc(-c3ccccc3C(=O)O)cc2)c2ccc(C(=O)N[C@@H](C)c3ccc(OC(C)(C)C)cc3)cc12]

Step 1: (S)-1-(4-(tert-butoxy)phenyl)ethanaminium chloride

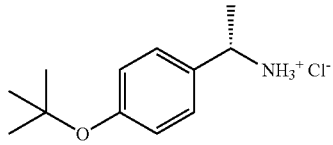

The title compound was prepared following the same general synthetic procedure as described in Steps 1-2, Example 2, using 4-(tert-butoxy)benzaldehyde instead of 4-(tert-butyl)benzaldehyde.

Step 2: (S)-4'-((5-((1-(4-(tert-butoxy)phenyl)ethyl)carbamoyl)-2,3-dimethyl-1H-indol-1-yl)methyl)-[1,1'-biphenyl]-2-carboxylic acid

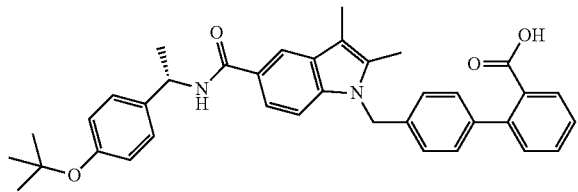 [SMILES: Cc1c(C)n(Cc2ccc(-c3ccccc3C(=O)O)cc2)c2ccc(C(=O)N[C@@H](C)c3ccc(OC(C)(C)C)cc3)cc12]

The title compound was prepared following the same general synthetic procedure as described in Steps 3-4, Example 2, starting with (S)-1-(4-(tert-butoxy)phenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 574 [M+1]$^+$.

Example 201: (S)-4'-((5-((1-(4-isopropoxyphenyl)ethyl)carbamoyl)-2,3-dimethyl-1H-indol-1-yl)methyl)-[1,1'-biphenyl]-2-carboxylic acid

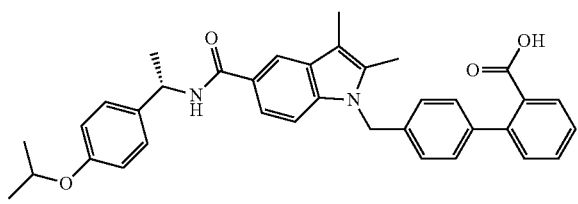 [SMILES: Cc1c(C)n(Cc2ccc(-c3ccccc3C(=O)O)cc2)c2ccc(C(=O)N[C@@H](C)c3ccc(OC(C)C)cc3)cc12]

Step 1: (S)-1-(4-isopropoxyphenyl)ethanaminium chloride

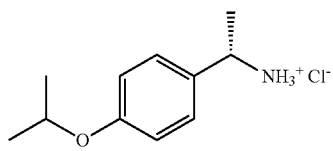

The title compound was prepared following the same general synthetic procedure as described in Steps 1-2, Example 2, using 4-isopropoxybenzaldehyde instead of 4-(tert-butyl)benzaldehyde.

Step 2: (S)-4'-((5-((1-(4-isopropoxyphenyl)ethyl)carbamoyl)-2,3-dimethyl-1H-indol-1-yl)methyl)-[1,1'-biphenyl]-2-carboxylic acid

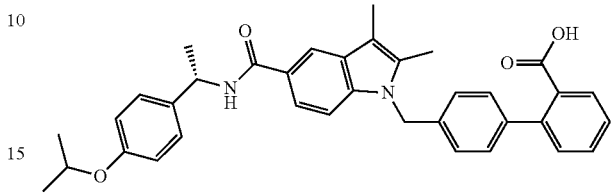

The title compound was prepared following the same general synthetic procedure as described in Steps 3-4, Example 2, starting with (S)-1-(4-isopropoxyphenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 560 [M+1]$^+$.

Example 202: (S)-4'-((5-((1-(1-((benzyloxy)carbonyl)piperidin-4-yl)ethyl)carbamoyl)-2,3-dimethyl-1H-indol-1-yl)methyl)-[1,1'-biphenyl]-2-carboxylic acid

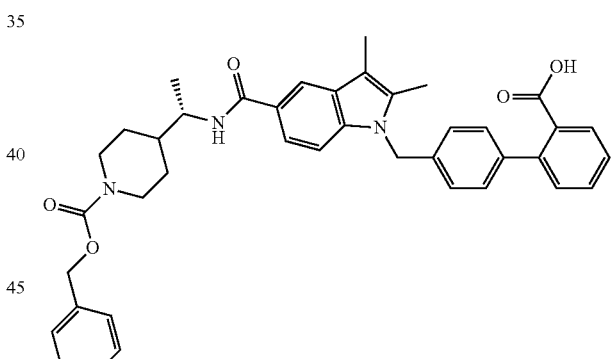

Step 1: (S)-1-(1-((benzyloxy)carbonyl)piperidin-4-yl)ethanaminium chloride

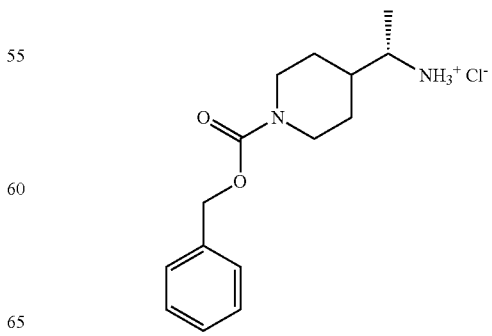

The title compound was prepared following the same general synthetic procedure as described in Steps 1-2, Example 2, using benzyl 4-formylpiperidine-1-carboxylate instead of 4-(tert-butyl)benzaldehyde. ESI-MS (m/z): 263 [M+1]+.

Step 2: (S)-4'-((5-((1-(1-((benzyloxy)carbonyl)piperidin-4-yl)ethyl)carbamoyl)-2,3-dimethyl-1H-indol-1-yl)methyl)-[1,1'-biphenyl]-2-carboxylic acid

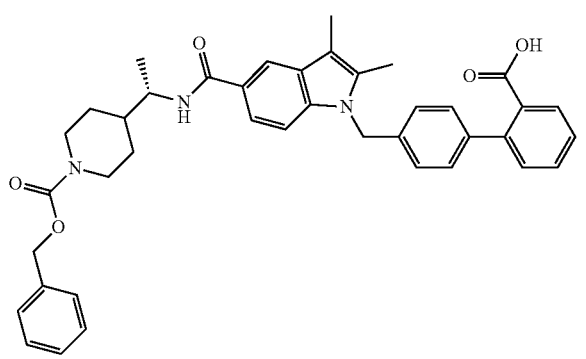 [SMILES: Cc1c(C)n(Cc2ccc(-c3ccccc3C(=O)O)cc2)c2ccc(C(=O)N[C@@H](C)C3CCN(C(=O)OCc4ccccc4)CC3)cc12]

The title compound was prepared following the same general synthetic procedure as described in Steps 3-4, Example 2, starting with ((S)-1-(1-((benzyloxy)carbonyl)piperidin-4-yl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 643 [M+1]+.

Example 203: (S)-4'-((5-((1-(1-(benzylcarbamoyl) piperidin-4-yl)ethyl)carbamoyl)-2,3-dimethyl-1H-indol-1-yl)methyl)[1,1'-biphenyl]-2-carboxylic acid 2753

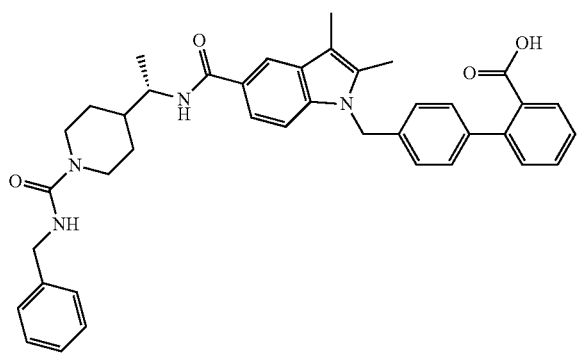 [SMILES: Cc1c(C)n(Cc2ccc(-c3ccccc3C(=O)O)cc2)c2ccc(C(=O)N[C@@H](C)C3CCN(C(=O)NCc4ccccc4)CC3)cc12]

The title compound was prepared from (S)-4'-((5-((1-(1-((benzyloxy)carbonyl)piperidin-4-yl)ethyl)carbamoyl)-2,3-dimethyl-1H-indol-1-yl)methyl)-[1,1'-biphenyl]-2-carboxylic-acid (0.175 g, 0.250 mmol) following palladium catalyzed hydrogenation (18 mg, 10% Pd/c) in AcOH (5 mL) and subsequent coupling of the resulting piperidine ((S)-tert-butyl-4'-((2,3-dimethyl-5-((1-(piperidin-4-yl)ethyl) carbamoyl)-1H-indol-1-yl)methyl)-[1,1'-biphenyl]-2-carboxylate) with benzyl isocyanate (6.8 mg, 0.049 mmol) in dicholoromethane (DCM) (1 mL)/di-isopropylethylamine (9.2 µL, 0.053 mmol) and then removal of t-butyl ester in TFA/DCM (1:1, 2 mL). Completion at each synthetic step was monitored by analytical HPLC and the title compound was isolated by reverse phase prep-HPLC (MeOH/Acetonitrile/water) ESI-MS (m/z): 642 [M+1]+.

Example 204: (S)-4'-((5-((1-((benzyloxy)carbonyl) pyrrolidin-3-yl)carbamoyl)-2,3-dimethyl-1H-indol-1-yl)methyl)-[1,1'-biphenyl]-2-carboxylic acid

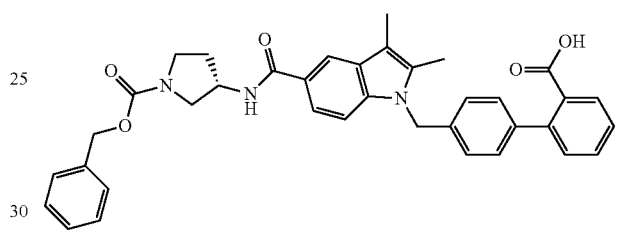

The title compound was prepared following the same general synthetic procedure as described in Steps 3-4, Example 2, starting with (S)-benzyl 3-aminopyrrolidine-1-carboxylate and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 601 [M+1]+.

Example 205: (R)-4'-((5-((1-(5-fluoro-2-methoxyphenyl)ethyl)carbamoyl)-2,3-dimethyl-1H-indol-1-yl)methyl)-[1,1'-biphenyl]-2-carboxylic acid

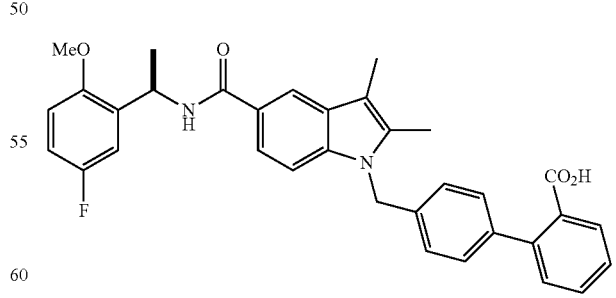

The title compound was prepared following the same general protocol as described in Steps 1-4, Example 1, using 5-fluoro-2-methoxybenzaldehyde and 1-((2'-(tert-butoxycarbonyl)biphenyl-4-yl)methyl)-2,3-dimethyl-1H-indole-5-carboxylic acid. LC-MS 551.2 (M+H).

Example 206: (S)-4'-((5-((1-(5-fluoro-2-methoxy-phenyl)ethyl)carbamoyl)-2,3-dimethyl-1H-indol-1-yl)methyl)-[1,1'-biphenyl]-2-carboxylic acid

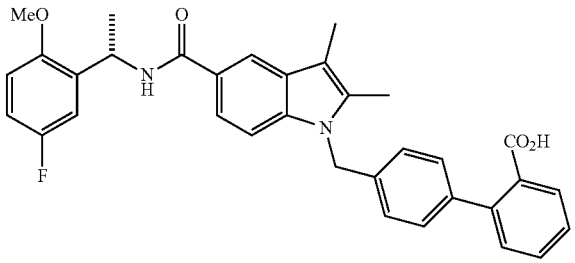 [SMILES: COc1ccc(F)cc1[C@H](C)NC(=O)c1ccc2c(c1)c(C)c(C)n2Cc1ccc(-c2ccccc2C(=O)O)cc1]

The title compound was prepared following the same general protocol as described in Steps 1-4, Example 1, using 5-fluoro-2-methoxybenzaldehyde and 1-((2'-(tert-butoxycarbonyl)biphenyl-4-yl)methyl)-2,3-dimethyl-1H-indole-5-carboxylic acid. LC-MS 551.2 (M+H).

Example 207: (R)-4'-((2,3-dimethyl-5-((1-(2-(trifluoromethyl)phenyl)ethyl)carbamoyl)-1H-indol-1-yl)methyl)-[1,1'-biphenyl]-2-carboxylic acid

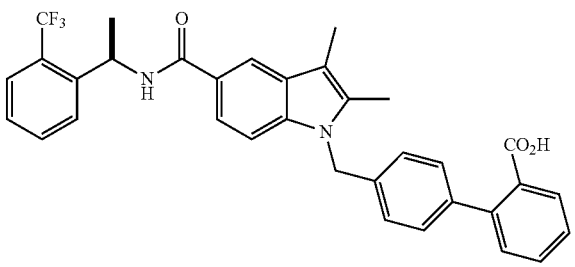 [SMILES: Cc1c(C)n(Cc2ccc(-c3ccccc3C(=O)O)cc2)c2ccc(C(=O)N[C@H](C)c3ccccc3C(F)(F)F)cc12]

The title compound was prepared following the same general protocol as described in Steps 1-4, Example 1, using 2-trifluoromethylbenzaldehyde and 1-((2'-(tert-butoxycarbonyl)biphenyl-4-yl)methyl)-2,3-dimethyl-1H-indole-5-carboxylic acid. LC-MS 571.2 (M+H).

Example 208: (S)-4'-((2,3-dimethyl-5-((1-(2-(trifluoromethyl)phenyl)ethyl)carbamoyl)-1H-indol-1-yl)methyl)-[1,1'-biphenyl]-2-carboxylic acid

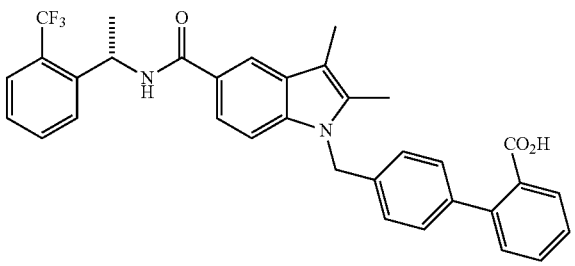 [SMILES: Cc1ccc(F)c([C@H](C)NC(=O)c2ccc3c(c2)c(C)c(C)n3Cc2ccc(-c3ccccc3C(=O)O)cc2)c1]

The title compound was prepared following the same general protocol as described in Steps 1-4, Example 1, using 2-trifluoromethylbenzaldehyde and 1-((2'-(tert-butoxycarbonyl)biphenyl-4-yl)methyl)-2,3-dimethyl-1H-indole-5-carboxylic acid. LC-MS 571.6 (M+H).

Example 209: (R)-4'-((5-((1-(2,4-bis(trifluoromethyl)phenyl)ethyl)carbamoyl)-2,3-dimethyl-1H-indol-1-yl)methyl)-[1,1'-biphenyl]-2-carboxylic acid

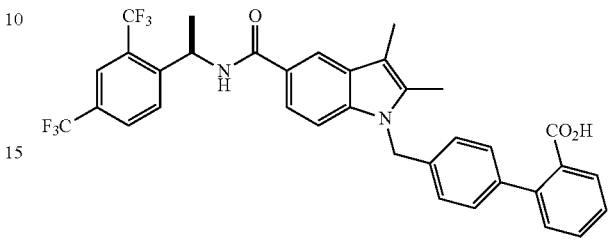

The title compound was prepared following the same general protocol as described in Steps 1-4, Example 1, using 2,4-bistrifluoromethylbenzaldehyde and 1-((2'-(tert-butoxycarbonyl)biphenyl-4-yl)methyl)-2,3-dimethyl-1H-indole-5-carboxylic acid. LC-MS 639.2 (M+H).

Example 210: (S)-4'-((5-((1-(2,4-bis(trifluoromethyl)phenyl)ethyl)carbamoyl)-2,3-dimethyl-1H-indol-1-yl)methyl)-[1,1'-biphenyl]-2-carboxylic acid

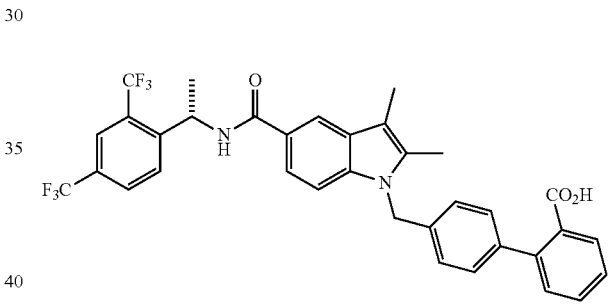

The title compound was prepared following the same general protocol as described in Steps 1-4, Example 1, using 2,4-bistrifluoromethylbenzaldehyde and 1-((2'-(tert-butoxycarbonyl)biphenyl-4-yl)methyl)-2,3-dimethyl-1H-indole-5-carboxylic acid. LC-MS 639.2 (M+−H).

Example 211: (S)-4'-((5-((1-(2-fluoro-5-methylphenyl)ethyl)carbamoyl)-2,3-dimethyl-1H-indol-1-yl)methyl)-[1,1'-biphenyl]-2-carboxylic acid

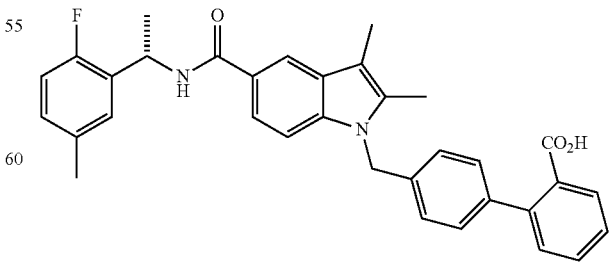

The title compound was prepared following the same general protocol as described in Steps 1-4, Example 1, using 2-fluoro-5-methylbenzaldehyde and 1-((2'-(tert-butoxycarbonyl)biphenyl-4-yl)methyl)-2,3-dimethyl-1H-indole-5-carboxylic acid. LC-MS 535.2 (M+H).

Example 212: (S)-4'-((5-((1-cyclohexylethyl)carbamoyl)-2,3-dimethyl-1H-indol-1-yl)methyl)-[1,1'-biphenyl]-2-carboxylic acid

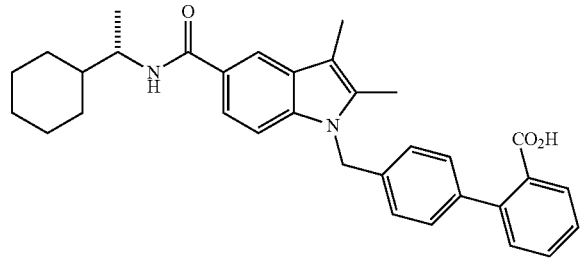 [SMILES: Cc1c(C)n(Cc2ccc(-c3ccccc3C(=O)O)cc2)c2ccc(C(=O)N[C@@H](C)C3CCCCC3)cc12]

The title compound was prepared following the same general protocol as described in Steps 1-4, Example 1, using cyclohexanecarboxaldehyde and 1-((2'-(tert-butoxycarbonyl)biphenyl-4-yl)methyl)-2,3-dimethyl-1H-indole-5-carboxylic acid. LC-MS 509.2 (M+H).

Example 213: 4'-((5-(((1R)-1-(2,3-dihydrobenzo[b][1,4]dioxin-2-yl)ethyl)carbamoyl)-2,3-dimethyl-1H-indol-1-yl)methyl)-[1,1'-biphenyl]-2-carboxylic acid

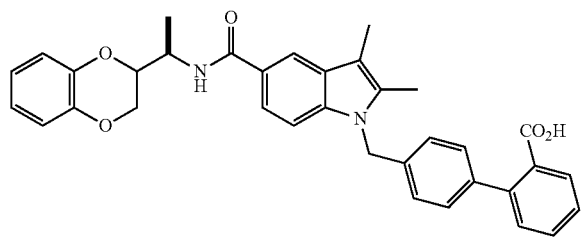 [SMILES: Cc1c(C)n(Cc2ccc(-c3ccccc3C(=O)O)cc2)c2ccc(C(=O)N[C@H](C)C3COc4ccccc4O3)cc12]

The title compound was prepared following the same general protocol as described in Steps 1-4, Example 1, using 2,3-dihydrobenzo[b][1,4]dioxine-2-carbaldehyde and 1-((2'-(tert-butoxycarbonyl)biphenyl-4-yl)methyl)-2,3-dimethyl-1H-indole-5-carboxylic acid. LC-MS 561.2 (M+H).

Example 214: 4'-((5-(((1S)-1-(2,3-dihydrobenzo[b][1,4]dioxin-2-yl)ethyl)carbamoyl)-2,3-dimethyl-1H-indol-1-yl)methyl)-[1,1'-biphenyl]-2-carboxylic acid

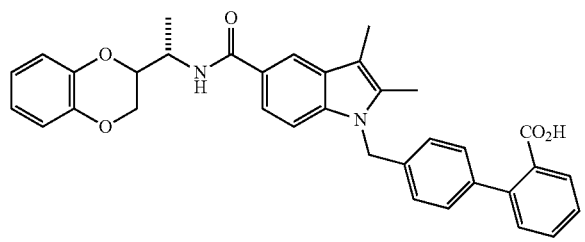 [SMILES: Cc1c(C)n(Cc2ccc(-c3ccccc3C(=O)O)cc2)c2ccc(C(=O)N[C@@H](C)C3COc4ccccc4O3)cc12]

The title compound was prepared following the same general protocol as described in Steps 1-4, Example 1, using 2,3-dihydrobenzo[b][1,4]dioxine-2-carbaldehyde and 1-((2'-(tert-butoxycarbonyl)biphenyl-4-yl)methyl)-2,3-dimethyl-1H-indole-5-carboxylic acid. LC-MS 561.2 (M+H).

Example 215: (R)-4'-((5-((1-(3,5-difluoropyridin-4-yl)ethyl)carbamoyl)-2,3-dimethyl-1H-indol-1-yl)methyl)-[1,1'-biphenyl]-2-carboxylic acid

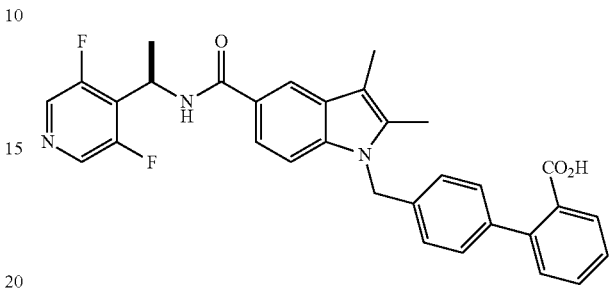

The title compound was prepared following the same general protocol as described in Steps 1-4, Example 1, using 3,5-difluoroisonicotinaldehyde and 1-((2'-(tert-butoxycarbonyl)biphenyl-4-yl)methyl)-2,3-dimethyl-1H-indole-5-carboxylic acid. LC-MS 540.2 (M+H).

Example 216: (S)-4'-((5-((1-(3,5-difluoropyridin-4-yl)ethyl)carbamoyl)-2,3-dimethyl-1H-indol-1-yl)methyl)-[1,1'-biphenyl]-2-carboxylic acid

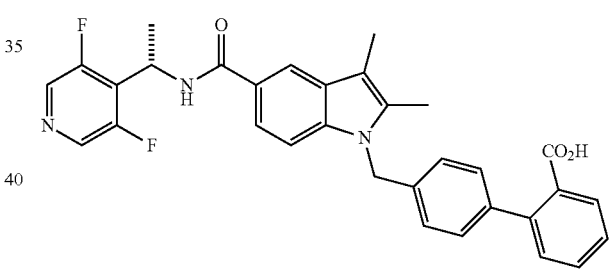

The title compound was prepared following the same general protocol as described in Steps 1-4, Example 1, using 3,5-difluoroisonicotinaldehyde and 1-((2'-(tert-butoxycarbonyl)biphenyl-4-yl)methyl)-2,3-dimethyl-1H-indole-5-carboxylic acid. LC-MS 540.2 (M+H).

Example 217: (S)-4'-((2,3-dimethyl-5-((1-(6-(trifluoromethyl)pyridin-3-yl)ethyl)carbamoyl)-1H-indol-1-yl)methyl)-[1,1'-biphenyl]-2-carboxylic acid

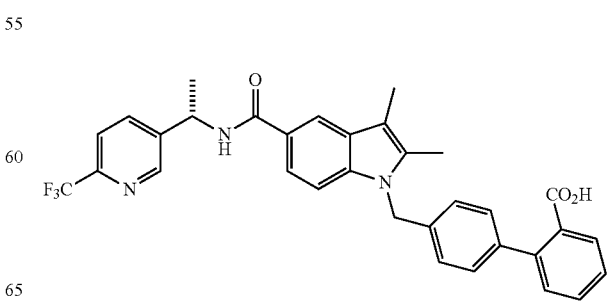

The title compound was prepared following the same general protocol as described in Steps 1-4, Example 1, using 6-(trifluoromethyl)nicotinaldehyde and 1-((2'-(tert-butoxycarbonyl)biphenyl-4-yl)methyl)-2,3-dimethyl-1H-indole-5-carboxylic acid. LC-MS 572.2 (M+H).

Example 218: (S)-4'-((5-((1-(2,3-dihydrobenzofuran-5-yl)ethyl)carbamoyl)-2,3-dimethyl-1H-indol-1-yl)methyl)-[1,1'-biphenyl]-2-carboxylic acid

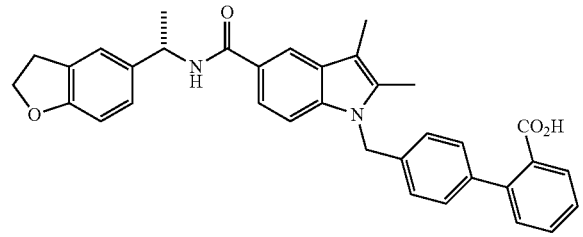 [SMILES: Cc1c(C)n(Cc2ccc(-c3ccccc3C(=O)O)cc2)c2ccc(C(=O)N[C@@H](C)c3ccc4c(c3)CCO4)cc12]

The title compound was prepared following the same general protocol as described in Steps 1-4, Example 1, using 2,3-dihydrobenzofuran-5-carbaldehyde and 1-((2'-(tert-butoxycarbonyl)biphenyl-4-yl)methyl)-2,3-dimethyl-1H-indole-5-carboxylic acid. LC-MS 545.2 (M+H).

Example 219: (S)-4'-((5-((1-(3,5-dichlorophenyl)ethyl)carbamoyl)-2,3-dimethyl-1H-indol-1-yl)methyl)-[1,1'-biphenyl]-2-carboxylic acid

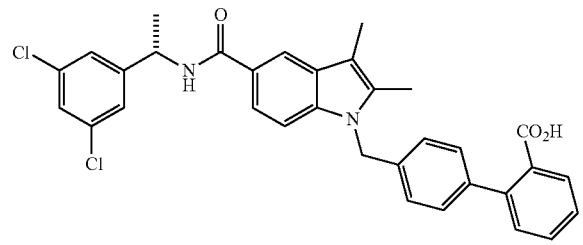 [SMILES: Cc1c(C)n(Cc2ccc(-c3ccccc3C(=O)O)cc2)c2ccc(C(=O)N[C@@H](C)c3cc(Cl)cc(Cl)c3)cc12]

The title compound was prepared following the same general protocol as described in Steps 1-4, Example 1, using 2,4-dichlorobenzaldehyde and 1-((2'-(tert-butoxycarbonyl)biphenyl-4-yl)methyl)-2,3-dimethyl-1H-indole-5-carboxylic acid. LC-MS 571.1 (M+H).

Example 220: (S)-4'-((5-((1-(3,4-dichlorophenyl)ethyl)carbamoyl)-2,3-dimethyl-1H-indol-1-yl)methyl)-[1,1'-biphenyl]-2-carboxylic acid

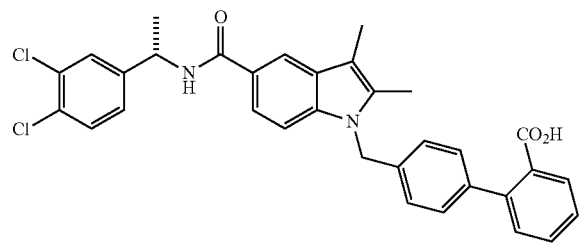 [SMILES: Cc1c(C)n(Cc2ccc(-c3ccccc3C(=O)O)cc2)c2ccc(C(=O)N[C@@H](C)c3ccc(Cl)c(Cl)c3)cc12]

The title compound was prepared following the same general protocol as described in Steps 1-4, Example 1, using 3,4-dichlorobenzaldehyde and 1-((2'-(tert-butoxycarbonyl)biphenyl-4-yl)methyl)-2,3-dimethyl-1H-indole-5-carboxylic acid. LC-MS 571.1 (M+).

Example 221: (S)-4'-((5-((1-(2-fluoro-5-(trifluoromethyl)phenyl)ethyl)carbamoyl)-2,3-dimethyl-1H-indol-1-yl)methyl)-[1,1'-biphenyl]-2-carboxylic acid

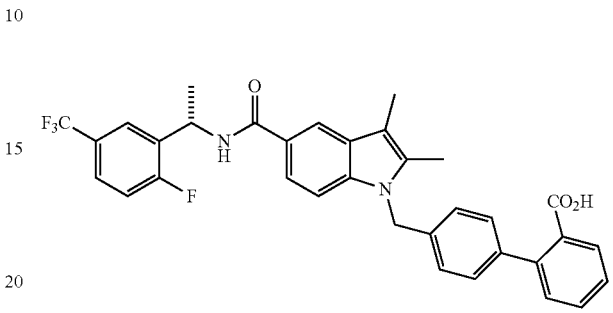

The title compound was prepared following the same general protocol as described in Steps 1-4, Example 1, using 2-fluoro-5-trifluoromethylbenzaldehyde and 1-((2'-(tert-butoxycarbonyl)biphenyl-4-yl)methyl)-2,3-dimethyl-1H-indole-5-carboxylic acid. LC-MS 589.1 (M+H).

Example 222: (S)-4'-((5-((1-(4-chloro-3-(trifluoromethyl)phenyl)ethyl)carbamoyl)-2,3-dimethyl-1H-indol-1-yl)methyl)-[1,1'-biphenyl]-2-carboxylic acid

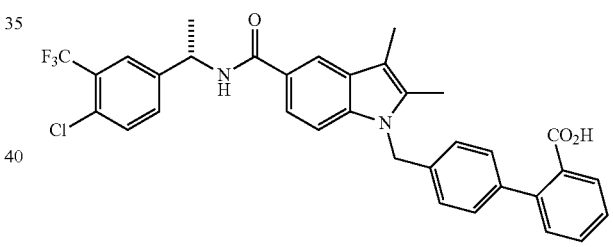

The title compound was prepared following the same general protocol as described in Steps 1-4, Example 1, using 3-trifluoromethyl-4-chlorobenzaldehyde and 1-((2'-(tert-butoxycarbonyl)biphenyl-4-yl)methyl)-2,3-dimethyl-1H-indole-5-carboxylic acid. LC-MS 606.1 (M+H).

Example 223: (S)-4'-((5-((1-(2-methoxy-4-(trifluoromethyl)phenyl)ethyl)carbamoyl)-2,3-dimethyl-1H-indol-1-yl)methyl)-[1,1'-biphenyl]-2-carboxylic acid

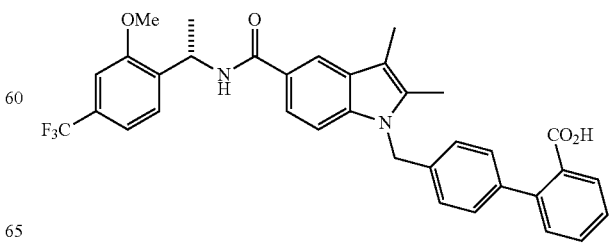

The title compound was prepared following the same general protocol as described in Steps 1-4, Example 1, using 2-methoxy-4-trifluoromethylbenzaldehyde and 1-((2'-(tert-butoxycarbonyl)biphenyl-4-yl)methyl)-2,3-dimethyl-1H-indole-5-carboxylic acid. LC-MS 601.2 (M+H).

Example 224: (R)-4'-((5-((1-(2-methoxy-4-(trifluoromethyl)phenyl)ethyl)carbamoyl)-2,3-dimethyl-1H-indol-1-yl)methyl)-[1,1'-biphenyl]-2-carboxylic acid

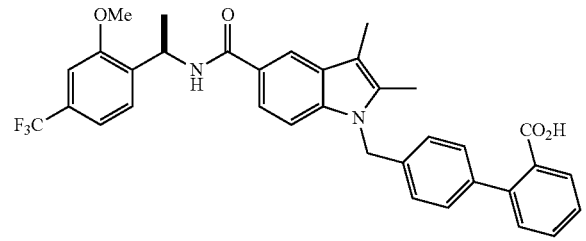

The title compound was prepared following the same general protocol as described in Steps 1-4, Example 1, using 2-methoxy-4-trifluoromethylbenzaldehyde and 1-((2'-(tert-butoxycarbonyl)biphenyl-4-yl)methyl)-2,3-dimethyl-1H-indole-5-carboxylic acid. LC-MS 601.2 (M+H).

Example 225: (S)-4'-((5-((1-(4-ethylphenyl)ethyl)carbamoyl)-2,3-dimethyl-1H-indol-1-yl)methyl)-[1,1'-biphenyl]-2-carboxylic acid

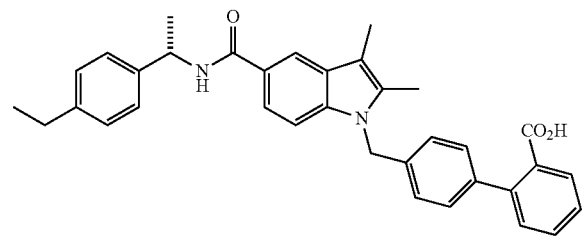 [SMILES: CCc1ccc([C@H](C)NC(=O)c2ccc3c(c2)c(C)c(C)n3Cc2ccc(-c3ccccc3C(=O)O)cc2)cc1]

The title compound was prepared following the same general protocol as described in Steps 1-4, Example 1, using 4-ethylbenzaldehyde and 1-((2'-(tert-butoxycarbonyl)biphenyl-4-yl)methyl)-2,3-dimethyl-1H-indole-5-carboxylic acid. LC-MS 531.2 (M+H).

Example 226: (S)-4'-((5-((1-(4-chloro-2-methylphenyl)ethyl)carbamoyl)-2,3-dimethyl-1H-indol-1-yl)methyl)-[1,1'-biphenyl]-2-carboxylic acid

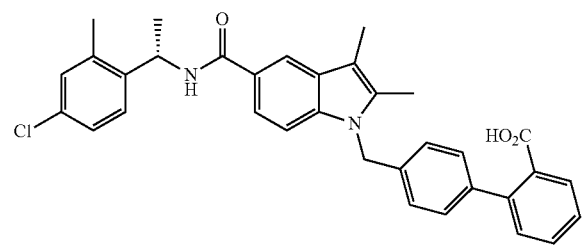

The title compound was prepared following the same general protocol as described in Step 8-9, Example 1, using the (S)-1-(4-chloro-2-methylphenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 551 [M+H]⁺.

Example 227: (S)-4'-((5-((1-(4-fluoro-2-(trifluoromethyl)phenyl)ethyl)carbamoyl)-2,3-dimethyl-1H-indol-1-yl)methyl)-[1,1'-biphenyl]-2-carboxylic acid

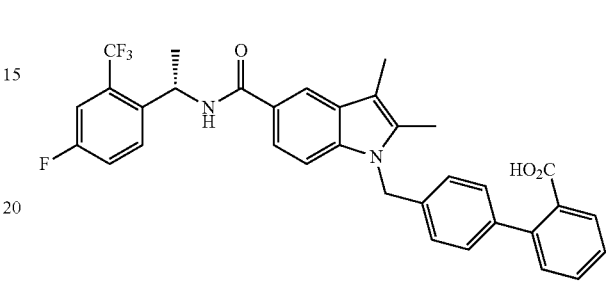

The title compound was prepared following the same general protocol as described in Step 8-9, Example 1, using the (S)-1-(4-fluoro-2-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]⁺.

Example 228: (S)-4'-((5-((1-(3-fluoro-4-(trifluoromethyl)phenyl)ethyl)carbamoyl)-2,3-dimethyl-1H-indol-1-yl)methyl)-[1,1'-biphenyl]-2-carboxylic acid

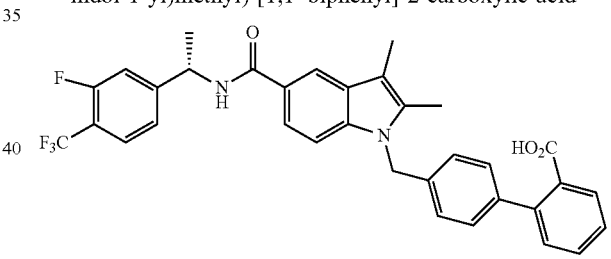

The title compound was prepared following the same general protocol as described in Step 8-9, Example 1, using the (S)-1-(3-fluoro-4-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]⁺.

Example 229: (S)-4'-((5-((1-(2,3-difluorophenyl)ethyl)carbamoyl)-2,3-dimethyl-1H-indol-1-yl)methyl)-[1,1'-biphenyl]-2-carboxylic acid

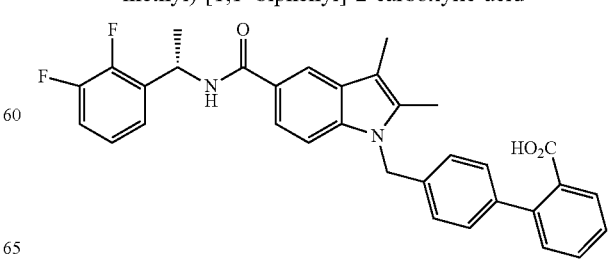

The title compound was prepared following the same general protocol as described in Step 8-9, Example 1, using the (S)-1-(2,3-difluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 539 [M+H]⁺.

Example 230: (S)-4'-((5-((1-(2-Chloro-3-(trifluoromethyl)phenyl)ethyl)carbamoyl)-2,3-dimethyl-1H-indol-1-yl)methyl)-[1,1'-biphenyl]-2-carboxylic acid

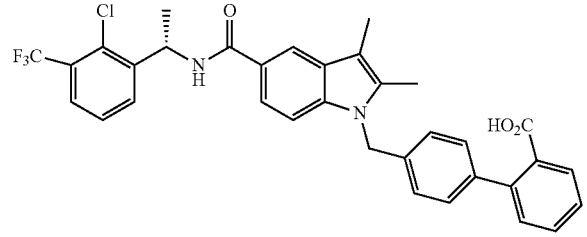 [SMILES: Cc1c(C)n(Cc2ccc(-c3ccccc3C(=O)O)cc2)c2ccc(C(=O)N[C@@H](C)c3cccc(C(F)(F)F)c3Cl)cc12]

The title compound was prepared following the same general protocol as described in Step 8-9, Example 1, using the (S)-1-(2-chloro-3-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 605 [M+H]⁺.

Example 231: (R)-4'-((5-((1-(2-chloro-3-(trifluoromethyl)phenyl)ethyl)carbamoyl)-2,3-dimethyl-1H-indol-1-yl)methyl)-[1,1'-biphenyl]-2-carboxylic acid

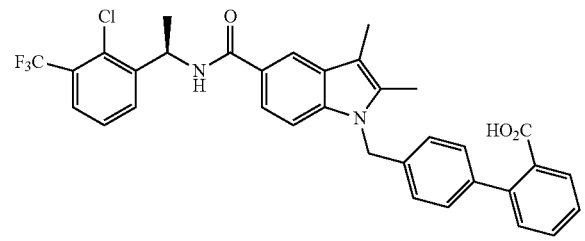 [SMILES: Cc1c(C)n(Cc2ccc(-c3ccccc3C(=O)O)cc2)c2ccc(C(=O)N[C@H](C)c3cccc(C(F)(F)F)c3Cl)cc12]

The title compound was prepared following the same general protocol as described in Step 8-9, Example 1, using the (R)-1-(2-chloro-3-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 605 [M+H]⁺.

Example 232: (S)-4'-((5-((1-(3-chloro-2-fluorophenyl)ethyl)carbamoyl)-2,3-dimethyl-1H-indol-1-yl)methyl)-[1,1'-biphenyl]-2-carboxylic acid

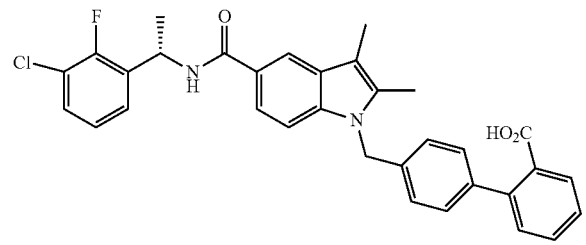 [SMILES: Cc1c(C)n(Cc2ccc(-c3ccccc3C(=O)O)cc2)c2ccc(C(=O)N[C@@H](C)c3cccc(Cl)c3F)cc12]

The title compound was prepared following the same general protocol as described in Step 8-9, Example 1, using (S)-1-(3-chloro-2-fluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 555 [M+H]⁺.

Example 233: (S)-4'-((5-((1-(3,4-difluorophenyl)ethyl)carbamoyl)-2,3-dimethyl-1H-indol-1-yl)methyl)-[1,1'-biphenyl]-2-carboxylic acid

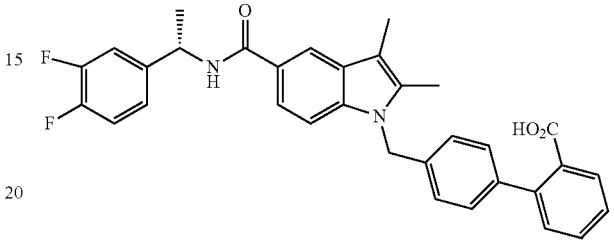

The title compound was prepared following the same general protocol as described in Step 8-9, Example 1, using the (S)-1-(3,4-difluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 539 [M+H]⁺.

Example 234: (R)-4'-((5-((1-(3-fluoro-4-(trifluoromethyl)phenyl)ethyl)carbamoyl)-2,3-dimethyl-1H-indol-1-yl)methyl)-[1,1'-biphenyl]-2-carboxylic acid

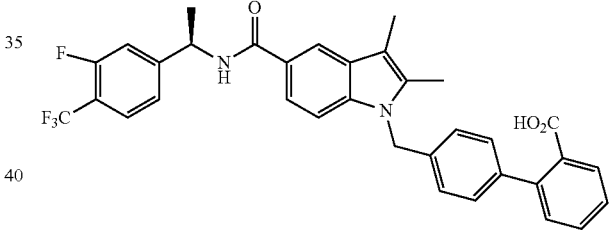

The title compound was prepared following the same general protocol as described in Step 8-9, Example 1, using the (R)-1-(3-fluoro-4-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]⁺.

Example 235: (R)-4'-((2,3-dimethyl-5-((1-(2,3,6-trifluorophenyl)ethyl)carbamoyl)-1H-indol-1-yl)methyl)-[1,1'-biphenyl]-2-carboxylic acid

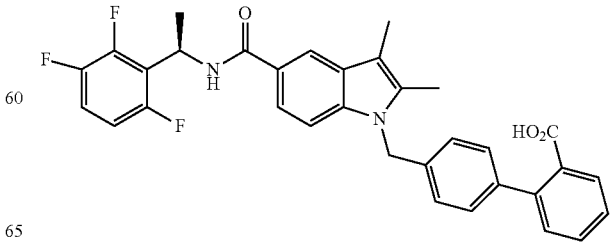

The title compound was prepared following the same general protocol as described in Step 8-9, Example 1, using the (R)-1-(2,3,6-trifluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 557 [M+H]+.

Example 236: (S)-4'-((2,3-dimethyl-5-((1-(2,3,6-trifluorophenyl)ethyl)carbamoyl)-1H-indol-1-yl)methyl)-[1,1'-biphenyl]-2-carboxylic acid

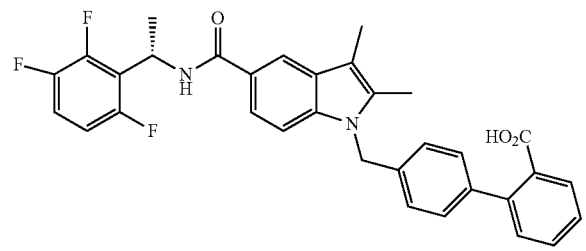

The title compound was prepared following the same general protocol as described in Step 8-9, Example 1, using the (S)-1-(2,3,6-trifluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 557 [M+H]+.

Example 237: 4'-((5-(((S)-1-((S)-1-((benzyloxy)carbonyl)pyrrolidin-2-yl)ethyl)carbamoyl)-2,3-dimethyl-1H-indol-1-yl)methyl)-[1,1'-biphenyl]-2-carboxylic acid

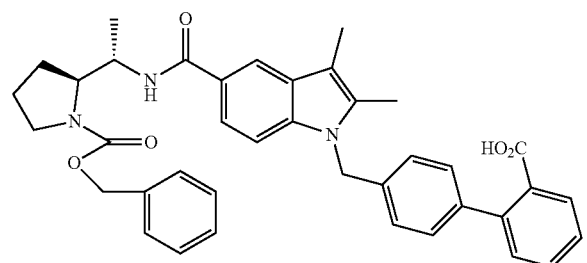

The title compound was prepared following the same general protocol as described in Step 8-9, Example 1, using the (S)-benzyl 2-((S)-1-aminoethyl)pyrrolidine-1-carboxylate hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 630 [M+H]+.

Example 238: 4'-((5-(((S)-1-((R)-1-((benzyloxy)carbonyl)pyrrolidin-2-yl)ethyl)carbamoyl)-2,3-dimethyl-1H-indol-1-yl)methyl)-[1,1'-biphenyl]-2-carboxylic acid

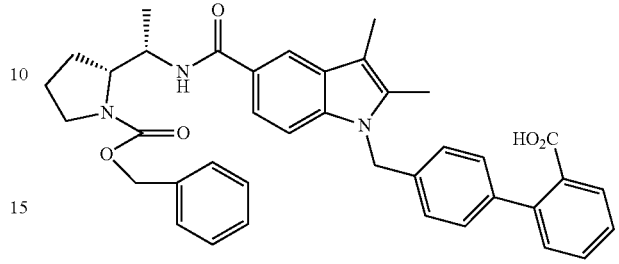

The title compound was prepared following the same general protocol as described in Step 8-9, Example 1, using the (R)-benzyl 2-((S)-1-aminoethyl)pyrrolidine-1-carboxylate hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 630 [M+H]+.

Example 239: (R)-4'-((5-((1-(5-fluoro-2-(trifluoromethyl)phenyl)ethyl)carbamoyl)-2,3-dimethyl-1H-indol-1-yl)methyl)-[1,1'-biphenyl]-2-carboxylic acid

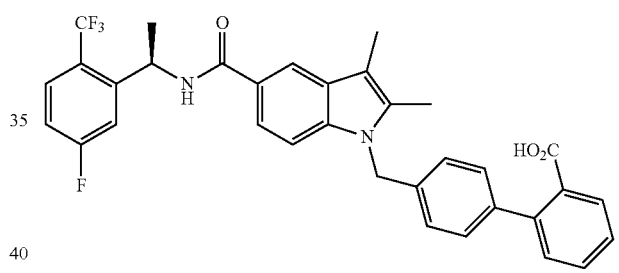

The title compound was prepared following the same general protocol as described in Step 8-9, Example 1, using the (R)-1-(5-fluoro-2-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]+.

Example 240: 4'-((5-(((S)-1-((R)-1-((benzyloxy)carbonyl)pyrrolidin-3-yl)ethyl)carbamoyl)-2,3-dimethyl-1H-indol-1-yl)methyl)-[1,1'-biphenyl]-2-carboxylic acid

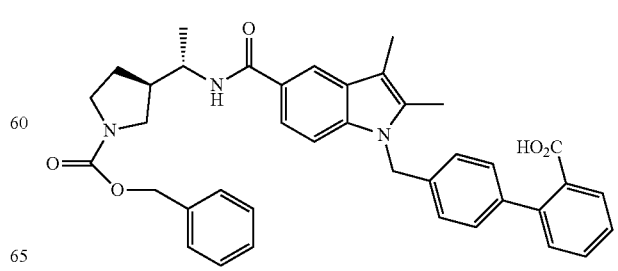

The title compound was prepared following the same general protocol as described in Step 8-9, Example 1, using the (R)-benzyl 3-((S)-1-aminoethyl)pyrrolidine-1-carboxylate hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 630 [M+H]⁺.

Example 241: (S)-4'-((5-((1-(5-fluoro-2-(trifluoromethyl)phenyl)ethyl)carbamoyl)-2,3-dimethyl-1H-indol-1-yl)methyl)-[1,1'-biphenyl]-2-carboxylic acid

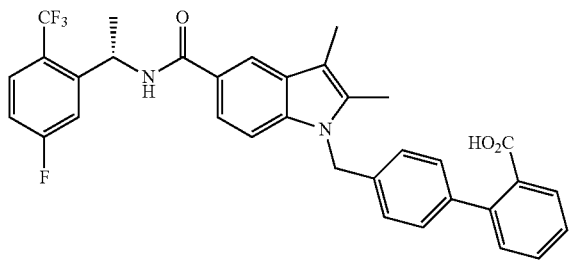 [SMILES: Cc1c(C)n(Cc2ccc(-c3ccccc3C(=O)O)cc2)c2ccc(C(=O)N[C@@H](C)c3cc(F)ccc3C(F)(F)F)cc12]

The title compound was prepared following the same general protocol as described in Step 8-9, Example 1, using the (S)-1-(5-fluoro-2-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]⁺.

Example 242: (S)-1-((2'-cyano-[1,1'-biphenyl]-4-yl)methyl)-N-(1-(3-isopropylphenyl)ethyl)-2,3-dimethyl-1H-indole-5-carboxamide

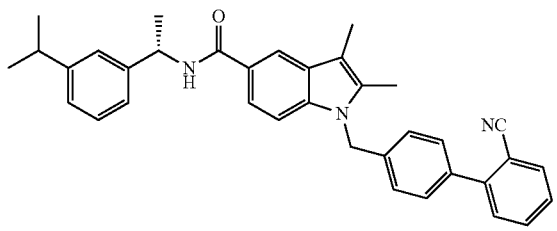 [SMILES: Cc1c(C)n(Cc2ccc(-c3ccccc3C#N)cc2)c2ccc(C(=O)N[C@@H](C)c3cccc(C(C)C)c3)cc12]

The title compound was prepared following the same general protocol as described in Step 8-9, Example 1, using the (S)-1-(5-fluoro-2-(trifluoromethyl)phenyl)ethanamine hydrochloride and the 4'-(bromomethyl)-[1,1'-biphenyl]-2-carbonitrile. ESI-MS (m/z): 526 [M+H]⁺.

Example 243: (S)-1-((2'-(2H-tetrazol-5-yl)-[1,1'-biphenyl]-4-yl)methyl)-N-(1-(3-isopropylphenyl)ethyl)-2,3-dimethyl-1H-indole-5-carboxamide

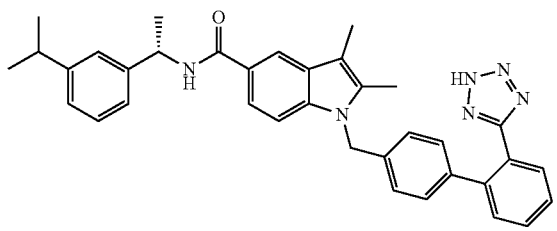 [SMILES: Cc1c(C)n(Cc2ccc(-c3ccccc3-c3nn[nH]n3)cc2)c2ccc(C(=O)N[C@@H](C)c3cccc(C(C)C)c3)cc12]

The mixture of (S)-1-((2'-cyano-[1,1'-biphenyl]-4-yl)methyl)-N-(1-(3-isopropylphenyl)ethyl)-2,3-dimethyl-1H-indole-5-carboxamide (0.1 g, 0.19 mmol), azidotrimethylsilane 90.05 mL, 0.38 mmol) and dibutylstannanone (0.005 g, 0.019 mmol) in toluene (3 mL) was heated at 110° C. oil bath for 16 hr. The solvent was removed and the residue was purified by preparative-HPLC to obtain the title compound. ESI-MS (m/z): 569 [M+H]⁺.

Example 244: (S)—N-(1-(3-isopropylphenyl)ethyl)-2,3-dimethyl-1-((2'-((5-oxo-4,5-dihydro-1,2,4-oxadiazol-3-yl)-[1,1'-biphenyl]-4-yl)methyl)-1H-indole-5-carboxamide

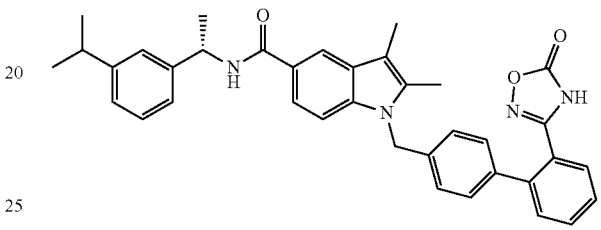

A mixture of hydroxylammoium chloride (0.2 g, 2.88 mmol), sodium hydrogen carbonate (0.3 g, 3.57 mmol) and dimethyl sulfoxide (2 mL) was stirred at 40° C. for 30 min. (S)-1-((2'-cyano-[1,1'-biphenyl]-4-yl)methyl)-N-(1-(3-isopropylphenyl)ethyl)-2,3-dimethyl-1H-indole-5-carboxamide (0.1 g, 0.19 mmol) was added, and the mixture was stirred at 90° C. for 16 hr. The reaction mixture was diluted with ethyl acetate, washed with water and then with brine, and dried over anhydrous sodium sulfate. Thvent was evaporated under reduced pressure, and the residue was dissolved in THF (3 mL), N, N'-carbonyldiimidazole (0.055 g, 0.29 mmol) and then 1,8-diazabicyclo[5,4,0] undec-7-ene (0.05 mL, 0.29 mmol) were added, and the mixture was stirred at room temperature for 2 hr. The reaction mixture was diluted with ethyl acetate, washed with saturated aqueous potassium hydrogensulfate solution and then with brine, and dried over anhydrous sodium sulfate. The solvent was evaporated under reduced pressure, and the residue was purified by preparative-HPLC to obtain the title compound. ESI-MS (m/z): 585 [M+H]⁺.

Example 245: (S)—N-(1-(3-isopropylphenyl)ethyl)-2,3-dimethyl-1-((2'-((5-oxo-4,5-dihydro-1,3,4-oxadiazol-2-yl)-[1,1'-biphenyl]-4-yl)methyl)-1H-indole-5-carboxamide

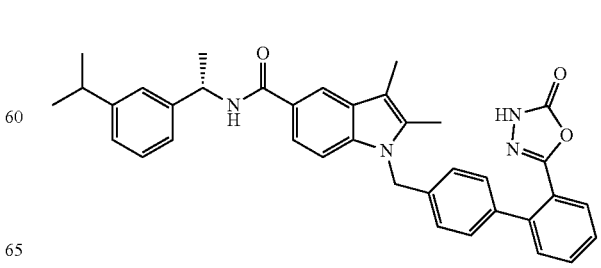

451

Step 1: (S)-1-((2'-(hydrazinecarbonyl)-[1,1'-biphenyl]-4-yl)methyl)-N-(1-(3-isopropylphenyl)ethyl)-2,3-dimethyl-1H-indole-5-carboxamide

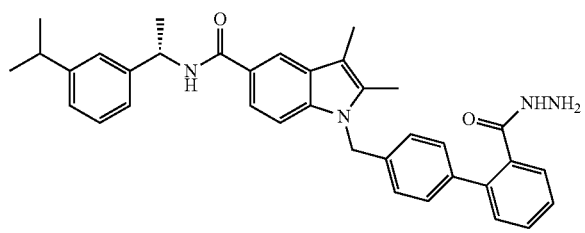 [SMILES: Cc1c(C)n(Cc2ccc(-c3ccccc3C(=O)NN)cc2)c2ccc(C(=O)N[C@@H](C)c3cccc(C(C)C)c3)cc12]

To the mixture of (S)-4'-((5-((1-(3-isopropylphenyl)ethyl)carbamoyl)-2,3-dimethyl-1H-indol-1-yl)methyl)-[1,1'-biphenyl]-2-carboxylic acid (0.11 g, 0.201 mmol), hydrazine hydrochloride (0.028 g, 0.402 mmol) and HATU (0.092 g, 0.24 mmol) in DCM (2 mL) was added DIEA (0.14 mL, 0.8 mmol). The mixture was stirred at room temperature for 16 h. The solvent was removed and the residue was purified by silica gel to obtain the title compound. ESI-MS (m/z): 559 [M+H]$^+$.

Step 2: (S)—N-(1-(3-isopropylphenyl)ethyl)-2,3-dimethyl-1-((2'-((5-oxo-4,5-dihydro-1,3,4-oxadiazol-2-yl)-[1,1'-biphenyl]-4-yl)methyl)-1H-indole-5-carboxamide The mixture of (S)-1-((2'-(hydrazinecarbonyl)-[1,1'-biphenyl]-4-yl)methyl)-N-(1-(3-isopropylphenyl)ethyl)-2,3-dimethyl-1H-indole-5-carboxamide (0.062 g, 0.11 mmol), N,N'-carbonyldiimidazole (0.027 g, 0.16 mmol) and DIEA (0.03 mL, 0.16 mmol) in DMF was stirred at room temperature for 1 h, and then stirred at 50° C. for 1 h. The reaction mixture was poured on to ice-water, and then extracted with ethyl acetate. The combined organic layers were washed with water and brine. Th solvent was remove and the residue was purified with preparative-HPLC to obtain the title compound. ESI-MS (m/z): 585 [M+H]$^+$.

Example 246: (S)-1-((2'-(N-(tert-butyl)sulfamoyl)-[1,1'-biphenyl]-4-yl)methyl)-N-(1-(3-isopropylphenyl)ethyl)-2,3-dimethyl-1H-indole-5-carboxamide

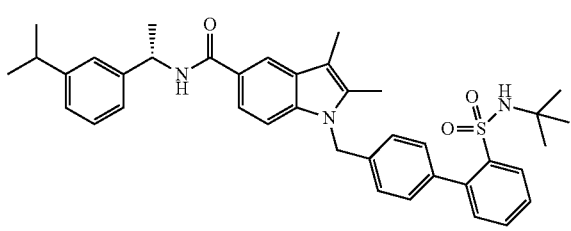 [SMILES: Cc1c(C)n(Cc2ccc(-c3ccccc3S(=O)(=O)NC(C)(C)C)cc2)c2ccc(C(=O)N[C@@H](C)c3cccc(C(C)C)c3)cc12]

452

Step 1: ethyl 1-((2'-(N-(tert-butyl)sulfamoyl)-[1,1'-biphenyl]-4-yl)methyl)-2,3-dimethyl-1H-indole-5-carboxylate

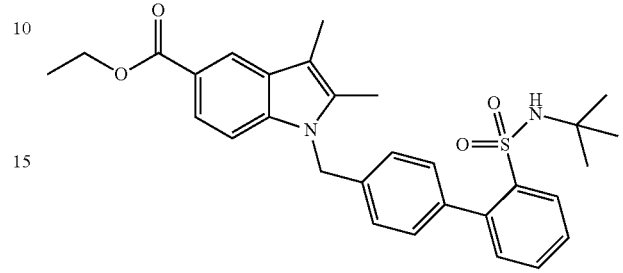

The title compound was prepared following the same general protocol as described in Step 6, Example 1, using the ethyl 2,3-dimethyl-1H-indole-5-carboxylate and 4'-(bromomethyl)-N-(tert-butyl)-[1,1'-biphenyl]-2-sulfonamide. ESI-MS (m/z): 519 [M+H]$^+$.

Step 2: 1-((2'-(N-(tert-butyl)sulfamoyl)-[1,1'-biphenyl]-4-yl)methyl)-2,3-dimethyl-1H-indole-5-carboxylic acid

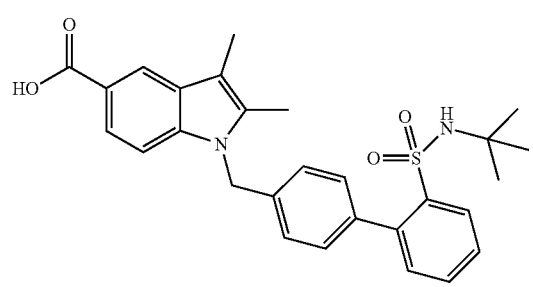 [SMILES: Cc1c(C)n(Cc2ccc(-c3ccccc3S(=O)(=O)NC(C)(C)C)cc2)c2ccc(C(=O)O)cc12]

The title compound was prepared following the same general protocol as described in Step 7, Example 1, using the ethyl 1-((2'-(N-(tert-butyl)sulfamoyl)-[1,1'-biphenyl]-4-yl)methyl)-2,3-dimethyl-1H-indole-5-carboxylate. ESI-MS (m/z): 491 [M+H]$^+$.

Step 3: (S)-1-((2'-(N-(tert-butyl)sulfamoyl)-[1,1'-biphenyl]-4-yl)methyl)-N-(1-(3-isopropylphenyl)ethyl)-2,3-dimethyl-1H-indole-5-carboxamide The title compound was prepared following the same general protocol as described in Step 8, Example 1, using the (S)-1-(3-isopropylphenyl)ethanamine hydrochloride and 1-((2'-(N-(tert-butyl)sulfamoyl)-[1,1'-biphenyl]-4-yl)methyl)-2,3-dimethyl-1H-indole-5-carboxylic acid. ESI-MS (m/z): 636 [M+H]$^+$.

Example 247: (S)—N-(1-(3-isopropylphenyl)ethyl)-2,3-dimethyl-1-((2'-sulfamoyl-[1,1'-biphenyl]-4-yl)methyl)-1H-indole-5-carboxamide

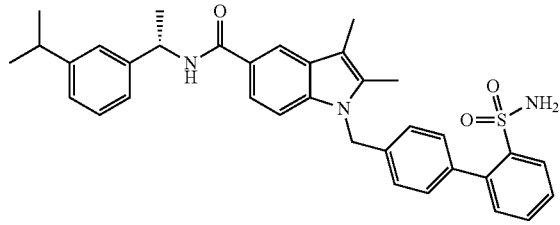 [SMILES: Cc1c(C)n(Cc2ccc(-c3ccccc3S(N)(=O)=O)cc2)c2ccc(C(=O)N[C@@H](C)c3cccc(C(C)C)c3)cc12]

The title compound was prepared following the same general protocol as described in Step 9, Example 1, using the (S)-1-((2'-(N-(tert-butyl)sulfamoyl)-[1,1'-biphenyl]-4-yl)methyl)-N-(1-(3-isopropylphenyl)ethyl)-2,3-dimethyl-1H-indole-5-carboxamide. ESI-MS (m/z): 580 [M+H]$^+$.

Example 248: (S)-1-((2'-(N-acetylsulfamoyl)-[1,1'-biphenyl]-4-yl)methyl)-N-(1-(3-isopropylphenyl)ethyl)-2,3-dimethyl-1H-indole-5-carboxamide

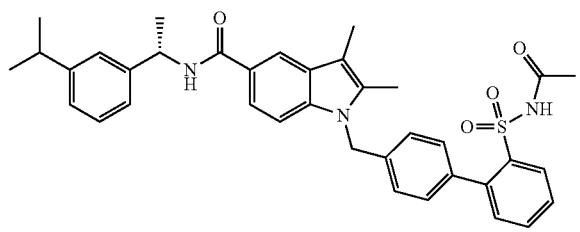 [SMILES: CC(=O)NS(=O)(=O)c1ccccc1-c1ccc(Cn2c(C)c(C)c3cc(C(=O)N[C@@H](C)c4cccc(C(C)C)c4)ccc32)cc1]

To the mixture of (S)—N-(1-(3-isopropylphenyl)ethyl)-2,3-dimethyl-1-((2'-sulfamoyl-[1,1'-biphenyl]-4-yl)methyl)-1H-indole-5-carboxamide (0.058 g, 0.1 mmol) and TEA (0.03 mL, 0.2 mmol) in DCM (0.5 mL) was slowly added acetyl chloride (0.009 g, 0.11 mmol). The mixture was stirred at room temperature for 1 h. The solvent was removed and the residue was purified by preparative-HPLC to obtain the title compound ESI-MS (m/z): 622 [M+H]$^+$.

Example 249: (R)-4'-((5-(chroman-3-ylcarbamoyl)-2,3-dimethyl-1H-indol-1-yl)methyl)-[1,1'-biphenyl]-2-carboxylic acid

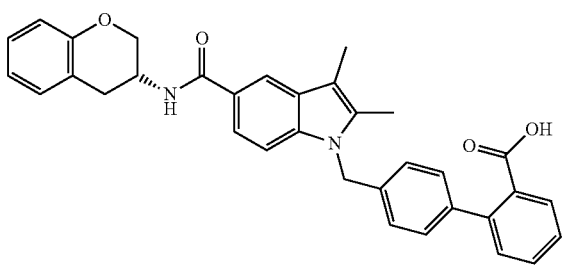

The title compound was prepared following the same protocol as described in Step 8 and 9, Example 1, using (R)-chroman-3-amine instead of the (S)-1-(4-bromophenyl)ethanamine.

Example 250: (S)-4'-((5-(chroman-3-ylcarbamoyl)-2,3-dimethyl-1H-indol-1-yl)methyl)-[1,1'-biphenyl]-2-carboxylic acid

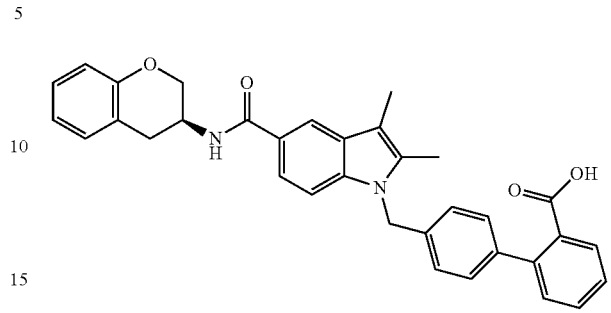

The title compound was prepared following the same protocol as described in Step 8 and 9, Example 1, using (S)-chroman-3-amine instead of the (S)-1-(4-bromophenyl)ethanamine.

Example 251: (S)-4'-((2,3-dimethyl-5-(1-(4-propylphenyl)ethylcarbamoyl)-1H-indol-1-yl)methyl)biphenyl-2-carboxylic acid

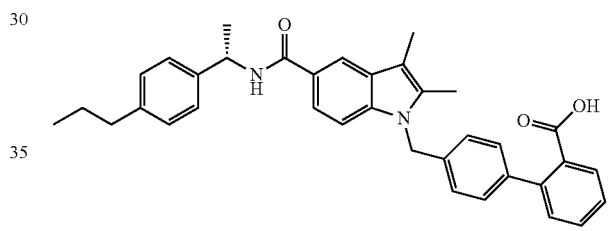

The title compound was prepared following the same protocol as described in Step 8 and 9, Example 1, using (S)-1-(4-propylphenyl)ethanaminium chloride instead of the (S)-1-(4-bromophenyl)ethanamine. ESI-MS (m/z): 545 [M+H]$^+$.

Example 252: (S)-4'-((2,3-dimethyl-5-(1-o-tolylethylcarbamoyl)-1H-indol-1-yl)methyl) biphenyl-2-carboxylic acid

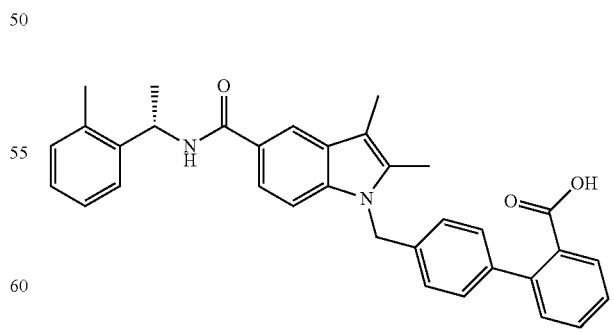

The title compound was prepared following the same protocol as described in Step 8 and 9, Example 1, using (S)-1-(o-tolyl)ethanaminium chloride instead of the (S)-1-(4-bromophenyl)ethanamine. ESI-MS (m/z): 517 [M+H]$^+$.

Example 253: (S)-4'-((5-(1-(4-ethoxyphenyl)ethyl-carbamoyl)-2,3-dimethyl-1H-indol-1-yl)methyl)biphenyl-2-carboxylic acid

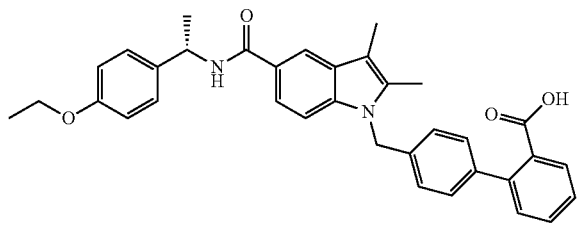 [SMILES: CCCc1ccc([C@H](C)NC(=O)c2ccc3c(c2)c(C)c(C)n3Cc2ccc(-c3ccccc3C(=O)O)cc2)cc1]

The title compound was prepared following the same protocol as described in Step 8 and 9, Example 1, using (S)-1-(4-ethoxyphenyl)ethanaminium chloride instead of the (S)-1-(4-bromophenyl)ethanamine. ESI-MS (m/z): 547 [M+H]$^+$.

Example 254: (S)-4'-((5-(1-(2-bromophenyl)ethyl-carbamoyl)-2,3-dimethyl-1H-indol-1-yl)methyl)biphenyl-2-carboxylic acid

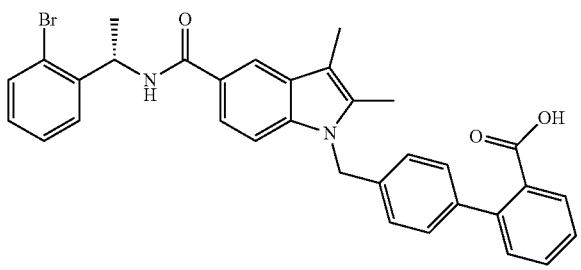 [SMILES: Cc1ccccc1[C@H](C)NC(=O)c1ccc2c(c1)c(C)c(C)n2Cc1ccc(-c2ccccc2C(=O)O)cc1]

The title compound was prepared following the same protocol as described in Step 8 and 9, Example 1, using (S)-1-(2-bromophenyl)ethanaminium chloride instead of the (S)-1-(4-bromophenyl)ethanamine. ESI-MS (m/z): 581 [M+H]$^+$.

Example 255: (S)-4'-((5-(1-(2-ethylphenyl)ethylcar-bamoyl)-2,3-dimethyl-1H-indol-1-yl)methyl)biphenyl-2-carboxylic acid

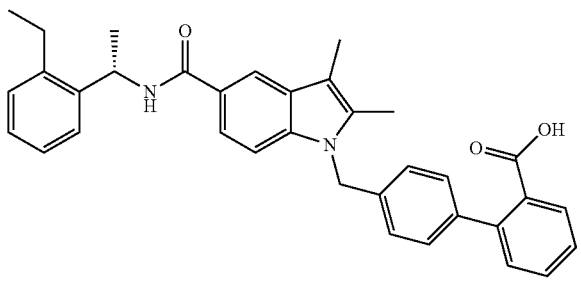 [SMILES: CCc1ccccc1[C@H](C)NC(=O)c1ccc2c(c1)c(C)c(C)n2Cc1ccc(-c2ccccc2C(=O)O)cc1]

The title compound was prepared following the same protocol as described in Step 8 and 9, Example 1, using (S)-1-(2-ethylphenyl)ethanaminium chloride instead of the (S)-1-(4-bromophenyl)ethanamine. ESI-MS (m/z): 531 [M+H]$^+$.

Example 256: (S)-4'-((2,3-dimethyl-5-(1-(2-(trifluoromethoxy)phenyl)ethylcarbamoyl)-1H-indol-1-yl)methyl)biphenyl-2-carboxylic acid

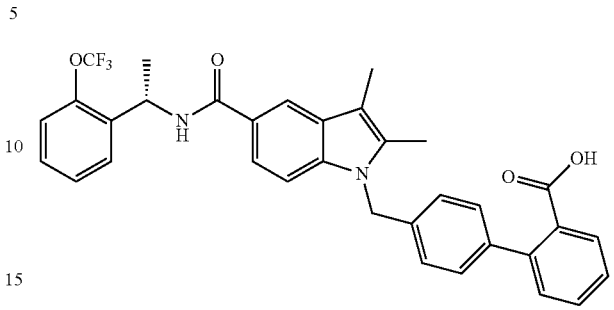

The title compound was prepared following the same protocol as described in Step 8 and 9, Example 1, using (S)-1-(2-(trifluoromethoxy)phenyl)ethanaminium chloride instead of the (S)-1-(4-bromophenyl)ethanamine. ESI-MS (m/z): 587 [M+H]$^+$.

Example 257: (S)-4'-((5-(1-(2-isopropoxyphenyl)ethylcarbamoyl)-2,3-dimethyl-1H-indol-1-yl)methyl)biphenyl-2-carboxylic acid

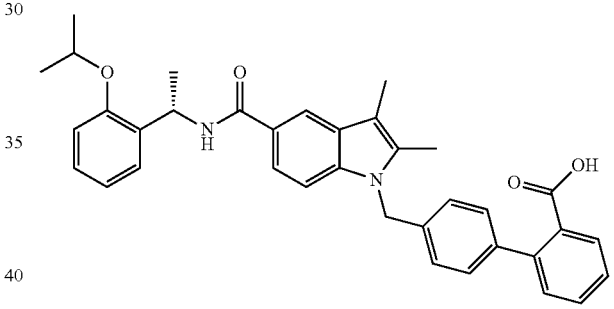

The title compound was prepared following the same protocol as described in Step 8 and 9, Example 1, using (S)-1-(2-isopropoxyphenyl)ethanaminium chloride instead of the (S)-1-(4-bromophenyl)ethanamine. ESI-MS (m/z): 561 [M+H]$^+$.

Example 258: (S)-4'-((2,3-dimethyl-5-(1-(4-(methylsulfonyl)phenyl)ethylcarbamoyl)-1H-indol-1-yl)methyl)biphenyl-2-carboxylic acid

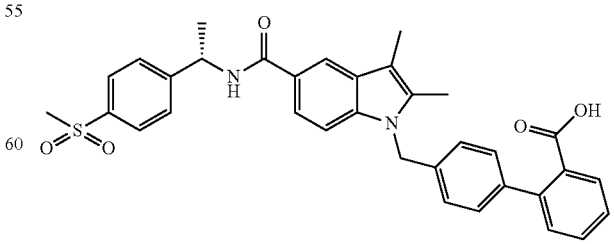

The title compound was prepared following the same protocol as described in Step 8 and 9, Example 1, using (S)-1-(4-(methylsulfonyl)phenyl)ethanaminium chloride instead of the (S)-1-(4-bromophenyl)ethanamine. ESI-MS (m/z): 581 [M+H]⁺.

Example 259: 4'-((5-(1-(5-cyclopropylpyridin-3-yl) ethylcarbamoyl)-2,3-dimethyl-1H-indol-1-yl) methyl)biphenyl-2-carboxylic acid

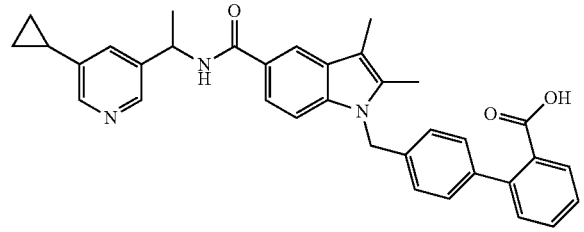 [SMILES: Cc1c(C)n(Cc2ccc(-c3ccccc3C(=O)O)cc2)c2ccc(C(=O)NC(C)c3cncc(C4CC4)c3)cc12]

Step 1: 1-(5-bromopyridin-3-yl)ethanaminium chloride

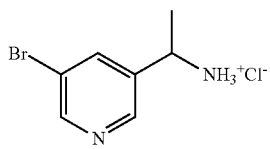

The title compound was prepared following the same general protocol as described in Step 1 and 2, Example 2, using 5-bromonicotinaldehyde instead of 4-t-butylbenzaldehyde.

Step 2: tert-butyl 4'-((5-((1-(5-bromopyridin-3-yl) ethyl)carbamoyl)-2,3-dimethyl-1H-indol-1-yl) methyl)-[1,1'-biphenyl]-2-carboxylate

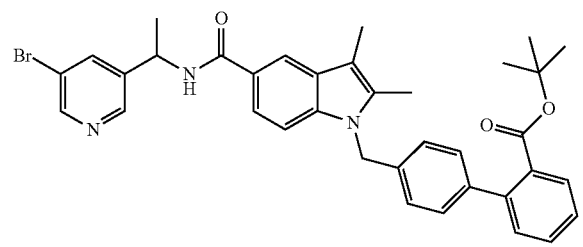 [SMILES: Cc1c(C)n(Cc2ccc(-c3ccccc3C(=O)OC(C)(C)C)cc2)c2ccc(C(=O)NC(C)c3cncc(Br)c3)cc12]

The title compound was prepared following the same general protocol as described in Step 8, Example 1, using 1-(5-bromopyridin-3-yl)ethanaminium chloride instead of (S)-1-(4-bromophenyl)ethanamine.

Step 3: tert-butyl 4'-((5-((1-(5-cyclopropylpyridin-3-yl)ethyl)carbamoyl)-2,3-dimethyl-1H-indol-1-yl) methyl)-[1,1'-biphenyl]-2-carboxylate

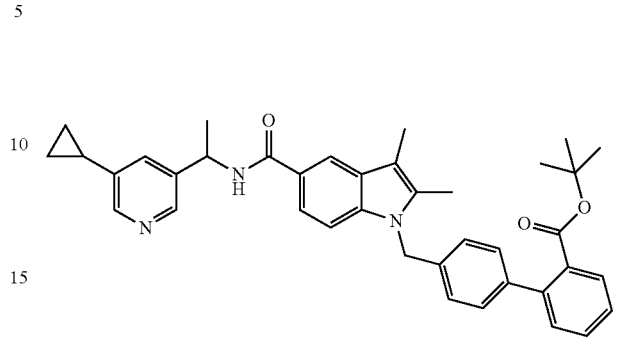

The title compound was prepared following the same general protocol as described in Step 1, Example 261, using tert-butyl 4'-((5-((1-(5-bromopyridin-3-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate.

Step 4: 4'-((5-((1-(5-cyclopropylpyridin-3-yl)ethyl) carbamoyl)-2,3-dimethyl-1H-indol-1-yl)methyl)-[1, 1'-biphenyl]-2-carboxylic acid

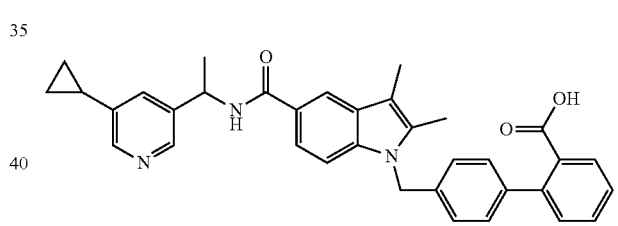

The title compound was prepared following the same general protocol as described in Step 9, Example 1. ESI-MS (m/z): 544 [M+H]⁺.

Example 260: (S)-4'-((5-((1-(5-bromopyridin-2-yl) ethyl)carbamoyl)-2,3-dimethyl-1H-indol-1-yl) methyl)-[1,1'-biphenyl]-2-carboxylic acid

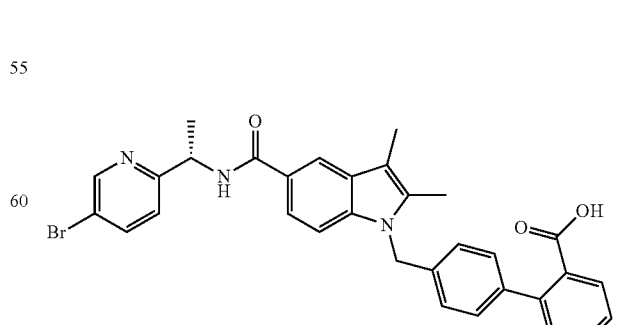

459

Step 1: (S)-1-(5-bromopyridin-2-yl)ethanaminium chloride

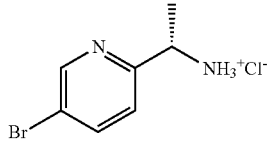

The title compound was prepared following the same general protocol as described in Step 1 and 2, Example 2, using 5-bromopicolinaldehyde instead of 4-t-butylbenzaldehyde.

Step 2: (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate

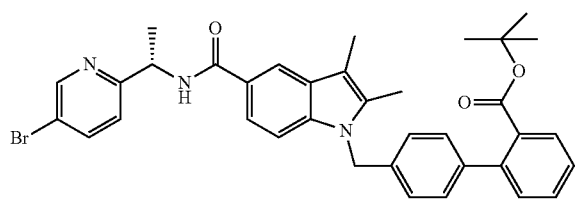

The title compound was prepared following the same general protocol as described in Step 8, Example 1, using (S)-1-(5-bromopyridin-2-yl)ethanaminium chloride instead of (S)-1-(4-bromophenyl)ethanamine.

460

Step 3: (S)-4'-((5-((1-(5-bromopyridin-2-yl)ethyl)carbamoyl)-2,3-dimethyl-1H-indol-1-yl)methyl)-[1,1'-biphenyl]-2-carboxylic acid

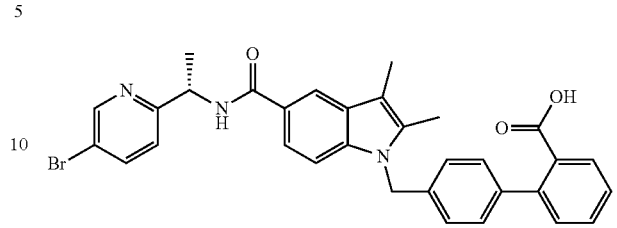

The title compound was prepared following the same general protocol as described in Step 9, Example 1. ESI-MS (m/z): 582 [M+H]$^+$.

Example 261: (S)-4'-((5-((1-(5-cyclopropylpyridin-2-yl)ethyl)carbamoyl)-2,3-dimethyl-1H-indol-1-yl)methyl)-[1,1'-biphenyl]-2-carboxylic acid

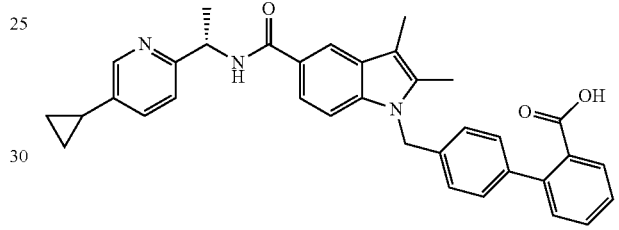

Step 1: (S)-tert-butyl 4'-((5-((1-(5-cyclopropylpyridin-2-yl)ethyl)carbamoyl)-2,3-dimethyl-1H-indol-1-yl)methyl)-[1,1'-biphenyl]-2-carboxylate

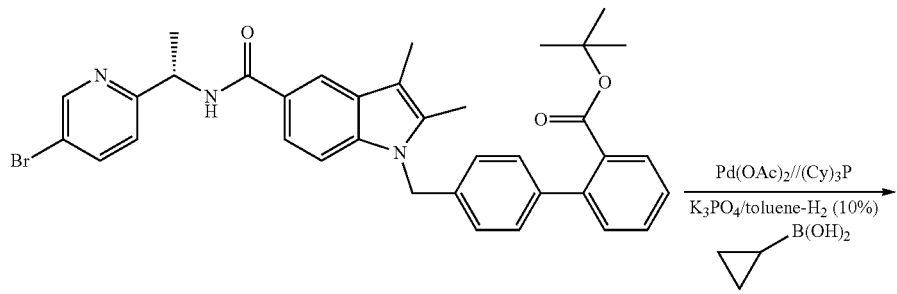

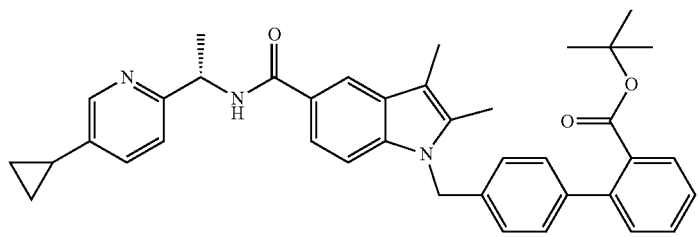

A high-pressure vial was filled with the (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate (50 mg, 0.078 mmol), cyclopropylboronic acid (8 mg, 0.09 mmol, 1.2 equiv), Pd(OAc)$_2$ (12 mg, 0.055 mmol, 0.7 equiv), (Cy)$_3$P (8.7 mg, 0.031 mmol, 0.4 equiv), K$_3$PO$_4$ (49 mg, 0.23 mmol, 3 equiv), in toluene-water (10%). The reaction mixture was heated at 100° C. for 3 h under microwaves. The mixture was evaporated in vacuo to obtain the crude which was purified by prep. HPLC (MeOH/Acetonitrile/water) to obtain the title compound.

Step 2: (S)-4'-((5-((1-(5-cyclopropylpyridin-2-yl)ethyl)carbamoyl)-2,3-dimethyl-1H-indol-1-yl)methyl)-[1,1'-biphenyl]-2-carboxylic acid

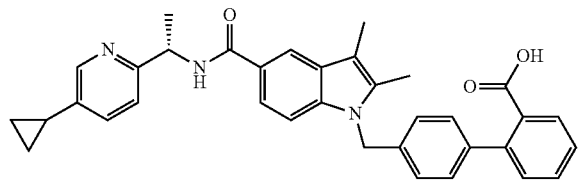 [SMILES: Cc1c(C)n(Cc2ccc(-c3ccccc3C(=O)O)cc2)c2ccc(C(=O)N[C@@H](C)c3ccc(C4CC4)cn3)cc12]

The title compound was prepared following the same general protocol as described in Step 9, Example 1. ESI-MS (m/z): 544 [M+H]$^+$.

Example 262: (S)-4'-((5-((1-(6-chloropyridin-3-yl)ethyl)carbamoyl)-2,3-dimethyl-1H-indol-1-yl)methyl)-[1,1'-biphenyl]-2-carboxylic acid

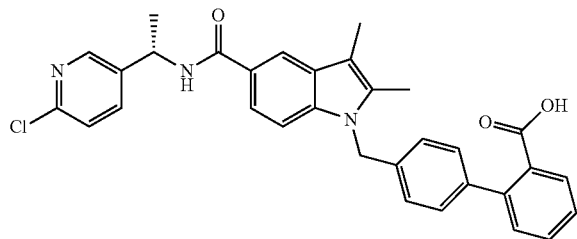 [SMILES: Cc1c(C)n(Cc2ccc(-c3ccccc3C(=O)O)cc2)c2ccc(C(=O)N[C@@H](C)c3ccc(Cl)nc3)cc12]

Step 1: (S)-1-(6-chloropyridin-3-yl)ethanaminium chloride

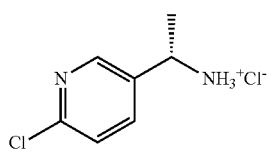

The title compound was prepared following the same general protocol as described in Step 1 and 2, Example 2, using 6-chloronicotinaldehyde instead of 4-t-butylbenzaldehyde.

Step 2: (S)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate

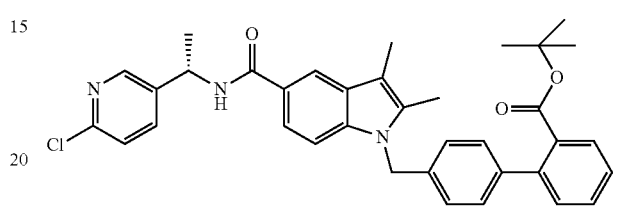

The title compound was prepared following the same general protocol as described in Step 8, Example 1, using (S)-1-(6-chloropyridin-3-yl)ethanaminium chloride instead of (S)-1-(4-bromophenyl)ethanamine.

Step 3: (S)-4'-((5-((1-(6-chloropyridin-3-yl)ethyl)carbamoyl)-2,3-dimethyl-1H-indol-1-yl)methyl)-[1,1'-biphenyl]-2-carboxylic acid

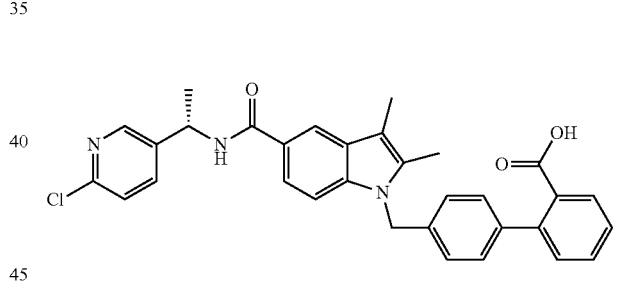

The title compound was prepared following the same general protocol as described in Step 9, Example 1. ESI-MS (m/z): 538 [M+H]$^+$.

Example 263: (S)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

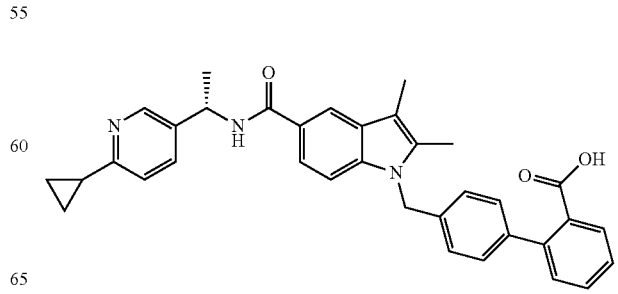

463

Step 1: (S)-tert-butyl 4'-((5-((1-(6-cyclopropylpyridin-3-yl)ethyl)carbamoyl)-2,3-dimethyl-1H-indol-1-yl)methyl)-[1,1'-biphenyl]-2-carboxylate

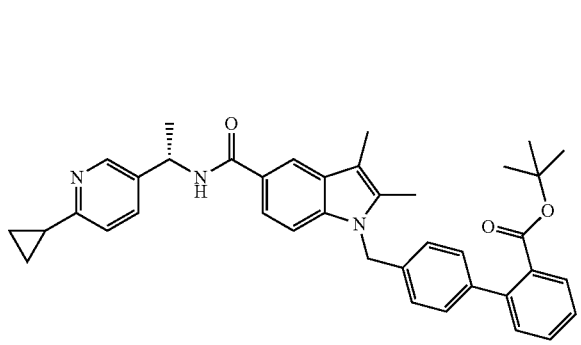 [SMILES: Cc1c(C)n(Cc2ccc(-c3ccccc3C(=O)OC(C)(C)C)cc2)c2ccc(C(=O)N[C@@H](C)c3ccc(C4CC4)nc3)cc12]

The title compound was prepared following the same general protocol as described in Step 1, Example 261, using (S)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate.

Step 2: (S)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

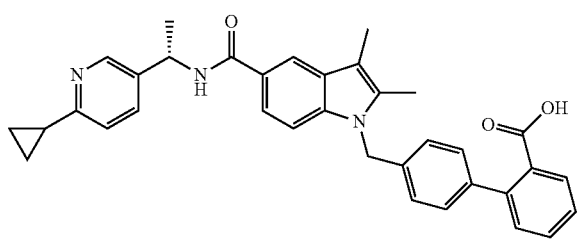 [SMILES: Cc1c(C)n(Cc2ccc(-c3ccccc3C(=O)O)cc2)c2ccc(C(=O)N[C@@H](C)c3ccc(C4CC4)nc3)cc12]

The title compound was prepared following the same general protocol as described in Step 9, Example 1. ESI-MS (m/z): 544 [M+H]+.

Example 264: (R)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

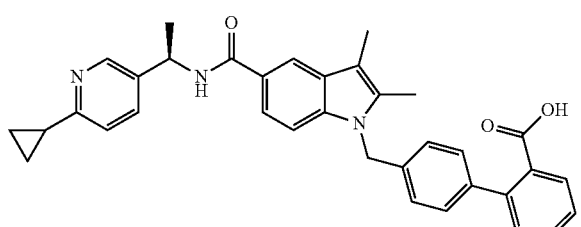

464

Step 1: (R)-1-(6-chloropyridin-3-yl)ethanaminium chloride

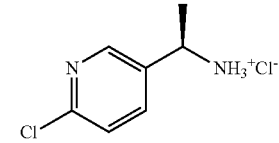

The title compound was prepared following the same general protocol as described in Step 1 and 2, Example 2, using 6-chloronicotinaldehyde instead of 4-t-butylbenzaldehyde.

Step 2: (R)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate

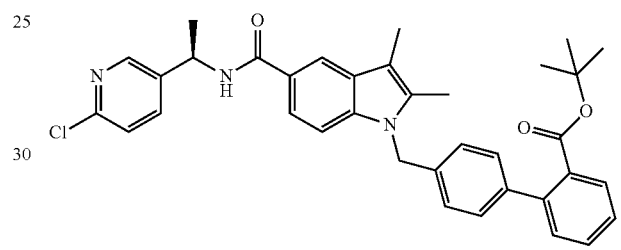

The title compound was prepared following the same general protocol as described in Step 8, Example 1, using (R)-1-(6-chloropyridin-3-yl)ethanaminium chloride instead of (S)-1-(4-bromophenyl)ethanamine.

Step 3: (R)-tert-butyl 4'-((5-((1-(6-cyclopropylpyridin-3-yl)ethyl)carbamoyl)-2,3-dimethyl-1H-indol-1-yl)methyl)-[1,1'-biphenyl]-2-carboxylate

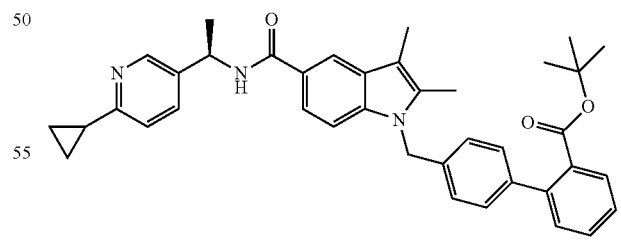

The title compound was prepared following the same general protocol as described in Step 1, Example 261, using (R)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate.

Step 4: (R)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

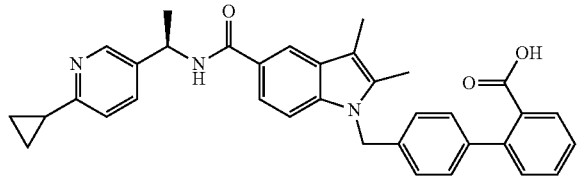 [SMILES: Cc1c(C)n(Cc2ccc(-c3ccccc3C(=O)O)cc2)c2ccc(C(=O)N[C@H](C)c3ccc(C4CC4)nc3)cc12]

The title compound was prepared following the same general protocol as described in Step 9, Example 1. ESI-MS (m/z): 544 [M+H]⁺.

Example 265: (S)-4'-((5-((1-(4-chloropyridin-2-yl)ethyl)carbamoyl)-2,3-dimethyl-1H-indol-1-yl)methyl)-[1,1'-biphenyl]-2-carboxylic acid

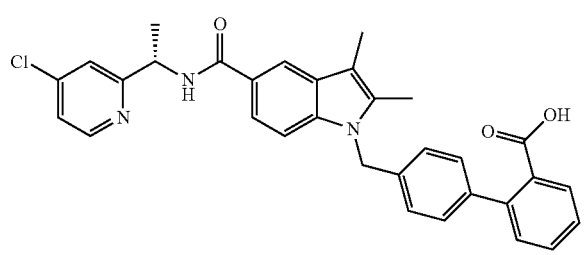 [SMILES: Cc1c(C)n(Cc2ccc(-c3ccccc3C(=O)O)cc2)c2ccc(C(=O)N[C@@H](C)c3cc(Cl)ccn3)cc12]

Step 1: (S)-1-(4-chloropyridin-2-yl)ethanaminium chloride

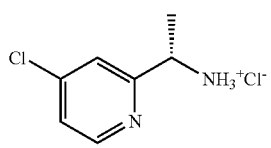

The title compound was prepared following the same general protocol as described in Step 1 and 2, Example 2, using 4-chloropicolinaldehyde instead of 4-t-butylbenzaldehyde.

Step 2: (S)-tert-butyl 4'-((5-((1-(4-chloropyridin-2-yl)ethyl)carbamoyl)-2,3-dimethyl-1H-indol-1-yl)methyl)-[1,1'-biphenyl]-2-carboxylate

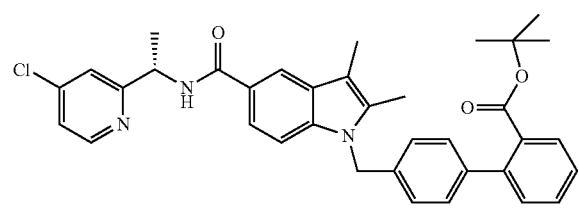 [SMILES: Cc1c(C)n(Cc2ccc(-c3ccccc3C(=O)OC(C)(C)C)cc2)c2ccc(C(=O)N[C@@H](C)c3cc(Cl)ccn3)cc12]

The title compound was prepared following the same general protocol as described in Step 8, Example 1, using (S)-1-(4-chloropyridin-2-yl)ethanaminium chloride instead of (S)-1-(4-bromophenyl)ethanamine.

Step 3: (S)-4'-((5-((1-(4-chloropyridin-2-yl)ethyl)carbamoyl)-2,3-dimethyl-1H-indol-1-yl)methyl)-[1,1'-biphenyl]-2-carboxylic acid

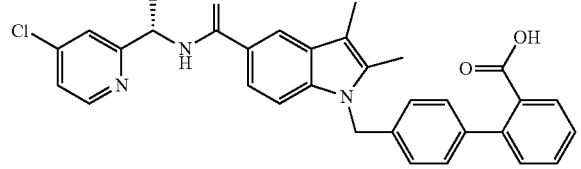

The title compound was prepared following the same general protocol as described in Step 9, Example 1. ESI-MS (m/z): 538 [M+H]⁺.

Example 266: (S)-4'-((5-((1-(4-cyclopropylpyridin-2-yl)ethyl)carbamoyl)-2,3-dimethyl-1H-indol-1-yl)methyl)-[1,1'-biphenyl]-2-carboxylic acid

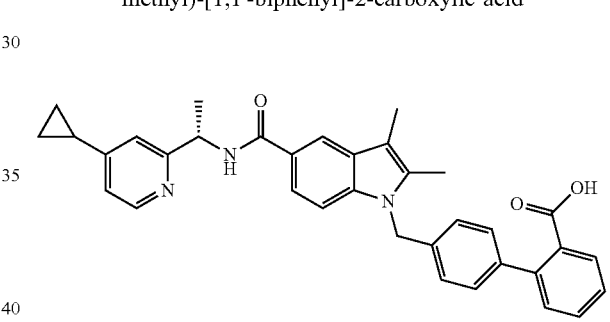

Step 1: (S)-tert-butyl 4'-((5-((1-(4-cyclopropylpyridin-2-yl)ethyl)carbamoyl)-2,3-dimethyl-1H-indol-1-yl)methyl)-[1,1'-biphenyl]-2-carboxylate

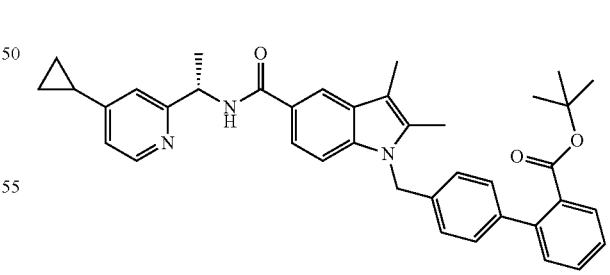

The title compound was prepared following the same general protocol as described in Step 1, Example 261, using (S)-tert-butyl 4'-((5-((1-(4-chloropyridin-2-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate.

Step 2: (S)-4'-((5-(((1-(4-cyclopropylpyridin-2-yl)ethyl)carbamoyl)-2,3-dimethyl-1H-indol-1-yl)methyl)-[1,1'-biphenyl]-2-carboxylic acid

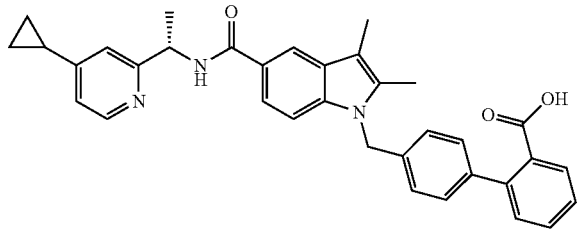 [SMILES: Cc1c(C)n(Cc2ccc(-c3ccccc3C(=O)O)cc2)c2ccc(C(=O)N[C@@H](C)c3cc(C4CC4)ccn3)cc12]

The title compound was prepared following the same general protocol as described in Step 9, Example 1. ESI-MS (m/z): 544 [M+H]⁺.

Example 267: (S)-4'-((5-(1-(2-bromopyridin-4-yl)ethylcarbamoyl)-2,3-dimethyl-1H-indol-1-yl)methyl)biphenyl-2-carboxylic acid

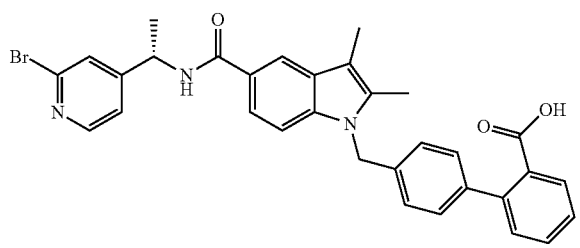 [SMILES: Cc1c(C)n(Cc2ccc(-c3ccccc3C(=O)O)cc2)c2ccc(C(=O)N[C@@H](C)c3ccnc(Br)c3)cc12]

Step 1: (S)-1-(2-bromopyridin-4-yl)ethanaminium chloride

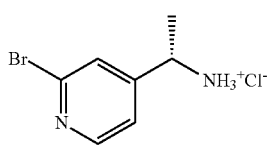

The title compound was prepared following the same general protocol as described in Step 1 and 2, Example 2, using 2-bromoisonicotinaldehyde instead of 4-t-butylbenzaldehyde.

Step 2: (S)-tert-butyl 4'-((5-((1-(2-bromopyridin-4-yl)ethyl)carbamoyl)-2,3-dimethyl-1H-indol-1-yl)methyl)-[1,1'-biphenyl]-2-carboxylate

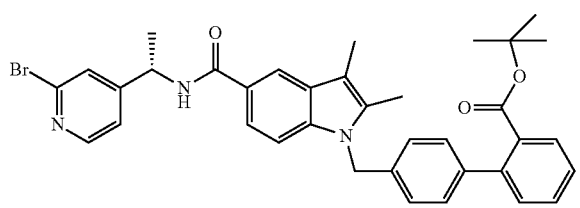

The title compound was prepared following the same general protocol as described in Step 8, Example 1, using (S)-1-(2-bromopyridin-4-yl)ethanaminium chloride instead of (S)-1-(4-bromophenyl)ethanamine.

Step 3: (S)-4'-((5-(1-(2-bromopyridin-4-yl)ethylcarbamoyl)-2,3-dimethyl-1H-indol-1-yl)methyl)biphenyl-2-carboxylic acid

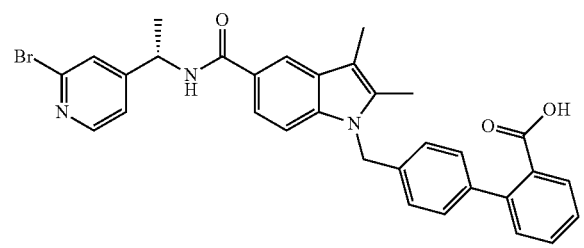 [SMILES: Cc1c(C)n(Cc2ccc(-c3ccccc3C(=O)O)cc2)c2ccc(C(=O)N[C@@H](C)c3ccnc(Br)c3)cc12]

The title compound was prepared following the same general protocol as described in Step 9, Example 1. ESI-MS (m/z): 582 [M+H]⁺.

Example 268: (S)-4'-((5-(1-(2-cyclopropylpyridin-4-yl)ethylcarbamoyl)-2,3-dimethyl-1H-indol-1-yl)methyl)biphenyl-2-carboxylic acid

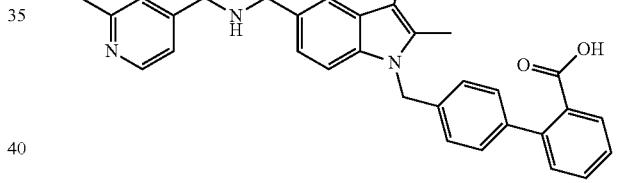

Step 1: (S)-tert-butyl 4'-((5-(((1-(2-cyclopropylpyridin-4-yl)ethyl)carbamoyl)-2,3-dimethyl-1H-indol-1-yl)methyl)-[1,1'-biphenyl]-2-carboxylate

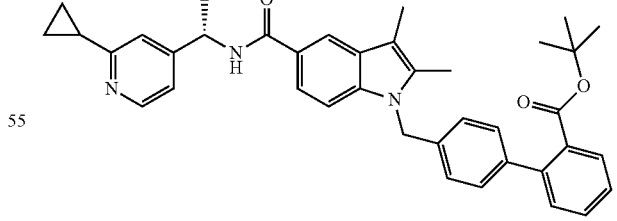

The title compound was prepared following the same general protocol as described in Step 1, Example 261, using (S)-tert-butyl 4'-((5-(((1-(2-bromopyridin-4-yl)ethyl)carbamoyl)-2,3-dimethyl-1H-indol-1-yl)methyl)-[1,1'-biphenyl]-2-carboxylate instead of (S)-tert-butyl 4'-((5-(((1-(5-bromopyridin-2-yl)ethyl) carbamoyl)-2,3-dimethyl-1H-indol-1-yl)methyl)-[1,1'-biphenyl]-2-carboxylate.

Step 2: (S)-4'-((5-(1-(2-cyclopropylpyridin-4-yl)ethylcarbamoyl)-2,3-dimethyl-1H-indol-1-yl)methyl)biphenyl-2-carboxylic acid

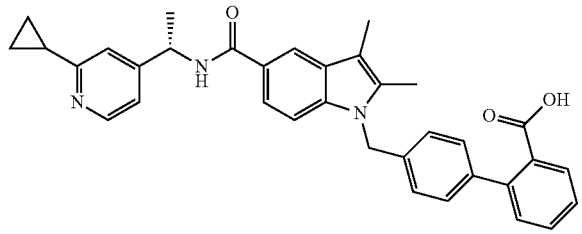 [SMILES: Cc1c(C)n(Cc2ccc(-c3ccccc3C(=O)O)cc2)c2ccc(C(=O)N[C@@H](C)c3ccnc(C4CC4)c3)cc12]

The title compound was prepared following the same general protocol as described in Step 9, Example 1. ESI-MS (m/z): 544 [M+H]⁺.

Example 269: (R)-4'-((5-(1-(2-bromopyridin-4-yl)ethylcarbamoyl)-2,3-dimethyl-1H-indol-1-yl)methyl)biphenyl-2-carboxylic acid

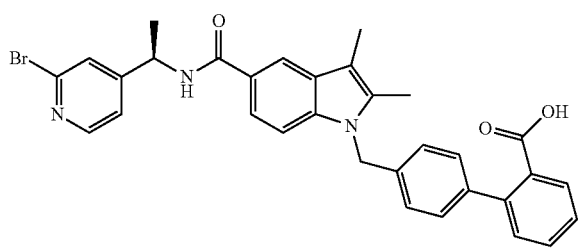 [SMILES: Cc1c(C)n(Cc2ccc(-c3ccccc3C(=O)O)cc2)c2ccc(C(=O)N[C@H](C)c3ccnc(Br)c3)cc12]

Step 1: (R)-1-(2-bromopyridin-4-yl)ethanaminium chloride

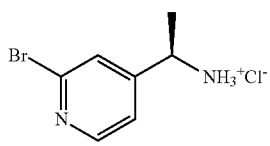

The title compound was prepared following the same general protocol as described in Step 1 and 2, Example 2, using 2-bromoisonicotinaldehyde instead of 4-t-butylbenzaldehyde.

Step 2: (R)-tert-butyl 4'-((5-((1-(2-bromopyridin-4-yl)ethyl)carbamoyl)-2,3-dimethyl-1H-indol-1-yl)methyl)-[1,1'-biphenyl]-2-carboxylate

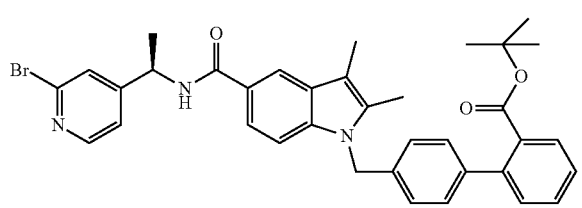

The title compound was prepared following the same general protocol as described in Step 8, Example 1, using (R)-1-(2-bromopyridin-4-yl)ethanaminium chloride instead of (S)-1-(4-bromophenyl)ethanamine.

Step 3: (R)-4'-((5-(1-(2-bromopyridin-4-yl)ethylcarbamoyl)-2,3-dimethyl-1H-indol-1-yl)methyl)biphenyl-2-carboxylic acid

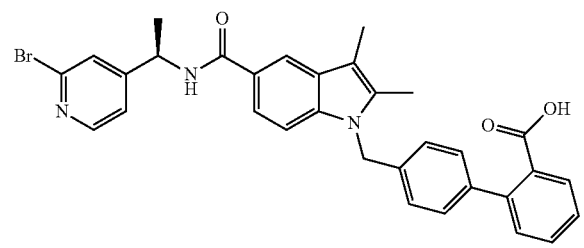

The title compound was prepared following the same general protocol as described in Step 9, Example 1. ESI-MS (m/z): 582 [M+H]⁺.

Example 270: (R)-4'-((5-(1-(2-cyclopropylpyridin-4-yl)ethylcarbamoyl)-2,3-dimethyl-1H-indol-1-yl)methyl)biphenyl-2-carboxylic acid

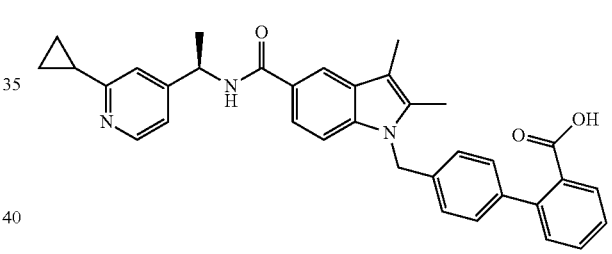

Step 1: (R)-tert-butyl 4'-((5-((1-(2-cyclopropylpyridin-4-yl)ethyl)carbamoyl)-2,3-dimethyl-1H-indol-1-yl)methyl)-[1,1'-biphenyl]-2-carboxylate

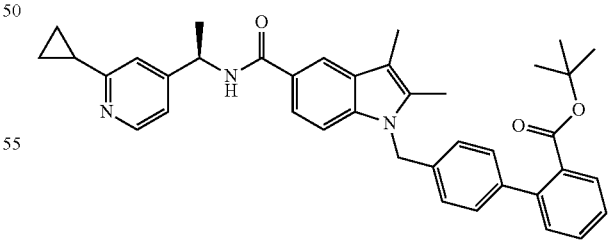

The title compound was prepared following the same general protocol as described in Step 1, Example 261, using (R)-tert-butyl 4'-((5-((1-(2-bromopyridin-4-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate.

Step 2: (R)-4'-((5-(1-(2-cyclopropylpyridin-4-yl)ethylcarbamoyl)-2,3-dimethyl-1H-indol-1-yl)methyl)biphenyl-2-carboxylic acid

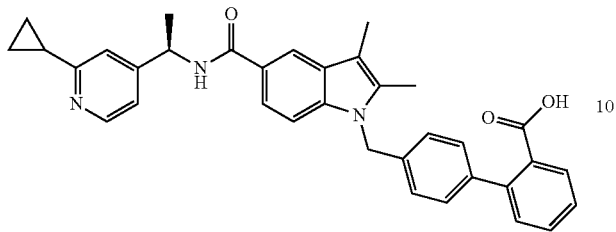

The title compound was prepared following the same general protocol as described in Step 9, Example 1. ESI-MS (m/z): 544 [M+H]+.

Example 271: (R)-4'-((5-(1-(6-bromopyridin-2-yl)ethylcarbamoyl)-2,3-dimethyl-1H-indol-1-yl)methyl)biphenyl-2-carboxylic acid

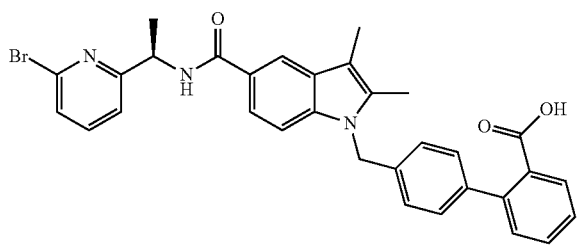 [SMILES: Cc1c(C)n(Cc2ccc(-c3ccccc3C(=O)O)cc2)c2ccc(C(=O)N[C@H](C)c3cccc(Br)n3)cc12]

Step 1: (R)-1-(6-bromopyridin-2-yl)ethanaminium chloride

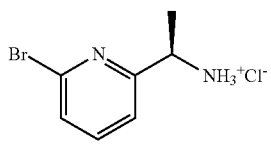

The title compound was prepared following the same general protocol as described in Step 1 and 2, Example 2, using 6-bromopicolinaldehyde instead of 4-t-butylbenzaldehyde.

Step 2: (R)-tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate

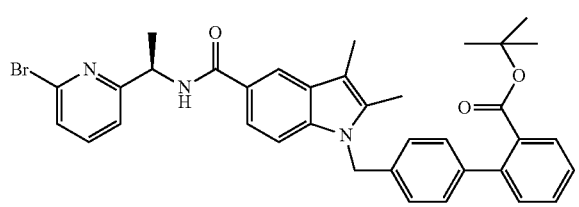 [SMILES: Cc1c(C)n(Cc2ccc(-c3ccccc3C(=O)OC(C)(C)C)cc2)c2ccc(C(=O)N[C@H](C)c3cccc(Br)n3)cc12]

The title compound was prepared following the same general protocol as described in Step 8, Example 1, using (R)-1-(6-bromopyridin-2-yl)ethanaminium chloride instead of (S)-1-(4-bromophenyl)ethanamine.

Step 3: (R)-4'-((5-(1-(6-bromopyridin-2-yl)ethylcarbamoyl)-2,3-dimethyl-1H-indol-1-yl)methyl)biphenyl-2-carboxylic acid The title compound was prepared following the same general protocol as described in Step 9, Example 1. ESI-MS (m/z): 582 [M+H]+.

Example 272: 4'-((5-(1-(6-cyclopropylpyridin-2-yl)ethylcarbamoyl)-2,3-dimethyl-1H-indol-1-yl)methyl)biphenyl-2-carboxylic acid Step 1: 1-(6-bromopyridin-2-yl)ethanaminium chloride

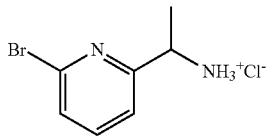

The title compound was prepared following the same general protocol as described in Step 1 and 2, Example 2, using 6-bromopicolinaldehyde instead of 4-t-butylbenzaldehyde.

Step 2: tert-butyl 4'-((5-(((1-(6-bromopyridin-2-yl)
ethyl)carbamoyl)-2,3-dimethyl-1H-indol-1-yl)
methyl)-[1,1'-biphenyl]-2-carboxylate

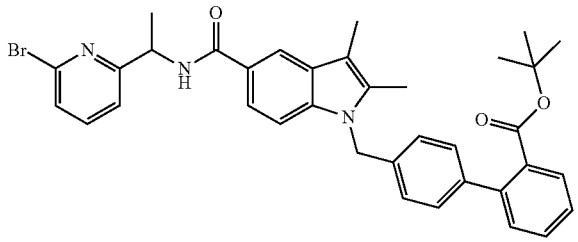 [SMILES: Cc1c(C)n(Cc2ccc(-c3ccccc3C(=O)OC(C)(C)C)cc2)c2ccc(C(=O)NC(C)c3cccc(Br)n3)cc12]

The title compound was prepared following the same general protocol as described in Step 8, Example 1, using (R)-1-(6-chloropyridin-3-yl)ethanaminium chloride instead of (S)-1-(4-bromophenyl)ethanamine.

Step 3: tert-butyl 4'-((5-(((1-(6-cyclopropylpyridin-2-yl)ethyl)carbamoyl)-2,3-dimethyl-1H-indol-1-yl)
methyl)-[1,1'-biphenyl]-2-carboxylate

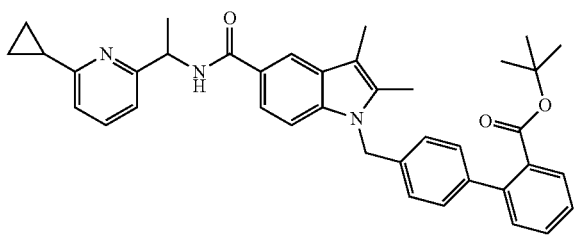 [SMILES: Cc1c(C)n(Cc2ccc(-c3ccccc3C(=O)OC(C)(C)C)cc2)c2ccc(C(=O)NC(C)c3cccc(C4CC4)n3)cc12]

The title compound was prepared following the same general protocol as described in Step 1, Example 261, using tert-butyl 4'-((5-(((1-(6-bromopyridin-2-yl)ethyl)carbamoyl)-2,3-dimethyl-1H-indol-1-yl)methyl)-[1,1'-biphenyl]-2-carboxylate instead of (S)-tert-butyl 4'-((5-(((1-(5-bromopyridin-2-yl)ethyl) carbamoyl)-2,3-dimethyl-1H-indol-1-yl)methyl)-[1,1'-biphenyl]-2-carboxylate.

Step 4: 4'-((5-(((1-(6-cyclopropylpyridin-2-yl)ethyl)
carbamoyl)-2,3-dimethyl-1H-indol-1-yl)methyl)-[1,
1'-biphenyl]-2-carboxylic acid

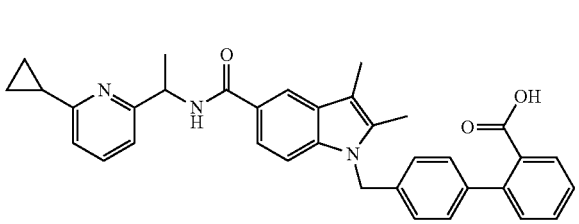 [SMILES: Cc1c(C)n(Cc2ccc(-c3ccccc3C(=O)O)cc2)c2ccc(C(=O)NC(C)c3cccc(C4CC4)n3)cc12]

The title compound was prepared following the same general protocol as described in Step 9, Example 1. ESI-MS (m/z): 544 [M+H]$^+$.

Example 273: (S)-4'-((5-(1-(6-bromopyridin-2-yl)
ethylcarbamoyl)-2,3-dimethyl-1H-indol-1-yl)
methyl)biphenyl-2-carboxylic acid

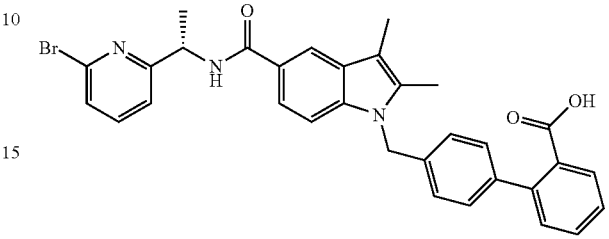

Step 1: (S)-1-(6-bromopyridin-2-yl)ethanaminium
chloride

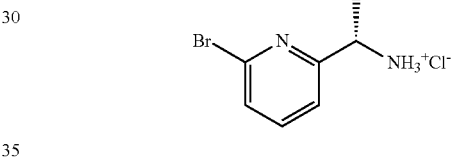

The title compound was prepared following the same general protocol as described in Step 1 and 2, Example 2, using 6-bromopicolinaldehyde instead of 4-t-butylbenzaldehyde.

Step 2: (S)-tert-butyl 4'-((5-(((1-(6-bromopyridin-2-yl)ethyl)carbamoyl)-2,3-dimethyl-1H-indol-1-yl)
methyl)-[1,1'-biphenyl]-2-carboxylate

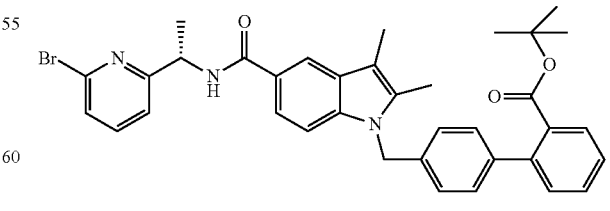

The title compound was prepared following the same general protocol as described in Step 8, Example 1, using (S)-1-(6-bromopyridin-2-yl)ethanaminium chloride instead of (S)-1-(4-bromophenyl)ethanamine.

475

Step 3: (S)-4'-((5-(1-(6-bromopyridin-2-yl)ethylcarbamoyl)-2,3-dimethyl-1H-indol-1-yl)methyl)biphenyl-2-carboxylic acid

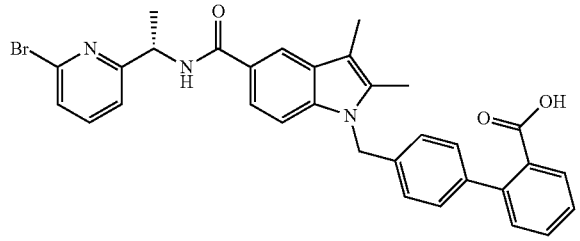 [SMILES: Cc1c(C)n(Cc2ccc(-c3ccccc3C(=O)O)cc2)c2ccc(C(=O)N[C@@H](C)c3cccc(Br)n3)cc12]

The title compound was prepared following the same general protocol as described in Step 9, Example 1. ESI-MS (m/z): 582 [M+H]⁺.

Example 274: (S)-4'-((5-(1-(6-cyclopropylpyridin-2-yl)ethylcarbamoyl)-2,3-dimethyl-1H-indol-1-yl)methyl)biphenyl-2-carboxylic acid Step 1: (S)-tert-butyl 4'-((5-((1-(6-cyclopropylpyridin-2-yl)ethyl)carbamoyl)-2,3-dimethyl-1H-indol-1-yl)methyl)-[1,1'-biphenyl]-2-carboxylate

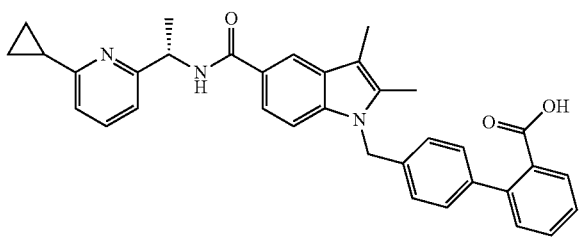 [SMILES: Cc1c(C)n(Cc2ccc(-c3ccccc3C(=O)O)cc2)c2ccc(C(=O)N[C@@H](C)c3cccc(C4CC4)n3)cc12]

The title compound was prepared following the same general protocol as described in Step 1, Example 261, using (S)-tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl) carbamoyl)-2,3-dimethyl-1H-indol-1-yl)methyl)-[1,1'-biphenyl]-2-carboxylate.

476

Step 2: (S)-4'-((5-(1-(6-cyclopropylpyridin-2-yl)ethylcarbamoyl)-2,3-dimethyl-1H-indol-1-yl)methyl)biphenyl-2-carboxylic acid

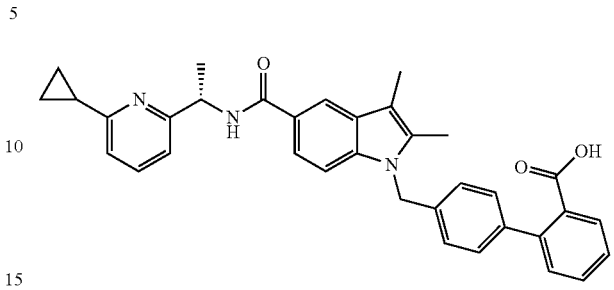

The title compound was prepared following the same general protocol as described in Step 9, Example 1. ESI-MS (m/z): 544 [M+H]⁺.

Example 275: 4'-((5-(1-(5-bromopyridin-3-yl)ethylcarbamoyl)-2,3-dimethyl-1H-indol-1-yl)methyl)biphenyl-2-carboxylic acid

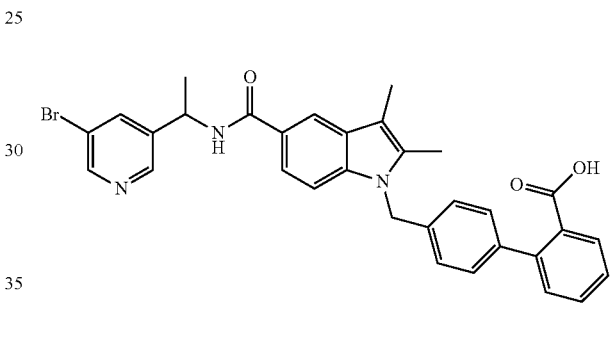

Step 1: 1-(5-bromopyridin-3-yl)ethanaminium chloride

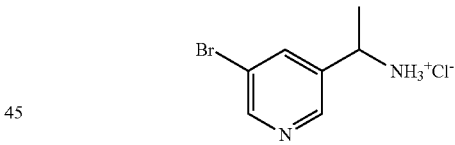

The title compound was prepared following the same general protocol as described in Step 1 and 2, Example 2, using 5-bromonicotinaldehyde instead of 4-t-butylbenzaldehyde.

Step 2: tert-butyl 4'-((5-((1-(5-bromopyridin-3-yl)ethyl)carbamoyl)-2,3-dimethyl-1H-indol-1-yl)methyl)-[1,1'-biphenyl]-2-carboxylate

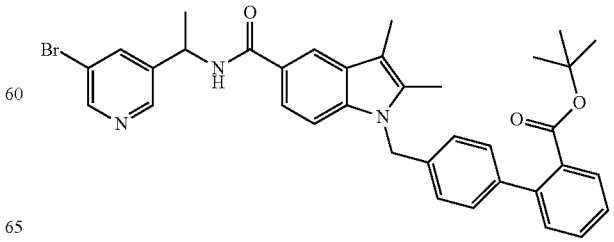

The title compound was prepared following the same general protocol as described in Step 8, Example 1, using 1-(5-bromopyridin-3-yl)ethanaminium chloride instead of (S)-1-(4-bromophenyl)ethanamine.

Step 3: 4'-((5-(1-(5-bromopyridin-3-yl)ethylcarbamoyl)-2,3-dimethyl-1H-indol-1-yl)methyl)biphenyl-2-carboxylic acid

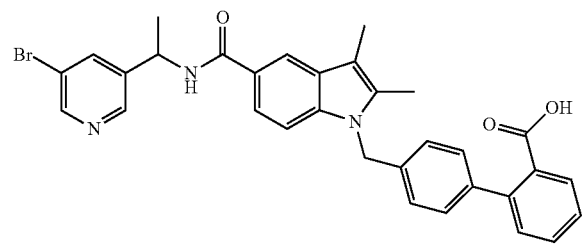

The title compound was prepared following the same general protocol as described in Step 9, Example 1. ESI-MS (m/z): 582 [M+H]$^+$.

Example 276: (R)-4'-((2,3-dimethyl-5-(1-(4-(methylsulfonyl)phenyl)ethylcarbamoyl)-1H-indol-1-yl)methyl)biphenyl-2-carboxylic acid

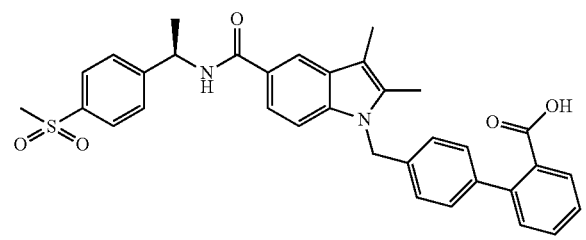 [SMILES: Cc1c(C)n(Cc2ccc(-c3ccccc3C(=O)O)cc2)c2ccc(C(=O)N[C@H](C)c3ccc(S(C)(=O)=O)cc3)cc12]

Step 1: (R)-1-(4-(methylsulfonyl)phenyl)ethanaminium chloride

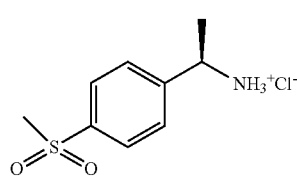

The title compound was prepared following the same general protocol as described in Step 1 and 2, Example 2, using 4-(methylsulfonyl)benzaldehyde instead of 4-t-butylbenzaldehyde.

Step 2: (R)-tert-butyl 4'-((2,3-dimethyl-5-((1-(4-(methylsulfonyl)phenyl)ethyl) carbamoyl)-1H-indol-1-yl)methyl)-[1,1'-biphenyl]-2-carboxylate

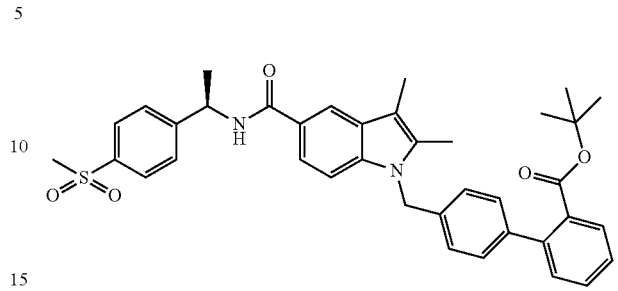

The title compound was prepared following the same general protocol as described in Step 8, Example 1, using (R)-1-(4-(methylsulfonyl)phenyl)ethanaminium chloride instead of (S)-1-(4-bromophenyl)ethanamine.

Step 3: (R)-4'-((2,3-dimethyl-5-(1-(4-(methylsulfonyl)phenyl)ethylcarbamoyl)-1H-indol-1-yl)methyl) biphenyl-2-carboxylic acid

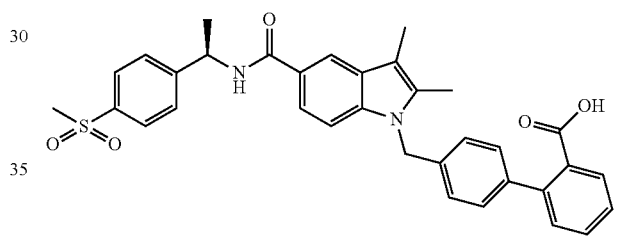

The title compound was prepared following the same general protocol as described in Step 9, Example 1. ESI-MS (m/z): 581 [M+H]$^+$.

Example 277: (S)-1-((2'-cyano-[1,1'-biphenyl]-4-yl)methyl)-2,3-dimethyl-N-(1-(4-(trifluoromethyl)phenyl)ethyl)-1H-indole-5-carboxamide

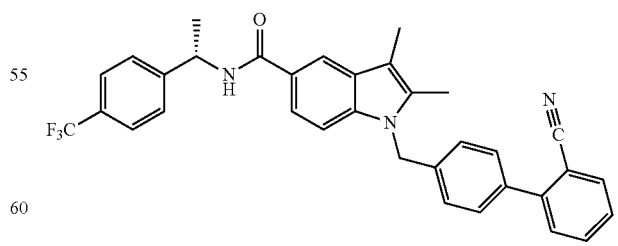

The title compound was prepared following the same protocol as described in Step 5, Example 34, using (S)-1-(4-(trifluoromethyl)phenyl)ethanamine instead of the 1-phenyl propan-1-amine. ESI-MS (m/z): 552 [M+H]$^+$.

Example 278: (S)-1-((2'-cyano-[1,1'-biphenyl]-4-yl) methyl)-N-(1-(4-isopropoxyphenyl) ethyl)-2,3-dimethyl-1H-indole-5-carboxamide

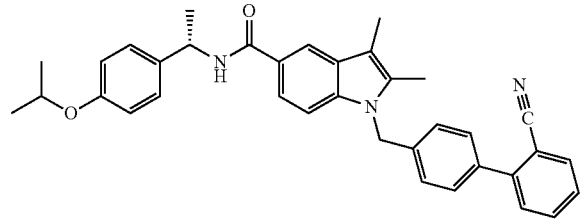 [SMILES: Cc1c(C)n(Cc2ccc(-c3ccccc3C#N)cc2)c2ccc(C(=O)N[C@@H](C)c3ccc(OC(C)C)cc3)cc12]

The title compound was prepared following the same protocol as described in Step 5, Example 34, using (S)-1-(4-isopropoxyphenyl)ethanamine instead of the 1-phenyl propan-1-amine. ESI-MS (m/z): 542 [M+H]$^+$.

Example 279: (S)-1-((2'-cyano-[1,1'-biphenyl]-4-yl) methyl)-2,3-dimethyl-N-(1-(4-(trifluoromethoxy) phenyl)ethyl)-1H-indole-5-carboxamide

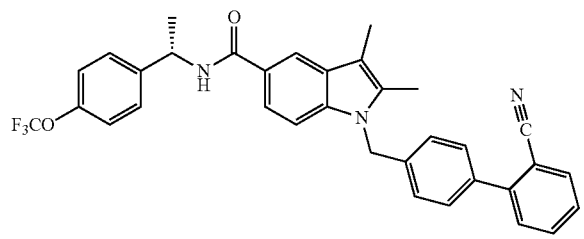 [SMILES: Cc1c(C)n(Cc2ccc(-c3ccccc3C#N)cc2)c2ccc(C(=O)N[C@@H](C)c3ccc(OC(F)(F)F)cc3)cc12]

The title compound was prepared following the same protocol as described in Step 5, Example 34, using (S)-1-(4-(trifluoromethoxy)phenyl)ethanamine instead of the 1-phenyl propan-1-amine. ESI-MS (m/z): 568 [M+H]$^+$.

Example 280: (S)-1-((2'-cyano-[1,1'-biphenyl]-4-yl) methyl)-N-(1-(3-ethoxyphenyl) ethyl)-2,3-dimethyl-1H-indole-5-carboxamide

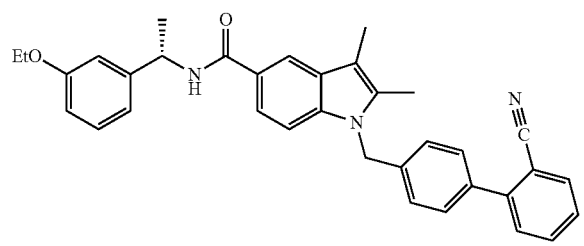 [SMILES: CCOc1cccc([C@H](C)NC(=O)c2ccc3c(c2)c(C)c(C)n3Cc2ccc(-c3ccccc3C#N)cc2)c1]

The title compound was prepared following the same protocol as described in Step 5, Example 34, using (S)-1-(3-ethoxyphenyl)ethanamine instead of the 1-phenyl propan-1-amine. ESI-MS (m/z): 528 [M+H]$^+$.

Example 281: (S)—N-(1-(3-chlorophenyl)ethyl)-1-((2'-cyano-[1,1'-biphenyl]-4-yl)methyl)-2,3-dimethyl-1H-indole-5-carboxamide

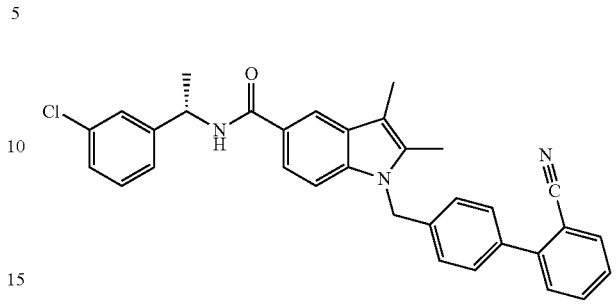

The title compound was prepared following the same protocol as described in Step 5, Example 34, using (S)-1-(3-chlorophenyl)ethanamine instead of the 1-phenyl propan-1-amine. ESI-MS (m/z): 518 [M+H]$^+$.

Example 282: (S)-1-((2'-cyano-[1,1'-biphenyl]-4-yl) methyl)-2,3-dimethyl-N-(1-(3-(trifluoromethyl)phenyl)ethyl)-1H-indole-5-carboxamide

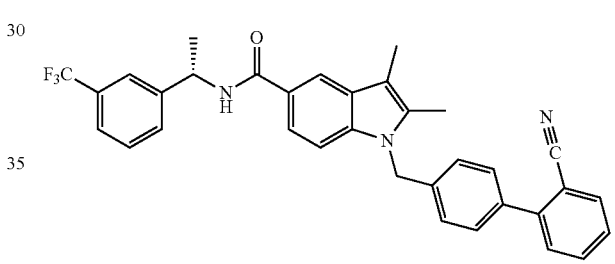

The title compound was prepared following the same protocol as described in Step 5, Example 34, using (S)-1-(3-(trifluoromethyl)phenyl)ethanamine instead of the 1-phenyl propan-1-amine. ESI-MS (m/z): 552 [M+H]$^+$.

Example 283: (S)—N-(1-(4-chlorophenyl)ethyl)-1-((2'-cyano-[1,1'-biphenyl]-4-yl)methyl)-2,3-dimethyl-1H-indole-5-carboxamide

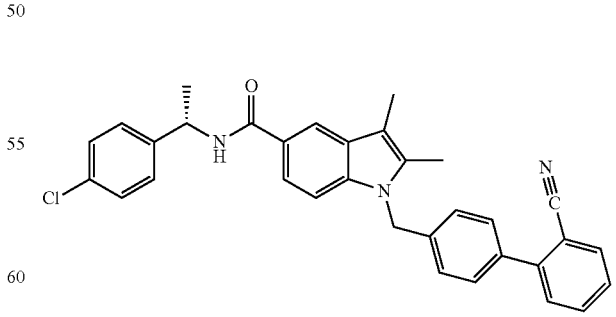

The title compound was prepared following the same protocol as described in Step 5, Example 34, using (S)-1-(4-chlorophenyl)ethanamine instead of the 1-phenyl propan-1-amine. ESI-MS (m/z): 518 [M+H]$^+$.

Example 284: (S)—N-(1-(3-bromophenyl)ethyl)-1-((2'-cyano-[1,1'-biphenyl]-4-yl)methyl)-2,3-dimethyl-1H-indole-5-carboxamide

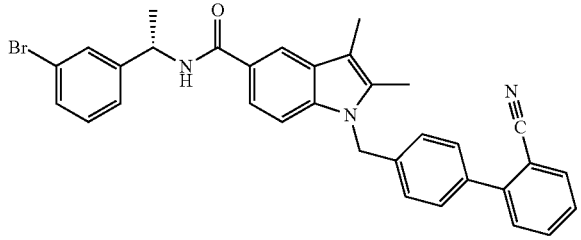 [SMILES: Cc1c(C)n(Cc2ccc(-c3ccccc3C#N)cc2)c2ccc(C(=O)N[C@@H](C)c3cccc(Cl)c3)cc12]

The title compound was prepared following the same protocol as described in Step 5, Example 34, using (S)-1-(3-bromophenyl)ethanamine instead of the 1-phenyl propan-1-amine. ESI-MS (m/z): 562 [M+H]$^+$.

Example 285: (S)-1-((2'-cyano-[1,1'-biphenyl]-4-yl)methyl)-N-(1-(4-methoxyphenyl) ethyl)-2,3-dimethyl-1H-indole-5-carboxamide

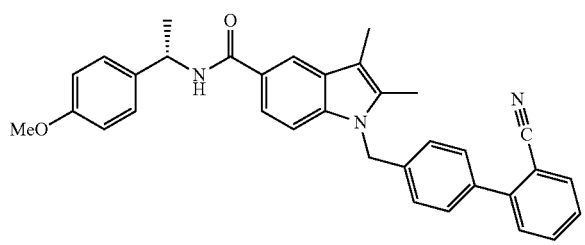 [SMILES: COc1ccc([C@H](C)NC(=O)c2ccc3c(c2)c(C)c(C)n3Cc2ccc(-c3ccccc3C#N)cc2)cc1]

The title compound was prepared following the same protocol as described in Step 5, Example 34, using (S)-1-(4-methoxyphenyl)ethanamine instead of the 1-phenyl propan-1-amine. ESI-MS (m/z): 514 [M+H]$^+$.

Example 286: (S)-1-((2'-cyano-[1,1'-biphenyl]-4-yl)methyl)-N-(1-(2,4-difluorophenyl) ethyl)-2,3-dimethyl-1H-indole-5-carboxamide

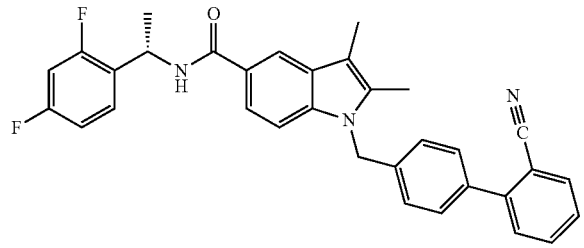 [SMILES: Cc1c(C)n(Cc2ccc(-c3ccccc3C#N)cc2)c2ccc(C(=O)N[C@@H](C)c3ccc(F)cc3F)cc12]

The title compound was prepared following the same protocol as described in Step 5, Example 34, using (S)-1-(2,4-difluorophenyl)ethanamine instead of the 1-phenyl propan-1-amine. ESI-MS (m/z): 520 [M+H]$^+$.

Example 287: (S)—N-(1-(2-chlorophenyl)ethyl)-1-((2'-cyano-[1,1'-biphenyl]-4-yl)methyl)-2,3-dimethyl-1H-indole-5-carboxamide

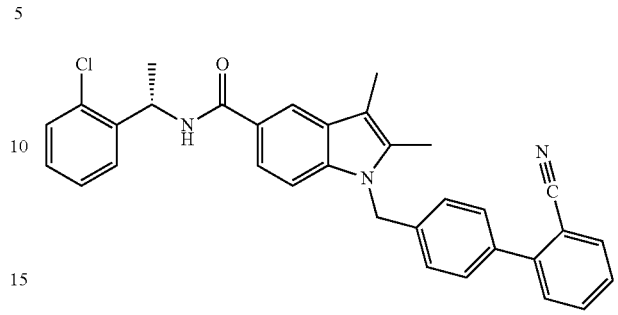

The title compound was prepared following the same protocol as described in Step 5, Example 34, using (S)-1-(2-chlorophenyl)ethanamine instead of the 1-phenyl propan-1-amine. ESI-MS (m/z): 518 [M+H]$^+$.

Example 288: (S)-1-((2'-cyano-[1,1'-biphenyl]-4-yl)methyl)-2,3-dimethyl-N-(1-(p-tolyl)ethyl)-1H-indole-5-carboxamide

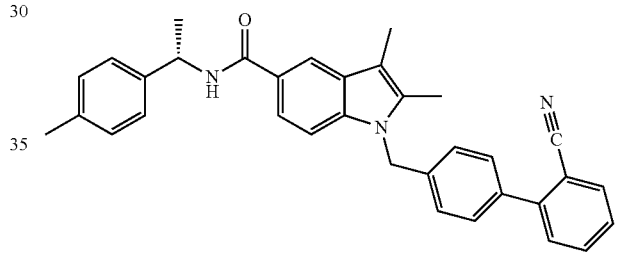

The title compound was prepared following the same protocol as described in Step 5, Example 34, using (S)-1-(4-methylphenyl)ethanamine instead of the 1-phenyl propan-1-amine. ESI-MS (m/z): 498 [M+H]$^+$.

Example 289: (S)-1-((2'-cyano-[1,1'-biphenyl]-4-yl)methyl)-N-(1-(4-ethylphenyl)ethyl)-2,3-dimethyl-1H-indole-5-carboxamide

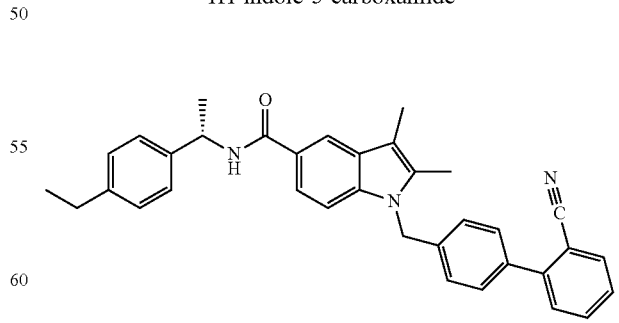

The title compound was prepared following the same protocol as described in Step 5, Example 34, using (S)-1-(4-ethylphenyl)ethanamine instead of the 1-phenyl propan-1-amine. ESI-MS (m/z): 512 [M+H]$^+$.

Example 290: (S)-1-((2'-cyano-[1,1'-biphenyl]-4-yl) methyl)-N-(1-(3,4-dichlorophenyl) ethyl)-2,3-dimethyl-1H-indole-5-carboxamide

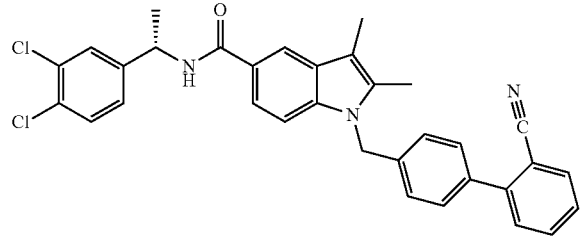 [SMILES: Cc1c(C)n(Cc2ccc(-c3ccccc3C#N)cc2)c2ccc(C(=O)N[C@@H](C)c3ccc(Cl)c(Cl)c3)cc12]

The title compound was prepared following the same protocol as described in Step 5, Example 34, using (S)-1-(3,4-dichlorophenyl)ethanamine instead of the 1-phenyl propan-1-amine. ESI-MS (m/z): 552 [M+H]+.

Example 291: (S)-1-((2'-cyano-[1,1'-biphenyl]-4-yl) methyl)-2,3-dimethyl-N-(1-phenylethyl)-1H-indole-5-carboxamide

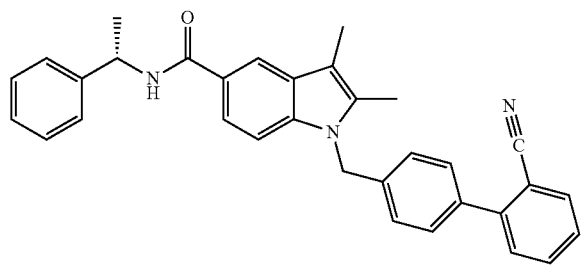 [SMILES: Cc1c(C)n(Cc2ccc(-c3ccccc3C#N)cc2)c2ccc(C(=O)N[C@@H](C)c3ccccc3)cc12]

The title compound was prepared following the same protocol as described in Step 5, Example 34, using (S)-1-phenylethanamine instead of the 1-phenyl propan-1-amine. ESI-MS (m/z): 484 [M+H]+.

Example 292: (S)-1-((2'-cyano-[1,1'-biphenyl]-4-yl) methyl)-N-(1-(2-methoxyphenyl) ethyl)-2,3-dimethyl-1H-indole-5-carboxamide

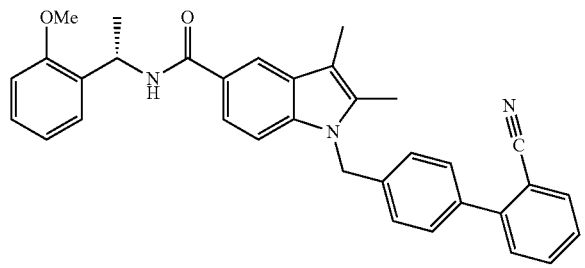 [SMILES: COc1ccccc1[C@H](C)NC(=O)c1ccc2c(c1)c(C)c(C)n2Cc1ccc(-c2ccccc2C#N)cc1]

The title compound was prepared following the same protocol as described in Step 5, Example 34, using (S)-1-(2-methoxyphenyl)ethanamine instead of the 1-phenyl propan-1-amine. ESI-MS (m/z): 514 [M+H]+.

Example 293: (S)-1-((2'-cyano-[1,1'-biphenyl]-4-yl) methyl)-N-(1-(3-fluorophenyl) ethyl)-2,3-dimethyl-1H-indole-5-carboxamide

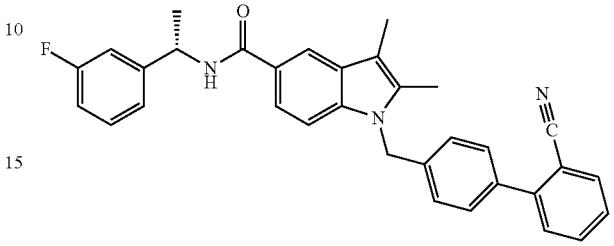

The title compound was prepared following the same protocol as described in Step 5, Example 34, using (S)-1-(3-fluorophenyl)ethanamine instead of the 1-phenyl propan-1-amine. ESI-MS (m/z): 502 [M+H]+.

Example 294: 4'-((2,3-Dimethyl-5-((((1R,2S)-2-phenylcyclopropyl)carbamoyl)-1H-indol-1-yl)methyl)-[1,1'-biphenyl]-2-carboxylic acid

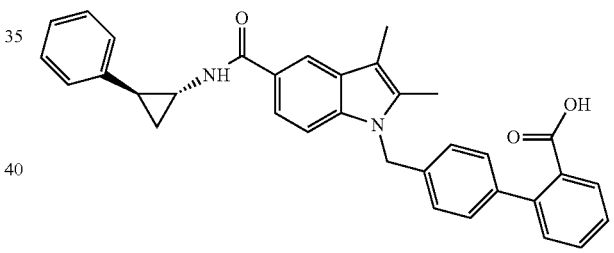

The title compound was prepared following the same general protocol as described in Step 8-9, Example 1, using (1R,2S)-2-phenylcyclopropanamine hydrochloride and 1-((2'-(tert-butoxycarbonyl)-[1,1'-biphenyl]-4-yl)methyl)-2,3-dimethyl-1H-indole-5-carboxylic acid. ESI-MS (m/z): 515 [M+H]+.

Example 295: (S)-4'-((2,3-Dimethyl-5-((1-(m-tolyl) ethyl)carbamoyl)-1H-indol-1-yl)methyl)-[1,1'-biphenyl]-2-carboxylic acid

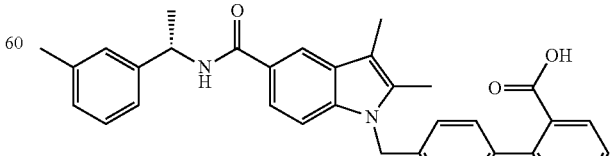

485

Step 1: (S)-tert-Butyl 4'-((2,3-dimethyl-5-((1-(m-tolyl)ethyl)carbamoyl)-1H-indol-1-yl)methyl)-[1,1'-biphenyl]-2-carboxylate

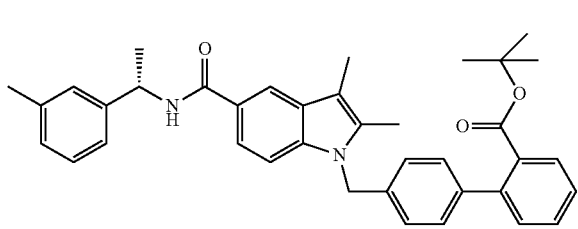 [SMILES: Cc1cccc([C@H](C)NC(=O)c2ccc3c(c2)c(C)c(C)n3Cc2ccc(-c3ccccc3C(=O)OC(C)(C)C)cc2)c1]

A mixture of (S)-tert-butyl 4'-((5-((1-(3-bromophenyl)ethyl)carbamoyl)-2,3-dimethyl-1H-indol-1-yl)methyl)-[1,1'-biphenyl]-2-carboxylate (24 mg, 0.038 mmol), trimethylboroxine (10 mL, 0.072 mmol), Pd(PPh₃)₄ (11 mg, 0.0095 mmol) and K₂CO₃ (15 mg, 0.11 mmol) in Dioxane (0.7 ml) were heated in a Biotage Microwave reactor at 100° C. for 2 h. The solvent was removed and the residue was purified by reverse phase prep-HPLC (MeOH/Acetonitrile/water) to obtain the title compound.

Step 2: (S)-4'-((2,3-Dimethyl-5-((1-(m-tolyl)ethyl)carbamoyl)-1H-indol-1-yl)methyl)-[1,1'-biphenyl]-2-carboxylic acid

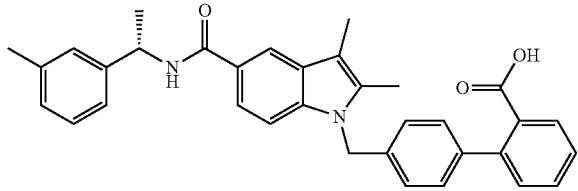 [SMILES: Cc1cccc([C@H](C)NC(=O)c2ccc3c(c2)c(C)c(C)n3Cc2ccc(-c3ccccc3C(=O)O)cc2)c1]

The title compound was prepared following the same general protocol as described in Step 9, Example 1. ESI-MS (m/z): 517 [M+H]⁺.

Example 296: (R)-4'-((5-((1-(3-Bromophenyl)ethyl)carbamoyl)-2,3-dimethyl-1H-indol-1-yl)methyl)-[1,1'-biphenyl]-2-carboxylic acid

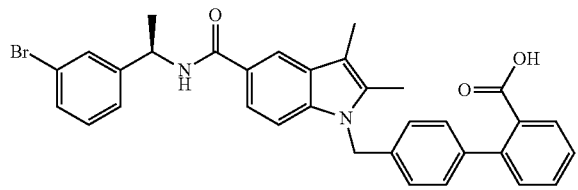 [SMILES: Cc1c(C)n(Cc2ccc(-c3ccccc3C(=O)O)cc2)c2ccc(C(=O)N[C@H](C)c3cccc(Br)c3)cc12]

486

Step 1: (R)-tert-Butyl 4'-((5-((1-(3-bromophenyl)ethyl)carbamoyl)-2,3-dimethyl-1H-indol-1-yl)methyl)-[1,1'-biphenyl]-2-carboxylate

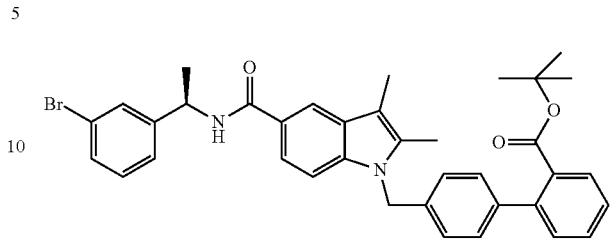

The title compound was prepared following the same general protocol as described in Step 8, Example 1, using (R)-1-(3-bromophenyl)ethanamine instead of (S)-1-(4-bromophenyl)ethanamine.

Step 2: (R)-4'-((5-((1-(3-Bromophenyl)ethyl)carbamoyl)-2,3-dimethyl-1H-indol-1-yl)methyl)-[1,1'-biphenyl]-2-carboxylic acid The title compound was prepared following the same general protocol as described in Step 9, Example 1. ESI-MS (m/z): 581/583 [M+H]⁺.

Example 297: (S)-4'-((5-((1-(3-Cyclopropylphenyl)ethyl)carbamoyl)-2,3-dimethyl-1H-indol-1-yl)methyl)-[1,1'-biphenyl]-2-carboxylic acid

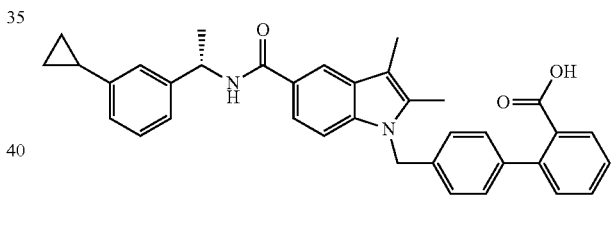

Step 1: (S)-tert-Butyl 4'-((5-((1-(3-cyclopropylphenyl)ethyl)carbamoyl)-2,3-dimethyl-1H-indol-1-yl)methyl)-[1,1'-biphenyl]-2-carboxylate

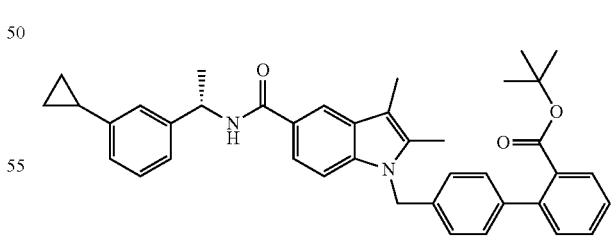

A mixture of (S)-tert-butyl 4'-((5-((1-(3-bromophenyl)ethyl)carbamoyl)-2,3-dimethyl-1H-indol-1-yl)methyl)-[1,1'-biphenyl]-2-carboxylate (24 mg, 0.038 mmol), cyclopropylboronic acid (7 mg, 0.081 mmol), Palladium(II) acetate (3.5 mg, 0.016 mmol) tricyclohexylphosphine (9 mg, 0.032 mmol) and potassium phosphate, tribasic, (23 mg, 0.11 mmol) in toluene (0.7 mL) and water (0.07 mL) was heated at 100° C. for 1 h in a Biotage Microwave reactor. The solvent was removed; the residue was filtered and purified by preparative HPLC to yield the title compound as a white solid.

Step 2: (S)-4'-((5-((1-(3-Cyclopropylphenyl)ethyl)carbamoyl)-2,3-dimethyl-1H-indol-1-yl)methyl)-[1,1'-biphenyl]-2-carboxylic acid

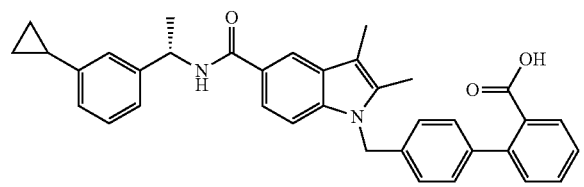

The title compound was prepared following the same general protocol as described in Step 9, Example 1. ESI-MS (m/z): 543 [M+H]$^+$.

Example 298: (S)-4'-((5-((1-(2-Fluoro-4-(trifluoromethyl)phenyl)ethyl)carbamoyl)-2,3-dimethyl-1H-indol-1-yl)methyl)-[1,1'-biphenyl]-2-carboxylic acid

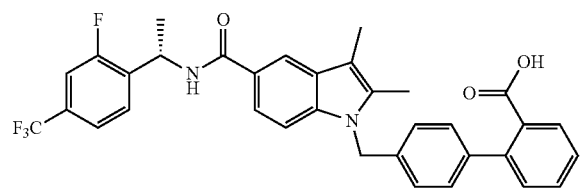 [SMILES: Cc1c(C)n(Cc2ccc(-c3ccccc3C(=O)O)cc2)c2ccc(C(=O)N[C@@H](C)c3ccc(C(F)(F)F)cc3F)cc12]

Step 1: (S)-tert-Butyl 4'-((5-((1-(2-fluoro-4-(trifluoromethyl)phenyl)ethyl)carbamoyl)-2,3-dimethyl-1H-indol-1-yl)methyl)-[1,1'-biphenyl]-2-carboxylate

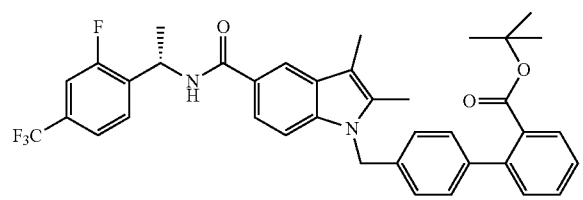 [SMILES: Cc1c(C)n(Cc2ccc(-c3ccccc3C(=O)OC(C)(C)C)cc2)c2ccc(C(=O)N[C@@H](C)c3ccc(C(F)(F)F)cc3F)cc12]

The title compound was prepared following the same general protocol as described in Step 8, Example 1, using (S)-1-(2-fluoro-4-(trifluoromethyl)phenyl)ethanamine instead of (S)-1-(4-bromophenyl)ethanamine Step 2: (S)-4'-((5-((1-(2-Fluoro-4-(trifluoromethyl)phenyl)ethyl)carbamoyl)-2,3-dimethyl-1H-indol-1-yl)methyl)-[1,1'-biphenyl]-2-carboxylic acid

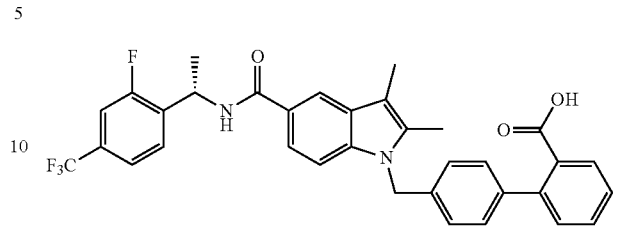

The title compound was prepared following the same general protocol as described in Step 9, Example 1. ESI-MS (m/z): 589 [M+H]$^+$.

Example 299: (S)-4'-((5-((1-(2-Fluoro-3-(trifluoromethyl)phenyl)ethyl)carbamoyl)-2,3-dimethyl-1H-indol-1-yl)methyl)-[1,1'-biphenyl]-2-carboxylic acid

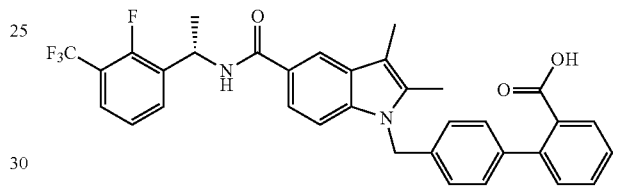

Step 1: (S)-tert-Butyl 4'-((5-((1-(2-fluoro-3-(trifluoromethyl)phenyl)ethyl)carbamoyl)-2,3-dimethyl-1H-indol-1-yl)methyl)-[1,1'-biphenyl]-2-carboxylate

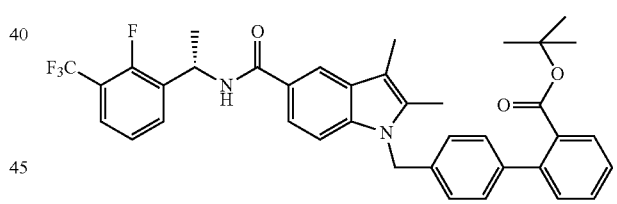

The title compound was prepared following the same general protocol as described in Step 8, Example 1, using (S)-1-(2-fluoro-3-(trifluoromethyl)phenyl)ethanamine instead of (S)-1-(4-bromophenyl)ethanamine.

Step 2: (S)-4'-((5-((1-(2-Fluoro-3-(trifluoromethyl)phenyl)ethyl)carbamoyl)-2,3-dimethyl-1H-indol-1-yl)methyl)-[1,1'-biphenyl]-2-carboxylic acid

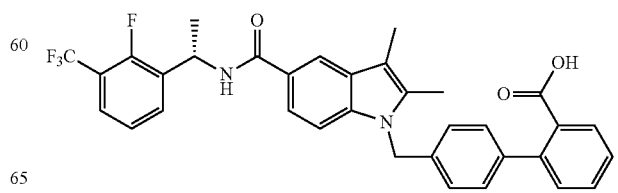

The title compound was prepared following the same general protocol as described in Step 9, Example 1. ESI-MS (m/z): 589 [M+H]⁺.

Example 300: (S)-4'-((5-((1-(2-Fluoro-6-(trifluoromethyl)phenyl)ethyl)carbamoyl)-2,3-dimethyl-1H-indol-1-yl)methyl)-[1,1'-biphenyl]-2-carboxylic acid

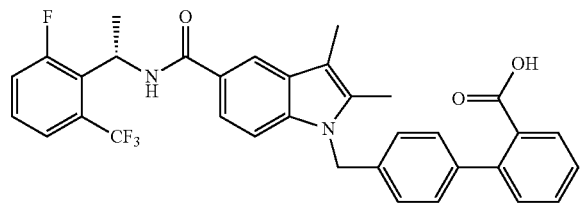 [SMILES: Cc1c(C)n(Cc2ccc(-c3ccccc3C(=O)O)cc2)c2ccc(C(=O)N[C@@H](C)c3c(F)cccc3C(F)(F)F)cc12]

Step 1: (S)-tert-Butyl 4'-((5-((1-(2-fluoro-6-(trifluoromethyl)phenyl)ethyl)carbamoyl)-2,3-dimethyl-1H-indol-1-yl)methyl)-[1,1'-biphenyl]-2-carboxylate

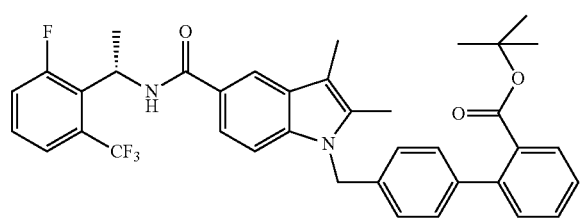 [SMILES: Cc1c(C)n(Cc2ccc(-c3ccccc3C(=O)OC(C)(C)C)cc2)c2ccc(C(=O)N[C@@H](C)c3c(F)cccc3C(F)(F)F)cc12]

The title compound was prepared following the same general protocol as described in Step 8, Example 1, using (S)-1-(2-fluoro-6-(trifluoromethyl)phenyl)ethanamine instead of (S)-1-(4-bromophenyl)ethanamine.

Step 2: (S)-4'-((5-((1-(2-Fluoro-6-(trifluoromethyl)phenyl)ethyl)carbamoyl)-2,3-dimethyl-1H-indol-1-yl)methyl)-[1,1'-biphenyl]-2-carboxylic acid

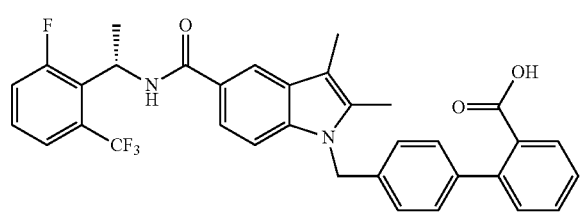 [SMILES: Cc1c(C)n(Cc2ccc(-c3ccccc3C(=O)O)cc2)c2ccc(C(=O)N[C@@H](C)c3c(F)cccc3C(F)(F)F)cc12]

The title compound was prepared following the same general protocol as described in Step 9, Example 1. ESI-MS (m/z): 589 [M+H]⁺.

Example 301: (S)-4'-((2,3-Dimethyl-5-((1-(2,4,5-trifluorophenyl)ethyl)carbamoyl)-1H-indol-1-yl)methyl)-[1,1'-biphenyl]-2-carboxylic acid

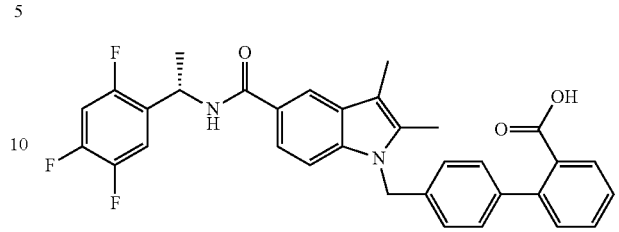

Step 1: (S)-tert-Butyl 4'-((2,3-dimethyl-5-((1-(2,4,5-trifluorophenyl)ethyl)carbamoyl)-1H-indol-1-yl)methyl)-[1,1'-biphenyl]-2-carboxylate

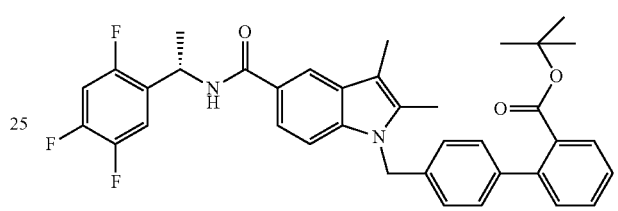

The title compound was prepared following the same general protocol as described in Step 8, Example 1, using (S)-1-(2,4,5-trifluorophenyl)ethanamine instead of (S)-1-(4-bromophenyl)ethanamine Step 2: (S)-4'-((2,3-Dimethyl-5-((1-(2,4,5-trifluorophenyl)ethyl)carbamoyl)-1H-indol-1-yl)methyl)-[1,1'-biphenyl]-2-carboxylic acid

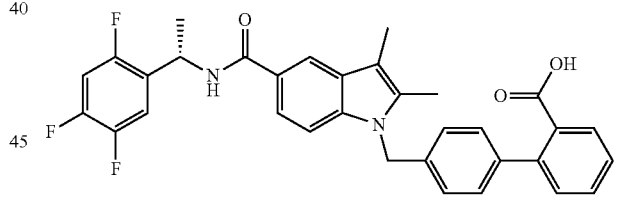

The title compound was prepared following the same general protocol as described in Step 9, Example 1. ESI-MS (m/z): 557 [M+H]⁺.

Example 302: (S)-4'-((5-((1-(2-Chloro-5-(trifluoromethyl)phenyl)ethyl)carbamoyl)-2,3-dimethyl-1H-indol-1-yl)methyl)-[1,1'-biphenyl]-2-carboxylic acid

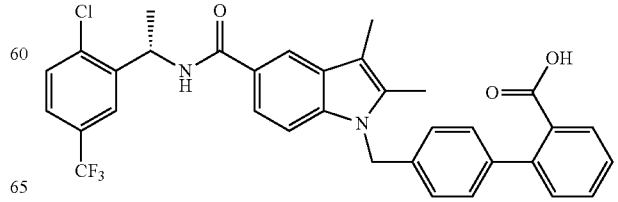

Step 1: (S)-tert-butyl 4'-((5-((1-(2-chloro-5-(trifluoromethyl)phenyl)ethyl)carbamoyl)-2,3-dimethyl-1H-indol-1-yl)methyl)-[1,1'-biphenyl]-2-carboxylate

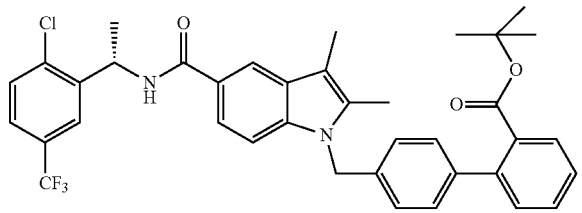 [SMILES: Cc1c(C)n(Cc2ccc(-c3ccccc3C(=O)OC(C)(C)C)cc2)c2ccc(C(=O)N[C@@H](C)c3cc(C(F)(F)F)ccc3Cl)cc12]

The title compound was prepared following the same general protocol as described in Step 8, Example 1, using (S)-1-(2-chloro-5-(trifluoromethyl)phenyl)ethanamine instead of (S)-1-(4-bromophenyl)ethanamine.

Step 2: (S)-4'-((5-((1-(2-Chloro-5-(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 9, Example 1. ESI-MS (m/z): 605 [M+H]$^+$.

Example 303: (S)-4'-((5-((1-(2,4-Dichlorophenyl)ethyl)carbamoyl)-2,3-dimethyl-1H-indol-1-yl)methyl)-[1,1'-biphenyl]-2-carboxylic acid

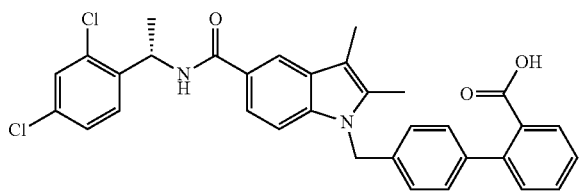 [SMILES: Cc1c(C)n(Cc2ccc(-c3ccccc3C(=O)O)cc2)c2ccc(C(=O)N[C@@H](C)c3ccc(Cl)cc3Cl)cc12]

Step 1: (S)-tert-Butyl 4'-((5-((1-(2,4-dichlorophenyl)ethyl)carbamoyl)-2,3-dimethyl-1H-indol-1-yl)methyl)-[1,1'-biphenyl]-2-carboxylate

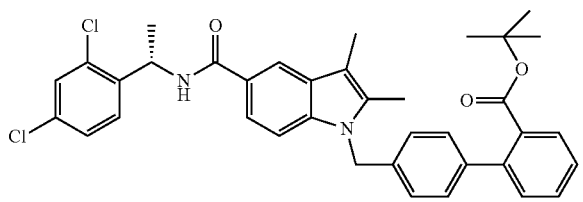 [SMILES: Cc1c(C)n(Cc2ccc(-c3ccccc3C(=O)OC(C)(C)C)cc2)c2ccc(C(=O)N[C@@H](C)c3ccc(Cl)cc3Cl)cc12]

The title compound was prepared following the same general protocol as described in Step 8, Example 1, using (S)-1-(2,4-dichlorophenyl)ethanamine instead of (S)-1-(4-bromophenyl)ethanamine.

Step 2: (S)-4'-((5-((1-(2,4-Dichlorophenyl)ethyl)carbamoyl)-2,3-dimethyl-1H-indol-1-yl)methyl)-[1,1'-biphenyl]-2-carboxylic acid

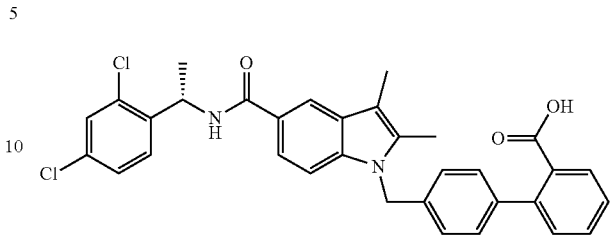

The title compound was prepared following the same general protocol as described in Step 9, Example 1. ESI-MS (m/z): 571 [M+H]$^+$.

Example 304: (S)-4'-((5-((1-(4-Cyclopropylphenyl)ethyl)carbamoyl)-2,3-dimethyl-1H-indol-1-yl)methyl)-[1,1'-biphenyl]-2-carboxylic acid

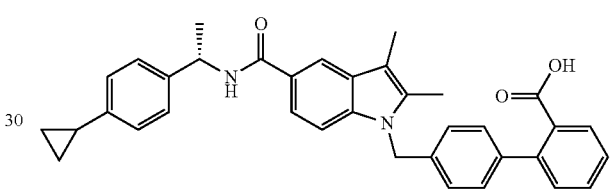

A mixture of (S)-4'-((5-((1-(4-bromophenyl)ethyl)carbamoyl)-2,3-dimethyl-1H-indol-1-yl)methyl)-[1,1'-biphenyl]-2-carboxylic acid (28 mg, 0.048 mmol), cyclopropylboronic acid (9 mg, 0.10 mmol), Palladium(II) acetate (3.9 mg, 0.017 mmol) tricyclohexylphosphine (10 mg, 0.036 mmol) and potassium phosphate, tribasic, (22 mg, 0.10 mmol) in toluene (2.5 mL) and water (0.3 mL) was heated at 100° C. for 1 h in a Biotage Microwave reactor. The solvent was removed; the residue was filtered and purified by preparative HPLC to yield the title compound as a white solid. ESI-MS (m/z): 543 [M+H]$^+$.

Example 305: (S)-1-((2'-(Cyclopropylcarbamoyl)-[1,1'-biphenyl]-4-yl)methyl)-N-(1-(3-isopropylphenyl)ethyl)-2,3-dimethyl-1H-indole-5-carboxamide

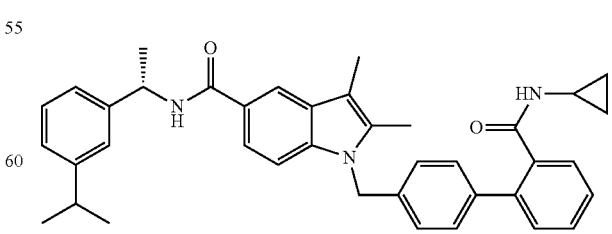

The title compound was prepared using the same general protocol as described in Step 8, Example 1. ESI-MS (m/z): 584 [M+H]$^+$.

Example 306: 1-((2'-((S)-3-Hydroxypyrrolidine-1-carbonyl)-[1,1'-biphenyl]-4-yl)methyl)-N—((S)-1-(3-isopropylphenyl)ethyl)-2,3-dimethyl-1H-indole-5-carboxamide

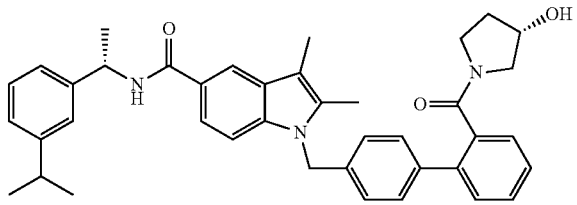 [SMILES: Cc1c(C)n(Cc2ccc(-c3ccccc3C(=O)N3CC[C@H](O)C3)cc2)c2ccc(C(=O)N[C@@H](C)c3cccc(C(C)C)c3)cc12]

The title compound was prepared using the same general protocol as described in Step 8, Example 1. ESI-MS (m/z): 614 [M+H]+.

Example 307: (S)-1-((2'-((2-Hydroxyethyl)carbamoyl)-[1,1'-biphenyl]-4-yl)methyl)-N-(1-(3-isopropylphenyl)ethyl)-2,3-dimethyl-1H-indole-5-carboxamide

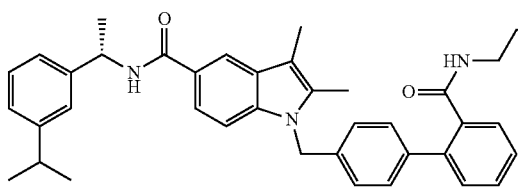

The title compound was prepared using the same general protocol as described in Step 8, Example 1. ESI-MS (m/z): 588 [M+H]+.

Example 308: (S)-1-((2'-(Cyclohexylcarbamoyl)-[1,1'-biphenyl]-4-yl)methyl)-N-(1-(3-isopropylphenyl)ethyl)-2,3-dimethyl-1H-indole-5-carboxamide

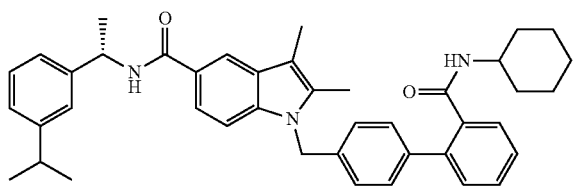 [SMILES: Cc1c(C)n(Cc2ccc(-c3ccccc3C(=O)NC3CCCCC3)cc2)c2ccc(C(=O)N[C@@H](C)c3cccc(C(C)C)c3)cc12]

The title compound was prepared using the same general protocol as described in Step 8, Example 1. ESI-MS (m/z): 626 [M+H]+.

Example 309: 1-((2'-(((R)-3-(Dimethylamino)-2-hydroxy-3-oxopropyl)carbamoyl)-[1,1'-biphenyl]-4-yl)methyl)-N—((S)-1-(3-isopropylphenyl)ethyl)-2,3-dimethyl-1H-indole-5-carboxamide

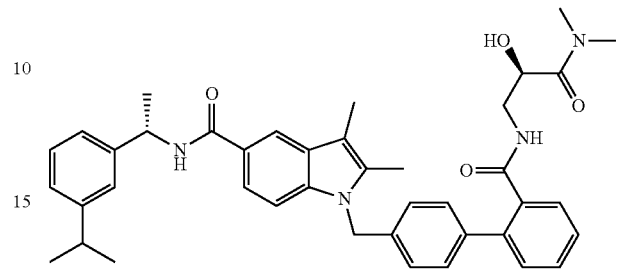

The title compound was prepared using the same general protocol as described in Step 8, Example 1. ESI-MS (m/z): 659 [M+H]+.

Example 310: (S)-1-((2'-((2-(Dimethylamino)ethyl)carbamoyl)-[1,1'-biphenyl]-4-yl)methyl)-N-(1-(3-isopropylphenyl)ethyl)-2,3-dimethyl-1H-indole-5-carboxamide

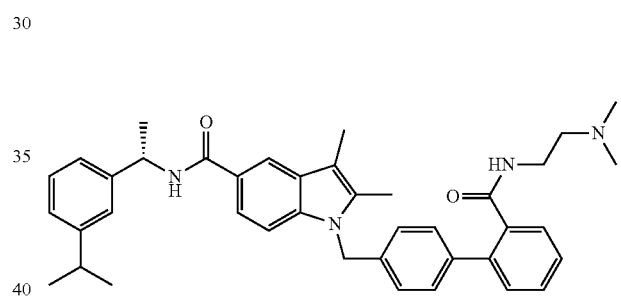

The title compound was prepared using the same general protocol as described in Step 8, Example 1. The TFA salt of the title compound was obtained. ESI-MS (m/z): 615 [M+H]+.

Example 311: (S)—N-(1-(3-Isopropylphenyl)ethyl)-2,3-dimethyl-1-((2'-(methylcarbamoyl)-[1,1'-biphenyl]-4-yl)methyl)-1H-indole-5-carboxamide

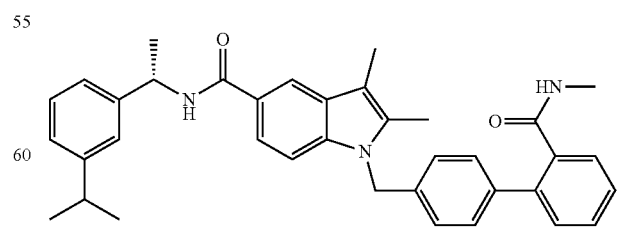

The title compound was prepared using the same general protocol as described in Step 8, Example 1. ESI-MS (m/z): 558 [M+H]+.

Example 312: (S)-1-((2'-(Dimethylcarbamoyl)-[1,1'-biphenyl]-4-yl)methyl)-N-(1-(3-isopropylphenyl)ethyl)-2,3-dimethyl-1H-indole-5-carboxamide

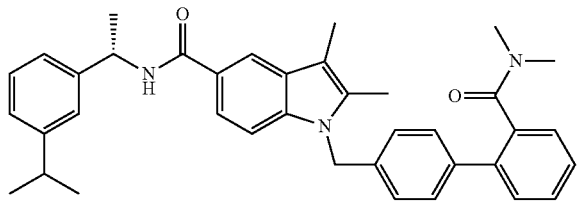 [SMILES: Cc1c(C)n(Cc2ccc(-c3ccccc3C(=O)N(C)C)cc2)c2ccc(C(=O)N[C@@H](C)c3cccc(C(C)C)c3)cc12]

The title compound was prepared using the same general protocol as described in Step 8, Example 1. ESI-MS (m/z): 572 [M+H]+.

Example 313: ((S)-1-((2'-(Hydroxycarbamoyl)-[1,1'-biphenyl]-4-yl)methyl)-N-(1-(3-isopropylphenyl)ethyl)-2,3-dimethyl-1H-indole-5-carboxamide

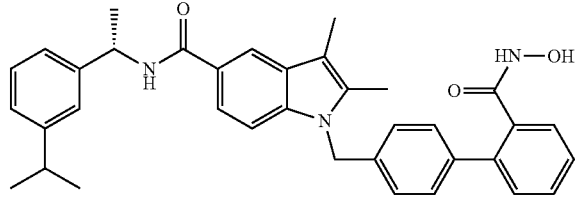 [SMILES: Cc1c(C)n(Cc2ccc(-c3ccccc3C(=O)NO)cc2)c2ccc(C(=O)N[C@@H](C)c3cccc(C(C)C)c3)cc12]

Step 1: (S)-1-((2'-(((tert-Butyldimethylsilyl)oxy)carbamoyl)-[1,1'-biphenyl]-4-yl)methyl)-N-(1-(3-isopropylphenyl)ethyl)-2,3-dimethyl-1H-indole-5-carboxamide

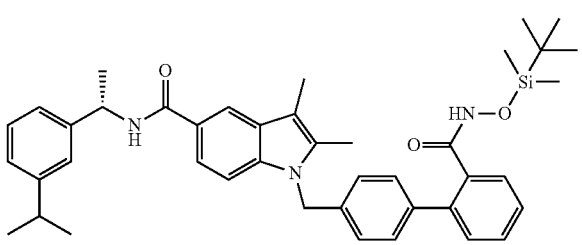 [SMILES: Cc1c(C)n(Cc2ccc(-c3ccccc3C(=O)NO[Si](C)(C)C(C)(C)C)cc2)c2ccc(C(=O)N[C@@H](C)c3cccc(C(C)C)c3)cc12]

The title compound was prepared using the same general protocol as described in Step 8, Example 1.

Step 2: ((S)-1-((2'-(Hydroxycarbamoyl)-[1,1'-biphenyl]-4-yl)methyl)-N-(1-(3-isopropylphenyl)ethyl)-2,3-dimethyl-1H-indole-5-carboxamide

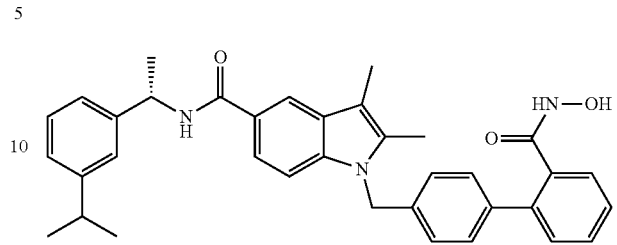

The solution of (S)-1-((2'-(((tert-Butyldimethylsilyl)oxy)carbamoyl)-[1,1'-biphenyl]-4-yl)methyl)-N-(1-(3-isopropylphenyl)ethyl)-2,3-dimethyl-1H-indole-5-carboxamide in DCM (3 mL) and TFA (0.5 mL) was stirred for 1 h at rt. The solvent was removed and the residue was purified by reverse phase prep-HPLC (MeOH/Acetonitrile/water) to obtain the title compound.
ESI-MS (m/z): 560 [M+H]+.

Example 314: (S)—N-(1-(3-Isopropylphenyl)ethyl)-2,3-dimethyl-1-((2'-((methylsulfonyl)carbamoyl)-[1,1'-biphenyl]-4-yl)methyl)-1H-indole-5-carboxamide

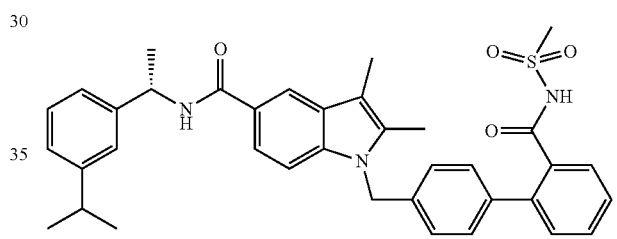

The mixture of (S)-4'-((5-((1-(3-isopropylphenyl)ethyl)carbamoyl)-2,3-dimethyl-1H-indol-1-yl)methyl)-[1,1'-biphenyl]-2-carboxylic acid (30 mg, 0.055 mmol), methanesulfonamide (15 mg, 0.16 mmol), EDAC (25 mg, 0.13 mmol) and DMAP (26 mg, 0.21 mmol) in DMF (3 mL) was stirred at rt for 15 h. The solvent was removed and the residue was purified by reverse phase prep-HPLC (MeOH/Acetonitrile/water) to obtain the title compound. ESI-MS (m/z): 622 [M+H]+.

Example 315: (S)-1-((2'-Carbamoyl-[1,1'-biphenyl]-4-yl)methyl)-N-(1-(3-isopropylphenyl)ethyl)-2,3-dimethyl-1H-indole-5-carboxamide

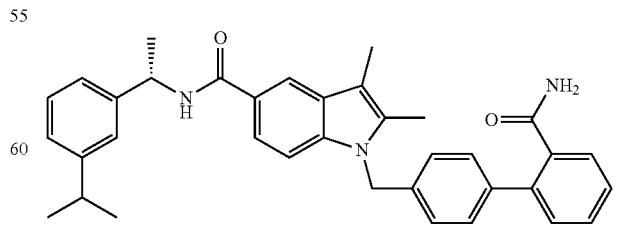

The title compound was prepared using the same general protocol as described in Step 8, Example 1. ESI-MS (m/z): 544 [M+H]+.

Bioassay Procedures
Lanthascreen PPARG Competitive Binding Assay (Invitrogen)

The assay was performed according to manufacturer protocol. A mixture of 5 nM GST-PPARG-LBD, 5 nM Tb-GST-antibody, 5 nM Fluormone Pan-PPAR Green, and serial dilutions of the experimental compound, beginning at 10 µM downwards, was added to wells of black 384-well low-volume plates (Greiner) to a total volume of 18 µL. All dilutions were made in TR-FRET assay buffer C. DMSO at 2% final concentration was used as a no-ligand control. Experiment was performed in triplicate, and incubated for 2 hours in the dark prior to assay read in Perkin Elmer ViewLux ultra HTS microplate reader. FRET signal was measured by excitation at 340 nm and emission at 520 nm for fluorescein and 490 nm for terbium. Fold change over DMSO was calculated using GraphPad Prism Software (La Jolla, Calif.) by calculating 520 nm/490 nm ratio. Graphs were plotted as fold change of FRET signal for compound treatment over DMSO-only control.

Cell-Based Transactivation Assay:

PPRE is a DNA that contains a binding site for PPARG; thus PPRE is a PPAR response element, used herein as a promoter reporter. The binding site is a DR1 response element with the sequence AGGTCA repeated 3 times in tandem and then fused to a construct for luciferase.

Thus, PPRE is the basis of the cell based transactivation assay described below. The plasmid DNA is co-transfected along with a plasmid for PPARG into COS-1 cells. After an overnight incubation, cells are treated with DMSO or compounds. In this assay rosiglitazone activates the reporter about 5 fold. Partial agonists such as MRL24 transactivate the reporter about 25% of rosiglitazone response. Compounds of the invention which are non-activators afford no transactivation of the reporter.

Confluent COS-1 cells were transfected with 4.5 µg murine PPARg2-pSV Sport or full-length human PPARg-pSport6, 4.5 µg 3×PPRE-luciferase reporter and 27 µL X-treme Gene 9 transfection reagent in serum-free opti-mem media (Gibco), followed by overnight incubation at 37° C., 5% $CO_2$. Transfected cells were plated in white Perkin Elmer 384-well plates and incubated 4 hours. Cells were treated with DMSO vehicle only or experimental compounds in increasing doses from 2 µM-220 pM for mouse receptor and 10 µM-111 fM for human. After 18 hour incubation, treated cells were developed with Brite Lite Plus (Perkin Elmer) and read in 384-well Luminescence Perkin Elmer EnVision Multilabel plate reader. Graphs were plotted in triplicate in GraphPad Prism Software as fold change of treated cells over DMSO control cells. The human PPAR nuclear receptor ligand binding domain (LBD) is fused to the DNA-Binding Domain of the yeast GAL4 transcription factor. The hybrid fusion-protein nuclear receptor can activate the luciferase reporter under the control of the GAL4 Upstream Activator Sequence (UAS).

The plasmid Gal4-PPAR DNA is co-transfected along with a plasmid for UAS-luc into HEK 293T cells. After an overnight incubation, cells are treated with DMSO or compounds. In this assay rosiglitazone activates the reporter about 100-fold. Partial agonists transactivate the reporter about 30-40% of rosiglitazone response. Compounds of the invention which are non-activators exhibit <5% transactivation of the receptor at 1 mM.

HEK 293T cells were transfected with 4.5 µg of Gal4-PPARg, 4.5 µg UAS-luciferase reporter and 27 µL X-treme Gene 9 transfection reagent in serum-free opti-mem media (Gibco), followed by overnight incubation at 37° C., 5% $CO_2$. Transfected cells were replated in white Perkin Elmer 384-well plates and incubated 4 hours. Cells were treated with DMSO vehicle only or experimental compounds in doses from 10 µM-111 fM. After 18 hour incubation, treated cells were developed with Brite Lite Plus (Perkin Elmer) and read in 384-well Luminescence Perkin Elmer EnVision Multilabel plate reader. Graphs were plotted in triplicate in GraphPad Prism Software as fold change of treated cells over DMSO control cells.

Biodata Tables 1-5, below, provides biological data for the specifically claimed compounds as shown in Table 1, above, listing compound examples of the invention covering almost all of compound examples 1-320. Each line of Biodata Tables 1-5 represents biodata for the corresponding single compound of the set listed in Table 1, with respect to $IC_{50}$ as determined by the Lanthascreen procedure, and EC50 as determined by the cell-based transactivation assay. A compound with a relatively low IC50 concentration is indicated to have potent PPARG binding activity, whereas a compound with a relatively high EC50 value in the cell-based transactivation assay is indicated to possess non-agonistic properties. In various embodiments, the invention provides compounds combining these two properties, non-agonistic and PPARG binding.

Evaluations

It is within ordinary skill to evaluate any compound disclosed and claimed herein for effectiveness in non-agonistic binding to PPARG and in the various cellular assays using the procedures described above or found in the scientific literature. Accordingly, the person of ordinary skill can prepare and evaluate any of the claimed compounds without undue experimentation.

Any compound found to be an effective non-agonist PPARG binding molecular entity can likewise be tested in animal models and in human clinical studies using the skill and experience of the investigator to guide the selection of dosages and treatment regimens.

Example 316: Binding Affinities

The purpose of this example was to determine binding affinities (IC50) of inventive compounds as determined by the Lantha Screen displacement assay (n=3) described above. The following table shows affinities for selected compounds in comparison with rosiglitazone:

| COMPOUND | $IC_{50}$ |
|---|---|
| Rosiglitazone | 60 |
| IB-72 (SR1663) | 2 |
| IB-73 (SR1664) | 80 |
| IB-2 (SR2595) | 30 |
| IA-58 (SR10221) | 15 |

Example 317: Pharmacokinetic Properties of Compounds of the Invention

The purpose of this example was to determine if pharmacological PPARγ repression would impair insulin sensitivity.

All animal experiments were performed according to procedures approved by Scripps-Florida IACUC Committee. Male $C_{57}BL/6J$ mice were purchased from the Jackson Laboratory (7-week-old) and fed a regular chow diet through experiments. The mice were dosed by oral gavage once daily with 5 mg $kg^{-1}$ rosiglitazone or 20 mg $kg^{-1}$ Compound IB-2 (SR2595) for 21 days. For insulin tolerance tests, mice were fasted overnight before i.p. injection of 0.75 U/kg insulin (Sigma). Glucose was then measured by tail vein bleeds at the indicated intervals using an OneTouch Ultra2 glucometer. Plasma insulin concentration was determined by ELISA (Millipore mouse/rat insulin. cat # EZRMI-13K).

Figure 12:
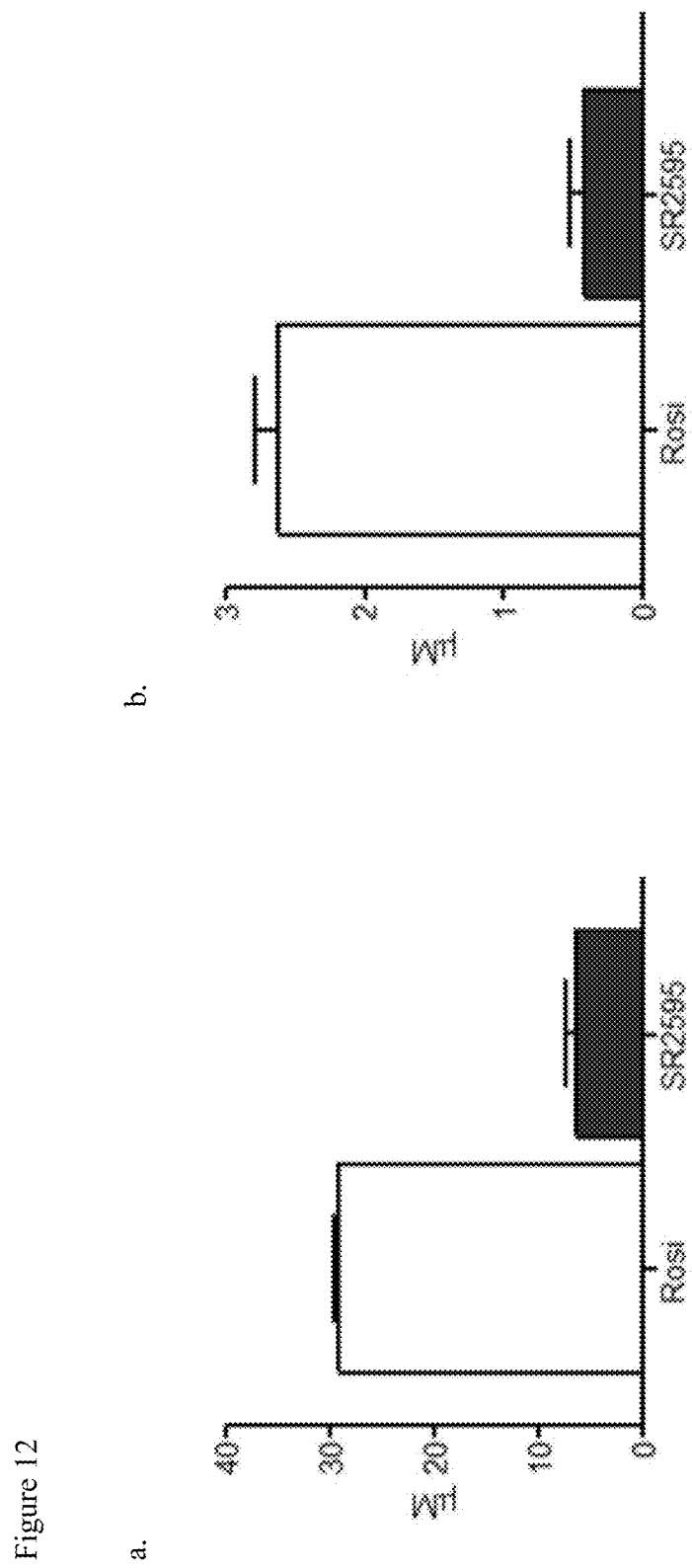
FIG. 12 shows pharmacokinetic properties of rosiglitazone and SR2595 concentration in lean C57BL/6J mice treated for 21 days, two hours following drug administration (n=5) (a) plasma concentration (b) epididymal WAT concentration. Error bars are s.e.m.
Figure 15:
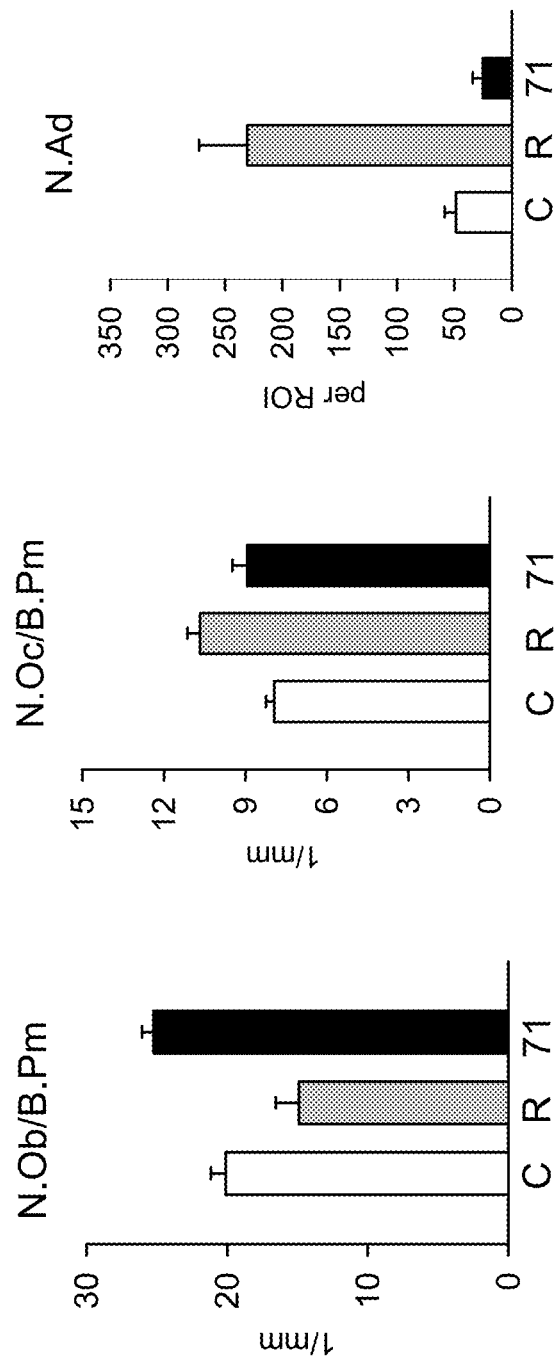
FIG. 15 shows static histomorphometry of trabecular bone in proximal tibia in lean C57BL/6 mice (N.Ob—number of osteoblasts per bone perimeter; N.Oc—number of osteoclasts per bone perimeter; N.Ad—number of adipocytes per region of interest; C=control; R=rosiglitazone; 71=SR10171).

The results are shown in FIG. 12, indicating that the pharmacokinetic properties of SR2595 were sufficient to support once daily oral dosing at 20 mg/kg.

Example 318: Increase of Bone Mass and Bone Formation

The purpose of this example is to demonstrate that the compounds of the invention increase bone mass in pathological conditions of bone loss or to increase bone formation in conditions that compromise fracture healing.

The compound IA-48 (SR10171) acts as an antagonist to PPARγ pro-adipocytic activity, and it has been further tested in vivo for its effect on bone. SR10171 was administered to hyperglycemic $C_{57}BL/6$ mice, 12 wks old males, that were purchased from the Jackson Laboratories (Bar Harbor, Me.). DIO mice: Animals were fed ad libitum for 11 wks high fat diet (HFD) providing 45 kcal % from fat (D12451; Research Diets, New Brunswick, N.J.) to develop diet induced obesity (DIO).

DIO mice were separated into three groups (n=8) and fed for 4 wks as follows: HFD (control), HFD supplemented with rosiglitazone at the dose 25 mg/kg/d, and HFD supplemented with SR10171 at the dose 25 mg/kg/d. The dose of SR10171 was calculated based on the following reasoning: SR10171 binding affinity to PPARγ is 10-fold lower and its 5273 phosphorylation blocking activity is 50% lower than rosiglitazone. This together with 2.5-fold higher than rosiglitazone retention levels in plasma of animals treated for 4 days resulted in the decision to treat animals with the same dose of each drug. The exact amount was decided based on our experience that a dose of rosiglitazone between 20-25 mg/kg/day administered for 4 weeks to DIO animals results in significant loss of trabecular bone in both, axial and appendicular skeleton (Kolli, V., et al. Partial Agonist, Telmisartan, Maintains PPARgamma Serine 112 Phosphorylation, and Does Not Affect Osteoblast Differentiation and Bone Mass. PLoS One 9, e96323 (2014). Ingested doses of SR10171 (22 mg/kg/d) and rosiglitazone (24 mg/kg/d) were calculated at the end of treatment based on food intake monitored throughout duration of entire experiment. In parallel, a group of sex- and age-matched control (n=5) was fed regular diet (RD) providing 12 kcal % from fat (2016 Teklad Global, Harlan Laboratories, Indianapolis, Ind.). Second experiment was conducted on 12 wks old males, lean C57BL/6 mice, which were fed for 8 weeks either non-supplemented RD, or RD supplemented with rosiglitazone, or RD supplemented with SR10171. Food intake was monitored during the entire experiment to calculate an ingested dose of SR10171 (12.7 mg/kg/d) and rosiglitazone (11.7 mg/kg/d). The animal treatment and care protocols conformed to the NIH Guidelines and were performed under the University of Toledo Health Science Campus Institutional Animal Care and Utilization Committee protocol.

Fat and lean mass were evaluated at the beginning and at the end of experiment using a Minispec mq10 NMR analyzer (Bruker, Billerica, Mass.). Glucose disposal (glucose tolerance test, GTT) was measured after ip injection of 2 g/kg glucose to animals fasted for 4 hrs. Blood glucose was measured using the AlphaTRAK system appropriate for mice (Abbott Laboratories, North Chicago, Ill.). For indirect calorimetry, mice were evaluated in metabolic cages (CLAMS; Columbus Instruments, Columbus, Ohio) for 4 days with a free access to food and water. Mice were housed individually at room temperature (22C) under an alternating 12-h light/dark cycle. After one day adaptation, oxygen (VO2) consumption, carbon dioxide (VCO2) production, physical activity, and heat production were measured to determine energy expenditure. Respiratory exchange ratio was calculated as a ratio of the $O_2$ consumption and the $CO_2$ production.

The effect of SRI0171 on bone mass was compared to the effect of rosiglitazone. At the end of experiment, bones (tibia, femur and vertebra) were isolated and their volume and microarchitecture was analyzed using micro-computed tomography.

Micro CT Imaging of Bone and Marrow Fat mCT of the tibiae was performed using the μCT-35 system (Scanco Medical AG, Bruettisellen, Switzerland) as previously described (Liu, L., et al. Rosiglitazone inhibits bone regeneration and causes significant accumulation of fat at sites of new bone formation. *Calcif Tissue Int* 91, 139-148 (2012). Briefly, scans were performed at 7 μm nominal resolution with the x-ray source operating at 70 kVp, and 113 μA settings. Scans consisted of 300 slices starting at the growth plate of proximal tibia and images of trabecular bone were segmented at 220 threshold value using per mille scale following manual contouring starting 10 slices below the growth plate and extending to the end of the image stack. Scans of cortical bone at tibia midshaft consisting of 55 slices were obtained at 7 μm nominal resolution with the x-ray source operating at 70 kVp and 113 μA. Images of cortical bone were contoured in the entire image stack and segmented at 260 threshold using per mille scale. The analysis of the trabecular bone microstructure and the cortical bone parameters was conducted using Evaluation Program V6.5-1 (Scanco Medical AG, Bruettisellen, Switzerland) and conformed to recommended guidelines (Bouxsein, M. L., et al. Guidelines for assessment of bone microstructure in rodents using micro-computed tomography. *J Bone Miner Res* 25, 1468-1486 (2010).

For lipid content evaluation, decalcified bone specimens were stained for 1 hr in solution containing 2% osmium tetroxide prepared in 0.1M sodium cacodylate buffer pH 7.4, according to the protocol (Liu et al., 2012). Staining was carried-out in an exhaust hood and away from light due to osmium tetroxide toxicity and light sensitivity. Images of lipid depositions were acquired at 70 kVp and 113 μA settings and 12 μm nominal resolution. Image segmentation was done under global threshold condition by applying a threshold of 480-1000 using permille scale with 3-dimensional noise filter set to sigma 1.2 and support 2.0. Lipid volumes were calculated directly from individual voxel volumes in 3-D reconstructions.

Bone Histomorphometry

To obtain static and dynamic bone histomorphometry, animals were injected with 2.5 mg/ml calcein solution in 2% sodium bicarbonate at a dose 20 mg/kg body weight. First injection was performed 10 days and second 2 days before sacrifice. Undecalcified tibiae were embedded in methyl methacrylate, sectioned and stained with either Golden Trichrome or Von Kossa/McNeal by Histology Core at the Department of Anatomy and Cell Biology, Indiana University (Indianapolis, Ind.). The histomorphometric examination was confined to the secondary spongiosa of proximal tibia and was performed using Nikon NIS-Elements BR3.1 system. The measurements were collected under 40× magnification from six representative fields per bone sample. The terminology and units used were those recommended by the Histomorphometry Nomenclature Committee of the American Society for Bone and Mineral Research (Parfitt, A. M., et al. Bone histomorphometry: standardization of nomenclature, symbols, and units. Report of the ASBMR Histomorphometry Nomenclature Committee. *J Bone Miner Res* 2, 595-610 (1987).

The measurements as described above showed that SR10171 compound increased bone mass and bone size and decreased bone marrow fat content in bone region of trabecular structure.

In contrast, rosiglitazone at the same pharmacological dose decreased trabecular bone mass by 70% and significantly increased fat content in the bone marrow. In addition, SR10171 increased overall bone size and bone area in midshaft tibia which contains cortical bone. These changes in the bone mass and bone geometry increased bone strength as measured by calculating tortional strength and bone bending strength.

These findings show that compounds such as SR10171, which do not possess PPARγ transcriptional pro-adipocytic activity can exert a beneficial effect on bone. The findings further indicate that the inventive compounds can be used as bone anabolic drugs to increase bone mass in pathological conditions of bone loss, e.g. osteoporosis, or to increase bone formation in conditions that compromise fracture healing, e.g. diabetes.

In addition, the data showed that beneficial effects on bone are independent of SR10171 metabolic activity. SR10171 increases energy metabolism and normalizes fat function in animals with diet induced obesity, but unlike rosiglitazone it is neutral in animals with balanced energy metabolism. Our data suggest that SR10171 modulates energy metabolism in an on-demand manner, while having sustained anabolic activity on bone regardless of animal metabolic status.

In lean mice, SR10171 exerted a more robust positive effect on bone. Trabecular bone mass in proximal tibia was increased by 26% as compared to non-treated animals, whereas animals receiving rosiglitazone-supplemented diet lost 30% of bone mass (FIG. 13). The increase in bone mass was due to increased number of trabeculae, but not their thickness (FIG. 13). In contrast to obese mice, lean mice treated with SR10171 did not experience effects on tibia cortical bone, neither cortical bone area nor cortical thickness.

What is claimed is:
1. A method for treatment of a patient afflicted by a progressive bone disease, comprising administering to the patient an effective dose of a compound of formula (I)

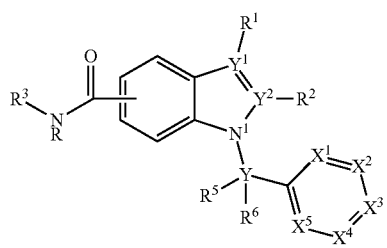

(I)

wherein:
R is H, $(C_1-C_6)$alkyl, $(C_3-C_9)$cycloalkyl, or $(C_3-C_9)$cycloalkyl$(C_1-C_6)$alkyl;
$Y^1$ or $Y^2$ are each independently C or N, provided that when $Y^1$ or $Y^2$ is N, $R^1$ or $R^2$, respectively, is absent;
$R^1$ is H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or multi-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, oxo, $(C_1-C_6)$haloalkyl, nitro, cyano-$(C_0-C_6)$alkyl, R'$O_2$C—$(C_0-C_6)$alkyl, methylenedioxy, R'O—$(C_0-C_6)$alkyl, $(R')_2$N—$(C_0-C_6)$alkyl, $(R')_2$NC(=O)—$(C_0-C_6)$alkyl, R'C(=O)N(R')—$(C_0-C_6)$alkyl, $(C_1-C_6)$alkyl-S(O)$_q$ $(C_0-C_6)$alkyl, aryl, aroyl, or $SO_2NR'_2$;
$R^2$ is H or $(C_1-C_6)$alkyl;
$R^3$ is optionally mono- or multi-substituted $(C_1-C_6)$alkyl, $(C_1-C_6)$alkenyl, $(C_1-C_6)$alkynyl, $(C_6-C_{10})$aryl, $(C_6-C_{10})$aryl$(C_1-C_6)$alkyl, (3-9 membered)heterocyclyl, (3-9 membered)heterocyclyl$(C_1-C_6)$alkyl, (3-9 membered)heteroaryl, or (3-9 membered)heteroaryl$(C_1-C_6)$alkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, oxo, haloalkyl, haloalkoxy, nitro, cyano, $CO_2R'$, methylenedioxy, OR', $N(R')_2$, C(O)N$(R')_2$, $(C_1-C_6)$alkyl-S(O)$_q$, $SO_2NR'_2$, and $(C_1-C_6)$alkoxyl; and provided that group $R^3N(R)C(=O)$— can be bonded to any one of the four carbon atoms of the phenyl ring not bonded to $N^1$ or $Y^1$;
wherein each R' is independently H, $(C_1-C_6)$ alkyl, $(C_3-C_9)$cycloalkyl, $(C_3-C_9)$cycloalkyl$(C_1-C_6)$alkyl, $(C_6-C_{10})$aryl, or $(C_6-C_{10})$aryl$(C_1-C_6)$ alkyl, or wherein two R' bonded to an atom together with the atom form a 3-9 membered ring optionally further comprising a heteroatom selected from the group consisting of O, NR', and $S(O)_q$;
wherein any alkyl, alkenyl, alkynyl, aryl, arylalkyl, or cycloalkyl of R' is optionally mono- or independently multi-substituted with $(C_1-C_6)$haloalkyl, $(C_1-C_6)$alkoxy, $(C_1-C_6)$haloalkoxy, halo, oxo, aryl, or aroyl;
each of $X^1$-$X^5$ is independently N or CH, or is C substituted with an independently selected $R^4$ or is C substituted with Z, provided that no more than two of $X^1$-$X^5$ are N, and provided that there is no more than one Z group bonded to the ring comprising $X^1$—$X^5$;
each $R^4$ is independently halo, nitro, $(C_1-C_6)$fluoroalkyl, R'—$(C_0-C_6)$alkyl, R'$O_2$C—$(C_0-C_6)$alkyl, NC—$(C_0-C_6)$alkyl, R'O—$(C_0-C_6)$alkyl, $(R')_2$N—$(C_0-C_6)$alkyl, $(R')_2$NC(=O)—$(C_0-C_6)$alkyl, R'C(=O)N(R')—$(C_0-C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1-C_6)$alkyl-S(O)$_q$$(C_0-C_6)$alkyl, R'S(O)$_2$NHC(O), R'C(O)NHS(O)$_2$, an unsubstituted or substituted aryl, an unsubstituted or substituted heteroaryl, $(C_1-C_6)$alkyl or $(C_3-C_9)$cycloalkyl-$(C_0-C_6)$ alkyl, wherein any alkyl or cycloalkyl is optionally mono- or independently multi-substituted with R', OR', N(R')$_2$, C-bonded tetrazolyl, (C$_1$-C$_6$)alkyl-S(O)$_q$(C$_0$-C$_6$)alkyl, an unsubstituted or substituted aryl, or an unsubstituted or substituted heteroaryl; or R$^4$ is —(C(R")$_2$)$_m$CO$_2$R', —(C(R")$_2$)$_m$CON(R')$_2$, —(C(R")$_2$)$_m$CN, —O(C(R")$_2$)$_m$CO$_2$R', —O(C(R")$_2$)$_m$CON(R')$_2$, or —O(C(R")$_2$)$_m$CN, wherein m is 1, 2, or 3;

R" is H, halo, (C$_1$-C$_6$) alkyl, (C$_1$-C$_6$) haloalkyl, (C$_3$-C$_9$) cycloalkyl, (C$_3$-C$_9$)cycloalkyl(C$_1$-C$_6$)alkyl, (C$_6$-C$_{10}$) aryl, or (C$_6$-C$_{10}$)aryl(C$_1$-C$_6$) alkyl, or two R" together with an atom to which they are bonded form a 3- to 9-membered ring;

Z is a group of formula

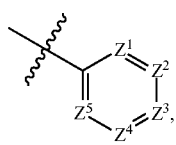

wherein a wavy line indicates a point of bonding, each of Z$^1$-Z$^5$ is independently N or is C substituted with an independently selected H or R$^4$; provided that no more than two of Z$^1$-Z$^5$ are N;

Y is (C$_1$-C$_2$) alkyl, or sulfur;

when Y is (C$_1$-C$_2$)alkyl, R$^5$ and R$^6$ are independently H or (C$_1$-C$_4$)alkyl or independently each R$^5$ and R$^6$ together with the carbon atom to which they are bonded form a carbonyl, or, one R$^5$ group can further be bonded to X$^5$ to form a 4- to 8-membered ring; and, when Y is sulfur, R$^5$ and R$^6$ are both oxygen;

or a pharmaceutically acceptable salt thereof;

wherein R$^3$—NRCO— is substituted at position 5 or 6 of the ring.

2. The method of claim 1, wherein Y$^1$ or Y$^2$ are each C and R$^1$ and R$^2$ are independently H or methyl.

3. The method of claim 1, wherein Y$^1$ is N and Y$^2$ is C, or wherein Y$^1$ is C and Y$^2$ is N.

4. The method of claim 1, wherein R$^3$ is benzyl, α-phenethyl, α-phenpropyl, cycloalkyl or cycloalkylalkyl, any of which is unsubstituted or substituted.

5. The method of claim 1, wherein R$^3$ is heterocyclyl, heterocyclylalkyl, heteroaryl, or heteroarylalkyl, any of which is unsubstituted or substituted.

6. The method of claim 1, wherein R$^3$ is any one of:

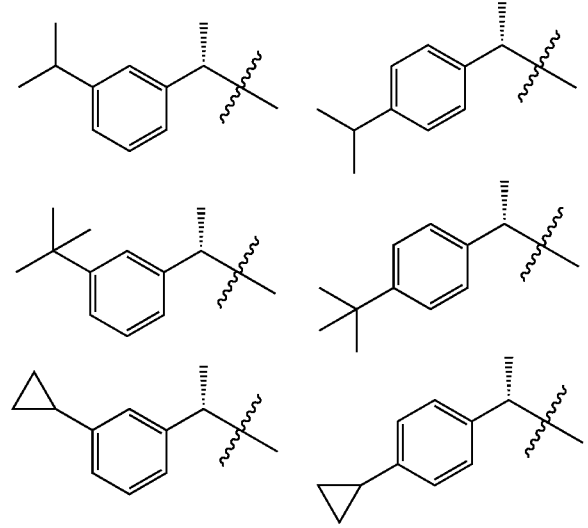

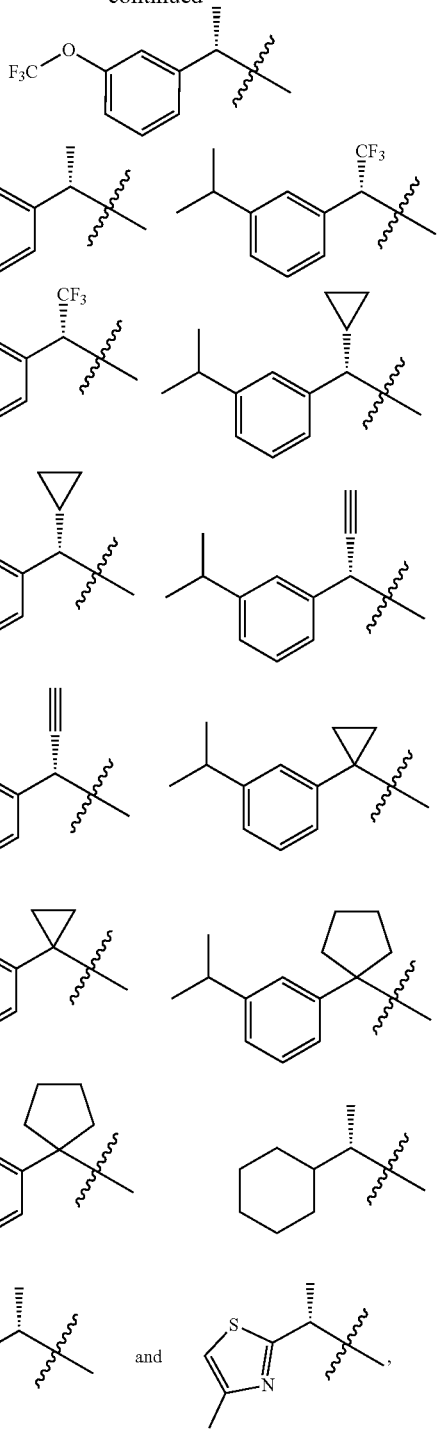

wherein a wavy line indicates a point of attachment.

7. The method of claim 1, wherein YR$^5$R$^6$ is SO$_2$.

8. The method of claim 1, wherein Y is C$_1$-alkyl; and R$^5$ and R$^6$ are H, or wherein Y is C$_2$-alkyl, and R$^5$ and R$^6$ are H.

9. The method of claim 1, wherein R$^4$ is —CO$_2$H, —(CH$_2$)$_m$CO$_2$H, —O(CH$_2$)$_m$CO$_2$H, —CN, —(CH$_2$)$_m$CN, —O(CH$_2$)$_m$CN, —C(CH$_3$)$_2$CO$_2$H, —C(CH$_3$)$_2$CN, —OC(CH$_3$)$_2$CO$_2$H, —OC(CH$_3$)$_2$CN, —CH(CH$_3$)CO$_2$H, —CH(CH$_3$)CN, —OCH(CH$_3$)CO$_2$H, —OCH(CH$_3$)CN; —CH(CH$_2$CH$_3$)CO$_2$H, —CH(CH$_2$CH$_3$)CN, —OCH(CH$_2$CH$_3$)

CO₂H, —OCH(CH₂CH₃)CN; —CH(i-Pr)CO₂H, —CH(i-Pr)CN, —OCH(i-Pr)CO₂H, —OCH(i-Pr)CN, wherein iPr indicates isopropyl; —CH(t-Bu)CO₂H, —CH(t-Bu)CN, —OCH(t-Bu)CO₂H, —OCH(t-Bu)CN, wherein t-Bu indicates t-butyl; —(CHR")$_m$C(=O)N(R")$_2$, —O(CHR")$_m$C(=O)N(R")$_2$,

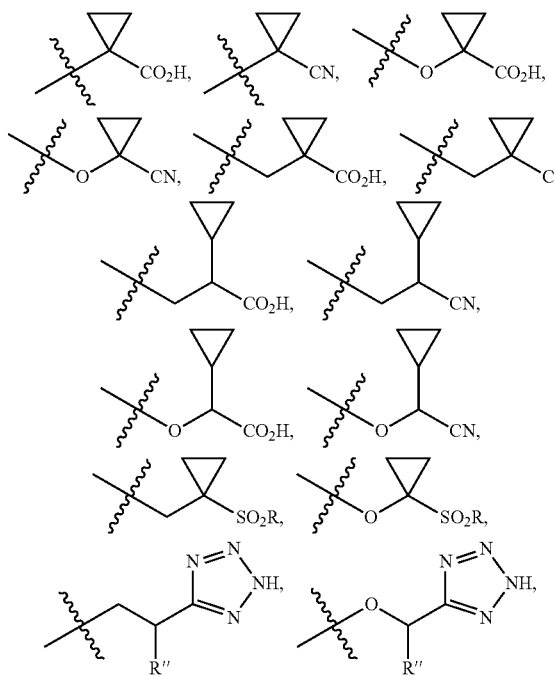

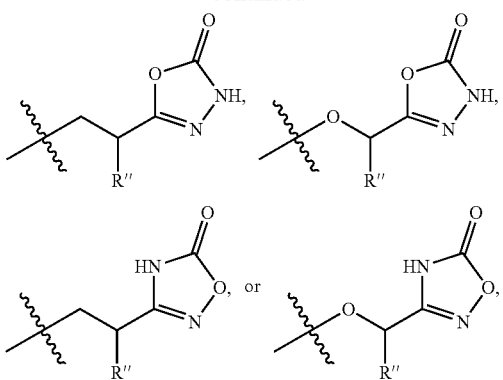

wherein a wavy line indicates a point of attachment.

10. The method of claim 1, wherein for the compound of formula (I), each of $X^1$-$X^5$ is independently N or CH, or is C substituted with an independently selected $R^4$.

11. The method of claim 1, wherein for the compound of formula (I), Z is present.

12. The method of claim 11, wherein $Z^1$-$Z^5$ are all carbon.

13. The method of claim 1, wherein the progressive bone disease is osteoporosis, Paget's Disease, multiple myeloma, or hyperparathyroidism.

14. The method of claim 1, wherein administration of the compound of formula (I) is an effective amount to increase FGF21.

* * * * *